US011110158B2

(12) United States Patent
Binder et al.

(10) Patent No.: US 11,110,158 B2
(45) **Date of Patent: *Sep. 7, 2021**

(54) PROSTATE-ASSOCIATED ANTIGENS AND VACCINE-BASED IMMUNOTHERAPY REGIMENS

(71) Applicant: Pfizer Inc., New York, NY (US)

(72) Inventors: Joseph John Binder, San Diego, CA (US); Helen Kim Cho, San Diego, CA (US); Michael Robert Dermyer, Carlsbad, CA (US); Karin Ute Jooss, San Diego, CA (US); Brian Gregory Pierce, Wayland, MA (US); Joyce Tsi Tan, Chapel Hill, NC (US); Van To Tsai, San Diego, CA (US); James Richard Merson, Rancho Santa Fe, CA (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/058,257

(22) Filed: Aug. 8, 2018

(65) Prior Publication Data

US 2019/0038728 A1 Feb. 7, 2019

Related U.S. Application Data

(60) Continuation of application No. 15/207,348, filed on Jul. 11, 2016, now abandoned, which is a continuation of application No. 14/657,302, filed on Mar. 13, 2015, now Pat. No. 9,468,672, which is a division of application No. 13/875,162, filed on May 1, 2013, now Pat. No. 9,066,898.

(60) Provisional application No. 61/642,844, filed on May 4, 2012.

(51) Int. Cl.

| | |
|---|---|
| ***A61K 39/00*** | (2006.01) |
| ***C07K 14/47*** | (2006.01) |
| ***C12N 9/48*** | (2006.01) |
| ***A61K 39/39*** | (2006.01) |
| ***A61K 39/395*** | (2006.01) |
| ***A61K 31/404*** | (2006.01) |
| ***C12N 9/64*** | (2006.01) |
| ***A61K 9/00*** | (2006.01) |
| ***A61K 31/7088*** | (2006.01) |
| ***C07K 16/28*** | (2006.01) |
| ***C07K 16/30*** | (2006.01) |

(52) U.S. Cl.

CPC .... *A61K 39/001193* (2018.08); *A61K 9/0019* (2013.01); *A61K 31/404* (2013.01); *A61K 31/7088* (2013.01); *A61K 39/001194* (2018.08); *A61K 39/001195* (2018.08); *A61K 39/39* (2013.01); *A61K 39/3955* (2013.01); *C07K 14/4748* (2013.01); *C07K 16/2818* (2013.01); *C07K 16/303* (2013.01); *C07K 16/3023* (2013.01); *C07K 16/3069* (2013.01); *C12N 9/485* (2013.01); *C12N 9/6445* (2013.01); *C12Y 304/17021* (2013.01); *A61K 2039/53* (2013.01); *A61K 2039/55561* (2013.01); *C07K 2317/21* (2013.01); *C07K 2317/76* (2013.01)

(58) Field of Classification Search

None

See application file for complete search history.

(56) References Cited

U.S. PATENT DOCUMENTS

| | | | |
|---|---|---|---|
| 5,538,866 A | 7/1996 | Israeli et al. | |
| 6,541,212 B2 | 4/2003 | Reiter et al. | |
| 6,825,326 B2 | 11/2004 | Reiter et al. | |
| 7,109,003 B2 | 9/2006 | Hanson et al. | |
| 7,288,251 B2 | 10/2007 | Bedian et al. | |
| 8,435,516 B2 | 5/2013 | Huang et al. | |
| 2003/0086930 A1 | 5/2003 | Mueller et al. | |
| 2005/0136055 A1 | 6/2005 | Gladue et al. | |
| 2005/0226875 A1 | 10/2005 | Gomez-Navaro et al. | |
| 2005/0272755 A1 | 12/2005 | Denis et al. | |
| 2007/0059315 A1 | 3/2007 | Jaffee et al. | |
| 2008/0193448 A1 | 8/2008 | Baum et al. | |
| 2008/0279865 A1 | 11/2008 | Gomez et al. | |
| 2009/0004213 A1 | 1/2009 | Singh et al. | |
| 2009/0074787 A1 | 3/2009 | Gomez et al. | |
| 2009/0117132 A1 | 5/2009 | Readett et al. | |
| 2010/0305196 A1 * | 12/2010 | Probst .................... | A61K 39/00 514/44 R |
| 2012/0263677 A1 | 10/2012 | Eagle et al. | |

FOREIGN PATENT DOCUMENTS

| | | |
|---|---|---|
| WO | WO2006048749 | 5/2006 |
| WO | WO2007113648 | 10/2007 |
| WO | WO20120042421 | 4/2012 |
| WO | WO2012065164 | 5/2012 |
| WO | WO2013006050 | 1/2013 |

OTHER PUBLICATIONS

Drake et al (Current Urol. Rep. 2010, 11:202-207).*
Kwek et al (Nature Reviews, 2012, 12:289-297).*
Furler et al (Gene Therapy, 2001,8:864-873).*
Fu et al (Biochmica et Biophysica Acta, 2012, 1825:140-152, published online Nov. 29, 2011).*

(Continued)

*Primary Examiner* — Laura B Goddard
(74) *Attorney, Agent, or Firm* — Austin W. Zhang

(57) ABSTRACT

The present disclosure provides (a) isolated immunogenic PAA polypeptides; (b) isolated nucleic acid molecules encoding immunogenic PAA polypeptides; (c) vaccine compositions comprising an immunogenic PAA polypeptide or an isolated nucleic acid molecule encoding an immunogenic PAA polypeptide; (d) methods relating to uses of the polypeptides, nucleic acid molecules, and compositions; and (e) vaccine-based immunotherapy regimens which involve co-administration of a vaccine in combination with an immune-suppressive-cell inhibitor and an immune-effector-cell enhancer.

17 Claims, 55 Drawing Sheets

Specification includes a Sequence Listing.

(56) References Cited

OTHER PUBLICATIONS

Ferraro et al (Human Vaccines, 2011, 7:120-127).*
Qin et al (Immunology Letters, 2005, 99:85-93).*
Schmittgen, T., et al., "Expression of Prostate Specific Membrane Antigen and Three Alternatively Spliced Variants of PSMA in Prostate Cancer Patients," Int. J. Cancer, 2003, vol. 107(2):323-9.
Schoenfeld, J. et al., "Active immunotherapy induces antibody responses that target tumor angiogenesis," Cancer Research, 2010, vol. 70:10150-10160.
Schroers, R., et al., "Identification of MHC class II-restricted T-cell epitopes in prostate-specific membrane antigen," Clinical Cancer Research, 2003, vol. 9(9):3260-71.
Sharma, R. et al., "4-1BB Ligand As an Effective Multifunctional Immunomodulator and Antigen Delivery Vehicle for the Development of Therapeutic Cancer Vaccines," Cancer Research, 2010 , vol. 70(10):3945-3954.
Shen, L., et al., "Cellular Protein Is the Source of Cross-Priming Antigen In Vivo," Proc Natl Acad Sci U S A., 2004, vol. 101(9):3035-3040.
Sonpavde, G., et al., "Recent Advances in Immunotherapy for the Treatment of Prostate Cancer." Expert Opinion on Biol. Ther., 2011, vol. 11(8):997-1009.
Stura E., et al., "Crystal Structure of Human Prostate-Specific Antigen in a Sandwich Antibody Complex.," Journal of Molecular Biology, 2011, vol. 414:530-544.
Terasawa, H. et al., "Identification and Characterization of a Human Agonist Cytotoxic T-Lymphocyte Epitope of Human Prostate-specific Antigen," Clinical Cancer Research, 2002, vol. 8:41-53.
Thomas-Kaskel, A., et al., "Vaccination of Advanced Prostate Cancer Patients With PSCA and PSA Peptide-Loaded Dendritic Cells Induces DTH Responses That Correlate With Superior Overall Survival," International Journal against Cancer, 2006, vol. 119, 2428-2434.
van den Eertwegh, A., et al., "Combined Immunotherapy With Granulocyte-Macrophage Colony-Stimulating Factor-Transduced Allogeneic Prostate Cancer Cells and Ipilimumab in Patients With Metastatic Castration-Resistant Prostate Cancer: A Phase 1 Dose-Escalation Trial," Lancet Oncology, 2012, vol. 13:509-17.
Villoutreix, B., et al., "A Structural Model for the Prostate Disease Marker, Human Prostate-Specific Antigen," Protein Science, 1994, vol. 3(11):2033-2044.
Zhang, J., et al., "A Small Composite Probasin Promoter Confers High Levels of Prostate-Specific Gene Expression Through Regulation by Androgens and Glucocorticoids In Vitro and In Vivo" Endocrinology, 2000, vol. 141 (12):4698-4710.
Houot, R., et al., "T-cell modulation combined with intratumoral CpG cures lymphoma in a mouse model without the need for chemotherapy," Blood, 2009, 3546-3552, vol. 113.
Olson, W., et al., "Clinical Trials of Cancer Therapies Targeting Prostate-Specific Membrane Antigen," Reviews on Recent Clinical Trials, 2007, 182-190, vol. 2.
Waeckerle-Men, Y., et al., "Dendritic cell-based multi-epitope immunotherapy of hormone-refractory prostate carcinoma", Cancer Immunology Immunotherapy, 2006, 1524-1533, vol. 55.
Sutmuller, R., et al., "Synergism of Cytotoxic T Lymphocyte-associated Antigen 4 Blockade and Depletion of CD25 Regulatory T Cells in Antitumor Therapy Reveals Alternative Pathways for Suppression of Autoreactive Cytotoxic T Lymphocyte Responses", J. Exp. Med., 2001, 825-832, vol. 194, No. 6.
Ahlers, J., et al., "A push-pull approach to maximize vaccine efficacy: Abrogating suppression with an IL-13 inhibitor while augmenting help with granulocyte/macrophage colony-stimulating factor and CD40L", PNAS, 2002, 13020-13025, vol. 99, No. 20.
Berzofsky, J., et al., "Progress on new vaccine strategies for the immunotherapy and prevention of cancer", The Journal of Clinical Investigation, 2004, 1515-1525, vol. 113, No. 11.
Mangsbo, S., et al., "Enhanced Tumor Eradication by Combining CTLA-4 or PD-1 Blockade with CpG Therapy," Journal of Immunotherapy, 2010, 225-235, vol. 33.
Database UniProt [Online], "Glutamate carboxypeptidase 2; EC=3.4.17.21; Cell growth-inhibiting gene 27 protein; Folate hydrolase 1; Folylpoly-gama-glutamate carboxypeptidase", retrieved from EBI accession No. UNIPROT:Q04609 Database accession No. Q04609 sequence, Jun. 1, 1994.
U.S. Appl. No. 13/875,162, filed May 1, 2013 (now U.S. Pat. No. 9,066,898).
U.S. Appl. No. 14/527,226, filed Oct. 29, 2014 (now U.S. Pat. No. 9,402,901).
U.S. Appl. No. 15/207,348, filed Jul. 11, 2016.
U.S. Appl. No. 15/146,578, filed May 4, 2016.
U.S. Appl. No. 14/657,302, filed Mar. 13, 2015 (now U.S. Pat. No. 9,468,672).
Ahmad, S. et al., "Prostate Stem Cell Antigen DNA Vaccination Breaks Tolerance to Self-Antigen and Inhibits Prostate Cancer Growth," American Society of Gene Therapy, 2009; vol. 17(6):1101-8.
Arlen, P. et al., "Clinical Safety of a Viral Vector Based Prostate Cancer Vaccine Strategy." The Journal of Urology, 2007, vol. 178:1515-1520.
Balk, S. et al., "Biology of Prostate-Specific Antigen," Journal of Clinical Onoclogy, 2003, vol. 21(2):383-391.
Barinka, C.et al., "Amino Acids at the N- and C-Termini of Human Glutamate Carboxypeptidase II Are Required for Enzymatic Activity and Proper Folding," Eur. J. Biochem, 2004, vol. 271:2782-2790.
Barinka, C. et al. "Identification of the N-glycosylation sites on glutamate carboxypeptidase II necessary for proteolytic activity." Protein Science, 2004, vol. 13(6): 1627-1635.
Bose, A. et al., "Combined Vaccine + Axitinib Therapy Yields Superior Antitumor Efficacy in a Murine Melanoma Model," Melanoma Research, 2012, vol. 22:236-243.
Cha, E., et al., "Therapeutic Vaccines for Prostate Cancer." Current Opinion in Molecular Therapeutics, 2010, vol. 12 (1): 77-85.
Chakraborty, M. et al., "The Combined Activation of Positive Costimulatory Signals With Modulation of a Negative Costimulatory Signal for the Enhancement of Vaccine-Mediated T-Cell Responses," Cancer Immunol Immunother, 2007, vol. 56:1471-1484.
Collins, D., et al., "Trastuzumab Induces Antibody-Dependent Cell-Mediated Cytotoxicity (ADCC) in HER-2-Non-Amplified Breast Cancer Cell Lines" Annals of Oncology, 2011, vol. 23:1788-1795.
Dall'Ozzo, S., et al.,"Rituximab-Dependent Cytotoxicity by Natural Killer Cells: Influence of FCGR3A Polymorphism on the Concentration-Effect Relationship." Cancer Research, 2004, vol. 64(13): 4664-4669.
Dannull J. et al., "Prostate Stem Cell Antigen is a Promising Candidate for Immunotherapy of Advanced Prostate Cancer.," Cancer Research, 2000, vol. 60:5522-28.
Davis, M., et al., "Crystal Structure of Prostate-Specific Membrane Antigen, A Tumor Marker and Peptidase," Proc Natl Acad Science, 2005, vol. 102(17):5981-6.
Drake, C. et al., "Update: immunological strategies for prostate cancer," Curr Urol Rep, 2010, vol. 11(3):202-7.
Durso, R., et al., "A Novel Alphavirus Vaccine Encoding Prostate-Specific Membrane Antigen Elicits Potent Cellular and Humoral Immune Responses." Clinical Cancer Research, 2007, vol. 13(13):3999-4008.
Elsasser-Beile, U., et al., "Targeted Therapies for Prostate Cancer Against the Prostate Specific Membrane Antigen," Current Drug Targets, 2009, vol. 10(2):118-25.
Farsaci, B. et al., "Consequence of Dose Scheduling of Sunitinib on Host Immune Response Elements and Vaccine Combination Therapy," International Journal of Cancer, 2011, vol. 0:1-12.
Ferraro, B., et al., "Co-delivery of PSA and PSMA DNA Vaccines With Electroporation Induces Potent Immune Responses," Human Vaccines, 2011, vol. 7:120-127.
Garcia-Hernandez , M.,, et al., "Prostate Stem Cell Antigen Vaccination Induces a Long-Term Protective Immune Response Against Prostate Cancer in the Absence of Autoimmunity." Cancer Research, 2008, vol. 68(3): 861-869.

(56) References Cited

OTHER PUBLICATIONS

Goodman, O., et al. "Interaction of prostate specific membrane antigen with clathrin and the adaptor protein complex-2," International Journal of Oncology , 2007, vol. 31(5): 1199-1203.
Gregor, P., et al., "Induction of autoantibodies to syngeneic prostate-specific membrane antigen by xenogeneic vaccination.," International Journal of Cancer, 2005, vol. 116(3): 415-21.
Gu, Z., et al., "Prostate Stem Cell Antigen (PSCA) Expression Increases With High Gleason Score, Advanced Stage and Bone Metastasis in Prostate Cancer." Oncogene, 2000, vol. 19(10): 1288-1296.
Harada, M., et al., "Prostate-Specific Antigen-Derived Epitopes Capable of Inducing Cellular and Humoral Responses in HLA-A24+ Prostate Cancer Patients," The Prostate, 2003, vol. 57:152-159.
Hirao, L.. et al., "Immune Modulation through 4-1BB Enhances SIV Vaccine Protection in Non-Human Primates against SIVmac251 Challenge," PLoS ONE, 2011, vol. 6(9): 1-11.
Hodge, J.. et al., "Multiple Costimulatory Modalities Enhance CTL Activity," The Journal of Immunology, 2005, vol. 174;5994-6004.
Horig , H. et al., "Prostate-Specific Antigen Vaccines for Prostate Cancer," Expert Opininion, 2002, vol. 2(4):395-408.
Houghton, C., et al., "Immunological validation of the EpitOptimizer program for streamlined design of heteroclitic epitopes." Vaccine, 2007, vol. 25(29): 5330-5342.
Karan, D., et al., "Dual Antigen Target-Based Immunotherapy for Prostate Cancer Eliminates the Growth of Established Tumors in Mice." Immunotherapy, 2011, vol. 3(6): 735-746.
Keler, T. et al., "Activity and Safety of CTLA-4 Blockade Combined with Vaccines in Cynomolgus Macaques.," The Journal of Immunology, 2003, vol. 171:6251-6259.
Kiessling, A., et al., "Advances in specific immunotherapy for prostate cancer.," European Urology, 2008. vol. 53 (4):694-708.
Kim, S., et al., "Vaccination With Recombinant Adenoviruses and Dendritic Cells Expressing Prostate-Specific Antigens Is Effective in Eliciting CTL and Suppresses Tumor Growth in the Experimental Prostate Cancer." The Prostate, 2009, vol. 69(9): 938-948.
Kobayashi, K., et al., "Identification of a Prostate-Specific Membrane Antigen-Derived Peptide Capable of Eliciting Both Cellular and Humoral Immune Responses in HLA-A24+ Prostate Cancer Patients," Cancer Sci, 2003, vol. 94(7): 622-7.
Kumar, A., et al. "Expression of Pro Form of Prostate-Specific Antigen by Mammalian Cells and Its Conversion to Mature, Active Form by Human Kallikrein 2," Cancer Research, 1997, vol. 57(15): 3111-3114.
Li, Betty et al., "Established B16 Tumors Are Rejected Following Treatment With GM-CSF-Secreting Tumor Cell Immunotherapy in Combination With Anti-4-1BB Mab," Clinical Immunology, 2007, vol. 125:76-87.
Li, Y., et al., "Cytotoxicity of Human Prostate Cancer Cell Lines In Vitro and Induction of Apoptosis Using 213Bi- Herceptin Alpha-Conjugate." Cancer Letters, 2004, vol. 205(2): 161-171.
Li, Y., et al., "Promising Tumor-Associated Antigens for Future Prostate Cancer Therapy." Medicinal Research Reviews, 2010, vol. 30(1):67-101.
Lu, J., et al.,, "Recognition of Prostate Tumor Cells by Cytotoxic T Lymphocytes Specific for Prostate-Specific Membrane Antigen," Cancer Research, 2002, vol. 62(20):5807-12.
Lubaroff, D., et al., "Phase I Clinical Trial of an Adenovirus/Prostate-Specific Antigen Vaccine for Prostate Cancer: Safety and Immunologic Results." Clinical Cancer Research, 2009, vol. 15(23): 7375-7380.
Lundwall, A., et al., "Molecular Cloning of Human Prostate Specific Antigen cDNA," FEBS Letters, 1987, vol. 214(2): 317-322.
Madan, R.. et al., "Ipilimumab and a Poxviral Vaccine Targeting Prostate-Specific Antigen in Metastatic Castration-Resistant Prostate Cancer: A Phase 1 Dose-Escalation Trial," Lancet Oncol, 2012; 13: 501-08.
Matsueda, S., et al., "Identification of peptide vaccine candidates for prostate cancer patients with HLA-A3 supertype alleles.," Clinical Cancer Research, 2005, vol. 11:6933-43.
McCormack, R., et al., "Molecular Forms of Prostate-Specific Antigen and the Human Kallikrein Gene Family: A New Era." Urology, 1995, vol. 45(5):729-744.
Mincheff, M., et al., "Immune Responses Against PSMA After Gene-Based Vaccination for Immunotherapy—A: Results From Immunizations in Animals," Cancer Gene Therapy, 2006, 13(4):436-44.
Qin, H., et al., "Specific Antitumor Immune Response Induced by a Novel DNA Vaccine Composed of Multiple CTL and T Helper Cell Epitopes of Prostate Cancer Associated Antigens," Immunology Letters, 2005, vol. 99(1):85-93.
Raff A., et al., "Prostate Stem Cell Antigen: A Prospective Therapeutic and Diagnostic Target," Cancer Letters, 2009, vol. 277:126-132.
Rajasekaran, S., et al., "A novel cytoplasmic tail MXXXL motif mediates the internalization of prostate-specific membrane antigen," Molecular Biology of the Cell, 2003, vol. 14(12):4835-4845.
Reiter, R., et al., "Prostate Stem Cell Antigen: A Cell Surface Marker Overexpressed in Prostate Cancer" Proc Natl Acad Sci U S A , 1994, vol. 95(4):1735-1740.
Rock, K., et al., "Cross-Presentation: Underlying Mechanisms and Role in Immune Surveillance." Immunology Reviews, 2005, vol. 207: 166-183.
Rountree, R., et al.,"Exosome targeting of tumor antigens expressed by cancer vaccines can improve antigen immunogenicity and therapeutic efficacy." Cancer Research, 2011, vol. 71:5235-5244.
Sacha, P., et al., "Expression of glutamate carboxypeptidase II in human brain," Neuroscience, 2007. vol. 144 (4):1361-72.
Sakamoto, H. et al., "Genetic variation in PSCA is associated with susceptibility to diffuse-type gastric cancer," Nature Genetics, 2008, vol.;40(6):730-40.
Database Geneseq [Online], Aug. 18, 2011 (Aug. 18, 2011), Human cancer antigen PSMA coding sequence, SEQ ID 17., XP002792814, retrieved from EBI accession No. GSN:AZK50829.
Partial European Search Report, completion date Jul. 10, 2019. (EP 19 15 9009, dated Feb. 25, 2019).
Extended European Search Report for European Application No. 19159009, filed Feb. 25, 2019, (document completion date Jul. 10, 2019 and dated Oct. 31, 2019.).

* cited by examiner

FIG. 2

```
                   10                  20
-----------------+-------------------+-
Q T L N F D L L K L A G D V E S N P G * P  FMDV 2A
- - E G R G S L L T C G D V E E N P G * P  TAV 2A
H Y A G Y F A D L L I H D I E T N P G * P  EMCV 2A
Q C T N Y A L L K L A G D V E S N P G * P  ERAV 2A
- A T N F S L L K Q A G D V E E N P G * P  PTV 2A
```

FIG. 3

5′UAACGUUACUGGCCGAAGCCGCUUGGAAUAAGGCCGGUGUGCGUUUGUCUAU
AUGUUAUUUUCCACCAUAUUGCCGUCUUUUGGCAAUGUGAGGGCCCGGAAACCU
GGCCCUGUCUUCUUGACGAGCAUUCCUAGGGGUCUUUCCCCUCUCGCCAAAGG
AAUGCAAGGUCUGUUGAAUGUCGUGAAGGAAGCAGUUCCUCUGGAAGCUUCUU
GAAGACAAACAACGUCUGUAGCGACCCUUUGCAGGCAGCGGAACCCCCCACCUG
GCGACAGGUGCCUCUGCGGCCAAAAGCCACGUGUAUAAGAUACACCUGCAAAGG
CGGCACAACCCCAGUGCCACGUUGUGAGUUGGAUAGUUGUGGAAAGAGUCAAAU
GGCUCUCCUCAAGCGUAUUCAACAAGGGGCUGAAGGAUGCCCAGAAGGUACCCC
AUUGUAUGGGAUCUGAUCUGGGGCCUCGGUGCACAUGCUUUACAUGUGUUUAG
UCGAGGUUAAAAAACGUCUAGGCCCCCCGAACCACGGGGACGUGGUUUUCCUUU
GAAAAACACGAUGAUAAU*<u>AUGGCCACAACCAUG3′</u>

Anti-PSMA Western (Abcam Ab66911)

Anti-PSCA Western (Clone1G8)

FIG. 31A rHer-2 specific polyfunctional CD8 T cells
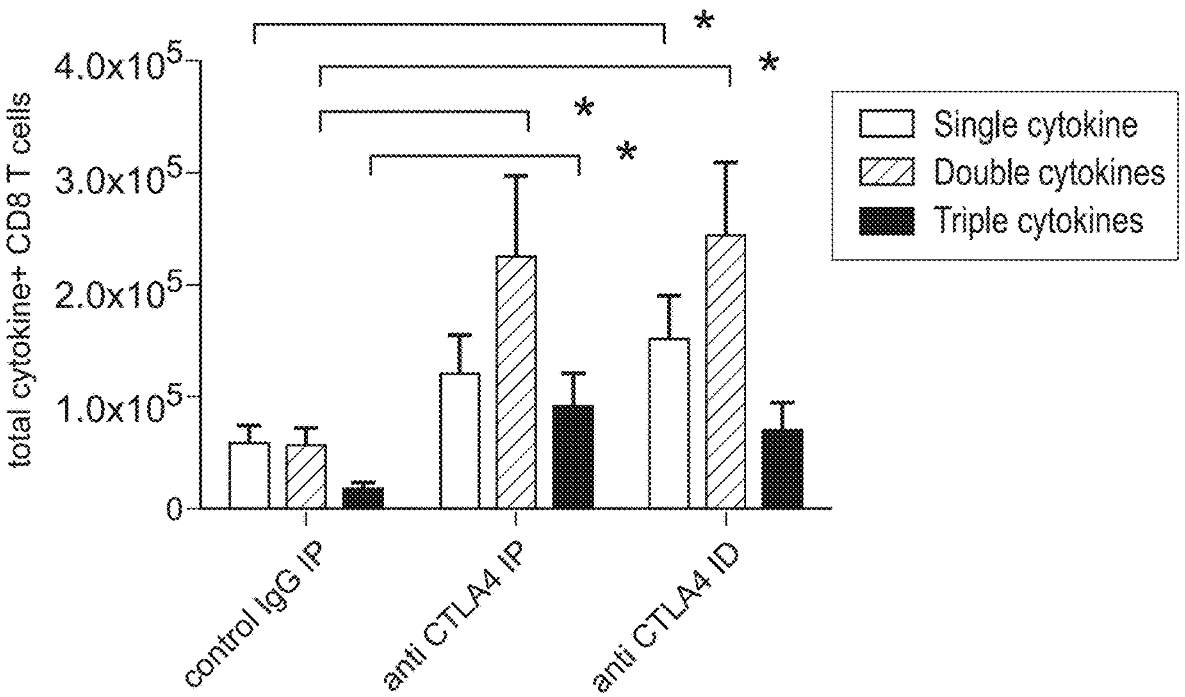
FIG. 31B rHer-2 specific polyfunctional CD4 T cells
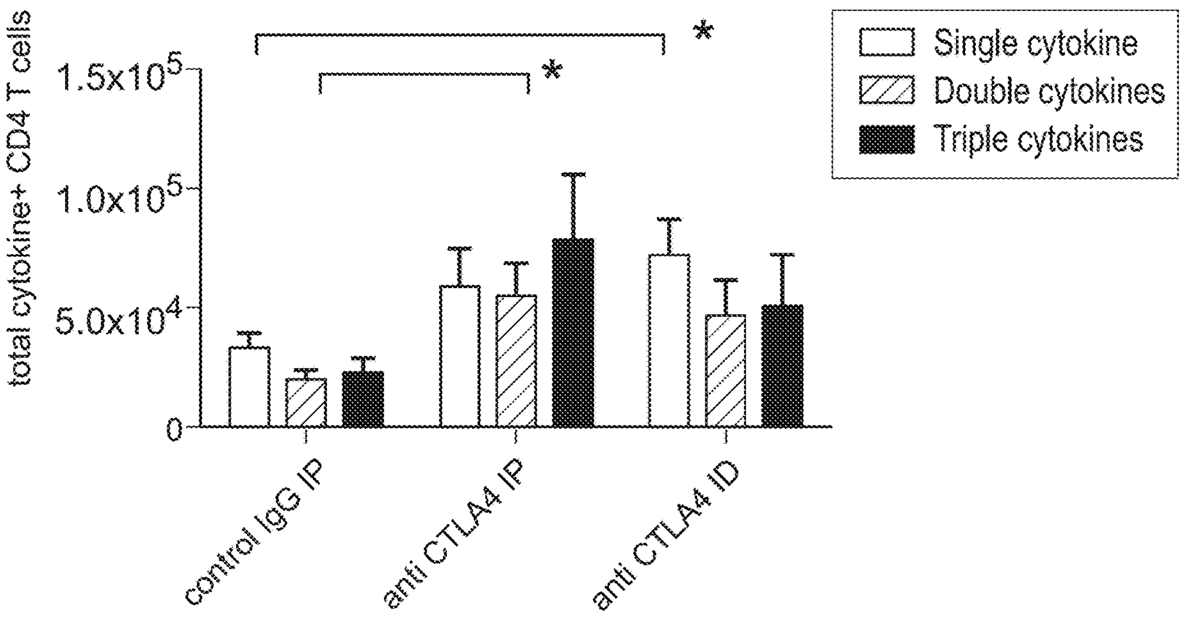

PROSTATE-ASSOCIATED ANTIGENS AND VACCINE-BASED IMMUNOTHERAPY REGIMENS

CROSS-REFERENCE TO RELATED APPLICATIONS

This application is a continuation of application Ser. No. 15/207,348 filed on Jul. 11, 2016, is a continuation of application Ser. No. 14/657,302 filed on Mar. 13, 2015, now U.S. Pat. No. 9,468,672, which is a division of application Ser. No. 13/875,162 filed on May 1, 2013, now U.S. Pat. No. 9,066,898, which claims benefit of U.S. Provisional Application No. 61/642,844 filed on May 4, 2012. The entire disclosures of application Ser. No. 13/875,162, application Ser. No. 14/657,302, application Ser. No. 15/207,348, and U.S. Provisional Application No. 61/642,844 are incorporated herein by reference.

REFERENCE TO SEQUENCE LISTING

This application is being filed along with a sequence listing in electronic format. The sequence listing is provided as a file in .txt format entitled "PC71854C_SEQLISTING_ST25.txt", created on Jul. 7, 2016 and having a size of 259 KB. The sequence listing contained in the .txt file is part of the specification and is herein incorporated by reference in its entity.

FIELD OF THE INVENTION

The present invention relates generally to immunotherapy and specifically to vaccines and methods for treating or preventing neoplastic disorders.

BACKGROUND OF THE INVENTION

Cancer is a leading cause of mortality worldwide. Traditional regimens of cancer management have been successful in the management of a selective group of circulating and solid cancers. However, many tumors are resistant to traditional approaches. In recent years, immunotherapy for the treatment of cancers has been explored, which involves the generation of an active systemic tumor-specific immune response of host origin by administering a vaccine composition at a site distant from the tumor. Various types of vaccines have been proposed, including those containing isolated tumor-associated antigens.

Prostate cancer is the second most commonly diagnosed cancer and the fourth leading cause of cancer-related death in men in the developed countries worldwide. Various prostate-associated antigens (PAA), such as prostate-specific antigen (PSA), prostate-specific membrane antigen (PSMA), and prostate stem cell antigen (PSCA) have been shown to be overexpressed by prostate cancer cells as compared to normal counterparts. These antigens, therefore, represent possible targets for inducing specific immune responses against cancers expressing the antigens via the use of vaccine-based immunotherapy. (see e.g. Marrari, A., M. Iero, et al. (2007). "Vaccination therapy in prostate cancer." Cancer Immunol Immunother 56(4): 429-45.)

PSCA is a 123-amino acid membrane protein. The amino acid sequence of the full length human PSCA consists of amino acids 4-123 of SEQ ID NO:21. PSCA has high tissue specificity and is expressed on more than 85% of prostate cancer specimens, with expression levels increasing with higher Gleason scores and androgen independence. It is expressed in 80-100% of bone metastasis of prostate cancer patients.

PSA is a kallikrein-like serine protease that is produced exclusively by the columnar epithelial cells lining the acini and ducts of the prostate gland. PSA mRNA is translated as an inactive 261-amino acid preproPSA precursor. PreproPSA has 24 additional residues that constitute the pre-region (the signal polypeptide) and the propolypeptide. Release of the propolypeptide results in the 237-amino acid, mature extracellular form, which is enzymatically active. The amino acid sequence of the human full length PSA is provided in SEQ ID NO: 15. PSA is organ-specific and, as a result, it is produced by the epithelial cells of benign prostatic hyperplastic (BPH) tissue, primary prostate cancer tissue, and metastatic prostate cancer tissue.

PSMA, also known as Folate hydrolase 1 (FOLH1), is composed of 750 amino acids. The amino acid sequence of the human full length PSMA is provided in SEQ ID NO:1. PSMA includes a cytoplasmic domain (amino acids 1-19), a transmembrane domain (amino acids 20-43), and an extracellular domain (amino acids 44-750). PSMA is a type II dimeric transmembrane protein expressed on the surface of prostate cancer cells and on neovasculature. It is also expressed on normal prostate cells, brain, salivary gland and biliary tree. However, in prostate cancer cells it was found to be expressed at 1000-fold higher levels than normal tissues. It is abundantly expressed on neovasculature of a variety of other solid tumors such as colon, breast, liver, bladder, pancreas, lung, renal cancers as well as melanoma and sarcomas. Thus, PSMA is considered a target not only specific for prostate cancer cells but also a pan-carcinoma target for other cancers. The expression of PSMA appears to be a universal feature of prostate carcinomas and its increased expression correlates with tumor aggressiveness. PSMA expression is highest in high-grade tumors, metastatic lesions and androgen-independent disease.

While a large number of tumor-associated antigens have been identified and many of these antigens have been explored as protein-based or DNA-based vaccines for the treatment or prevention of cancers, most clinical trials so far have failed to produce a therapeutic product. One of the challenges in developing cancer vaccines resides in the fact that the cancer antigens are usually self-derived and, therefore, poorly immunogenic because the immune system is self-regulated not to recognize self-proteins. Accordingly, a need exists for a method to enhance the immunogenicity or therapeutic effect of cancer vaccines.

Numerous approaches have been explored for enhancing the immunogenicity or enhancing anti-tumor efficacy of cancer vaccines. One of such approach involves the use of various immune modulators, such as TLR agonists, TNFR agonists, CTLA-4 inhibitors, and protein kinase inhibitors.

Toll-like receptors (TLRs) are type 1 membrane receptors that are expressed on hematopoietic and non-hematopoietic cells. At least 11 members have been identified in the TLR family. These receptors are characterized by their capacity to recognize pathogen-associated molecular patterns (PAMP) expressed by pathogenic organisms. It has been found that triggering of TLR elicits profound inflammatory responses through enhanced cytokine production, chemokine receptor expression (CCR2, CCR5 and CCR7), and costimulatory molecule expression. As such, these receptors in the innate immune systems exert control over the polarity of the ensuing acquired immune response. Among the TLRs, TLR9 has been extensively investigated for its functions in immune responses. Stimulation of the TLR9 receptor directs antigen-presenting cells (APCs) towards priming potent, $T_H1$-dominated T-cell responses, by increasing the production of pro-inflammatory cytokines and the presentation of co-stimulatory molecules to T cells. CpG oligonucleotides, ligands for TLR9, were found to be a class of potent immunostimulatory factors. CpG therapy has been tested against a wide variety of tumor models in mice, and has consistently been shown to promote tumor inhibition or regression.

Cytotoxic T-Lymphocyte Antigen 4 (CTLA-4) is a member of the immunoglobulin superfamily and is expressed on the surface of Helper T cells. CTLA-4 is a negative regulator of CD28 dependent T cell activation, and acts as an inhibitory checkpoint for the adaptive immune response. Similar to the T-cell costimulatory protein CD28, CTLA-4 binds to CD80 and CD86 on antigen-presenting cells. CTLA-4 transmits an inhibitory signal to T cells, whereas CD28 transmits a stimulatory signal. Human antibodies against human CTLA-4 have been described as immunostimulation modulators in a number of disease conditions, such as treating or preventing viral and bacterial infection and for treating cancer (WO 01/14424 and WO 00/37504). Various preclinical studies have shown that CTLA-4 blockade by monoclonal antibodies enhances the host immune response against immunogenic tumors, and can even reject established tumors. Two fully human anti-human CTLA-4 monoclonal antibodies (mAbs), ipilimumab (MDX-010) and Tremelimumab (also known as CP-675206), have been investigated in clinical trials in the treatment of various types of solid tumors.

The tumor necrosis factor (TNF) superfamily is a group of cytokines that engage specific cognate cell surface receptors, the TNF receptor (TNFR) superfamily. Members of the tumor necrosis factor superfamily act through ligand-mediated trimerization, causing recruitment of several intracellular adaptors to activate multiple signal transduction pathways, such as apoptosis, NF-kB pathway, JNK pathway, as well as immune and inflammatory responses. Examples of the TNF Superfamily include CD40 ligands, OX40 ligands, 4-1BB ligands, CD27, CD30 ligand (CD153), TNF-alpha, TNF-beta, RANK ligands, LT-alpha, LT-beta, GITR ligands, and LIGHT. The TNFR Superfamily includes, for example, CD40, OX40, 4-1BB, CD70 (CD27 ligand), CD30, TNFR2, RANK, LT-beta R, HVEM, GITR, TROY, and RELT. CD40 is found on the surface of B lymphocytes, dendritic cells, follicular dendritic cells, hematopoietic progenitor cells, epithelial cells, and carcinomas. CD40 binds to a ligand (CD40-L), which is a glycoprotein and expressed on activated T cells, mostly CD4+ but also some CD8+ as well as basophils/mast cells. Because of the role of CD40 in innate and adaptive immune responses, CD40 agonists, including various CD40 agonistic antibodies, such as the fully human agonist CD40 monoclonal antibody CP870893, have been explored for usage as vaccine adjuvants and in therapies.

Protein kinases are a family of enzymes that catalyze the phosphorylation of specific residues in proteins. Protein kinases are key elements in signal transduction pathways responsible for transducing extracellular signals, including the action of cytokines on their receptors, to the nuclei, triggering various biological events. The many roles of protein kinases in normal cell physiology include cell cycle control and cell growth, differentiation, apoptosis, cell mobility and mitogenesis. Kinases such as c-Src, c-Abl, mitogen activated protein (MAP) kinase, phosphotidylinositol-3-kinase (PI3K) AKT, and the epidermal growth factor (EGF) receptor are commonly activated in cancer cells, and are known to contribute to tumorigenesis. Logically, a number of kinase inhibitors are currently being developed for anti-cancer therapy, in particular tyrosine kinase inhibitors (TKIs): cyclin-dependent kinase inhibitors, aurora kinase inhibitors, cell cycle checkpoint inhibitors, epidermal growth factor receptor (EGFR) inhibitors, FMS-like tyrosine kinase inhibitors, platelet-derived growth factor receptor (PDGFR) inhibitors, kinase insert domain inhibitors, inhibitors targeting the PI3K/Akt/mTOR pathway, inhibitors targeting the Ras-Raf-MEK-ERK (ERK) pathway, vascular endothelial growth factor receptor (VEGFR) kinase inhibitors, c-kit inhibitors and serine/threonine kinase inhibitors. A number of kinase inhibitors have been investigated in clinical investigation for use in anti-cancer therapies, which includes, for example, MK0457, VX-680, ZD6474, MLN8054, AZD2171, SNS-032, PTK787/ZK222584, Sorafenib (BAY43-9006), SU5416, SU6668 AMG706, Zactima (ZD6474), MP-412, Dasatinib, CEP-701, (Lestaurtinib), XL647, XL999, Tykerb, (Lapatinib), MLN518, (formerly known as CT53518), PKC412, ST1571, AMN107, AEE 788, OSI-930, OSI-817, Sunitinib malate (Sutent; SU11248), Vatalanib (PTK787/ZK 222584), SNS-032, SNS-314 and Axitinib (AG-013736). Gefitinib and Erlotinib are two orally available EGFR-TKIs.

The immune modulators that have been explored are typically administered systemically to the patients, for example, by oral administration, intravenous injection or infusion, or intramuscular injection. One major factor that limits the effective use of some of the immune modulators is toxicity caused by high systemic exposure to the administered agents. For example, with respect to CD40 agonists, it has been reported that 0.3 mg/kg is the maximum tolerated dose for an exemplified agonistic CD40 antibody and that higher doses may elicit side effects including venous thromboembolism, grade 3 headache, cytokine release resulting in toxic effects such as chills and the like, and transient liver toxicity. (Vanderheide et al., J Clin. Oncol. 25(7): 876-8833 (March 2007). In a clinical trial to investigate combinations of intravenous Tremelimumab (an anti-CTLA-4 antibody) plus oral sunitinib in patients with metastatic renal cell carcinoma, rapid onset of renal failure was observed and, as a result, further investigation of Tremelimumab at doses higher than 6 mg/kg plus sunitinib at 37.5 mg daily was not recommended. See: Brian 1. Rini et al.: Phase 1 Dose-Escalation Trial of Tremelimumab Plus Sunitinib in Patients With Metastatic Renal Cell Carcinoma. Cancer 117(4):758-767 (2011)]. Therefore, there is a need for vaccine-based immunotherapy regimens where the immune modulators are administered at effective doses which do not elicit severe adverse side effects such as liver toxicity or renal failure.

SUMMARY OF THE INVENTION

In some aspects, the present disclosure provides isolated immunogenic PSMA polypeptides and immunogenic PSA polypeptides, which are useful, for example, for eliciting an immune response in vivo (e.g. in an animal, including humans) or in vitro, generating antibodies, or for use as a component in vaccines for treating cancers, including prostate cancer. In one aspect, the present disclosure provides isolated immunogenic PSMA polypeptides which have at least 90% identity to amino acids 15-750 of the human PSMA of SEQ ID NO:1 and comprise the amino acids of at least 10, 11, 12, 13, 14, 15, 16, 17, 18, or 19 of the conserved T cell epitopes of the human PSMA at corresponding positions.

In other aspects, the present disclosure provides nucleic acid molecules that encode immunogenic PAA polypeptides. In some embodiments, the present disclosure provides isolated nucleic acid molecules, or degenerate variants thereof, which comprise a nucleotide sequence encoding an immunogenic PSMA polypeptide, or a functional variant of said polypeptide, provided by the present disclosure.

In some other aspects, the present disclosure provides multi-antigen nucleic acid constructs that each encode two or more immunogenic PAA polypeptides.

The disclosure also provides vectors containing one or more nucleic acid molecules of the invention. The vectors are useful for cloning or expressing the immunogenic PAA polypeptides encoded by the nucleic acid molecules, or for delivering the nucleic acid molecules in a composition, such as a vaccine, to a host cell or to a host animal, such as a human.

In some further aspects, the present disclosure provides compositions comprising one or more immunogenic PAA polypeptides, isolated nucleic acid molecules encoding immunogenic PAA polypeptides, or vectors or plasmids containing nucleic acid molecules encoding immunogenic PAA polypeptides. In some embodiments, the composition is an immunogenic composition useful for eliciting an immune response against a PAA in a mammal, such as a mouse, dog, monkey, or human. In some embodiments, the composition is a vaccine composition useful for immunization of a mammal, such as a human, for inhibiting abnormal cell proliferation, for providing protection against the development of cancer (used as a prophylactic), or for treatment of disorders (used as a therapeutic) associated with PAA over-expression, such as cancer, particularly prostate cancer.

In still other aspects, the present disclosure provides methods of using the immunogenic PAA polypeptides, isolated nucleic acid molecules, and compositions comprising an immunogenic PAA polypeptide or isolated nucleic acid molecules described herein above. In some embodiments, the present disclosure provides a method of eliciting an immune response against a PAA in a mammal, particularly a human, comprising administering to the mammal an effective amount of a polypeptide provided by the invention that is immunogenic against the target PAA, an effective amount of an isolated nucleic acid molecule encoding such an immunogenic polypeptide, or a composition comprising such an immunogenic PAA polypeptide or an isolated nucleic acid molecule encoding such an immunogenic PAA polypeptide. The polypeptide or nucleic acid vaccines may be used together with one or more adjuvants.

In yet other aspects, the present disclosure provides vaccine-based immunotherapy regimens (or "VBIR") that involve co-administration of a vaccine delivering various tumor associated antigens (TAAs) for inducing TAA specific immune responses to treat a variety of cancers in combination with at least one immune-suppressive-cell inhibitor and at least one immune-effector-cell enhancer. Specifically, in some aspects, the disclosure provides a method of enhancing the immunogenicity or therapeutic effect of a vaccine for the treatment of a neoplastic disorder in a mammal, comprising administering to the mammal receiving the vaccine an effective amount of at least one immune-suppressive-cell inhibitor and at least one immune-effector-cell enhancer. In a further aspect, the disclosure provides a method of treating a neoplastic disorder in a mammal, comprising administering to the mammal a vaccine, at least one immune-suppressive-cell inhibitor, and at least one immune-effector-cell enhancer.

BRIEF DESCRIPTION OF THE DRAWINGS

FIG. 2. Amino acid alignment of five viral 2A cassettes. The skipped glycine-proline bonds are indicated by asterisks.

FIG. 3. Sequence of the preferred EMCV IRES. The translation initiation site is indicated by the asterisk. The minimal IRES element excludes the underlined first 5 codons of the EMCV L protein.

FIG. 5A) and full length human PSCA (FIG. 5B) in HEK293 cells transfected with dual antigen vaccine constructs as measured by western blotting with PSMA and PSCA specific monoclonal antibodies.

FIGS. 31A and 31B. Graphs depicting results of a representative study that evaluates the immunomodulatory activity of anti-murine CTLA-4 monoclonal antibody (clone 9H10) on the quality of the immune responses induced by a rat Her-2 DNA vaccine using an intracellular cytokine staining assay, in which (a) cytokine positive CD8 T cells (FIG. 31A) and (b) cytokine positive CD4 T cells (FIG. 31B) were measured.

FIG. 35A) and Treg containing CD25+CD4+ cells (FIG. 35B) in the periphery blood of the groups of mice from the study described FIGS. 33A-33D.

FIG. 36A), (b) myeloid derived suppressor cells (Gr1+CD11b+; FIG. 36B), and (c) PD-1+CD8 T cells (FIG. 36C) isolated from tumors of the mice.

DETAILED DESCRIPTION OF THE INVENTION

A. Definitions

Figure 1:
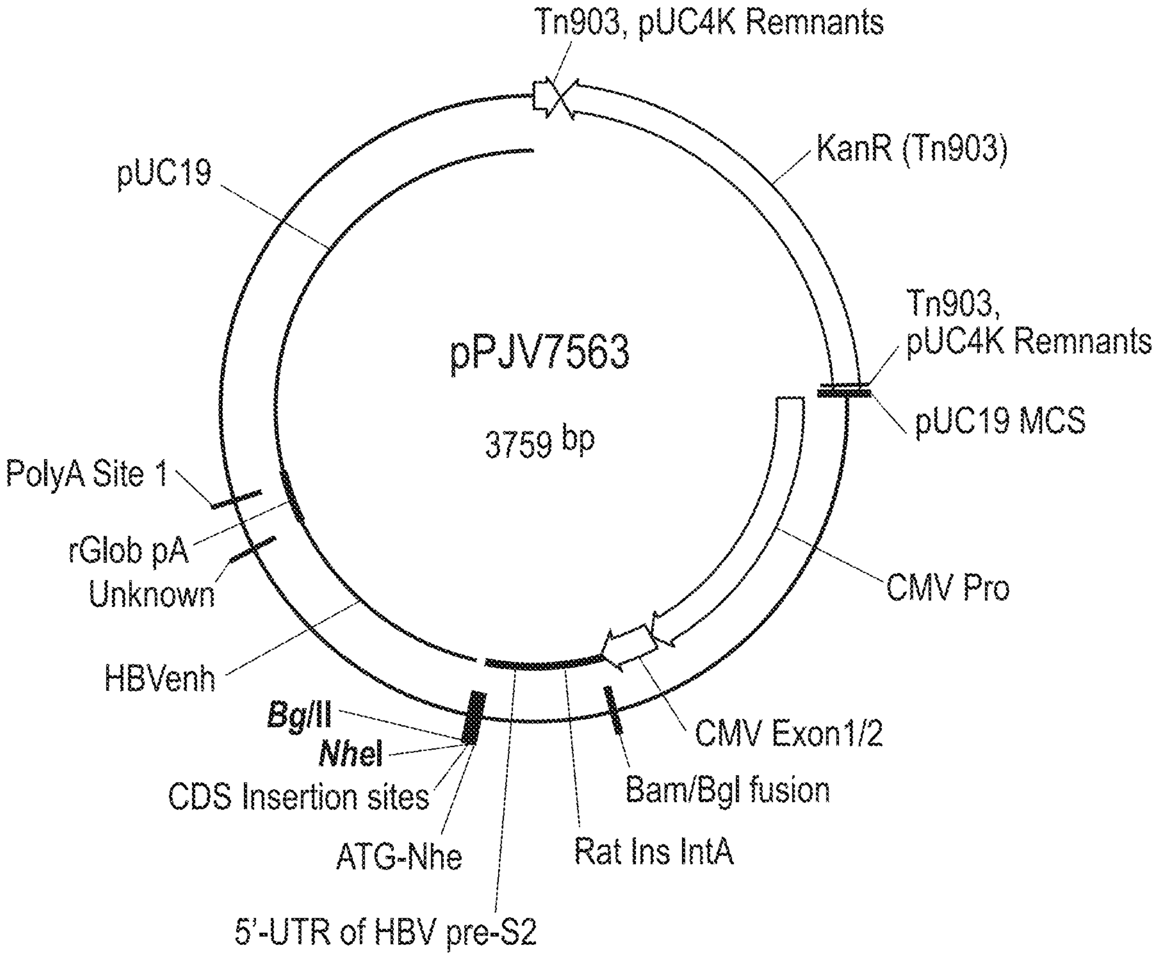
FIG. 1. Schematic illustration of PJV7563 vector.
Figure 4:
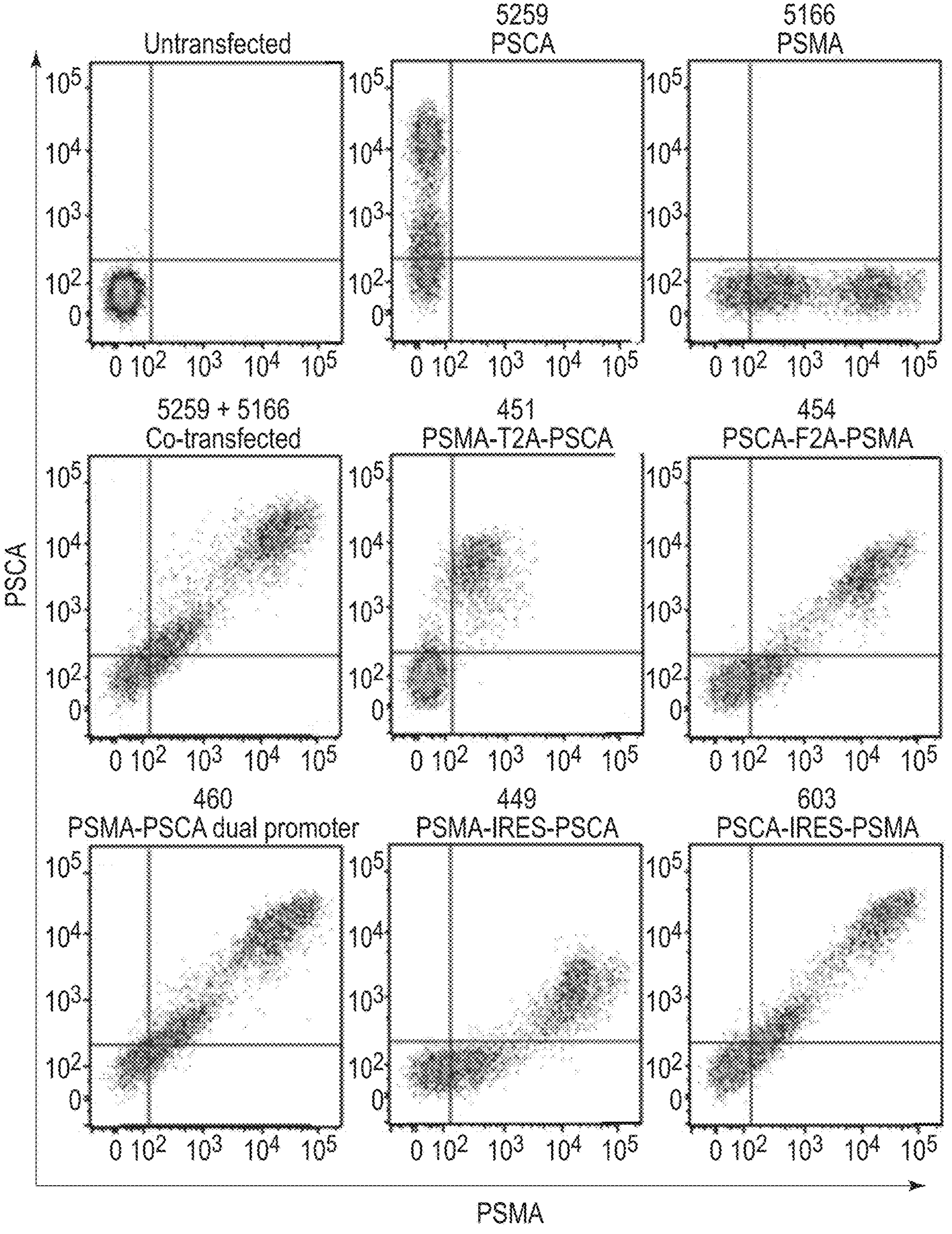
FIG. 4. Dot plots showing expression of the human PSMA modified antigen (amino acids 15-750) and full length human PSCA on the surface of HEK293 cells transfected with dual antigen vaccine constructs as measured by flow cytometry.
Figure 5A:
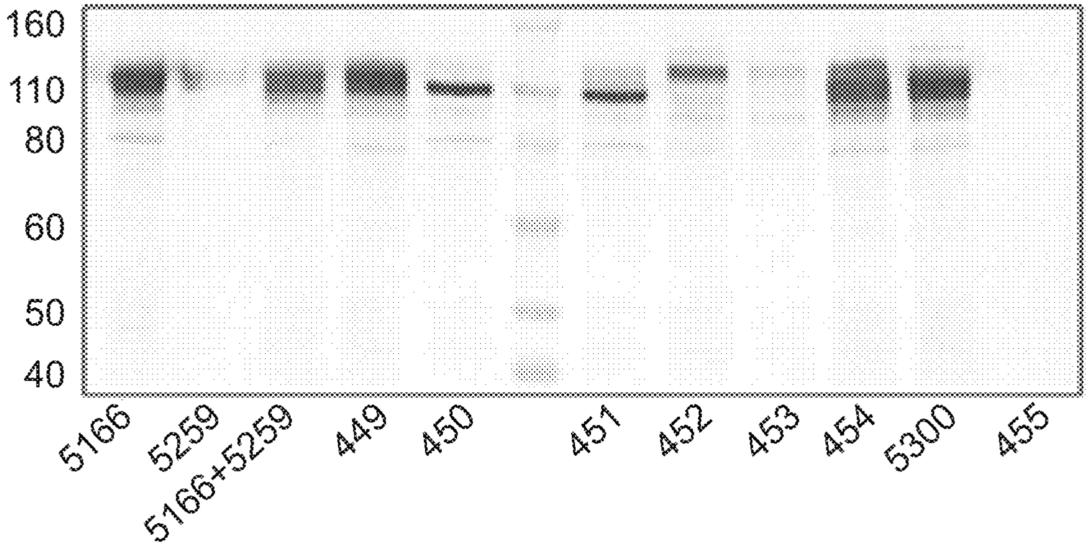
FIGS. 5A and 5B. Image of Western blots showing expression of the human PSMA modified antigen (amino acids 15-750.
Figure 5B:
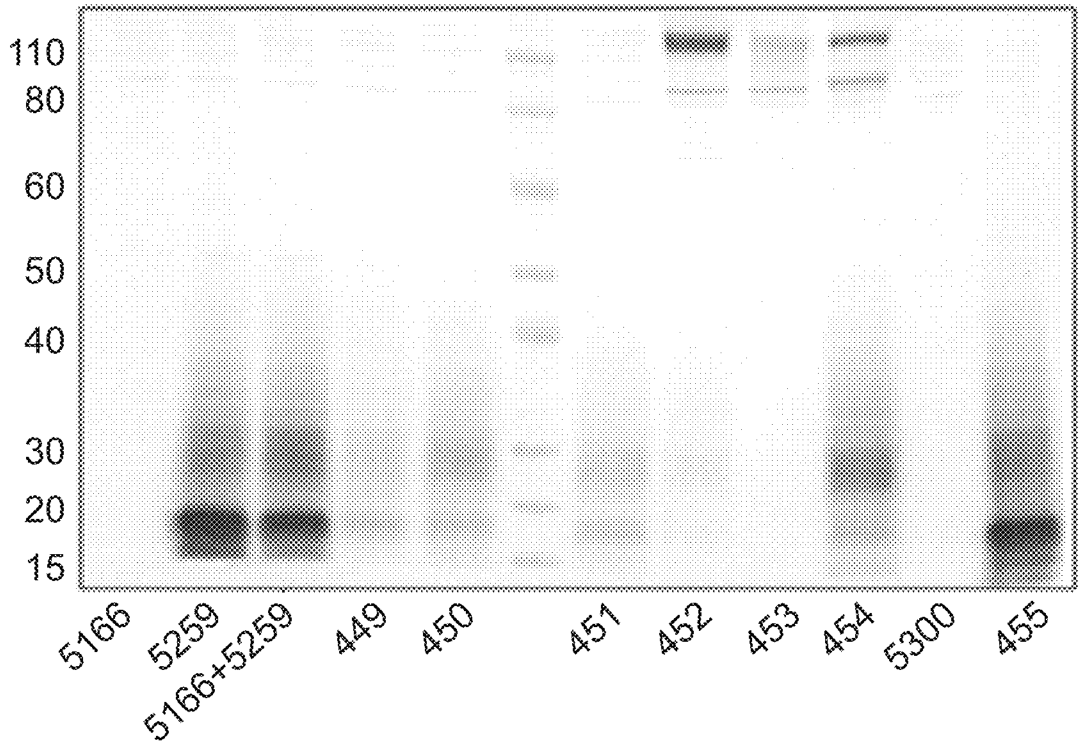
Figure 6:
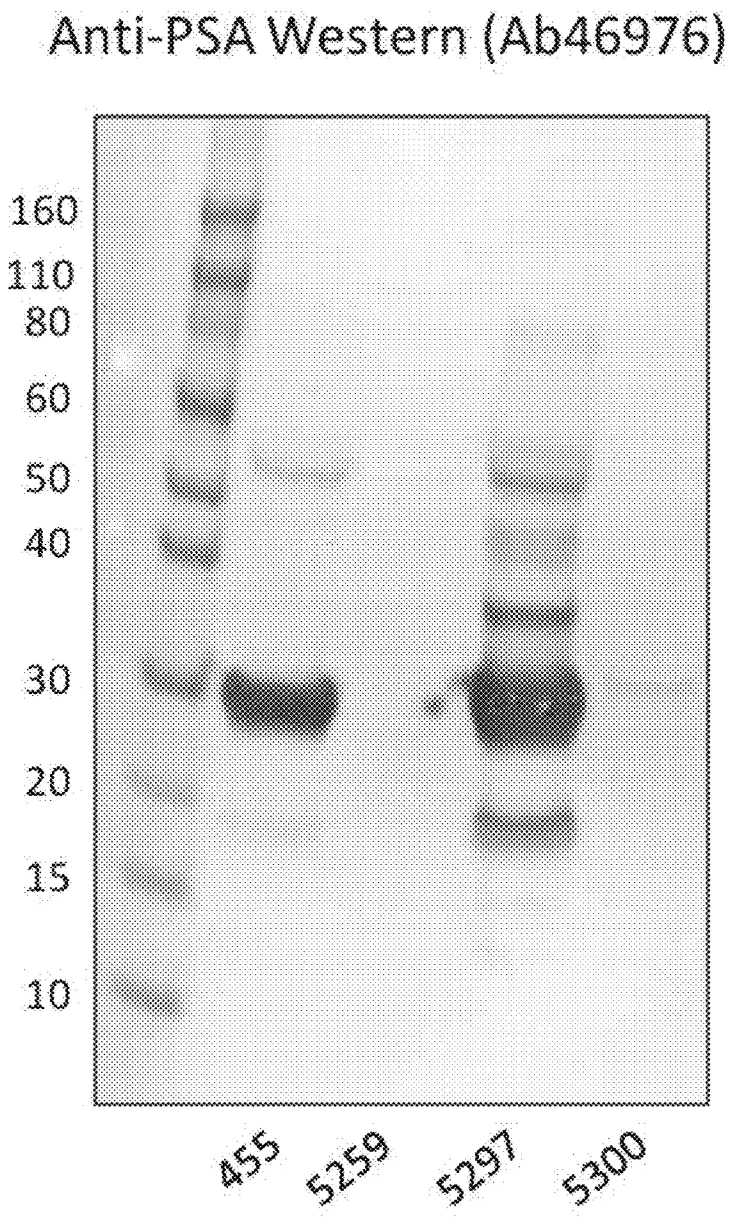
FIG. 6. Image of Western blots showing expression of human PSA cytosolic antigen (amino acids 25-261) in HEK293 cells transfected with dual antigen vaccine constructs as measured by western blotting with a PSA specific monoclonal antibody. Lane 5300 exhibited a faint band about 2 kD larger than PSA, consistent with a C-terminal fusion of the 2A peptide.

The term "adjuvant" refers to a substance that is capable of enhancing, accelerating, or prolonging an immune response when given with a vaccine immunogen. The term "agonist" refers to is a substance which promotes (induces, causes, enhances or increases) the activity of another molecule or a receptor. The term agonist encompasses substances which bind receptor (e.g., an antibody, a homolog of a natural ligand from another species) and substances which promote receptor function without binding thereto (e.g., by activating an associated protein).

The term "antagonist" or "inhibitor" refers to a substance that partially or fully blocks, inhibits, or neutralizes a biological activity of another molecule or receptor.

The term "co-administration" refers to administration of two or more agents to the same subject during a treatment period. The two or more agents may be encompassed in a single formulation and thus be administered simultaneously. Alternatively, the two or more agents may be in separate physical formulations and administered separately, either sequentially or simultaneously to the subject. The term "administered simultaneously" or "simultaneous administration" means that the administration of the first agent and that of a second agent overlap in time with each other, while the term "administered sequentially" or "sequential administration" means that the administration of the first agent and that of a second agent does not overlap in time with each other.

The term "conserved T cell epitope" refers to one of the following amino acid sequences of the human PSMA protein as set forth in SEQ ID NO. 1:

```
amino acids    168-176   (GMPEGDLVY),
amino acids    347-356   (HSTNGVTRIY),
amino acids    557-566   (ETYELVEKFY),
amino acids    207-215   (KVFRGNKVK),
amino acids    431-440   (STEWAEENSR),
amino acids      4-12    (LLHETDSAV),
amino acids     27-35    (VLAGGFFLL),
amino acids    168-177   (GMPEGDLVYV),
amino acids    441-450   (LLQERGVAYI),
amino acids    469-477   (LMYSLVHNL),
amino acids    711-719   (ALFDIESKV),
amino acids    663-671   (MNDQVMFL),
amino acids    178-186   (NYARTEDFF),
```

-continued

```
amino acids,   227-235   (LYSDPADYF),
amino acids    624-632   (TYSVSFDSL),
amino acids    334-348   (TGNFSTQKVKMHIHS),
amino acids    459-473   (NYTLRVDCTPLMYSL),
amino acids    687-701   (YRHVIYAPSSHNKYA),
and
amino acids    730-744   (RQIYVAAFTVQAAAE).
```

The term "cytosolic" means that after a nucleotide sequence encoding a particular polypeptide is expressed by a host cell, the expressed polypeptide is retained inside the host cell.

The terms "degenerate variant" refers to DNA sequences that have substitutions of bases but encode the same polypeptide.

The term "effective amount" refers to an amount administered to a mammal that is sufficient to cause a desired effect in the mammal.

The term "fragment" of a given polypeptide refers to a polypeptide that is shorter than the given polypeptide and shares 100% identity with the sequence of the given polypeptide.

The term "identical" or percent "identity," in the context of two or more nucleic acid or polypeptide sequences, refers to two or more sequences or subsequences that are the same or have a specified percentage of amino acid residues or nucleotides that are the same, when compared and aligned for maximum correspondence.

The term "immune-effector-cell enhancer" or "IEC enhancer" refers to a substance capable of increasing or enhancing the number, quality, or function of one or more types of immune effector cells of a mammal. Examples of immune effector cells include cytolytic CD8 T cells, CD40 T cells, NK cells, and B cells.

The term "immune modulator" refers to a substance capable of altering (e.g., inhibiting, decreasing, increasing, enhancing or stimulating) the working of any component of the innate, humoral or cellular immune system of a mammal. Thus, the term "immune modulator" encompasses the "immune-effector-cell enhancer" as defined herein and the "immune-suppressive-cell inhibitor" as defined herein, as well as substance that affects other components of the immune system of a mammal.

The term "immune response" refers to any detectable response to a particular substance (such as an antigen or immunogen) by the immune system of a host vertebrate animal, including, but not limited to, innate immune responses (e.g., activation of Toll receptor signaling cascade), cell-mediated immune responses (e.g., responses mediated by T cells, such as antigen-specific T cells, and non-specific cells of the immune system), and humoral immune responses (e.g., responses mediated by B cells, such as generation and secretion of antibodies into the plasma, lymph, and/or tissue fluids). Examples of immune responses include an alteration (e.g., increase) in Toll-like receptor activation, lymphokine (e.g., cytokine (e.g., Th1, Th2 or Th17 type cytokines) or chemokine) expression or secretion, macrophage activation, dendritic cell activation, T cell (e.g., CD4+ or CD8+ T cell) activation, NK cell activation, B cell activation (e.g., antibody generation and/or secretion), binding of an immunogen (e.g., antigen (e.g., immunogenic polypolypeptide)) to an MHC molecule, induction of a cytotoxic T lymphocyte ("CTL") response, induction of a B cell response (e.g., antibody production), and, expansion (e.g., growth of a population of cells) of cells of the immune system (e.g., T cells and B cells), and increased processing and presentation of antigen by antigen presenting cells. The term "immune response" also encompasses any detectable response to a particular substance (such as an antigen or immunogen) by one or more components of the immune system of a vertebrate animal in vitro.

The term "immunogenic" refers to the ability of a substance to cause, elicit, stimulate, or induce an immune response, or to improve, enhance, increase or prolong a pre-existing immune response, against a particular antigen, whether alone or when linked to a carrier, in the presence or absence of an adjuvant.

The term "immunogenic PSA polypeptide" refers to a polypeptide that is immunogenic against human PSA protein or against cells expressing human PSA protein.

The term "immunogenic PSCA polypeptide" refers to a polypeptide that is immunogenic against human PSCA protein or against cells expressing human PSCA protein.

The term "immunogenic PSMA polypeptide" refers to a polypeptide that is immunogenic against human PSMA protein or against cells expressing human PSMA protein.

The term "immunogenic PAA polypeptide" refers to an "immunogenic PSA polypeptide," an "immunogenic PSCA polypeptide," or an "immunogenic PSMA polypeptide" as defined herein above.

The term "immunogenic PSA nucleic acid molecule" refers to a nucleic acid molecule that encodes an immunogenic PSA polypeptide as defined herein.

The term "immunogenic PSCA nucleic acid molecule" refers to a nucleic acid molecule that encodes an "immunogenic PSCA polypeptide" as defined herein.

The term "immunogenic PSMA nucleic acid molecule" refers to a nucleic acid molecule that encodes an "immunogenic PSMA polypeptide" as defined herein.

The term "immunogenic PAA nucleic acid molecule" refers to a nucleic acid molecule that encodes an "immunogenic PSA polypeptide," an "immunogenic PSCA polypeptide," or an "immunogenic PSMA polypeptide" as defined herein above.

The term "immune-suppressive-cell inhibitor" or "ISC inhibitor" refers to a substance capable of reducing or suppressing the number or function of immune suppressive cells of a mammal. Examples of immune suppressive cells include regulatory T cells ("T regs"), myeloid-derived suppressor cells, and tumor-associated macrophages.

The term "intradermal administration," or "administered intradermally," in the context of administering a substance, such as a therapeutic agent or an immune modulator, to a mammal including a human, refers to the delivery of the substance into the dermis layer of the skin of the mammal. The skin of a mammal is composed of three layers—the epidermis, dermis, and subcutaneous layer. The epidermis is the relatively thin, tough, outer layer of the skin. Most of the cells in the epidermis are keratinocytes.

The dermis, the skin's next layer, is a thick layer of fibrous and elastic tissue (made mostly of collagen, elastin, and fibrillin) that gives the skin its flexibility and strength. The dermis contains nerve endings, sweat glands and oil (sebaceous) glands, hair follicles, and blood vessels. The dermis varies in thickness depending on the location of the skin. In humans it is about 0.3 mm on the eyelid and about 3.0 mm on the back. The subcutaneous layer is made up of fat and connective tissue that houses larger blood vessels and nerves. The thickness of this layer varies throughout the body and from person to person. The term "intradermal administration" refers to delivery of a substance to the inside of the dermis layer. In contrast, "subcutaneous administration" refers to the administration of a substance into the subcutaneous layer and "topical administration" refers to the administration of a substance onto the surface of the skin.

The term "local administration" or "administered locally" encompasses "topical administration," "intradermal administration," and "subcutaneous administration," each as defined herein above. This term also encompasses "intratumoral administration," which refers to administration of a substance to the inside of a tumor. Local administration is intended to allow for high local concentrations around the site of administration for a period of time until systemic biodistribution has been achieved with of the administered substance, while "systemic administration" is intended for the administered substance to be absorbed into the blood and attain systemic exposure rapidly by being distributed through the circulatory system to organs or tissues throughout the body.

The term "mammal" refers to any animal species of the Mammalia class. Examples of mammals include: humans; non-human primates such as monkeys; laboratory animals such as rats, mice, guinea pigs; domestic animals such as cats, dogs, rabbits, cattle, sheep, goats, horses, and pigs; and captive wild animals such as lions, tigers, elephants, and the like.

The term "membrane-bound" means that after a nucleotide sequence encoding a particular polypeptide is expressed by a host cell, the expressed polypeptide is bound to, attached to, or otherwise associated with, the membrane of the cell.

The term "neoplastic disorder" refers to a condition in which cells proliferate at an abnormally high and uncontrolled rate, the rate exceeding and uncoordinated with that of the surrounding normal tissues. It usually results in a solid lesion or lump known as "tumor." This term encompasses benign and malignant neoplastic disorders. The term "malignant neoplastic disorder", which is used interchangeably with the term "cancer" in the present disclosure, refers to a neoplastic disorder characterized by the ability of the tumor cells to spread to other locations in the body (known as "metastasis"). The term "benign neoplastic disorder" refers to a neoplastic disorder in which the tumor cells lack the ability to metastasize.

The term "operably linked" refers to a juxtaposition wherein the components so described are in a relationship permitting them to function in their intended manner. A control sequence "operably linked" to a transgene is ligated in such a way that expression of the transgene is achieved under conditions compatible with the control sequences.

The term "ortholog" refers to genes in different species that are similar to each other and originated from a common ancestor.

The term "pharmaceutically acceptable excipient" refers to a substance in an immunogenic or vaccine composition, other than the active ingredients (e.g., the antigen, antigen-coding nucleic acid, immune modulator, or adjuvant) that is compatible with the active ingredients and does not cause significant untoward effect in subjects to whom it is administered.

The terms "peptide," "polypeptide," and "protein" are used interchangeably herein, and refer to a polymeric form of amino acids of any length, which can include coded and non-coded amino acids, chemically, or biochemically modified or derivatized amino acids, and polypeptides having modified polypeptide backbones.

The term "preventing" or "prevent" refers to (a) keeping a disorder from occurring or (b) delaying the onset of a disorder or onset of symptoms of a disorder.

The term "prostate-associated-antigen" (or PAA) refers to the TAA (as defined herein) that is specifically expressed on prostate tumor cells or expressed at a higher frequency or density by tumor cells than by non-tumor cells of the same tissue type. Examples of PAA include PSA, PSCA, and PSMA.

The term "secreted" in the context of a polypeptide means that after a nucleotide sequence encoding the polypeptide is expressed by a host cell, the expressed polypeptide is secreted outside of the host cell.

The term "suboptimal dose" when used to describe the amount of an immune modulator, such as a protein kinase inhibitor, refers to a dose of the immune modulator that is below the minimum amount required to produce the desired therapeutic effect for the disease being treated when the immune modulator is administered alone to a patient.

The term "treating," "treatment," or "treat" refers to abrogating a disorder, reducing the severity of a disorder, or reducing the severity or occurrence frequency of a symptom of a disorder.

The term "tumor-associated antigen" or "TAA" refers to an antigen which is specifically expressed by tumor cells or expressed at a higher frequency or density by tumor cells than by non-tumor cells of the same tissue type. Tumor-associated antigens may be antigens not normally expressed by the host; they may be mutated, truncated, misfolded, or otherwise abnormal manifestations of molecules normally expressed by the host; they may be identical to molecules normally expressed but expressed at abnormally high levels; or they may be expressed in a context or milieu that is abnormal. Tumor-associated antigens may be, for example, proteins or protein fragments, complex carbohydrates, gangliosides, haptens, nucleic acids, or any combination of these or other biological molecules.

The term "vaccine" refers to an immunogenic composition for administration to a mammal for eliciting an immune response against a particular antigen.

The term "variant" of a given polypeptide refers to a polypeptide that shares less than 100% but more than 80% identity to the amino acid sequence of that given polypeptide and exhibits at least some of the immunogenic activity of that given polypeptide.

The term "vector" refers to a nucleic acid molecule capable of transporting or transferring a foreign nucleic acid molecule. The term encompasses both expression vectors and transcription vectors. The term "expression vector" refers to a vector capable of expressing the insert in the target cell, and generally contain control sequences, such as enhancer, promoter, and terminator sequences, that drive expression of the insert. The term "transcription vector" refers to a vector capable of being transcribed but not translated. Transcription vectors are used to amplify their insert. The foreign nucleic acid molecule is referred to as "insert" or "transgene." A vector generally consists of an insert and a larger sequence that serves as the backbone of the vector. Based on the structure or origin of vectors, major types of vectors include plasmid vectors, cosmid vectors, phage vectors such as lambda phage, viral vectors such as adenovirus (Ad) vectors, and artificial chromosomes.

B. Immunogenic Prostate-Associated-Antigen (PAA) Polypeptides

In some aspects, the present disclosure provides isolated immunogenic PSA polypeptides and PSMA polypeptides, which are useful, for example, for eliciting an immune response in vivo (e.g. in an animal, including humans) or in vitro, activating effector T cells, or generating antibodies specific for PSA and PSMA, respectively, or for use as a component in vaccines for treating cancer, particularly prostate cancer. These polypeptides can be prepared by methods known in the art in light of the present disclosure. The capability of the polypeptides to elicit an immune response can be measured in in vitro assays or in vivo assays. In vitro assays for determining the capability of a polypeptide or DNA construct to elicit immune responses are known in the art. One example of such in vitro assays is to measure the capability of the polypeptide or nucleic acid expressing an polypeptide to stimulate T cell response as described in U.S. Pat. No. 7,387,882, the disclosure of which is incorporated in this application. The assay method comprises the steps of: (1) contacting antigen presenting cells in culture with an antigen thereby the antigen can be taken up and processed by the antigen presenting cells, producing one or more processed antigens; (2) contacting the antigen presenting cells with T cells under conditions sufficient for the T cells to respond to one or more of the processed antigens; (3) determining whether the T cells respond to one or more of the processed antigens. The T cells used may be CD8+ T cells or CD4+ T cells. T cell response may be determined by measuring the release of one of more of cytokines, such as interferon-gamma and interleukin-2, lysis of the antigen presenting cells (tumor cells), and production of antibodies by B cells.

B-1. Immunogenic PSMA Polypeptides

In one aspect, the present disclosure provides isolated immunogenic PSMA polypeptides which have at least 90% identity to amino acids 15-750 of the human PSMA of SEQ ID NO:1 and comprise the amino acids of at least 10, 11, 12, 13, 14, 15, 16, 17, 18, or 19 of the conserved T cell epitopes of the human PSMA at corresponding positions.

In some embodiments, the immunogenic PSMA polypeptides comprise at least 15, 16, 17, 18, or 19 of the conserved T cell epitopes of the human PSMA.

In some embodiments, the present disclosure provides an immunogenic PSMA polypeptide consisting of the amino acid sequence of SEQ ID NO:9, or an immunogenic PSMA polypeptide having 93%-99%, 94%-98%, or 94%-97% identity to the amino acid sequence of SEQ ID NO:9.

Examples of some particular immunogenic PSMA polypeptides include:

1) a polypeptide consisting of amino acids 15-750 of SEQ ID NO: 1;

2) a polypeptide comprising the amino acids 4-739 of SEQ ID NO: 3;

3) a polypeptide comprising the amino acids 4-739 of SEQ ID NO:5;

4) a polypeptide comprising the amino acids 4-739 of SEQ ID NO:7;

2) a polypeptide comprising the amino acid sequence of SEQ ID NO:3;

3) a polypeptide comprising the amino acid sequence of SEQ ID NO:5; and 4) a polypeptide comprising the amino acid sequence of SEQ ID NO:7.

In other embodiments, the present disclosure provides an immunogenic PSMA polypeptide selected from the group consisting of:

1) a polypeptide consisting of the amino acid sequence of SEQ ID NO:11

2) a polypeptide consisting of the amino acid sequence of SEQ ID NO:13; and 3) a polypeptide comprising the amino acid sequence of SEQ ID NO:13.

In some other embodiments, the present disclosure provides isolated immunogenic PSMA polypeptides that are variants of any of the following polypeptides:

2) a polypeptide comprising the amino acids 4-739 of SEQ ID NO: 3;

3) a polypeptide comprising the amino acids 4-739 of SEQ ID NO: 5; and 4) a polypeptide comprising the amino acids 4-739 of SEQ ID NO: 7, wherein the amino acid sequence of the variant has 93%-99% identity to the sequence of SEQ ID NO:1 and share at least 80%, at least 85%, at least 90%, at least 95%, or at least 99% identity with the amino acid sequence of SEQ ID NO: 3, 5, or 7.

The variants of a given PAA polypeptide can be obtained by deleting, inserting, or substituting one or more amino acids in the parent immunogenic PAA polypeptide. An example for the production of such variants is the conservative substitution of individual amino acids of the polypeptides, that is, by substituting one amino acid for another having similar properties.

An immunogenic PSMA polypeptide of the invention may be constructed by conserving some or all of the conserved T cell epitopes of the human PSMA of SEQ ID NO:1 while substituting certain amino acids in the remaining regions of the human PSMA with amino acids found in one or more orthologs of human PSMA at corresponding positions. Sequences of various PSMA orthologs that may be utilized to make the immunogenic PSMA polypeptides are available from the GeneBank database. These orthologs along with their NCBI ID numbers are provided in Table 18. Substitutions of amino acids of human PSMA with amino acids from one or more of the orthologs may be conservative substitutions or non-conservative substitutions, or both, and may be selected based on a number of factors known in the art, including the divergence needed to be achieved, MHC binding, the presence of ortholog amino acids at the site of substitution, surface exposure, and maintaining the 3-D structure of the protein for optimal processing and presentation.

B-2. Immunogenic PSA Polypeptides

In another aspect, the present disclosure provides isolated immunogenic PSA polypeptides. In one embodiment, the isolated immunogenic PSA polypeptide is a polypeptide consisting of the amino acid sequence of SEQ ID NO:15 or amino acids 4-263 of SEQ ID NO: 15, or a variant thereof. In another embodiment, the isolated immunogenic PSA polypeptide is a polypeptide consisting of the amino acid sequence of SEQ ID NO:17 or amino acids 4-240 of SEQ ID NO: 17, or a variant thereof. In a further embodiment, the isolated immunogenic PSA polypeptide is a polypeptide consisting of the amino acid sequence of SEQ ID NO:19 or amino acids 4-281 of SEQ ID NO: 19, or a variant thereof.

C. Nucleic Acid Molecules Encoding Immunogenic PAA Polypeptides

In some aspects, the present disclosure provides nucleic acid molecules that encode immunogenic PAA polypeptides. The nucleic acid molecules can be deoxyribonucleotides (DNA) or ribonucleotides (RNA). Thus, a nucleic acid molecule can comprise a nucleotide sequence disclosed herein wherein thymidine (T) can also be uracil (U), which reflects the differences between the chemical structures of DNA and RNA. The nucleic acid molecules can be modified forms, single or double stranded forms, or linear or circular forms. The nucleic acid molecules can be prepared using methods known in the art light of the present disclosure.

C-1. Nucleic Acid Molecules Encoding Immunogenic PSMA Polypeptides

In one aspect, the present disclosure provides isolated nucleic acid molecules, or degenerate variants thereof, which comprise a nucleotide sequence encoding an immunogenic PSMA polypeptide, including the immunogenic PSMA polypeptides provided by the present disclosure or a functional variant thereof In some embodiments, the nucleotide sequence encodes a membrane-bound immunogenic PSMA polypeptide. In some particular embodiments, the isolated nucleic acid molecule comprises a nucleotide sequence, or a degenerate variant thereof, selected from the group consisting of:

1) a nucleotide sequence encoding the amino acid sequence of SEQ ID NO:9;

2) a nucleotide sequence encoding amino acids 4-739 of SEQ ID NO:3;

3) a nucleotide sequence encoding amino acids 4-739 of SEQ ID NO:5; and 4) a nucleotide sequence encoding amino acids 4-739 of SEQ ID NO:7.

In some other particular embodiments, the nucleotide sequence encodes a variant of an immunogenic PSMA polypeptide of SEQ ID NO:3, SEQ ID NO:5, SEQ ID NO:7, or SEQ ID NO:9, wherein the variant has an amino acid sequence that has (a) 93% to 99% identity with the amino acid sequence of SEQ ID NO:1 and (b) at least 80%, at least 85%, at least 90%, at least 95%, or at least 99% identity with the amino acid sequence of SEQ ID NO: 3, 5, or 7.

In still some other particular embodiments, the isolated nucleic acid molecule comprises a nucleotide sequence, or a degenerate variant thereof, selected from the group consisting of:

1) a nucleotide sequence comprising nucleotides 10-2217 of SEQ ID NO:4;

2) a nucleotide sequence comprising nucleotides 10-2217 of SEQ ID NO:6;

3) a nucleotide sequence comprising nucleotides 10-2217 of SEQ ID NO:8; and 4) a nucleotide sequence comprising nucleotides 10-2217 of SEQ ID NO:10.

C-2. Nucleic Acid Molecules Encoding Immunogenic PSA Polypeptides

In another aspect, the present disclosure provides isolated nucleic acid molecules, or degenerate variants thereof, which encode an immunogenic PSA polypeptide, including the immunogenic PSA polypeptides provided by the present disclosure.

In some embodiments, the isolated nucleic acid molecule comprises or consists of a nucleotide sequence encoding a cytosolic immunogenic PSA polypeptide. In one embodiment, the nucleotide sequence encodes a cytosolic immunogenic PSA polypeptide consisting of consecutive amino acid residues 4-240 of SEQ ID NO:17. In another embodiment, the nucleotide sequence encodes a cytosolic immunogenic PSA polypeptide comprising the amino acid sequence of SEQ ID NO:17. In still another embodiment, the nucleotide sequence encodes a cytosolic immunogenic PSA polypeptide consisting of the amino acid sequence of SEQ ID NO:17. In yet another embodiment, the nucleotide sequence encodes a functional variant of any of said cytosolic immunogenic polypeptides provided herein above.

In some other embodiments, the isolated nucleic acid molecule comprises a nucleotide sequence encoding a membrane-bound immunogenic PSA polypeptide. In one embodiment, the nucleotide sequence encodes a membrane-bound immunogenic PSA polypeptide comprising consecutive amino acid residues 4-281 of SEQ ID NO:19.

In another embodiment, the nucleotide sequence encodes a membrane-bound immunogenic PSA polypeptide comprising the amino acid sequence of SEQ ID NO:19.

In still another embodiment, the nucleotide sequence encodes a membrane-bound immunogenic PSA polypeptide consisting of the amino acid sequence of SEQ ID NO:19. In yet other embodiments, the nucleotide sequence encodes a functional variant of any of said membrane-bound immunogenic PSA polypeptides provided herein above.

Examples of particular nucleic acid molecules provided by the present disclosure include:

1) a nucleic acid molecule consisting of the nucleotide sequence of SEQ ID NO: 18;

2) a nucleic acid molecule comprising the nucleotide sequence of SEQ ID NO; 18;

3) a nucleic acid molecule consisting of the nucleotide sequence of SEQ ID NO; 20;

4) a nucleic acid molecule comprising the nucleotide sequence of SEQ ID NO: 20; and 5) a degenerate variant of any of the nucleic acid molecules 1)-4) above.

C-3. Nucleic Acid Molecules Encoding Two or More Immunogenic PAA Polypeptides

In another aspect, the present disclosure provides a nucleic acid molecule that encodes more than one immunogenic PAA polypeptide, for example at least two, at least three, or at least four immunogenic PAA polypeptides. Such nucleic acid molecules are also be referred to as "multi-antigen constructs," "multi-antigen vaccine," "multi-antigen plasmid," and the like, in the present disclosure. Thus, in some aspects, one nucleic acid molecule carries two coding nucleotide sequences wherein each of the coding nucleotide sequences expresses an individual immunogenic PAA polypeptide. Such a nucleic acid molecule is also referred to as "dual antigen construct," "dual antigen vaccine," or "dual antigen plasmid," etc., in this disclosure. In some other aspects, one nucleic acid molecule carries three coding nucleotide sequences wherein each of the coding nucleotide sequences expresses an individual immunogenic PAA polypeptide. Such a nucleic acid molecule is also referred to as "triple antigen construct," "triple antigen vaccine," or "triple antigen plasmid" in this disclosure. The individual PAA polypeptides encoded by a multi-antigen construct may be immunogenic against the same antigen, such as PSMA, PSA, or PSCA. The individual PAA polypeptides encoded by a multi-antigen construct may be immunogenic against different antigens, for example, one PAA polypeptide being a PSMA polypeptide and another one a PSA polypeptide. Specifically, one multi-antigen construct may encode two or more immunogenic PAA polypeptides in any one of the following combinations:

1) at least one immunogenic PSMA polypeptide and at least one immunogenic PSA polypeptide;

2) at least one immunogenic PSMA polypeptide and at least one immunogenic PSCA polypeptide;

3) at least one immunogenic PSA polypeptide and at least one immunogenic PSCA polypeptide; and 4) at least one immunogenic PSMA polypeptide, at least one immunogenic PSA polypeptide, and at least one immunogenic PSCA polypeptide.

The immunogenic PSMA polypeptides encoded by a multi-antigen construct may be either cytosolic, secreted, or membrane-bound, but preferably membrane-bound. Similarly, the immunogenic PSA polypeptide encoded by a multi-antigen construct may be either cytosolic, secreted, or membrane-bound, but preferably cytosolic. The immunogenic PSCA polypeptide encoded by a multi-antigen construct is preferably the full length human PSCA protein, the amino acid sequence of which is set forth in SEQ ID No:21.

In some embodiments, the present disclosure provides a multi-antigen construct that encodes at least one membrane-bound immunogenic PSMA polypeptide and at least one membrane-bound immunogenic PSA polypeptide.

In some other embodiments, the present disclosure provides a multi-antigen construct that encodes at least one membrane-bound immunogenic PSMA polypeptide, at least one cytosolic immunogenic PSA polypeptide, and at least one immunogenic PSCA polypeptide, wherein the at least one cytosolic immunogenic PSA polypeptide comprises amino acids 4-240 of SEQ ID NO:17, wherein the at least one immunogenic PSCA polypeptide is the full length human PSCA protein of SEQ ID NO:21, and wherein the at least one immunogenic PSMA polypeptide is selected from the group consisting of:

1) a polypeptide comprising amino acids 15-750 of SEQ ID NO: 1;

2) a polypeptide comprising the amino acid sequence of SEQ ID NO:3;

3) a polypeptide comprising the amino acid sequence of SEQ ID NO:5;

4) a polypeptide comprising the amino acid sequence of SEQ ID NO:7;

5) a polypeptide comprising the amino acids 4-739 of SEQ ID NO:9;

6) a polypeptide comprising the amino acids 4-739 of SEQ ID NO:3;

7) a polypeptide comprising the amino acids 4-739 of SEQ ID NO:5;

8) a polypeptide comprising the amino acids 4-739 of SEQ ID NO:7; and 9) polypeptide comprising the amino acid sequence of SEQ ID NO: 9.

In some particular embodiments, the present disclosure provides a multi-antigen construct comprising at least one nucleotide sequence encoding an immunogenic PSMA polypeptide, at least one nucleotide sequence encoding an immunogenic PSA polypeptide, and at least one nucleotide sequence encoding an immunogenic PSCA polypeptide, wherein the nucleotide sequence encoding the immunogenic PSA polypeptide is selected from the nucleotide sequence of SEQ ID NO: 18 or SEQ ID NO: 20, wherein the nucleotide sequence encoding the immunogenic PSCA polypeptide is set forth in SEQ ID NO:22, and wherein the nucleotide sequence encoding the immunogenic PSMA polypeptide is selected from the group consisting of:

1) the nucleotide sequence of SEQ ID NO:2;

2) the nucleotide sequence of SEQ ID NO:4;

3) the nucleotide sequence of SEQ ID NO:6;

4) the nucleotide sequence of SEQ ID NO:8;

5) the nucleotide sequence of SEQ ID NO:10;

6) a nucleotide sequence comprising nucleotides 10-2217 of SEQ ID NO:4;

7) a nucleotide sequence comprising nucleotides 10-2217 of SEQ ID NO:6;

8) a nucleotide sequence comprising nucleotides 10-2217 of SEQ ID NO:8; and 9) a nucleotide sequence comprising nucleotides 10-2217 of SEQ ID NO:10.

Examples of specific multi-antigen constructs provided by the present disclosure include the nucleic acid molecules that comprise a nucleotide sequence set forth in SEQ ID NOs:23-36.

Multi-antigen constructs provided by the present disclosure can be prepared using various techniques known in the art in light of the disclosure. For example, a multi-antigen construct can be constructed by incorporating multiple independent promoters into a single plasmid (Huang, Y., Z. Chen, et al. (2008). "Design, construction, and characterization of a dual-promoter multigenic DNA vaccine directed against an HIV-1 subtype C/B' recombinant." J Acquir Immune Defic Syndr 47(4): 403-411; Xu, K., Z. Y. Ling, et al. (2011). "Broad humoral and cellular immunity elicited by a bivalent DNA vaccine encoding HA and NP genes from an H5N1 virus." Viral Immunol 24(1): 45-56). The plasmid can be engineered to carry multiple expression cassettes, each consisting of a) a eukaryotic promoter for initiating RNA polymerase dependent transcription, with or without an enhancer element, b) a gene encoding a target antigen, and c) a transcription terminator sequence. Upon delivery of the plasmid to the transfected cell nucleus, transcription will be initiated from each promoter, resulting in the production of separate mRNAs, each encoding one of the target antigens. The mRNAs will be independently translated, thereby producing the desired antigens.

Multi-antigen constructs provided by the present disclosure can also be constructed using a single vector through the use of viral 2A-like polypeptides (Szymczak, A. L. and D. A. Vignali (2005). "Development of 2A peptide-based strategies in the design of multicistronic vectors." Expert Opin Biol Ther 5(5): 627-638; de Felipe, P., G. A. Luke, et al. (2006). "E unum pluribus: multiple proteins from a self-processing polyprotein." Trends Biotechnol 24(2): 68-75; Luke, G. A., P. de Felipe, et al. (2008). "Occurrence, function and evolutionary origins of '2A-like' sequences in virus genomes." J Gen Virol 89(Pt 4): 1036-1042; Ibrahimi, A., G. Vande Velde, et al. (2009). "Highly efficient multicistronic lentiviral vectors with peptide 2A sequences." Hum Gene Ther 20(8): 845-860; Kim, J. H., S. R. Lee, et al. (2011). "High cleavage efficiency of a 2A peptide derived from porcine teschovirus-1 in human cell lines, zebrafish and mice." PLoS One 6(4): e18556). These polypeptides, also called cleavage cassettes or CHYSELs (cis-acting hydrolase elements), are approximately 20 amino acids long with a highly conserved carboxy terminal D-V/I-EXNPGP motif (FIG. 2). The cassettes are rare in nature, most commonly found in viruses such as Foot-and-mouth disease virus (FMDV), Equine rhinitis A virus (ERAV), Encephalomyocarditis virus (EMCV), Porcine teschovirus (PTV), and Thosea asigna virus (TAV) (Luke, G. A., P. de Felipe, et al. (2008). "Occurrence, function and evolutionary origins of '2A-like' sequences in virus genomes." J Gen Virol 89(Pt 4): 1036-1042). With a 2A-based multi-antigen expression strategy, genes encoding multiple target antigens can be linked together in a single open reading frame, separated by 2A cassettes. The entire open reading frame can be cloned into a vector with a single promoter and terminator. Upon delivery of the constructs to a host cell, mRNA encoding the multiple antigens will be transcribed and translated as a single polyprotein. During translation of the 2A cassettes, ribosomes skip the bond between the C-terminal glycine and proline. The ribosomal skipping acts like a cotranslational autocatalytic "cleavage" that releases upstream from downstream proteins. The incorporation of a 2A cassette between two protein antigens results in the addition of ~20 amino acids onto the C-terminus of the upstream polypeptide and 1 amino acid (proline) to the N-terminus of downstream protein. In an adaptation of this methodology, protease cleavage sites can be incorporated at the N terminus of the 2A cassette such that ubiquitous proteases will cleave the cassette from the upstream protein (Fang, J., S. Yi, et al. (2007). "An antibody delivery system for regulated expression of therapeutic levels of monoclonal antibodies in vivo." Mol Ther 15(6): 1153-1159).

Another strategy for constructing the multi-antigen constructs provided by the present disclosure involves the use of an internal ribosomal entry site, or IRES. Internal ribosomal entry sites are RNA elements (FIG. 3) found in the 5' untranslated regions of certain RNA molecules (Bonnal, S., C. Boutonnet, et al. (2003). "IRESdb: the Internal Ribosome Entry Site database." Nucleic Acids Res 31(1): 427-428). They attract eukaryotic ribosomes to the RNA to facilitate translation of downstream open reading frames. Unlike normal cellular 7-methylguanosine cap-dependent translation, IRES-mediated translation can initiate at AUG codons far within an RNA molecule. The highly efficient process can be exploited for use in multi-cistronic expression vectors (Bochkov, Y. A. and A. C. Palmenberg (2006). "Translational efficiency of EMCV IRES in bicistronic vectors is dependent upon IRES sequence and gene location." Biotechniques 41(3): 283-284, 286, 288). Typically, two transgenes are inserted into a vector between a promoter and transcription terminator as two separate open reading frames separated by an IRES. Upon delivery of the constructs to a host cell, a single long transcript encoding both transgenes will be transcribed. The first ORF will be translated in the traditional cap-dependent manner, terminating at a stop codon upstream of the IRES. The second ORF will be translated in a cap-independent manner using the IRES. In this way, two independent proteins can be produced from a single mRNA transcribed from a vector with a single expression cassette.

Although the multi-antigen expression strategies are described here in the context of a DNA vaccine construct, the principles apply similarly in the context of viral vector genetic vaccines.

D. Vectors Containing a Nucleic Acid Molecule Encoding an Immunogenic PAA Polypeptide Another aspect of the invention relates to vectors containing one or more nucleic acid molecules of the invention. The vectors are useful for cloning or expressing the immunogenic PAA polypeptides encoded by the nucleic acid molecules, or for delivering the nucleic acid molecule in a composition, such as a vaccine, to a host cell or to a host animal, such as a human. A wide variety of vectors may be prepared to contain and express a nucleic acid molecule of the invention, such as plasmid vectors, cosmid vectors, phage vectors, and viral vectors.

In some embodiments, the disclosure provides a plasmid-based vector containing a nucleic acid molecule of the invention. Representative examples of suitable plasmid vectors include pBR325, pUC18, pSKF, pET23D, and pGB-2. Other representative examples of plasmid vectors, as well as method of constructing such vectors, are described in U.S. Pat. Nos. 5,580,859, 5,589,466, 5,688,688, 5,814,482 and 5,580,859.

In other embodiments, the present invention provides vectors that are constructed from viruses, such as retroviruses, alphaviruses, adenoviruses. Representative examples of retroviral vectors are described in more detail in EP 0,415,731; PCT Publication Nos. WO 90/07936; WO 91/0285, WO 9311230; WO 9310218, WO 9403622; WO 9325698; WO 9325234; and U.S. Pat. Nos. 5,219,740, 5,716,613, 5,851,529, 5,591,624, 5,716,826, 5,716,832, and 5,817,491. Representative examples of vectors that can be generated from alphaviruses are described in U.S. Pat. Nos. 5,091,309 and 5,217,879, 5,843,723, and 5,789,245. In some particular embodiments, the present disclosure provides adenoviral vectors derived from non-human primate adenoviruses, such as simian adenoviruses. Examples of such adenoviral vectors, as well as their preparation, are described in PCT application publication WO2005/071093 and WO 2010/086189, and include non-replicating vectors such as ChAd3, ChAd4, ChAd5, ChAd7, ChAd8, ChAd9, ChAd10, ChAd11, ChAdl6, ChAdl7, ChAdl9, ChAd20, ChAd22, ChAd24, ChAd26, ChAd30, ChAd31, ChAd37, ChAd38, ChAd44, ChAd63, ChAd68, ChAd82, ChAd55, ChAd73, ChAd83, ChAd146, ChAd147, PanAd1, Pan Ad2, and Pan Ad3, and replication-competent vectors such as Ad4 and Ad7 vectors. It is preferred that in constructing the adenoviral vectors from the simian adenoviruses one or more of the early genes from the genomic region of the virus selected from E1A, E1B, E2A, E2B, E3, and E4 are either deleted or rendered non-functional by deletion or mutation. In a particular embodiment, the vector is constructed from ChAd3 or ChAd68. Suitable vectors can also be generated from other viruses such as: pox viruses, such as canary pox virus or vaccinia virus (Fisher-Hoch et al., PNAS 86:317-321, 1989; Flexner et al., Ann. N.Y. Acad. Sci. 569:86-103, 1989; Flexner et al., Vaccine 8:17-21, 1990; U.S. Pat. Nos. 4,603,112, 4,769,330 and 5,017,487; WO 89/01973); adeno-associated vectors (see, e.g., U.S. Pat. No. 5,872,005); SV40 (Mulligan et al., Nature 277:108-114, 1979); herpes (Kit, Adv. Exp. Med. Biol. 215:219-236, 1989; U.S. Pat. No. 5,288,641); and lentivirus such as HIV (Poznansky, J. Virol. 65:532-536, 1991).

Methods of constructing vectors are well known in the art. Expression vectors typically include one or more control elements that are operatively linked to the nucleic acid sequence to be expressed. The term "control elements" refers collectively to promoter regions, polyadenylation signals, transcription termination sequences, upstream regulatory domains, origins of replication, internal ribosome entry sites ("IRES"), enhancers, and the like, which collectively provide for the replication, transcription, and translation of a coding sequence in a recipient cell. Not all of these control elements need always be present so long as the selected coding sequence is capable of being replicated, transcribed, and translated in an appropriate host cell. The control elements are selected based on a number of factors known to those skilled in that art, such as the specific host cells and source or structures of other vector components, For enhancing the expression of an immunogenic PAA polypeptide, a Kozak sequence can be provided upstream of the sequence encoding the immunogenic PAA polypeptide. For vertebrates, a known Kozak sequence is (GCC)NCCATGG, wherein N is A or G and GCC is less conserved. Exemplary Kozak sequences that can be used include ACCAUGG and ACCATGG.

E. Compositions Comprising an Immunogenic PAA Polypeptide (Polypeptide Compositions)

In another aspect, the present disclosure provides compositions comprising one or more isolated immunogenic PAA polypeptides provided by the present disclosure ("polypeptide composition"). In some embodiments, the polypeptide composition is an immunogenic composition useful for eliciting an immune response against a PAA protein in a mammal, such as a mouse, dog, nonhuman primates or human. In some other embodiments, the polypeptide composition is a vaccine composition useful for immunization of a mammal, such as a human, for inhibiting abnormal cell proliferation, for providing protection against the development of cancer (used as a prophylactic), or for treatment of disorders (used as a therapeutic) associated with PAA over expression, such as cancers, particularly prostate cancer.

A polypeptide composition provided by the present disclosure may contain a single type of immunogenic PAA polypeptide, such an immunogenic PSMA polypeptide, an immunogenic PSA polypeptide, or an immunogenic PSCA polypeptide. A composition may also contain a combination of two or more different types of immunogenic PAA polypeptides. For example, a polypeptide composition may contain immunogenic PAA polypeptides in any of the following combinations:

1) an immunogenic PSMA polypeptide and an immunogenic PSA polypeptide;

2) an immunogenic PSMA polypeptide and a PSCA polypeptide; or 3) an immunogenic PSMA polypeptide, an immunogenic PSA polypeptide, and a PSCA polypeptide.

An immunogenic composition or vaccine composition provided by the present disclosure may further comprise a pharmaceutically acceptable excipient. Pharmaceutically acceptable excipients for immunogenic or vaccine compositions are known in the art. Examples of suitable excipients include biocompatible oils, such as rape seed oil, sunflower oil, peanut oil, cotton seed oil, jojoba oil, squalan, squalene, physiological saline solution, preservatives and osmotic pressure controlling agents, carrier gases, pH-controlling agents, organic solvents, hydrophobic agents, enzyme inhibitors, water absorbing polymers, surfactants, absorption promoters, pH modifiers, and anti-oxidative agents.

The immunogenic PAA polypeptide in a composition, particularly an immunogenic composition or a vaccine composition, may be linked to, conjugated to, or otherwise incorporated into a carrier for administration to a recipient. The term "carrier" refers to a substance or structure that an immunogenic polypeptide can be attached to or otherwise associated with for delivery of the immunogenic polypeptide to the recipient (e.g., patient). The carrier itself may be immunogenic. Examples of carriers include immunogenic polypeptides, immune CpG islands, limpet hemocyanin (KLH), tetanus toxoid (TT), cholera toxin subunit B (CTB), bacteria or bacterial ghosts, liposome, chitosome, virosomes, microspheres, dendritic cells, or their like. One or more immunogenic PAA polypeptide molecules may be linked to a single carrier molecule. Methods for linking an immunogenic polypeptide to a carrier are known in the art, A vaccine composition or immunogenic composition provided by the present disclosure may be used in conjunction with one or more immune modulators or adjuvants. The immune modulators or adjuvants may be formulated separately from the vaccine composition, or they may be part of the same vaccine composition formulation. Thus, in one embodiment, the vaccine composition further comprises one or more immune modulators or adjuvants. Examples of immune modulators and adjuvants are provided herein below.

The polypeptide compositions, including the immunogenic and vaccine compositions, can be prepared in any suitable dosage forms, such as liquid forms (e.g., solutions, suspensions, or emulsions) and solid forms (e.g., capsules, tablets, or powder), and by methods known to one skilled in the art.

F. Compositions Comprising an Immunogenic PAA Nucleic Acid Molecule (Nucleic Acid Compositions)

The present disclosure also provides a composition comprising an isolated nucleic acid molecule or vector provided by the present disclosure (herein "nucleic acid composition"). The nucleic acid compositions are useful for eliciting an immune response against a PAA protein in vitro or in vivo in a mammal, including a human.

In some particular embodiments, the nucleic acid composition is a DNA vaccine composition for administration to humans for inhibiting abnormal cell proliferation, providing protection against the development of cancer (used as a prophylactic), or for treatment of cancer (used as a therapeutic) associated with PAA over-expression, or for eliciting an immune response to a particular human PAA, such as PSMA, PSA, and PSCA. The nucleic acid molecule in the composition may be a "naked" nucleic acid molecule, i.e. simply in the form of an isolated DNA free from elements that promote transfection or expression. Alternatively, the nucleic acid molecule in the composition can be incorporated into a vector.

A nucleic acid composition provided by the present disclosure may comprise individual isolated nucleic acid molecules that each encode only one type of immunogenic PAA polypeptide, such as an immunogenic PSMA polypeptide, an immunogenic PSA polypeptide, or an immunogenic PSCA polypeptide.

A nucleic acid composition may comprise a multi-antigen construct provided by the present disclosure that encodes two or more types of immunogenic PAA polypeptides. A multi-antigen construct may encode two or more immunogenic PAA polypeptides in any of the following combinations:

1) an immunogenic PSMA polypeptide and an immunogenic PSA polypeptide;

2) an immunogenic PSMA polypeptide and an immunogenic PSCA polypeptide;

3) an immunogenic PSA polypeptide and an immunogenic PSCA polypeptide; and 4) an immunogenic PSMA polypeptide, an immunogenic PSA polypeptide, and an immunogenic PSCA polypeptide.

The nucleic acid compositions, including the DNA vaccine compositions, may further comprise a pharmaceutically acceptable excipient. Examples of suitable pharmaceutically acceptable excipients for nucleic acid compositions, including DNA vaccine compositions, are well known to those skilled in the art and include sugars, etc. Such excipients may be aqueous or non aqueous solutions, suspensions, and emulsions. Examples of non-aqueous excipients include propylene glycol, polyethylene glycol, vegetable oils such as olive oil, and injectable organic esters such as ethyl oleate. Examples of aqueous excipient include water, alcoholic/aqueous solutions, emulsions or suspensions, including saline and buffered media. Suitable excipients also include agents that assist in cellular uptake of the polynucleotide molecule. Examples of such agents are (i) chemicals that modify cellular permeability, such as bupivacaine, (ii) liposomes or viral particles for encapsulation of the polynucleotide, or (iii) cationic lipids or silica, gold, or tungsten microparticles which associate themselves with the polynucleotides. Anionic and neutral liposomes are well-known in the art (see, e.g., Liposomes: A Practical Approach, RPC New Ed, IRL press (1990), for a detailed description of methods for making liposomes) and are useful for delivering a large range of products, including polynucleotides. Cationic lipids are also known in the art and are commonly used for gene delivery. Such lipids include Lipofectin™ also known as DOTMA (N—[I-(2,3-dioleyloxy) propyls N,N, N-trimethylammonium chloride), DOTAP (1,2-bis (oleyloxy)-3 (trimethylammonio) propane), DDAB (dimethyldioctadecyl-ammonium bromide), DOGS (dioctadecylamidologlycyl spermine) and cholesterol derivatives such as DCChol (3 beta-(N—(N',N'-dimethyl aminomethane)-carbamoyl) cholesterol). A description of these cationic lipids can be found in EP 187,702, WO 90/11092, U.S. Pat. No. 5,283,185, WO 91/15501, WO 95/26356, and U.S. Pat. No. 5,527,928. A particular useful cationic lipid formulation that may be used with the nucleic vaccine provided by the disclosure is VAXFECTIN, which is a commixture of a cationic lipid (GAP-DMORIE) and a neutral phospholipid (DPyPE) which, when combined in an aqueous vehicle, self-assemble to form liposomes.

Cationic lipids for gene delivery are preferably used in association with a neutral lipid such as DOPE (dioleyl phosphatidylethanolamine), as described in WO 90/11092 as an example. In addition, a DNA vaccine can also be formulated with a nonionic block copolymer such as CRL1005.

G. Uses of the Immunogenic PAA Polypeptides, Nucleic Acid Molecules, and Compositions In other aspects, the present disclosure provides methods of using the immunogenic PAA polypeptides, isolated nucleic acid molecules, and compositions comprising an immunogenic PAA polypeptide or isolated nucleic acid molecule described herein above.

In one aspect, the present disclosure provides a method of eliciting an immune response against a PAA in a mammal, particularly a human, comprising administering to the mammal an effective amount of (1) an immunogenic PAA polypeptide provided by the disclosure that is immunogenic against the target PAA, (2) an isolated nucleic acid molecule encoding such an immunogenic PAA polypeptide, (3) a composition comprising such an immunogenic PAA polypeptide, or (4) a composition comprising an isolated nucleic acid molecule encoding such an immunogenic PAA polypeptide.

In some embodiments, the disclosure provides a method of eliciting an immune response against PSMA in a human, comprising administering to the human an effective amount of an immunogenic PSMA composition provided by the present disclosure, wherein the immunogenic PSMA composition is selected from: (1) an immunogenic PSMA polypeptide, (2) an isolated nucleic acid molecule encoding an immunogenic PSMA polypeptide, (3) a composition comprising an immunogenic PSMA polypeptide, or (4) a composition comprising an isolated nucleic acid molecule encoding an immunogenic PSMA polypeptide.

In some other embodiments, the disclosure provides a method of eliciting an immune response against PSA in a human, comprising administering to the human an effective amount of an immunogenic PSA composition provided by the present disclosure, wherein the immunogenic PSA composition is selected from: (1) an immunogenic PSA polypeptide, (2) an isolated nucleic acid molecule encoding an immunogenic PSA polypeptide, (3) a composition comprising an immunogenic PSA polypeptide, or (4) a composition comprising an isolated nucleic acid molecule encoding an immunogenic PSA polypeptide.

In another aspect, the present disclosure provides a method of inhibiting abnormal cell proliferation in a human, wherein the abnormal cell proliferation is associated with over-expression of a PAA. The method comprises administering to the human an effective amount of immunogenic PAA composition provided by the present disclosure that is immunogenic against the over-expressed PAA. The immunogenic PAA composition may be (1) an immunogenic PAA polypeptide, (2) an isolated nucleic acid molecule encoding one or more immunogenic PAA polypeptides, (3) a composition comprising an immunogenic PAA polypeptide, or (4) a composition comprising an isolated nucleic acid molecule encoding one or more immunogenic PAA polypeptides. In some embodiments, the method is for inhibiting abnormal cell proliferation in prostate in a human. In a particular embodiment, the present disclosure provide a method of inhibiting abnormal cell proliferation in prostate over-expressing PSMA, comprising administering to the human effective amount of (1) an immunogenic PSMA polypeptide, (2) an isolated nucleic acid molecule encoding one or more immunogenic PSMA polypeptides, (3) a composition comprising an immunogenic PSMA polypeptide, or (4) a composition comprising an isolated nucleic acid molecule encoding one or more immunogenic PSMA polypeptide.

In another aspect, the present disclosure provides a method of treating cancer in a human wherein cancer is associated with over-expression of a PAA. The method comprises administering to the human an effective amount of immunogenic PAA composition capable of eliciting an immune response against the over-expressed PAA. The immunogenic PAA composition may be (1) an immunogenic PAA polypeptide, (2) an isolated nucleic acid molecule encoding one or more immunogenic PAA polypeptides, (3) a composition comprising an immunogenic PAA polypeptide, or (4) a composition comprising an isolated nucleic acid molecule encoding one or more immunogenic PAA polypeptides. Examples of cancers that may be treated with the method include breast cancer, stomach cancer, ovarian cancer, lung cancer, bladder cancer, colorectal cancer, renal cancer, pancreatic cancer and prostate cancer.

In some embodiments, the disclosure provides a method of treating prostate cancer in a human, comprising administering to the human an effective amount of a nucleic acid composition provided herein above. The nucleic acids in the composition may encode only one particular immunogenic PAA polypeptide, such an immunogenic PSMA polypeptide, an immunogenic PSA polypeptide, or an immunogenic PSCA polypeptide. The nucleic acids in the composition may also encode two or more different immunogenic PAA polypeptides, such as: (1) an immunogenic PSMA polypeptide and an immunogenic PSA polypeptide; (2) an immunogenic PSMA polypeptide and an immunogenic PSCA polypeptide; (3) an immunogenic PSA polypeptide and an immunogenic PSCA polypeptide; (4) an immunogenic PSMA polypeptide, an immunogenic PSA polypeptide, and an immunogenic PSCA polypeptide. Each individual nucleic acid molecule in the composition may encode only one particular immunogenic PAA polypeptide, such as a PSMA polypeptide, a PSA polypeptide, or a PSCA polypeptide. Alternatively, an individual nucleic acid molecule in the composition may be a multi-antigen constructs encoding two different types of immunogenic PAA polypeptides, such as: (1) an immunogenic PSMA polypeptide and an immunogenic PSA polypeptide; (2) an immunogenic PSMA polypeptide and an immunogenic PSCA polypeptide; (3) an immunogenic PSCA polypeptide and an immunogenic PSA polypeptide; or (4) an immunogenic PSMA polypeptide, an immunogenic PSA polypeptide, and an immunogenic PSCA polypeptide. In some particular embodiments, the nucleic acid composition comprises a multi-antigen construct that encode at least (4) an immunogenic PSMA polypeptide, an immunogenic PSA polypeptide, and an immunogenic PSCA polypeptide. The immunogenic PSCA polypeptide contained in vaccine compositions or expressed by a nucleic acid in vaccine compositions for the treatment of prostate cancer in human is preferably the human full length PSCA protein.

The polypeptide and nucleic acid compositions can be administered to an animal, including human, by a number of methods known in the art. Examples of suitable methods include: (1) intramuscular, intradermal, intraepidermal, intravenous, intraarterial, subcutaneous, or intraperitoneal administration, (2) oral administration, and (3) topical application (such as ocular, intranasal, and intravaginal application). One particular method of intradermal or intraepidermal administration of a nucleic acid vaccine composition that may be used is gene gun delivery using the Particle Mediated Epidermal Delivery (PMED™) vaccine delivery device marketed by PowderMed. PMED is a needle-free method of administering vaccines to animals or humans. The PMED system involves the precipitation of DNA onto microscopic gold particles that are then propelled by helium gas into the epidermis. The DNA-coated gold particles are delivered to the APCs and keratinocytes of the epidermis, and once inside the nuclei of these cells, the DNA elutes off the gold and becomes transcriptionally active, producing encoded protein. This protein is then presented by the APCs to the lymphocytes to induce a T-cell-mediated immune response. Another particular method for intramuscular administration of a nucleic acid vaccine provided by the present disclosure is electroporation. Electroporation uses controlled electrical pulses to create temporary pores in the cell membrane, which facilitates cellular uptake of the nucleic acid vaccine injected into the muscle. Where a CpG is used in combination with a nucleic acid vaccine, it is preferred that the CpG and nucleic acid vaccine are co-formulated in one formulation and the formulation is administered intramuscularly by electroporation.

The effective amount of the immunogenic PAA polypeptide or nucleic acid encoding an immunogenic PAA polypeptide in the composition to be administered in a given method provided by the present disclosure can be readily determined by a person skilled in the art and will depend on a number of factors. In a method of treating cancer, such as prostate cancer, factors that may be considered in determining the effective amount of the immunogenic PAA polypeptide or nucleic acid include, but not limited: (1) the subject to be treated, including the subject's immune status and health, (2) the severity or stage of the cancer to be treated, (3) the specific immunogenic PAA polypeptides used or expressed, (4) the degree of protection or treatment desired, (5) the administration method and schedule, and (6) other therapeutic agents (such as adjuvants or immune modulators) used. In the case of nucleic acid vaccine compositions, including the multi-antigen vaccine compositions, the method of formulation and delivery are among the key factors for determining the dose of the nucleic acid required to elicit an effective immune response. For example, the effective amounts of the nucleic acid may be in the range of 2 μg/dose-10 mg/dose when the nucleic acid vaccine composition is formulated as an aqueous solution and administered by hypodermic needle injection or pneumatic injection, whereas only 16 ng/dose-16 μg/dose may be required when the nucleic acid is prepared as coated gold beads and delivered using a gene gun technology. The dose range for a nucleic acid vaccine by electroporation is generally in the range of 0.5-10 mg/dose. In the case where the nucleic acid vaccine is administered together with a CpG by electroporation in a co-formulation, the dose of the nucleic acid vaccine may be in the range of 0.5-5 mg/dose and the dose of CpG is typically in the range of 0.05 mg-5 mg/dose, such as 0.05, 0.2, 0.6, or 1.2 mg/dose per person.

The nucleic acid or polypeptide vaccine composition of the present invention can be used in a prime-boost strategy to induce robust and long-lasting immune response. Priming and boosting vaccination protocols based on repeated injections of the same immunogenic construct are well known. In general, the first dose may not produce protective immunity, but only "primes" the immune system. A protective immune response develops after the second or third dose (the "boosts). The boosts are performed according to conventional techniques, and can be further optimized empirically in terms of schedule of administration, route of administration, choice of adjuvant, dose, and potential sequence when administered with another vaccine. In one embodiment, the nucleic acid or polypeptide vaccines of the present invention are used in a conventional homologous prime-boost strategy, in which the same vaccine is administered to the animal in multiple doses. In another embodiment, the nucleic acid or polypeptide vaccine compositions are used in a heterologous prime-boost vaccination, in which different types of vaccines containing the same antigens are administered at predetermined time intervals. For example, a nucleic acid construct may be administered in the form of a plasmid in the initial dose ("prime") and as part of a vector in the subsequent doses ("boosts"), or vice versa.

For the treatment of prostate cancer, the polypeptide or nucleic acid vaccines of the present invention may be used together with prostate cancer vaccines based on other antigens, such as prostatic acid phosphatase-based antigens and androgen receptor.

The polypeptide or nucleic acid vaccine composition of the present invention may be used together with one or more adjuvants. Examples of suitable adjuvants include: (1) oil-in-water emulsion formulations (with or without other specific immunostimulating agents such as muramyl polypeptides or bacterial cell wall components), such as for example (a) MF59™ (PCT Publication No. WO 90/14837; Chapter 10 in *Vaccine design: the subunit and adjuvant approach*, eds. Powell & Newman, Plenum Press 1995), containing 5% Squalene, 0.5% Tween 80 (polyoxyethylene sorbitan monooleate), and 0.5% Span 85 (sorbitan trioleate) formulated into submicron particles using a microfluidizer, (b) SAF, containing 10% Squalene, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS) (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS); (2) saponin adjuvants, such as QS21, STIMULON™ (Cambridge Bioscience, Worcester, Mass.), Abisco® (Isconova, Sweden), or Iscomatrix® (Commonwealth Serum Laboratories, Australia); (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (PCT Publication No. WO 99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3 dMPL), optionally in the substantial absence of alum when used with pneumococcal saccharides (e.g. GB-2220221, EP-A-0689454, WO 00/56358); (6) combinations of 3 dMPL with, for example, QS21 and/or oil-in-water emulsions (e.g. EP-A-0835318, EP-A-0735898, EP-A-0761231); (7) oligonucleotides comprising CpG motifs, i.e. containing at least one CG dinucleotide, where the cytosine is unmethylated (e.g., Krieg, *Vaccine* (2000) 19:618-622; Krieg, *Curr Opin Mol Ther* (2001) 3:15-24; WO 98/40100, WO 98/55495, WO 98/37919 and WO 98/52581); (8) a polyoxyethylene ether or a polyoxyethylene ester (e.g. WO 99/52549); (9) a polyoxyethylene sorbitan ester surfactant in combination with an octoxynol (e.g., WO 01/21207) or a polyoxyethylene alkyl ether or ester surfactant in combination with at least one additional non-ionic surfactant such as an octoxynol (e.g., WO 01/21152); (10) a saponin and an immunostimulatory oligonucleotide (e.g. a CpG oligonucleotide) (e.g., WO 00/62800); (11) metal salt including aluminum salts (such as alum, aluminum phosphate, aluminum hydroxide); (12) a saponin and an oil-in-water emulsion (e.g. WO 99/11241); (13) a saponin (e.g. QS21)+3 dMPL+IM2 (optionally+a sterol)(e.g. WO 98/57659); (14) other substances that act as immunostimulating agents to enhance the efficacy of the composition, such as Muramyl polypeptides including N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), (15) ligands for toll-like receptors (TLR), natural or synthesized (e.g. Kanzler et al., *Nature Med.* 13:1552-1559 (2007)), including TLR3 ligands such as polyl:C and similar compounds such as Hiltonol and Ampligen.

The polypeptide or nucleic acid vaccine compositions of the present invention may be used together with one or more immune modulators. Examples of suitable immune modulators include protein tyrosine kinase inhibitors (such as afatinib, axitinib, cediranib, erlotinib, gefitinib, grandinin, lapatinib, lestaurtinib, neratinib, pazopanib, quizartinib, regorafenib, semaxanib, sorafenib, sunitinib, tivozanib, toceranib, bosutinib and vandetanib), CD40 agonists (such as CD40 agonist antibody), OX40 agonists (such as OX40 agonist antibody), CTLA-4 inhibitors (such as antiCTLA-4 antibody Ipilimumab and Tremelimumab), TLR agonists, 4-1BB agonists, Tim-1 antagonists, LAGE-3 antagonists and PD-L1 & PD-1 antagonists.

H. Vaccine-Based Immunotherapy Regimens (VBIR)

In a further aspect, the present disclosure provides a method of enhancing the immunogenicity or therapeutic effect of a vaccine for the treatment of a neoplastic disorder in a mammal, particularly a human. The method comprises administering to the mammal receiving the vaccine for the treatment of a neoplastic disorder (1) an effective amount of at least one immune-suppressive-cell inhibitor (ISC inhibitor) and (2) an effective amount of at least one immune-effector-cell enhancer (IEC enhancer). The method may be used in combination with a vaccine in any form or formulation, for example, a subunit vaccine, a protein-based vaccine, a peptide-based vaccine, or a nucleic acid-based vaccines such as a DNA-based vaccine, a RNA-based vaccine, a plasmid-based vaccine, or a vector-based vaccine. In addition, the method is not limited to any particular types of vaccines or any particular types of cancer. Rather, the method may be used in combination with any vaccine intended for the treatment of neoplastic disorder, including benign, pre-malignant, and malignant neoplastic disorders. For example, the method may be used in combination a vaccine that is intended for the treatment of any of the following neoplastic disorders: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genito-urinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyosarcoma, and osteosarcoma; other tumors including melanoma, xenoderma pigmentosum, keratoactanthoma, seminoma, thyroid follicular cancer, and teratocarcinoma; melanoma, unresectable stage III or IV malignant melanoma, squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, bone cancer, bone tumors, adult malignant fibrous histiocytoma of bone; childhood malignant fibrous histiocytoma of bone, sarcoma, pediatric sarcoma, sinonasal natural killer, neoplasms, plasma cell neoplasm; myelodysplastic syndromes; neuroblastoma; testicular germ cell tumor, intraocular melanoma, myelodysplastic syndromes; myelodysplastic/myeloproliferative diseases, synovial sarcoma, chronic myeloid leukemia, acute lymphoblastic leukemia, philadelphia chromosome positive acute lymphoblastic leukemia (Ph+ ALL), multiple myeloma, acute myelogenous leukemia, chronic lymphocytic leukemia, and mastocytosis.

In some embodiments, present disclosure provides a method of enhancing the immunogenicity or therapeutic effect of a vaccine for the treatment of prostate cancer in a human. The vaccine administered may be capable of eliciting an immune response against any human PAA, such as PSMA, PSA, or PSCA. In some particular embodiments, the vaccine administered comprises a nucleic acid molecule encoding an antigen capable of eliciting immunogenicity against a human PAA, such as PSMA, PSA, or PSCA. Examples of specific nucleic acid molecules that may be contained in the vaccine include the following provided by the present disclosure:

1) a nucleic acid molecule encoding an immunogenic PSMA polypeptide, an immunogenic PSA polypeptide, or an immunogenic PSCA polypeptide;

2) a nucleic acid molecule encoding two immunogenic PAA polypeptides provided by the present disclosure, such as a) an immunogenic PSMA polypeptide and an immunogenic PSA polypeptide; b) an immunogenic PSMA polypeptide and an immunogenic PSCA polypeptide; or c) an immunogenic PSA polypeptide and an immunogenic PSCA polypeptide; and 3) a nucleic acid molecule encoding three immunogenic PAA polypeptides, which are an immunogenic PSMA polypeptide, an immunogenic PSA polypeptide, and an immunogenic PSCA polypeptide.

In another further aspect, the present disclosure provides a method of treating a neoplastic disorder in a mammal, particularly a human. The method comprises administering to the mammal (1) an effective amount of a vaccine capable of eliciting an immune response against a TAA associated with the neoplastic disorder, (2) an effective amount of at least one immune-suppressive-cell inhibitor (ISC inhibitor), and (3) an effective amount of at least one immune-effector-cell enhancer (IEC enhancer). Any vaccine that is capable of eliciting an immune response against a particular TAA may be used in the method. Many TAAs are known in the art. In addition to the prostate-associated antigens, the following are examples of TAAs that are known in the art: CEA, MUC-1, Ep-CAM, 5T4, hCG-b, K-ras, and TERT for colorectal cancer; CEA, Muc-1, p53, mesothelin, Survivin, and NY-ESO-1 for ovarian cancer; Muc-1, 5T4, WT-1, TERT, CEA, EGF-R and MAGE-A3 for non-small cell lung cancer; 5T4 for renal cell carcinoma; and Muc-1, mesothelin, K-Ras, Annexin A2, TERT, and CEA for pancreatic cancer. New TAAs continue to be identified. A vaccine that is capable of eliciting an immune response against any of the known or new TAAs can be used in the method. In addition, the vaccine administered may be in any form or formulation, for example, subunit vaccines, protein-based vaccine, peptide based vaccines, or nucleic acid-based vaccines such DNA-based vaccines, RNA-based vaccines, plasmid-based vaccines, or vector-based vaccines.

In some embodiments, the present disclosure provides a method of treating a prostate cancer in a human, the method comprising administering to the human a vaccine capable of eliciting an immune response against any human PAA, such as PSMA, PSA, or PSCA. In some particular embodiments, the vaccine administered comprises a nucleic acid molecule encoding an antigen capable of eliciting immunogenicity against a human PAA, such as PSMA, PSA, or PSCA. Examples of specific nucleic acid molecules that may be contained in the vaccine include the following provided by the present disclosure:

1) a nucleic acid molecule encoding an immunogenic PSMA polypeptide, an immunogenic PSA polypeptide, or an immunogenic PSCA polypeptide;

2) a nucleic acid molecule encoding two immunogenic PAA polypeptides provided by the present disclosure, such as a) an immunogenic PSMA polypeptide and an immunogenic PSA polypeptide; b) an immunogenic PSMA polypeptide and an immunogenic PSCA polypeptide; or c) an immunogenic PSA polypeptide and an immunogenic PSCA polypeptide; and 3) a nucleic acid molecule encoding three immunogenic PAA polypeptides, which are an immunogenic PSMA polypeptide, an immunogenic PSA polypeptide, and an immunogenic PSMA polypeptide.

The method of treating a neoplastic disorder in a mammal and the method of enhancing the immunogenicity or therapeutic effect of a vaccine for the treatment of a neoplastic disorder in a mammal described herein above are alternatively referred to as "vaccine-based immunotherapy regimens" (or "VBIR").

In the vaccine-based immunotherapy regimens, the IEC enhancers and ISC inhibitors may be administered by any suitable methods and routes, including (1) systemic administration such as intravenous, intramuscular, or oral administration, and (2) local administration such intradermal and subcutaneous administration. Where appropriate or suitable, local administration is generally preferred over systemic administration. Local administration of any IEC enhancer and ISC inhibitor can be carried out at any location of the body of the mammal that is suitable for local administration of pharmaceuticals; however, it is more preferable that these immune modulators are administered locally at close proximity to the vaccine draining lymph node.

Two or more specific IEC enhancers from a single class of IEC enhancers (for examples, two CTLA-agonists) may be administered in combination with the ISC inhibitors. In addition, two or more specific IEC enhancers from two or more different classes of IEC enhancers (for example, one CTLA-4 antagonist and one TLR agonist) may be administered together. Similarly, two or more specific ISC inhibitors from a single class of ISC inhibitors (for examples, two or more protein kinase inhibitors) may be administered in combination with the IEC enhancers. In addition, two or more specific ISC inhibitors from two or more different classes of ISC inhibitors (for example, one protein kinase inhibitor and one COX-2 inhibitor) may be administered together.

In the vaccine-based immunotherapy regimens the vaccine may be administered simultaneously or sequentially with any or all of the immune modulators (i.e., ISC inhibitors and IEC enhancers) used. Similarly, when two or more immune modulators are used, they may be administered simultaneously or sequentially with respect to each other. In some embodiments, a vaccine is administered simultaneously (e.g., in a mixture) with respect to one immune modulator, but sequentially with respect to one or more additional immune modulators. Co-administration of the vaccine and the immune modulators in the vaccine-based immunotherapy regimen can include cases in which the vaccine and at least one immune modulator are administered so that each is present at the administration site, such as vaccine draining lymph node, at the same time, even though the antigen and the immune modulators are not administered simultaneously. Co-administration of the vaccine and the immune modulators also can include cases in which the vaccine or the immune modulator is cleared from the administration site, but at least one cellular effect of the cleared vaccine or immune modulator persists at the administration site, such as vaccine draining lymph node, at least until one or more additional immune modulators are administered to the administration site. In cases where a nucleic acid vaccine is administered in combination with a CpG, the vaccine and CpG may be contained in a single formulation and administered together by any suitable method. In some embodiments, the nucleic acid vaccine and CpG in a co-formulation (mixture) is administered by intramuscular injection in combination with electroporation.

Any ISC inhibitors may be used in the vaccine-based immunotherapy regimens. Examples of classes of SIC inhibitors include protein kinase inhibitors, cyclooxygenase-2 (COX-2) inhibitors, phosphodiesterase type 5 (PDE5) inhibitors, and DNA crosslinkers. Examples COX-2 inhibitors include celecoxib and rofecoxib. Examples of PDE5 inhibitors include avanafil, lodenafil, mirodenafil, sildenafil, tadalafil, vardenafil, udenafil, and zaprinast. An example of DNA crosslinkers is cyclophosphamide. Examples of specific protein kinase inhibitors are described in details below.

The term "protein kinase inhibitor" refers to any substance that acts as a selective or non-selective inhibitor of a protein kinase. The term "protein kinases" refers to the enzymes that catalyze the transfer of the terminal phosphate of adenosine triphosphate to tyrosine, serine or threonine residues in protein substrates. Protein kinases include receptor tyrosine kinases and non-receptor tyrosine kinases. Examples of receptor tyrosine kinases include EGFR (e.g., EGFR/HER1/ErbB1, HER2/Neu/ErbB2, HER3/ErbB3, HER4/ErbB4), INSR (insulin receptor), IGF-IR, IGF-II1R, IRR (insulin receptor-related receptor), PDGFR (e.g., PDGFRA, PDGFRB), c-KIT/SCFR, VEGFR-1/FLT-1, VEGFR-2/FLK-1/KDR, VEGFR-3/FLT-4, FLT-3/FLK-2, CSF-1R, FGFR 1-4, CCK4, TRKA-C, MET, RON, EPHA 1-8, EPHB 1-6, AXL, MER, TYRO3, TIE, TEK, RYK, DDR 1-2, RET, c-ROS, LTK (leukocyte tyrosine kinase), ALK (anaplastic lymphoma kinase), ROR 1-2, MUSK, AATYK 1-3, and RTK 106. Examples of non-receptor tyrosine kinases include BCR-ABL, Src, Frk, Btk, Csk, Abl, Zap70, Fes/Fps, Fak, Jak, Ack, and LIMK. In the vaccine-based immunotherapy regimen provided by the present disclosure, the protein kinase inhibitors are administered to the mammal at a suboptimal dose. The term "suboptimal dose" refers to the dose amount that is below the minimum effective dose when the tyrosine kinase inhibitor is administered in a monotherapy (i.e., where the protein kinase inhibitor is administered alone without any other therapeutic agents) for the target neoplastic disorder.

Examples of specific protein kinase inhibitors suitable for use in the vaccine-based immunotherapy regimen include Lapatinib, AZD 2171, ET180CH 3, Indirubin-3'-oxime, NSC-154020, PD 169316, Quercetin, Roscovitine, Triciribine, ZD 1839, 5-Iodotubercidin, Adaphostin, Aloisine, Alsterpaullone, Aminogenistein, API-2, Apigenin, Arctigenin, ARRY-334543, Axitinib (AG-013736), AY-22989, AZD 2171, Bisindolylmaleimide IX, CCI-779, Chelerythrine, DMPQ, DRB, Edelfosine, ENMD-981693, Erbstatin analog, Erlotinib, Fasudil, Gefitinib (ZD1839), H-7, H-8, H-89, HA-100, HA-1004, HA-1077, HA-1100, Hydroxyfasudil, Kenpaullone, KN-62, KY12420, LFM-A13, Luteolin, LY294002, LY-294002, Mallotoxin, ML-9, MLN608, NSC-226080, NSC-231634, NSC-664704, NSC-680410, NU6102, Olomoucine, Oxindole I, PD 153035, PD 98059, Phloridzin, Piceatannol, Picropodophyllin, PKI, PP1, PP2, PTK787/ZK222584, PTK787/ZK-222584, Purvalanol A, Rapamune, Rapamycin, Ro 31-8220, Rottlerin, SB202190, SB203580, Sirolimus, SL327, SP600125, Staurosporine, STI-571, SU1498, SU4312, SU5416, SU5416 (Semaxanib), SU6656, SU6668, syk inhibitor, TBB, TCN, Tyrphostin AG 1024, Tyrphostin AG 490, Tyrphostin AG 825, Tyrphostin AG 957, U0126, W-7, Wortmannin, Y-27632, Zactima (ZD6474), ZM 252868. gefitinib (Iressa®), sunitinib malate (Sutent®; SU11248), erlotinib (Tarceva®; OSI-1774), lapatinib (GW572016; GW2016), canertinib (CI 1033), semaxinib (SU5416), vatalanib (PTK787/ZK222584), sorafenib (BAY 43-9006), imatinib (Gleevec®; ST1571), dasatinib (BMS-354825), leflunomide (SU101), vandetanib (Zactima®; ZD6474), and nilotinib. Additional protein kinase inhibitors suitable for use in the present invention are described in, e.g., U.S. Pat. Nos. 5,618,829, 5,639,757, 5,728,868, 5,804,396, 6,100,254, 6,127,374, 6,245,759, 6,306,874, 6,313,138, 6,316,444, 6,329,380, 6,344,459, 6,420,382, 6,479,512, 6,498,165, 6,544,988, 6,562,818, 6,586,423, 6,586,424, 6,740,665, 6,794,393, 6,875,767, 6,927,293, and 6,958,340.

In some embodiments, the protein kinase inhibitor is a multi-kinase inhibitor, which is an inhibitor that acts on more than one specific kinase. Examples of multi-kinase inhibitors include imatinib, sorafenib, lapatinib, BIRB-796, and AZD-1152, AMG706, Zactima (ZD6474), MP-412, sorafenib (BAY 43-9006), dasatinib, CEP-701 (lestaurtinib), XL647, XL999, Tykerb (lapatinib), MLN518, (formerly known as CT53518), PKC412, ST1571, AEE 788, OSI-930, OSI-817, sunitinib malate (Sutent), axitinib (AG-013736), erlotinib, gefitinib, axitinib, bosutinib, temsirolismus and nilotinib (AMN107). In some particular embodiments, the tyrosine kinase inhibitor is sunitinib, sorafenib, or a pharmaceutically acceptable salt or derivative (such as a malate or a tosylate) of sunitinib or sorafenib.

Sunitinib malate, which is marketed by Pfizer Inc. under the trade name SUTENT, is described chemically as butanedioic acid, hydroxy-, (2S)-, compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1). The compound, its synthesis, and particular polymorphs are described in U.S. Pat. No. 6,573,293, U.S. Patent Publication Nos. 2003-0229229, 2003-0069298 and 2005-0059824, and in J. M. Manley, M. J. Kalman, B. G. Conway, C. C. Ball, J. L Havens and R. Vaidyanathan, "Early Amidation Approach to 3-[(4-amido)pyrrol-2-yl]-2-indolinones," J. Org. Chew. 68, 6447-6450 (2003). Formulations of sunitinib and its L-malate salt are described in PCT Publication No. WO 2004/024127. Sunitinib malate has been approved in the U.S. for the treatment of gastrointestinal stromal tumor, advanced renal cell carcinoma, and progressive, well-differentiated pancreatic neuroendocrine tumors in patients with unresectable locally advanced or metastatic disease. The recommended dose of sunitinib malate for gastrointestinal stromal tumor (GIST) and advanced renal cell carcinoma (RCC) for humans is 50 mg taken orally once daily, on a schedule of 4 weeks on treatment followed by 2 weeks off (Schedule 4/2). The recommended dose of sunitinib malate for pancreatic neuroendocrine tumors (pNET) is 37.5 mg taken orally once daily.

In the vaccine-based immunotherapy regimen, sunitinib malate may be administered orally in a single dose or multiple doses. Typically, sunitinib malate is delivered for two, three, four or more consecutive weekly doses followed by a "off" period of about 1 or 2 weeks, or more where no sunitinib malate is delivered. In one embodiment, the doses are delivered for about 4 weeks, with 2 weeks off. In another embodiment, the sunitinib malate is delivered for two weeks, with 1 week off. However, it may also be delivered without a "off" period for the entire treatment period. The effective amount of sunitinib malate administered orally to a human in the vaccine-based immunotherapy regimen is typically below 40 mg per person per dose. For example, it may be administered orally at 37.5, 31.25, 25, 18.75, 12.5, 6.25 mg per person per day. In some embodiments, sunitinib malate is administered orally in the range of 1-25 mg per person per dose. In some other embodiments, sunitinib malate is administered orally in the range of 6.25, 12.5, or 18.75 mg per person per dose. Other dosage regimens and variations are foreseeable, and will be determined through physician guidance.

Sorafenib tosylate, which is marketed under the trade name NEXAVAR, is also a multi-kinase inhibitor. Its chemical name is 4-(4-{3-[4-Chloro-3-(trifluoromethyl) phenyl] ureido}phenoxy)-N-methylpyrid-ine-2-carboxamide. It is approved in the U.S. for the treatment of primary kidney cancer (advanced renal cell carcinoma) and advanced primary liver cancer (hepatocellular carcinoma). The recommended daily dose is 400 mg taken orally twice daily. In the vaccine-based immunotherapy regimen provided by the present disclosure, the effective amount of sorafenib tosylate administered orally is typically below 400 mg per person per day. In some embodiments, the effective amount of sorafenib tosylate administered orally is in the range of 10-300 mg per person per day. In some other embodiments, the effective amount of sorafenib tosylate administered orally is between 10-200 mg per person per day, such as 10, 20, 60, 80, 100, 120, 140, 160, 180, or 200 mg per person per day.

Axitinib, which is marketed under the trade name INLYTA, is a selective inhibitor of VEGF receptors 1, 2, and 3. Its chemical name is (N-Methyl-2-[3-((E)-2-pyridin-2-yl-vinyl)-1H-indazol-6-ylsulfanyl]-benzamide. It is approved for the treatment of advanced renal cell carcinoma after failure of one prior systemic therapy. The starting dose is 5 mg orally twice daily. Dose adjustments can be made based on individual safety and tolerability. In the vaccine-based immunotherapy regimen provided by the present disclosure, the effective amount of axitinib administered orally is typically below 5 mg twice daily. In some other embodiments, the effective amount of axitinib administered orally is between 1-5 mg twice daily. In some other embodiments, the effective amount of axitinib administered orally is between 1, 2, 3, 4, or 5 mg twice daily.

In the vaccine-based immunotherapy regimens any IEC enhancers may be used. They may be small molecules or large molecules (such as protein, polypeptide, DNA, RNA, and antibody). Examples of IEC enhancers that may be used include TNFR agonists, CTLA-4 antagonists, TLR agonists, programmed cell death protein 1 (PD-1) antagonists (such as BMS-936558), anti-PD-1 antibody CT-011), and programmed cell death protein 1 ligand 1 (PD-L1) antagonists (such as BMS-936559), lymphocyte-activation gene 3 (LAG3) antagonists, and T cell Immunoglobulin- and mucin-domain-containing molecule-3 (TIM-3) antagonists. Examples of specific TNFR agonists, CTLA-4 antagonists, and TLR agonists are provided in details herein below.

TNFR Agonists.

Examples of TNFR agonists include agonists of OX40, 4-1BB (such as BMS-663513), GITR (such as TRX518), and CD40. Examples of specific CD40 agonists are described in details herein below.

CD40 agonists are substances that bind to a CD40 receptor on a cell and is capable of increasing one or more CD40 or CD40L associated activities. Thus, CD40 "agonists" encompass CD40 "ligands".

Examples of CD40 agonists include CD40 agonistic antibodies, fragments CD40 agonistic antibodies, CD40 ligands (CD40L), and fragments and derivatives of CD40L such as oligomeric (e.g., bivalent, trimeric CD40L), fusion proteins containing and variants thereof.

CD40 ligands for use in the present invention include any peptide, polypeptide or protein, or a nucleic acid encoding a peptide, polypeptide or protein that can bind to and activate one or more CD40 receptors on a cell. Suitable CD40 ligands are described, for example, in U.S. Pat. Nos. 6,482, 411, 6,410,711; 6,391,637; and 5,981,724, all of which patents and application and the CD40L sequences disclosed therein are incorporated by reference in their entirety herein. Although human CD40 ligands will be preferred for use in human therapy, CD40 ligands from any species may be used in the invention. For use in other animal species, such as in veterinary embodiments, a species of CD40 ligand matched to the animal being treated will be preferred. In certain embodiments, the CD40 ligand is a gp39 peptide or protein oligomer, including naturally forming gp39 peptide, polypeptide or protein oligomers, as well as gp39 peptides, polypeptides, proteins (and encoding nucleic acids) that comprise an oligomerization sequence. While oligomers such as dimers, trimers and tetramers are preferred in certain aspects of the invention, in other aspects of the invention larger oligomeric structures are contemplated for use, so long as the oligomeric structure retains the ability to bind to and activate one or more CD40 receptor(s).

In certain other embodiments, the CD40 agonist is an anti-CD40 antibody, or antigen-binding fragment thereof. The antibody can be a human, humanized or part-human chimeric anti-CD40 antibody. Examples of specific anti-CD40 monoclonal antibodies include the G28-5, mAb89, EA-5 or S2C6 monoclonal antibody, and CP870893. In a particular embodiment, the anti-CD40 agonist antibody is CP870893 or dacetuzumab (SGN-40).

CP-870,893 is a fully human agonistic CD40 monoclonal antibody (mAb) that has been investigated clinically as an anti-tumor therapy. The structure and preparation of CP870,893 is disclosed in WO2003041070 (where the antibody is identified by the internal identified "21.4.1"). The amino acid sequences of the heavy chain and light chain of CP-870,893 are set forth in SEQ ID NO: 40 and SEQ ID NO: 41, respectively. In clinical trials, CP870,893 was administered by intravenous infusion at doses generally in the ranges of 0.05-0.25 mg/kg per infusion. In a phase I clinical study, the maximum tolerated dose (MTD) of CP-870893 was estimated to be 0.2 mg/kg and the dose-limiting toxicities included grade 3 CRS and grade 3 urticaria. [Jens Ruter et al.: Immune modulation with weekly dosing of an agonist CD40 antibody in a phase I study of patients with advanced solid tumors. Cancer Biology & Therapy 10:10, 983-993; Nov. 15, 2010.]. In the vaccine-based immunotherapy regimen provided by the present disclosure, CP-870,893 can be administered intradermally, subcutaneously, or topically. It is preferred that it is administered intradermally. The effective amount of CP870893 to be administered in the regimen is generally below 0.2 mg/kg, typically in the range of 0.01 mg-0.15 mg/kg, or 0.05-0.1 mg/kg.

Dacetuzumab (also known as SGN-40 or huS2C6; CAS number 88-486-59-9) is another anti-CD40 agonist antibody that has been investigated in clinical trials for indolent lymphomas, diffuse large B cell lymphomas and Multiple Myeloma. In the clinical trials, dacetuzumab was administered intravenously at weekly doses ranging from 2 mg/kg to 16 mg/kg. In the vaccine-based immunotherapy regimen provided by the present disclosure, dacetuzumab can be administered intradermally, subcutaneously, or topically. It is preferred that it is administered intradermally. The effective amount of dacetuzumab to be administered in the vaccine-based immunotherapy regimen is generally below 16 mg/kg, typically in the range of 0.2 mg-14 mg/kg, or 0.5-8 mg/kg, or 1-5 mg/kg.

CTLA-4 Inhibitors.

Suitable anti-CTLA-4 antagonist agents for use in the vaccine-based immunotherapy regimen provided by the disclosure include, without limitation, anti-CTLA-4 antibodies (such as human anti-CTLA-4 antibodies, mouse anti-CTLA-4 antibodies, mammalian anti-CTLA-4 antibodies, humanized anti-CTLA-4 antibodies, monoclonal anti-CTLA-4 antibodies, polyclonal anti-CTLA-4 antibodies, chimeric anti-CTLA-4 antibodies, anti-CTLA-4 domain antibodies), fragments of anti-CTLA-4 antibodies (such as (single chain anti-CTLA-4 fragments, heavy chain anti-CTLA-4 fragments, and light chain anti-CTLA-4 fragments), and inhibitors of CTLA-4 that agonize the co-stimulatory pathway. In some embodiments, the CTLA-4 inhibitor is Ipilimumab or Tremelimumab.

Ipilimumab (also known as MEX-010 or MDX-101), marketed as YERVOY, is a human anti-human CTLA-4 antibody. Ipilimumab can also be referred to by its CAS Registry No. 477202-00-9, and is disclosed as antibody 10DI in PCT Publication No. WO 01/14424, incorporated herein by reference in its entirety and for all purposes. Examples of pharmaceutical composition comprising Ipilimumab are provided in PCT Publication No. WO 2007/67959. Ipilimumab is approved in the U.S. for the treatment of unresectable or metastatic melanoma. The recommended dose of Ipilimumab as monotherapy is 3 mg/kg by intravenous administration every 3 weeks for a total of 4 doses. In the methods provided by the present invention, Ipilimumab is administered locally, particularly intradermally or subcutaneously. The effective amount of Ipilimumab administered locally is typically in the range of 5-200 mg/dose per person. In some embodiments, the effective amount of Ipilimumab is in the range of 10-150 mg/dose per person per dose. In some particular embodiments, the effective amount of Ipilimumab is about 10, 25, 50, 75, 100, 125, 150, 175, or 200 mg/dose per person.

Tremelimumab (also known as CP-675,206) is a fully human IgG2 monoclonal antibody and has the CAS number 745013-59-6. Tremelimumab is disclosed as antibody 11.2.1 in U.S. Pat. No. 6,682,736, incorporated herein by reference in its entirety and for all purposes. The amino acid sequences of the heavy chain and light chain of Tremelimumab are set forth in SEQ ID NOs:42 and 43, respectively. Tremelimumab has been investigated in clinical trials for the treatment of various tumors, including melanoma and breast cancer; in which Tremelimumab was administered intravenously either as single dose or multiple doses every 4 or 12 weeks at the dose range of 0.01 and 15 mg/kg. In the regimens provided by the present invention, Tremelimumab is administered locally, particularly intradermally or subcutaneously. The effective amount of Tremelimumab administered intradermally or subcutaneously is typically in the range of 5-200 mg/dose per person. In some embodiments, the effective amount of Tremelimumab is in the range of 10-150 mg/dose per person per dose. In some particular embodiments, the effective amount of Tremelimumab is about 10, 25, 50, 75, 100, 125, 150, 175, or 200 mg/dose per person.

Toll-like Receptor (TLR) Agonists.

The term "toll-like receptor agonist" or "TLR agonist" refers to a compound that acts as an agonist of a toll-like receptor (TLR). This includes agonists of TLR1, TLR2, TLR3, TLR4, TLR5, TLR6, TLR7, TLR8, TLR9, TLR10, and TLR11 or a combination thereof. Unless otherwise indicated, reference to a TLR agonist compound can include the compound in any pharmaceutically acceptable form, including any isomer (e.g., diastereomer or enantiomer), salt, solvate, polymorph, and the like. In particular, if a compound is optically active, reference to the compound can include each of the compound's enantiomers as well as racemic mixtures of the enantiomers. Also, a compound may be identified as an agonist of one or more particular TLRs (e.g., a TLR7 agonist, a TLR8 agonist, or a TLR7/8 agonist).

The TLR agonism for a particular compound may be assessed in any suitable manner known in the art. Regardless of the particular assay employed, a compound can be identified as an agonist of a particular TLR if performing the assay with a compound results in at least a threshold increase of some biological activity mediated by the particular TLR. Conversely, a compound may be identified as not acting as an agonist of a specified TLR if, when used to perform an assay designed to detect biological activity mediated by the specified TLR, the compound fails to elicit a threshold increase in the biological activity. Unless otherwise indicated, an increase in biological activity refers to an increase in the same biological activity over that observed in an appropriate control. An assay may or may not be performed in conjunction with the appropriate control. With experience, one skilled in the art may develop sufficient familiarity with a particular assay (e.g., the range of values observed in an appropriate control under specific assay conditions) that performing a control may not always be necessary to determine the TLR agonism of a compound in a particular assay.

Certain TLR agonists useful in the method of the present invention are small organic molecules, as opposed to large biological molecules such as proteins, peptides, and the like. Examples of small molecule TLR agonists include those disclosed in, for example, U.S. Pat. Nos. 4,689,338; 4,929,624; 4,988,815; 5,037,986; 5,175,296; 5,238,944; 5,266,575; 5,268,376; 5,346,905; 5,352,784; 5,367,076; 5,389,640; 5,395,937; 5,446,153; 5,482,936; 5,693,811; 5,741,908; 5,756,747; 5,939,090; 6,039,969; 6,083,505; 6,110,929; 6,194,425; 6,245,776; 6,331,539; 6,376,669; 6,451,810; 6,525,064; 6,545,016; 6,545,017; 6,558,951; and 6,573,273. Examples of specific small molecule TLR agonists useful in the methods provided by the present invention include 4-amino-alpha, alpha,2-trimethyl-IH-imidazo[4,5-c]qumolin-I-ethanol, N-(2-{2-[4-amino-2-(2-methoxyethyl)-IH-imidazo[4,5-c]quinolin-1-yl]ethoxy-}ethyl)-N-methylmorpholine-4-carboxamide, l-(2-amino-2-methylpropyl)-2-(ethoxymethyl-)-IH-imidazo[4,5-c]quinolin-4-arnine, N-[4-(4-amino-2-ethyl-IH-imidazo[4,5-c]quinolin-1-yl)butyl]methanesulfonamide, N-[4-(4-amino-2-propyl-IH-imidazo[4,5-c]quinolin-1-yl)butyl]methanesulfonamide, and imiquimod. Some TLR agonists particularly useful in the methods or regimen provided by the present disclosure are discussed in review article: Folkert Steinhagen, et al.: TLR-based immune adjuvants. Vaccine 29 (2011): 3341-3355.

In some embodiments, the TLR agonists are TLR9 agonists, particularly CpG oligonucleotides (or CpG.ODN). A CpG oligonucleotide is a short nucleic acid molecule containing a cytosine followed by a guanine linked by a phosphate bond in which the pyrimidine ring of the cytosine is unmethylated. A CpG motif is a pattern of bases that include an unmethylated central CpG surrounded by at least one base flanking (on the 3' and the 5' side of) the central CpG. CpG oligonucleotides include both D and K oligonucleotides. The entire CpG oligonucleotide can be unmethylated or portions may be unmethylated. Examples of CpG oligonucleotides useful in the methods provided by the present disclosure include those disclosed in U.S. Pat. Nos. 6,194,388, 6,207,646, 6,214,806, 628,371, 6,239,116, and 6,339,068.

The CpG oligonucleotides can encompass various chemical modifications and substitutions, in comparison to natural RNA and DNA, involving a phosphodiester internucleoside bridge, a beta-D-ribose (deoxyhbose) unit and/or a natural nucleoside base (adenine, guanine, cytosine, thymine, uracil). Examples of chemical modifications are known to the skilled person and are described, for example in Uhlmann E. et al. (1990), Chem. Rev. 90:543; "Protocols for Oligonucleotides and Analogs", Synthesis and Properties and Synthesis and Analytical Techniques, S. Agrawal, Ed., Humana Press, Totowa, USA 1993; Crooke, S T. et al. (1996) Annu. Rev. Pharmacol. Toxicol. 36:107-129; and Hunziker J. et al., (1995), Mod. Synth. Methods 7:331-417. Specifically, a CpG oligonucleotide can contain a modified cytosine. A modified cytosine is a naturally occurring or non-naturally occurring pyrimidine base analog of cytosine which can replace this base without impairing the immunostimulatory activity of the oligonucleotide. Modified cytosines include but are not limited to 5-substituted cytosines (e.g. 5-methylcytosine, 5-fluorocytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g. N4-ethyl-cytosine), 5-aza-cytosine, 2-mercapto-cytosine, isocytosine, pseudo-isocytosine, cytosine analogs with condensed ring systems (e.g. N,N'-propylene cytosine or phenoxazine), and uracil and its derivatives (e.g. 5-fluoro-uracil, 5-bromo-uracil, 5-bromovinyl-uracil, 4-thio-uracil, 5-hydroxy-uracil, 5-propynyl-uracil). Some of the preferred cytosines include 5-methylcytosine, 5-fluoro-cytosine, 5-hydroxy-cytosine, 5-hydroxymethyl-cytosine, and N4-ethyl-cytosine.

A CpG oligonucleotide can also contain a modified guanine. A modified guanine is a naturally occurring or non-naturally occurring purine base analog of guanine which can replace this base without impairing the immunostimulatory activity of the oligonucleotide. Modified guanines include but are not limited to 7-deeazaguanine, 7-deaza-7-substituted guanine, hypoxanthine, N2-substituted guanines (e.g. N2-methyl-guanine), 5-amino-3-methyl-3H,6H-thiazolo[4,5-d]pyhmidine-2,7-dione, 2,6-diaminopuhne, 2-aminopuhne, purine, indole, adenine, substituted adenines (e.g. N6-methyl-adenine, 8-oxo-adenine), 8-substituted guanine (e.g. 8-hydroxyguanine and 8-bromoguanine), and 6-thioguanine. In some embodiments of the disclosure, the guanine base is substituted by a universal base (e.g. 4-methylindole, 5-nitro-indole, and K-base), an aromatic ring system (e.g. benzimidazole or dichloro-benzimidazole, 1-methyl-1H-[1,2,4]triazole-3-carboxylic acid amide) or a hydrogen atom.

In certain aspects, the CpG oligonucleotides include modified backbones. It has been demonstrated that modification of the nucleic acid backbone provides enhanced activity of nucleic acids when administered in vivo. Secondary structures, such as stem loops, can stabilize nucleic acids against degradation. Alternatively, nucleic acid stabilization can be accomplished via phosphate backbone modifications. A preferred stabilized nucleic acid has at least a partial phosphorothioate modified backbone. Phosphorothioates may be synthesized using automated techniques employing either phosphoramidate or H-phosphonate chemistries. Aryl- and alkyl-phosphonates can be made, e.g. as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described (Uhlmann, E. and Peyman, A. (1990) Chem. Rev. 90:544; Goodchild, J. (1990) Bioconjugate Chem. 1:165). 2'-O-methyl nucleic acids with CpG motifs also cause immune activation, as do ethoxy-modified CpG nucleic acids. In fact, no backbone modifications have been found that completely abolish the CpG effect, although it is greatly reduced by replacing the C with a 5-methyl C. Constructs having phosphorothioate linkages provide maximal activity and protect the nucleic acid from degradation by intracellular exo- and endo-nucleases. Other modified oligonucleotides include phosphodiester modified oligonucleotides, combinations of phosphodiester and phosphorothioate oligonucleotides, methylphosphonate, methylphosphorothioate, phosphorordithioate, p-ethoxy, and combinations thereof. Each of these combinations and their particular effects on immune cells is discussed in more detail with respect to CpG nucleic acids in PCT Publication Nos. WO 96/02555 and WO 98/18810 and in U.S. Pat. Nos. 6,194,388 and 6,239,116.

The CpG oligonucleotides may have one or two accessible 5' ends. It is possible to create modified oligonucleotides having two such 5' ends, for instance, by attaching two oligonucleotides through a 3'-3' linkage to generate an oligonucleotide having one or two accessible 5' ends. The 3'-3'-linkage may be a phosphodiester, phosphorothioate or any other modified internucleoside bridge. Methods for accomplishing such linkages are known in the art. For instance, such linkages have been described in Seliger, H. et al., Oligonucleotide analogs with terminal 3'-3'- and 5'-5'-internucleotidic linkages as antisense inhibitors of viral gene expression, Nucleosides and Nucleotides (1991), 10(1-3), 469-77 and Jiang, et al., Pseudo-cyclic oligonucleotides: in vitro and in vivo properties, Bioorganic and Medicinal Chemistry (1999), 7(12), 2727-2735.

Additionally, 3'-3'-linked oligonucleotides where the linkage between the 3'-terminal nucleosides is not a phosphodiester, phosphorothioate or other modified bridge, can be prepared using an additional spacer, such as tri- or tetra-ethyleneglycol phosphate moiety (Durand, M. et al., Triple-helix formation by an oligonucleotide containing one (dA) 12 and two (dT)12 sequences bridged by two hexaethylene glycol chains, Biochemistry (1992), 31 (38), 9197-204, U.S. Pat. Nos. 5,658,738 and 5,668,265). Alternatively, the non-nucleotidic linker may be derived from ethanediol, propanediol, or from an abasic deoxyhbose (dSpacer) unit (Fontanel, Marie Laurence et al., Nucleic Acids Research (1994), 22(11), 2022-7) using standard phosphoramidite chemistry. The non-nucleotidic linkers can be incorporated once or multiple times, or combined with each other allowing for any desirable distance between the 3'-ends of the two oligonucleotides to be linked.

A phosphodiester internucleoside bridge located at the 3' and/or the 5' end of a nucleoside can be replaced by a modified internucleoside bridge, wherein the modified internucleoside bridge is for example selected from phosphorothioate, phosphorodithioate, $NRiR_2$-phosphoramidate, boranophosphate, a-hydroxybenzyl phosphonate, phosphate-$(C_1$-$C_{21})$—O-alkyl ester, phosphate-[$(C_6$-$C_{21})$aryl-$(C_1$-$C_{21})$—O-alkyl]ester, $(C_1$-$C_8)$alkylphosphonate and/or $(C_6$-$C_{12})$arylphosphonate bridges, $(C_7$—$O_{12})$-a-hydroxymethyl-aryl (e.g. disclosed in PCT Publication No. WO 95/01363), wherein $(C_6$-$C_{12})$aryl, $(C_6$-$C_{20})$aryl and $(C_6$-$C_{14})$aryl are optionally substituted by halogen, alkyl, alkoxy, nitro, cyano, and where Ri and $R_2$ are, independently of each other, hydrogen, $(C_1$-$C_{18})$-alkyl, $(C_6$-$C_{20})$-aryl, $(C_6$-$C_{14})$-aryl, $(C_1$-$C_8)$-alkyl, preferably hydrogen, $(C_1$-$C_8)$-alkyl, preferably $(C_1$-$C_4)$-alkyl and/or methoxyethyl, or $R_1$ and $R_2$ form, together with the nitrogen atom carrying them, a 5 to 6-membered heterocyclic ring which can additionally contain a further heteroatom selected from the group O, S and N.

The replacement of a phosphodiester bridge located at the 3' and/or the 5' end of a nucleoside by a dephospho bridge (dephospho bridges are described, for example, in Uhlmann E. and Peyman A. in "Methods in Molecular Biology", Vol. 20, "Protocols for Oligonucleotides and Analogs", S. Agrawal, Ed., Humana Press, Totowa 1993, Chapter 16, pp. 355 ff), wherein a dephospho bridge is for example selected from the dephospho bridges formacetal, 3'-thioformacetal, methylhydroxylamine, oxime, methylenedimethyl-hydrazo, dimethylenesulfone and/or silyl groups.

The CpG oligonucleotides for use in the methods or regimen provided by the disclosure may optionally have chimeric backbones. A chimeric backbone is one that comprises more than one type of linkage. In one embodiment, the chimeric backbone can be represented by the formula: 5' Y1 N1ZN2Y2 3'. Y1 and Y2 are nucleic acid molecules having between 1 and 10 nucleotides. Y1 and Y2 each include at least one modified internucleotide linkage. Since at least 2 nucleotides of the chimeric oligonucleotides include backbone modifications these nucleic acids are an example of one type of "stabilized immunostimulatory nucleic acids".

With respect to the chimeric oligonucleotides, Y1 and Y2 are considered independent of one another. This means that each of Y1 and Y2 may or may not have different sequences and different backbone linkages from one another in the same molecule. In some embodiments, Y1 and/or Y2 have between 3 and 8 nucleotides. N1 and N2 are nucleic acid molecules having between 0 and 5 nucleotides as long as N1ZN2 has at least 6 nucleotides in total. The nucleotides of N1ZN2 have a phosphodiester backbone and do not include nucleic acids having a modified backbone. Z is an immunostimulatory nucleic acid motif, preferably selected from those recited herein.

The center nucleotides (N1ZN2) of the formula Y1 N1ZN2Y2 have phosphodiester internucleotide linkages and Y1 and Y2 have at least one, but may have more than one or even may have all modified internucleotide linkages. In preferred embodiments, Y1 and/or Y2 have at least two or between two and five modified internucleotide linkages or Y1 has five modified internucleotide linkages and Y2 has two modified internucleotide linkages. The modified internucleotide linkage, in some embodiments, is a phosphorothioate modified linkage, a phosphorodithioate linkage or a p-ethoxy modified linkage.

Examples of particular CpG oligonucleotides useful in the methods provided by the present disclosure include:

```
5' TCGTCGTTTTGTCGTTTTGTCGTT3'   (CpG 7909);

5' TCGTCGTTTTTCGGTGCTTTT3'      (CpG 24555);
and

5' TCGTCGTTTTTCGGTCGTTTT3'      (CpG 10103).
```

CpG7909, a synthetic 24mer single stranded, has been extensively investigated for the treatment of cancer as a monotherapy and in combination with chemotherapeutic agents, as well as adjuvant as an adjuvant for vaccines against cancer and infectious diseases. It was reported that a single intravenous dose of CpG 7909 was well tolerated with no clinical effects and no significant toxicity up to 1.05 mg/kg, while a single dose subcutaneous CpG 7909 had a maximum tolerated dose (MTD) of 0.45 mg/kg with dose limiting toxicity of myalgia and constitutional effects. [See Zent, Clive S, et al: Phase I clinical trial of CpG oligonucleotide 7909 (PF-03512676) in patients with previously treated chronic lymphocytic leukemia. Leukemia and Lymphoma, 53(2):211-217(7)(2012). In the regimens provided by the present disclosure, CpG7909 may be administered by injection into the muscle or any other suitable methods. It is preferred that it is administered locally in proximity to the vaccine draining lymph node, particularly by intradermal or subcutaneous administration. For use with a nucleic acid vaccine, such as a DNA vaccine, a CpG may be preferably co-formulated with the vaccine in a single formulation and administered by intramuscular injection coupled with electroporation. The effective amount of CpG7909 by intramuscular, intradermal, or subcutaneous administration is typically in the range of 10 μg/dose-10 mg/dose. In some embodiments, the effective amount of CpG7909 is in the range of 0.05 mg-14 mg/dose. In some particular embodiments, the effective amount of CpG7909 is about 0.05, 0.1, 0.2, 0.3, 0.4, 0.5, 05 1 mg/dose. Other CpG oligonucleotides, including CpG 24555 and CpG 10103, may be administered in similar manner and dose levels.

In some particular embodiments, the present disclosure provides a method of enhancing the immunogenicity or therapeutic effect of a vaccine for the treatment of a neoplastic disorder in a human, comprising administering the human (1) an effective amount of at least one ISC inhibitor and (2) an effective amount of at least one IEC enhancer, wherein the at least one ISC inhibitor is protein kinase inhibitor selected from sorafenib tosylate, sunitinib malate, axitinib, erlotinib, gefitinib, axitinib, bosutinib, temsirolismus, or nilotinib and wherein the at least one IEC enhancer is selected from a CTLA-4 inhibitor, a TLR agonist, or a CD40 agonist. In some preferred embodiments, regimen comprises administering to the human (1) an effective amount of at least one ISC inhibitor and (2) effective amount of at least one IEC enhancer, wherein the at least one ISC inhibitor is a protein kinase inhibitor selected from axitinib, sorafenib tosylate, or sunitinib malate and wherein the wherein the at least one IEC enhancer is a CTLA-4 inhibitor selected from Ipilimumab or Tremelimumab. In some further preferred embodiments, the regimen comprises administering to the human (1) an effective amount of at least one ISC inhibitor and (2) an effective amount of at least two IEC enhancers, wherein the at least one ISC inhibitor is a protein kinase inhibitor selected from sunitinib or axitinib and wherein the at least two IEC enhancers are Tremelimumab and a TLR agonist selected from CpG7909, CpG2455, or CpG10103.

In some other embodiments, the present disclosure provides a method of treating prostate cancer in a human, comprising administering to the human (1) an effective amount of a vaccine capable of eliciting an immune response against a human PAA, (2) an effective amount of at least one ISC inhibitor, and (3) an effective amount of at least one IEC enhancer, wherein the at least one ISC inhibitor is a protein kinase inhibitor selected from sorafenib tosylate, sunitinib malate, axitinib, erlotinib, gefitinib, axitinib, bosutinib, temsirolismus, or nilotinib, and wherein the at least one IEC enhancer is selected from a CTLA-4 inhibitor, a TLR agonist, or a CD40 agonist. In some preferred embodiments, the method comprises administering to the human (1) an effective amount of a vaccine capable of eliciting an immune response against a human PAA, (2) an effective amount of at least one ISC inhibitor, and (3) an effective amount of at least one IEC enhancer, wherein the at least one ISC inhibitor is a protein kinase inhibitor selected from sorafenib tosylate, sunitinib malate, or axitinib and wherein the at least one IEC enhancer is a CTLA-4 inhibitor selected from Ipilimumab or Tremelimumab.

In some further specific embodiments, the method comprises administering to the human (1) an effective amount of at least one ISC inhibitor and (2) an effective amount of at least two IEC enhancers, wherein the at least one ISC inhibitor is a protein kinase inhibitor selected from sunitinib or axitinib and wherein the at least two IEC enhancers are Tremelimumab and a TLR agonist selected from CpG7909, CpG2455, or CpG10103.

Additional Therapeutic Agents.

The vaccine-based immunotherapy regimen provided by the present disclosure may further comprise an additional therapeutic agent. A wide variety of cancer therapeutic agents may be used, including chemotherapeutic agents and hormone therapeutic agents. One of ordinary skill in the art will recognize the presence and development of other cancer therapies which can be used in VBIR provided by the present disclosure, and will not be restricted to those forms of therapy set forth herein.

The term "chemotherapeutic agent" refers to a chemical or biological substance that can cause death of cancer cells, or interfere with growth, division, repair, and/or function of cancer cells. Examples of chemotherapeutic agents include those that are disclosed in WO2006/088639, WO2006/129163, and US 20060153808, the disclosures of which are incorporated herein by reference. Examples of particular chemotherapeutic agents include: (1) alkylating agents, such as chlorambucil (LEUKERAN), cyclophosphamide (CYTOXAN), ifosfamide (IFEX), mechlorethamine hydrochloride (MUSTARGEN), thiotepa (THIOPLEX), streptozotocin (ZANOSAR), carmustine (BICNU, GLIADEL WAFER), lomustine (CEENU), and dacarbazine (DTIC-DOME); (2) alkaloids or plant vinca alkaloids, including cytotoxic antibiotics, such as doxorubicin (ADRIAMYCIN), epirubicin (ELLENCE, PHARMORUBICIN), daunorubicin (CERUBIDINE, DAUNOXOME), nemorubicin, idarubicin (IDAMYCIN PFS, ZAVEDOS), mitoxantrone (DHAD, NOVANTRONE). dactinomycin (actinomycin D, COSMEGEN), plicamycin (MITHRACIN), mitomycin (MUTAMYCIN), and bleomycin (BLENOXANE), vinorelbine tartrate (NAVELBINE)), vinblastine (VELBAN), vincristine (ONCOVIN), and vindesine (ELDISINE); (3) antimetabolites, such as capecitabine (XELODA), cytarabine (CYTOSAR-U), fludarabine (FLUDARA), gemcitabine (GEMZAR), hydroxyurea (HYDRA), methotrexate (FOLEX, MEXATE, TREXALL), nelarabine (ARRANON), trimetrexate (NEUTREXIN), and pemetrexed (ALIMTA); (4) Pyrimidine antagonists, such as 5-fluorouracil (5-FU); capecitabine (XELODA), raltitrexed (TOMUDEX), tegafur-uracil (UFTORAL), and gemcitabine (GEMZAR); (5) taxanes, such as docetaxel (TAXOTERE), paclitaxel (TAXOL); (6) platinum drugs, such as cisplatin (PLATINOL) and carboplatin (PARAPLATIN), and oxaliplatin (ELOXATIN); (7) topoisomerase inhibitors, such as irinotecan (CAMPTOSAR), topotecan (HYCAMTIN), etoposide (ETOPOPHOS, VEPESSID, TOPOSAR), and teniposide (VUMON); (8) epipodophyllotoxins (podophyllotoxin derivatives), such as etoposide (ETOPOPHOS, VEPESSID, TOPOSAR); (9) folic acid derivatives, such as leucovorin (WELLCOVORIN); (10) nitrosoureas, such as carmustine (BiCNU), lomustine (CeeNU); (11) inhibitors of receptor tyrosine kinase, including epidermal growth factor receptor (EGFR), vascular endothelial growth factor (VEGF), insulin receptor, insulin-like growth factor receptor (IGFR), hepatocyte growth factor receptor (HGFR), and platelet-derived growth factor receptor (PDGFR), such as gefitinib (IRESSA), erlotinib (TARCEVA), bortezomib (VELCADE), imatinib mesylate (GLEEVEC), genefitinib, lapatinib, sorafenib, thalidomide, sunitinib (SUTENT), axitinib, rituximab (RITUXAN, MABTHERA)Z, trastuzumab (HERCEPTIN), cetuximab (ERBITUX), bevacizumab (AVASTIN), and ranibizumab (LUCENTIS), lym-1 (ONCOLYM), antibodies to insulin-like growth factor-1 receptor (IGF-1R) that are disclosed in WO2002/053596); (12) angiogenesis inhibitors, such as bevacizumab (AVASTIN), suramin (GERMANIN), angiostatin, SU5416, thalidomide, and matrix metalloproteinase inhibitors (such as batimastat and marimastat), and those that are disclosed in WO2002055106; and (13) proteasome inhibitors, such as bortezomib (VELCADE).

The term "hormone therapeutic agent" refers to a chemical or biological substance that inhibits or eliminates the production of a hormone, or inhibits or counteracts the effect of a hormone on the growth and/or survival of cancer cells. Examples of such agents suitable for the VBIR include those disclosed in US20070117809. Examples of particular hormone therapeutic agents include tamoxifen (NOLVADEX), toremifene (Fareston), fulvestrant (FASLODEX), anastrozole (ARIMIDEX), exemestane (AROMASIN), letrozole (FEMARA), megestrol acetate (MEGACE), goserelin (ZOLADEX), leuprolide (LUPRON), abiraterone, and MDV3100.

The VBIR provided by this disclosure may also be used in combination with other therapies, including (1) surgical methods that remove all or part of the organs or glands which participate in the production of the hormone, such as the ovaries, the testicles, the adrenal gland, and the pituitary gland, and (2) radiation treatment, in which the organs or glands of the patient are subjected to radiation in an amount sufficient to inhibit or eliminate the production of the targeted hormone.

I. Examples

The following examples are provided to illustrate certain embodiments of the invention. They should not be construed to limit the scope of the invention in any way. From the above discussion and these examples, one skilled in the art can ascertain the essential characteristics of the invention, and without departing from the spirit and scope thereof, can make various changes and modifications of the invention to adapt it to various usage and conditions.

Example 1. Antigens in Cytosolic, Secreted, and Membrane-Bound Formats Derived from the Human PSMA Protein Example 1 illustrates the construction of three immunogenic PSMA polypeptides referred to an "human PSMA cytosolic antigen," "human PSMA secreted antigen," and "human PSMA membrane-bound antigen," respectively, and biological properties of these polypeptides.

1A. Design of Immunogenic PSMA Polypeptides

DNA constructs encoding immunogenic PSMA polypeptides in cytosolic, secreted, and modified formats were constructed based on the native human PSMA protein sequence and tested for their ability to induce anti-tumor effector immune responses. The structure and preparation of each of the human PSMA antigen formats are provided as follows.

1A1. Human PSMA Cytosolic Antigen.

An immunogenic PSMA polypeptide in cytosolic form was designed to retain the immunogenic polypeptide inside the cell once it is expressed. The cytoplasmic domain (amino acids 1-19) and the transmembrane domain (amino acids 20-43) of the human PSMA were removed, resulting in a cytosolic PSMA polypeptide that consists of amino acids 44-750 (extracellular domain or ECD) of the human PSMA of SEQ ID NO: 1. The optimal Kozak sequence "MAS" may be added to the N-terminus of the polypeptide for enhancing the expression.

1A2. Human PSMA Secreted Antigen.

An immunogenic PSMA polypeptide in secreted form was designed to secret the polypeptide outside of the cell once it is expressed. The secreted polypeptide is made with amino acids 44-750 (ECD) of the human PSMA of SEQ ID NO:1 and the Ig Kappa secretory element that has the amino acid sequence ETDTLLLWVLLLWVPGSTGD and a two-amino acid linker (AA) in the N-terminal in order to maximize the secretion of the PSMA antigen once it is expressed.

1A3. Human PSMA Membrane-Bound Antigen.

An immunogenic PSMA membrane-bound polypeptide was designed to stabilize the polypeptide on the cell surface. The first 14 amino acids of the human PSMA protein were removed and the resultant immunogenic polypeptide consists of amino acids 15-750 of the human PSMA protein of SEQ ID NO:1. The immunogenic polypeptide that consists of amino acids 15-750 of the native human PSMA protein of SES ID NO: 1 and share 100% sequence identity with the native human PSMA protein is also referred to as "human PSMA modified," "hPSMA modified," or "hPSMAmod" antigen in the present disclosure.

1B. Preparation of DNA Plasmids for Expressing the PSMA Antigens

DNA constructs encoding the PSMA cytosolic, PSMA secreted, and PSMA modified antigens were cloned individually into PJV7563 vector that was suitable for in vivo testing in animals (FIG. 1). Both strands of the DNA in the PJV7563 vectors were sequenced to confirm the design integrity.

A large scale plasmid DNA preparation (Qiagen/CsCl) was produced from a sequence confirmed clone. The quality of the plasmid DNA was confirmed by high 260/280 ratio, high super coiled/nicked DNA ratio, low endotoxin levels (<10 U/mg DNA) and negative bio burden.

1C. Expression of PSMA Constructs in Mammalian Cells

The expression of the PSMA cytosolic, secreted, and modified antigens was determined by FACS. Mammalian 293 cells were transfected with the PJV7563 PMED vectors encoding the various immunogenic PSMA polypeptides. Three days later, the 293 cells were stained with mouse anti-PSMA antibody, followed with a fluorescent conjugated (FITC) rat anti-mouse secondary antibody. The data below, which were reported as mean fluorescent intensity (MFI) over negative controls, confirmed that human PSMA modified antigen is expressed on the cell surface.

| Samples | Average mean fluorescent intensity |
|---|---|
| Untransfected 293 cells | 231 |
| 293 cells transfected with full length human PSMA (SEQ ID NO: 1) | 6425 |
| 293 cells transfected with human PSMA modified antigen (SEQ ID NO: 9) | 12270 |

1D. Formulations of PSMA Plasmids onto Gold Particles (for ND10/X15)

Particle Mediated Epidermal Delivery technology (PMED) is a needle-free method of administering vaccines to animals or to patients. The PMED system involves the precipitation of DNA onto microscopic gold particles that are then propelled by helium gas into the epidermis. The ND10, a single use device, uses pressurized helium from an internal cylinder to deliver gold particles and the X15, a repeater delivery device, uses an external helium tank which is connected to the X15 via high pressure hose to deliver the gold particles. Both of these devices were used in studies to deliver the PSMA DNA plasmids. The gold particle was usually 1-3 μm in diameter and the particles were formulated to contain 2 μg of PSMA plasmids per 1 mg of gold particles. (Sharpe, M. et al.: P. Protection of mice from H5N1 influenza challenge by prophylactic DNA vaccination using particle mediated epidermal delivery. Vaccine, 2007, 25(34): 6392-98: Roberts L K, et al.: Clinical safety and efficacy of a powdered Hepatitis B nucleic acid vaccine delivered to the epidermis by a commercial prototype device. Vaccine, 2005; 23(40):4867-78).

1E. Transgenic Mice Used for In Vivo Studies

Two human HLA transgenic mouse models were used to evaluate the presentation of various PSMA antigens by different HLAs and a human PSMA transgenic mouse model was used to assess the breaking of immune tolerance to human PSMA. The first HLA transgenic mouse model utilizes the HLA A2/DR1 mice (from the Pasteur Institute, Paris, France; also referred to as "Pasteur mice"). Pasteur mice are knock out for murine β-2-microglobulin and do not express functional H-2b molecules; therefore this model is believed to represent the presentation of antigen in the human HLA A2 and DR1 context (Pajot, A., M.-L. Michel, N. Faxilleau, V. Pancre, C. Auriault, D. M. Ojcius, F. A. Lemonnier, and Y.-C. Lone. A mouse model of human adaptive immune functions: HLA-A2.1-/HLA-DR1-transgenic H-2 class I-/class II-knockout mice. *Eur. J. Immunol.* 2004, 34:3060-69.). The second HLA transgenic mouse model uses mice that are knock in with human HLA A24 that is covalently linked to the human β-2-microglobulin at the H2bk locus. These mice lack murine β-2-microglobulin and do not express functional H-2b molecules. This model allows evaluation of antigen presentation in the context of human HLA A24.

1F. Immunogenicity of the Human PSMA Proteins in Cytosolic, Secreted and Modified Formats Study Design.

Eight-to-10 week-old transgenic mice were immunized using PMED method with various PSMA DNA constructs in a prime/boost/boost regimen, two weeks apart between each vaccination. Alternatively, mice were primed with adenovirus vectors encoding the PSMA antigen at $1\times10^9$ viral particles in 50 μl (PBS) by intramuscular injection. The adenovirus vector (pShuttle-CMV vector from Stratagene) was modified to contain NheI and BglII restriction sites within the multiple cloning site. The DNA encoding human PSMA modified was then restriction digested with NheI and BglII, ligated into this vector and sequence confirmed. The pShuttle human PSMA modified vector was then recombined with the pAdEasy-1 vector and virus was propagated according to the AdEasy system (Stratagene). Twenty-days later, they were boosted with PMED as described above. In each of the regimens used, antigen specific T cell response was measured 7 days after the last immunization in an interferon-gamma (IFNγ) ELISPOT assay. The ELISPOT assay is similar to the sandwich enzyme-linked immunosorbent assay (ELISA). Briefly, a capture antibody specific to IFNγ BD Bioscience, #51-2525kc) is coated onto a polyvinylidene fluoride (PVDF) membrane in a microplate overnight at 4° C. The plate is blocked with serum/protein to prevent nonspecific binding to the antibody. After blocking, effector cells (such as splenocytes isolated from PSMA immunized mice) and targets (such as PSMA peptides from peptide library, target cells pulsed with peptides or tumor cells expressing the relevant antigens) or mitogen (which will stimulate splenocytes non-specifically to produce IFNγ□ are added to the wells and incubated overnight at 37° C. in a 5% $CO_2$ incubator. Cytokine secreted by effector cells are captured by the coating antibody on the surface of the PVDF membrane. After removing the cells and culture media, 100 μl of a biotinylated polyclonal anti-mouse IFNγ antibody (0.5 mg/ml-BD Bioscience, #51-1818 kz) was added to each of the wells for detection. The spots are visualized by adding streptavidin-horseradish peroxidase (HRP, BD Bioscience, #557630) and the precipitate substrate, 3-amino-9-ethylcarbazole (AEC), to yield a red color spot. Each spot represents a single cytokine producing T cell. In general, in the studies disclosed here the ELISpot assay was set up as follows: $5\times10^5$ splenocytes from PSMA immunized mice were cultured (1) in the presence of PSMA specific peptides derived from a PSMA peptide library (see Table 16) made of 15-amino acid peptides overlapping by 11 amino acids, (2) with known HLA A2.1 restricted PSMA specific peptides, or (3) with tumor cells. To measure the recognition of endogenous antigen presentation, splenocytes were cultured with a human HLA A2 prostate cancer cells (i.e. LNCaP, available from ATCC) that naturally express PSMA or cultured with HLA A2 tumor cells transduced with adenovirus encoding and thus expressing the human PSMA modified antigen. In addition, human PSMA ECD protein was added to the ELISpot assay to measure specifically CD4 IFNγ□ producing cells. For controls where appropriate, HLA A2 restricted HER-2 specific peptide p168-175 or tumor cells not expressing PSMA or irrelevant protein such as BSA were used as a negative control in the IFNγ □ELISpot assay. Data results are given in normalized format for the number of spot forming cells (SFC) that secrete IFNγ □in $1\times10^6$ splenocytes. At least three studies were performed for each of the PSMA antigen peptides tested.

Results.

Data from the ELISpot assay with splenocytes of Pasteur mice cultured with peptides derived from a PSMA peptide library are presented in Table 1. A positive response is defined as having SFC>100. As shown in Table 1, the immunogenic PMSA polypeptides made with all three antigen formats, the human PSMA cytosolic, secreted, and modified antigens described in Example 1A above, are capable of inducing T cell responses. The human PSMA modified antigen format induced the best breadth and magnitude of T cell responses.

TABLE 1

T cell response induced by the human PSMA cytosolic, secreted, and modified antigens in Pasteur mice

| aa sequence coverage of target peptide pools from PSMA peptide | IFN-γ SFC/1 × $10^6$ splenocytes (SD) | | |
|---|---|---|---|
| library | PSMA cytosolic | PSMA modified | PSMA secreted |
| 13-35 | 1 (14) | 809 (78) | 44 (6) |
| 97-117 | 1 (1) | 96 (17) | 0 |
| 109-131 | 8 (9) | 923 (21) | 179 (24) |
| 121-243 | 21 (4) | 1329 (109) | 320 (28) |
| 145-167 | 23 (4) | 1499 (1) | 312 (14) |
| 169-191 | 497 (4) | 248 (14) | 183 (13) |
| 181-203 | 43 (21) | 70 (20) | 19 (10) |
| 205-227 | 5 (1) | 112 (0) | 9 (13) |
| 217-239 | 44 (13) | 1627 (38) | 351 (10) |
| 265-287 | 23 (4) | 527 (100) | 10 (6) |

TABLE 1-continued

T cell response induced by the human PSMA cytosolic, secreted, and modified antigens in Pasteur mice

| aa sequence coverage of target peptide pools from PSMA peptide library | IFN-γ SFC/1 × $10^6$ splenocytes (SD) | | |
|---|---|---|---|
| | PSMA cytosolic | PSMA modified | PSMA secreted |
| 277-299 | 39 (1) | 1143 (86) | 151 (4) |
| 289-311 | 27 (1) | 429 (4) | 28 (11) |
| 409-431 | 14 (9) | 281 (18) | 12 (9) |
| 421-443 | 4 (0) | 676 (45) | 48 (14) |
| 433-455 | 339 (18) | 713 (64) | 119 (21) |
| 481-503 | 22 | 288 (9) | 1 (1) |
| 577-599 | 227 (27) | 131 (16) | 33 (16) |
| 589-611 | 187 (13) | 27 (10) | 6 (9) |
| 613-635 | 418 (6) | 437 (1) | 55 (1) |
| 637-659 | 222 (31) | 49 (10) | 95 (16) |
| 649-671 | 203 (21) | 1625 (33) | 420 (11) |
| 661-683 | 102 (14) | 1633 (140) | 366 (48) |
| 697-719 | 179 (4) | 1357 (58) | 342 (6) |
| 709-731 | 40 (11) | 1162 (59) | 223 (4) |
| 721-743 | 56 (6) | 1409 (103) | 344 (23) |
| 733-750 | 50 (11) | 1512 (51) | 365 (27) |

( ) = standard deviation

Data from the ELISpot assay on T cell responses induced by various PSMA vaccine formats in Pasteur mice (which that recognized HLA A2.1 restricted PSMA peptide pulsed target cells as well as PSMA+ HLA A2.1 LNCaP tumor cells) are presented in Table 2. PC3, which is a human prostate cancer cell line that does not express PSMA, was used here as a negative control. A positive response is defined as having SFC>50. As shown in Table 2, the various PSMA constructs tested are capable of inducing T cells that recognize known HLA A2 restricted PSMA epitopes as well as PSMA protein and human prostate cancer cells LNCaP. However, the PSMA modified construct was shown to induce the best breadth and magnitude T cell response.

TABLE 2

T cell responses induced by the human PSMA cytosolic, secreted, and modified antigens in Pasteur mice that recognized HLA A2.1 restricted PSMA peptide pulsed target cells as well as PSMA+ HLA A2.1 LNCaP tumor cells.

| HLA A2.1 restricted peptides | IFN-γ SFC/1 × $10^6$ splenocytes | | |
|---|---|---|---|
| | PSMA cytosolic | PSMA modified | PSMA secreted |
| Target peptide or protein | | | |
| PSMA p663 | 1554 (4) | 1524.9 (45) | 444 (23) |
| PSMA p275 | 14 (10) | 304 (21) | 3 (1) |
| PSMA p662 | 41 (15) | 925.1 (77) | 455 (25) |
| PSMA p627 | 1 (1) | 222 (14) | 9 (8) |
| PSA p64 | 0 | 2 (4) | 1 (1) |
| Protein or tumor cells | | | |
| PSMA ECD protein | 45 (11) | 731 (16) | 13 (5) |
| LNCap | 4 (2) | 96 (12) | 5 (3) |
| PC3 | 0 | 1 (1) | 1 (1) |

( ) = standard deviation

1G. Humoral Immune Response Measured in Pasteur Mice or Nonhuman Primates

1G1. Sandwich ELISA Assay.

The standard sandwich ELISA assay was done using an automated Biotek system. The plates were coated with 25 µl of native PSMA protein at a 1.0 µg/ml in PBS overnight, the plates were washed and blocked with 35 µl/well of 5% FBS 1×PBS-T 0.05% and incubated for 1 hour at RT on a shaker at 600 RPM. The blocking media was decanted and serial dilute vaccinated mouse serum with half log dilutions in 5% FBS 1×PBS-T 0.05% starting at 1:100 or 1:500 were made and 25µ samples of the diluted serum were added to each well of the 96 well plates and incubated for 1 hour at RT on a shaker at 600 RPM. The plates were washed 3 times with 75 ul/well in 1×PBS-T 0.05% using the Biotek ELx405, and 25 µl/well of 1:30,000 diluted anti-mouse IgG HRP (AbCam cat #ab20043) secondary antibody (diluted in 1×PBS-T 0.05%) was added to each well of the 96 well plates and incubated for 1 hour at RT on a shaker at 600 RPM. Plates were washed 5× with 75 ul/well in 1×PBS-T 0.05% using the Biotek EIx405. TMB Substrate was diluted at 1:10 and 25 µl was added to each well and incubated at RT for 30 minutes. The reaction was stopped by adding 12.5 µl/well of 1M H2SO4. Plates were read using the Spectramax Plus at 450 nm wavelength. Data were reported as titers and these could be reported as first positive (average and both values above 5% FBS PBS+3 time Standard Deviation) and/or as calculated titers at OD of 0.5 or 1.0. Serum from irrelevant vaccinated mice were used as negative controls.

TABLE 3

Induction of anti-PSMA antibody response by human PSMA antigens as measured by an ELISA assay.

| Antigen format | ELISA (OD = 1) Average (+/−SD) | N | # of positive |
|---|---|---|---|
| PSMA cytosolic | 499 (0) | 4 | 0/4 |
| PSMA modified | 1067 (518) | 4 | 4/4 |
| PSMA secreted | 959 (920) | 4 | 1/4 |

Results.

Data presented in Table 3 shows that the human PSMA cytosolic antigen did not induce any anti-PSMA responses, while the human PSMA modified antigen consistently induced good anti-PSMA antibody responses in all mice.

Data presented in Table 5 shows that antibodies induced by the human PSMA antigens reacted to multiple peptide epitopes in the PSMA library. Serum from the individual mice in each group was pooled in equal amounts and tested at a 1:500 dilution in an ELISA assay. A negative control group of mice vaccinated with anti-diphtheria (CRM) toxoid was tested in parallel. Each well of the 96 well ELISA plate was coated with 0.03 µg of a single 15aa peptide derived from the PSMA peptide library. An OD value above 0.10 is considered positive.

1G2. FACS Cell Binding Assay.

Various prostate cancer cell lines were used for this assay. LNCaP (ATCC) was used as human prostate cancer cells expressing PSMA and PC3 (ATCC) was used as negative human prostate cancer cells that do not expressing PSMA. In some assays, a TRAMP-C2 cell line engineered to stably express the human native full length PSMA and the parental TRAMP-C2 cell line that does not express PSMA (negative control) were used for the cell binding assay. The cell binding assay was performed as follows: LNCaP and PC3 cells (or TRAMP-C2PSMA and TRAMP C2) were plated in separate wells at 2×$10^5$ cells/well (50 µL) in a 96 well plate. Sera from PSMA vaccinated mice, as described in if, were diluted 1:50 with FACS buffer (PBS pH 7.4, 1% FBS, 25 mM HEPES, and 1 mM EDTA). Fifty µL of diluted J591-A antibody (mouse anti-human PSMA antibody, clone J591-A from ATCC) were added to the diluted test sera or FACS buffer (unstained samples) to achieve the appropriate cell numbers per well in the staining plate. All was mixed by pipetting and then kept on ice for 20 min. The cells were washed twice with FACS buffer; each wash was by centrifugation at 1200 RPM at 5° C. for 5 minutes. Fifty μL of secondary staining solution were added containing a 1:200 dilution of PE-labeled goat anti-mouse Ig (Sigma, cat P9670-5) and 0.25 μl of Live/Dead Aqua stain (Invitrogen, cat. #L34957) to each of the cell containing wells and kept on ice for 20 min. Cells were washed twice as described earlier. Washed cell pellets were resuspended in 125 uL FACS buffer and then 75 uL 4% paraformaldehyde solution were added to each well to fix the cells. Samples were kept on ice and protected from light for at least 15 min. Samples were run on FACS Canto II. Ten thousand live cell events were recorded for each sample. Control samples for each cell type were 1) unstained cells, 2) cells with secondary antibody only, 3) Cells with J591 plus secondary antibody, and 4) cells with naïve serum plus secondary antibody. Data were reported as mean fluorescent intensity (MFI) over negative controls.

Results of FACS Cell Binding Assay.

Table 4 shows that antibodies induced by both human PSMA secreted and modified antigens are capable of binding to human PSMA positive prostate cancer cells (LNCaP) and not to PSMA negative prostate cancer cells (PC3). The PSMA modified antigen consistently induced good anti-PSMA antibody response in all mice.

TABLE 4

Binding of anti-PSMA antibodies to human prostate cancer cells as measured by FACS.

| Antigen Format | Fold over background Average (+/−SD) | N | # of positive |
|---|---|---|---|
| PSMA cytosolic | 1.40 (0.12) | 4 | 0/4 |
| PSMA modified | 6.01 (0.38) | 4 | 4/4 |
| PSMA secreted | 5.50 (4.10) | 4 | 3/4 |
| background (PC3) | 1.36 (0.04) | 4 | NA |

TABLE 5

Antibodies induced by PSMA vaccine reacted to multiple peptides in the PSMA library. Based on this result, four B cell epitopes of PSMA were identified, 1: aa 138-147, 2: aa 119-123, 3: aa 103-106, 4: aa 649-659.

| Target peptide or protein | | ELISA O.D. results: PSMA vaccinated serum | ELISA O.D. results: CRM-197 vaccinated serum |
|---|---|---|---|
| Peptides | 93 | 0.21 | 0.05 |
| from PSMA | 101 | 0.27 | 0.05 |
| library (no. | 133 | 0.58 | 0.05 |
| of first aa) | 137 | 0.89 | 0.05 |
| | 141 | 0.12 | 0.05 |
| | 645 | 0.17 | 0.05 |
| PSMA protein | | 3.87 | 0.05 |

1G3. Antibody-Dependent Cell-Mediated Cytotoxicity (ADCC) Assay

Study Design.

An Indian rhesus macaque was immunized with a nucleic acid encoding a human PSMA modified antigen delivered by adenovirus (1e11 V.P. injected intramuscularly) followed by 2 PMED immunizations (8 actuations/immunization, 4 actuations per each right and left side of the lower abdomen) with 8 and 6 week intervals respectively. The animal also received intradermal injections of 3 mg of CpG (PF-03512676) in proximity to each inguinal draining lymph node at the time of the second PMED immunization. The antibody dependent cell-mediated cytotoxicity was determined from the plasma collected from the blood before any immunizations (pre-immune plasma) and 8 days after the last PMED immunization (immune plasma).

Antibody-Dependent Cell-Mediated Cytotoxicity Assay.

Antibody-dependent cell-mediated cytotoxicity was determined using the standard chromium 51 release assay. Human prostate cancer cell lines LNCaP and PC3 were used as target cells. Freshly isolated human PBMC cells were used as effector cells. Effectors to target cells were set at 30:1. Briefly, for one labeling reaction, $1.5 \times 10^6$ target cells in 200 ul were incubated with 200 μCi $^{51}Cr$ (37° C., 5% $CO_2$ for 1 hour). Cells were washed three times and the cell concentration was adjusted to $2 \times 10^5$ cells/ml. Control monoclonal antibodies (mAb) or test plasma (1:50) were made at 2× concentration and 175 ul of each of the (depending on the size of the assay) mAb/plasma dilution were added to 175 ul of target cells. The mixture was incubated for 30 minutes at 4° C. in an Eppendorf tube. Cells were washed once to free unbound antibodies. At this time, 100 ul of freshly isolated effector cells were added to each well of the 96 well plate along with 100 ul of monoclonal antibodies or test plasma bound target cells and incubated at 37° C. and 5% $CO_2$ for 4 hrs. Samples were tested in duplicates. 100 μl 2N HCl were added to the target wells for maximum release and 100 μl of media were added to the target wells for spontaneous release. Specific lysis was calculated as follows: Percent release=(ER-SR)/(MR-SR)×100 where ER (effectors+target cells release) was experimental release, SR (target cells alone incubated with media) was spontaneous release, and MR (target cells alone incubated with 2N HCl) was maximum release. Percent specific lysis was calculated by subtracting irrelevant target (PC3) release from antigen specific target (LNCaP) release.

TABLE 6

Antibody dependent cytotoxicity activity measured in plasma from human PSMA modified vaccinated animal.

| Targets | Percent specific lysis at E:T of 30:1 (based on type of antibodies and targets used in an ADCC assay): Herceptin | Rituxan | Pre-immune plasma (naive) | Post-immune plasma | None |
|---|---|---|---|---|---|
| LNCaP | 56.14 | 8.99 | 0 | 49.9 | 0 |
| PC3 | 8.04 | 0 | 0 | 0 | 0 |

Results.

The data from the antibody dependent cytotoxicity assay are presented in Table 6. LNCaP, a human prostate PSMA+ cancer cell line coated with immune plasma derived from the hPSMA immunized animal, was lysed by effector cells while PC3, a human prostate PSMA-cancer cell line coated with the same immune serum, was not lysed by effector cells. Similarly, LNCaP coated with pre-immune plasma was not lysed by effector cells. Herceptin, a monoclonal antibody against HER-2 was used as a positive control since LNCaP cells are known to express HER-2 (Li, Cozzi et al. 2004). Rituxan, a monoclonal against B cell antigen (CD20) was used as a negative control antibody since LNCaP cells do not express CD20. Both monoclonal antibodies are reported to have ADCC activities (Dall'Ozzo, Tartas et al. 2004; Collins, O'Donovan et al. 2011).

Example 2. Construction of PSMA Shuffled Antigens

This example illustrates the construction and certain biological properties of various immunogenic PSMA polypeptides that are variants of the human PSMA modified antigen (SEQ ID NO:9) as described in Example 1.

2A. Design of PSMA Shuffled Antigens

Various immunogenic PSMA polypeptides that are variants of the human PSMA modified antigen (SEQ ID NO:9) as described in Example 1 were designed. These variants were created by introducing mutations selected from orthologs of the human PSMA into the human PSMA modified antigen sequence. These variants are referred to, interchangeably, as "PSMA shuffled antigens" or "shuffled PSMA modified antigens" in the disclosure. The principle and procedure used in creating these variants are provided below.

A computational algorithm was written to select point mutations for the shuffled variant. First, a multiple sequence alignment of PSMA and 12 orthologs (Appendix 2a) was assembled using NCBI's PSI-BLAST. The output from PSI-BLAST included propensities for each residue at each PSMA position among the orthologs. The perl script then used these propensities to select point mutations as follows:

1) Among all positions, the most commonly observed residue is selected that does not match the identity in the native human PSMA.

2) Verify that this mutation position does not overlap with identified Class I or II human PSMA epitopes to ensure that the point mutation is not within a conserved T cell epitope as defined herein above (Table 19).

3) Calculate similarity of mutation to the human residue via the BLOSUM62 matrix to verify that the BLOSUM62 similarity score for the residue substitution is within the range of 0-1 (inclusive).

This iterative procedure is followed until a certain percent sequence identity (below 100) is reached with respect to the human PSMA.

To serve as the input to this algorithm, the PSMA orthologs were assembled to construct a position-specific probability matrix using PSI-BLAST from NCBI. Additionally, the identified epitope regions of PSMA were listed in a file which was also provided to the shuffle algorithm. The non-shuffling regions were also extended to the cytosolic and transmembrane regions of the protein to avoid membrane-bound functionality problems.

The orthologous PSMA protein sequences, BLOSUM62 matrix, and PSI-BLAST program were downloaded from the NCBI site.

The shuffling script was then run using these input data and produced a variant of human PSMA with 94% sequence identity with the original human PSMA. Additionally, three mutations to improve HLA-A2 binding were introduced based on their performance in the Epitoptimizer algorithm (Houghton, Engelhorn et al. 2007). These mutations are M664L (epitope: 663-671), 1676V (epitope: 668-676), and N76L (epitope: 75-83). The resultant antigen is referred to as "shuffled PSMA modified antigen 1," "shuffled PSMA modified 1," or "PSMA shuffled antigen 1".

Results based on epitopes with consensus rank <1% and IC50 by neural Network (single best method)<500 showed that predicted epitopes from HLA A2.1, HLA A3, HLA All, HLA A24, and HLA B7 were highly conserved in this shuffled antigen. Two additional variants of the human PSMA modified antigen described in Example 1 were designed 'with higher sequence identities and a more restrictive BLOSUM score cutoff of 1 to remove all non-conservative substitutions. These two variants are also referred to as "shuffled PSMA modified antigen 2" and "shuffled PSMA modified antigen 3," respectively. Percent identities of shuffled PSMA modified antigens 1-3 with respect to the human PSMA modified construct (e.g., amino acids 15-750 of the human PSMA) are approximately 93.6%, 94.9%, and 96.4%, respectively.

The shuffled PSMA modified antigen 1 has the amino acid sequence of SEQ ID NO:3 and has the following mutations relative to the human PSMA modified antigen: N47S, T53S, K55Q, M58V, L65M, N76L, S98A, Q99E, K122E, N132D, V1541, 1157V, F161Y, D191E, M192L, V201L, V2251, 1258V, G282E, 1283L, R320K, L3621, S380A, E408K, L4171, H475Y, K482Q, M509V, S513N, E542K, M583L, N589D, R598Q, S613N, 1614L, S615A, Q620E, M622L, S647N, E648Q, S656N, 1659L, V660L, L661V, M664L, 1676V The shuffled PSMA modified antigen 2 has the amino acid sequence of SEQ ID NO:5 and has the following mutations relative to the human PSMA modified antigen: Mutations: N47S, K55Q, M58V, Q91E, S98A, A111S, K122E, N132D, V1541, 1157V, F161Y, V201L, V2251, 1258V, S312A, R320K, K324Q, R363K, S380A, E408K, H475Y, K482Q, Y494F, E495D, K499E, M509L, N540D, E542K, N544S, M5831, 1591V, R598Q, R605K, S613N, S647N, E648Q, S656N, V660L The shuffled PSMA modified antigen 3 has the amino acid sequence of SEQ ID NO:7 and has the following mutations relative to the human PSMA modified antigen: Mutations: T339A, V342L, M344L, T349N, N350T, E351K, S401T, E408K, M470L, Y471H, H475Y, F506L, M509L, A531S, N540D, E542K, N544S, G548S, V5551, E563V, V603A, R605K, K606N, Y607H, D609E, K610N, 1611L 2B. Immune Responses Measured Post Vaccination in Pasteur Mice Study Design.

Eight- to 10-week old Pasteur mice were immunized using PMED method with the various plasmid DNAs expressing shuffled PSMA modified antigens in a prime/boost/boost regimen, two weeks apart between each vaccination as described in Example 1F. Antigen specific T and B cell responses were measured 7 days after the last immunization in an interferon-gamma (IFNγ) ELISPOT assay and sandwich ELISA respectively.

TABLE 7

T cell responses induced by various shuffled PSMA modified antigens to peptide pools in PSMA peptide library

| Amino acid | IFN-γ SFC/1 × $10^6$ splenocytes (SD) | | | |
|---|---|---|---|---|
| sequence coverage of target peptide pools from PSMA peptide library | Human PSMA modified antigen | Shuffled PSMA modified antigen1 | Shuffled PSMA modified antigen 2 | Shuffled PSMA modified antigen 3 |
| 13-35 | 608 (31) | 135 (4) | 539 (33) | 339 (16) |
| 109-131 | 132 (14) | 97 (21) | 49 (13) | 360 (40) |
| 121-243 | 275 (7) | 146 (17) | 104 (17) | 542 (119) |
| 145-167 | 218 (6) | 158 (8) | 98 (8) | 505 (16) |
| 157-179 | 212 (14) | 293 (24) | 800 (0)* | 800 (0)* |
| 169-191 | 50 (11) | 52 (14) | 814 (23) | 804 (65) |
| 181-203 | 415 (33) | 8 (0) | 243 (18) | 103 (1) |
| 205-227 | 125 (7) | 1 (1) | 17 (7) | 7 (4) |
| 217-239 | 883 (47) | 302 (0) | 467 (52) | 538 (14) |
| 229-251 | 565 (24) | 188 (23) | 150 (17) | 460 (122) |
| 265-287 | 418 (8) | 2 (0) | 154 (25) | 168 (23) |
| 277-299 | 908 (79) | 132 (3) | 574 (25) | 670 (74) |
| 289-311 | 417 (27) | 20 (8) | 260 (3) | 374 (51) |
| 409-431 | 377 (7) | 61 (10) | 38 (3) | 48 (11) |
| 421-443 | 720 (34) | 110 (9) | 720 (17) | 38 (17) |

TABLE 7-continued

T cell responses induced by various shuffled PSMA modified antigens to peptide pools in PSMA peptide library

| Amino acid sequence coverage of target peptide pools from PSMA peptide library | IFN-γ SFC/1 × $10^6$ splenocytes (SD) Human PSMA modified antigen | Shuffled PSMA modified antigen1 | Shuffled PSMA modified antigen 2 | Shuffled PSMA modified antigen 3 |
|---|---|---|---|---|
| 433-455 | 974 (51) | 211 (16) | 800 (0)* | 771 (52) |
| 481-503 | 400 (59) | 0 (0) | 116 (6) | 100 (34) |
| 589-611 | 60 (14) | 245 (30) | 679 (35) | 364 (11) |
| 601-623 | 70 (9) | 79 (13) | 344 (20) | 27 (1) |
| 613-635 | 629 (41) | 102 (11) | 772 (93) | 634 (9) |
| 637-659 | 226 (17) | 292 (0) | 539 (16) | 420 (198) |
| 649-671 | 530 (74) | 319 (16) | 614 (20) | 644 (65) |
| 661-683 | 507 (52) | 248 (9) | 330 (3) | 661 (16) |

Results.

ELISpot data presented in Table 7 demonstrates that overall the shuffled PSMA modified antigens are capable of inducing T cell responses in breadth and magnitude very similar to the human PSMA modified antigen. SFC>100 is considered positive. The "*" symbol represents too numerous to accurately count.

TABLE 8

T cell responses induced by shuffled PSMA modified antigens to HLA A2 targets and PSMA protein.

| IFNγ ELISPOT targetstargets | IFN-γ SFC/1 × $10^6$ splenocytes (SD) Human PSMA modified antigen | Shuffled PSMA modified antigen 1 | Shuffled PSMA modified antigen 2 | Shuffled PSMA modified antigen 3 |
|---|---|---|---|---|
| PSMA p168 | 261 (21) | 337 (16) | 800+ (0) | 800+ (0) |
| PSMA p275 | 540 (66) | 2 (2) | 181 (17) | 134 (17) |
| PSMA p663 | 441 (46) | 152 (10) | 219 (6) | 600 (48) |
| HER-2 p106 | 1 (1) | 1 (1) | 1 (1) | 1 (1) |
| PSMA ECD protein | 839 (70) | 165 (31) | 569 (44) | 319 (6) |
| BSA protein | 1 (1) | 1 (1) | 1 (1) | 2 (0) |
| LNCaP | 229 (45) | 40 (3) | 137 (23) | 45 (6) |
| MeWo | 3 (1) | 1 (1) | 2 (2) | 1 (1) |
| MeWo-Ad-hPSMA | 365 (33) | 31 (10) | 341 (46) | 415 (128) |

As shown in Table 8, all the shuffled PSMA antigens are capable of inducing T cells that recognized known HLA A2 restricted PSMA epitopes as well as human HLA A2 tumor cells transduced with adenovirus bearing the PSMA transgene to express PSMA. The tumor cells that did not express PSMA served as negative controls and were not recognized. SFC>50 is considered positive.

TABLE 9

T cell responses induced by shuffled PSMA modified antigens to specific to CD4 T cells.

| aa sequence coverage of target peptide pools from PSMA peptide library | IFN-γ SFC/1 × $10^6$ CD8 depleted splenocytes (SD) Human PSMA modified antigen | Shuffled PSMA modified antigen 1 | Shuffled PSMA modified antigen 2 | Shuffled PSMA modified antigen 3 |
|---|---|---|---|---|
| 17-31 | 396 (51) | 49 (33) | 294 (3) | 209 (13) |
| 281-295 | 528 (6) | 51 (1) | 592 (9) | 461 (24) |
| 285-299 | 512 (34) | 55 (18) | 529 (38) | 471 (38) |

TABLE 9-continued

T cell responses induced by shuffled PSMA modified antigens to specific to CD4 T cells.

| aa sequence coverage of target peptide pools from PSMA peptide library | IFN-γ SFC/1 × $10^6$ CD8 depleted splenocytes (SD) Human PSMA modified antigen | Shuffled PSMA modified antigen 1 | Shuffled PSMA modified antigen 2 | Shuffled PSMA modified antigen 3 |
|---|---|---|---|---|
| 429-443 | 552 (51) | 51 (1) | 524 (17) | 0 |
| 581-595 | 11 (1) | 0 | 199 (24) | 0 |

ELISpot data shown in Table 9 were obtained with splenocytes that were depleted of CD8; therefore the data represents T cell responses to specific to CD4 T cells. The data show that the CD4 response elicited by shuffled PSMA modified antigen 2 is very similar to that induced by the human PSMA modified antigen. SFC>50 is considered positive.

TABLE 10

Induction of anti-PSMA antibody response as measured by an ELISA assay

| Antigen | ELISA (OD = 0.5) | # of positive |
|---|---|---|
| Human PSMA modified antigen | 1159 (802) | 7/7 |
| Shuffled PSMA modified antigen 1 | 899 (1016) | 4/7 |
| Shuffled PSMA modified antigen 2 | 4898 (3636) | 6/6 |
| Shuffled PSMA modified antigen 3 | 1482 (3092) | 1/5 |

Data in Table 10 demonstrates that all the shuffled PSMA modified antigens are capable of inducing anti-human PSMA antibody responses. Shuffled PSMA modified antigen 2 and the human PSMA modified antigen induced consistent antibody responses in all mice.

TABLE 11

T cell responses in HLA A24 mice induced by the human PSMA modified antigen and shuffled PSMA modified antigen 2.

| Amino acid sequence coverage of target peptide pools from PSMA peptide library | IFN-γ SFC/1 × $10^6$ splenocytes (SD) Human PSMA modified antigen | Shuffled PSMA modified antigen 2 |
|---|---|---|
| 217-231 | 280 (10) | 271 (7) |
| 233-247 | 219 (2) | 0 |
| 237-251 | 197 (1) | 228 (1) |
| 249-263 | 203 (1) | 28 (1) |
| 273-287 | 57 (2) | 323 (3) |
| 277-291 | 194 (24) | 337 (18) |
| 293-307 | 147 (6) | 379 (11) |
| 309-323 | 17 (1) | 441 (14) |
| 401-415 | 256 (1) | 292 (3) |
| 429-443 | 255 (7) | 0 |
| 433-447 | 59 (1) | 179 (6) |
| 481-495 | 167 (11) | 475 (21) |
| 557-571 | 194 (14) | 297 (1) |
| 601-615 | 500 (35) | 166 (10) |
| 605-619 | 500 (28) | 143 (7) |
| 613-627 | 218 (4) | 0 |
| 697-711 | 0 | 141 (8) |
| 729-743 | 0 | 140 (1) |
| 733-747 | 0 | 271 (3) |
| 737-750 | 0 | 401 (8) |

ELISpot data in Table 11 demonstrates that overall the T cell response induced by shuffled PSMA modified antigen 2 in HLA A24 mice is very similar in breadth and magnitude to the human PSMA modified antigen. SFC>100 is considered positive.

2C. Breaking of Immune Tolerance to Human PSMA by Shuffled PSMA Modified Antigens Study Design.

The human PSMA transgenic mouse model uses mice that were made using the minimal rat probasin promoter driving the expression of PSMA specifically in the prostate gland (Zhang, Thomas et al. 2000) Endocrinology 141(12): 4698-4710. These mice were made in the C57BL/6 background. RT-PCR and immune histochemistry staining data confirmed the expression of PSMA in the ventral and dorsolateral roots of the prostate gland in these PSMA transgenic mice. The endogenous expression of human PSMA protein in these mice is expected to generate immune tolerance.

Results.

As shown in Table 12, only 20% of the PSMA transgenic mice were able to mount a T cell response to human PSMA using the human PSMA modified antigen. However, 67% of the PSMA transgenic mice were able to mount a PSMA specific T cell response using the shuffled PSMA modified antigen 2. The data suggests that the inclusion of non-self amino acid sequences in the shuffled PSMA modified antigen 2 improved the breaking tolerance to the self human PSMA antigen. SFC>50 is considered positive.

TABLE 12

T cell responses in human PSMA transgenic mice to known PSMA epitope
(PADYFAPGVKSYPDG; Durso RJ, Clin Cancer Res. 2007 Jul 1;13(13):3999-400).

| Antigen | IFN-γ SFC/1 × 10⁶ splenocytes (SD) | | | | | | | | | | # of positive |
|---|---|---|---|---|---|---|---|---|---|---|---|
| Human PSMA modified antigen | 7 (3) | 126 (20) | 1 (2) | 3 (1) | 10 (5) | 22 (5) | 30 (3) | 12 (0) | 7 (2) | 404 (4) | 2/10 |
| Shuffled PSMA modified antigen 2 | 474 (52) | 104 (18) | 7 (3) | 111 (8) | 12 (2) | 21 (2) | 139 (12) | 246 (9) | 226 (11) | NA | 6/9 |

Example 3. Design of Various Immunogenic PSA Polypeptides

Example 3 illustrates the construction and certain biological properties of immunogenic PSA polypeptides in cytosolic, secreted, and membrane-bound forms.

3A. Construction of Various PSA Antigen Forms

Similar to what was described in Example 1 for the three different immunogenic PSMA polypeptide forms (e.g., the cytosolic, membrane-bound, and secreted forms), immunogenic PSA polypeptides in the three forms were also designed based on the human PSA sequence. An immunogenic PSA polypeptide in cytosolic form, which consists of amino acids 25-261 of the native human PSA, is constructed by deleting the secretory signal and the pro domain (amino acids 1-24). The amino acid sequence of this cytosolic immunogenic PSA polypeptide is provided in SEQ ID NO: 17. The secreted form of the PSA polypeptide is the native full length human PSA (amino acids 1-261). An immunogenic PSA polypeptide in membrane-bound form is constructed by linking the immunogenic PSA polypeptide cytosolic form (amino acids 25-261 of the native human PSA) to the human PSMA transmembrane domain (amino acids 15-54 of the human PSMA).

3B. Immune responses in Pasteur and HLA A24 mice

Study Design.

Eight to 10 week old HLA A2 Pasteur mice or HLA A24 mice were immunized with DNA expressing the various PSA antigens using PMED provided in Example 3A in a prime/boost/boost regimen with two week intervals between each vaccination as described in Example 1. The antigen specific T and B cell responses were measured 7 days after the last immunization in an interferon-gamma (IFNγ) ELISPOT assay and sandwich ELISA.

TABLE 13

Induction of T cell responses in Pasteur mice and HLA A24 mice vaccinated with PSA polypeptides

| Amino acid sequence coverage of target peptide pools from PSA peptide library | IFN-γ SFC/1 × 10⁶ splenocytes (SD) | | |
|---|---|---|---|
| | PSA cytosolic | PSA membrane-bound | PSA secreted |
| T cell response detected in HLA A2 Pasteur mice | | | |
| 25-47 | 12 (0) | 134 (6) | 27 (1) |
| 49-71 | 150 (0) | 23 (1) | 151 (10) |
| 61-83 | 904 (17) | 27 (7) | 452 (14) |

TABLE 13-continued

Induction of T cell responses in Pasteur mice and HLA A24 mice vaccinated with PSA polypeptides

| Amino acid sequence coverage of target peptide pools from PSA peptide library | IFN-γ SFC/1 × 10⁶ splenocytes (SD) | | |
|---|---|---|---|
| | PSA cytosolic | PSA membrane-bound | PSA secreted |
| 73-95 | 128 (25) | 8 (6) | 78 (14) |
| 85-107 | 17 (7) | 205 (18) | 11 (1) |
| 97-117 | 26 (3) | 378 (25) | 13 (1) |
| 217-239 | 16 (8) | 234 (8) | 6 (6) |
| 229-251 | 96 (34) | 844 (6) | 35 (12) |
| T cell response detected in HLA A24 mice | | | |
| 145-167 | 357 (2) | Not determined | Not determined |

Results.

Table 13 shows ELISpot data derived from splenocytes isolated from HLA A2 Pasteur mice or HLA A24 mice cultured with peptides derived from the PSA peptide library. T cell responses can be detected in both HLA A2 and HLA A24 mice. SFC>100 is considered positive.

TABLE 14

The induction of T cell responses by PSA antigens in Pasteur mice to PSA+ HLA A2.1+ SKmel5 human cancer cells

| HLA A2.1+ human cancer cells or protein | IFN-γ SFC/1 × $10^6$ splenocytes (SD) PSA cytosolic | PSA membrane-bound | PSA secreted |
|---|---|---|---|
| SKmel5-Ad-eGFP | 7.7 (9.6) | 1.2 (1.4) | 2.9 (2.7) |
| SKmel5-Ad-PSA | 112.0 (169.3) | 546.1 (379.6) | 18.7 (18.5) |
| PSA protein | 108.8 (161.0) | 536.9 (380.9) | 20.6 (21) |

ELISpot data shown in table 14 indicates that immunogenic PSA polypeptides in both cytosolic and membrane-bound forms are capable of inducing T cells that recognize human tumor cells transduced with adenovirus to express the cytosolic PSA antigen (SKmel5-Ad-PSA) but not cells transduced with adenovirus to express eGFP (SKmel5-Ad-eGFP). These two antigens also elicited response to PSA protein. The PSA secreted antigen failed to induce T cells to both SKmel5-Ad-PSA or PSA protein. SFC>50 is considered positive.

TABLE 15

The induction of anti-PSA antibody response as measured by a sandwich ELISA assay

| Antigen Forms | ELISA (OD = 1.0) Average (SD) | # of positive |
|---|---|---|
| PSA cytosolic | 99 (0) | 0/6 |
| PSA membrane-bound | 4838 (835) | 6/6 |
| PSA secreted | 1151 2410) | 2/6 |

Data in Table 15 demonstrates that immunogenic PSA polypeptides in both secreted and membrane-bound forms are capable of inducing anti-PSA antibody responses.

TABLE 16

Human PSMA Peptide Library peptide pools and corresponding amino acid sequences

| PSMA peptide pool (aa no.) | aa sequences of individual peptides |
|---|---|
| 1-23 | MWNLLHETDSAVATA<br>LHETDSAVATARRPR<br>DSAVATARRPRWLCA |
| 13-35 | ATARRPRWLCAGALV<br>RPRWLCAGALVLAGG<br>LCAGALVLAGGFFLL |
| 25-47 | ALVLAGGFFLLGFLF<br>AGGFFLLGFLFGWFI<br>FLLGFLFGWFIKSSN |
| 37-59 | FLFGWFIKSSNEATN<br>WFIKSSNEATNITPK<br>SSNEATNITPKHNMK |
| 49-71 | ATNITPKHNMKAFLD<br>TPKHNMKAFLDELKA<br>NMKAFLDELKAENIK |
| 61-83 | FLDELKAENIKKFLY<br>LKAENIKKFLYNFTQ<br>NIKKFLYNFTQIPHL |
| 73-95 | FLYNFTQIPHLAGTE<br>FTQIPHLAGTEQNFQ<br>PHLAGTEQNFQLAKQ |

TABLE 16-continued

Human PSMA Peptide Library peptide pools and corresponding amino acid sequences

| PSMA peptide pool (aa no.) | aa sequences of individual peptides |
|---|---|
| 85-107 | GTEQNFQLAKQIQSQ<br>NFQLAKQIQSQWKEF<br>AKQIQSQWKEFGLDS |
| 97-117 | QSQWKEFGLDSVELA<br>KEFGLDSVELAHYDV<br>LDSVELAHYDVLLSY |
| 109-131 | ELAHYDVLLSYPNKT<br>YDVLLSYPNKTHPNY<br>LSYPNKTHPNYISII |
| 121-243 | NKTHPNYISIINEDG<br>PNYISIINEDGNEIF<br>SIINEDGNEIFNTSL |
| 133-155 | EDGNEIFNTSLFEPP<br>EIFNTSLFEPPPPGY<br>TSLFEPPPPGYENVS |
| 145-167 | EPPPPGYENVSDIVP<br>PGYENVSDIVPPFSA<br>NVSDIVPPFSAFSPQ |
| 157-179 | IVPPFSAFSPQGMPE<br>FSAFSPQGMPEGDLV<br>SPQGMPEGDLVYVNY |
| 169-191 | MPEGDLVYVNYARTE<br>DLVYVNYARTEDFFK<br>VNYARTEDFFKLERD |
| 181-203 | RTEDFFKLERDMKIN<br>FFKLERDMKINCSGK<br>ERDMKINCSGKIVIA |
| 193-215 | KINCSGKIVIARYGK<br>SGKIVIARYGKVFRG<br>VIARYGKVFRGNKVK |
| 205-227 | YGKVFRGNKVKNAQL<br>FRGNKVKNAQLAGAK<br>KVKNAQLAGAKGVIL |
| 217-239 | AQLAGAKGVILYSDP<br>GAKGVILYSDPADYF<br>VILYSDPADYFAPGV |
| 229-251 | SDPADYFAPGVKSYP<br>DYFAPGVKSYPDGWN<br>PGVKSYPDGWNLPGG |
| 241-263 | SYPDGWNLPGGGVQR<br>GWNLPGGGVQRGNIL<br>PGGGVQRGNILNLNG |
| 253-275 | VQRGNILNLNGAGDP<br>NILNLNGAGDPLTPG<br>LNGAGDPLTPGYPAN |
| 265-287 | GDPLTPGYPANEYAY<br>TPGYPANEYAYRRGI<br>PANEYAYRRGIAEAV |
| 277-299 | YAYRRGIAEAVGLPS<br>RGIAEAVGLPSIPVH<br>EAVGLPSIPVHPIGY |
| 289-311 | LPSIPVHPIGYYDAQ<br>PVHPIGYYDAQKLLE<br>IGYYDAQKLLEKMGG |

TABLE 16-continued

| Human PSMA Peptide Library peptide pools and corresponding amino acid sequences | |
|---|---|
| PSMA peptide pool (aa no.) | aa sequences of individual peptides |
| 301-323 | DAQKLLEKMGGSAPP<br>LLEKMGGSAPPDSSW<br>MGGSAPPDSSWRGSL |
| 313-335 | APPDSSWRGSLKVPY<br>SSWRGSLKVPYNVGP<br>GSLKVPYNVGPGFTG |
| 325-347 | VPYNVGPGFTGNFST<br>VGPGFTGNFSTQKVK<br>FTGNFSTQKVKMHIH |
| 337-359 | FSTQKVKMHIHSTNE<br>KVKMHIHSTNEVTRI<br>HIHSTNEVTRIYNVI |
| 349-371 | TNEVTRIYNVIGTLR<br>TRIYNVIGTLRGAVE<br>NVIGTLRGAVEPDRY |
| 361-383 | TLRGAVEPDRYVILG<br>AVEPDRYVILGGHRD<br>DRYVILGGHRDSWVF |
| 373-395 | ILGGHRDSWVFGGID<br>HRDSWVFGGIDPQSG<br>WVFGGIDPQSGAAVV |
| 385-407 | GIDPQSGAAVVHEIV<br>QSGAAVVHEIVRSFG<br>AVVHEIVRSFGTLKK |
| 397-419 | EIVRSFGTLKKEGWR<br>SFGTLKKEGWRPRRT<br>LKKEGWRPRRTILFA |
| 409-431 | GWRPRRTILFASWDA<br>RRTILFASWDAEEFG<br>LFASWDAEEFGLLGS |
| 421-443 | WDAEEFGLLGSTEWA<br>EFGLLGSTEWAEENS<br>LGSTEWAEENSRLLQ |
| 433-455 | EWAEENSRLLQERGV<br>ENSRLLQERGVAYIN<br>LLQERGVAYINADSS |
| 445-467 | RGVAYINADSSIEGN<br>YINADSSIEGNYTLR<br>DSSIEGNYTLRVDCT |
| 457-479 | EGNYTLRVDCTPLMY<br>TLRVDCTPLMYSLVH<br>DCTPLMYSLVHNLTK |
| 469-491 | LMYSLVHNLTKELKS<br>LVHNLTKELKSPDEG<br>LTKELKSPDEGFEGK |
| 481-503 | LKSPDEGFEGKSLYE<br>DEGFEGKSLYESWTK<br>EGKSLYESWTKKSPS |
| 493-515 | LYESWTKKSPSPEFS<br>WTKKSPSPEFSGMPR<br>SPSPEFSGMPRISKL |
| 505-527 | EFSGMPRISKLGSGN<br>MPRISKLGSGNDFEV<br>SKLGSGNDFEVFFQR |

TABLE 16-continued

| Human PSMA Peptide Library peptide pools and corresponding amino acid sequences | |
|---|---|
| PSMA peptide pool (aa no.) | aa sequences of individual peptides |
| 517-539 | SGNDFEVFFQRLGIA<br>FEVFFQRLGIASGRA<br>FQRLGIASGRARYTK |
| 529-551 | GIASGRARYTKNWET<br>GRARYTKNWETNKFS<br>YTKNWETNKFSGYPL |
| 541-563 | WETNKFSGYPLYHSV<br>KFSGYPLYHSVYETY<br>YPLYHSVYETYELVE |
| 553-575 | HSVYETYELVEKFYD<br>ETYELVEKFYDPMFK<br>LVEKFYDPMFKYHLT |
| 565-587 | FYDPMFKYHLTVAQV<br>MFKYHLTVAQVRGGM<br>HLTVAQVRGGMVFEL |
| 577-599 | AQVRGGMVFELANSI<br>GGMVFELANSIVLPF<br>FELANSIVLPFDCRD |
| 589-611 | NSIVLPFDCRDYAVV<br>LPFDCRDYAVVLRKY<br>CRDYAVVLRKYADKI |
| 601-623 | AVVLRKYADKIYSIS<br>RKYADKIYSISMKHP<br>DKIYSISMKHPQEMK |
| 613-635 | SISMKHPQEMKTYSV<br>KHPQEMKTYSVSFDS<br>EMKTYSVSFDSLFSA |
| 625-647 | YSVSFDSLFSAVKNF<br>FDSLFSAVKNFTEIA<br>FSAVKNFTEIASKFS |
| 637-659 | KNFTEIASKFSERLQ<br>EIASKFSERLQDFDK<br>KFSERLQDFDKSNPI |
| 649-671 | RLQDFDKSNPIVLRM<br>FDKSNPIVLRMMNDQ<br>NPIVLRMMNDQLMFL |
| 661-683 | LRMMNDQLMFLERAF<br>NDQLMFLERAFIDPL<br>MFLERAFIDPLGLPD |
| 673-695 | RAFIDPLGLPDRPFY<br>DPLGLPDRPFYRHVI<br>LPDRPFYRHVIYAPS |
| 685-707 | PFYRHVIYAPSSHNK<br>HVIYAPSSHNKYAGE<br>APSSHNKYAGESFPG |
| 697-719 | HNKYAGESFPGIYDA<br>AGESFPGIYDALFDI<br>FPGIYDALFDIESKV |
| 709-731 | YDALFDIESKVDPSK<br>FDIESKVDPSKAWGE<br>SKVDPSKAWGEVKRQ |
| 721-743 | PSKAWGEVKRQIYVA<br>WGEVKRQIYVAAFTV<br>KRQIYVAAFTVQAAA |

TABLE 16-continued

| Human PSMA Peptide Library peptide pools and corresponding amino acid sequences | |
|---|---|
| PSMA peptide pool (aa no.) | aa sequences of individual peptides |
| 733-750 | YVAAFTVQAAAETLS<br>FTVQAAAETLSEVA |

TABLE 17

| Human PSA Peptide Library | |
|---|---|
| PSA peptide pool (aa no.) | aa sequences of individual peptides |
| 1-23 | MWVPVVFLTLSVTWI<br>VVFLTLSVTWIGAAP<br>TLSVTWIGAAPLILS |
| 13-35 | TWIGAAPLILSRIVG<br>AAPLILSRIVGGWEC<br>ILSRIVGGWECEKHS |
| 25-47 | IVGGWECEKHSQPWQ<br>WECEKHSQPWQVLVA<br>KHSQPWQVLVASRGR |
| 37-59 | PWQVLVASRGRAVCG<br>LVASRGRAVCGGVLV<br>RGRAVCGGVLVHPQQ |
| 49-71 | VCGGVLVHPQWVLTA<br>VLVHPQWVLTAAHCI<br>PQWVLTAAHCIRNKS |
| 61-83 | LTAAHCIRNKSVILL<br>HCIRNKSVILLGRHS<br>NKSVILLGRHSLFHP |
| 73-95 | ILLGRHSLFHPEDTG<br>RHSLFHPEDTGQVFQ<br>FHPEDTGQVFQVSHS |
| 85-107 | DTGQVFQVSHSFPHP<br>VFQVSHSFPHPLYDM<br>SHSFPHPLYDMSLLK |
| 97-117 | PHPLYDMSLLKNRFL<br>YDMSLLKNRFLRPGD<br>LLKNRFLRPGDDSSH |
| 109-131 | RFLRPGDDSSHDLML<br>PGDDSSHDLMLLRLS<br>SSHDLMLLRLSEPAE |
| 121-243 | LMLLRLSEPAELTDA<br>RLSEPAELTDAVKVM<br>PAELTDAVKVMDLPT |
| 133-155 | TDAVKVMDLPTQEPA<br>KVMDLPTQEPALGTT<br>LPTQEPALGTTCYAS |
| 145-167 | EPALGTTCYASGWGS<br>GTTCYASGWGSIEPE<br>YASGWGSIEPEEFLT |
| 157-179 | WGSIEPEEFLTPKKL<br>EPEEFLTPKKLQCVD<br>FLTPKKLQCVDLHVI |
| 169-191 | KKLQCVDLHVISNDV<br>CVDLHVISNDVCAQV<br>HVISNDVCAQVHPQK |

TABLE 17-continued

| Human PSA Peptide Library | |
|---|---|
| PSA peptide pool (aa no.) | aa sequences of individual peptides |
| 181-203 | NDVCAQVHPQKVTKF<br>AQVHPQKVTKFMLCA<br>PQKVTKFMLCAGRWT |
| 193-215 | TKFMLCAGRWTGGKS<br>LCAGRWTGGKSTCSG<br>RWTGGKSTCSGDSGG |
| 205-227 | GKSTCSGDSGGPLVC<br>CSGDSGGPLVCNGVL<br>SGGPLVCNGVLQGIT |
| 217-239 | LVCNGVLQGITSWGS<br>GVLQGITSWGSEPCA<br>GITSWGSEPCALPER |
| 229-251 | WGSEPCALPERPSLY<br>PCALPERPSLYTKVV<br>PERPSLYTKVVHYRK |
| 241-263 | SLYTKVVHYRKWIKD<br>KVVHYRKWIKDTIVA<br>YRKWIKDTIVANP |

TABLE 18

| PSMA Orthologs | | |
|---|---|---|
| PSMA species | NCBI ID | % ID with human |
| human | 2897946 | 100 |
| chimpanzee | 114639743 | 99 |
| macaque | 109108238 | 97 |
| dog | 73987958 | 93 |
| horse | 149719573 | 92 |
| pig | 47523822 | 90 |
| cow | 156120365 | 89 |
| rat | 149069047 | 84 |
| mouse | 20138153 | 84 |
| opossum | 126327828 | 80 |
| chicken | 118085215 | 78 |
| platypus | 149635150 | 76 |
| zebra fish | 41053648 | 69 |

TABLE 19

| Conserved T Cell Epitopes in the Human PSMA as Set Forth in SEQ ID NO: 1. | | |
|---|---|---|
| Amino acid Start | Amino acid End | Sequence |
| 168 | 176 | GMPEGDLVY |
| 347 | 356 | HSTNGVTRIY |
| 557 | 566 | ETYELVEKFY |
| 207 | 215 | KVFRGNKVK |
| 431 | 440 | STEWAEENSR |
| 4 | 12 | LLHETDSAV |
| 27 | 35 | VLAGGFFLL |
| 168 | 177 | GMPEGDLVYV |
| 441 | 450 | LLQERGVAYI |

TABLE 19-continued

Conserved T Cell Epitopes in the Human PSMA as Set Forth in SEQ ID NO: 1.

| Amino acid Start | Amino acid End | Sequence |
|---|---|---|
| 469 | 477 | LMYSLVHNL |
| 711 | 719 | ALFDIESKV |
| 663 | 671 | MNDQVMFL |
| 178 | 186 | NYARTEDFF |
| 227 | 235 | LYSDPADYF |
| 624 | 632 | TYSVSFDSL |
| 334 | 348 | TGNFSTQKVKMHIHS |
| 459 | 473 | NYTLRVDCTPLMYSL |
| 687 | 701 | YRHVIYAPSSHNKYA |
| 730 | 744 | RQIYVAAFTVQAAAE |

Example 4. Construction of Multi-Antigen Vaccine Constructs

In this Example, several strategies for expressing multiple antigens from single component DNA vaccine construct are described. These multi-antigen DNA vaccine constructs share the same general plasmid backbone as pPJV7563. Although the multi-antigen expression strategies are described here in the context of a DNA vaccine, the principles will apply similarly in the context of viral vector genetic vaccines (such as adenovirus vectors). Unless otherwise specified, the genes included in the multi-antigen constructs encode the human PSMA modified antigen (noted as PSMA), full length human PSCA (noted as PSCA), and the human PSA cytosolic antigen (noted as PSA), as described in the examples herein above.

Example 4A. Dual Antigen Constructs

4A1. Construction of Dual Antigen Constructs Utilizing Multiple Promoters

General Strategy.

One strategy for creating multivalent nucleic acid vaccine constructs is to incorporate multiple independent promoters into a single plasmid (Huang, Y., Z. Chen, et al. (2008). "Design, construction, and characterization of a dual-promoter multigenic DNA vaccine directed against an HIV-1 subtype C/B' recombinant." J Acquir Immune Defic Syndr 47(4): 403-411; Xu, K., Z. Y. Ling, et al. (2011). "Broad humoral and cellular immunity elicited by a bivalent DNA vaccine encoding HA and NP genes from an H5N1 virus." Viral Immunol 24(1): 45-56). The plasmid can be engineered to carry multiple expression cassettes, each consisting of a) a eukaryotic promoter for initiating RNA polymerase dependent transcription, with or without an enhancer element, b) a gene encoding a target antigen, and c) a transcription terminator sequence. Upon delivery of the plasmid to the transfected cell nucleus, transcription will be initiated from each promoter, resulting in the production of separate mRNAs, each encoding one of the target antigens. The mRNAs will be independently translated, thereby producing the desired antigens.

Plasmid 460 (PSMA/PSCA Dual Promoter).

Plasmid 460 was constructed using the techniques of site-directed mutagenesis, PCR, and restriction fragment insertion. First, a Kpn I restriction site was introduced upstream of the CMV promoter in plasmid 5259 using site-directed mutagenesis with MD5 and MD6 primers according to manufacturer's protocol (Quickchange kit, Agilent Technologies, Santa Clara, Calif.). Second, an expression cassette consisting of a minimal CMV promoter, human PSMA, and rabbit B globulin transcription terminator was amplified by PCR from plasmid 5166 using primers that carried Kpn I restriction sites (MD7 and MD8). The PCR amplicon was digested with Kpn I and inserted into the newly introduced Kpn I site of calf intestinal alkaline phosphatase (CIP)-treated plasmid 5259.

4A2. Construction of Dual Antigen Constructs Utilizing 2A Peptides

General Strategy.

Multiple protein antigens can also be expressed from a single vector through the use of viral 2A-like peptides (Szymczak, A. L. and D. A. Vignali (2005). "Development of 2A peptide-based strategies in the design of multicistronic vectors." Expert Opin Biol Ther 5(5): 627-638; de Felipe, P., G. A. Luke, et al. (2006). "E unum pluribus: multiple proteins from a self-processing polyprotein." Trends Biotechnol 24(2): 68-75; Luke, G. A., P. de Felipe, et al. (2008). "Occurrence, function and evolutionary origins of '2A-like' sequences in virus genomes." J Gen Virol 89(Pt 4): 1036-1042; Ibrahimi, A., G. Vande Velde, et al. (2009). "Highly efficient multicistronic lentiviral vectors with peptide 2A sequences." Hum Gene Ther 20(8): 845-860; Kim, J. H., S. R. Lee, et al. (2011). "High cleavage efficiency of a 2A peptide derived from porcine teschovirus-1 in human cell lines, zebrafish and mice." PLoS One 6(4): e18556). These peptides, also called cleavage cassettes or CHYSELs (cis-acting hydrolase elements), are approximately 20 amino acids long with a highly conserved carboxy terminal D-V/I-EXNPGP motif (FIG. 2). The cassettes are rare in nature, most commonly found in viruses such as Foot-and-mouth disease virus (FMDV), Equine rhinitis A virus (ERAV), Encephalomyocarditis virus (EMCV), Porcine teschovirus (PTV), and Thosea asigna virus (TAV) (Luke, G. A., P. de Felipe, et al. (2008). "Occurrence, function and evolutionary origins of '2A-like' sequences in virus genomes." J Gen Virol 89(Pt 4): 1036-1042). With a 2A-based multi-antigen expression strategy, genes encoding multiple target antigens can be linked together in a single open reading frame, separated by 2A cassettes. The entire open reading frame can be cloned into a vector with a single promoter and terminator. Upon delivery of the genetic vaccine to a cell, mRNA encoding the multiple antigens will be transcribed and translated as a single polyprotein. During translation of the 2A cassettes, ribosomes skip the bond between the C-terminal glycine and proline. The ribosomal skipping acts like a cotranslational autocatalytic "cleavage" that releases upstream from downstream proteins. The incorporation of a 2A cassette between two protein antigens results in the addition of ~20 amino acids onto the C-terminus of the upstream polypeptide and 1 amino acid (proline) to the N-terminus of downstream protein. In an adaptation of this methodology, protease cleavage sites can be incorporated at the N terminus of the 2A cassette such that ubiquitous proteases will cleave the cassette from the upstream protein (Fang, J., S. Yi, et al. (2007). "An antibody delivery system for regulated expression of therapeutic levels of monoclonal antibodies in vivo." Mol Ther 15(6): 1153-1159).

Plasmid 451 (PSMA-T2A-PSCA).

Plasmid 451 was constructed using the techniques of overlapping PCR and restriction fragment exchange. First, the gene encoding human PSMA amino acids 15-750 was amplified by PCR using plasmid 5166 as a template with primers 119 and 117. The gene encoding full-length human PSCA was amplified by PCR using plasmid 5259 as a template with primers 118 and 120. PCR resulted in the addition of overlapping TAV 2A (T2A) sequences at the 3' end of PSMA and 5' end of PSCA. The amplicons were mixed together and amplified by PCR with primers 119 and 120. The PSMA-T2A-PSCA amplicon was digested with Nhe I and Bgl II and inserted into similarly digested plasmid 5166. A glycine-serine linker was included between PSMA and the T2A cassette to promote high cleavage efficiency.

Plasmid 454 (PSCA-F2A-PSMA).

Plasmid 454 was created using the techniques of PCR and restriction fragment exchange. First, the gene encoding full-length human PSCA was amplified by PCR using plasmid 5259 as a template with primers 42 and 132. The amplicon was digested with BamH I and inserted into similarly digested, CIP-treated plasmid 5300. A glycine-serine linker was included between PSCA and the FMDV 2A (F2A) cassette to promote high cleavage efficiency.

Plasmid 5300 (PSA-F2A-PSMA)

Plasmid 5300 was constructed using the techniques of overlapping PCR and restriction fragment exchange. First, the gene encoding PSA amino acids 25-261 was amplified by PCR from plasmid 5297 with primers MD1 and MD2. The gene encoding human PSMA amino acids 15-750 was amplified by PCR from plasmid 5166 with primers MD3 and MD4. PCR resulted in the addition of overlapping F2A sequences at the 3' end of PSA and 5' end of PSMA. The amplicons were mixed together and extended by PCR. The PSA-F2A-PSMA amplicon was digested with Nhe I and Bgl II and inserted into similarly digested plasmid pPJV7563.

4A3. Dual Antigen Constructs Utilizing Internal Ribosomal Entry Sites

General Strategy:

A third strategy for expressing multiple protein antigens from a single plasmid or vector involves the use of an internal ribosomal entry site, or IRES. Internal ribosomal entry sites are RNA elements (FIG. 3) found in the 5' untranslated regions of certain RNA molecules (Bonnal, S., C. Boutonnet, et al. (2003). "IRESdb: the Internal Ribosome Entry Site database." Nucleic Acids Res 31(1): 427-428). They attract eukaryotic ribosomes to the RNA to facilitate translation of downstream open reading frames. Unlike normal cellular 7-methylguanosine cap-dependent translation, IRES-mediated translation can initiate at AUG codons far within an RNA molecule. The highly efficient process can be exploited for use in multi-cistronic expression vectors (Bochkov, Y. A. and A. C. Palmenberg (2006). "Translational efficiency of EMCV IRES in bicistronic vectors is dependent upon IRES sequence and gene location." Biotechniques 41(3): 283-284, 286, 288). Typically, two transgenes are inserted into a vector between a promoter and transcription terminator as two separate open reading frames separated by an IRES. Upon delivery of the genetic vaccine to the cell, a single long transcript encoding both transgenes will be transcribed. The first ORF will be translated in the traditional cap-dependent manner, terminating at a stop codon upstream of the IRES. The second ORF will be translated in a cap-independent manner using the IRES. In this way, two independent proteins can be produced from a single mRNA transcribed from a vector with a single expression cassette.

Plasmid 449 (PSMA-mIRES-PSCA).

Plasmid 449 was constructed using the techniques of overlapping PCR and restriction fragment exchange. First, the gene encoding full length human PSCA was amplified by PCR from plasmid 5259 with primers 124 and 123. The minimal EMCV IRES was amplified by PCR from pShuttle-IRES with primers 101 and 125. The overlapping amplicons were mixed together and amplified by PCR with primers 101 and 123. The IRES-PSCA amplicon was digested with Bgl II and BamH I and inserted into Bgl II-digested, CIP-treated plasmid 5166. In order to fix a spontaneous mutation within the IRES, the IRES containing Avr II to Kpn I sequence was replaced with an equivalent fragment from pShuttle-IRES.

Plasmid 603 (PSCA-pIRES-PSMA).

Plasmid 603 was constructed using the techniques of PCR and seamless cloning. The gene encoding full length human PSCA attached at its 3' end to a preferred EMCV IRES was amplified from plasmid 455 by PCR with primers SD546 and SD547. The gene encoding human PSMA amino acids 15-750 was amplified by PCR from plasmid 5166 using primers SD548 and SD550. The two overlapping PCR amplicons were inserted into Nhe I and Bgl II-digested pPJV7563 by seamless cloning according to manufacturer's instructions (Invitrogen, Carlsbad, Calif.).

Plasmid 455 (PSCA-mIRES-PSA).

Plasmid 455 was constructed using the techniques of overlapping PCR and restriction fragment exchange. First, the gene encoding human PSA amino acids 25-261 was amplified by PCR from plasmid 5297 with primers 115 and 114. The minimal EMCV IRES was amplified by PCR from pShuttle-IRES with primers 101 and 116. The overlapping amplicons were mixed together and amplified by PCR with primers 101 and 114. The IRES-PSA amplicon was digested with Bgl II and BamH I and inserted into Bgl II-digested, CIP-treated plasmid 5259. In order to fix a spontaneous mutation within this clone, the Bgl II to BstE II sequence was replaced with an equivalent fragment from a fresh overlapping PCR reaction.

Example 4B. Triple Antigen DNA Constructs

General Strategy.

Figure 7A:
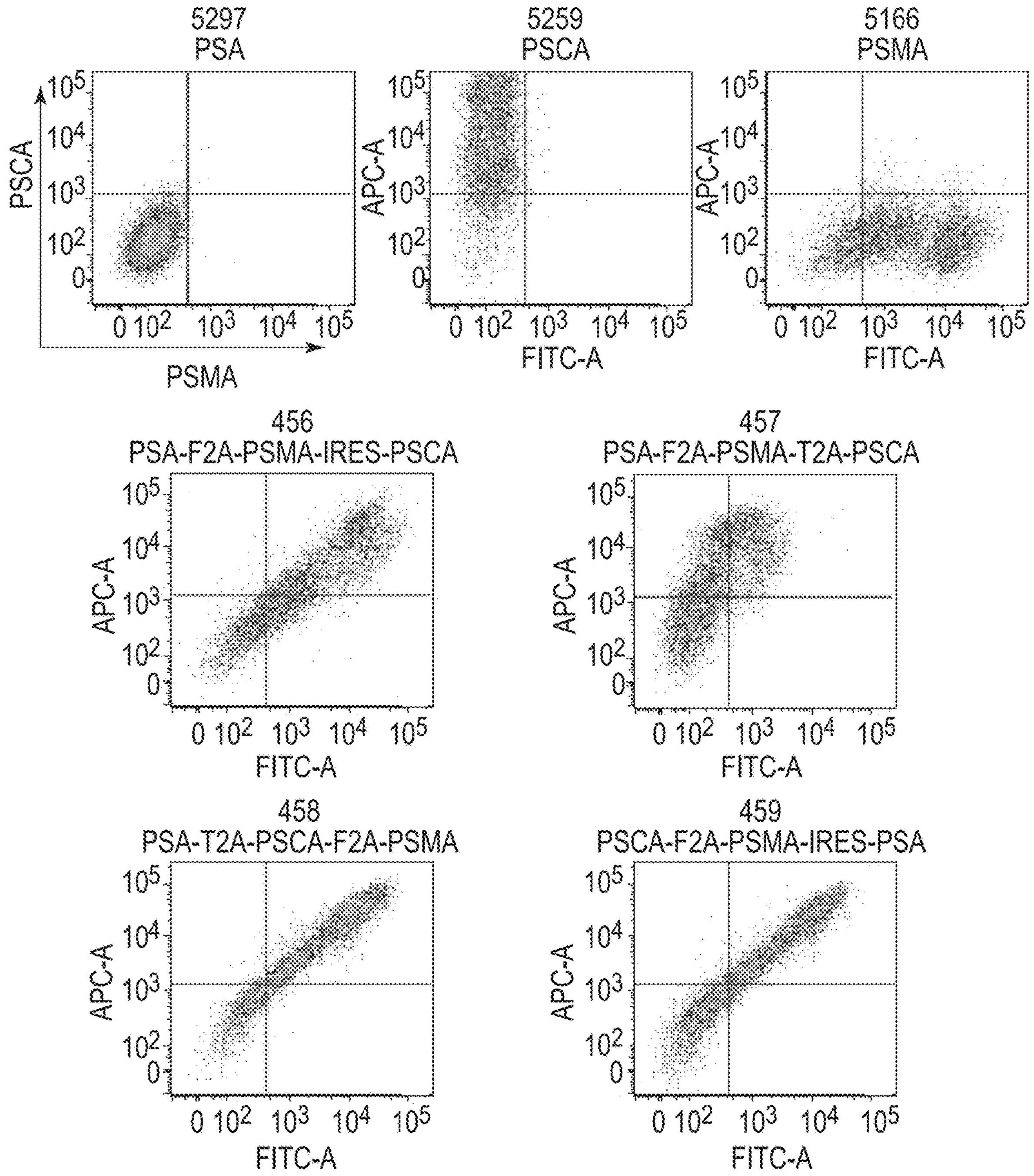
FIGS. 7A, 7B. Dot plots showing expression of human PSMA modified antigen (amino acids 15-750) and full length human PSCA on the surface of HEK293 cells transfected with either single promoter triple antigen constructs (FIG. 7A) or dual promoter triple antigen vaccine constructs (FIG. 7B) as measured by flow cytometry.
Figure 7B:
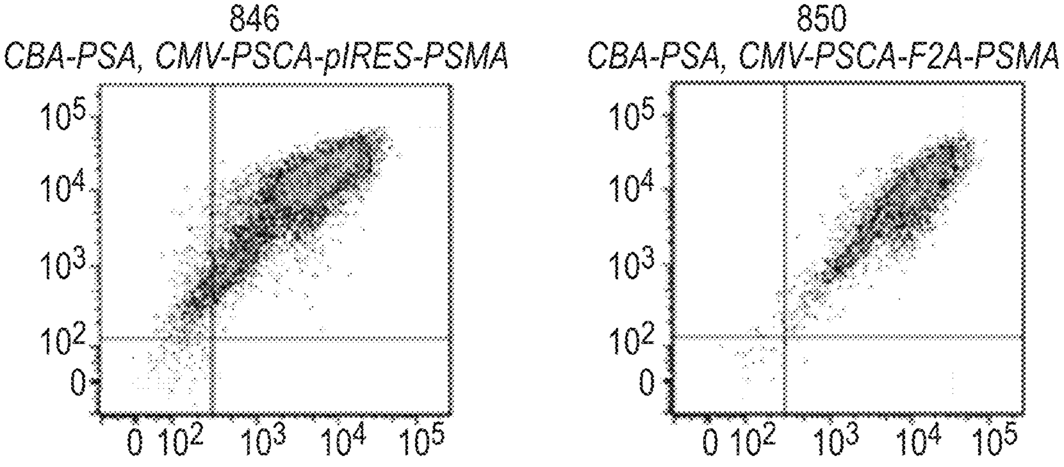
Figure 8A:
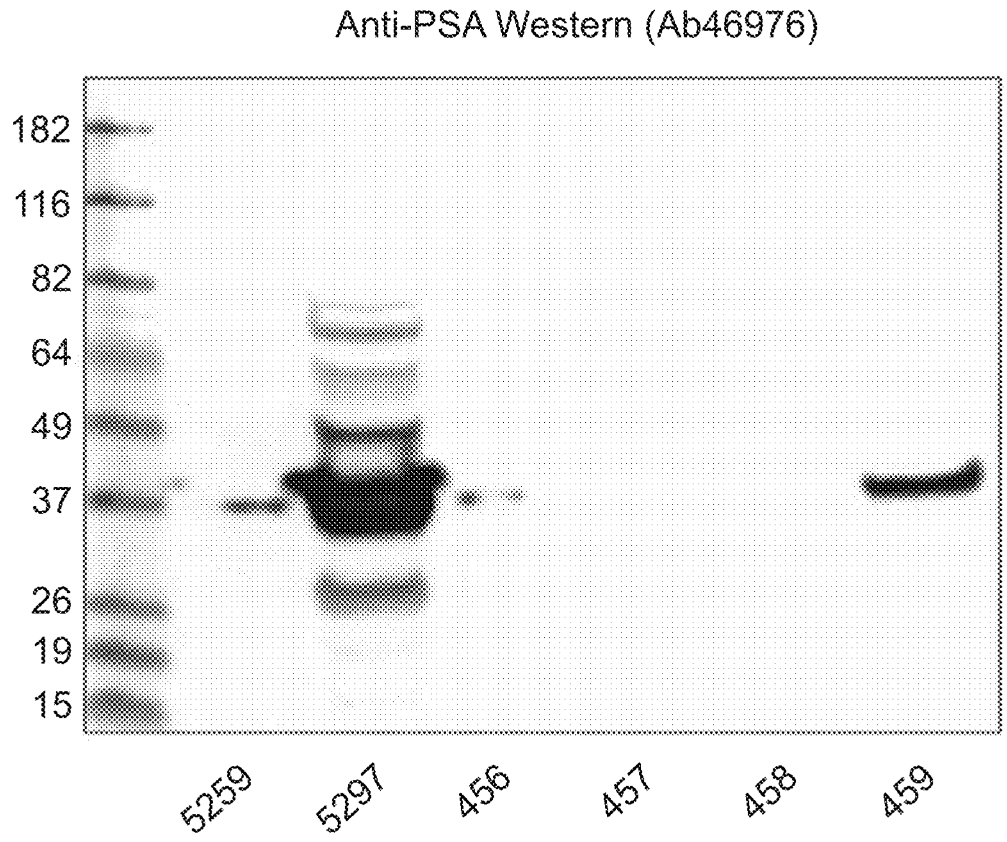
FIGS. 8A, 8B. Images of Western blots showing expression of human PSA in HEK293 cells transfected with either single promoter triple antigen constructs (FIG. 8A) or dual promoter triple antigen vaccine constructs (FIG. 8B) as measured by western blotting with a PSA specific monoclonal antibody. The bands in lanes 5259 and 456 are spillover from lane 5297. Although not visible in the scanned gel, lanes 456, 457, and 458 exhibited a band about 2 kD larger than PSA.
Figure 8B:
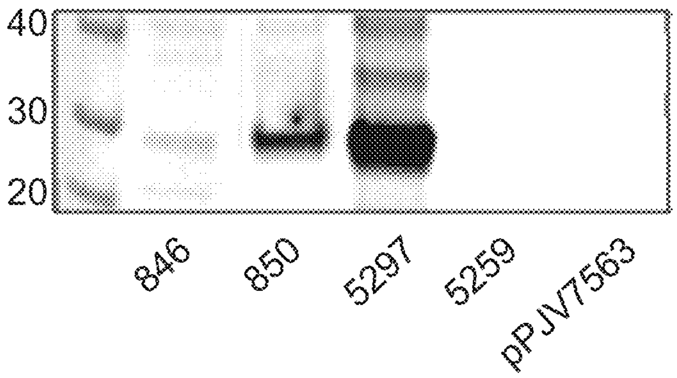
Figure 9A:
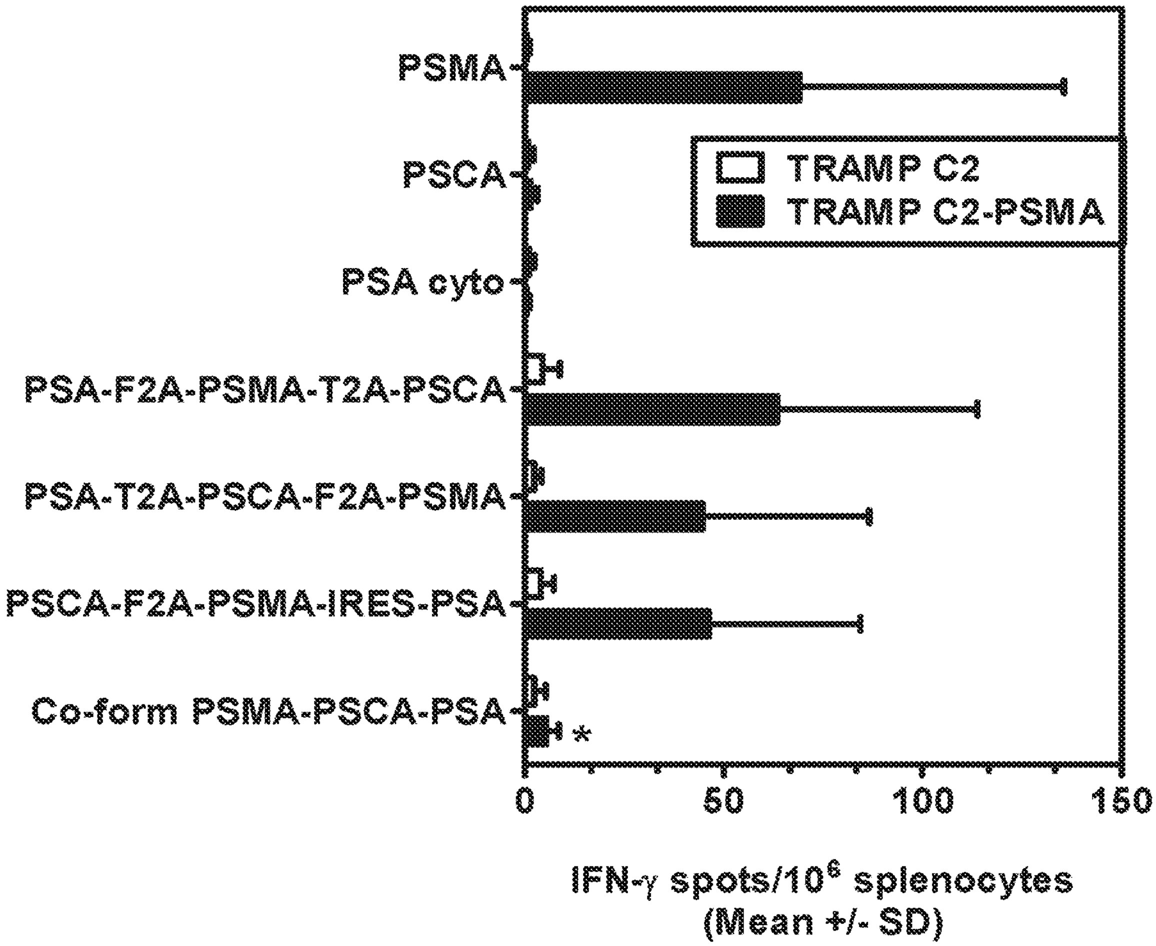
FIGS. 9A-9D. Graphs depicting results of a representative study that evaluates the immunogenicity of the triple antigen vaccines by IFN-γ ELISPOT assay, in which recognition of endogenous prostate antigens was assessed by examining T cell responses to (a) TRAMP C2 cells expressing PSMA (FIG. 9A), (b) TRAMP C2 cells expressing PSCA (FIG. 9B), (c) TRAMP C2 cells expressing PSA (FIG. 9C), and (d) TRAMP C2 cells expressing PSMA, PSA, and PSCA (FIG. 9D).
Figure 9B:
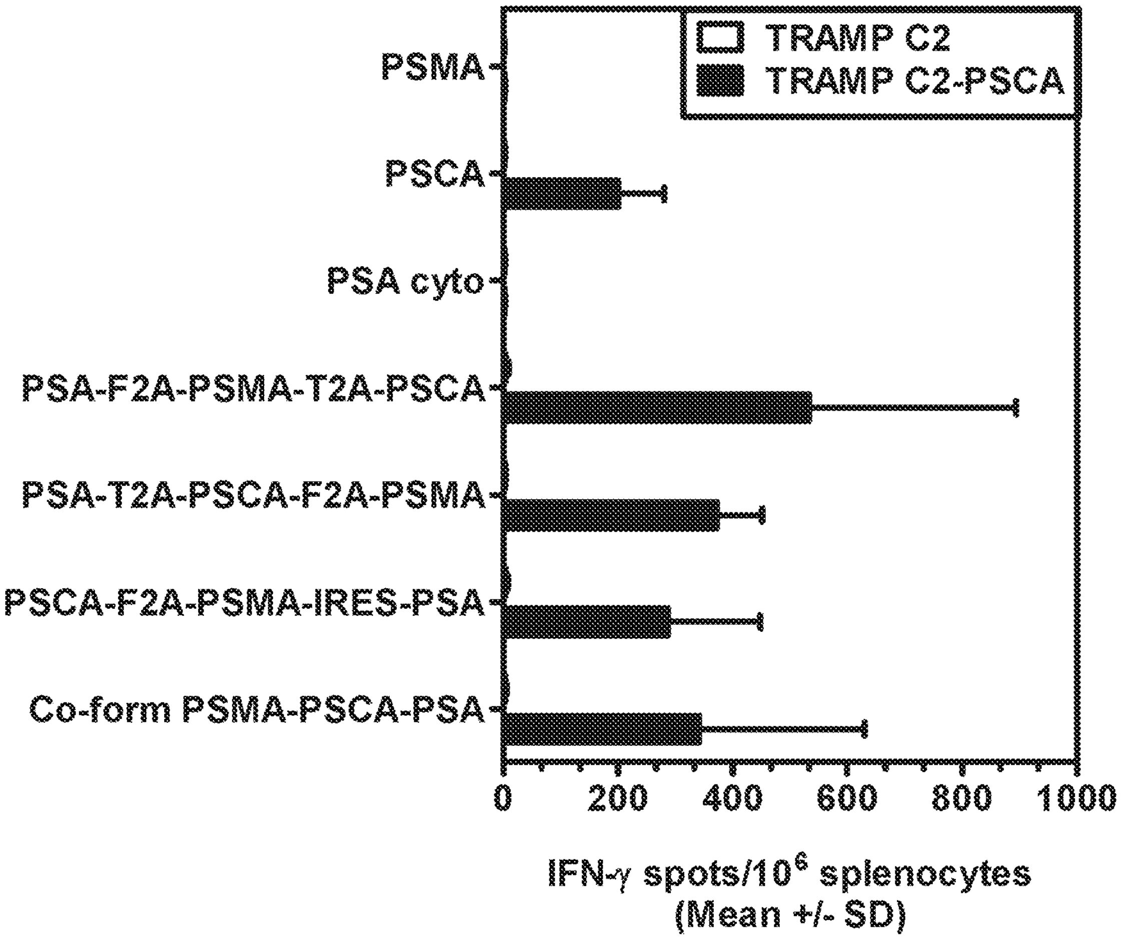
Figure 9C:
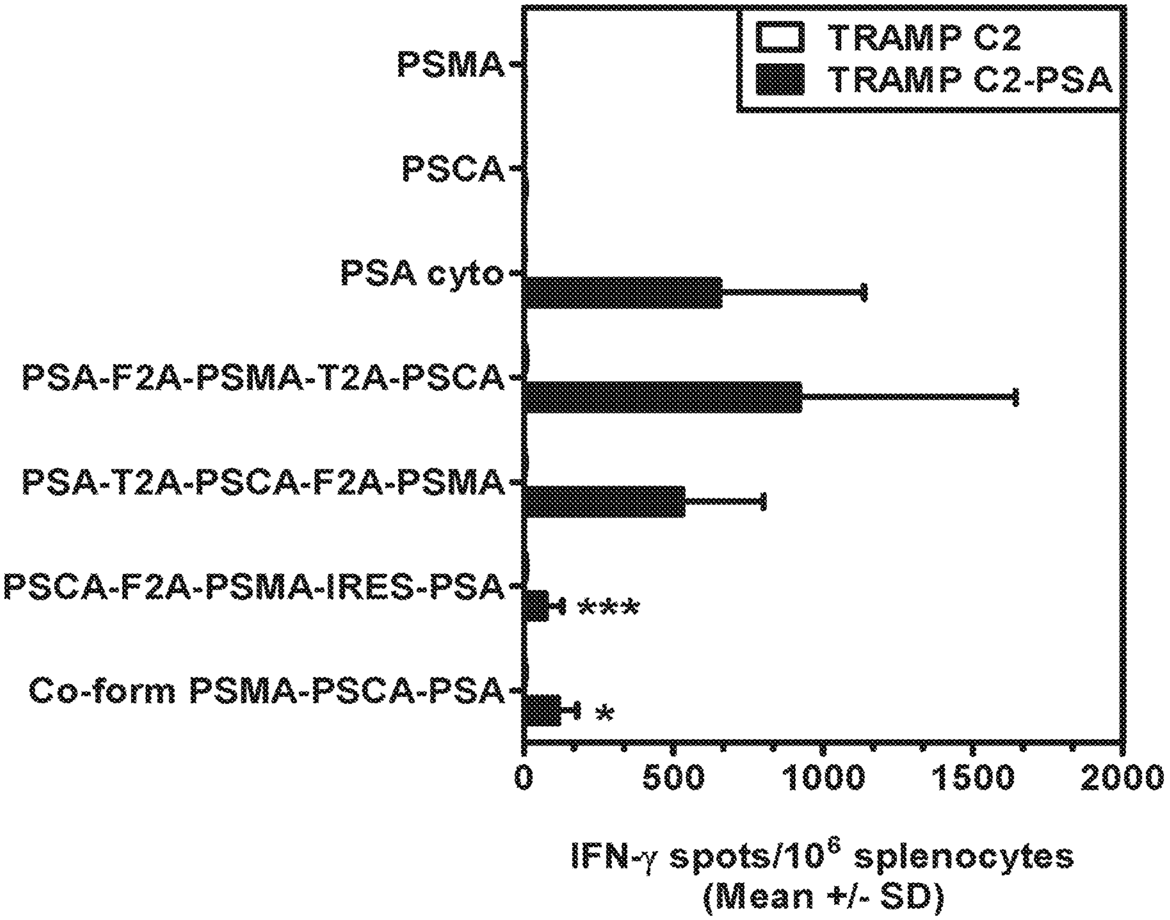
Figure 9D:
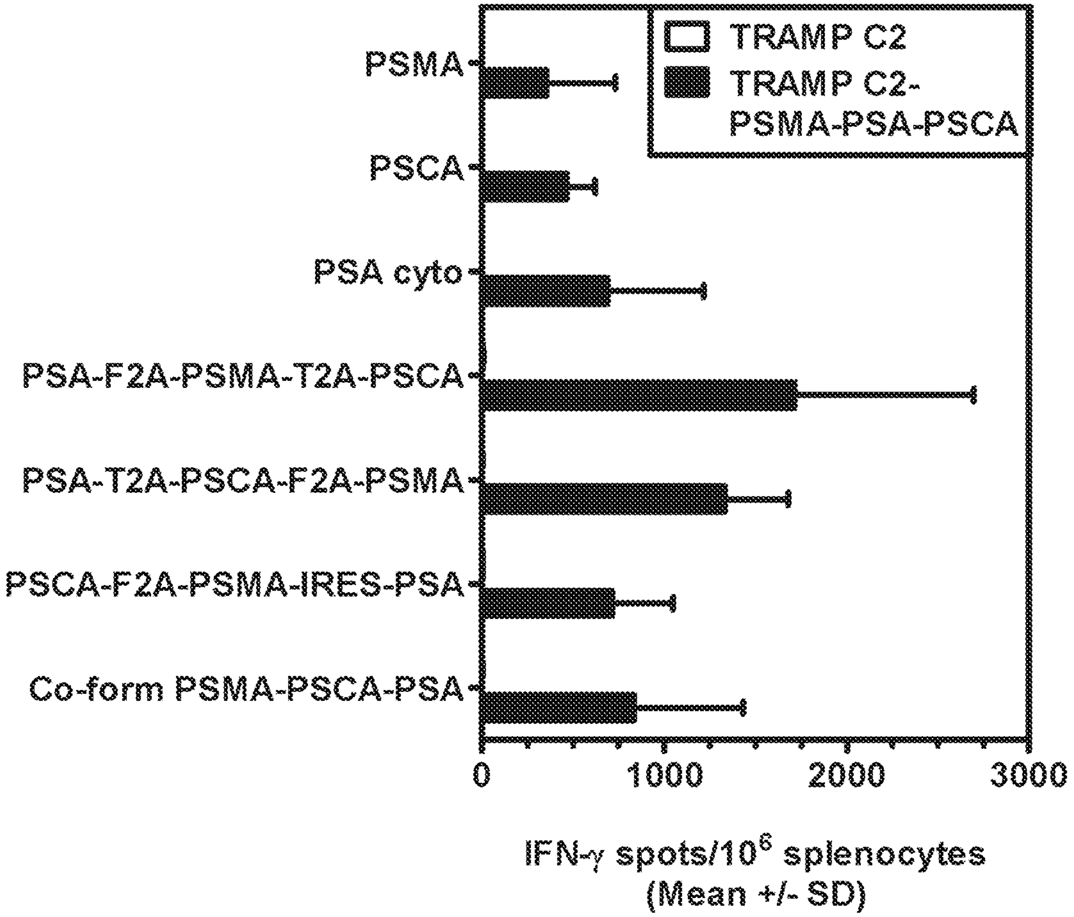
Figure 10A:
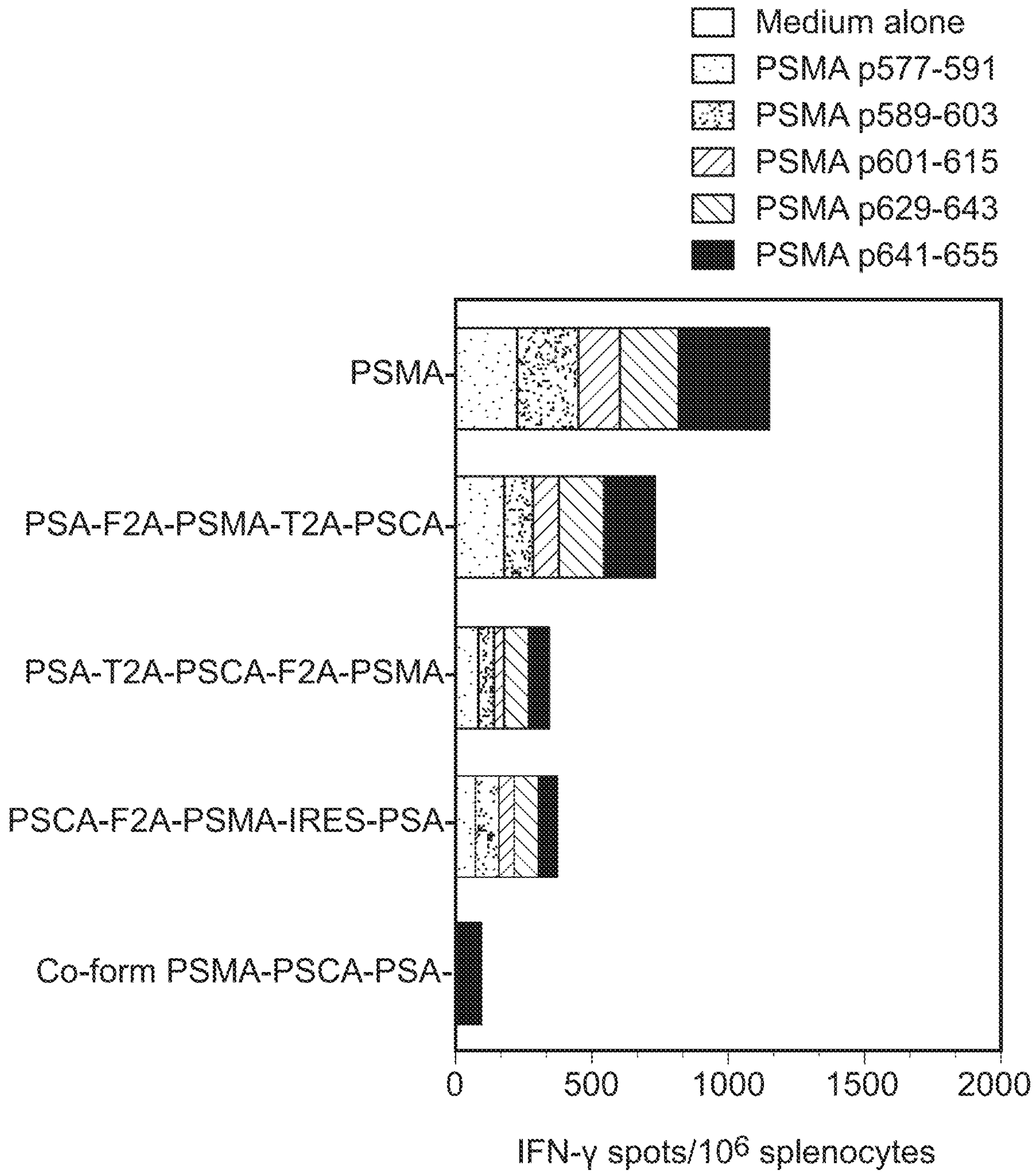
FIGS. 10A-10D. Graphs depicting results of a representative study that evaluates the immunogenicity of the triple antigen vaccines by IFN-γ ELISPOT assay, in which T cell responses to (a) individual PSMA peptides (FIG. 10A), (b) three PSMA peptide pools (FIG. 10B), (c) a PSCA peptide (FIG. 10C), and (d) PSA peptides (FIG. 10D) were assessed.
Figure 10B:
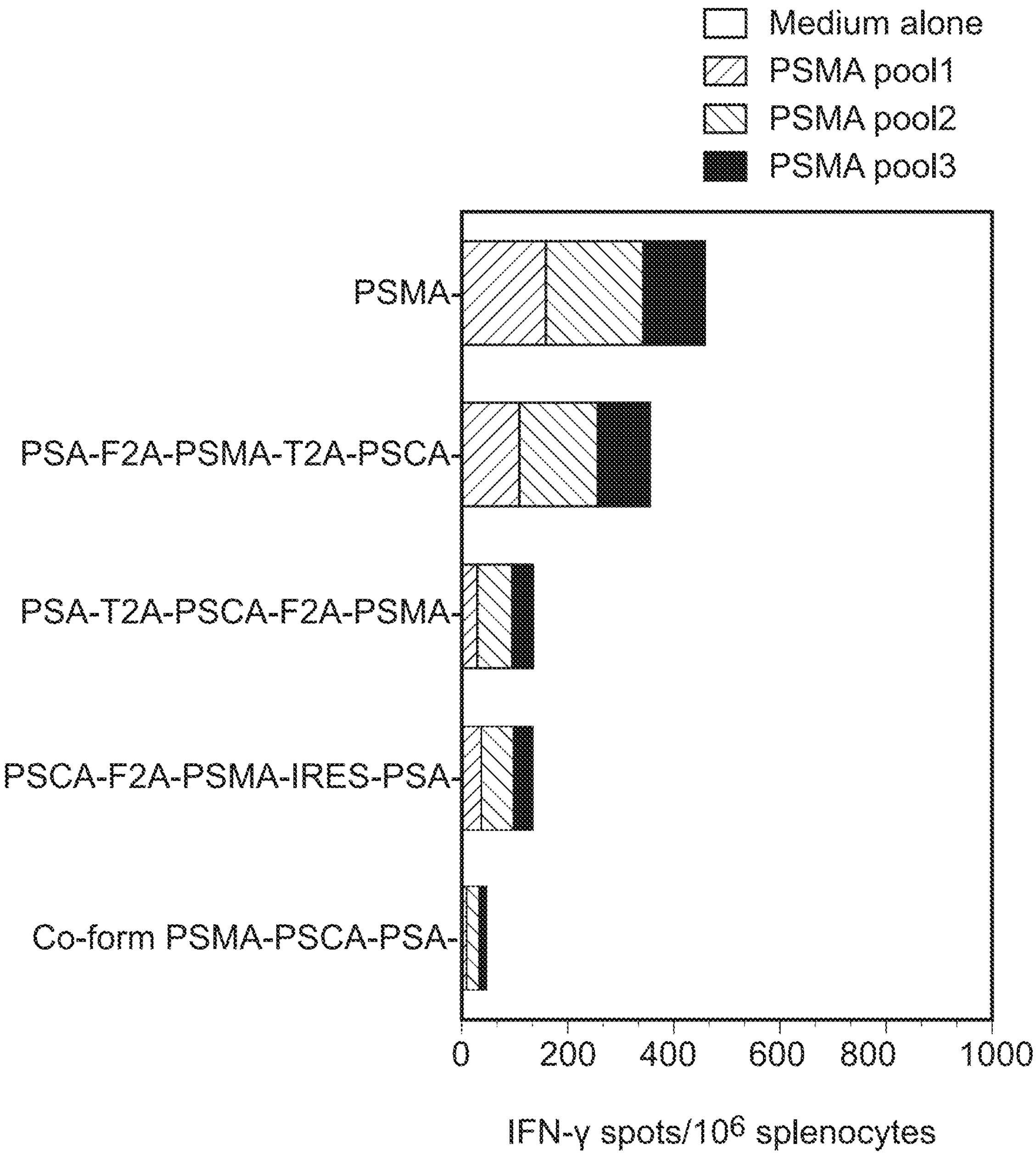
Figure 10C:
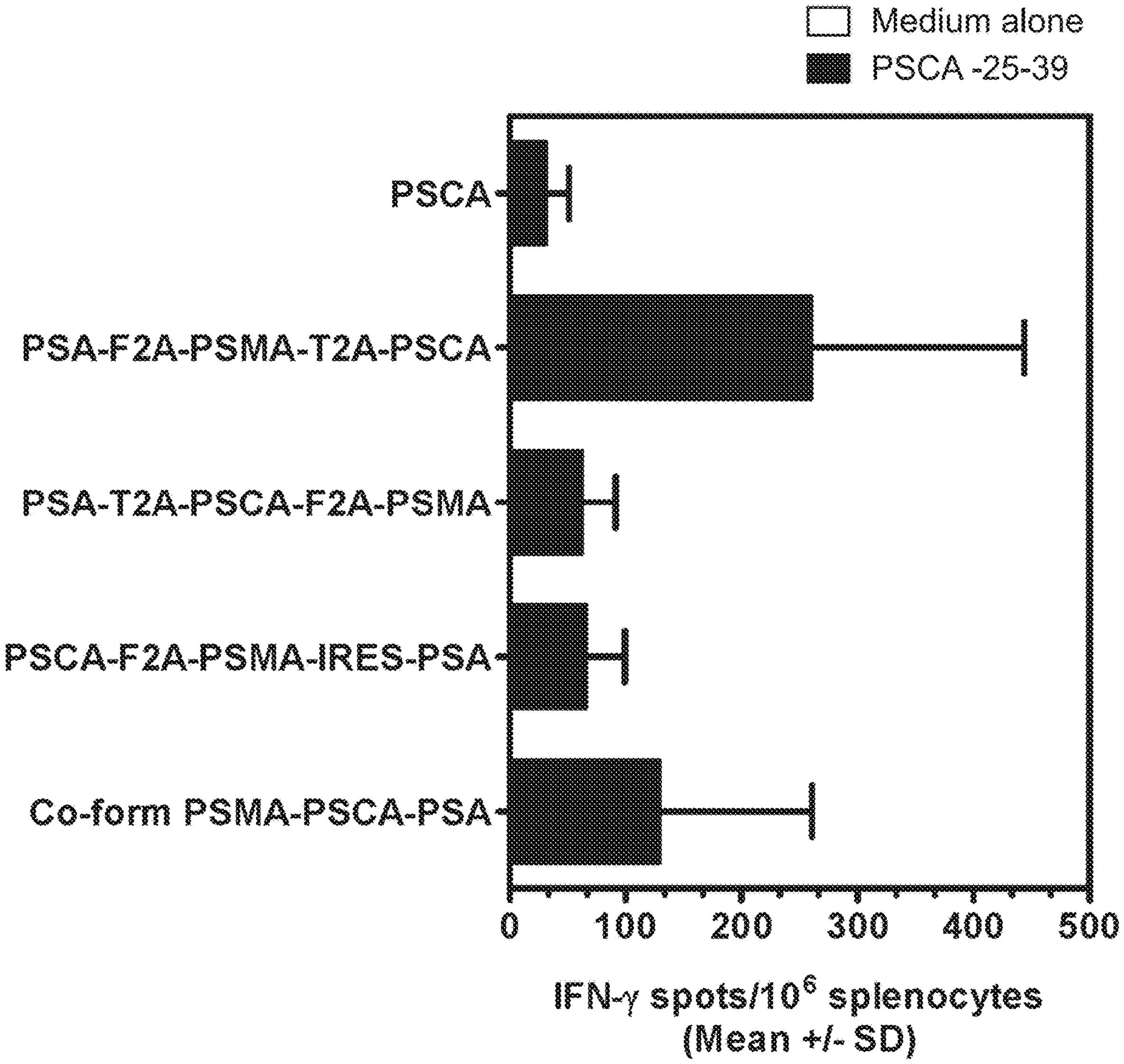
Figure 10D:
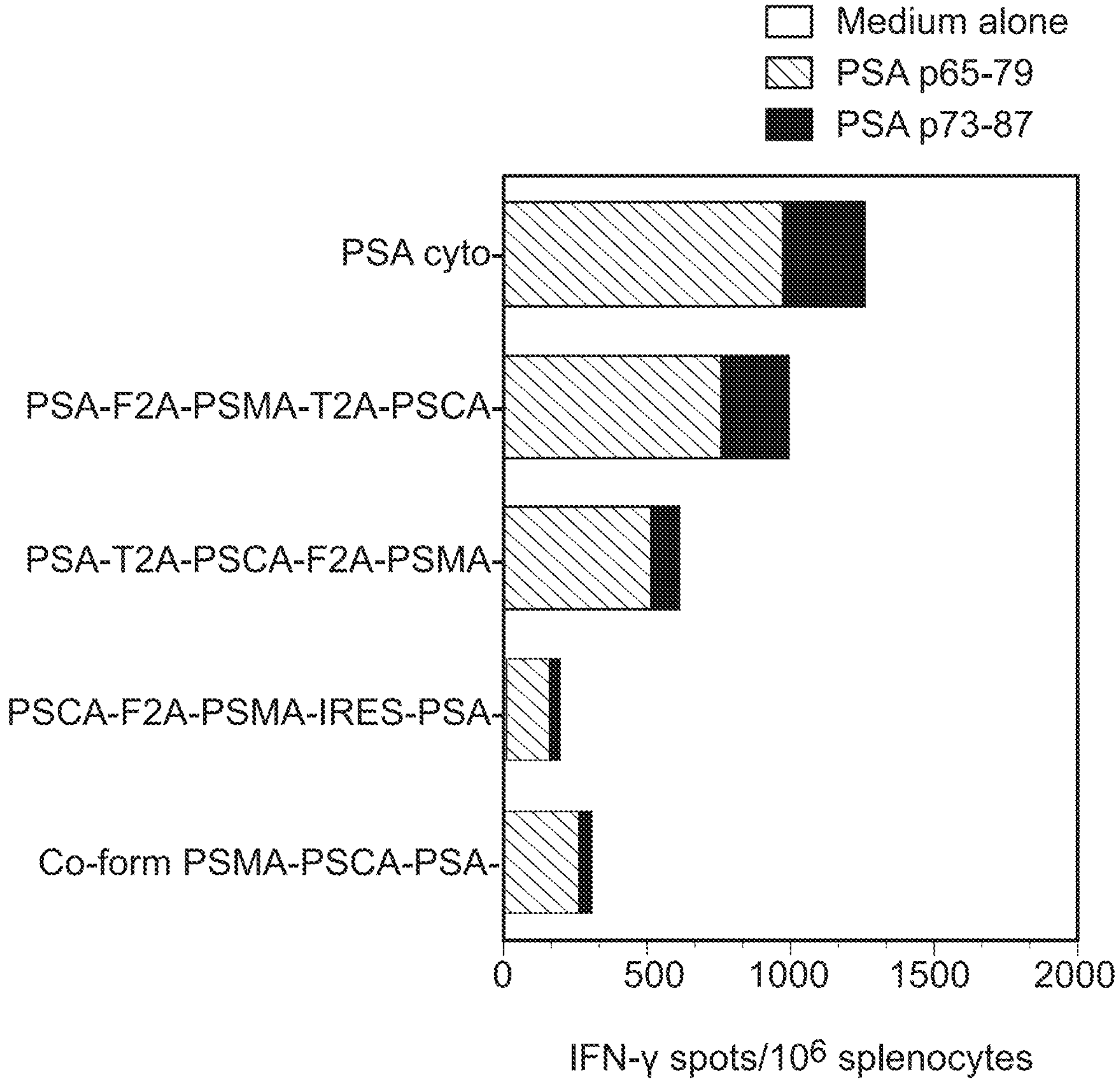

The abilities of the dual antigen expression vectors to direct the expression of PSMA, PSCA, and/or PSA were characterized in transfected HEK293 cells (FIGS. 4, 5A, 5B, and 6). A number of dual antigen expression cassettes, including PSA-F2A-PSMA, PSMA-mIRES-PSCA, PSMA-T2A-PSCA, PSA-T2A-PSCA, PSCA-F2A-PSMA, PSCA-pIRES-PSMA, and PSMA-mIRES-PSA, were selected for incorporation in various combinations into triple antigen expression vectors. In all cases, the vectors were based on the parental pPJV7563 plasmid backbone. Four vectors (plasmids 456, 457, 458, and 459) utilized a single full CMV promoter with a rabbit B globulin transcription terminator to drive expression of all three antigens. Two other vectors (plasmids 846 and 850) incorporated a dual promoter strategy in combination with either an IRES or 2A to drive expression of the three antigens. Vectors with multiple 2A cassettes were engineered to carry different cassettes to minimize the likelihood of recombination between the first and second cassette during plasmid/vector amplification. Antigen expression was demonstrated by flow cytometry (FIGS. 7A and 7B) and western blotting (FIGS. 8A and 8B).

Plasmid 456 (PSA-F2A-PSMA-mIRES-PSCA).

Plasmid 456 was constructed by restriction fragment exchange. Plasmid 5300 was digested with Nhe I and Hpa I and the ~1.8 kb insert was ligated into similarly digested plasmid 449.

Plasmid 457 (PSA-F2A-PSMA-T2A-PSCA).

Plasmid 457 was constructed by restriction fragment exchange. Plasmid 5300 was digested with Nhe I and Hpa I and the ~1.8 kb insert was ligated into similarly digested plasmid 451.

Plasmid 458 (PSA-T2A-PSCA-F2A-PSMA).

Plasmid 458 was constructed using the techniques of PCR and restriction fragment exchange. The gene encoding human PSA amino acids 25-261 was amplified by PCR from plasmid 5297 with primers 119 and 139, resulting in the addition of a T2A sequence and Nhe I restriction site at the 3' end. The amplicon was digested with Nhe I and inserted into similarly digested plasmid 454.

Plasmid 459 (PSCA-F2A-PSMA-mIRES-PSA).

Plasmid 459 was constructed by restriction fragment exchange. Plasmid 454 was digested with Nhe I and Bgl II and the PSCA-F2A-PSMA containing insert was ligated into similarly digested plasmid 455.

Plasmid 846 (CBA-PSA, CMV-PSCA-pIRES-PSMA).

Plasmid 846 was constructed using the techniques of PCR and seamless cloning. First, an expression cassette was synthesized that consisted of 1) the promoter and 5' untranslated region from the chicken beta actin (CBA) gene, 2) a hybrid chicken beta actin/rabbit beta globin intron, 3) the gene encoding human PSA amino acids 25-261, and 4) the bovine growth hormone terminator. This PSA expression cassette was amplified by PCR from plasmid 796 with primers 3SalICBA and 5SalIBGH. The amplicon was cloned into the Sail site of plasmid 603 using a GeneArt Seamless Cloning and Assembly Kit (Invitrogen, Carlsbad, Calif.). Upon delivery of this plasmid into a cell, PSA expression will be driven off the CBA promoter while PSCA and PSMA expression will be driven off the CMV promoter.

Plasmid 850 (CBA-PSA, CMV-PSCA-F2A-PSMA).

Plasmid 850 was constructed using the techniques of PCR and seamless cloning. First, the CBA promoter-driven PSA expression cassette was amplified by PCR from plasmid 796 with primers 3SalICBA and 5SalIBGH. The amplicon was cloned into the Sail site of plasmid 454 using GeneArt Seamless Cloning. Upon delivery of this plasmid into a cell, PSA expression will be driven off the CBA promoter while PSCA and PSMA expression will be driven off the CMV promoter.

TABLE 20

List of Plasmids Expressing Multiple-Antigens

| $1^{st}$ Antigen | Expression strategy | $2^{nd}$ Antigen | Expression strategy | $3^{rd}$ Antigen | Plasmid ID # |
|---|---|---|---|---|---|
| PSMA | | | | | 5166 |
| PSCA | | | | | 5259 |
| PSA | | | | | 5297 |
| PSMA | 2 promoters | PSCA | | | 460 |
| PSMA | T2A | PSCA | | | 451 |
| PSCA | F2A | PSMA | | | 454 |
| PSA | F2A | PSMA | | | 5300 |
| PSMA | IRES | PSCA | | | 449 |
| PSCA | IRES | PSMA | | | 603 |
| PSCA | IRES | PSA | | | 455 |
| PSA | F2A | PSMA | mIRES | PSCA | 456 |
| PSA | F2A | PSMA | T2A | PSCA | 457 |
| PSA | T2A | PSCA | F2A | PSMA | 458 |

TABLE 20-continued

List of Plasmids Expressing Multiple-Antigens

| $1^{st}$ Antigen | Expression strategy | $2^{nd}$ Antigen | Expression strategy | $3^{rd}$ Antigen | Plasmid ID # |
|---|---|---|---|---|---|
| PSCA | F2A | PSMA | mIRES | PSA | 459 |
| PSA | 2 promoters | PSCA | pIRES | PSMA | 796 |
| PSA | 2 promoters | PSCA | pIRES | PSMA | 846 |
| PSA | 2 promoters | PSCA | F2A | PSMA | 850 |

TABLE 21

List of Primers Used in the Construction of the Multi-antigen Plasmids

| Primer | Sequence (5' to 3') | Strand |
|---|---|---|
| 42 | CGTTGACGCAAATGGGCGGTAGG | Sense |
| 101 | TCAGAGATCTGACCCCCTAACGTTACTGGC | Sense |
| 114 | TATAGGATCCTCAGGGGTTGGCCACGATG | Antisense |
| 115 | GAAAAACACGATGATAATATGGCCAGCATT GTGGGAGGCTGGGAGTG | Sense |
| 116 | CCACAATGCTGGCCATATTATCATCGTGTT TTTCAAAGGAAAACCACGTCC | Antisense |
| 117 | CATCTCCACAGGTCAATAATGAACCCCTAC CTTCGGATCCGGCTACTTCACTCAAAGTC | Antisense |
| 118 | GTTCATTATTGACCTGTGGAGATGTCGAAG AAAACCCAGGACCCGCAAGCAAGGCTGTGC TGCTTGCCCTG | Sense |
| 119 | TTGCCTCTCACATCTCGTCAATCTCCGCGA GGAC | Sense |
| 120 | GATCTTTTGTACAATATGATCTTGTGGCAA TGTCCC | Antisense |
| 123 | TATAGGATCCCTATAGCTGGCCGGGTCC | Antisense |
| 124 | CACGATGATAATATGGCCAGCAAGGCTGTG CTGCTTGCC | Sense |
| 125 | CACAGCCTTGCTGGCCATATTATCATCGTG TTTTTCAAAGGAAAACCACGTCC | Antisense |
| 132 | TATAGGATCCTAGCTGGCCGGGTCCCCAGAG | Antisense |
| 139 | ATATGCTAGCGGGTCCTGGGTTTTCTTCGA CATCTCCACAGGTCAATAATGAACCCCTAC CTTCGGATCCGGGG TTGGCCACGATGGTGTCC | Antisense |
| SD546 | CTGTGACGAACATGGCTAGCAAGG | Sense |
| SD547 | ATTATCATCGTGTTTTTCAAAGGAAAACC | Antisense |
| SD548 | AAACACGATGATAATATGGCCACAACCATG GCGCGCCGCCCGC | Sense |
| SD550 | TTTTGTTAGGGCCCAGATCTTTAGGC | Antisense |
| MD1 | GACGAACATGGCTAGCATTGTGGGAGGCTG | Sense |
| MD2 | CCACATCGCCTGCCAGTTTCAGCAGATCAA AGTTCAGGGTCTGGGATCCGGGGTTGGCCA CGATGGTGTC | Antisense |

TABLE 21-continued

List of Primers Used in the Construction of the Multi-antigen Plasmids

| Primer | Sequence (5' to 3') | Strand |
|---|---|---|
| MD3 | GATCTGCTGAAACTGGCAGGCGATGTGGAAA GCAACCCAGGCCCAATGGCAAGCGCGCCG CCCGCGCTG | Sense |
| MD4 | GTTAGGGCCCAGATCTTTAGGCTACTTCACT CAAAGTC | Antisense |
| MD5 | CTTGTATTACTGTTTATGTAAGCAGACAGGG TACCAATATTGGCTATTGGCCATTGCATAC | Sense |
| MD6 | GTATGCAATGGCCAATAGCCAATATTGGTAC CCTGTCTGCTTACATAAACAGTAATACAAG | Antisense |
| MD7 | CATGCATGGGTACCAATCTTCCGAGTGAGAG ACACAAAAAATTCC | Sense |
| MD8 | GATCGATCGGTACCCTGCAGGTCGAGCACCA AAATCAACGGG | Antisense |
| 5SalIBG H | GTTTATGTAAGCAGACAGGTCGACCCATAGA GCCCACCGCATCCCCAGC | Antisense |
| 3SalICBA | TGGCCAATAGCCAATATTGTCGACTGGGTCG AGGTGAGCCCCACGTTCTG | Sense |

Example 4C. Triple Antigen Adenovirus Constructs

General Strategy. As with DNA plasmids, viral vaccine vectors can be engineered to deliver multiple prostate cancer antigens. The three multi-antigen expression strategies described above for DNA vaccines—dual promoters, 2A peptides, and internal ribosome entry sites—were incorporated in various combinations to create triple antigen adenovirus vectors. Briefly, the multi-antigen expression cassettes were cloned into a pShuttle-CMV plasmid modified to carry two copies of the tetracycline operator sequence (TetO2). Recombinant adenovirus serotype 5 vectors were created using the AdEasy Vector System according to manufacturer's protocols (Agilent Technologies, Inc., Santa Clara, Calif.). Viruses were amplified in HEK293 cells and purified by double cesium chloride banding according to standard protocols. Prior to in vivo studies, viral stocks were thoroughly characterized for viral particle concentration, infectivity titer, sterility, endotoxin, genomic and transgene integrity, transgene identity and expression.

Adenovirus-733 (PSA-F2A-PSMA-T2A-PSCA).

Ad-733 is the viral equivalent of plasmid 457. Expression of the three antigens is driven off a single CMV promoter with a tetracycline operator for repressing transgene expression during large scale production in Tet repressor expressing HEK293 lines. Multi-antigen expression strategies include two different 2A sequences.

Adenovirus-734 (PSA-T2A-PSCA-F2A-PSMA).

Ad-734 is the viral equivalent of plasmid 458. Expression of the three antigens is driven off a single CMV promoter with a tetracycline operator for repressing transgene expression during large scale production in Tet repressor expressing HEK293 lines. Multi-antigen expression strategies include two different 2A sequences.

Adenovirus-735 (PSCA-F2A-PSMA-mIRES-PSA).

Ad-735 is the viral equivalent of plasmid 459. Expression of the three antigens is driven off a single CMV promoter with a tetracycline operator for repressing transgene expression during large scale production in Tet repressor expressing HEK293 lines. Multi-antigen expression strategies include a 2A sequence and an IRES.

Adenovirus-796 (CBA-PSA, CMV-PSCA-pIRES-PSMA).

Ad-796 is the viral equivalent of plasmid 846. Expression of PSA is driven off the chicken beta actin promoter while PSCA and PSMA expression is driven off the CMV-TetO2 promoter. Multi-antigen expression strategies include two promoters and an IRES.

Adenovirus-809 (CBA-PSA, CMV-PSCA-F2A-PSMA).

Ad-809 is the viral equivalent of plasmid 850. Expression of PSA is driven off the chicken beta actin promoter while PSCA and PSMA expression is driven off the CMV-TetO2 promoter. Multi-antigen expression strategies include two promoters and a 2A sequence.

Example 5. Immunogenicity of Triple Antigen DNA Vaccines

Example 5 illustrates the capability of triple antigen nucleic acid vaccine constructs expressing PSMA, PSCA and PSA to elicit antigen-specific T and B cell responses to all three encoded prostate antigens.

Cellular Immune Response Study.

Immunogenicity of triple antigen constructs containing PSMA, PSCA and PSA, as described in Example 5, was studied in C57BL/6 mice according to the procedure described below.

Female C57BL/6 mice were primed on day 0 and boosted on days 14, 28 and 49 with DNA vaccine constructs encoding human-PSMA, PSCA and PSA antigens by PMED administration. In total, four different triple antigen vaccination strategies were evaluated, which included three DNA vaccines that co-expressed the target proteins and one co-formulation approach. For co-expression, single DNA plasmids encoding all three prostate antigens linked by 2A peptides or internal ribosome entry sites (IRES) were used as follows: PSA-F2A-PSMA-T2A-PSCA (plasmid ID #457), PSA-T2A-PSCA-F2A-PSMA (plasmid ID #458) and PSCA-F2A-PSMA-IRES-PSA (plasmid ID #459). For the co-formulation approach, three different DNA plasmids, each individually encoding PSMA, PSCA or PSA, were co-formulated onto a single gold particle for PMED delivery. With the exception of co-formulation, the DNA elements that control co-expression (2A and IRES) differ in length, transgene expression efficiency and the presence of foreign genetic material attached to the target transgenes. As controls, C57BL/6 mice were vaccinated with DNA expressing a single prostate antigen, either PSMA, PSCA or PSA. For the co-expressed triple or single antigen DNA vaccines, a dose 2 μg of DNA vaccine plasmid was given per PMED administration, whereas 1 μg of each of the co-formulated triple antigen DNA vaccines (a total of 3 μg) was administered per PMED administration. Cellular immune responses against the triple and single antigen vaccines were measured by collecting the spleens from each animal on day 56, seven days after the final PMED vaccination. Splenocytes were isolated and subjected to an IFN-γ ELISPOT assay to measure the PSMA, PSCA and PSA-specific T cell responses. Briefly, $2\times10^5$ splenocytes from individual animals were plated per well with $5\times10^4$ per well of TRAMP-C2 (transgenic adenocarcinoma mouse prostate) cells stably expressing a single human prostate antigen or PSMA, PSCA and PSA together, or with individual or pools of human PSMA, PSCA and PSA-specific peptides at 10 μg/ml (see Table 22 for peptides and peptide pool composition), or medium alone as a control. Each condition was performed in triplicate. The plates were incubated for 20 h at 37° C. and 5% $CO_2$, washed and developed after incubation as per the manufacturer's instructions. The number of IFN-γ spot forming cells (SFC) was counted by a Cellular Technology Ltd. (CTL) reader. The results are presented in FIGS. 9 and 10, which show the average number of PSMA, PSCA or PSA-specific SFCs+/−the standard deviation of five mice per group, normalized to $1\times10^6$ splenocytes.

TABLE 22

The 15mer PSMA, PSCA and PSA peptides that were tested in the ELISPOT assay. The amino acid position of the N and C-terminal end of each peptide is indicated.

| Prostate antigen | Peptides | Tested individually or pool |
|---|---|---|
| PSMA | 577-591 | Individual |
| PSMA | 589-603 | Individual |
| PSMA | 601-615 | Individual |
| PSMA | 629-643 | Individual |
| PSMA | 641-655 | Individual |
| PSMA | 77-91 | Pool 1 |
| | 91-111 | |
| | 153-167 | |
| | 229-243 | |
| | 365-379 | |
| PSMA | 401-415 | Pool 2 |
| | 429-443 | |
| | 521-535 | |
| | 613-627 | |
| PSMA | 657-671 | Pool 3 |
| | 685-699 | |
| | 701-715 | |
| | 733-747 | |
| PSCA | 25-39 | Individual |
| PSA | 65-79 | Individual |
| PSA | 73-87 | Individual |

Antibody Response Study.

Antibody responses against the triple and single antigen vaccines were measured by collecting the serum from each animal on day 56, seven days after the final PMED vaccination. Serum was subjected to enzyme-linked immunosorbent assays (ELISA) to determine the anti-PSMA and anti-PSCA antibody titers. In brief, ELISA plates were coated with 1 μg/ml of human PSMA or PSCA and incubated overnight at 4° C. Plates were then blocked and incubated at RT for 1 h with 1% bovine serum albumin (BSA). Each serum sample was serially diluted in duplicate starting at a 1:100 dilution and incubated for 1 h at RT. After washing, a horseradish-peroxidise (HRP)-conjugated goat anti-mouse polyclonal IgG antibody was incubated at RT for 1 h. After washing, the TMB Peroxidase EIA-Substrate was incubated at RT for 30 min. The colorimetric reaction was stopped by addition 1N sulfuric acid and the absorbance then read at 450 nm. Titration curves were plotted for each serum sample (sample dilution versus absorbance). The serum titer (subsequently transformed into reciprocal titer) was then taken as the most dilute serum sample tested with an optical density (OD) value of above the lower limit of detection (LLOD; background plus 3 standard deviations) or the serum dilution calculated to achieve an OD value of 1.0. The results are presented in FIGS. 11 and 12, which show the average titers+/−the standard deviation of five mice per group.

Serum was also subjected to a fluorescence-activated cell sorting (FACS) assay to measure antibody binding to either human PSMA or PSCA expressed on the cell surface of appropriate cell lines, thus determining whether antibodies generated by the multi-antigen vaccines were capable of recognizing native PSMA and PSCA conformations, respectively. LNCaP (human prostate adenocarcinoma) cells were utilized to measure antibody binding to native PSMA. PC3 (human prostate cancer) cells served as a control in the FACS assay, as these cells do not express human PSMA. MIA-PaCa-2 (human pancreatic carcinoma) cells transduced with an adenovirus expressing human PSCA (Ad-PSCA) were utilized to measure antibody binding to native PSCA. Untransduced MIA-PaCa-2 cells served as the control. In brief, to measure anti-PSMA antibody binding, $2\times10^5$ LNCaP or PC3 cells were incubated with a 1:100 dilution of mouse serum or 15 μg/ml of the control mouse-anti-human PSMA monoclonal antibody (mAb) (clone J591-A) for 20 min at 4° C. To measure anti-PSCA antibody binding, $2\times10^5$ Ad-PSCA transduced and untransduced MIA-PaCa-2 cells were incubated with a 1:30 dilution of mouse serum or 4 μg/ml of the control mouse anti-human PSCA mAb (clone 7F5) for 20 min at 4° C. Subsequently, cells were washed and incubated with a secondary Phycoerythrin (PE)-conjugated goat-anti-mouse IgG antibody and a live/dead dye for an additional 20 min at 4° C. After the incubation, cells were washed and resuspended in 1.5% paraformaldehyde, and 10,000 live cells were acquired on a FACS Canto II. The results are presented in FIGS. 13 and 14, which show the average fold change in mean fluorescence intensity (MFI) of the mouse serum over the secondary anti-mouse antibody alone+/−the standard deviation of five mice per group. Antibody titers were not measured because PSA was expressed as a cytoplasmic protein by the multi-antigen vaccines investigated in this study.

Results:

FIGS. 9A-9D show the results of a representative study that evaluates the cellular immune responses of the triple antigen vaccines by IFN-γ ELISPOT assay. Briefly, 5 mice per group were primed on day 0 and boosted with PMED on days 14, 28 and 49. On day 56, seven days after the last PMED vaccination, recognition of the endogenous prostate antigens was assessed by examining T cell responses to (A) TRAMP C2-PSMA, (B) TRAMP C2-PSCA, (C) TRAMP C2-PSA, and (D) TRAMP C2-PSMA-PSA-PSCA cells by IFN-□γ ELISPOT assay. The TRAMP C2 cells served as a background control for the assay. For IFN-γ T cell responses to endogenous PSMA, a significant response to TRAMP C2-PSMA was observed following the single PSMA PMED vaccination, which was consistent with responses seen in other studies. Similar PSMA-specific IFN-γ T cell response to TRAMP C2-PSMA was detected following the triple antigen vaccinations. In contrast, complete ablation of the response was observed following co-formulated PSMA, PSCA and PSA vaccination (* indicates $p<0.05$ by two-way ANOVA). For IFN-γ T cell responses to endogenous PSCA, no significant difference in response to the TRAMP C2-PSCA cells was observed when comparing the single PSCA vaccine to the four different triple antigen vaccines. For IFN-□γ T cell responses to endogenous PSA, a significant decrease in the response magnitude to TRAMP C2-PSA was detected when comparing the immunogenicity of the single PSA vaccine to either PSCA-F2A-PSMA-IRES-PSA (*** indicates $p<0.001$ by two-way ANOVA) or the co-formulated vaccine (* indicates $p<0.05$ by two-way ANOVA). When examining the response to TRAMP C2-PSMA-PSCA-PSA, the highest magnitude IFN-γ T cell response was observed following the PSA-F2A-PSMA-T2A-PSCA vaccine. Taken together, these data demonstrate recognition of endogenous PSMA, PSCA and PSA and generation of antigen-specific T cell responses to all three prostate antigens using a co-expression DNA vaccination strategy, especially with the PSA-F2A-PSMA-T2A-PSCA vaccine construct. However, the co-formulation DNA vaccination strategy resulted in a loss of antigen-specific IFN-γ T cell responses to PSMA and PSA.

FIGS. 10A-10D show the results of a representative study that evaluates the immunogenicity of the triple antigen vaccines by IFN-γ ELISPOT assay. Briefly, 5 mice per group were primed on day 0 and boosted with PMED on days 14, 28 and 49. On day 56, T cell responses to (A) PSMA peptides, (B) PSMA peptide pools, (C) PSCA peptides and (D) PSA peptides (see Table 22) were assessed by IFN-γ ELISPOT assay. Medium alone served as a background control for the assay. For IFN-γ T cell responses to both the individual and pools of PSMA peptides, compared to the single PSMA vaccine, the highest magnitude response was observed following administration of the PSA-F2A-PSMA-T2A-PSCA triple antigen vaccine. Similarly, the highest magnitude IFN-γ T cell response to PSCA and PSA-specific peptides was detected following administration of the PSA-F2A-PSMA-T2A-PSCA vaccine. The co-formulated PSMA, PSCA and PSA vaccine resulted in low to no T cell responses to the PSMA-specific peptides and low magnitude responses to the PSCA and PSA-specific peptides. These data also demonstrate generation of T cell responses to PSMA, PSCA and PSA when co-expressed from the same vaccine construct. There was consistent and robust IFN-γ T cell responses to all three prostate antigens following PSA-F2A-PSMA-T2A-PSCA vaccination, and significant decreases in the magnitude of IFN-γ T cell responses to the prostate antigens following PSA-T2A-PSCA-F2A-PSMA, PSMA-F2A-PSMA-IRES-PSA and co-formulated PSMA, PSCA and PSA vaccinations.

Figure 11:
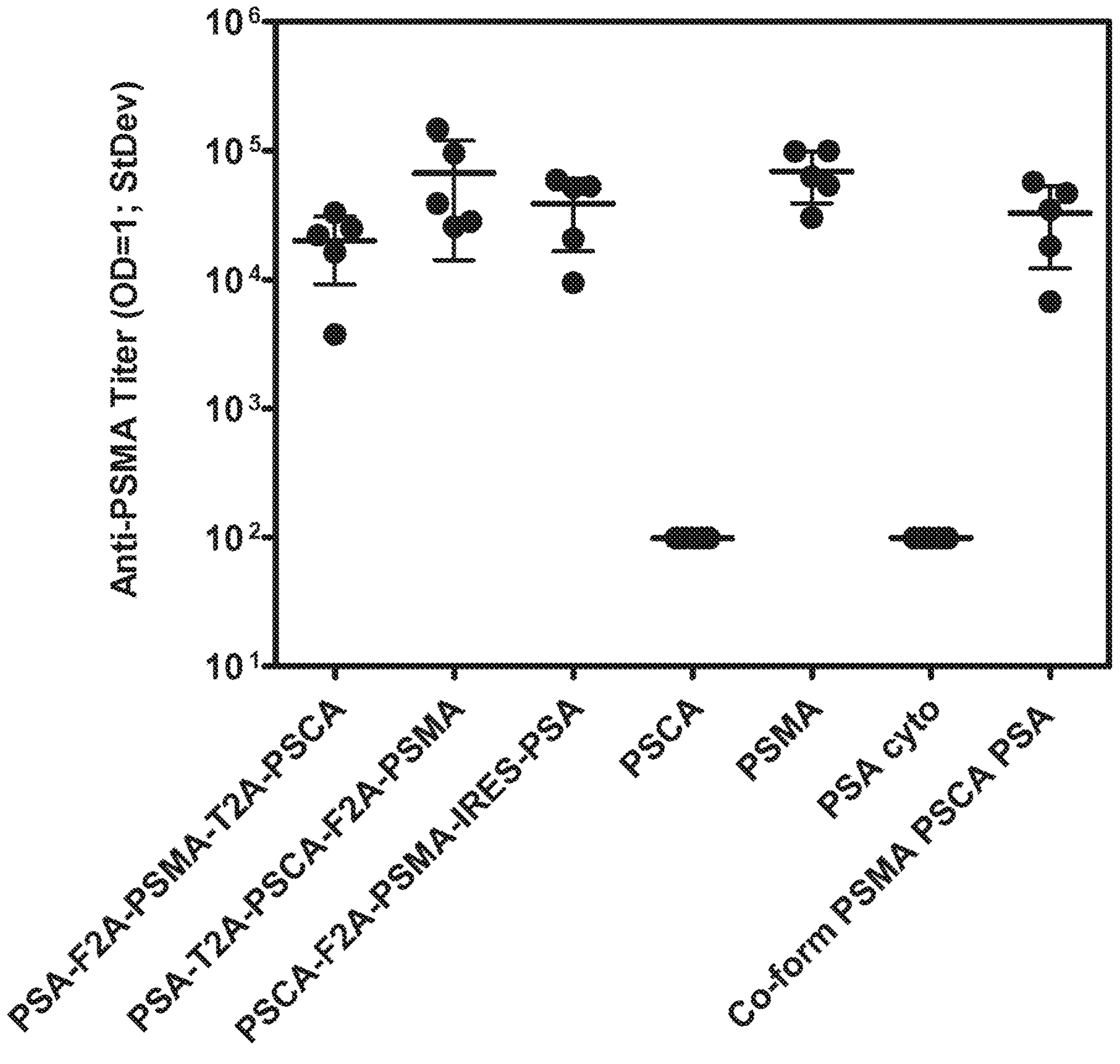
FIG. 11. Graph depicting results of a representative study that evaluates the immunogenicity of the triple antigen vaccines by anti-PSMA antibody titers.

FIG. 11 shows the results of a representative study that evaluates the immunogenicity of the triple antigen vaccines by anti-PSMA antibody titers. Briefly, 5 mice per group were primed on day 0 and boosted with PMED on days 14, 28 and 49. On day 56, serum anti-PSMA antibody titers were assessed by ELISA. All animals vaccinated with PSMA generated significant anti-PSMA antibody titers. There were no significant differences between titers, although vaccination with PSA-F2A-PSMA-T2A-PSCA resulted in slightly lower titers compared to the other groups vaccinated with PSMA. These data demonstrate the generation of anti-PSMA-specific antibodies following triple antigen vaccination, using both co-expression and co-formulation vaccine strategies.

Figure 12:
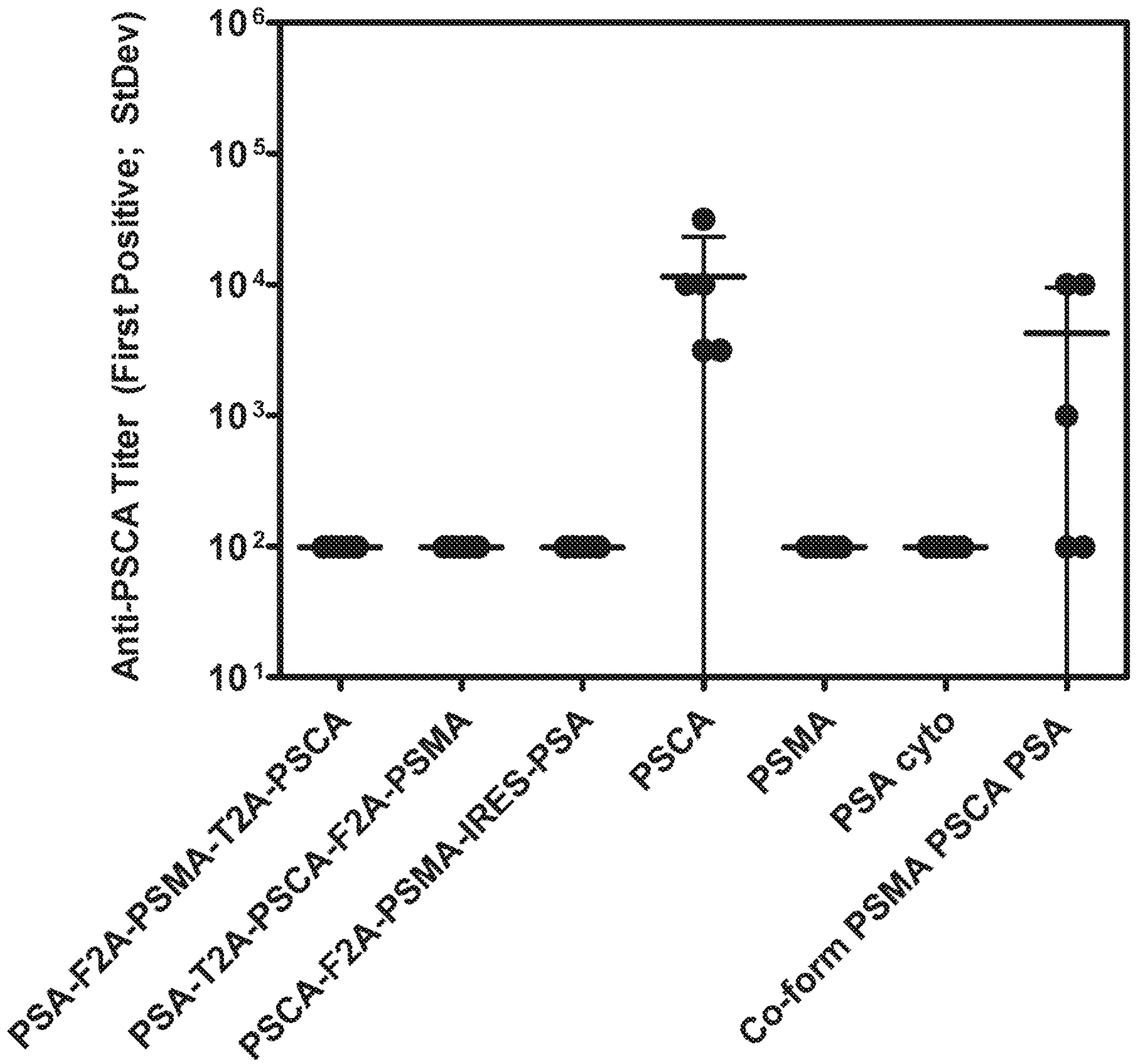
FIG. 12. Graph depicting results of a representative study that evaluates the immunogenicity of the triple antigen vaccines by anti-PSCA antibody titers.

FIG. 12 shows the results of a representative study that evaluates the immunogenicity of the triple antigen vaccines by anti-PSCA antibody titers. Briefly, 5 mice per group were primed on day 0 and boosted with PMED on days 14, 28 and 49. On day 56, serum anti-PSCA antibody titers were assessed by ELISA. Antibody titers were detected in mice vaccinated with PSCA alone and co-formulated PSMA, PSCA and PSA. These results indicate that co-formulation of PSMA, PSCA and PSA elicits a detectable anti-PSCA antibody titer compared to the co-expressed DNA vaccination strategies.

Figure 13:
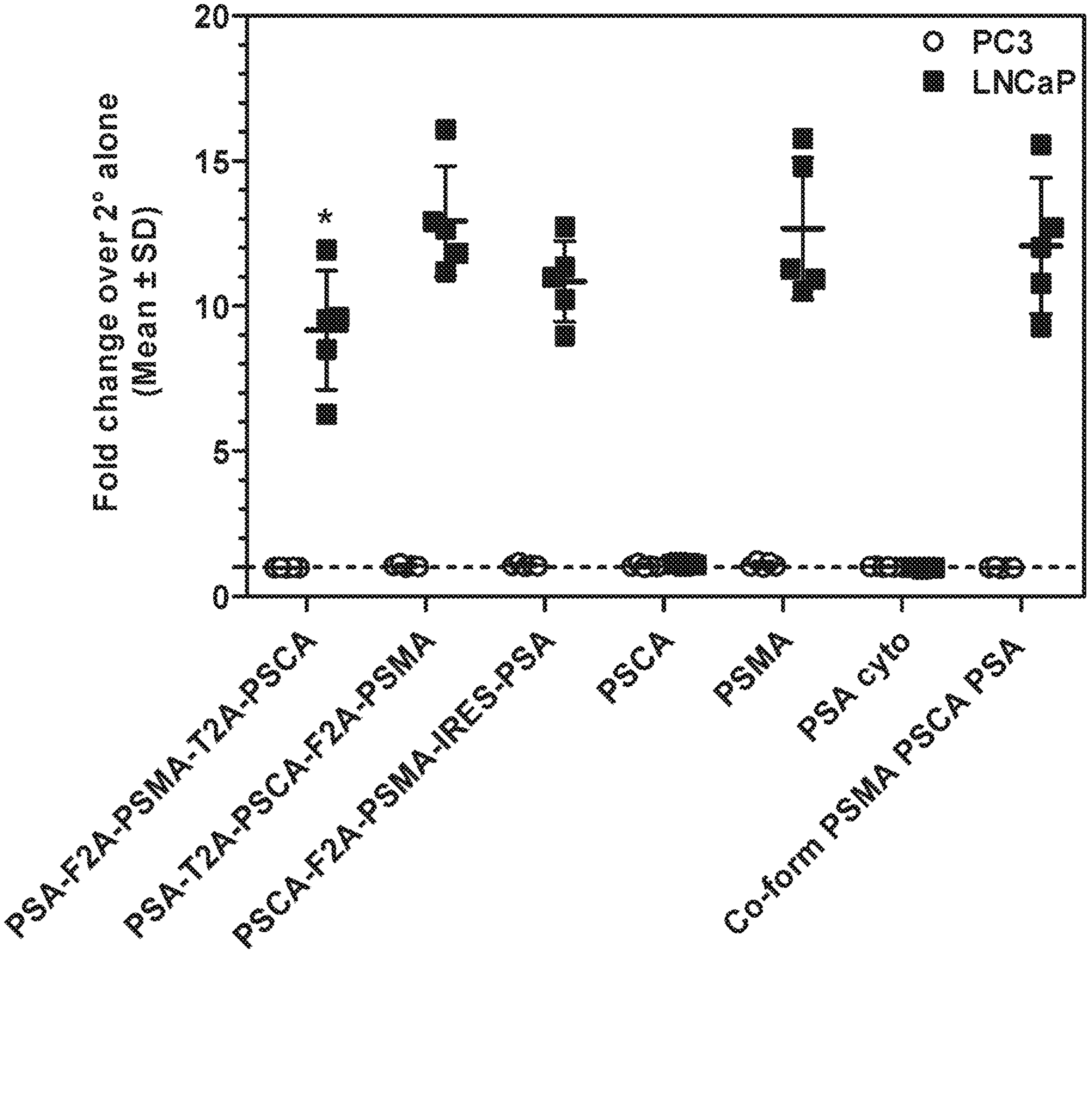
FIG. 13. Graph depicting results of a representative study that evaluates the immunogenicity of the triple antigen vaccines by anti-PSMA antibody cell-surface binding.

FIG. 13 shows the results of a representative study that evaluates the immunogenicity of the triple antigen vaccines by anti-PSMA antibody cell-surface binding. Briefly, 5 mice per group were primed on day 0 and boosted with PMED on days 14, 28 and 49. On day 56, recognition of cell-surface native PSMA was assessed by serum antibody binding to LNCaP and PC3 cells. The PC3 cells served as a background control for the assay. PSA-F2A-PSMA-T2A-PSCA vaccination resulted in anti-PSMA antibodies with a significantly lower binding capacity to LNCaP cells compared to mice vaccinated with PSA-T2A-PSCA-F2A-PSMA and PSMA alone (* indicates p-value <0.05 by one-way ANOVA). All other PSMA vaccinated groups showed no significant difference in anti-PSMA antibody binding. The fold-change over secondary antibody alone for the J591-A mAb was 45.3 (data not shown). Overall, these data demonstrate generation of anti-PSMA-specific antibodies that recognize native PSMA following triple antigen vaccination, using both co-expression and co-formulation DNA vaccination strategies.

Figure 14:
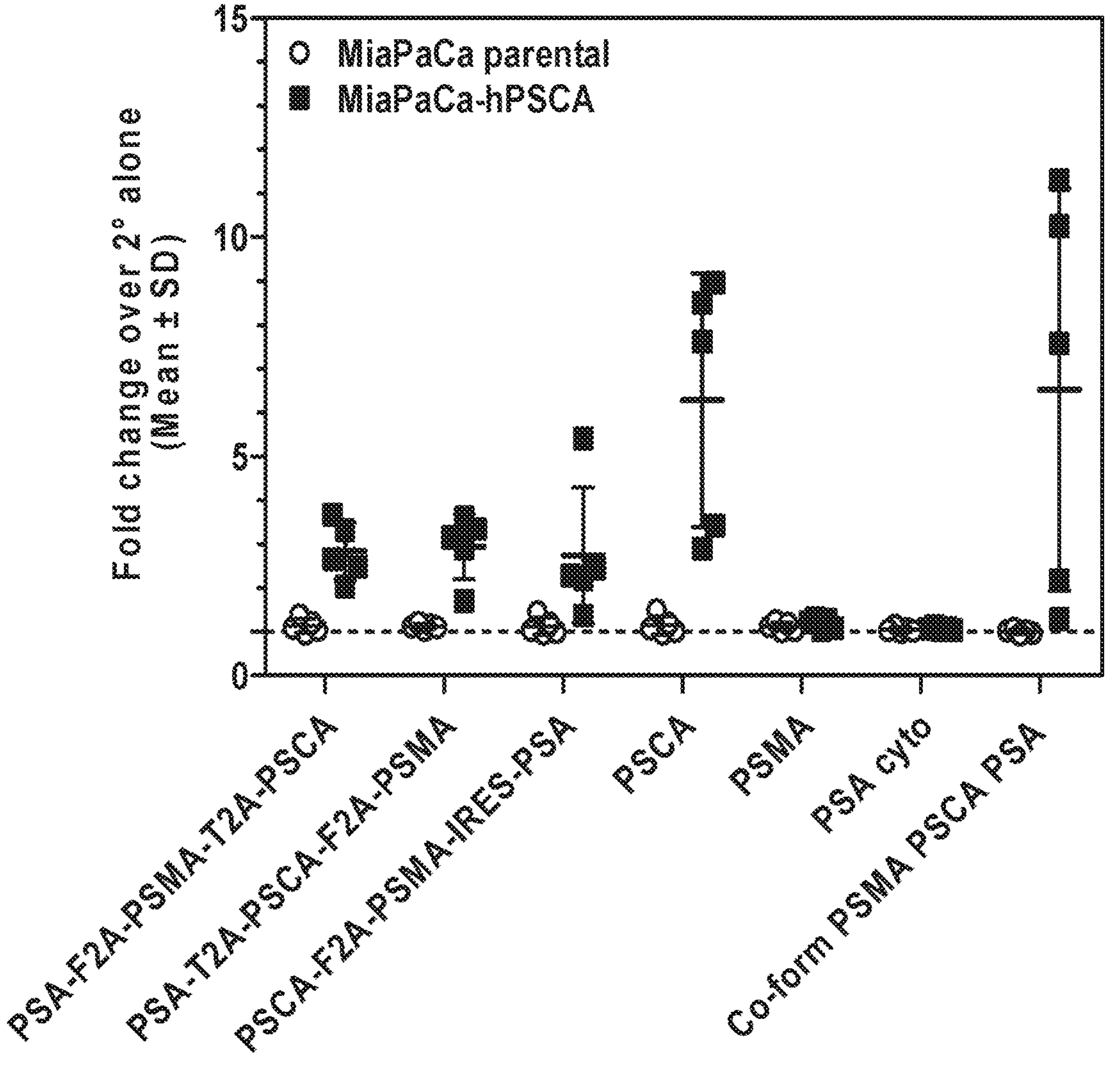
FIG. 14. Graph depicting results of a representative study that evaluates the immunogenicity of the triple antigen vaccines by anti-PSCA antibody cell-surface binding.

FIG. 14 shows the results of a representative study that evaluates the immunogenicity of the triple antigen vaccines by anti-PSCA antibody cell-surface binding. Briefly, 5 mice per group were primed on day 0 and boosted with PMED on days 14, 28 and 49. On day 56, recognition of cell-surface native PSCA was assessed by serum antibody binding to Ad-PSCA transduced and untransduced MIA-PaCa-2 cells. The untransduced, parental cells served as a background control for the assay. With the exception of the single PSMA and single PSA cyto vaccines, all vaccine regimens with PSCA resulted in significant anti-PSCA antibody binding to Ad-PSCA transduced MIA-PaCa-2 cells compared to the parental cells. There were no significant differences in the anti-PSCA antibody binding to Ad-PSCA transduced MIA-PaCa-2 cells between the PSCA-vaccinated groups (one-way ANOVA, p-value >0.05). The fold change over secondary antibody alone for the 7F5 mAb was 18.7 (data not shown). Overall, these data demonstrate the generation of anti-PSCA-specific antibodies that recognize native PSCA following triple antigen vaccination, using both co-expression and co-formulation DNA vaccination strategies.

Example 6. Immunogenicity of Dual Antigen Vaccines

The following examples are provided to illustrate the capability of dual antigen vaccines expressing two prostate antigens to elicit antigen-specific T and B cell responses to the two encoded prostate antigens.

6A. Immunogenicity of Dual Antigen Vaccines Containing PSMA and PSCA in C57BL/6:

Study procedure.

Cellular Immune Response Study.

Female C57BL/6 mice were primed on day 0 and boosted on days 14, 28, 42 and 70 with human PSMA and PSCA expressing DNA by PMED epidermal injection. In total, five different dual antigen DNA vaccination strategies were evaluated, which included four DNA vaccines that co-expressed the antigens and one co-formulation approach. For co-expression, single DNA vaccine plasmids encoding two prostate antigens, PSMA and PSCA, linked by a dual promoter, 2A peptides or IRES were administered. These included PSMA-PSCA dual promoter (plasmid ID #460), PSMA-T2A-PSCA (plasmid ID #451), PSCA-F2A-PSMA (plasmid ID #454) and PSCA-IRES-PSMA (plasmid ID #603). For co-formulation, two different DNA plasmids, each individually encoding PSMA and PSCA, were co-formulated onto a single gold particle for PMED delivery. With the exception of co-formulation, the DNA elements that control co-expression (dual promoter, 2A and IRES) differ in length, transgene expression efficiency and the presence of foreign genetic material attached to the target transgenes. As controls, C57BL/6 mice were vaccinated with DNA expressing a single prostate antigen, PSMA or PSCA. For the co-expressed dual or single antigen DNA vaccines, a total dose of 2 μg of DNA vaccine was given per PMED administration, whereas 2 μg of each DNA vaccine plasmid (total of 4 μg of DNA per administration) was given for the co-formulation. Cellular immune responses of the dual and single antigen vaccines were measured by collecting the spleens from each animal on day 77, seven days after the final PMED vaccination. Splenocytes were isolated and subjected to an IFN-γ ELISPOT assay to measure the PSMA and PSCA-specific T cell responses. Briefly, $2\times10^5$ splenocytes from individual animals were plated per well with $5\times10^4$ per well of TRAMP-C2 cells expressing a single endogenous human prostate antigen or PSMA, PSCA and PSA together, or with individual or pools of human PSMA and PSCA-specific peptides at 10 μg/ml (see Table 22 for peptides and peptide pool composition), or medium alone as a control. Each condition was performed in triplicate. The plates were incubated for 20 h at 37° C. and 5% $CO_2$, washed and developed after incubation as per the manufacturer's instructions. The number of IFN-γ SFC was counted by a CTL reader. The results are presented in FIGS. 15 and 16, which show the average number of PSMA or PSCA-specific SFCs+/−the standard deviation of five mice per group, normalized to $1\times10^6$ splenocytes.

Antibody Response Study.

Antibody responses against the dual and single antigen vaccines were measured by collecting the serum from each animal on day 77, seven days after the final PMED vaccination. The anti-PSMA and anti-PSCA antibody titers in the serum was determined using ELISA as described in Example 5. The results are presented in FIGS. 17 and 18, which show the average titers+/−the standard deviation of five mice per group.

Figure 19:
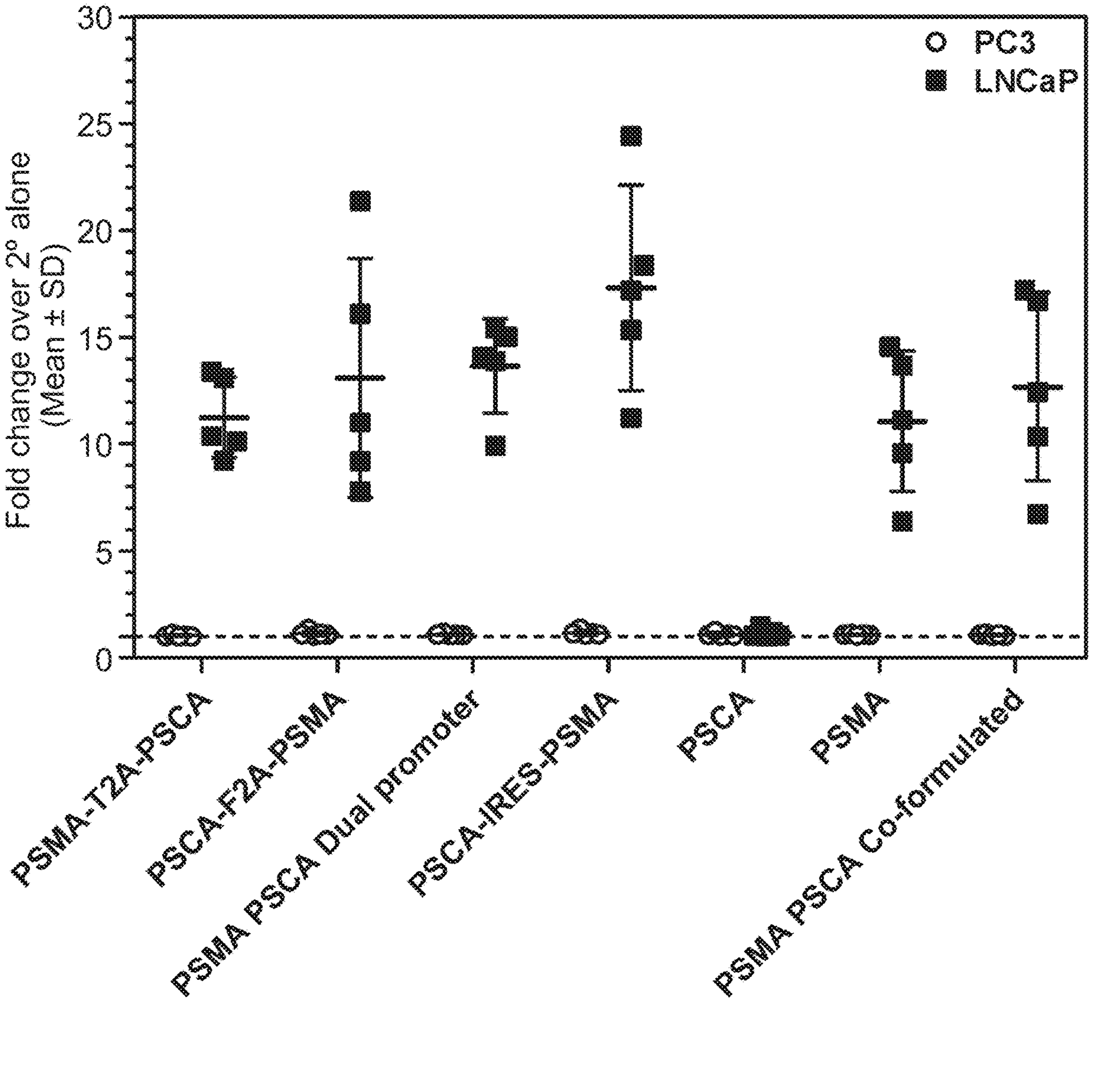
FIG. 19. Graph depicting results of a representative study that evaluates the immunogenicity of the dual antigen vaccines by anti-PSMA antibody cell-surface binding.
Figure 20:
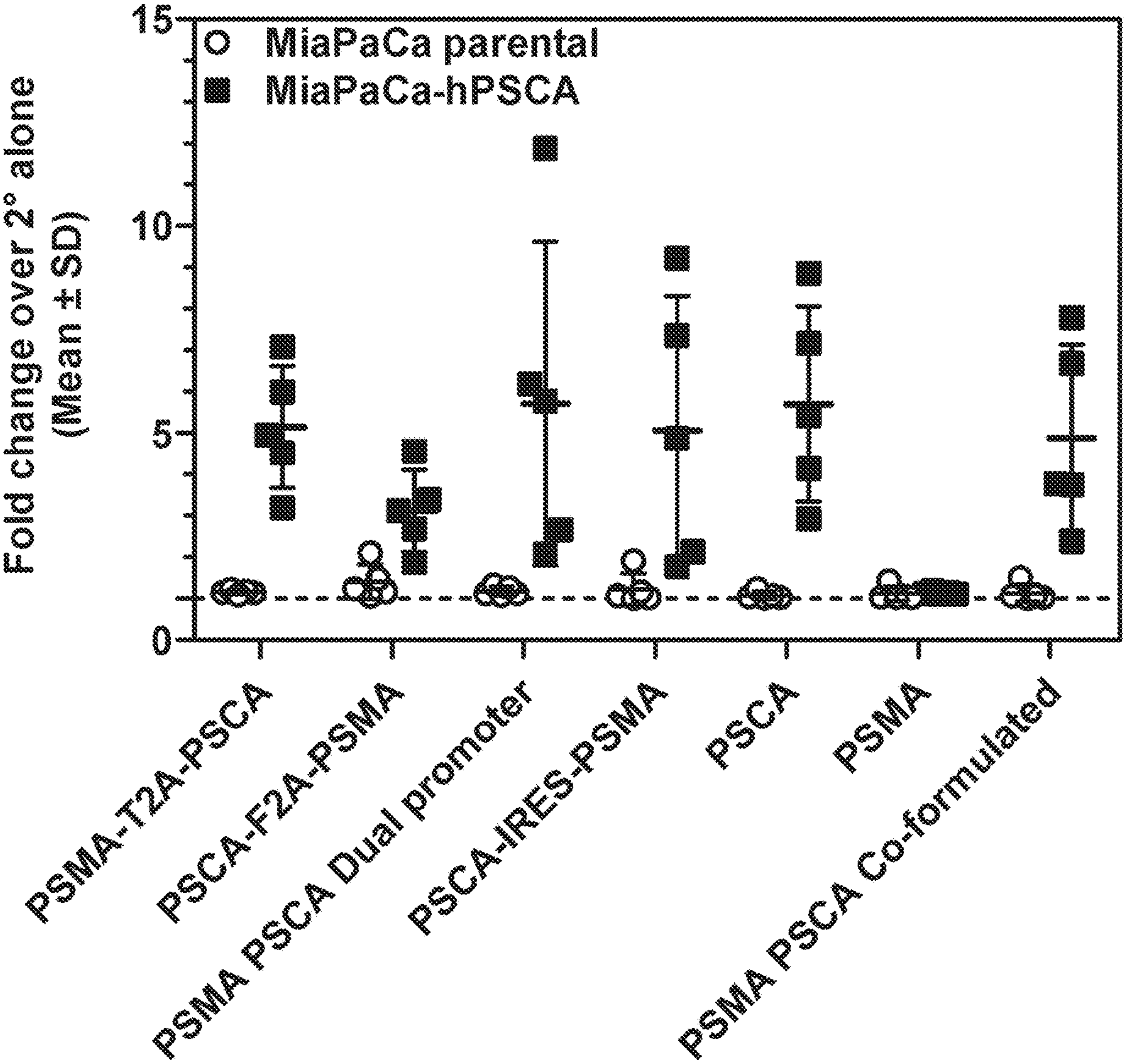
FIG. 20. Graph depicting results of a representative study that evaluates the immunogenicity of the dual antigen vaccines by anti-PSCA antibody cell-surface binding.
Figure 21A:
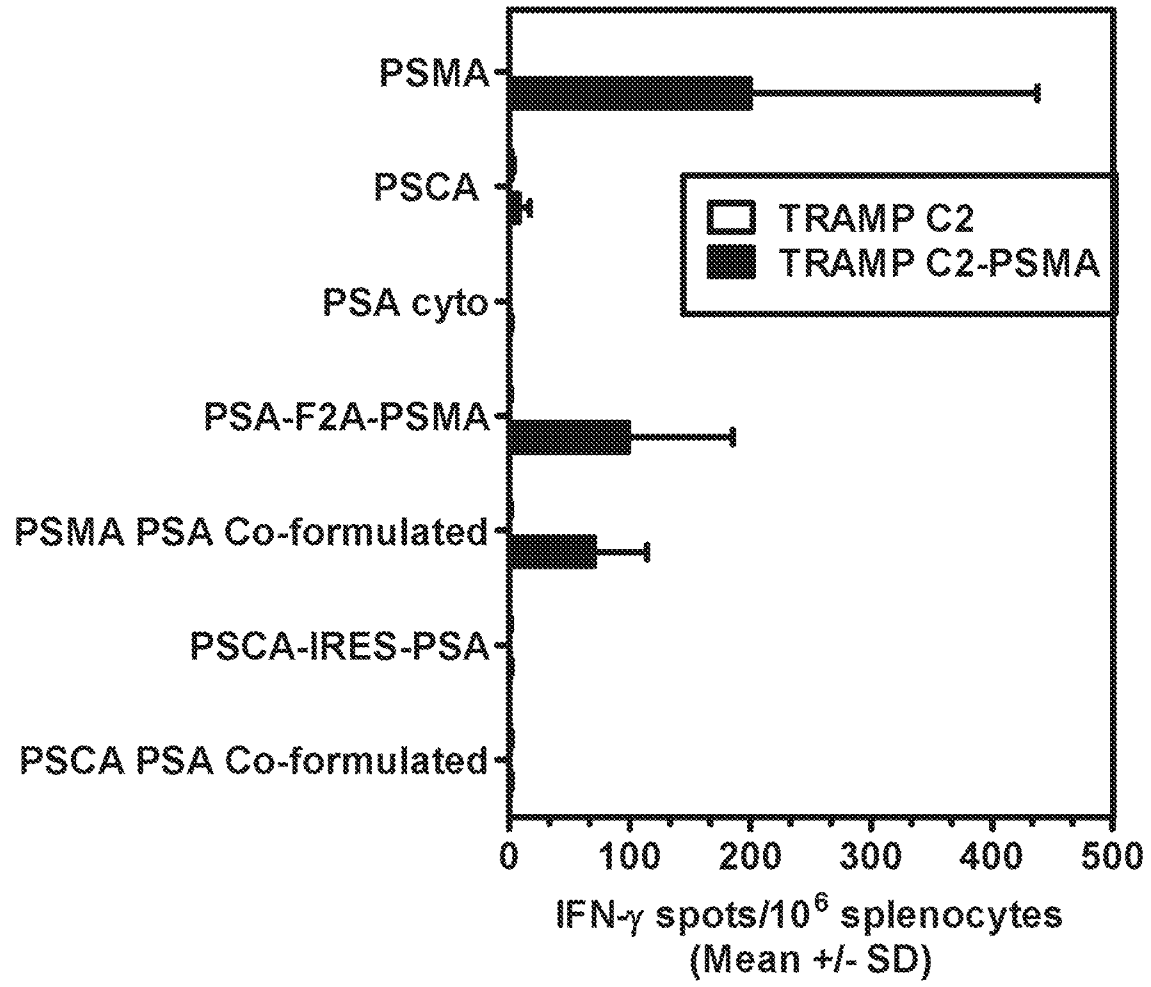
FIGS. 21A-21D. Graphs depicting results of a representative study that evaluates the immunogenicity of the dual antigen vaccines by IFN-γ ELISPOT assay, in which recognition of endogenous PSMA, PSCA, and PSA was assessed by examining T cell responses to (a) TRAMP C2 cells expressing PSMA (FIG. 21A), (b) TRAMP C2 cells expressing PSCA (FIG. 21B), (c) TRAMP C2 cells expressing PSA (FIG. 21C), and (d) TRAMP C2 cells expressing PSMA, PSA, and PSCA (FIG. 21D).
Figure 21B:
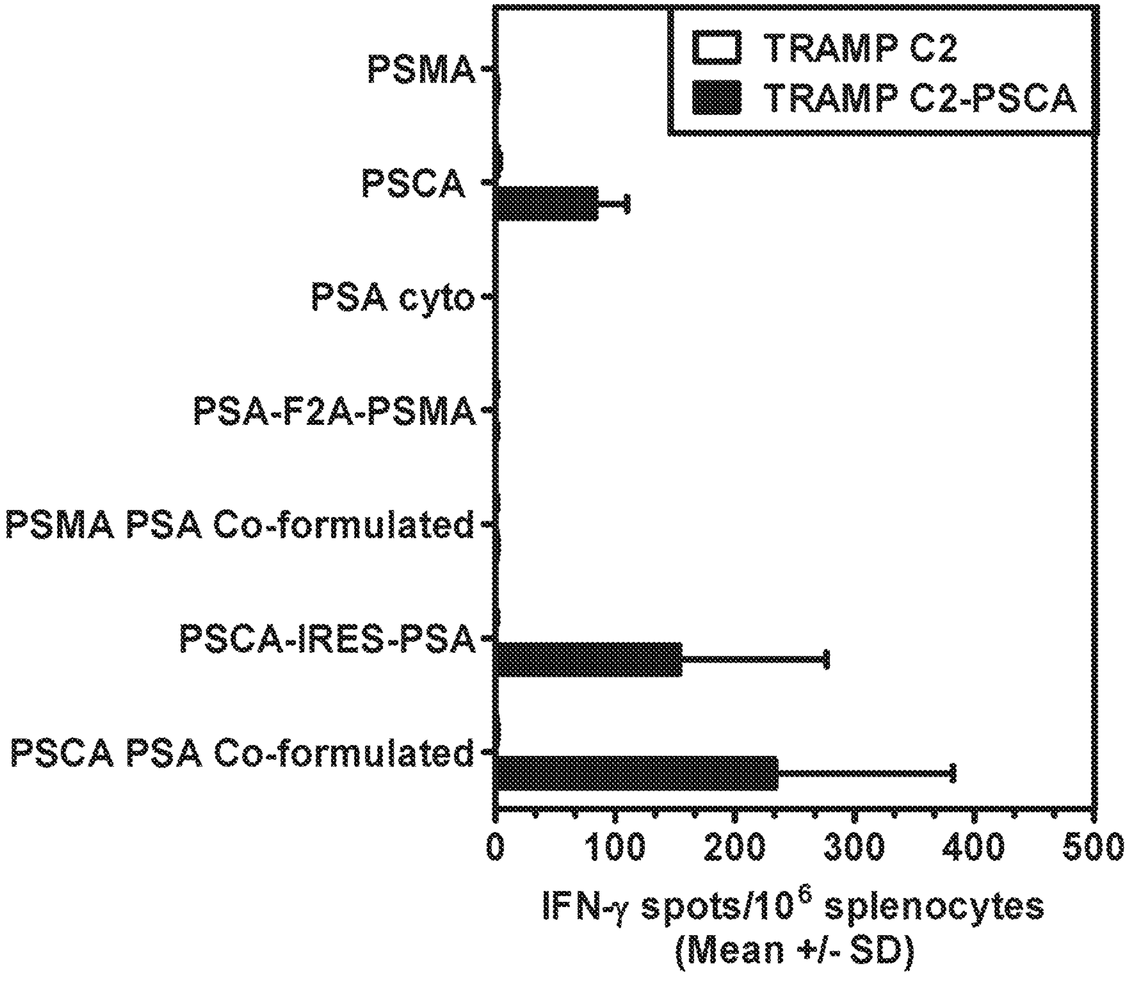
Figure 21C:
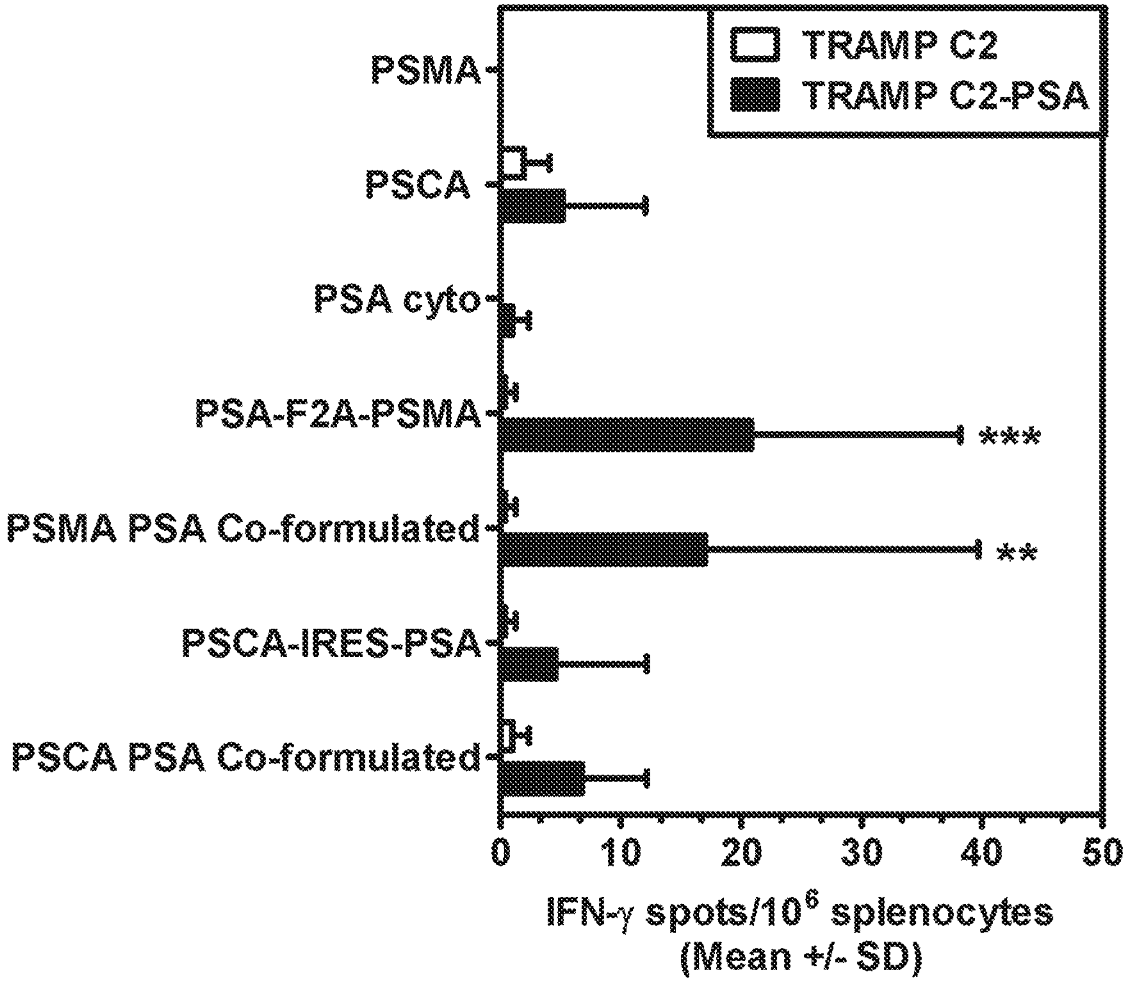
Figure 21D:
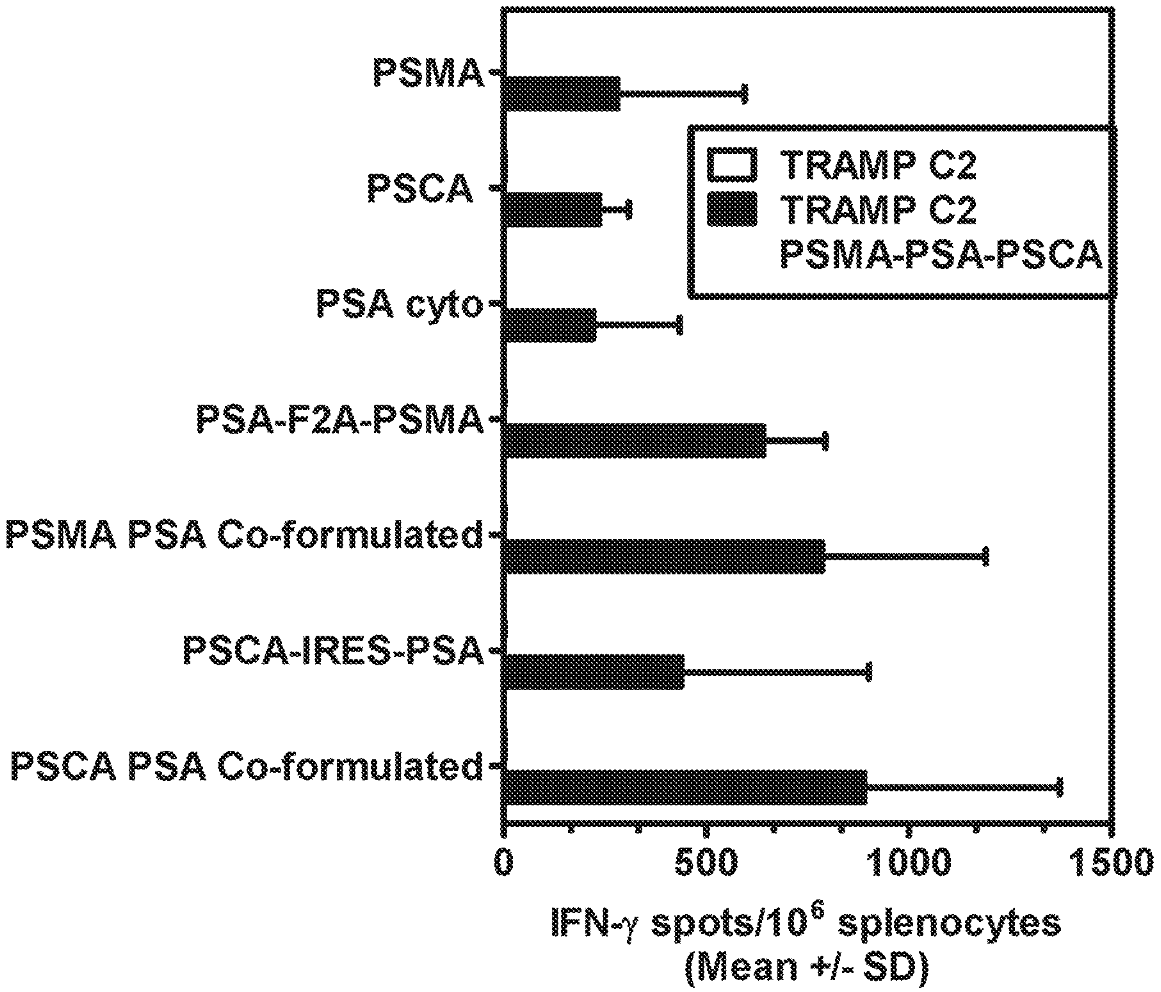

Serum was also subjected to a FACS assay to measure antibody binding to either human PSMA or PSCA expressed on the cell surface of appropriate cell lines, thus determining whether antibodies generated by the multi-antigen vaccines were capable of recognizing native PSMA and PSCA conformations, respectively. Antibody binding to cell-surface native PSA was not measured because PSA was expressed as a cytoplasmic protein by the multi-antigen vaccines investigated in this study. The FACS assay was conducted according to procedure as described in Example 5. The results presented in FIGS. 19 and 20, show the average fold-change in MFI of the mouse serum over the secondary anti-mouse antibody alone+/−the standard deviation of five mice per group. Antibody titers and binding to cell-surface native PSA were not measured because PSA was expressed as a cytoplasmic protein by the multi-antigen vaccines investigated in this study.

Results.

Figure 15A:
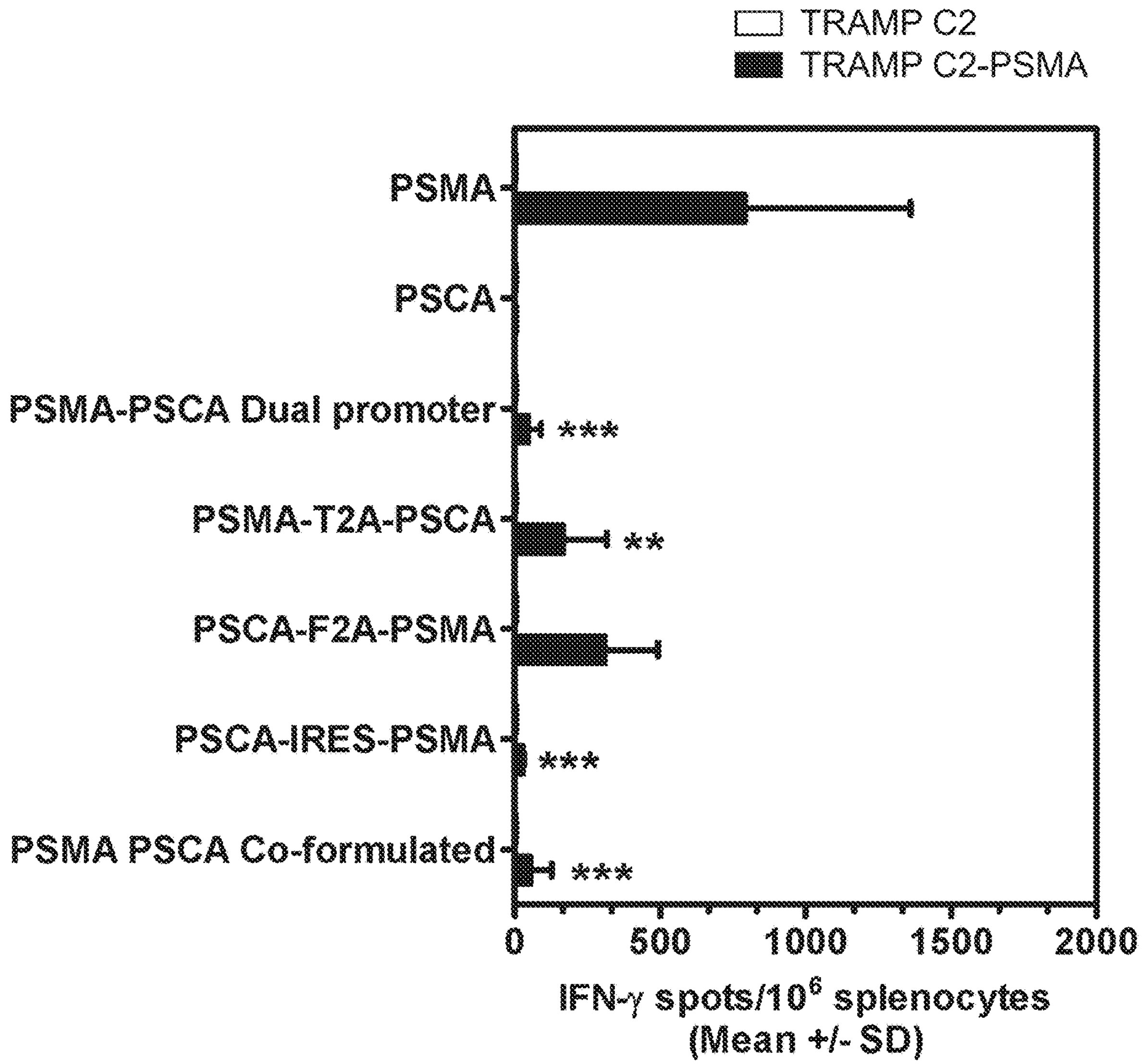
FIGS. 15A-15C. Graphs depicting results of a representative study that evaluates the immunogenicity of the dual antigen vaccines by IFN-γ ELISPOT assay, in which recognition of endogenous prostate antigens was assessed by examining T cell responses to (a) TRAMP C2 cells expressing PSMA (FIG. 15A), (b) TRAMP C2 cells expressing PSCA (FIG. 15B), and (c) TRAMP C2 cells expressing PSMA, PSA, and PSCA (FIG. 15C).
Figure 15B:
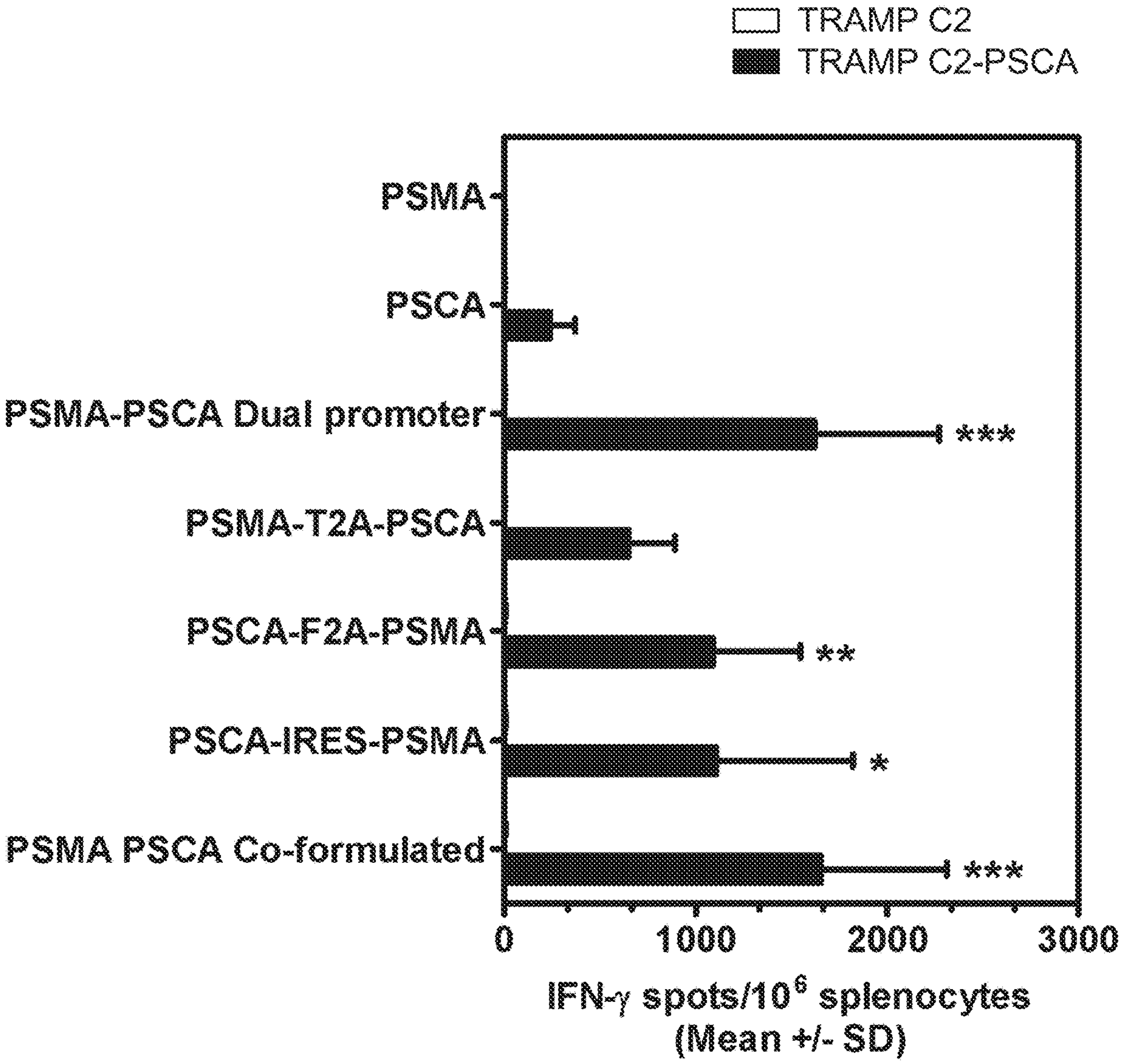
Figure 15C:
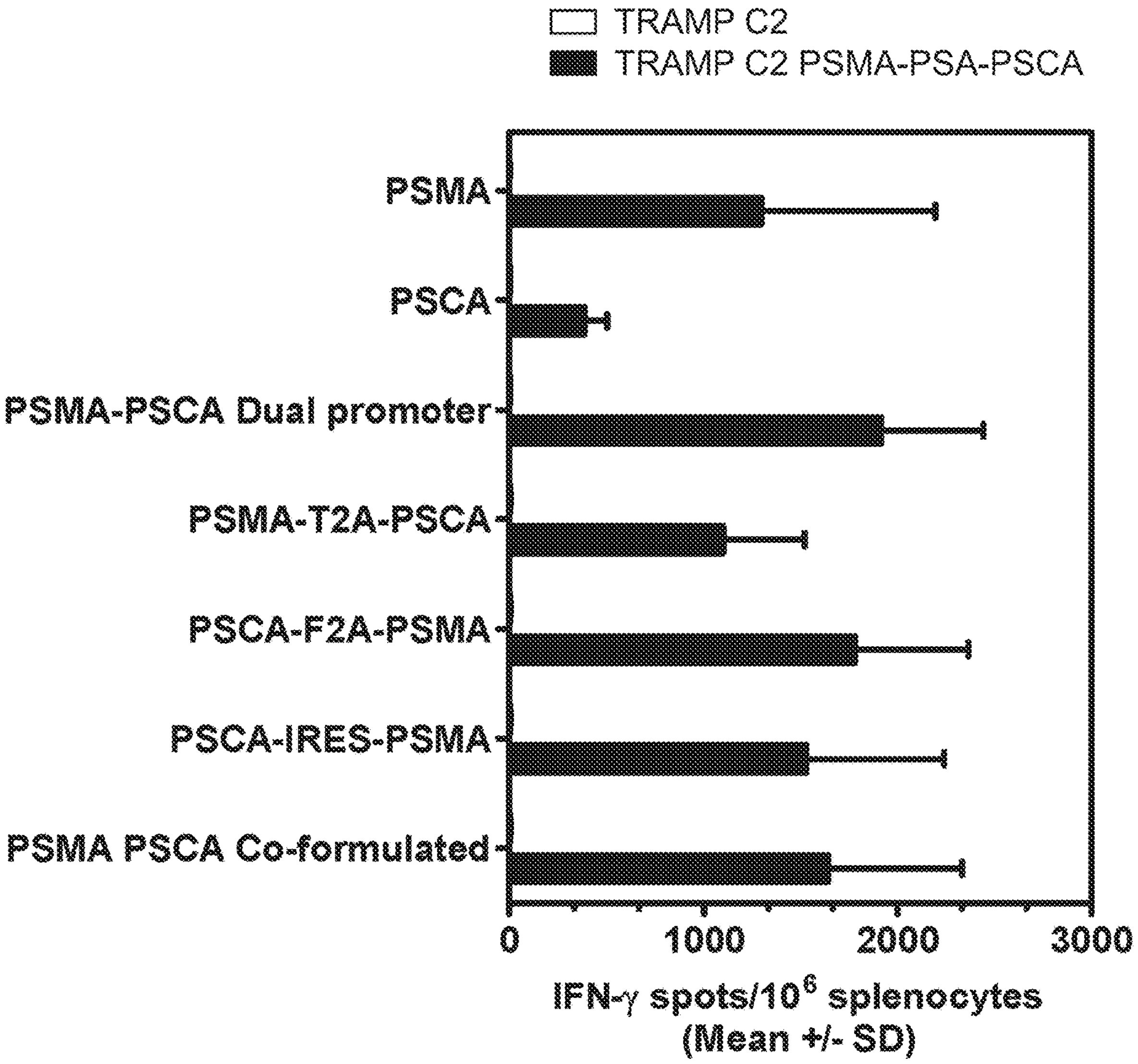

FIGS. 15A-15C show the results of a representative study that evaluates the immunogenicity of the dual antigen vaccines by IFN-γ ELISPOT assay. Briefly, 5 mice per group were primed on day 0 and boosted with PMED on days 14, 28, 42 and 70. On day 77, recognition of endogenous PSMA and PSCA was assessed by examining T cell responses to (A) TRAMP C2-PSMA, (B) TRAMP C2-PSCA and (C) TRAMP C2-PSMA-PSA-PSCA cells by IFN-□γ ELISPOT assay. The TRAMP C2 cells served as a background control for the assay. For IFN-γ T cell responses to endogenous PSMA, the magnitude of the response TRAMP C2-PSMA was significantly decreased following vaccination with PSMA-PSCA dual promoter, PSMA-T2A-PSCA, PSCA-IRES-PSMA and co-formulated PSMA PSCA compared to vaccination with PSMA alone ( and * indicate p-values <0.01 and <0.001, respectively, by two-way ANOVA). However, the PSCA-F2A-PSMA vaccine construct elicited a similar magnitude IFN-γ T cell response to the TRAMP C2-PSMA cells as the single PSMA vaccine. For IFN-□γ T cell responses to endogenous PSCA, significantly increased responses were observed following vaccination with several of the dual antigen vaccines, including PSMA-PSCA dual promoter, PSCA-F2A-PSMA, PSCA-IRES-PSMA and co-formulated PSMA PSCA compared to the PSCA vaccine alone (*,  and * indicate p-values of <0.05, 0.01 and 0.001, respectively, by two-way ANOVA). The PSCA-T2A-PSMA vaccine construct elicited a similar magnitude IFN-γ T cell response to the TRAMP C2-PSCA cells as the single PSCA vaccine. Comparing the IFN-γ T cell responses to TRAMP C2-PSMA-PSA-PSCA, there were no significant differences between the groups vaccinated with different dual antigen vaccines. Taken together, these data demonstrate generation of PSMA and PSCA-specific T cell responses following dual antigen vaccination, using both co-expression and co-formulation DNA vaccination strategies.

Figure 16A:
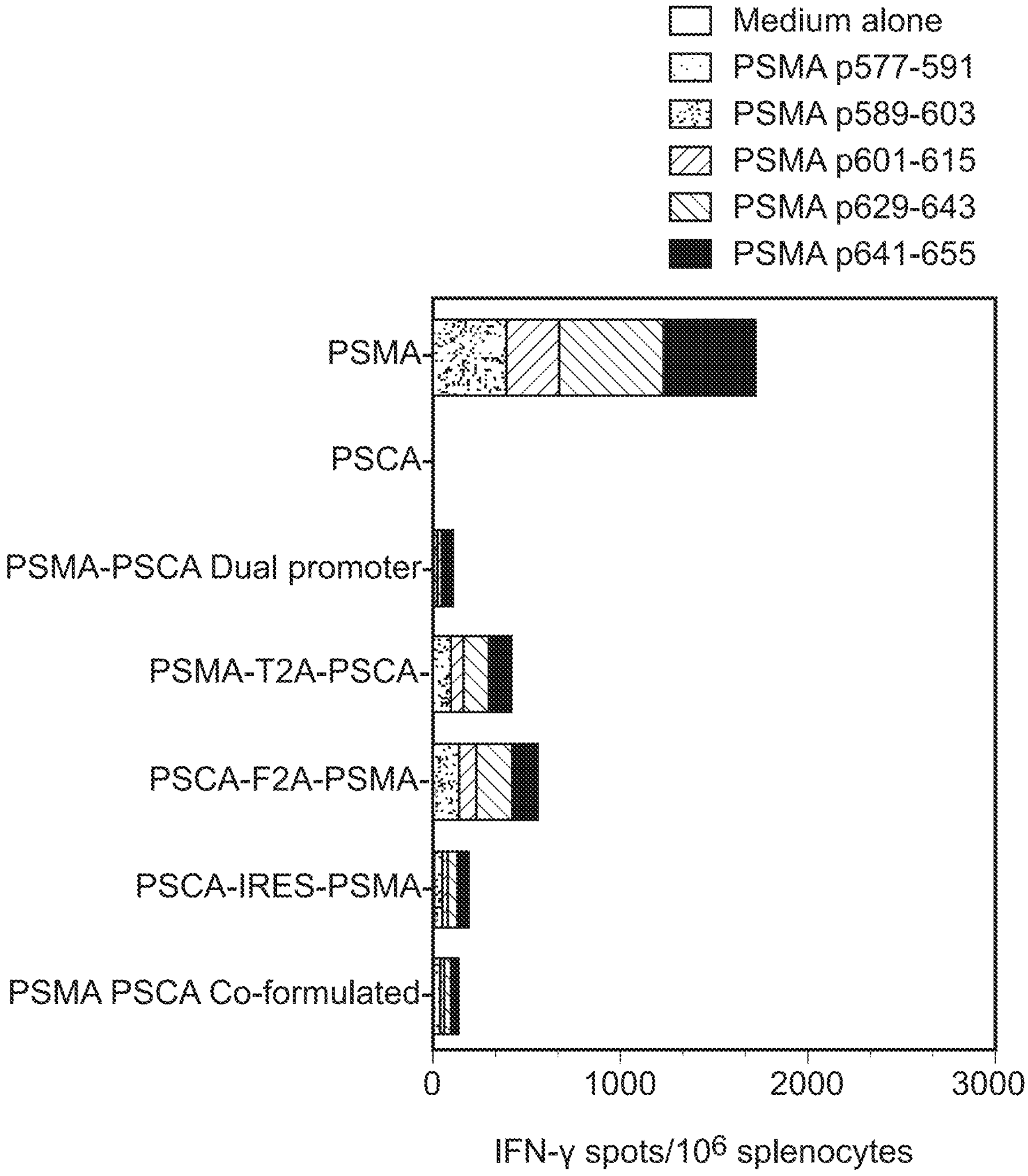
FIGS. 16A-16C. Graphs depicting results of a representative study that evaluates the immunogenicity of the dual antigen vaccines by IFN-γ ELISPOT assay, in which T cell responses to (a) individual PSMA peptides (FIG. 16A), (b) three different PSMA peptide pools (FIG. 16B), and (c) a PSCA peptide (FIG. 16C) were assessed.
Figure 16B:
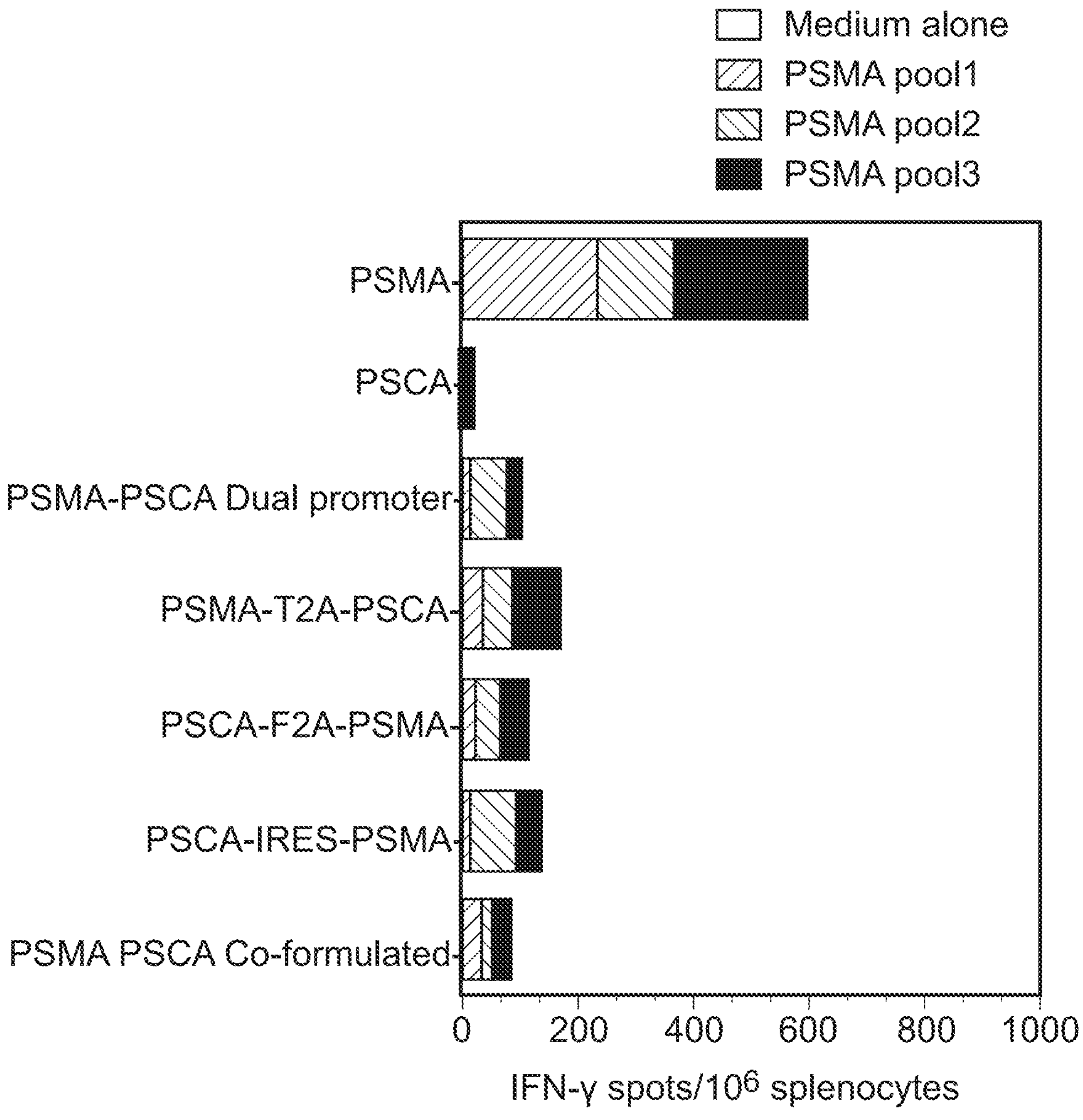
Figure 16C:
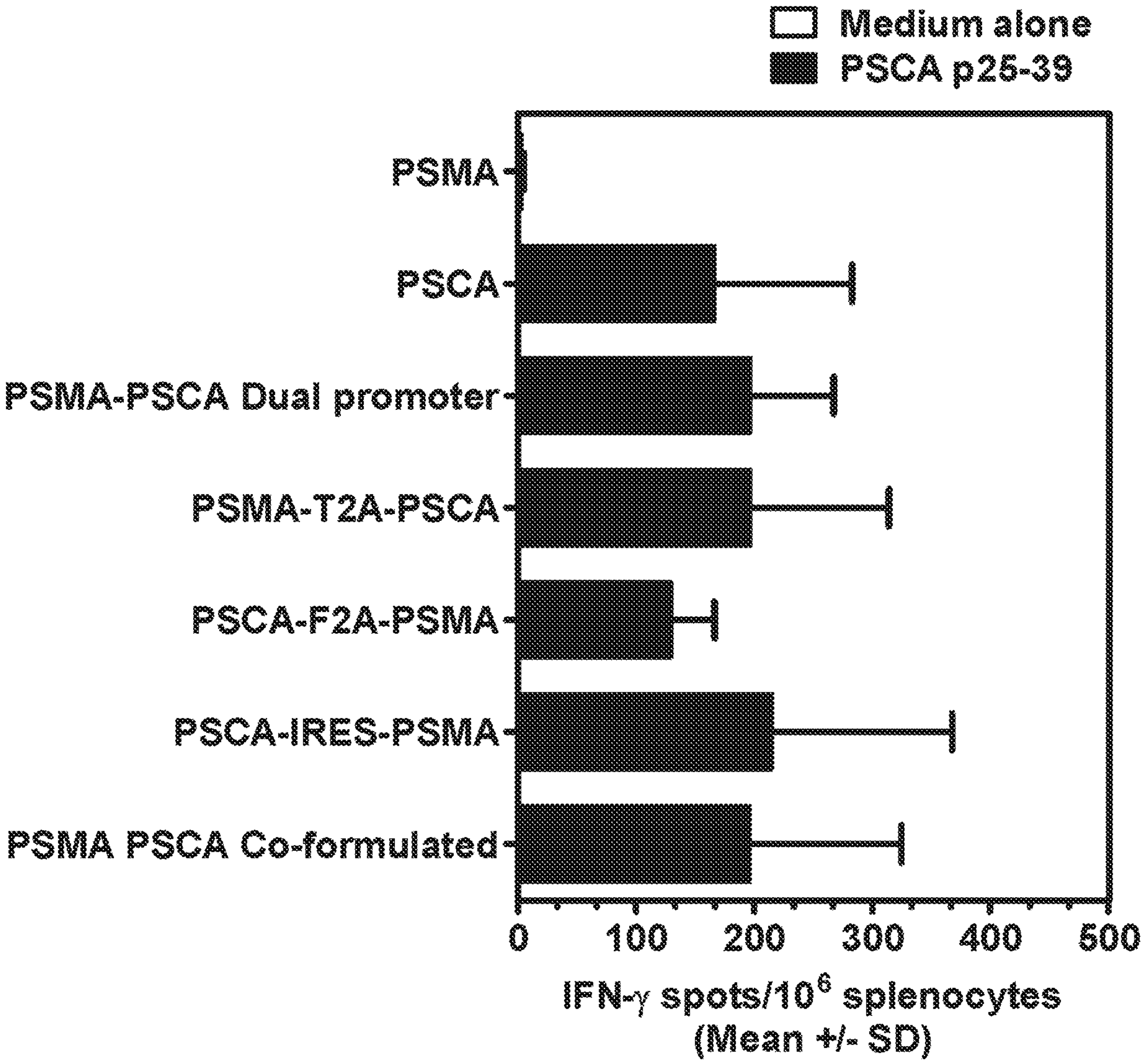

FIGS. 16A-16C show the results of a representative study that evaluates the immunogenicity of the dual antigen vaccines by IFN-γ ELISPOT assay. Briefly, 5 mice per group were primed on day 0 and boosted with PMED on days 14, 28, 42 and 70. On day 77, T cell responses to (A) PSMA peptides, (B) PSMA peptide pools and (C) PSCA peptides (see Table 22) were assessed by IFN-γ ELISPOT assay. Medium alone served as a background control for the assay. For IFN-γ T cell responses to both the individual and pools of PSMA peptides, the highest magnitude responses compared to the single PSMA vaccine were observed following the PSMA-T2A-PSCA and PSCA-F2A-PSMA dual antigen vaccinations. A significant reduction in the IFN-γ T cell response to the individual PSMA peptides was observed following vaccination with PSMA-PSCA dual promoter, PSCA-IRES-PSMA and co-formulated PSMA PSCA. The IFN-γ T cell response to the PSCA-specific peptide was similar between the groups vaccinated with the different dual antigen vaccines. These data also demonstrate generation of T cell responses to both PSMA and PSCA when co-expressed on the same DNA vaccine construct, or delivered as a co-formulation.

Figure 17:
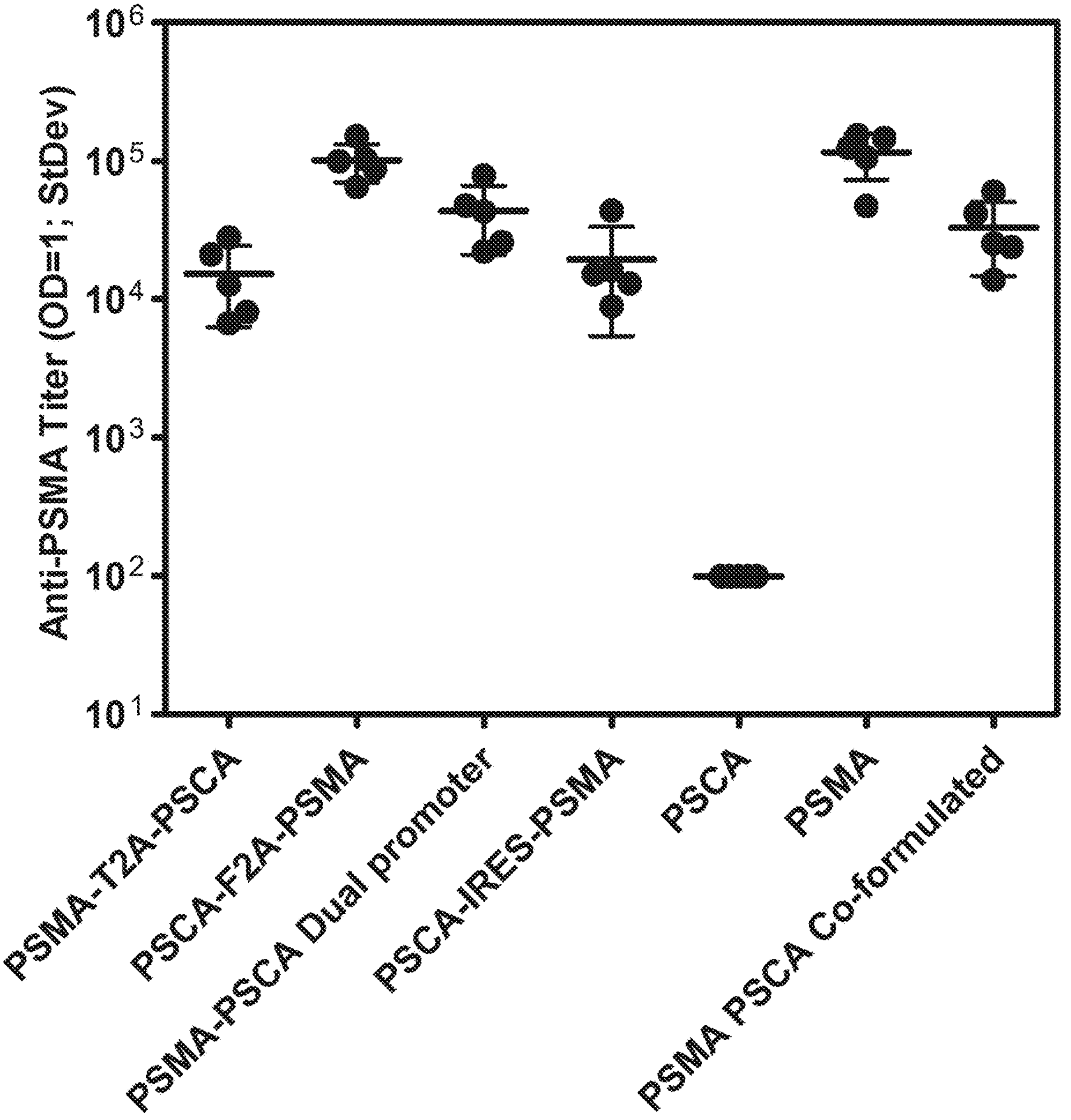
FIG. 17. Graph depicting results of a representative study that evaluates the immunogenicity of the dual antigen vaccines by anti-PSMA antibody titers.

FIG. 17 shows the results of a representative study that evaluates the immunogenicity of the dual antigen vaccines by anti-PSMA antibody titers. Briefly, 5 mice per group were primed on day 0 and boosted with PMED on days 14, 28, 42 and 70. On day 77, serum anti-PSMA antibody titers were assessed by ELISA. All animals vaccinated with PSMA generated significant anti-PSMA antibody titers. Mice vaccinated with the dual vaccine construct, PSCA-F2A-PSMA, and the single PSMA vaccine generated significantly higher antibody titers compared to all other groups of mice vaccinated with PSMA (one-way ANOVA, p-value <0.05). Vaccination with PSMA-PSCA dual promoter and co-formulated PSMA and PSCA resulted in higher antibody titers compared to mice that received the PSMA-T2A-PSCA vaccine. Taken together, these data demonstrate generation of anti-PSMA-specific antibodies following dual antigen DNA vaccination with PSMA and PSCA, using both co-expression and co-formulation vaccination strategies.

Figure 18:
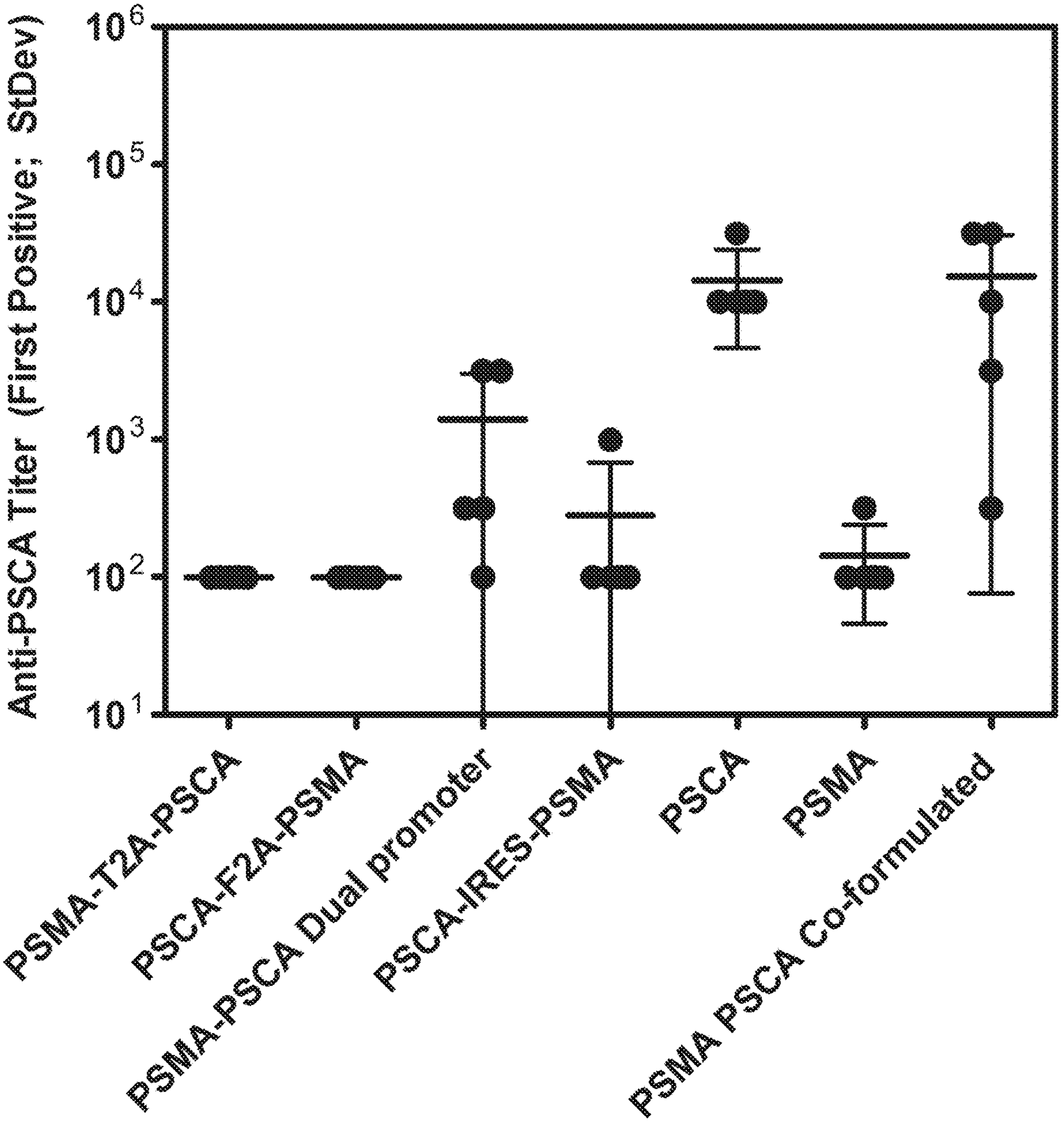
FIG. 18. Graph depicting results of a representative study that evaluates the immunogenicity of the dual antigen vaccines by anti-PSCA antibody titers.

FIG. 18 shows the results of a representative study that evaluates the immunogenicity of the dual antigen vaccines by anti-PSCA antibody titers. Briefly, 5 mice per group were primed on day 0 and boosted with PMED on days 14, 28, 42 and 70. On day 77, serum anti-PSCA antibody titers were assessed by ELISA. Mice vaccinated with the co-formulated PSMA and PSCA, and the single PSCA vaccine generated significantly higher antibody titers compared to all other groups of mice vaccinated with PSCA (one-way ANOVA). Vaccination with PSMA-PSCA dual promoter resulted in higher antibody titers compared to vaccination with PSMA- T2A-PSCA, PSCA-F2A-PSMA and PSCA-IRES-PSMA. These results indicate that co-expression or co-formulation of PSMA and PSCA elicits anti-PSCA antibodies.

FIG. 19 shows the results of a representative study that evaluates the immunogenicity of the dual antigen vaccines by anti-PSMA antibody cell-surface binding. Briefly, 5 mice per group were primed on day 0 and boosted with PMED on days 14, 28, 42 and 70. On day 77, recognition of cell-surface native PSMA was assessed by serum antibody binding to LNCaP and PC3 cells. The PC3 cells served as a background control for the assay. With the exception of the single PSCA vaccine, all vaccine regimens with PSMA resulted in significant anti-PSMA antibody binding to LNCaP cells compared to the control PC3 cells. There were no significant differences in the anti-PSMA antibody binding to LNCaP cells between the PSMA-vaccinated groups (one-way ANOVA, p-value >0.05). The fold change over secondary antibody alone for the J591-A mAb was 45.3 (data not shown). These data demonstrate generation of anti-PSMA-specific antibodies that recognized native PSMA following dual antigen DNA vaccination, using both co-expression and co-formulation vaccination strategies.

FIG. 20 shows the results of a representative study that evaluates the immunogenicity of the dual antigen vaccines by anti-PSCA antibody cell-surface binding. Briefly, 5 mice per group were primed on day 0 and boosted with PMED on days 14, 28, 42 and 70. On day 77, recognition of cell-surface native PSCA was assessed by serum antibody binding to Ad-PSCA transduced and untransduced MIA-PaCa-2 cells. The untransduced, parental cells served as a background control for the assay. With the exception of the single PSMA vaccine, all vaccine regimens with PSCA resulted in significant anti-PSCA antibody binding to Ad-PSCA transduced MIA-PaCa-2 cells compared to the control cells. There were no significant differences in the anti-PSCA antibody binding to Ad-PSCA transduced MIA-PaCa-2 cells between the PSCA-vaccinated groups (one-way ANOVA, p-value >0.05). The fold change over secondary antibody alone for the 7F5 mAb was 18.7 (data not shown). Overall, these data demonstrate generation of anti-PSCA-specific antibodies that recognized native PSCA following dual antigen DNA vaccination, using both co-expression and co-formulation vaccination strategies.

6B. Immunogenicity of Dual Antigen Vaccines Containing Either PSMA and PSA or PSCA and PSA in C57BL/6

Study Procedure.

Cellular Immune Response Study.

Female C57BL/6 mice were primed on day 0 and boosted on days 14 and 28 with human PSMA, PSCA and PSA expressing DNA by PMED epidermal injection. In total, four different dual antigen vaccines strategies were evaluated, which included two co-expression approaches and two co-formulation strategies. For co-expression, a single DNA plasmid encoding two prostate antigens, PSMA and PSA linked a 2A peptide (plasmid ID #5300) or PSCA and PSA linked by IRES (plasmid ID #455) were administered. For co-formulation, plasmids individually encoding PSMA, PSCA or PSA were co-formulated onto a single gold particle for PMED delivery. Specifically, these included PSMA and PSA co-formulated and PSCA and PSA co-formulated. As controls, C57BL/6 mice were vaccinated with DNA expressing a single prostate antigen, PSMA, PSCA or PSA. For the co-expressed dual or single antigen vaccines, a dose 2 μg of DNA was given per PMED administration, whereas 2 μg of each DNA vaccine plasmid (total of 4 μg of DNA per administration) was given for the co-formulation. Cellular immune responses of the dual and single antigen vaccines were measured by collecting the spleens from each animal on day 35. Splenocytes were isolated and subjected to an IFN-γ ELISPOT assay to measure the PSMA, PSCA and PSA-specific T cell responses. Briefly, $2\times10^5$ splenocytes from individual animals were plated per well with $5\times10^4$ per well of TRAMP-C2 cells expressing a single endogenous human prostate antigen or PSMA, PSCA and PSA together, or with individual or pools of human PSMA, PSCA and PSA-specific peptides at 10 μg/ml (see Table 22 for peptides and peptide pool composition), or medium alone as a control. Each condition was performed in triplicate. The plates were incubated for 20 h at 37° C. and 5% $CO_2$, washed and developed after incubation as per manufacturer's instructions. The number of IFN-γ SFC was counted by a CTL reader. The results are presented in FIGS. 21 and 22, which show the average number of PSMA, PSCA and PSA-specific SFCs+/−the standard deviation of five mice per group, normalized to $1\times10^6$ splenocytes.

Antibody Response Study.

Female C57BL/6 mice were primed on day 0 and boosted on days 14, 28 and 49 with human PSMA, PSCA and PSA expressing DNA by PMED. Antibody responses against the dual and single antigen vaccines were measured by collecting the serum from each animal on day 56, seven days after the final PMED vaccination. The anti-PSMA and anti-PSCA antibody titers in the serum was determined using ELISA assay as described in Example 5. The results are presented in FIGS. 23 and 24, which show the average titers+/−the standard deviation of five mice per group.

Serum was also subjected to a FACS assay to measure antibody binding to either human PSMA or PSCA expressed on the cell surface of appropriate cell lines, thus determining whether antibodies generated by the multi-antigen vaccines were capable of recognizing native PSMA and PSCA conformations, respectively. Antibody binding to cell-surface native PSA was not measured because PSA was expressed as a cytoplasmic protein by the multi-antigen vaccines investigated in this study. The FACS assay was conducted according to the procedure as described in Example 5. The results are presented in FIGS. 25 and 26, which show the average fold change in MFI of the mouse serum over the secondary anti-mouse antibody alone+/−the standard deviation of five mice per group. Antibody titers and binding to cell-surface native PSA were not measured because PSA was expressed as a cytoplasmic protein by the multi-antigen vaccines investigated in this study.

Results.

FIGS. 21A-21D show the results of a representative study that evaluates the immunogenicity of the dual antigen vaccines by IFN-γ ELISPOT assay. Briefly, 5 mice per group were primed on day 0 and boosted with PMED on days 14 and 28. On day 35, recognition of endogenous PSMA, PSCA and PSA was assessed by examining T cell responses to (A) TRAMP C2-PSMA, (B) TRAMP C2-PSCA, (C) TRAMP C2-PSA and (D) TRAMP C2-PSMA-PSA-PSCA cells by IFN-□γ ELISPOT assay. The TRAMP C2 cells served as a background control for the assay. For IFN-□γ T cell responses to endogenously expressed PSMA on cells, no significant differences were observed between responses to TRAMP C2-PSMA following vaccination with dual antigens containing PSMA (PSA-F2A-PSMA and co-formulated PSMA and PSA) and PSMA alone. Likewise, for IFN-□γ T cell responses to endogenous PSCA, there were no observed differences in response magnitude to TRAMP C2-PSCA between the dual PSCA-IRES-PSA and co-formulated PSCA and PSA vaccines compared to the single PSCA vaccine. For IFN-□γ T cell responses to endogenous PSA, a significant increase in the response magnitude to TRAMP C2-PSA was detected when comparing the immunogenicity of the single PSA vaccine to either PSA-F2A-PSMA (* indicates $p<0.001$ by two-way ANOVA) and co-formulated PSMA and PSA ( indicates $p<0.01$ by two-way ANOVA). There were no observed differences in response magnitude to TRAMP C2-PSA when comparing animals that received the dual PSCA and PSA vaccines to the single PSA vaccine. When examining the IFN-γ T cell response to TRAMP C2-PSMA-PSA-PSCA, there were no significant differences in the response between the groups vaccinated with different dual antigen vaccines. Taken together, these data demonstrate the generation of PSMA and PSA-specific T cell responses, as well as PSCA and PSA-specific T cell responses following dual antigen DNA vaccination, using both co-expression and co-formulation vaccine strategies.

Figure 22:
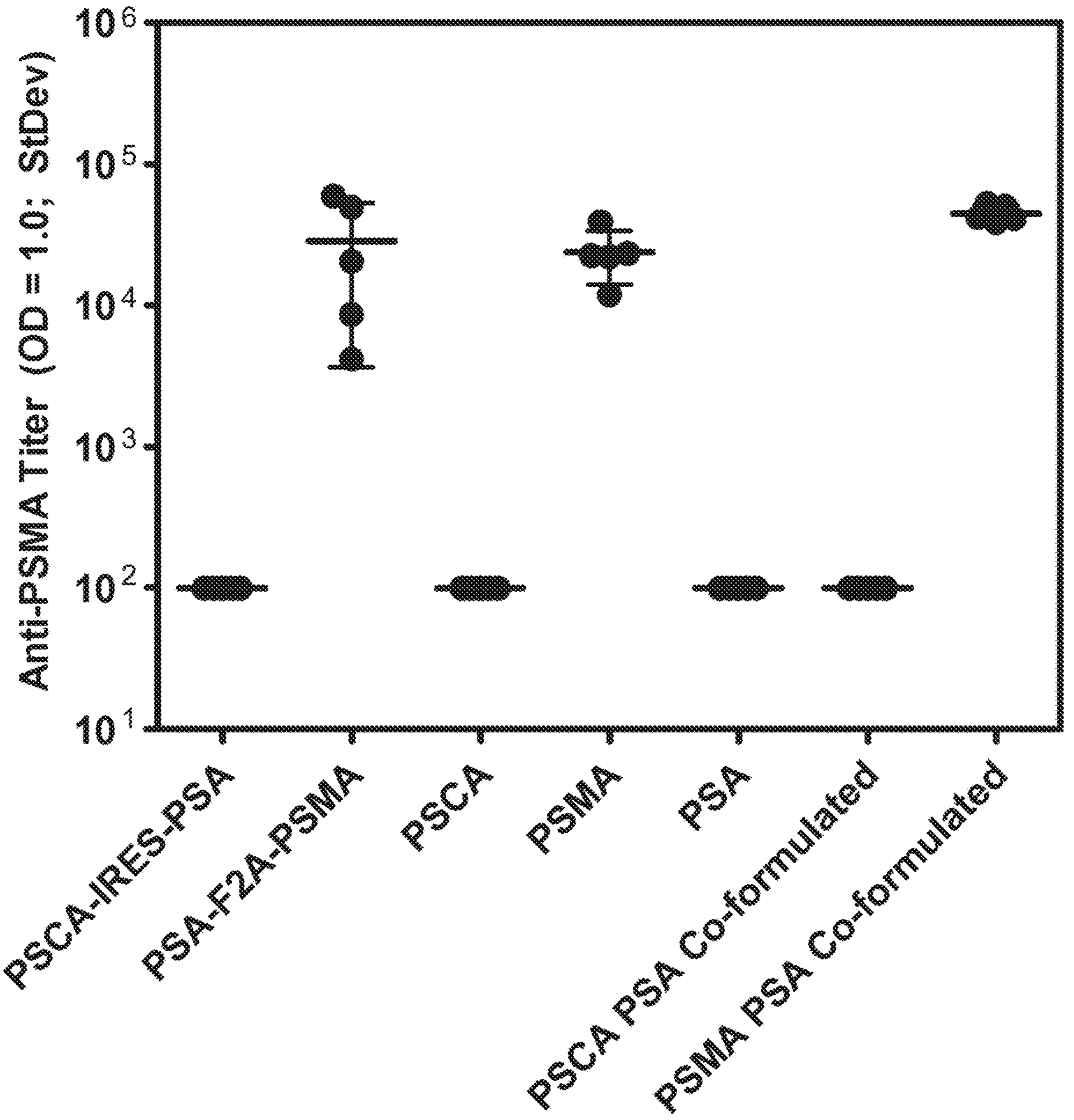
FIG. 22. Graph depicting results of a representative study that evaluates the immunogenicity of the dual antigen vaccines by anti-PSMA antibody titers.

FIG. 22 shows the results of a representative study that evaluates the immunogenicity of the dual antigen vaccines by anti-PSMA antibody titers. Briefly, 5 mice per group were primed on day 0 and boosted with PMED on days 14, 28 and 49. On day 56, serum anti-PSMA antibody titers were assessed by ELISA. All animals vaccinated with PSMA generated significant anti-PSMA antibody titers. There was no significant difference in the antibody titers between mice vaccinated with PSA-F2A-PSMA, co-formulated PSMA and PSA, and PSMA alone (one-way ANOVA, p-value >0.05). Taken together, these data demonstrate the generation of anti-PSMA-specific antibodies following dual antigen DNA vaccination with PSMA and PSA, using both co-expression and co-formulation vaccine strategies.

Figure 23:
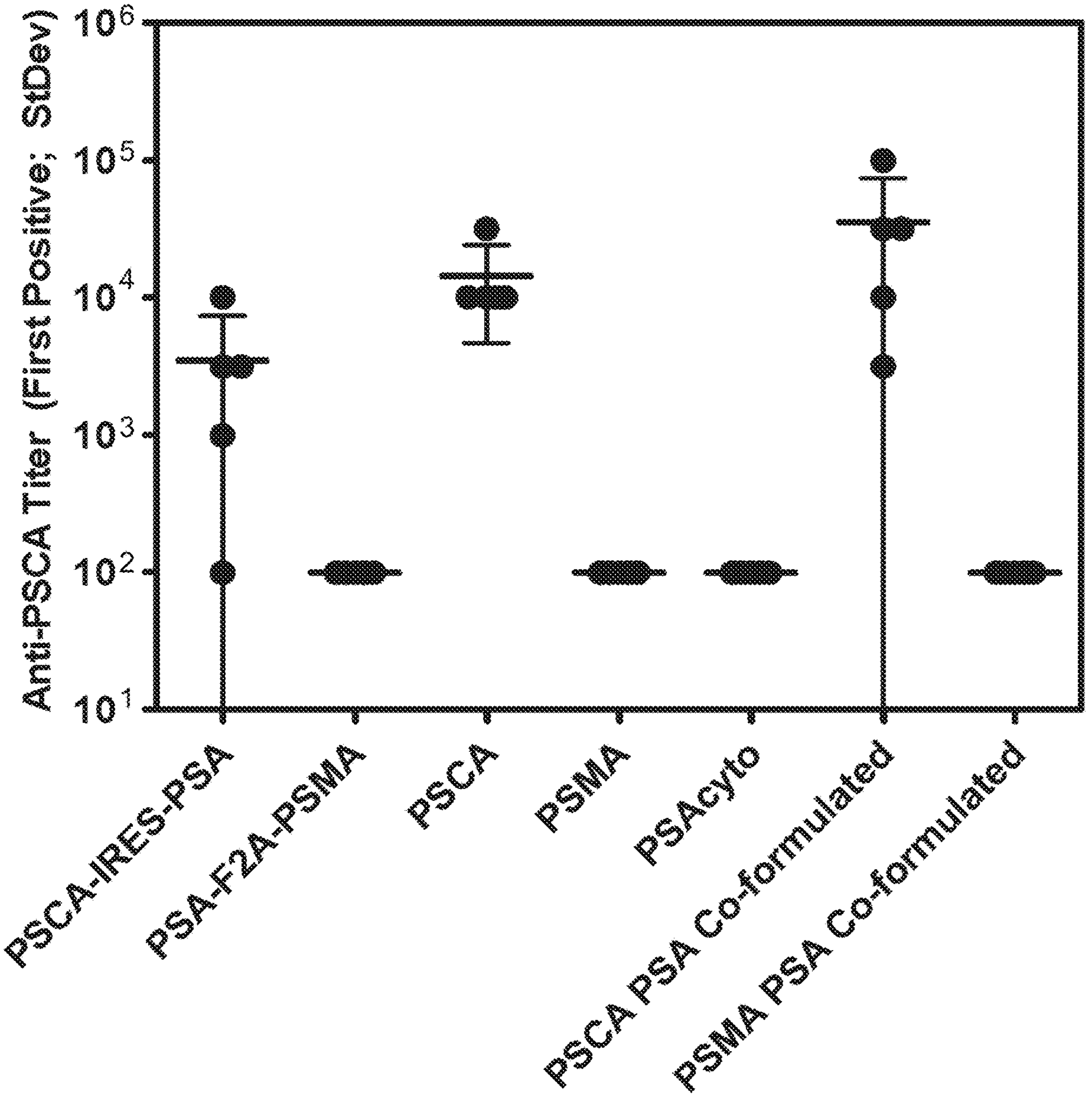
FIG. 23. Graph depicting results of a representative study that evaluates the immunogenicity of the dual antigen vaccines by anti-PSCA antibody titers.

FIG. 23 shows the results of a representative study that evaluates the immunogenicity of the dual antigen vaccines by anti-PSCA antibody titers. Briefly, 5 mice per group were primed on day 0 and boosted with PMED on days 14, 28 and 49. On day 56, serum anti-PSCA antibody titers were assessed by ELISA. All animals vaccinated with PSCA generated significant anti-PSCA antibody titers. There was no significant difference in the antibody titers between mice vaccinated with PSCA-IRES-PSA, co-formulated PSCA and PSA, and PSCA alone (one-way ANOVA, p-value >0.05), although the antibody titers generated following PSCA-IRES-PSA vaccination trended lower than the other groups vaccinated with PSCA. These results indicate that co-expression or co-formulation of PSCA and PSA elicits anti-PSCA antibodies.

Figure 24:
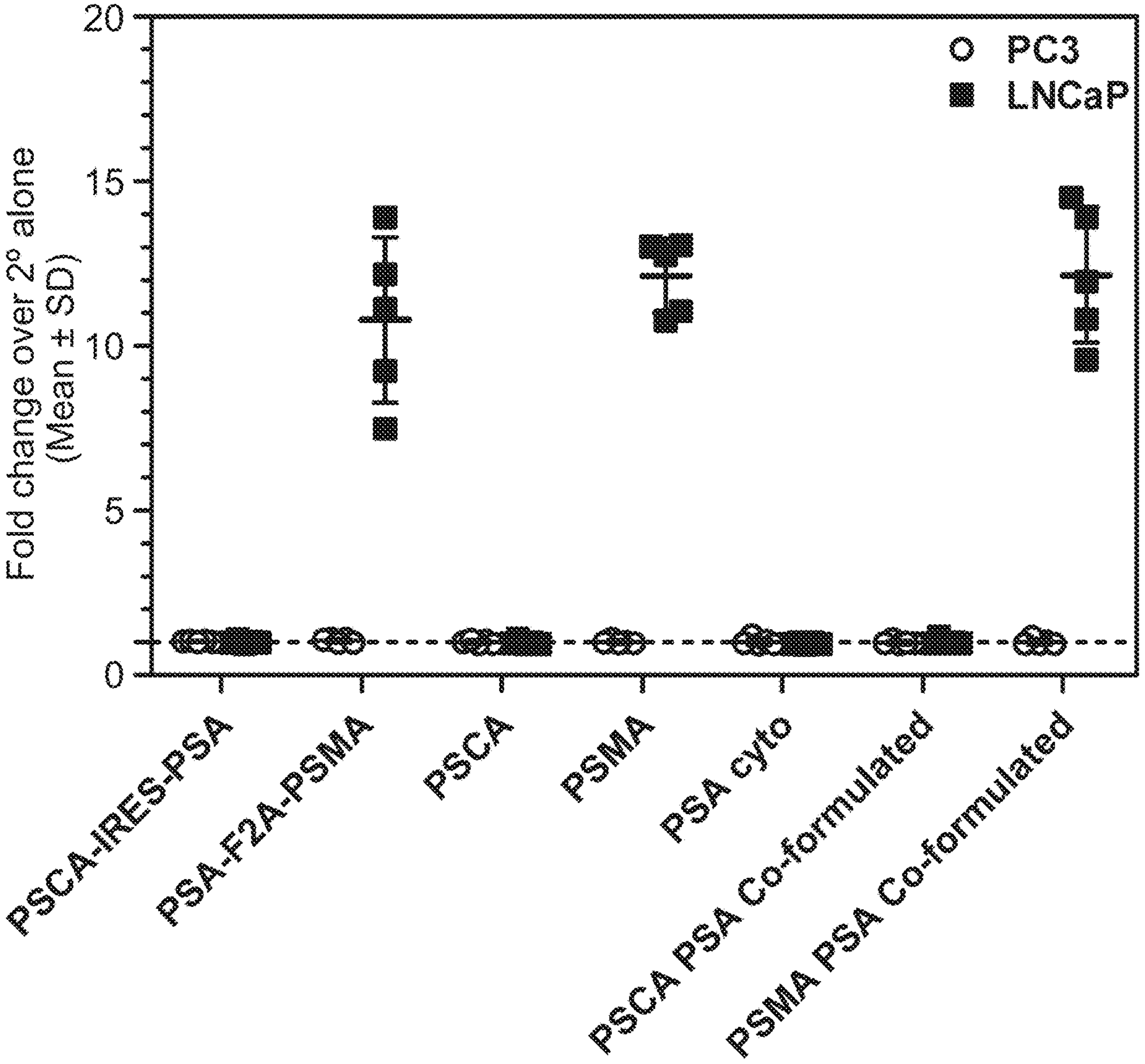
FIG. 24. Graph depicting results of a representative study that evaluates the immunogenicity of the dual antigen vaccines by anti-PSMA antibody cell-surface binding.

FIG. 24 shows the results of a representative study that evaluates the immunogenicity of the dual antigen vaccines by anti-PSMA antibody cell-surface binding. Briefly, 5 mice per group were primed on day 0 and boosted with PMED on days 14, 28 and 49. On day 56, recognition of cell-surface native PSMA was assessed by serum antibody binding to LNCaP and PC3 cells. The PC3 cells served as a background control for the assay. There were no significant differences in the anti-PSMA antibody binding to LNCaP cells between the PSMA-vaccinated groups (one-way ANOVA, p-value >0.05). The fold change over secondary antibody alone for the J591-A mAb was 45.3 (data not shown). Overall, these data demonstrate the generation of anti-PSMA-specific antibodies that recognized native PSMA following dual antigen vaccination, using both co-expression and co-formulation vaccine strategies.

Figure 25:
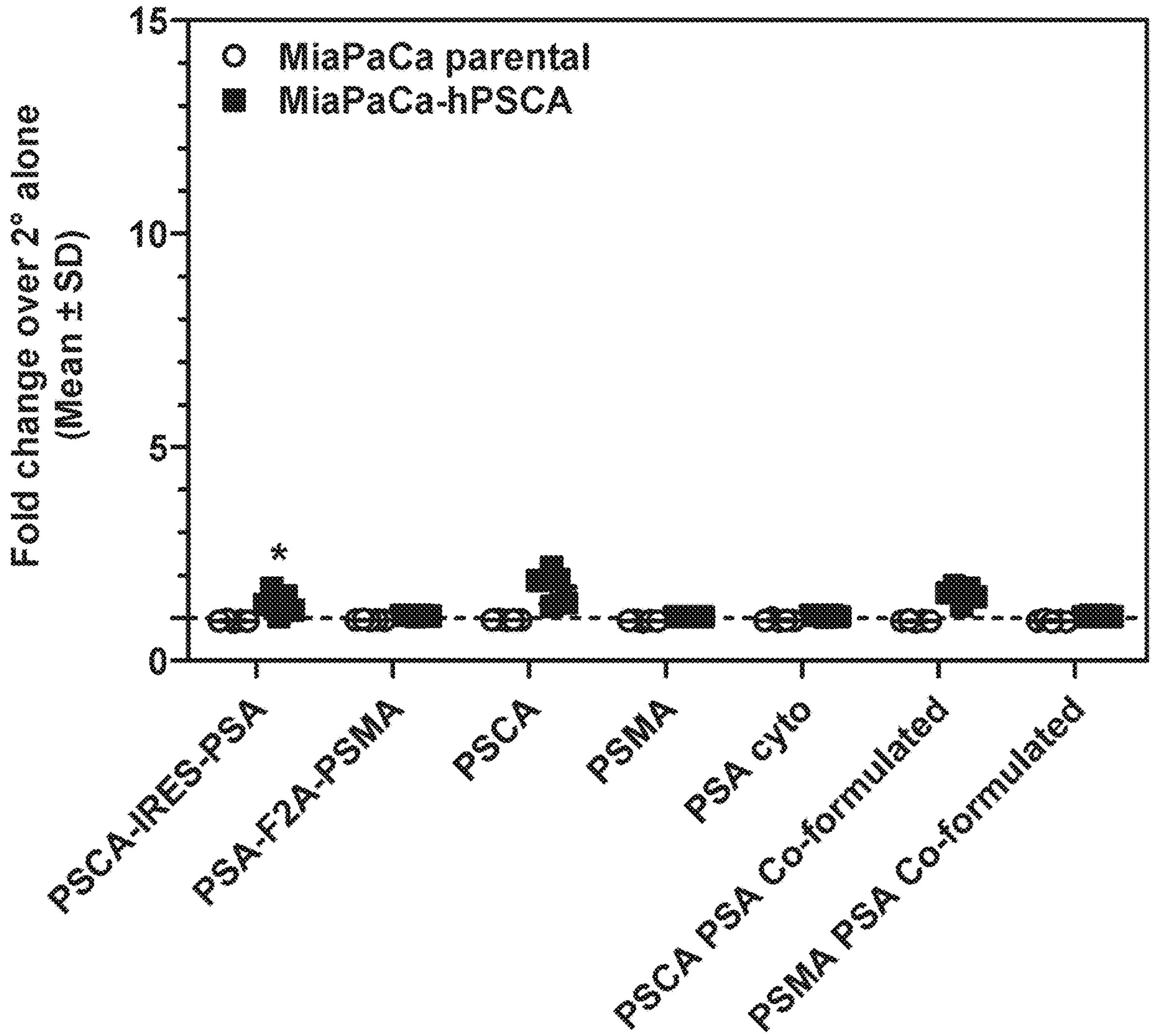
FIG. 25. Graph depicting results of a representative study that evaluates the immunogenicity of the dual antigen vaccines by anti-PSCA antibody cell-surface binding.

FIG. 25 shows the results of a representative study that evaluates the immunogenicity of the dual antigen vaccines by anti-PSCA antibody cell-surface binding. Briefly, 5 mice per group were primed on day 0 and boosted with PMED on days 14, 28 and 49. On day 56, recognition of cell-surface native PSCA was assessed by serum antibody binding to Ad-PSCA transduced and untransduced MIA-PaCa-2 cells. The untransduced, parental cells served as a background control for the assay. All groups of mice vaccinated with PSCA demonstrated very low anti-PSCA antibody binding to Ad-PSCA transduced MIA-PaCa-2 cells. PSCA-IRES-PSA vaccination resulted in significantly decreased binding to Ad-PSCA transduced MIA-PaCa-2 cells compared to mice vaccinated with PSCA alone (* indicates $p<0.05$ by one-way ANOVA). Taken together, these data demonstrate that co-expression or co-formulation of PSCA and PSA results in very low recognition of native PSCA by anti-PSCA-specific antibodies.

Example 7. Immunogenicity of the Human PSMA Modified Antigen

Study Design.

The immune responses induced by DNA vaccination using a construct encoding an immunogenic PSMA polypeptide (the "human PSMA modified antigen" or "hPSMA modified") consisting 15-750 amino acids (aa) of the native human PSMA protein of SEQ ID NO: 1 were compared with those induced by the native human full-length PSMA protein (hPSMA full length). Groups of female C57BL/6 mice or female Pasteur (HLA-A2/DR1) transgenic mice were primed on day 0 and boosted on days 14, 28 by PMED administration with a 2 μg dose of a DNA vaccine encoding either hPSMA full-length or hPSMA modified protein. Mice were bled and sacrificed on day 35 (7 days after the third vaccination) and T cell immune responses against the hPSMA full-length protein were determined in splenocytes by IFN-γ ELISPOT assay. For C57BL/6 mice, single cell suspensions of $5\times10^5$ splenocytes from individual animals were plated per well with 10 g purified hPSMA protein, $5\times10^4$ TRAMP-C2 cells alone, or TRAMP-C2 cells expressing hPSMA or a PSMA-PSA-PSCA fusion protein. For Pasteur (HLA-A2/DR1) transgenic mice, single cell suspensions of $5\times10^5$ splenocytes from individual animals were plated per well with $5\times10^4$ K562 cells expressing human HLA-A2 that had been pulsed with known HLA-A2-restricted $CD8^+$ T cell epitopes derived from the human PSMA protein sequence (Table 23). Responses in Pasteur mice were also determined using 10 μg/ml purified PSMA protein or $5\times10^4$ SK-Mel5 cells that had been transduced with Adenoviral vectors expressing a control protein (Ad-eGFP) or the full-length human PSMA protein (Ad-hPSMA). Each condition was performed in triplicate. The plates were incubated for 20 h at 37° C. and 5% $CO_2$, washed and developed after incubation as per the manufacturer's instruction. The number of IFN-γ SFC was counted by a CTL reader. The results are presented in FIGS. 19 and 20, which show the average number of PSMA-specific SFC/million splenocytes+/−the standard deviation per group.

ELISA Assay.

Antibody responses induced by the modified and full-length PSMA vaccines were measured in serum from each animal collected on day 35. Serum from was subjected to ELISA to determine the anti-PSMA antibody titers in the serum was determined using the ELISA assay as described in Example 5. The results are presented in FIG. 26, which shows the average titers+/−the standard deviation of the number of mice per group.

FACS Assay.

Serum was also subjected to a FACS assay to measure antibody binding to either human PSMA expressed on the cell surface of appropriate cell lines, thus determining whether antibodies generated by the modified and full-length PSMA vaccines were capable of recognizing native PSMA conformation. The FACS assay was conducted according to the procedure as described in Example 5. The results are presented in FIG. 29, which show the average fold change in MFI of the mouse serum over the secondary anti-mouse antibody alone+/−the standard deviation of the number of mice per group.

TABLE 23

HLA-A2 restricted peptide epitopes tested in the assays conducted for the Pasteur (HLA-A2/DR1) transgenic mice. Peptides were tested individually at a concentration of 10 μg/ml. The amino acid position of the N and C-terminal end of each peptide is indicated.

| Prostate antigen | Peptides | Purpose |
|---|---|---|
| hHer2 | 106-114 | HLA-A2-restricted control peptide derived from the human Her2 protein |
| PSMA | 168-177 | HLA-A2-restricted PSMA test peptide |
| PSMA | 663-671 | HLA-A2-restricted PSMA test peptide |
| PSMA | 275-289 | HLA-A2-restricted PSMA test peptide |

Results.

Figure 26:
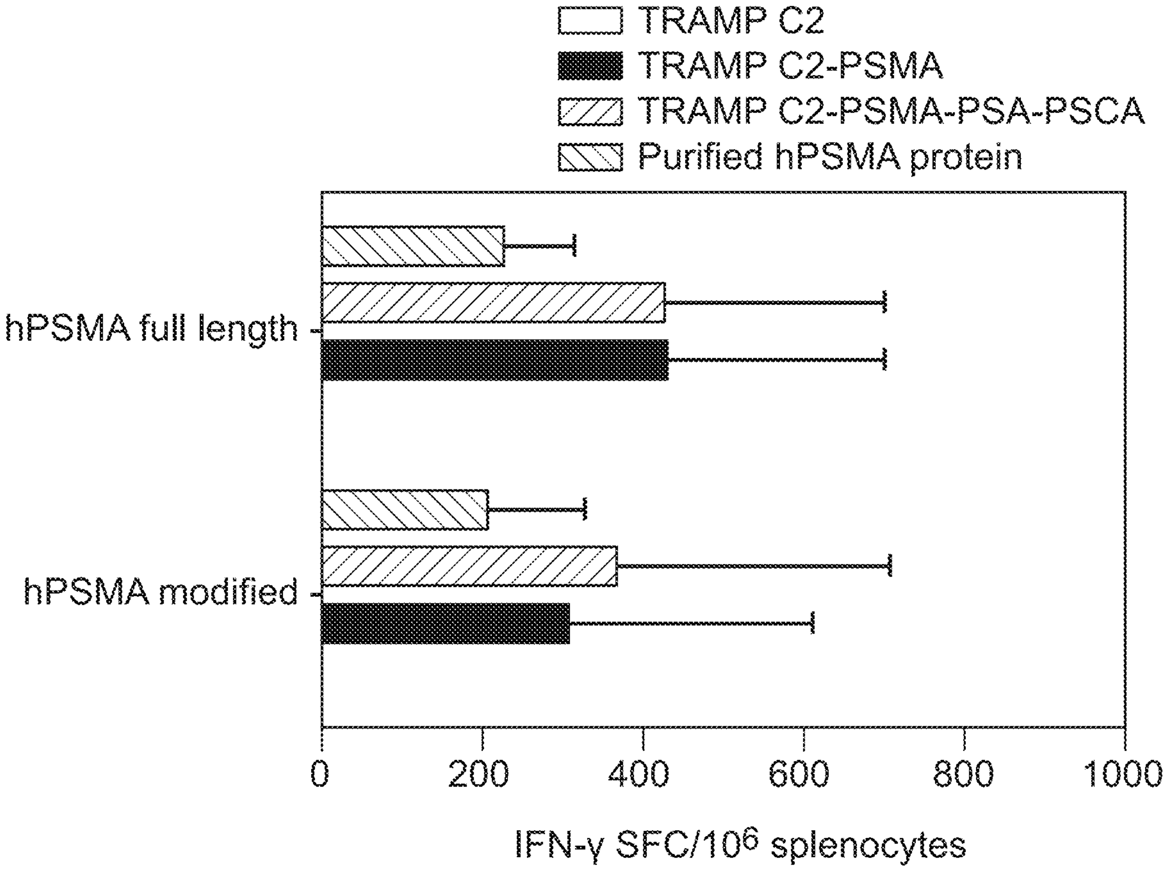
FIG. 26. Graph depicting results of a representative study that evaluates the T cell immune response elicited by human PSMA modified antigen (amino acids 15-750) versus full-length human PSMA (amino acids 1-750) in C57BL/6 mice.

FIG. 26 shows the results of a representative study to evaluate the T cell immune response elicited by the human PSMA modified (aa 15-750) versus full-length human PSMA (aa 1-750) in C57BL/6 mice determined by IFN-γ ELISPOT assay. Five (5) mice per group were primed on day 0 and boosted PMED with DNA vaccines expressing hPSMA modified or hPSMA full-length proteins on days 14 and 28. On day 35, the response elicited against the hPSMA full-length protein were compared by determining T cell responses to TRAMP C2-PSMA or purified human PSMA ECD protein (referred to Purified hPSMA protein in FIG. 26) by IFNγ ELISPOT assay. TRAMP C2 cells served as a background control for the assay. The magnitude of the IFN-γ T cell responses elicited to TRAMP C2-PSMA or purified hPSMA protein were not significantly different (two-way ANOVA, p-value >0.05) between groups. These results indicate that the DNA vaccines expressing hPSMA modified and hPSMA full-length proteins elicit equivalent T cell immune responses in C57BL/6 mice.

Figure 27A:
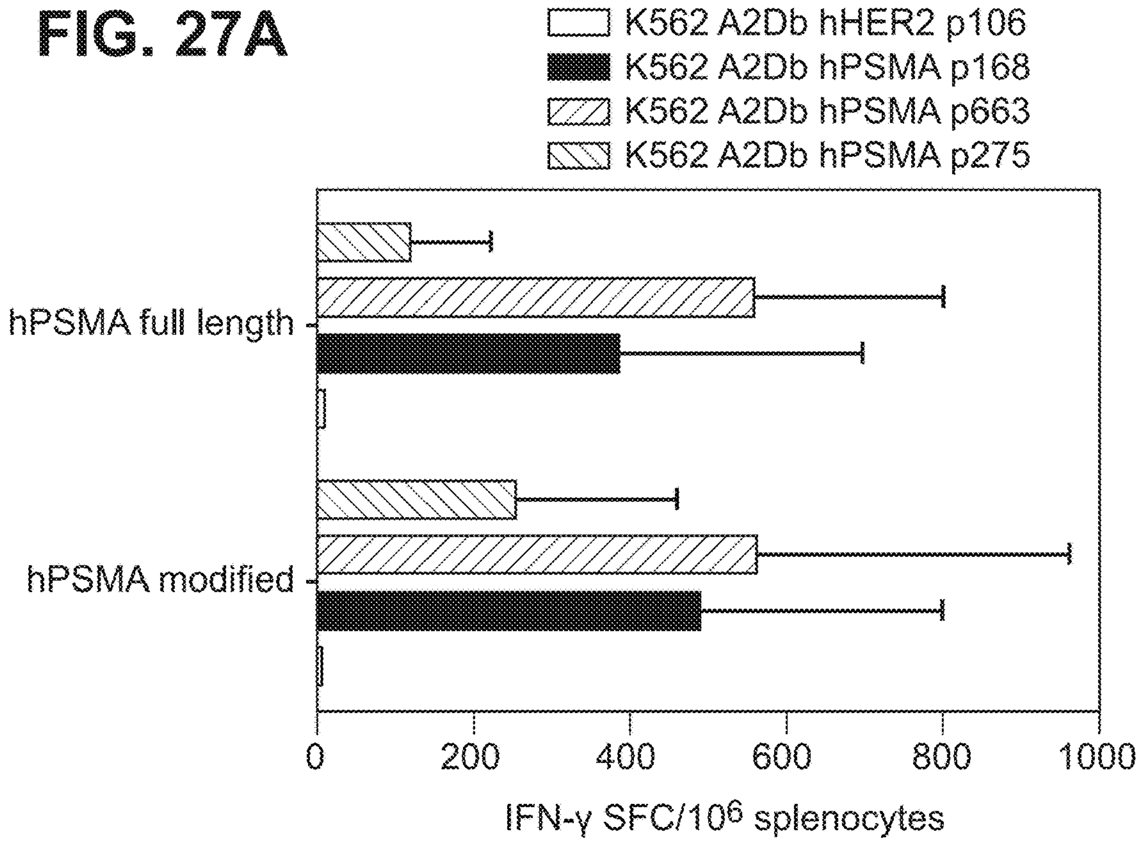
FIGS. 27A, 27B. Graphs depicting results of a representative study that evaluates the T cell immune response of human PSMA modified antigen (amino acids 15-750) versus full-length human PSMA antigen (amino acids 1-750) in Pasteur (HLA-A2/DR1) transgenic mice by IFN-γ ELISPOT assay using (a) PSMA derived HLA-A2-restricted peptides (FIG. 27A) or (b) SK-Mel5 cells transduced with Ad-hPSMA or purified hPSMA full-length protein (FIG. 27B).
Figure 27B:
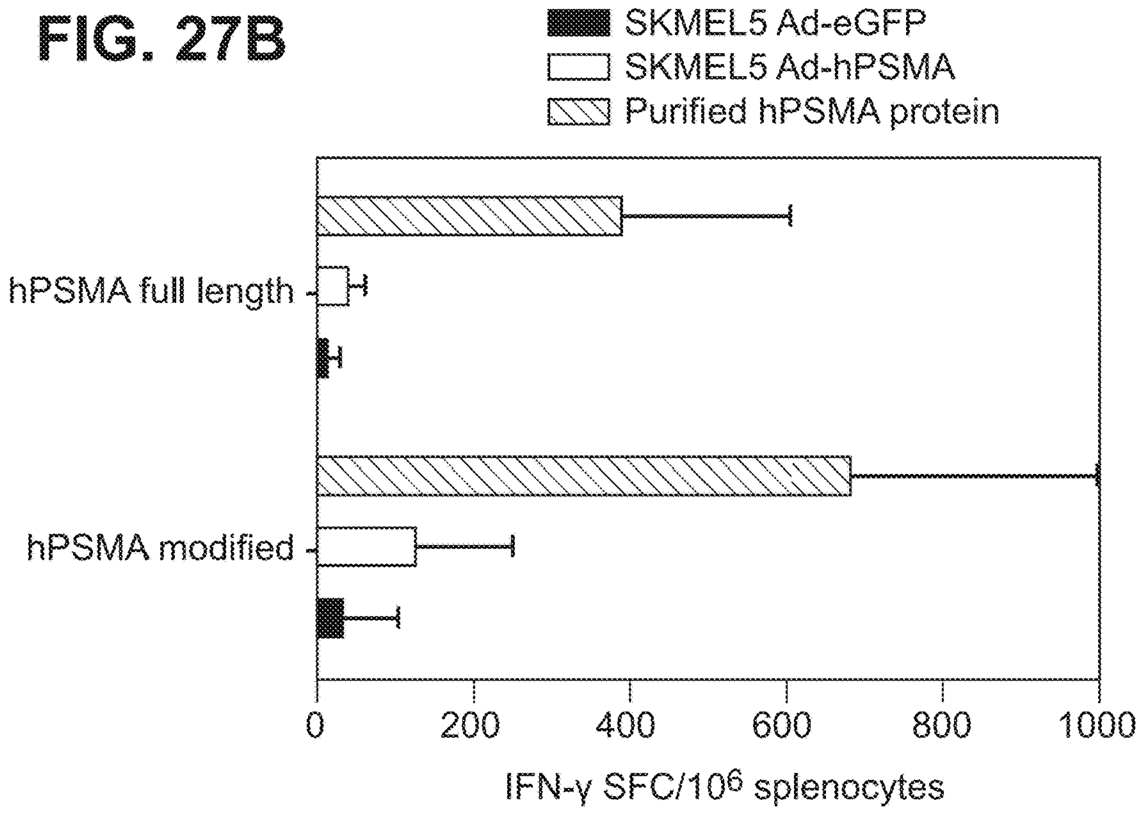

FIGS. 27A and 27B show the results of a representative study to evaluate the T cell immune response of human PSMA modified antigen (aa 15-750) versus full-length human PSMA antigen (aa 1-750) in Pasteur (HLA-A2/DR1) transgenic mice by IFN-γ ELISPOT assay. Ten (10) mice per group were primed on day 0 and boosted PMED with DNA vaccines encoding hPSMA modified or hPSMA full-length protein on days 14 and 28. On day 35, the T cell response elicited against the hPSMA full-length protein was determined by IFN-□□ E ELISPOT assay using (A) PSMA derived HLA-A2-restricted peptides representing known $CD8^+$ epitopes and (B) SK-Mel5 cells transduced with Ad-hPSMA or purified hPSMA full-length protein. The hHER2 106 peptide and SK-Mel5 Ad-eGFP served as negative controls in the assays. The hPSMA modified vaccine elicited the highest magnitude of IFN-γ T cell immune responses to the HLA-A2-restricted $CD8^+$ T cell epitopes, although the difference between groups was not significant (two-way ANOVA, p-value >0.05). Similarly, the hPSMA modified vaccine elicited the highest magnitude of immune response against the SK-Mel5 cells transduced with Ad-hPSMA and significantly (two-way ANOVA, p-value >0.05) higher frequencies of IFN-γ SFC to the purified hPSMA protein. These results demonstrate that the DNA vaccine expressing the hPSMA modified protein is more potent in inducing T cell responses to the hPSMA protein than the hPSMA full-length protein in Pasteur (HLA-A2/DR1) transgenic mice.

Figure 28:
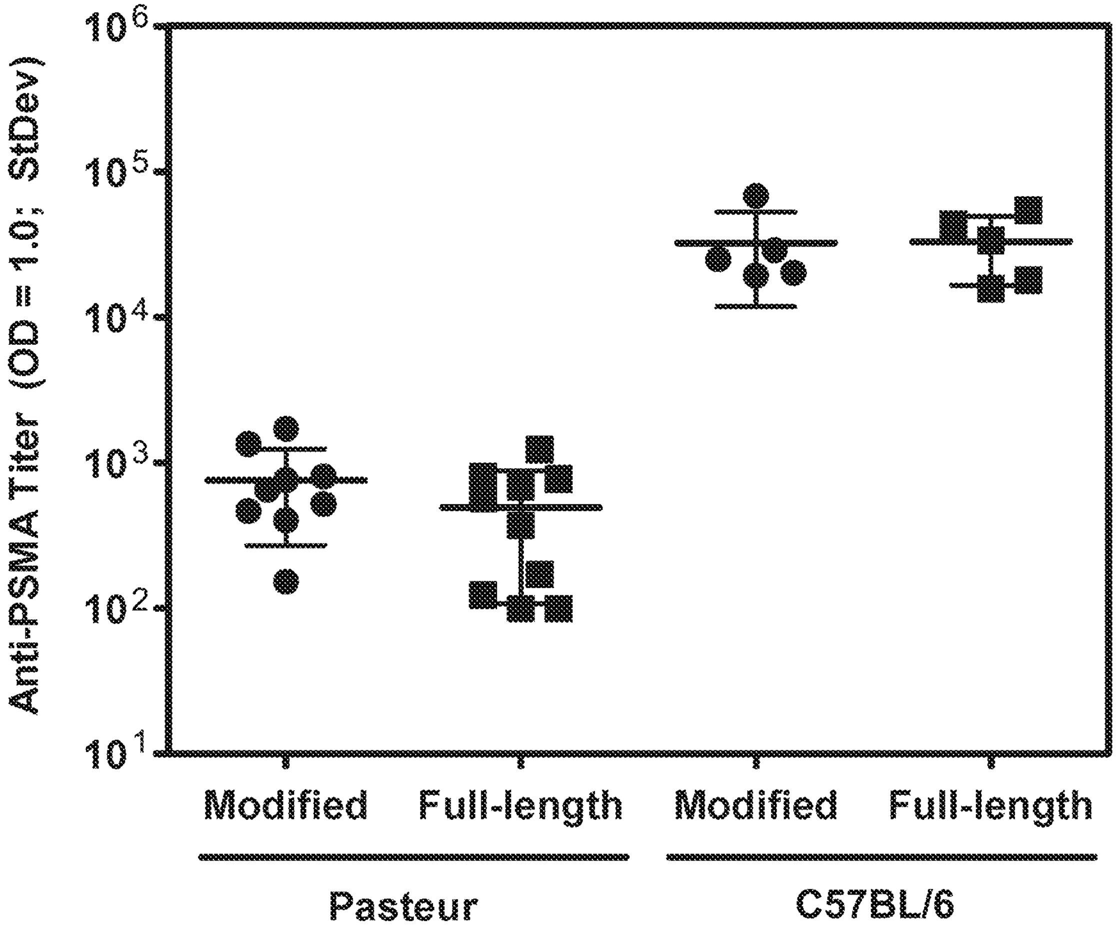
FIG. 28. Graph depicting results of a representative study that evaluates the immunogenicity of the human modified and full-length PSMA vaccines by anti-PSMA antibody titers.

FIG. 28 shows the results of a representative study that evaluates the immunogenicity of the human modified and full-length PSMA vaccines by anti-PSMA antibody titers. Briefly, mice were primed on day 0 and boosted with PMED on days 14 and 28. Nine Pasteur mice were vaccinated with modified PSMA, 10 Pasteur mice were vaccinated with full-length PSMA, and 5 C57BL/6 mice per group were vaccinated with either modified or full-length PSMA. On day 35, serum anti-PSMA antibody titers were assessed by ELISA. As expected, C57BL/6 mice generated significantly greater anti-PSMA antibody titers compared to Pasteur mice (one-way ANOVA). Comparing antibody titers between the same strains of mice, there was no significant difference in the antibody titers between mice vaccinated with modified and full-length PSMA (one-way ANOVA, p-value >0.05). Overall, these results demonstrate that vaccination with the full-length version of human PSMA generates an equivalent anti-PSMA antibody titer compared to the human modified PSMA vaccine.

Figure 29:
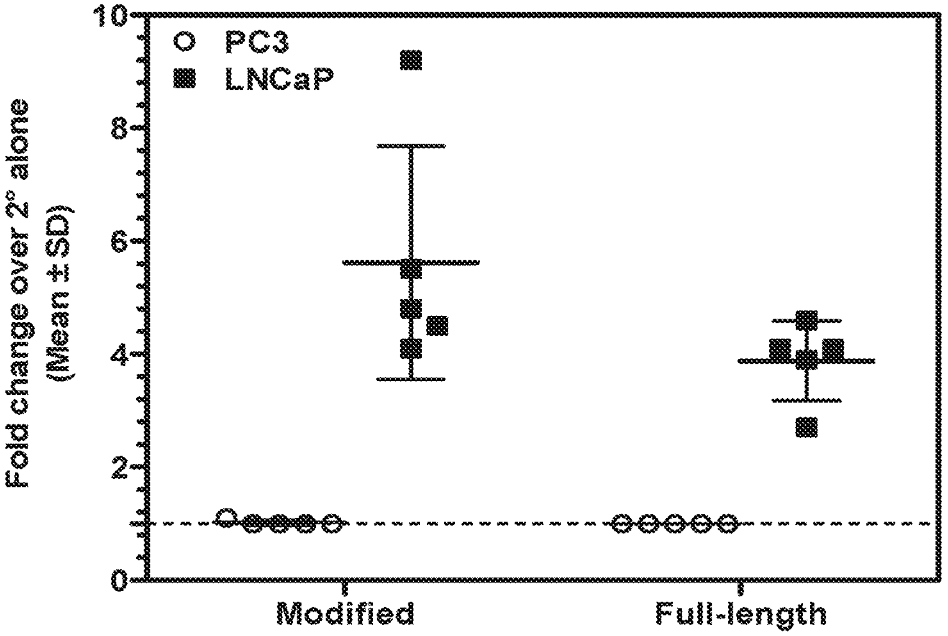
FIG. 29. Graph depicting results of a representative study that evaluates the immunogenicity of the human modified and full-length PSMA vaccines by anti-PSMA antibody cell-surface binding.

FIG. 29 shows the results of a representative study that evaluates the immunogenicity of the human modified and full-length PSMA vaccines by anti-PSMA antibody cell-surface binding. Briefly, 5 C57BL/6 mice per group were primed on day 0 and boosted with PMED on days 14 and 28. On day 35, recognition of cell-surface native PSMA was assessed by serum antibody binding to LNCaP and PC3 cells. The PC3 cells served as a background control for the assay. There were no significant differences in the anti-PSMA antibody binding to LNCaP cells between mice vaccinated with modified or full-length PSMA (one-way ANOVA, p-value >0.05). The fold change over secondary antibody alone for the J591-A mAb was 14.3 (data not shown). Overall, these data demonstrate that it is feasible to generate anti-PSMA-specific antibodies that recognized native PSMA following either modified or full-length PSMA vaccination.

Example 8. Effect of Anti-CTLA-4 Antibody on Vaccine-Induced Immune Response

The effect of local administration of anti-CTLA-4 monoclonal antibody (CP-675, 206) on the immune responses induced by a human PSMA nucleic acid molecule provided by the invention was investigated in a monkey study, in which the immune response was assessed by measuring PSMA specific T cell responses using an IFNγ ELISPOT assay.

Animal Treatment and Sample Collection.

Three groups of male Indian rhesus macaques, five to six (#1 to 5 or 6) per each test group, were immunized with a nucleic acid (SEQ ID NO: 10) that encodes a human PSMA modified antigen (SEQ ID NO: 9) delivered by adenovirus (1e11 V.P. injected intramuscularly) followed by 2 DNA immunizations (8 actuations/immunization, 4 actuations per each right and left side of the lower abdomen) by PMED with 6 and 9 week intervals respectively. Animals in Groups 2 and 3 additionally received bilateral intradermal injections of 3 mg of CpG (PF-03512676) subsequently after the PMED immunization in proximity to each inguinal draining lymph node. Group 2 also received intravenous injections of anti-CTLA-4 monoclonal antibody (CP-675, 206) at 10 mg/kg and group 3 received intradermal injections of anti-CTLA-4 monoclonal antibody (CP-675, 206) at 5 mg/kg in proximity to each left and right inguinal vaccine draining lymph node at the time of the second PMED immunization.

Peripheral blood samples were collected from each animal sixteen days after the last PMED immunization. Peripheral blood mononuclear cells (PBMCs) were isolated from the samples and were subjected to an IFNγ ELISPOT assay to measure the PSMA specific T cell responses. Briefly, 4e5 PBMCs from individual animals were plated per well with pools of PSMA specific peptides each at 2 ug/ml hPSMA ECD protein at 10 ug/ml, rhesus PSMA ECD protein at 10 ug/ml or nonspecific control peptides (human HER2 peptide pool) each at 2 ug/ml in IFNγ ELISPOT plates. The composition of each of the PSMA specific peptide pools is provided in Table 24A. The plates were incubated for 16 hrs at 37° C. and 5% CO2 and washed and developed after incubation as per manufacturer's instruction. The number of IFNγ spot forming cells (SFC) were counted by CTL reader. Each condition was performed in duplicates. The results are presented in Table 24B, which shows the average number of the PSMA specific SFC from the triplicates subtracting the average number of SFC from the nonspecific control peptides normalized to 1e6 PBMCs. ^ indicates that the count is not accurate because the numbers of spots were too numerous to count.

IFNγ ELISPOT Assay Procedure.

A capture antibody specific to IFNγ(□BD Bioscience, #51-2525kc) is coated onto a polyvinylidene fluoride (PVDF) membrane in a microplate overnight at 4° C. The plate is blocked with serum/protein to prevent nonspecific binding to the antibody. After blocking, effector cells (such as splenocytes isolated from immunized mice or PBMCs isolated from rhesus macaques) and targets (such as PSMA peptides from peptide library, target cells pulsed with antigen specific peptides or tumor cells expressing the relevant antigens) are added to the wells and incubated overnight at 37° C. in a 5% $CO_2$ incubator. Cytokine secreted by effector cells are captured by the coating antibody on the surface of the PVDF membrane. After removing the cells and culture media, 100 μl of a biotinylated polyclonal anti-humanIFNγ antibody was added to each of the wells for detection. The spots are visualized by adding streptavidin-horseradish peroxidase and the precipitate substrate, 3-amino-9-ethylcarbazole (AEC), to yield a red color spot as per manufacturer's (Mabtech) protocol. Each spot represents a single cytokine producing T cell.

Results.

Table 24B. shows the results of a representative IFNγ ELISPOT assay that evaluates and compares the T cell responses induced by the vaccine without (group 1) or with anti-CTLA-4 monoclonal antibody (CP-675, 206) given either systemically by intravenous injections (group 2) or locally by intradermal injections in proximity to the vaccine draining lymph node (group 3). As shown in Table 1B, PSMA vaccine induced measurable IFNγ T cell responses to multiple PSMA specific peptides and proteins in the absence of CpG (PF-03512676) and anti-CTLA-4 monoclonal antibody (CP-675, 206). The responses were modestly enhanced by the addition of CpG (PF-03512676) and systemic delivery of the anti-CTLA-4 antibody (CP-675, 206; group 2). However, a more potent and significant enhancement of the response to multiple PSMA peptides and PSMA protein was observed when the anti-CTLA-4 monoclonal antibody (CP-675, 206) was delivered locally by intradermal injections in proximity to the vaccine draining lymph node (group 3).

TABLE 24A

PSMA peptide pools: Each peptide pool (i.e., P1, P2, P3, H1, H2, R1, and R2) is composed of 15mer peptides from either human PSMA protein (hPMSA protein) or rhesus PSMA protein (rPMSA protein) sequences as indicated below. The amino acid position of the N and C-terminal end of each peptide is indicated.

| P1 | P2 | P3 | H1 | H2 | R1 | R2 |
|---|---|---|---|---|---|---|
| h 1-15 | h 249-263 | h 449-463 | h 33-47 | h 465-479 | r 33-47 | r 465-479 |
| h 5-19 | h 253-267 | h 453-467 | h 37-51 | h 469-483 | r 37-51 | r 469-483 |
| h 9-23 | h 257-271 | h 457-471 | h 41-55 | h 473-487 | r 41-55 | r 473-487 |
| h 13-27 | h 261-275 | h 485-499 | h 45-59 | h 477-491 | r 45-59 | r 477-491 |
| h 17-31 | h 265-279 | h 489-503 | h 61-75 | h 481-495 | r 61-75 | r 481-495 |
| h 21-35 | h 269-283 | h 493-507 | h 65-79 | h 537-551 | r 65-79 | r 537-551 |
| h 25-39 | h 273-287 | h 497-511 | h 69-83 | h 541-555 | r 69-83 | r 541-555 |
| h 29-43 | h 277-291 | h 501-515 | h 73-87 | h 545-559 | r 73-87 | r 545-559 |
| h 49-63 | h 281-295 | h 505-519 | h 97-111 | h 577-591 | r 97-111 | r 577-591 |
| h 53-67 | h 285-299 | h 509-523 | h 101-115 | h 581-595 | r 101-115 | r 581-595 |
| h 57-71 | h 289-303 | h 513-527 | h 105-119 | h 585-599 | r 105-119 | r 585-599 |
| h 77-91 | h 293-307 | h 517-531 | h 109-123 | h 589-603 | r 109-123 | r 589-603 |
| h 81-95 | h 297-311 | h 521-535 | h 137-151 | h 601-615 | r 137-151 | r 601-615 |
| h 85-99 | h 317-331 | h 525-539 | h 141-155 | h 605-619 | r 141-155 | r 605-619 |
| h 89-103 | h 321-335 | h 529-543 | h 145-159 | h 609-623 | r 145-159 | r 609-623 |
| h 93-107 | h 325-339 | h 533-547 | h 149-163 | h 613-627 | r 149-163 | r 613-627 |
| h 113-127 | h 329-343 | h 549-563 | h 209-223 | h 637-651 | r 209-223 | r 637-651 |
| h 117-131 | h 333-347 | h 553-567 | h 213-227 | h 641-655 | r 213-227 | r 641-655 |
| h 121-135 | h 353-367 | h 557-571 | h 217-231 | h 645-659 | r 217-231 | r 645-659 |
| h 125-139 | h 357-371 | h 561-575 | h 221-235 | h 649-663 | r 221-235 | r 649-663 |
| h 129-143 | h 361-375 | h 565-579 | h 301-315 | h 653-667 | r 301-315 | r 653-667 |
| h 133-147 | h 365-379 | h 569-583 | h 305-319 | h 657-671 | r 305-319 | r 657-671 |
| h 153-167 | h 369-383 | h 573-587 | h 309-323 | h 709-723 | r 309-323 | r 709-723 |
| h 157-171 | h 373-387 | h 593-607 | h 313-327 | h 713-727 | r 313-327 | r 713-727 |
| h 161-175 | h 377-391 | h 597-611 | h 337-351 | h 717-731 | r 337-351 | r 717-731 |
| h 165-179 | h 381-395 | h 617-631 | h 341-355 | h 721-735 | r 341-355 | r 721-735 |
| h 169-183 | h 385-399 | h 621-635 | h 345-359 | h 725-739 | r 345-359 | r 725-739 |
| h 173-187 | h 389-403 | h 625-639 | h 349-363 | h 729-743 | r 349-363 | r 729-743 |
| h 177-191 | h 393-407 | h 629-643 | h 461-475 | h 733-747 | r 461-475 | r 733-747 |
| h 181-195 | h 397-411 | h 633-647 | | | | |
| h 185-199 | h 401-415 | h 661-675 | | | | |
| h 189-203 | h 405-419 | h 665-679 | | | | |
| h 193-207 | h 409-423 | h 669-683 | | | | |

TABLE 24A-continued

PSMA peptide pools: Each peptide pool (i.e., P1, P2, P3, H1, H2, R1, and R2) is composed of 15mer peptides from either human PSMA protein (hPMSA protein) or rhesus PSMA protein (rPMSA protein) sequences as indicated below. The amino acid position of the N and C-terminal end of each peptide is indicated.

| P1 | P2 | P3 | H1 | H2 | R1 | R2 |
|---|---|---|---|---|---|---|
| h 197-211 | h 413-427 | h 673-687 | | | | |
| h 201-215 | h 417-431 | h 677-691 | | | | |
| h 205-219 | h 421-435 | h 681-695 | | | | |
| h 225-239 | h 425-439 | h 685-699 | | | | |
| h 229-243 | h 429-443 | h 689-703 | | | | |
| h 233-247 | h 433-447 | h 693-707 | | | | |
| h 237-251 | h 437-451 | h 697-711 | | | | |
| h 241-255 | h 441-455 | h 701-715 | | | | |
| h 245-259 | h 445-459 | h 705-719 | | | | |
| | | h 737-750 | | | | |

TABLE 24B

T cell responses induced by the vaccine without (Group 1) or with anti-CTLA-4 antibody Tremelimumab (CP-675, 206) given systemically by intravenous injections (Group 2) or local intradermal injections (Group 3).

| | | recall antigen | | | | | | | | |
|---|---|---|---|---|---|---|---|---|---|---|
| Group | animal ID | P1 | P2 | P3 | H1 | H2 | hPSMA protein | R1 | R2 | rPSMA protein |
| 1. | #1 | 7.5 | 62.5 | 0.0 | 210.0 | 172.5 | 455.0 | 3.8 | 1.3 | 0.0 |
| no | #2 | 11.3 | 48.8 | 0.0 | 17.5 | 146.3 | 111.3 | 0.0 | 3.8 | 0.0 |
| immune | #3 | 12.5 | 342.5 | 13.8 | 115.0 | 517.5 | 705.0 | 12.5 | 40.0 | 138.8 |
| modulator | #4 | 6.3 | 23.8 | 0.0 | 211.3 | 38.8 | 45.0 | 5.0 | 7.5 | 7.5 |
| | #5 | 0.0 | 16.3 | 0.0 | 0.0 | 52.5 | 45.0 | 0.0 | 0.0 | 0.0 |
| | #6 | 6.3 | 442.5 | 21.3 | 42.5 | 238.8 | 736.3 | 11.3 | 8.8 | 93.8 |
| 2. | #1 | 23.8 | 57.5 | 1.3 | 71.3 | 292.5 | 278.8 | 6.3 | 6.3 | 0.0 |
| with | #2 | 0.0 | 61.3 | 0.0 | 2.5 | 108.8 | 78.8 | 0.0 | 6.3 | 3.8 |
| aCTLA4 | #3 | 58.8 | 41.3 | 7.5 | 1063.8 | 82.5 | 1197.5 | 22.5 | 7.5 | 1.3 |
| (IV) | #4 | 25.0 | 318.8 | 27.5 | 147.5 | 983.8 | 1046.3 | 26.3 | 86.3 | 2.5 |
| | #5 | 15.0 | 312.5 | 5.0 | 402.5 | 573.8 | 707.5 | 97.5 | 25.0 | 20.0 |
| 3. | #1 | 48.8 | 1236.3^ | 38.8 | 405.0 | 1236.3^ | 1236.8^ | 218.8 | 490.0 | 1120.0 |
| with | #2 | 113.8 | 946.3 | 17.5 | 293.8 | 1247.5^ | 1247.5^ | 162.5 | 86.3 | 5.0 |
| aCTLA4 | #3 | 16.3 | 1248.8^ | 6.3 | 465.0 | 1248.8^ | 1248.8^ | 187.5 | 295.0 | 11.3 |
| (ID) | #4 | 6.3 | 828.8 | 6.3 | 1006.3 | 1247.5^ | 1247.5^ | 142.5 | 30.0 | 17.5 |
| | #5 | 152.5 | 566.3 | 18.8 | 757.5 | 1173.8 | 1242.5^ | 287.5 | 57.5 | 110.0 |

Example 9. Systemic Exposure of CTLA-4 Antibody after Administration in Monkeys The blood levels of anti-CTLA-4 antibody Tremelimumab (CP675206) were investigated in Indian Rhesus macaques after the antibody was administered by intradermal or intravenous injections.

Animal Treatment and Sample Collection.

Three animals per treatment group were injected with the anti-CTLA-4 antibody Tremelimumab at 10 mg/kg, either with a single intravenous injection into the saphenous vein or multiple 0.2 ml intradermal bilateral injections in the upper thigh in proximity to the inguinal draining lymph nodes. Blood samples were collected at 0, 1, 2, 4, 8, 12, 24, and 48 hrs post injection into 2.0 ml vaccutainer tubes containing lithium heparin as the anticoagulant. Plasma was collected from the supernatant in the vaccutainer tubes after centrifugation at 1500×g at 4° C. for 10 min. The levels of Tremelimumab in the plasma was measured by a quantitative ELISA assay according to the procedure provided below.

Tremelimumab Quantitative ELISA Assay Procedure. The 384-well high bind assay plates (VWR-Greiner Bio-One Cat #82051-264) were coated with 25 μl/well of CD-152 (CTLA-4; Ancell Immunology Research Products Cat #501-020) at 1.0 μg/ml in 100 mM carbonate-bicarbonate coating buffer and incubated overnight at 4° C. Plates were washed ×6 with 1×PBS-Tween (0.01M PBS pH 7.4/0.05% Tween 20) and blocked using 40 μL/well of 5% FBS/1×PBS-Tween and incubated shaking at 600 rpm RT for 1 hour. Standards were prepared by making the following dilutions of Tremelimumab: 200, 67, 22, 7.4, 2.5, 0.82, 0.27, 0.09 and 0.03 ng/mL. The samples were diluted to 1:100, 1:1,000 and 1:10,000. The diluent consisted of 1% naïve cynomolgus macaque sera and 5% FBS in 1×PBS-Tween (0.01M PBS pH 7.4/0.05% Tween 20). 25 μL/well of each standard, sample and diluent control were transferred in duplicate into the plate and incubated shaking at 600 rpm RT for 1 hour. After washing×6 with 1×PBS-Tween, 25 μL/well of secondary antibody (goat anti-human IgG HRP, Southern Biotech Cat #9042-05) at a 1:5,000 dilution with 1×PBS-Tween was added and then incubated shaking at 600 rpm room temperature for 1 hour. After washing×6 with 1×PBS-Tween, 25 μL/well of TMB Peroxidase EIA-Substrate (solution A+B) (Bio-Rad Cat #172-1067) were added and the plates were incubated at RT for 4 minutes. The colorimetric reaction was stopped by addition of 12.5 μL/well 1N Sulfuric acid and the absorbance then read at 450 nm. The amount of Tremelimumab in each sample was quantified using the standard curve with 0.27 to 67 ng/mL used as the quantitative range.

Results.

Figure 30:
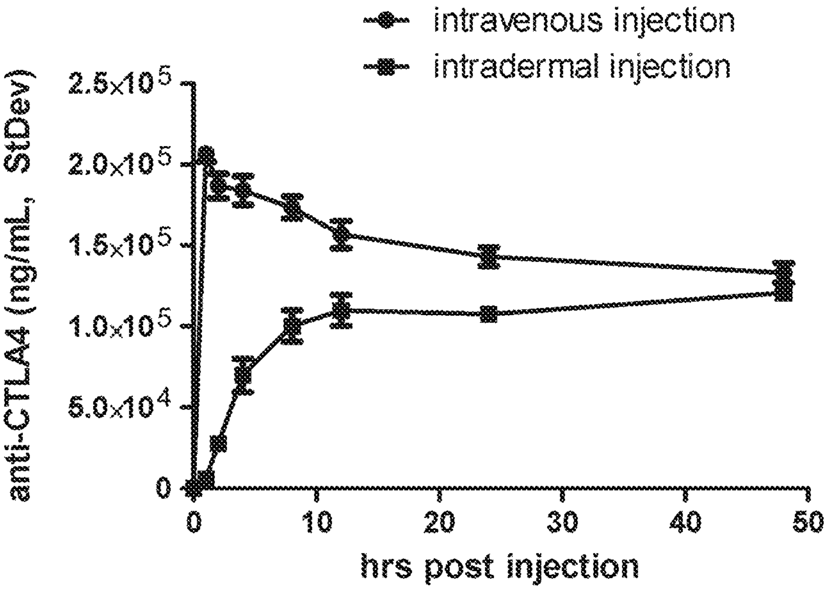
FIG. 30. Graph depicting results of a representative study that evaluates the blood anti-CTLA-4 monoclonal antibody levels measured by competitive ELISA in Indian Rhesus macaques injected with anti-CTLA-4 (CP-675, 206) at 10 mg/kg.

The plasma anti-CTLA-4 levels from a representative study are presented in FIG. 30. As shown, intradermal injection of the anti-CTLA-4 antibody Tremelimumab displays a slower release kinetics of the antibody in the blood and a lower systemic exposure ($AUC_{0-24}$=4.9×$10^6$ ng·hr/ml) profile than intravenous injections ($AUC_{0-24}$=7.2×$10^6$ ng·hr/ml).

Example 10. Effect of Anti-CTLA-4 Antibody on Vaccine-Induced Immune Responses in Mice Study Procedure.

Female BALB/c mice, 6 per group, were primed and boosted with rHer-2 expressing DNA by PMED separated by a four week interval. 150 μg of the monoclonal antibody specific to mouse CTLA-4 (clone 9H10, Bioxcell or #BE0131) or isotype control monoclonal antibodies (Bioxcell #BE0091) was administered on the days of PMED actuation and 100 μg on the days after PMED by local intradermal or systemic intraperitoneal injections as indicated in the legends. The polyfunctional (multi-cytokine positive) T cell immune responses were measured from splenocytes isolated from individual mice 7 days after the last PMED immunizations by ICS assay. After a 5 hr stimulation with a vaccine specific epitope peptide (rHer-2 specific antigen specific CD8 (p66), CD4 (p169) epitope or irrelevant peptide HBV (core antigen p87)) at 10 μg/ml, the splenocytes were first stained for CD4, CD3 and CD8 which was followed by permeabilization and staining for IFNα, TNFα and IL-2 expression that was analyzed by flow cytometry. The total number of antigen specific single, double or triple cytokine positive T cells per total spleen of each animal is calculated by subtracting the responses to the irrelevant peptide HBV from the vaccine specific responses and normalized by the total number of splenocytes isolated per spleen.

Results.

FIGS. 31A and 31B show the results of a representative study that evaluates the immunomodulatory activity of anti-CTLA-4 monoclonal antibody (clone 9H10) on the quality of the vaccine induced immune responses by intracellular cytokine staining assay. Seven days after the last PMED, significant increases in antigen specific single and double cytokine positive CD8 T cell responses by the local intradermal delivery of anti-CTLA-4 and double and triple cytokine positive CD8 T cell responses by the systemic delivery was observed. Additionally, significant increases in antigen specific single cytokine positive CD4 T cells by intradermal delivery and double cytokine positive cells by systemic delivery of anti-CTLA-4 was observed (*indicates $P<0.05$ by Student's T-test).

Example 11. Synergistic Effect of Sunitinib in Combination with an Anti-Cancer Vaccine Study Procedure.

The Anti-tumor efficacy of sunitinib malate in combination with an anti-cancer DNA vaccine was investigated in BALB/neuT transgenic female mice. Heterozygote BALB/neuT transgenic female mice that express rat Her-2 (rHer-2) tumor associate antigen were implanted subcutaneously with 1e6 TUBO cells expressing rHer-2 which are derived from the spontaneous mammary tumors of BALB/neuT mice. After 7 days post tumor cell implantation, the mice were dosed once a day orally with either vehicle or sunitinib malate at doses as indicated in the legends. Three days after the initiation of sunitinib malate therapy, the mice were immunized with regimens comprised of either (a) control vaccine that expresses an antigen that is not expressed in the tumor or the mouse or (b) DNA cancer vaccine construct that expresses a rat Her-2 antigen of SEQ ID NO: 54 (rHER2) which is expressed in the tumor and the mouse. The tumor growth rate was analyzed by measuring the long (a) and short diameter (b) of the subcutaneous TUBO tumors twice a week and calculating the volume as a×$b^2$×0.5 $mm^3$. The average and standard error of the mean of the tumor volumes from 10 mice per each treatment group are plotted against the days after tumor implantation.

Results.

Figure 32:
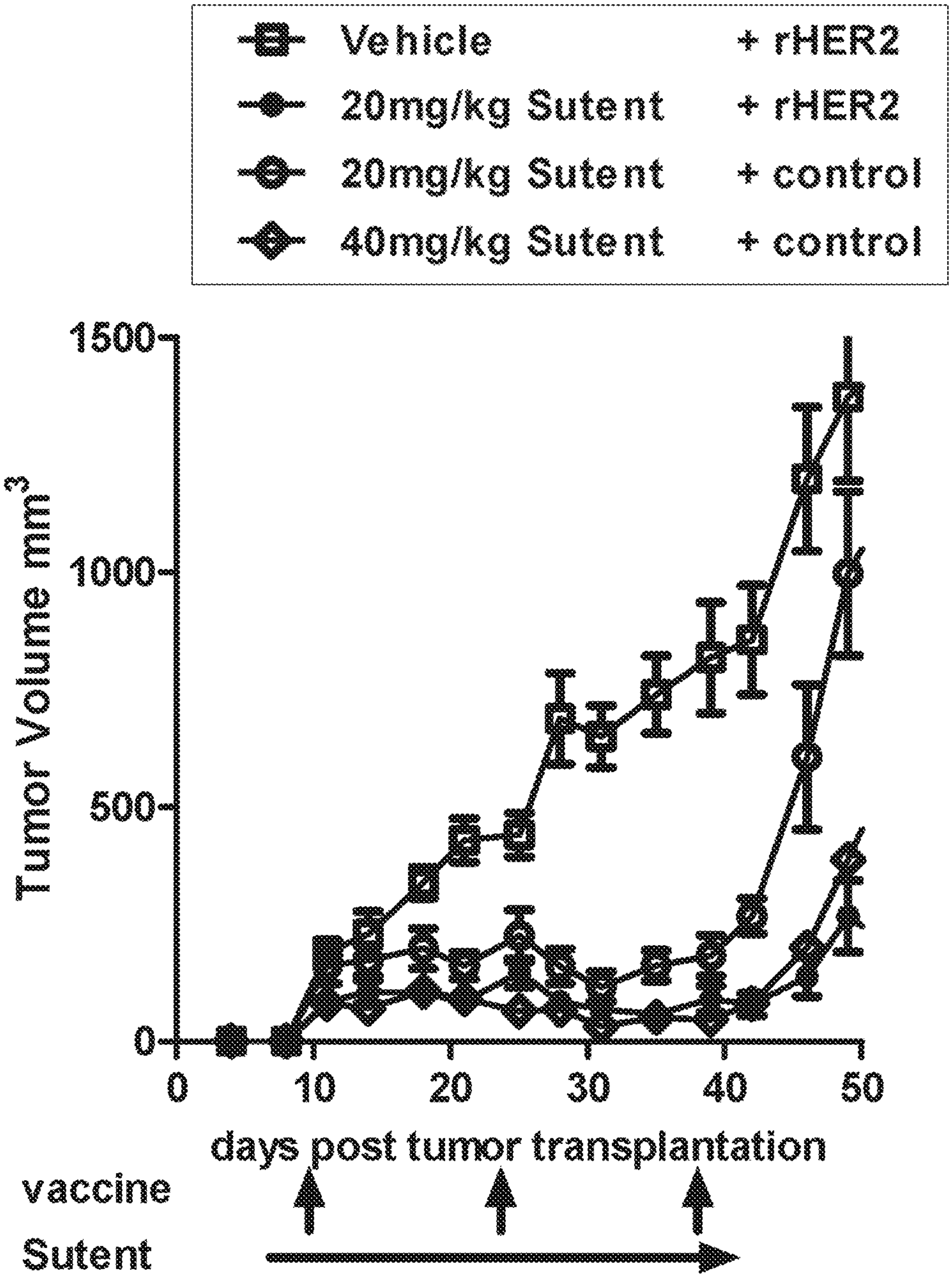
FIG. 32. Graph depicting results of a representative study that evaluates the effect of sunitinib malate (Sutent) on the anti-tumor efficacy of a cancer vaccine (rHER2) in mice, in which the subcutaneous tumor growth rate was measured.
Figure 33A:
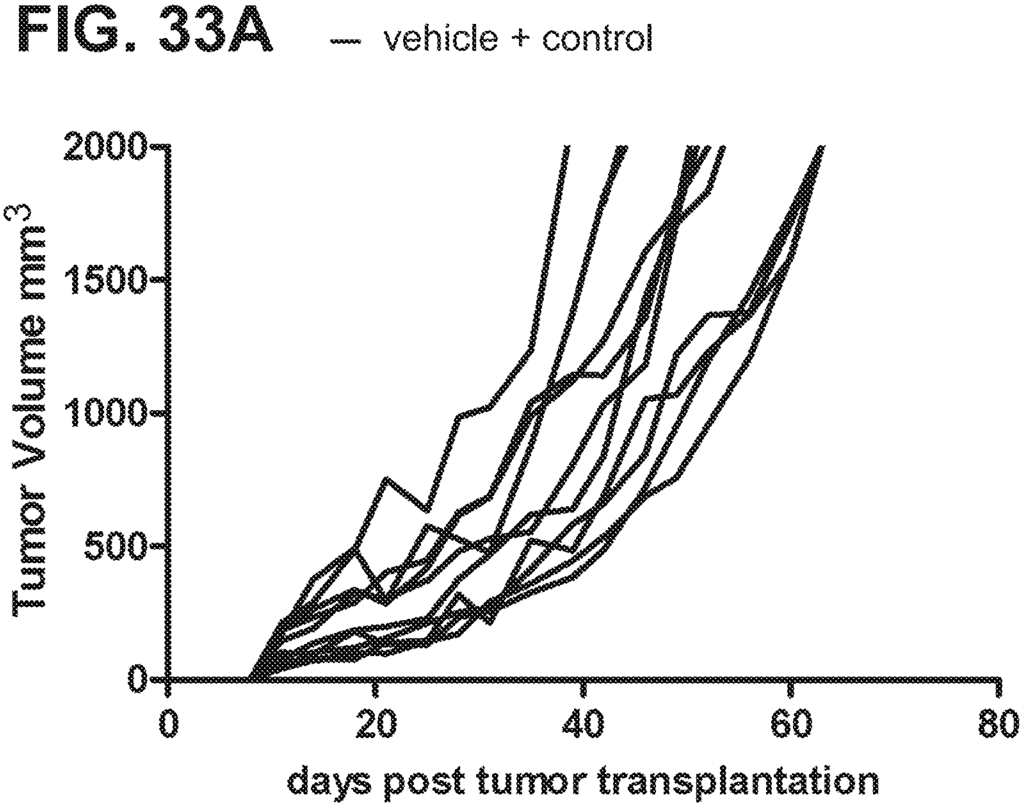
FIGS. 33A-33D. Graphs depicting results from a representative study that evaluates the effect of sunitinib malate (Sutent) on the anti-tumor efficacy of a cancer vaccine (rHER2), in which individual tumor growth rates were measured in mice treated with (a) the control agents (FIG. 33A), (b) sunitinib malate and the control vaccine (FIG. 33B), (c) the vehicle and the cancer vaccine (FIG. 33C), or (d) sunitinib malate and the cancer vaccine (FIG. 33D).
Figure 33B:
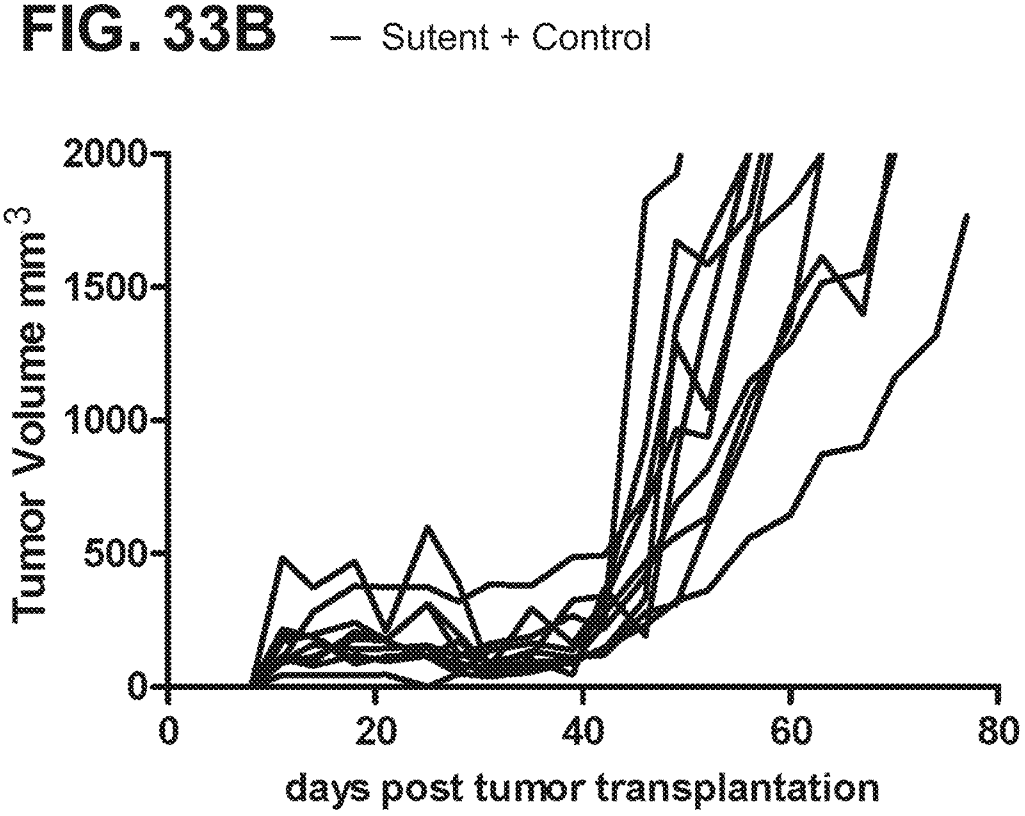
Figure 33C:
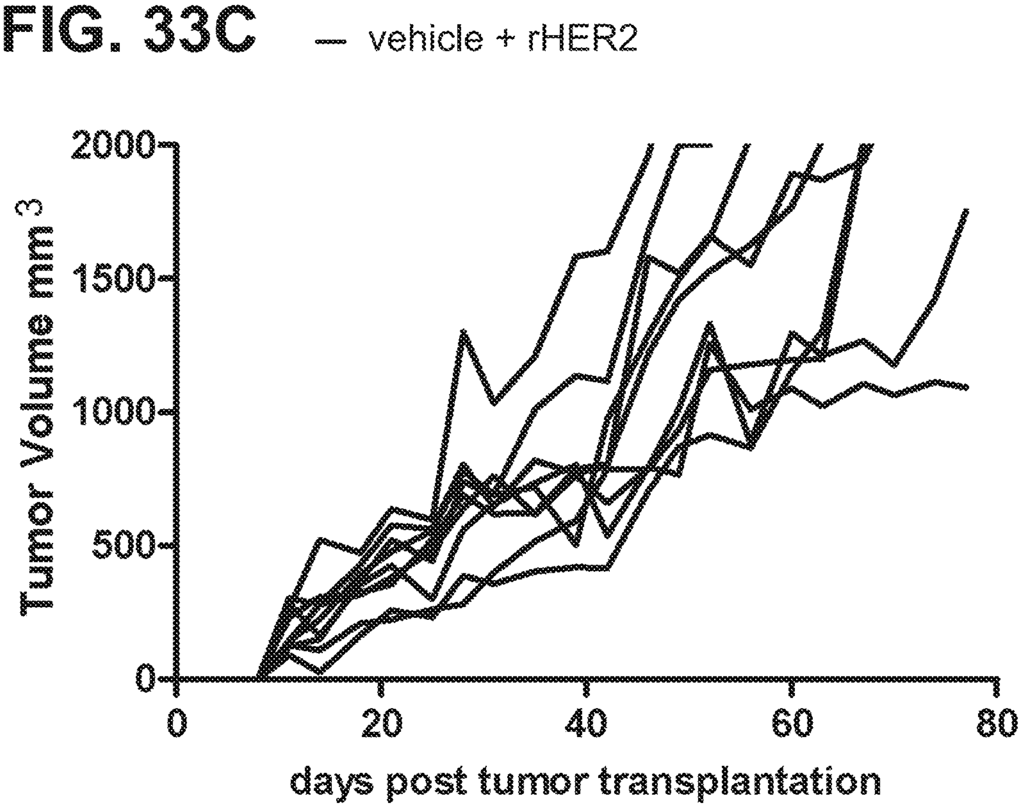
Figure 33D:
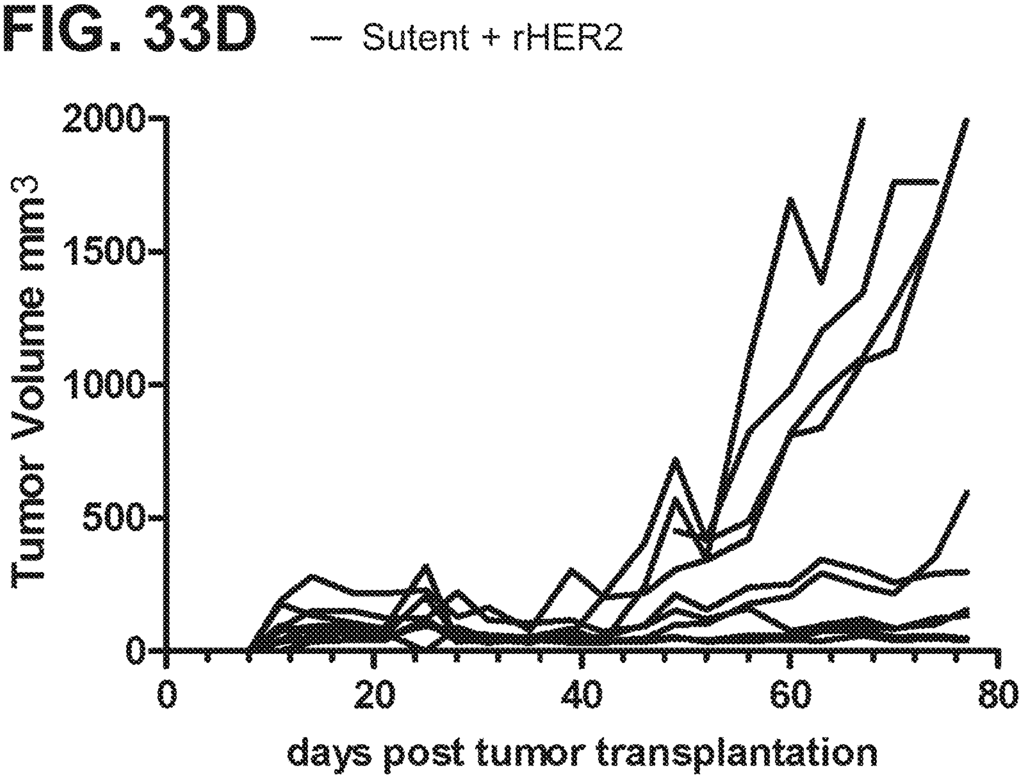

FIG. 32 shows the results of a representative study that evaluates and compares the subcutaneous tumor growth rate upon treatment with sunitinib malate as a monotherapy or in combination with the DNA cancer vaccine. While the tumors from mice that received the DNA cancer vaccine (rHER2: intramuscular injection of 1e9 V.P. of rHer-2 expressing adenovirus followed by two biweekly actuations of rHer-2 expressing DNA by PMED) continued to grow rapidly, the tumors from mice that received sunitinib malate at either 20 mg/kg or 40 mg/kg doses with control vaccines (control: intramuscular injection of 1e9 V.P. of eGFP expressing adenovirus followed by two biweekly, actuations of HBV core antigen expressing DNA by PMED) significantly decreased the tumor growth rate, with 20 mg/kg displaying suboptimal efficacy compared to the 40 mg/kg dose. However when the cancer vaccine was co-administered with the suboptimal dose of sunitinib malate at 20 mg/kg, the tumors grew at a much slower growth rate than in mice treated with the same dose of sunitinib malate co-administered with a control vaccine and similar to that of mice treated with sunitinib malate at a higher dose. Cancer vaccine provides additional therapeutic benefit to mice that received suboptimal doses of sunitinib malate.

FIGS. 33A-33D show the individual tumor growth rates of mice from a representative study that evaluates and compares the anti-tumor efficacy of sunitinib malate at 20 mg/kg with control (control) or the DNA cancer vaccine (rHER2). Briefly, after 7 days post tumor cell implantation, ten mice per treatment group were daily orally dosed with either vehicle or 20 mg/kg sunitinib malate (Sutent) for 34 days. Three days after the initiation of Sutent dosing, a series of immunizations, primed by Adenovirus followed by PMED, were initiated that continued after the discontinuation of Sutent therapy. Specifically the mice were immunized with either control vaccine comprised of an intramuscular injection of 1e9 V.P. of eGFP expressing adenovirus subsequently followed by two biweekly, two 9 days and four weekly actuations of DNA expressing HBV core and surface antigens by PMED or cancer vaccine comprised of rHer-2 expressing adenovirus and DNA instead. The tumors of the animals that received vehicle with the control vaccine became measurable around day 7 and continued growing reaching 2000 $mm^3$ after 50 days post tumor implant. The tumor growth of the animals that received Sutent with control vaccine was significantly impaired until Sutent therapy was discontinued. The tumors displayed a rapid growth rate immediately after the discontinuation of Sutent, the majority reaching 2000 $mm^3$ after 50 days post tumor implant. The tumor growth rate of animals that only received the cancer vaccinations was modestly slower than the animals that did not receive cancer vaccine or Sutent. The combination of cancer vaccine with Sutent not only suppressed the tumor growth during Sutent therapy (FIG. 33)

but also significantly impaired the progression of the tumor in 60% of the animals after discontinuation of Sutent treatment.

Figure 34:
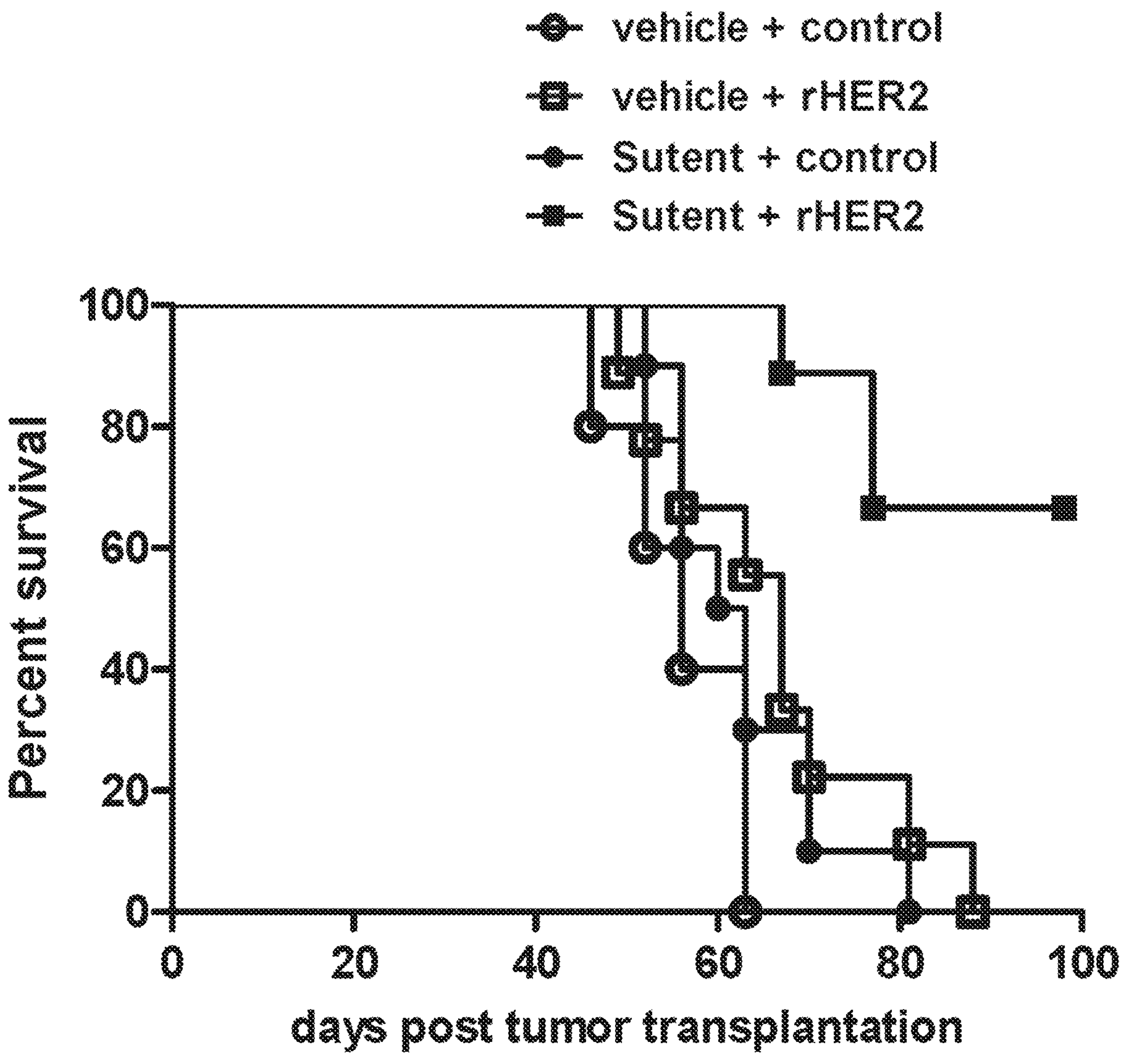
FIG. 34. Graph showing the Kaplan-Meier survival curves of the groups of mice from the study described in FIGS. 33A-33D that evaluates the effect of sunitinib malate (Sutent) on the anti-tumor efficacy of a cancer vaccine (rHER2).
Figure 35A:
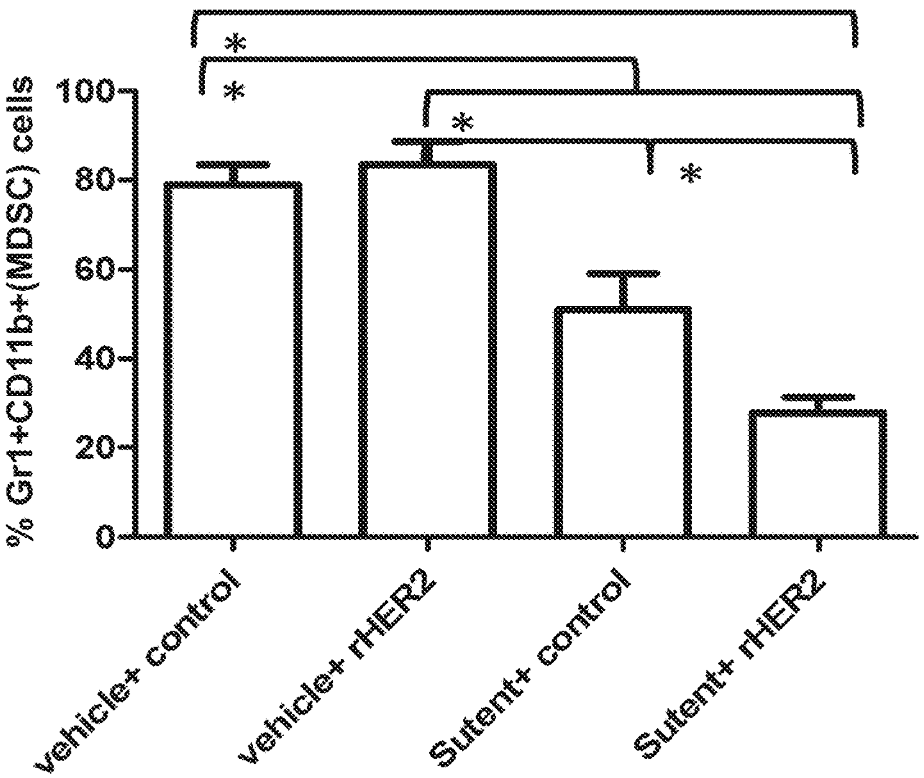
FIGS. 35A, 35B. Graphs showing changes in myeloid derived suppressor cells (Gr1+CD11b+.
Figure 35B:
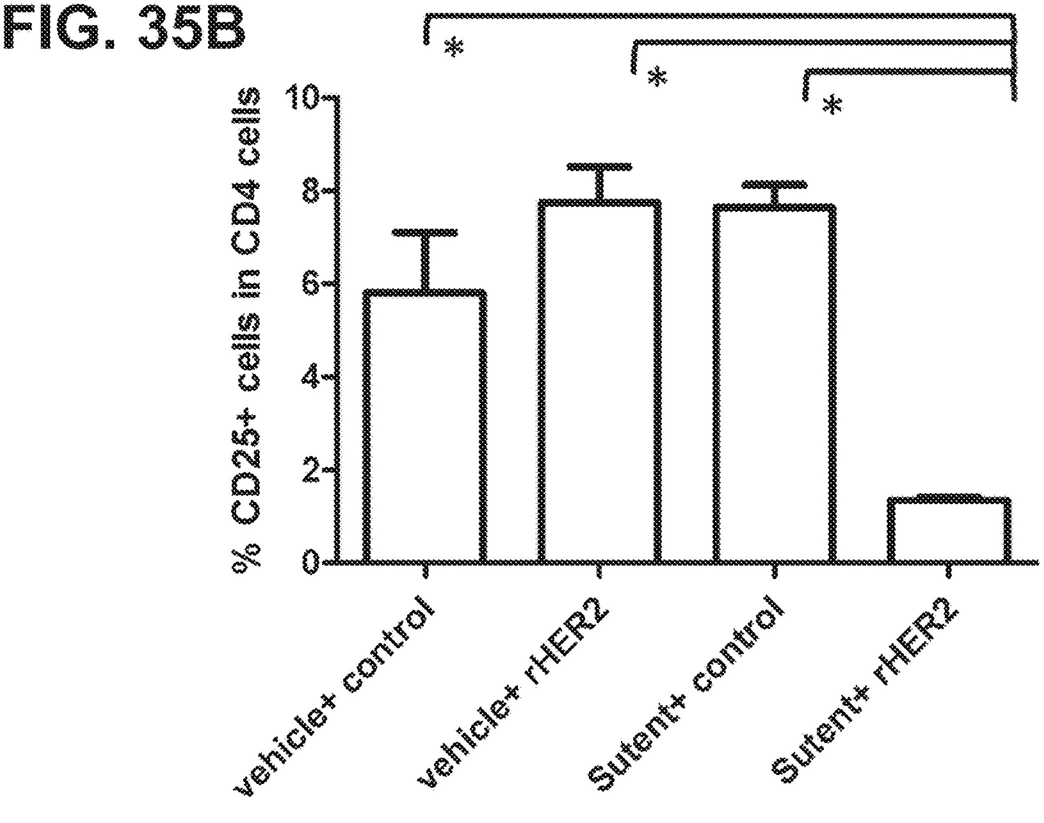

FIG. 34 shows the Kaplan-Meier survival curve of the groups of mice from the study described in FIGS. 33A-33D that evaluates the anti-tumor efficacy of Sutent with the control (control) or cancer vaccine (rHER2). The mice were sacrificed when the tumor volume reached 2000 $mm^3$ according to IAUCUC guidelines. Only mice treated with Sutent (at 20 mg/kg) and cancer vaccine displayed a significantly prolonged survival compared to mice either treated with vehicle and control vaccine, cancer vaccine without Sutent or Sutent without cancer vaccine (*P<0.01 by Log-rank Test).

FIGS. 35A-35D show the percentage of myeloid derived suppressor cells (Gr1+CD11b+) and Treg containing CD25+CD4+ cells in the periphery blood from the groups of mice from the study described in FIGS. 33A-33D. Briefly, PBMCs were stained and analyzed by flow cytometry for the expression of Gr1, CD1 b, CD3, CD4, and CD25 from submandibular bleeds of five mice from each group on d27 (20 days post the initiation of Sutent or vehicle treatment). The mean and standard error of the mean of each treatment group is shown. A statistically significant reduction of % myeloid derived suppressor cells was observed in mice that were treated by Sutent with either control or cancer vaccine compared to mice that did not receive Sutent nor cancer vaccine (vehicle+control). However significantly lower myeloid derived suppressor cells were observed in mice treated with the combination of Sutent with cancer vaccine (Sutent+rHER2) compared to mice that were treated with cancer vaccine without Sutent (vehicle+rHER2) or Sutent without cancer vaccine (Sutent+control). A statistically significant reduction of Treg containing CD25+CD4+ T cells in the CD4 population was observed by Sutent with cancer vaccine. These mice had significantly lower % of Treg containing CD25+CD4+ T cells in the CD4 population than mice that were treated with cancer vaccine without Sutent or Sutent without cancer vaccine in their blood. * indicates P<0.05 by Student's T-test.

Figure 36A:
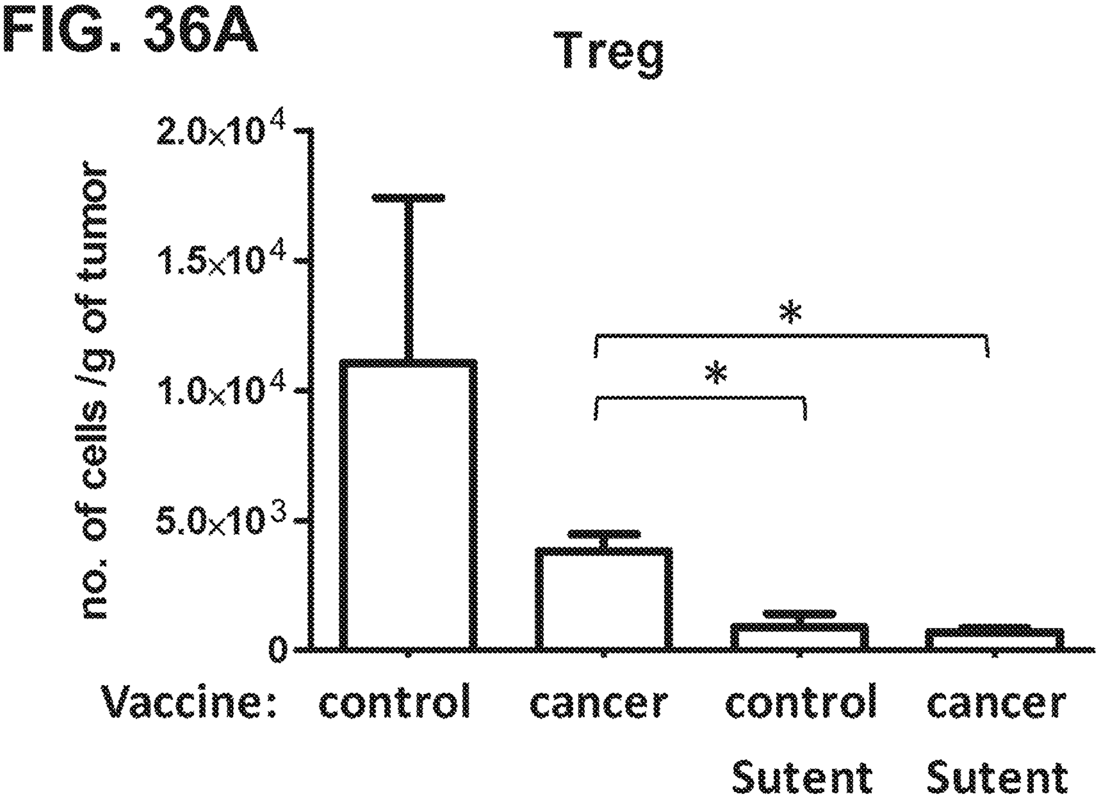
FIGS. 36A-36C. Graphs depicting results of a representative study in a mouse tumor model that evaluates the effect of sunitinib malate (Sutent) on the total number of (a) Tregs (CD4+CD25+Foxp3+.
Figure 36B:
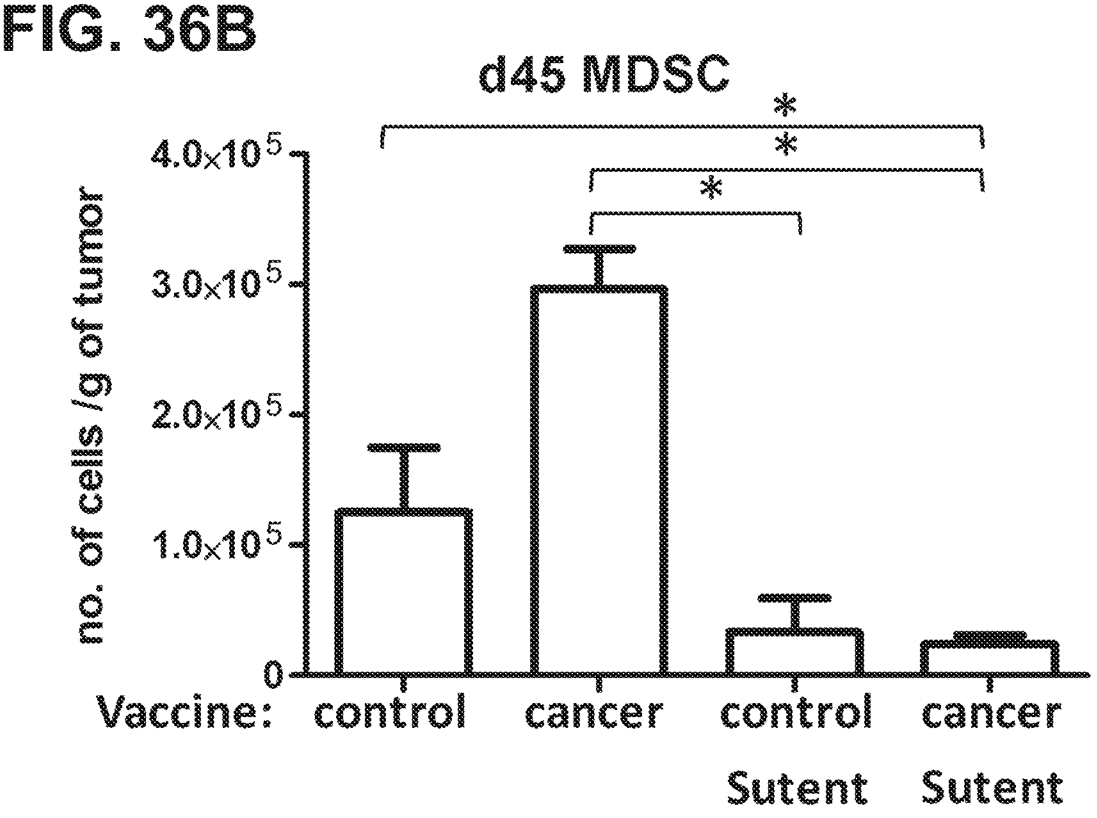
Figure 36C:
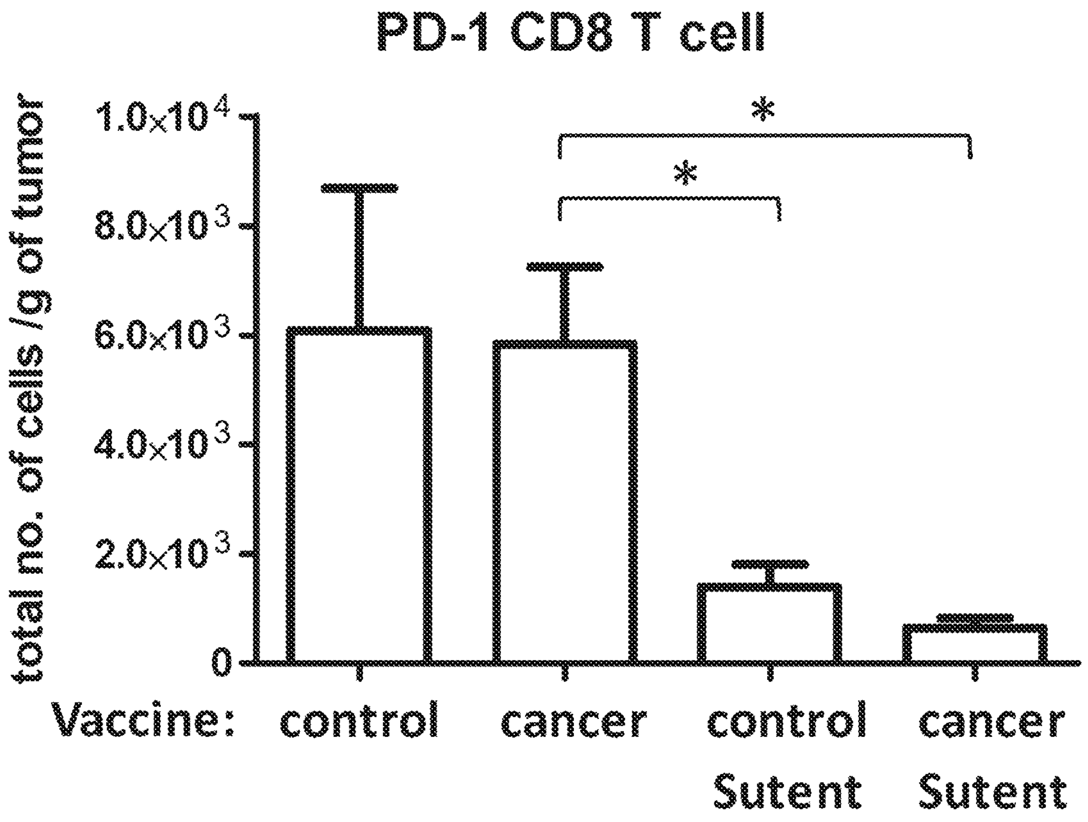

FIGS. 36A-36C show the total number of myeloid derived suppressor cells (Gr1+CD11b+), Tregs (CD4+CD25+Foxp3+) and PD-1+CD8 T cells isolated from tumors of mice. Briefly, the mice were given a single daily oral dose of either vehicle or Sutent at 20 mg/kg three days after implantation with TUBO cells for 28 days. The same mice were immunized with either control vaccine comprised of an intramuscular injection of 1e9 V.P. of eGFP expressing adenovirus subsequently followed by two biweekly administrations of DNA expressing HBV core antigen delivered by PMED or cancer vaccine comprised of rHer-2 expressing adenovirus and DNA. An intradermal injection of 50 µg of CpG (PF-03512676) was given with the PMED administrations in proximity to the right side inguinal draining lymph node. Seven days after the second PMED and CpG administration, individual tumors were isolated, from 6 mice per treatment group.

The single cell suspension prepared from the isolated subcutaneous tumors were stained by antibodies specific for Gr1, CD11b, CD3, CD8, CD25, FoxP3, and PD-1 and analyzed by flow cytometry. The mean and standard error of the mean of the total number of specific cells as indicated in the figures per µg of tumor from each treatment group is plotted. (*indicates P<0.05 by Student's T-test) While there was no significant difference in the frequency of immune suppressive Tregs or MDSC found in the tumor when mice were given cancer vaccine (A and B) compared to mice that received control vaccine (A and B), a significant reduction was observed when the mice were treated with Sutent (A and B) compared to mice that received cancer vaccine only. A reduction of PD-1+CD8 T cells was also observed in mice that were treated with Sutent (C) compared to mice that received cancer vaccine (C) only. Taken together, these data demonstrate that agents that reduce Tregs, MDSCs or CD8+PD-1+Tcells in combination with the vaccine would be beneficial in reducing tumor burden in tumor bearing animals.

Example 12. Anti-Cancer Efficacy of Vaccine in Combination with Sunitinib and Anti-CTLA-4 Antibody The anti-tumor efficacy of a cancer vaccine in combination with sunitinib and anti-CTLA-4 monoclonal antibody (clone 9D9) was investigated in subcutaneous TUBO tumor bearing BALB/neuT mice.

Study Procedure.

Briefly, ten mice per each group were daily orally dosed with either vehicle or sunitinib malate at 20 mg/kg starting at day 10 post tumor implant until day 64. Vaccination with DNA constructs that either encode no antigen (control vaccine) or a rat Her-2 antigen of SEQ Id NO: 54 (cancer vaccine) as adenovirus vectors initiated on day 13 subsequently followed by two weekly immunizations, two biweekly immunizations, and seven weekly immunizations of respective antigens (HBV antigens or rHer-2) by DNA. The groups of mice (closed circle and open triangle) that were treated with anti-murine CTLA-4 monoclonal antibody were intraperitoneally injected with 250 µg of the antibody on day 20, 27, 41, 55, 62, 69, 76, 83, 90, and 97 right after the PMED injections.

Results.

Figure 37:
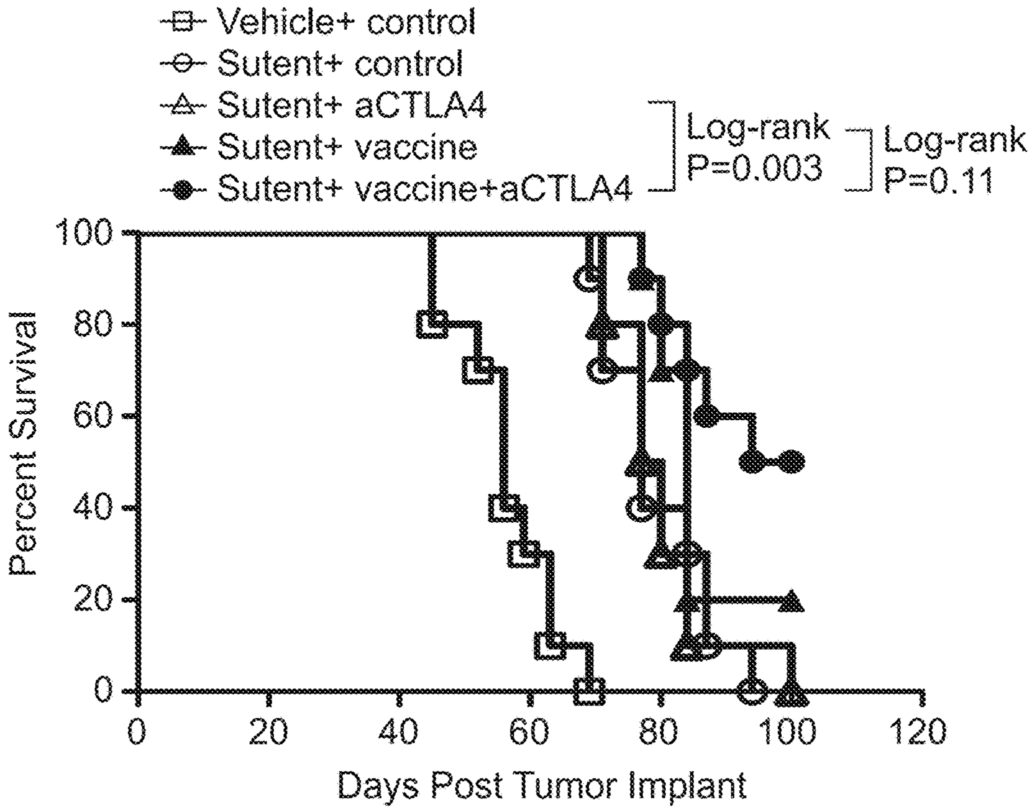
FIG. 37. Graph showing the Kaplan-Meier survival curves of the groups of mice from a representative study evaluating the effect of sunitinib malate (Sutent) and an anti-murine CTLA-4 monoclonal antibody (clone 9D9) on the anti-tumor efficacy of a cancer vaccine (vaccine) in subcutaneous TUBO tumor bearing BALB/neuT mice.

FIG. 37 shows the Kaplan-Meier survival curve of the groups of mice from a representative study evaluating the anti-tumor efficacy of sunitinib and anti-murine CTLA-4 monoclonal antibody (clone 9D9) in combination with a cancer vaccine. Increased survival time was observed in mice treated with Sutent with control vaccine (open circle), anti-murine CTLA-4 monoclonal antibody (open triangle) or cancer vaccine (closed triangle). A further increase of survival was observed in mice treated with Sutent and cancer vaccine in combination with anti-murine CTLA-4 (closed circle). P values were calculated by log-rank test.

Example 13. Systemic Exposure of Sunitinib and Anti-Cancer Efficacy of Anti-Cancer Vaccine in Combination with Low Dose Sunitinib Sunitinib Systemic Exposure Study.

The kinetics of blood sunitinib was investigated in BALB/neuT mice with subcutaneous TUBO tumors. Briefly, 20 mice per each treatment group were given Sutent orally, at 20 mg/kg once a day (SID) or at 10 mg/kg twice a day (BID) with 6 hr intervals, 6 days after tumor implantation. Submandibular blood from 2-3 mice was collected into lithium heparin tubes at several time points after Sutent dosing as indicated (0, 2, 4, 6, 8, 10, 12, and 24 hr). The plasma supernatant was recovered from the tubes after centrifugation at ×1000 g for 15 min. and the sunitinib levels from the plasma samples were measured by LC/MS/MS. The mean and standard error of the mean of each group at each time point is plotted.

Figure 38:
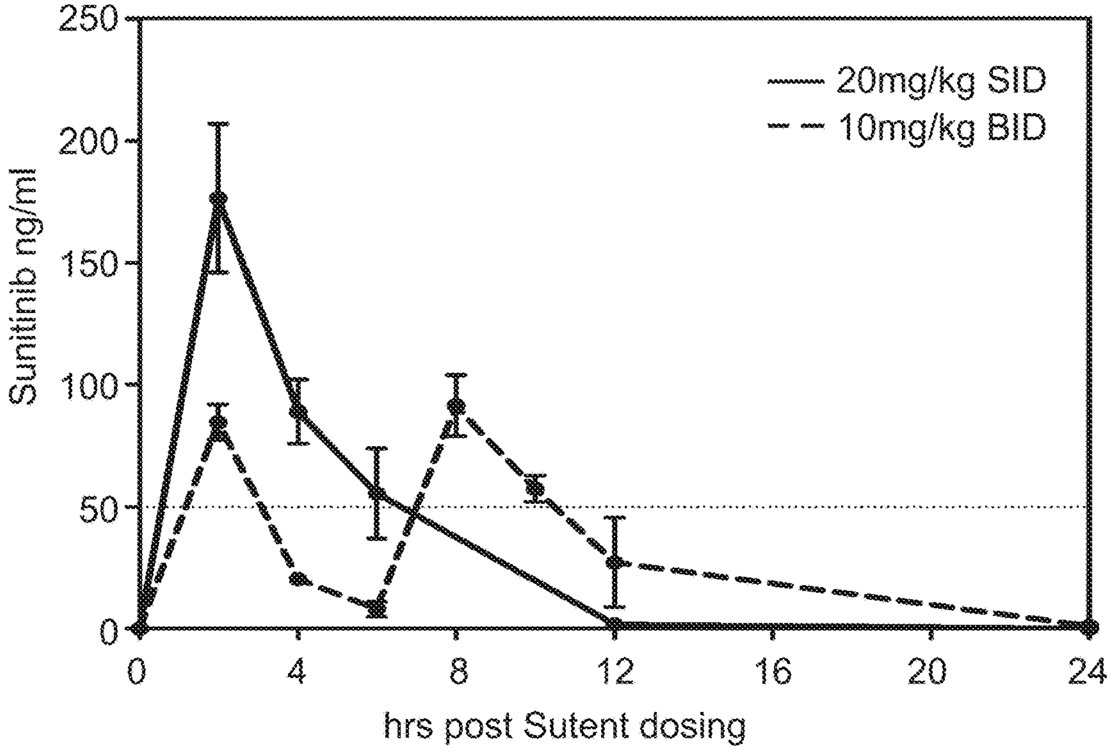
FIG. 38. Graph showing kinetics of the blood sunitinib levels of BALB/neuT mice with subcutaneous TUBO tumors.

Results are presented in FIG. 38. The mean and standard error of the mean of each group at each time point is plotted.

The dotted horizontal line marks the minimum sunitinib blood level, 50 ng/ml, that is necessary to effectively inhibit tumor growth in monotherapy (Mendel, D., et al.: "In vivo antitumor activity of SU11248, a novel tyrosine kinase inhibitor targeting vascular endothelial growth factor and platelet-derived growth factor receptors: determination of a pharmacokinetic/pharmacodynamic relationship". Clinical Cancer Research, 203, 9:327-337). As shown, the blood suntinib levels in the mice that received either 20 mg/kg SID or 10 mg/kg BID only maintain the target effective dose of 50 ng/ml that effectively inhibits tumor growth transiently within 24 hr. The blood levels in 20 mg/kg SID group peaked above 50 ng/ml at 2 hrs, dropped to 50 ng/ml at 6 hrs and cleared the blood by 12 hrs post Sutent dosing the levels in the group that received 10 mg/kg BID peaked above 50 ng/ml at 2 hrs but rapidly dropped below 50 ng/ml by 4 hrs that peaked again 2 hrs after the second dose. The levels rapidly dropped to 50 ng/ml by 4 hrs and cleared the blood by 18 hrs after the second dose. Despite the bi-daily dosing regimen, the animals that received 10 mg/kg, remained to display lower duration of exposure at target concentration than the 20 mg/kg single daily dosing regimen.

Anti-Tumor Efficacy Study.

Anti-tumor efficacy of long term administration of low dose sunitinib in combination with an anti-cancer vaccine was investigated in BALB/neuT mice with subcutaneous TUBO tumors. Briefly, the mice were given sunitinib malate (Sutent) for 31 days at 20 mg/kg SID or for 104 days at 10 mg/kg BID and received either control vaccine or cancer vaccine. The control vaccine, which delivers no antigen, and the cancer vaccine, which delivers a rat her-2 antigen (rHer-2) of SEQ ID NO: 54, was given by adenovirus on day 9 subsequently followed by five biweekly administrations of the DNA by PMED delivering HBV antigens or rHer-2 respectively.

Figure 39:
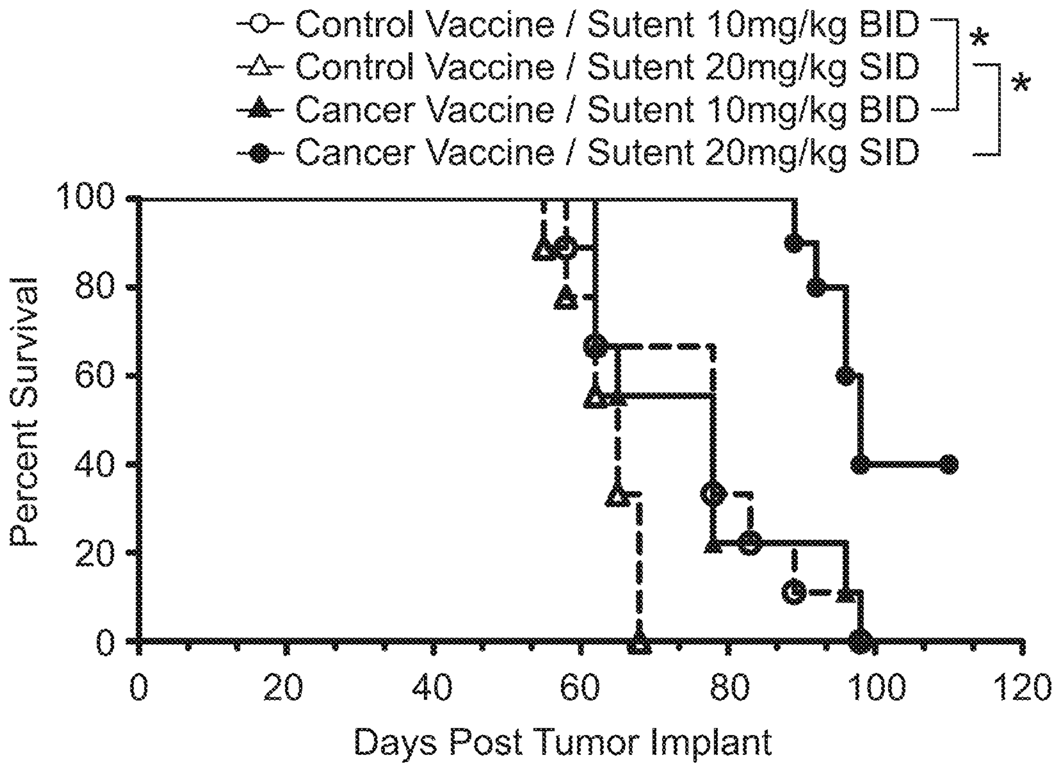
FIG. 39. Graph showing the Kaplan-Meier survival curves of the groups of mice from a representative study that evaluates the effect of sunitinib malate (Sutent) on the anti-tumor efficacy of a cancer vaccine in BALB/neuT mice with subcutaneous TUBO tumors.

The results are presented in FIG. 39. While the cancer vaccine improved the survival of mice given Sutent at 20 m/kg, there was even significant improvement of the survival of mice given Sutent at 10 mg/kg (*P=0.05 by Log rank test).

Example 14. Effect of CPG or CD40 Agonist on the Immune Responses Induced by Cancer Vaccine Immunogenicity Studies in BALB/c Mice The effect of local administration of immune modulators on the magnitude and quality of antigen specific immune responses induced by a cancer was investigated in BALB/c mice, in which the immune response was assessed by measuring rHER2 specific T cell responses using the IFNγ ELISPOT assay or intracellular cytokine staining assay. Briefly, 4 to 6 female BALB/c mice per group as indicated were immunized with DNA plasmid expression constructs encoding rHER2 antigen sequences (SEQ ID NO:54) by PMED delivery system. The immune modulators, CpG7909 (PF-03512676) and anti-CD40 monoclonal agonistic antibody, were administered locally by intradermal injections in proximity to the vaccine draining inguinal lymph node subsequently after the PMED actuations. Antigen specific T cell responses were measured by IFNγ □ELISPOT or intracellular cytokine staining assay according to the procedure described below.

Intracellular Cytokine Staining (ICS) Assay

The rHer-2 specific polyfunctional (multi-cytokine positive) T cell immune responses were measured from splenocytes or PBMCs isolated from individual animals by ICS assay. Typically 1e6 splenocytes were incubated with Brefeldin A at 1 μg/ml and peptide stimulant (rHer-2 specific CD8 p66, rHer-2 specific CD4 p169 or irrelevant HBV p87) at 10 μg/ml for 5 hr at 37° C. in a 5% $CO_2$ incubator. After the stimulation, the splenocytes were washed and blocked with Fcγ block (anti-mouse CD16/CD32) for 10 min. at 4° C. followed by a 20 min staining with Live/dead aqua stain, anti-mouse CD3ePE-Cy7, anti-mouse CD8a Pacific blue, and anti-mouse CD45R/B220 PerCP-Cy5.5. The cells were washed, fixed with 4% paraformaldehyde overnight at 4° C., permeabilized with BD fix/perm solution for 30 min at RT and incubated with anti-mouse IFNγ APC, anti-mouse TNFα Alexa488 and anti-mouse IL-2 PE for 30 min at RT. The cells were washed and 20,000 CD4 or CD8 T cells were acquired for analysis by flow cytometry. The total number of antigen specific single, double or triple cytokine positive T cells per total spleen of each animal is calculated by subtracting the rHer-2 specific responses to the irrelevant peptide HBV from the vaccine specific responses and normalized to the total number of splenocytes isolated from the spleen.

IFNγELISPOT Assay Results

Figure 40:
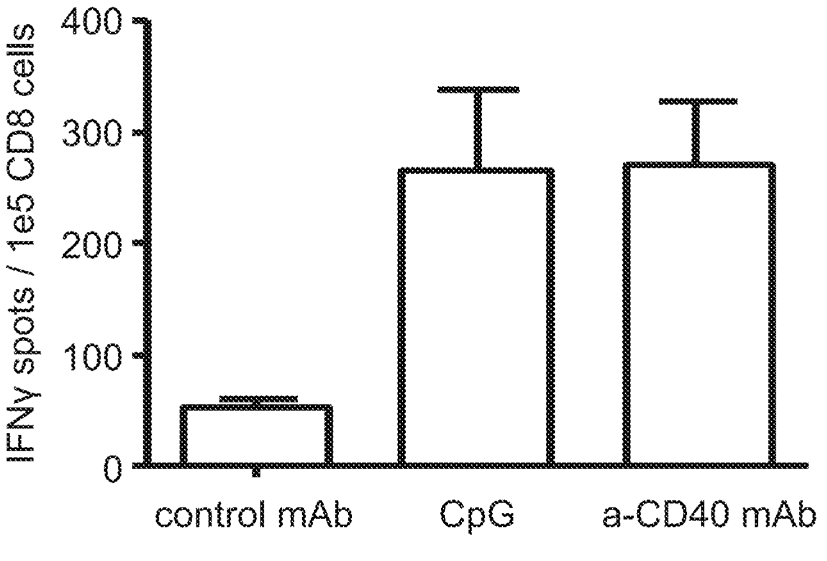
FIG. 40. Graph depicting the IFNγ ELISPOT results from a representative study evaluating the effect of CpG7909 and an anti-CD40 antibody (Bioxcell #BE0016-2) on the antigen specific T cell responses induced by a cancer vaccine (rHER2).

FIG. 40 shows the IFNγ ELISPOT results from groups of mice from a representative study evaluating the magnitude of antigen specific T cell responses induced by the rHER2 vaccine when given with the immune modulators as indicated. Briefly, each mouse per treatment group (n=4) was immunized with DNA plasmid expression constructs encoding rHER2 antigen sequences (SEQ ID NO:54) by PMED immediately followed by either 100 ug of control rat IgG monoclonal antibody (Bioxcell #BE0089: control mAb) or 50 g CpG7909 or 100 ug of anti-CD40 monoclonal antibody (Bioxcell #BE0016-2: a-CD40 mAb) as indicated. The antigen specific immune responses were measured by IFNγ ELISPOT assay from 5e5 splenocytes mixed with control or rHer-2 specific p66 peptides at 10 g/ml concentration, 7 days after the PMED actuation. The number of total IFNγ secreting cells from splenocytes containing 1e5 CD8 T cells were calculated from the ELISPOT results from individual animals and the % of CD8 T cells in splenocytes and mean and standard mean of error of each group are plotted. As shown, both CpG7909 and the anti-CD40 monoclonal antibody both significantly enhanced the magnitude of antigen specific immune responses induced by rHer-2 DNA compared to mice that received control antibodies.

Intracellular Cytokine Staining (ICS) Assay Results.

Figure 41A:
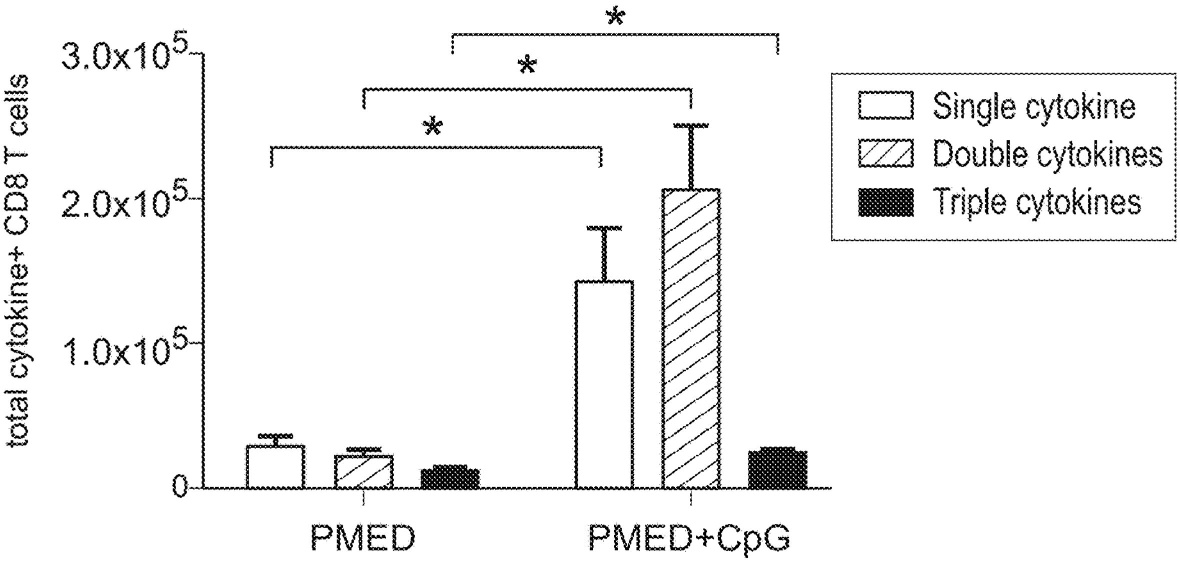
FIGS. 41A, 41B. Graphs depicting results of a representative study that evaluates the immunomodulatory activity of CpG7909 on the quality of the immune responses induced by a cancer vaccine (PMED) using intracellular cytokine staining assay, in which cytokine positive CD8 T cells (FIG. 41A) and cytokine positive CD4 T cells (FIG. 41B) were measured.
Figure 41B:
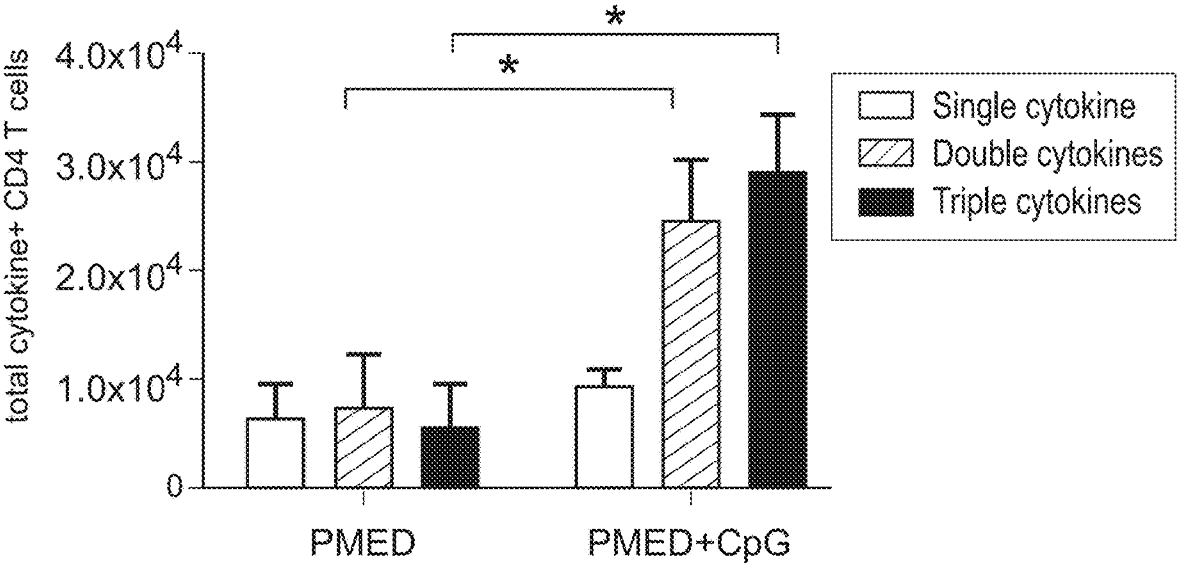

FIGS. 41A and 41B show the results of a representative study that evaluates the immunomodulatory activity of CpG 7909 on the quality of the vaccine induced immune responses by intracellular cytokine staining assay. Briefly, each animal was immunized twice with the DNA plasmid expression constructs encoding rHER2 antigen sequences (SEQ ID NO:54) delivered by PMED with a 4-week interval. The mice in each group (n=5) were given intradermal injections of either PBS (PMED group) or 50 g of CpG 7909 (PMED+CpG group) in proximity to the right side vaccine draining inguinal node immediately following both DNA immunizations by PMED. Seven days after the last immunization by PMED, an ICS assay was performed on the splenocytes isolated from each individual mice to detect antigen specific polyfunctional CD8 or CD4 T cells that secrete IFNγ, TNFα and/or IL-2. A significant increase in rHer-2 specific multi-cytokine positive CD8 and CD4 T cell responses were detected from mice treated with the local delivery of CpG 7909 compared to PBS. An increase in the single cytokine positive CD8 population was observed in the animals that received local delivery of CpG7909 administration compared to PBS (*indicates P<0.05 by Student's T-test).

Figure 42A:
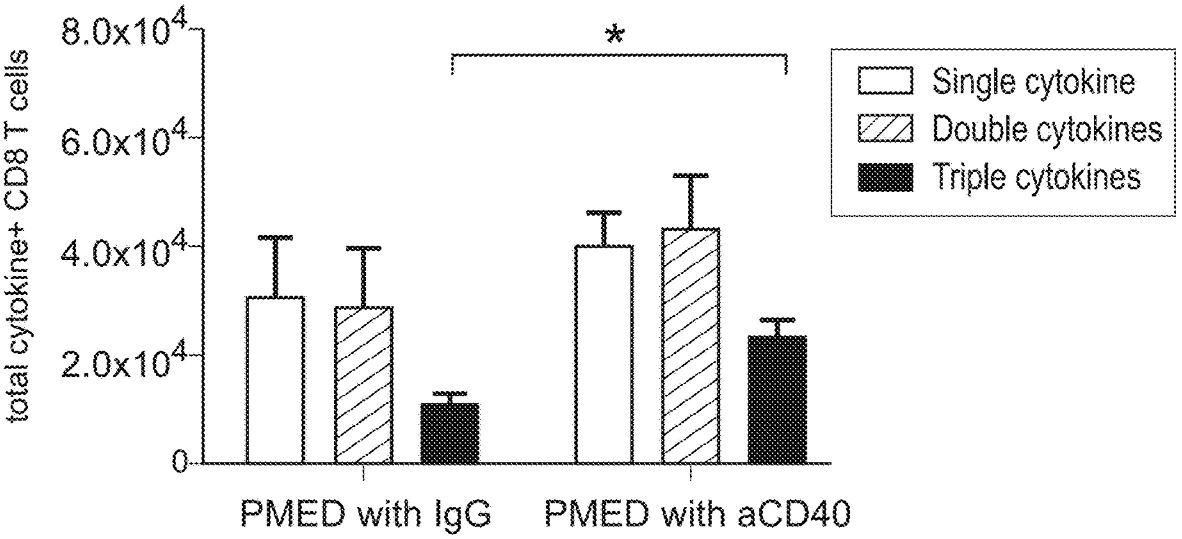
FIGS. 42A, 42B. Graphs depicting results of a representative study that evaluates the immunomodulatory activity of an agonistic anti-murine CD40 monoclonal antibody on the quality of the immune responses induced by a cancer vaccine (PMED) using intracellular cytokine staining assay, in which cytokine positive CD8 T cells (FIG. 42A) and cytokine positive CD4 T cells (FIG. 42B) were measured.
Figure 42B:
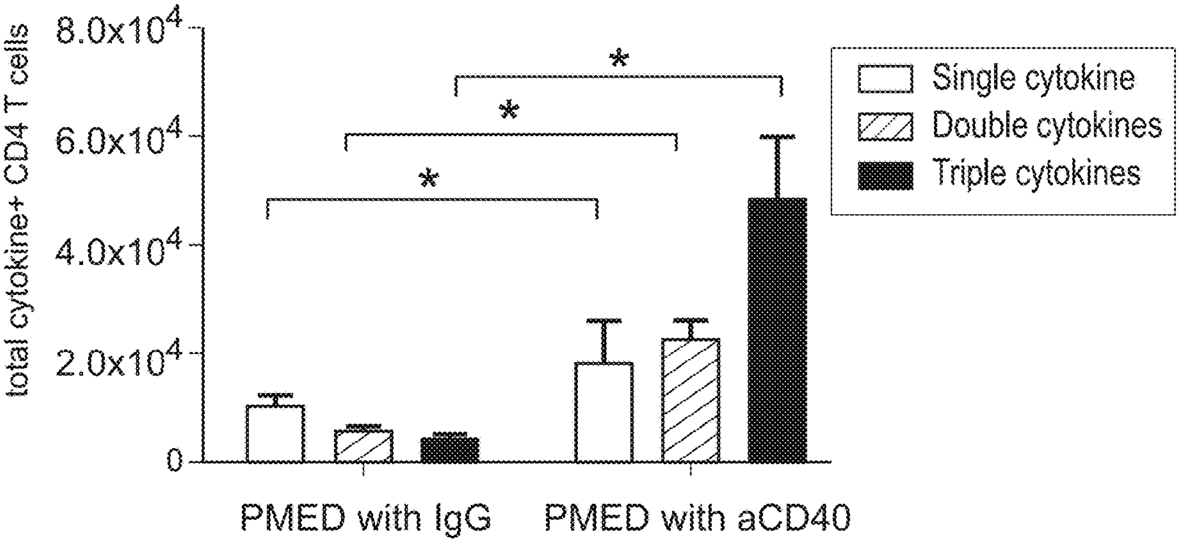

FIGS. 42A and 42B show the results of a representative study that evaluates the immunomodulatory activity of an agonistic anti-CD40 monoclonal antibody on the quality of the vaccine induced immune responses by intracellular cytokine staining assay. Briefly, each animal was immunized twice by DNA plasmid expression constructs encoding rHER2 antigen sequences (SEQ ID NO:54) delivered by PMED with a 4 week interval. The mice in each group (n=6) were given 100 μg of intradermal injections of either isotype IgG control (PMED with IgG) or anti-CD40 monoclonal antibody (PMED with aCD40) in proximity to the right side vaccine draining inguinal node, one day after the first immunization was administered by PMED. Seven days after the last PMED, an ICS assay was performed on the splenocytes isolated from each individual mice to detect rHer-2 specific polyfunctional CD8 or CD4 T cells that secrete IFNγ, TNFα and/or IL-2. A significant increase in the rHer-2 specific triple-cytokine positive CD8 and CD4 T cell responses were detected from mice treated with the local delivery of anti-CD40 monoclonal antibody compared to isotype IgG control. There were also significant increases in rHer-2 specific single and double cytokine positive CD4 T cells by anti-CD40 monoclonal antibody given locally (*indicates P<0.05 by Student's T-test).

Example 15. Anti-Cancer Efficacy of Cancer Vaccine in Combination with Low Dose Sunitinib Anti-tumor efficacy of anti-cancer vaccine in combination with low dose sunitinib was investigated in BALB/neuT mice with spontaneous mammary pad tumors.

Animal treatment.

Figure 43:
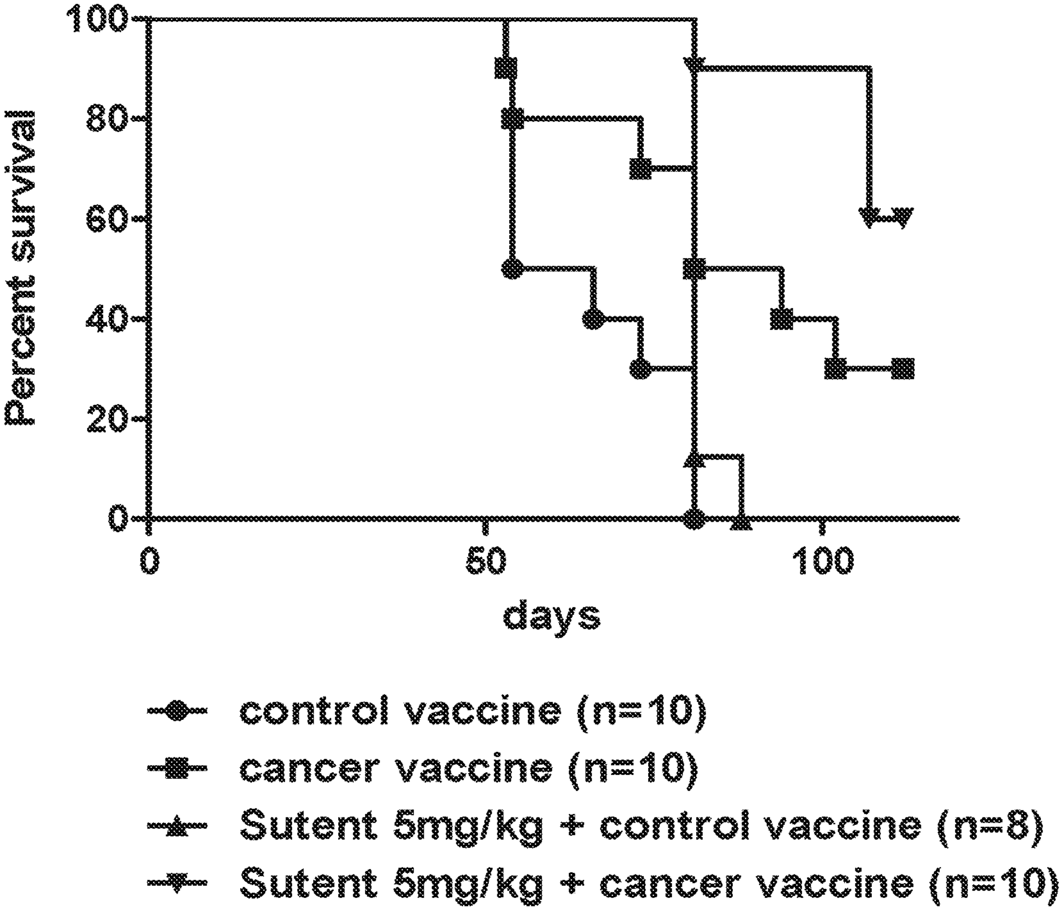
FIG. 43. Graph showing the Kaplan-Meier survival curves of the groups of mice from a representative study that evaluates the effect of low dose sunitinib malate (Sutent) on the anti-tumor efficacy of a cancer vaccine in spontaneous mammary tumor bearing BALB/neuT mice.

Briefly, 13-14 weeks old female mice were orally given sunitinib malate (Sutent) at 5 mg/kg for 112 days twice a day. The control vaccine, which delivers no antigen, and cancer vaccine which delivers a rat Her-2 antigen of SEQ ID NO: 54 (rHer-2), were given by adenovirus injections on day 3 as a prime followed by 7 biweekly administrations by PMED of DNA delivering HBV antigens (control vaccine) or rHer-2 (cancer vaccine) respectively. The survival end point was determined when all ten mammary pads became tumor positive or when the volume of any of the mammary tumors reach 2000 $mm^3$. The results are presented in FIG. 43.

Results.

Compared to previously published pharmacokinetic profile of Sutent (Mendel, D., Laird, D., et al.: "In vivo antitumor activity of SU11248, a novel tyrosine kinase inhibitor targeting vascular endothelial growth factor and platelet-derived growth factor receptors: determination of a pharmacokinetic/pharmacodynamic relationship". Clinical Cancer Research, 203, 9:327-337) and previous data (FIG. 38), the $C_{Max}$ of Sutent in mice dosed twice a day at 5 mg/kg is expected to be significantly lower than the minimum blood levels necessary to achieve efficient anti-tumor efficacy in mice and man. The data shows a quick and temporary improvement in the survival of the mice treated with low dose Sutent monotherapy. However when given with the cancer vaccine, a more persistent and significant improvement of survival was observed (P<0.0001 by Log rank test).

Example 16. Enhancement of Vaccine-Induced Immune Responses by Local Administration of CPG The immune enhancement of local administration of CpG (PF-03512676) on the immune responses induced by a human PSMA nucleic acid provided by the invention was investigated in a monkey study, in which the immune response was assessed by measuring PSMA specific T cell responses using an IFNγ ELISPOT assay.

Animal Treatment and Sample Collection.

Six groups of Chinese cynomolgus macaques, six (#1 to 6) per each test group, were immunized with a plasmid DNA encoding the human PSMA modified antigen (amino acids 15-750 of SEQ ID NO:1) delivered by electroporation. Briefly, all animals received bilateral intramuscular injections of 5 mg of plasmid DNA followed by electroporation (DNA EP) on day 0. Subsequently right after the electroporation, group 2 received bilateral intramuscular injections of 2 mg of CpG mixed with 1 mg Alum in proximity to the DNA injection sites. Group 3 and 4 received bilateral intramuscular injections of 2 mg of CpG delivered without alum in proximity to the DNA injection sites either on day 0 or day 3, respectively. Group 5 received 2 mg of bilateral intradermal injections of CpG delivered in proximity to the vaccine draining inguinal nodes on day 3. Group 6 received bilateral injections of 200 μg of CpG mixed with the DNA solution which was co-electroporated into the muscle on day 0.

IFNγ ELISPOT Assay Procedure.

Peripheral blood samples were collected from each animal fifteen days after the DNA immunization. Peripheral blood mononuclear cells (PBMCs) were isolated from the blood samples and were subjected to an IFNγELISPOT assay to measure the PSMA specific T cell responses. Briefly, 4e5 PBMCs from individual animals were plated per well with pools of PSMA specific peptides or nonspecific control peptides (human HER2 peptide pool) each at 2 ug/ml in IFNγELISPOT plates. The composition of each of the PSMA specific peptide pool is provided in Table 1A. The plates were incubated for 16 hrs at 37° C. and 5% CO2 and washed and developed after incubation as per manufacturer's instruction. The number of IFNγ spot forming cells (SFC) were counted by CTL reader. Each condition was performed in duplicates. The result of a representative experiment is presented in Table 1B. The reported PSMA specific response is calculated by subtracting the average number of the SFC to the nonspecific control peptides (human HER2 peptide pool) from the average number of SFC to the PSMA peptide pools and normalized to the SFC observed with 1e6 PBMCs. ^ indicates that the count is not accurate because the numbers of spots were too numerous to count. ND indicates not determined.

Results.

Table 28 shows the result of a representative IFNγ ELISPOT assay that evaluates and compares the IFNγT cell responses induced by the vaccine without (group 1) or with CpG (PF-03512676) given locally by intramuscular (groups 2, 3, 4, and 5) or intradermal injections (group 6). There results in Table 1B is plotted in FIG. 1. As shown in Table 1B and FIG. 1, the PSMA specific IFNγ T cell responses were detected to multiple PSMA specific peptide pools in the absence of CpG (PF-03512676) in all six animals (group 1). The total response to the PSMA peptides measured were modestly higher in a few animals that additionally received CpG (PF-03512676) either by intramuscular (group 4: 3/6) or intradermal (group 5: 2/6) injections 3 days after DNA electroporation. However, when CpG was delivered subsequently right after electroporation on the same day (groups 2 and 3), there were several animals that failed to produce high responses (group 2: 4/6 and group 3: 3/6) whether mixed or not mixed with Alum. However higher net responses were detected in 4/6 animals when a ten-fold lower dose of CpG was co-electroporated with the DNA solution into the muscle (group 6) with a statistically higher response ($P<0.05$) to peptide pools H1 and R1 compared to animals that did not receive CpG (group 1). The data shows that low dose of CpG can effectively enhance IFNγ T cell responses induced by a DNA vaccine when co-electroporated into the muscle.

TABLE 28

PSMA specific IFNγ T cell responses induced by the DNA vaccine without (Group 1) or with CpG (Groups 2, 3, 4, 5 and 6) is measured by IFNγ ELISPOT assay from PBMCS, 15 days after DNA electroporation

| | | Recall Antigen | | | | | | |
|---|---|---|---|---|---|---|---|---|
| Group | Animal ID | P1 | P2 | P3 | H1 | H2 | R1 | R2 |
| 1 | #1 | 36 | 31 | 1 | 126 | 183 | 5 | 14 |
| | #2 | 6 | 3 | 13 | 61 | 524 | 6 | 141 |
| | #3 | 11 | 4 | 8 | 108 | 1049 | 3 | 56 |
| | #4 | 10 | 0 | 13 | 20 | 151 | 13 | 10 |
| | #5 | 8 | 6 | 11 | 39 | 469 | 14 | 18 |
| | #6 | 26 | 5 | 0 | 145 | 356 | 8 | 30 |
| 2 | #1 | 3 | 10 | 0 | 15 | 35 | 0 | 0 |
| | #2 | 0 | 0 | 8 | 4 | 6 | 13 | 0 |
| | #3 | 3 | 0 | 0 | 0 | 10 | 11 | 0 |
| | #4 | 6 | 209 | 4 | 111 | 414 | 23 | 9 |
| | #5 | 15 | 5 | 30 | 171 | 104 | 68 | 6 |
| | #6 | 0 | 0 | 0 | 9 | 9 | 6 | 8 |
| 3 | #1 | 14 | 19 | 8 | 123 | 1066 | 10 | 60 |
| | #2 | 14 | 16 | 20 | 384 | 393 | 104 | 8 |
| | #3 | 0 | 0 | 15 | 0 | 6 | 0 | 0 |
| | #4 | 0 | 0 | 0 | 33 | 21 | 0 | 4 |
| | #5 | 4 | 91 | 1 | 875 | ^1235 | 233 | 109 |
| | #6 | 0 | 0 | 0 | 0 | 3 | 0 | 0 |
| 4 | #1 | 0 | 33 | 15 | 1025 | ^1209 | 280 | 90 |
| | #2 | 0 | 313 | 3 | 23 | 656 | 6 | 31 |
| | #3 | 61 | 120 | 61 | 428 | 1190 | 143 | 53 |
| | #4 | 0 | 0 | 8 | 599 | 870 | 34 | 111 |
| | #5 | 0 | 1 | 8 | 19 | 226 | 10 | 36 |
| | #6 | 111 | 55 | 39 | 231 | 613 | 121 | 99 |
| 5 | #1 | 21 | 9 | 0 | 355 | 1131 | 73 | 5 |
| | #2 | 0 | 0 | 0 | 118 | 233 | 0 | 0 |
| | #3 | 0 | 0 | 0 | 18 | 129 | 0 | 0 |
| | #4 | 0 | 28 | 78 | 68 | 294 | 58 | 8 |
| | #5 | 25 | 0 | 28 | 329 | 1125 | 134 | 5 |
| | #6 | 0 | 0 | 0 | 23 | 39 | 4 | 0 |
| 6 | #1 | 0 | 0 | 13 | 650 | 1096 | 270 | 5 |
| | #2 | 34 | 1 | 74 | 124 | 474 | 29 | 15 |
| | #3 | 0 | 3 | 14 | 684 | 1074 | 126 | 64 |
| | #4 | 8 | 9 | 0 | 136 | 321 | 49 | 1 |
| | #5 | 13 | 23 | 35 | ND | ^1235 | 333 | 195 |
| | #6 | 0 | 0 | 0 | 421 | ^1201 | 138 | 29 |

Example 17. Enhancement of Vaccine-Induced Immune Responses by Local Administration of Anti-CTLA-4 Antibody The effect of low dose subcutaneous administration of anti-CTLA-4 monoclonal antibody (CP-675, 206) on the immune responses induced by a rhesus PSMA nucleic acid was investigated in a monkey study, in which the immune response was assessed by measuring PSMA specific T cell responses using an IFNγ ELISPOT assay. The rhesus PSMA nucleic acid used in the study has the sequence as set forth in SEQ ID NO: 56) and encodes an immunogenic PSMA polypeptide of SEQ ID NO: 55.

Animal Treatment and Sample Collection.

Five groups of male Indian rhesus macaques, seven (#1 to 7) per each test group, were immunized with an adenovirus encoding a rhesus PSMA modified polypeptide delivered by bilateral intramuscular injections (2×5e10 V.P.). Immediately following the adenovirus injections, group 1 received vehicle, and groups 2 to 4 received bilateral subcutaneous injections of anti-CTLA-4 antibody (CP-675, 206) at doses 2×25 mg, 2×16.7 mg and 2×8.4 mg respectively in proximity to the vaccine draining lymph node.

Nine days after the immunization, peripheral blood mononuclear cells (PBMCs) were isolated from each animal and were subjected to an IFNγ ELISPOT assay to measure the rhesus PSMA specific T cell responses. Briefly, 4e5 PBMCs from individual animals were plated per well with pools of rhesus PSMA specific peptides (P1, P2, P3 or R1+R2 defined in table 24A) or nonspecific control peptides (human HER2 peptide pool) each at 2 ug/ml in IFNγ ELISPOT plates. The plates were incubated for 16 hrs at 37° C. and 5% CO2 and washed and developed after incubation as per manufacturer's instruction. The number of IFNγ spot forming cells (SFC) were counted by CTL reader. Each condition was performed in duplicates. The average of the duplicates from the background adjusted SFC of the rhesus PSMA specific peptide pools was normalized to the response in 1e6 PBMCs. The individual and sum responses to the peptide pools from each individual animal are presented in Table 29.

IFNγ ELISPOT Assay Procedure.

A capture antibody specific to IFNγ □BD Bioscience, #51-2525kc) is coated onto a polyvinylidene fluoride (PVDF) membrane in a microplate overnight at 4° C. The plate is blocked with serum/protein to prevent nonspecific binding to the antibody. After blocking, effector cells (such as splenocytes isolated from immunized mice or PBMCs isolated from rhesus macaques) and targets (such as PSMA peptides from peptide library, target cells pulsed with antigen specific peptides or tumor cells expressing the relevant antigens) are added to the wells and incubated overnight at 37° C. in a 5% $CO_2$ incubator. Cytokine secreted by effector cells are captured by the coating antibody on the surface of the PVDF membrane. After removing the cells and culture media, 100 µl of a biotinylated polyclonal anti-humanIFNγ antibody was added to each of the wells for detection. The spots are visualized by adding streptavidin-horseradish peroxidase and the precipitate substrate, 3-amino-9-ethylcarbazole (AEC), to yield a red color spot as per manufacturer's (Mabtech) protocol. Each spot represents a single cytokine producing T cell.

Results.

Table 29. shows the results of a representative IFNγ ELISPOT assay that compares the T cell responses induced by the vaccine without (group 1) or with (groups 2-4) anti-CTLA-4 monoclonal antibody (CP-675, 206) given locally by subcutaneous injections in proximity to the vaccine draining lymph node. The vaccine generated an immune response (group 1) that was significantly enhanced by the local administration of the anti-CTLA-4 antibody (CP-675, 206) at a dose of 50 mg (group 2, P=0.001 by Student's T-test using underestimated values). The response was also significantly enhanced by low doses of anti-CTLA-4 antibody at 33.4 mg (group 3: P=0.004 by Student T-test using underestimated values) and 16.7 mg (group 4: P=0.05 by Student T-test) respectively. The data suggests that low doses of anti-CTLA-4 delivered by subcutaneous injection can significantly enhance the vaccine induced immune responses.

TABLE 29

IFNγ T cell responses induced by the vaccine without (Group 1) or with subcutaneous injections of anti-CTLA-4 antibody (CP-675, 206).

| Group | aCTLA4 dose, mg | animal ID | peptide pool P1 | P2 | P3 | R1 + R2 | SUM |
|---|---|---|---|---|---|---|---|
| 1 | NA | 1 | 21 | 0 | 0 | 108 | 129 |
| | | 2 | 59 | 480 | 28 | 353 | 920 |
| | | 3 | 133 | 29 | 359 | 305 | 826 |
| | | 4 | 0 | 28 | 1 | 35 | 64 |
| | | 5 | 41 | 6 | 30 | 99 | 176 |
| | | 6 | 1 | 0 | 849 | 169 | 1019 |
| | | 7 | 0 | 0 | 0 | 23 | 23 |
| 2 | 50.0 | 1 | ^1105 | 704 | ^1116 | ^1116 | ^4041 |
| | | 2 | 371 | 26 | 661 | 779 | 1837 |
| | | 3 | 393 | 559 | 216 | 198 | 1366 |
| | | 4 | ^1100 | ^1100 | 406 | 1078 | ^3684 |
| | | 5 | 778 | 325 | 554 | 419 | 2076 |
| | | 6 | ^1079 | ^1079 | 844 | ^1079 | ^4081 |
| | | 7 | 423 | 103 | 535 | 398 | 1459 |
| 3 | 33.4 | 1 | ^425 | ^425 | ^425 | ^425 | ^1700 |
| | | 2 | ^580 | ^580 | ^580 | ^580 | ^2320 |
| | | 3 | TNTC | TNTC | TNTC | TNTC | TNTC |
| | | 4 | 321 | 778 | 370 | 409 | 1878 |
| | | 5 | 331 | 466 | 311 | 446 | 1554 |
| | | 6 | 545 | 121 | ^631 | ^1194 | ^2491 |
| | | 7 | 446 | 299 | ^1078 | ^1060 | ^2883 |
| 4 | 16.7 | 1 | ^964 | 296 | ^964 | ^964 | ^3188 |
| | | 2 | 76 | 76 | 76 | 76 | 304 |
| | | 3 | ^984 | ^984 | ^984 | ^984 | ^3936 |
| | | 4 | 260 | 489 | 648 | ^1109 | ^2506 |
| | | 5 | 119 | 45 | 28 | 140 | 332 |
| | | 6 | 55 | 76 | 43 | 198 | 372 |
| | | 7 | 146 | 726 | 141 | 400 | 1413 |

^indicates that the count is underestimated due to the high spot numbers.

TNTC means too numerous to count.

Example 18. Immunomodulation of Myeloid Derived Suppressor Cells by Low Dose Sunitinib The following example is provided to illustrate the immunomodulatory effects of low dose sunitinib on Myeloid Derived Suppressor Cells (MDSC) in vivo, in a non-tumor mouse model.

Study Procedures.

To generate MDSC enriched splenocytes, TUBO cells ($1\times10^6$) were implanted into the flanks of 5 BALB/neuT mice, and left for approx. 20-30 days until tumor volume reached between 1000-1500 $mm^3$. Mice were then sacrificed, spleens removed and the MDSC enriched splenocytes recovered. Splenocytes were labeled for 10 minutes with 5 µM CFSE, washed with PBS and counted. Labeled cells were subsequently resuspended at $5\times10^7$ splenocytes/ml in PBS solution and adoptively transferred via an i.v. tail vein injection into naïve BALB/c recipient mice. Three days prior to adoptive transfer, the recipient mice began bi-daily dosing with vehicle or sunitinib malate (Sutent) at 5 mg/kg, 10 mg/kg and 20 mg/kg. Following adoptive transfer, recipient mice continued to receive bi-daily dosing of Vehicle or sunitinib for two further days, after which point the mice were sacrificed, spleens removed, splenocytes recovered and processed for phenotypic analysis.

Splenocytes were counted and resuspended at $5\times10^6$ cells/ml in FACS staining buffer (PBS, 0.2% (w/v) bovine serum albumin, and 0.02% (w/v) Sodium Azide). For flow cytometry staining of splenocytes, $2.5\times10^6$ cells were first incubated with anti-bodies to CD16/CD32, 10 minutes at 4° C., to block Fc receptors and minimize non-specific binding. Splenocytes were then stained for 20 minutes at 4° C. with appropriate fluorophore conjugated antibodies (Biolegend) to murine cell surface markers. For T cells (anti-CD3 (Pacific Blue), clone 17A2) and for MDSC (anti-GR-1 (APC), clone RB6-8C5 and anti-CD11b (PerCp Cy5.5), clone M1/70). A live/dead stain was also included. Following antibody incubation, stained splenocytes were washed with 2 mls of FACS buffer, pelleted by centrifugation and resuspended in 0.2 ml of FACS buffer prior to data acquisition on a BD CANTO II flow cytometer. To monitor the effect of Sunitinib or Vehicle on the adoptively transferred MDSC survival, we calculated the percentage of CFSE+, CD3−,GR1+,CD11b+ in the live, singlet gate. We then determined the number of adoptively transferred MDSC per spleen by calculating what actual cell number the percentage represented of total splenocytes count. Data was analyzed by FloJo and Graph pad software.

Results.

The data presented in Table 31 represents the mean number of adoptively transferred CSFE+,CD3−,GR1+, CD11b+ cells recovered per spleen (n=7/group), 2 days post adoptive transfer, from mice bi-daily dosed with either Vehicle or 5 mg/kg, 10 mg/kg and 20 mg/kg Sunitinib. The data demonstrates that Sunitinib, dosed bi-daily, in vivo, has an immunomodulatory effect on MDSCs, even when dosed as low as 5 mg/kg, resulting in a statistically significant reduction in the numbers recovered when compared to the vehicle treated control group.

TABLE 31

Mean number of CFSE+, CD3−, GR1+, CD11b+ MDSCs recovered from the spleen, 7 mice per group, and the corresponding standard error. Statistical significance was determined by one-way ANOVA using the Dunnett's multiple comparison test, comparing the Sunitinib dosed groups against the 0 mg/kg (vehicle) group.

| | Sunitinib Dose (mg/kg) | | | |
|---|---|---|---|---|
| | 0 (Vehicle) | 5 | 10 | 20 |
| MDSC #/spleen Mean +/− SEM | 17470 +/− 2017 | 10980 +/− 1082 | 4207 +/− 338 | 4440 +/− 440 |
| Statistical significance, p < 0.05 [[?]] | NA | Yes | Yes | Yes |

Example 19. Immunogenicity of Triple Antigen Adenovirus and DNA Constructs

The following example is provided to illustrate the capability of triple antigen vaccine constructs (either in the form of adenovirus vector or DNA plasmid) expressing three antigens PSMA, PSCA and PSA provided by the invention to elicit specific T cell responses to all three encoded antigens in nonhuman primates.

In Vivo Study Procedures.

The T cell immunogenicity of five adenovirus vectors each expressing three antigens (PSMA, PSCA and PSA; Ad-733, Ad-734, Ad-735, Ad-796 and Ad-809) provided by the invention were compared to the mix of three adenovirus vectors each only expressing a single antigen (PSMA, PSA or PSCA), 9 days post prime. The response to single adenovirus expressing a single antigen (groups 1-3) was evaluated to demonstrate the specificity. Briefly, Indian rhesus macaques (n=6 for groups 1 and 3, n=7 for group 2 and n=8 for groups 4-9) were intramuscularly injected with a total of 1e11 V.P. followed by intradermal injections of anti-CTLA-4 at 10 mg/kg on the same day. Nine days after the injections, peripheral blood mononuclear cells (PBMCs) were isolated from each animal and were subjected to an IFNγ ELISPOT assay to measure the PSMA, PSA and PSCA specific T cell responses.

Thirteen weeks after the adenovirus and anti-CTLA-4 injections when the T cell responses have contracted, the monkeys received DNA (Group 1: PSMA, plasmid 5166; Group 2: PSA, plasmid 5297; Group 3: PSCA, plasmid 5259; Group 4: mix of PSMA, PSA and PSCA, plasmids 5166, 5259 and 5297; Group 4: plasmid 457; Group 6: plasmid 458; Group 7: plasmid 459; Group 8: plasmid 796 and Group 9: plasmid 809) boost vaccinations delivered by electroporation. In summary, each animal received a total 5 mg of plasmid DNA provided by the invention which delivers the same expression cassette encoded in the adenovirus used in the prime. Nine days after the boost vaccination, peripheral blood mononuclear cells (PBMCs) were isolated from each animal and were subjected to an IFNγ ELISPOT assay.

IFNγ ELISPOT Assay.

Briefly, 4e5 PBMCs from individual animals were plated per well with PSMA specific peptide pools P1, P2, P3 or H1 and H2 (Table 24A), PSA specific pool 1 or 2 (Table 25), PSCA specific pool (Table 26) or nonspecific control peptides (human HER2 peptide pool) each at 2 ug/ml in IFNγ ELISPOT plates. The plates were incubated for 16 hrs at 37° C. and 5% CO2 and washed and developed after incubation as per manufacturer's instruction. The number of IFNγ spot forming cells (SFC) were counted by CTL reader. Each condition was performed in duplicates. The average of the duplicates from the background adjusted SFC of the antigen specific peptide pools was normalized to the response in 1e6 PBMCs. The antigen specific responses in the tables present the sum of the responses to the corresponding antigen specific peptides or peptide pools.

Results:

Table 27 represents a study that evaluates the T cell immunogenicity of five different adenoviruses each expressing all three antigens in comparison to the mixture of three adenoviruses each expressing a single antigen in Indian rhesus macaques by IFNγ ELISPOT. The majority of animals that only received Ad-PSMA (group 1) injections induced specific responses to PSMA but not to PSA or PSCA (Student's T-test, P<0.03. One animal (#4) that induced responses to PSCA preferentially was removed from the statistical analysis). The animals that only received injections of Ad-PSA (group 2) induced specific responses to PSA but not to PSMA or PSCA (Student's T-test, P<0.02). The animals that only received injections of Ad-PSCA (group 3) induced specific responses to PSCA but not to PSMA or PSA (Student's T-test, P<0.03). All five triple-antigen expressing adenovirus vectors (groups 5-9) induced IFNγT cell responses to all three antigens which the magnitude varied by animal. The magnitude of the responses to PSCA induced by the triple antigen expressing adenoviruses were similar to the mix of individual vectors (group 4). However the magnitude of responses to PSMA induced by Ad-809 (group 9) and responses to PSA induced by Ad-796 (group 8) were each significantly superior to the mix (Student's T-test, P=0.04 and P=0.02) respectively. These results indicate that vaccinating with an adenovirus expressing triple antigens can elicit equivalent or superior T cell immune responses to vaccinating with the mix of individual adenoviruses in nonhuman primates.

Table 28 shows the IFNγ ELISPOT results represents a study that evaluates the immunogenicity of the five different triple antigen expression cassettes provided in the invention delivered by an adenovirus prime in combination with anti-CTLA-4 followed by an electroporation boost of the corresponding plasmid DNA. The immune responses are compared to the mix of three constructs expressing a single antigen delivered similarly by an adenovirus prime with anti-CTLA-4 and DNA electroporation boost immunizations.

All of the animals that only received Ad-PSMA with anti-CTLA-4 followed by plasmid-PSMA (group 1) immunizations induced specific responses to PSMA but not to PSA or PSCA. Similarly all of the animals that only received Ad-PSA with anti-CTLA-4 followed by plasmid-PSA immunizations (group 2) induced specific responses to PSA but not to PSMA or PSCA and finally all of the animals that only received Ad-PSCA with anti-CTLA-4 followed by plasmid-PSCA (group 3) immunizations induced specific responses to PSCA but not to PSMA or PSA (Student's T-test, P<0.01).

All animals that have been immunized with either the triple-antigen expressing vectors (groups 5-9) or the mix (group 4) induced IFNγ T cell responses to all three antigens. The frequency of PSCA or PSA specific IFNγ T cells detected were similar in all of these groups (groups 4-9) respectively. However construct groups 7 and 9 that received triple antigen expression vector vaccinations produced significantly higher frequency of responses to PSMA than the mix of three single antigen expressing constructs (group 4). These results indicate that adenovirus and DNA vaccines expressing triple antigens in one cassette can elicit equivalent or superior IFNγ T cell responses to the mix of adenoviruses and DNAs expressing the single antigens in nonhuman primates.

TABLE 25

PSA peptide pools: The amino acid position and sequence of fifteen amino acid peptides overlapping by thirteen amino acids from PSA peptide library is shown.

| PSA peptide pool 1 | | PSA peptide pool 2 | |
|---|---|---|---|
| amino acid no. | PSA peptide sequence | amino acid no. | PSA peptide sequence |
| 5-19 | VVFLTLSVTWIGAAP | 129-143 | PAELTDAVKVMDLPT |
| 9-23 | TLSVTWIGAAPLILS | 131-145 | ELTDAVKVMDLPTQE |
| 11-25 | SVTWIGAAPLILSRI | 133-147 | TDAVKVMDLPTQEPA |
| 13-27 | TWIGAAPLILSRIVG | 135-149 | AVKVMDLPTQEPALG |

TABLE 25-continued

PSA peptide pools: The amino acid position and sequence of fifteen amino acid peptides overlapping by thirteen amino acids from PSA peptide library is shown.

| PSA peptide pool 1 | | PSA peptide pool 2 | |
|---|---|---|---|
| amino acid no. | PSA peptide sequence | amino acid no. | PSA peptide sequence |
| 15-29 | IGAAPLILSRIVGGW | 137-151 | KVMDLPTQEPALGTT |
| 17-31 | AAPLILSRIVGGWEC | 139-153 | MDLPTQEPALGTTCY |
| 19-33 | PLILSRIVGGWECEK | 141-155 | LPTQEPALGTTCYAS |
| 21-35 | ILSRIVGGWECEKHS | 143-157 | TQEPALGTTCYASGW |
| 23-37 | SRIVGGWECEKHSQP | 145-159 | EPALGTTCYASGWGS |
| 25-39 | IVGGWECEKHSQPWQ | 147-161 | ALGTTCYASGWGSIE |
| 27-41 | GGWECEKHSQPWQVL | 149-163 | GTTCYASGWGSIEPE |
| 29-43 | WECEKHSQPWQVLVA | 151-165 | TCYASGWGSIEPEEF |
| 31-45 | CEKHSQPWQVLVASR | 153-167 | YASGWGSIEPEEFLT |
| 33-47 | KHSQPWQVLVASRGR | 155-169 | SGWGSIEPEEFLTPK |
| 35-49 | SQPWQVLVASRGRAV | 157-171 | WGSIEPEEFLTPKKL |
| 37-51 | PWQVLVASRGRAVCG | 159-173 | SIEPEEFLTPKKLQC |
| 39-53 | QVLVASRGRAVCGGV | 161-175 | EPEEFLTPKKLQCVD |
| 41-55 | LVASRGRAVCGGVLV | 163-177 | EEFLTPKKLQCVDLH |
| 43-57 | ASRGRAVCGGVLVHP | 165-179 | FLTPKKLQCVDLHVI |
| 45-59 | RGRAVCGGVLVHPQW | 167-181 | TPKKLQCVDLHVISN |
| 47-61 | RAVCGGVLVHPQWVL | 169-183 | KKLQCVDLHVISNDV |
| 49-63 | VCGGVLVHPQWVLTA | 171-185 | LQCVDLHVISNDVCA |
| 51-65 | GGVLVHPQWVLTAAH | 173-187 | CVDLHVISNDVCAQV |
| 53-67 | VLVHPQWVLTAAHCI | 175-189 | DLHVISNDVCAQVHP |
| 55-69 | VHPQWVLTAAHCIRN | 177-191 | HVISNDVCAQVHPQK |
| 57-71 | PQWVLTAAHCIRNKS | 179-193 | ISNDVCAQVHPQKVT |
| 59-73 | WVLTAAHCIRNKSVI | 181-195 | NDVCAQVHPQKVTKF |
| 61-75 | LTAAHCIRNKSVILL | 183-197 | VCAQVHPQKVTKFML |
| 63-77 | AAHCIRNKSVILLGR | 185-199 | AQVHPQKVTKFMLCA |
| 65-79 | HCIRNKSVILLGRHS | 187-201 | VHPQKVTKFMLCAGR |
| 67-81 | IRNKSVILLGRHSLF | 189-203 | PQKVTKFMLCAGRWT |
| 69-83 | NKSVILLGRHSLFHP | 191-205 | KVTKFMLCAGRWTGG |
| 71-85 | SVILLGRHSLFHPED | 193-207 | TKFMLCAGRWTGGKS |
| 73-87 | ILLGRHSLFHPEDTG | 195-209 | FMLCAGRWTGGKSTC |
| 75-89 | LGRHSLFHPEDTGQV | 197-211 | LCAGRWTGGKSTCSG |
| 77-91 | RHSLFHPEDTGQVFQ | 199-213 | AGRWTGGKSTCSGDS |
| 79-93 | SLFHPEDTGQVFQVS | 201-215 | RWTGGKSTCSGDSGG |
| 81-95 | FHPEDTGQVFQVSHS | 203-217 | TGGKSTCSGDSGGPL |
| 83-97 | PEDTGQVFQVSHSFP | 205-219 | GKSTCSGDSGGPLVC |

TABLE 25-continued

PSA peptide pools: The amino acid position and sequence of fifteen amino acid peptides overlapping by thirteen amino acids from PSA peptide library is shown.

| PSA peptide pool 1 | | PSA peptide pool 2 | |
|---|---|---|---|
| amino acid no. | PSA peptide sequence | amino acid no. | PSA peptide sequence |
| 85-99 | DTGQVFQVSHSFPHP | 207-221 | STCSGDSGGPLVCNG |
| 87-101 | GQVFQVSHSFPHPLY | 209-223 | CSGDSGGPLVCNGVL |
| 89-103 | VFQVSHSFPHPLYDM | 211-225 | GDSGGPLVCNGVLQG |
| 91-105 | QVSHSFPHPLYDMSL | 213-227 | SGGPLVCNGVLQGIT |
| 93-107 | SHSFPHPLYDMSLLK | 215-229 | GPLVCNGVLQGITSW |
| 95-109 | SFPHPLYDMSLLKNR | 217-231 | LVCNGVLQGITSWGS |
| 97-111 | PHPLYDMSLLKNRFL | 219-233 | CNGVLQGITSWGSEP |
| 99-113 | PLYDMSLLKNRFLRP | 221-235 | GVLQGITSWGSEPCA |
| 101-115 | YDMSLLKNRFLRPGD | 223-237 | LQGITSWGSEPCALP |
| 103-117 | MSLLKNRFLRPGDDS | 225-239 | GITSWGSEPCALPER |
| 105-119 | LLKNRFLRPGDDSSH | 227-241 | TSWGSEPCALPERPS |
| 107-121 | KNRFLRPGDDSSHDL | 229-243 | WGSEPCALPERPSLY |
| 109-123 | RFLRPGDDSSHDLML | 231-245 | SEPCALPERPSLYTK |
| 111-125 | LRPGDDSSHDLMLLR | 233-247 | PCALPERPSLYTKVV |
| 113-127 | PGDDSSHDLMLLRLS | 235-249 | ALPERPSLYTKVVHY |
| 115-129 | DDSSHDLMLLRLSEP | 237-251 | PERPSLYTKVVHYRK |
| 117-131 | SSHDLMLLRLSEPAE | 239-253 | RPSLYTKVVHYRKWI |
| 119-133 | HDLMLLRLSEPAELT | 241-255 | SLYTKVVHYRKWIKD |
| 121-135 | LMLLRLSEPAELTDA | 243-257 | YTKVVHYRKWIKDTI |
| 123-137 | LLRLSEPAELTDAVK | 245-259 | KVVHYRKWIKDTIVA |
| 125-139 | RLSEPAELTDAVKVM | 247-261 | VHYRKWIKDTIVANP |
| 127-141 | SEPAELTDAVKVMDL | 249-261 | YRKWIKDTIVANP |
| | | 251-261 | KWIKDTIVANP |

TABLE 26

PSCA peptide pool: The amino acid position and sequence of fifteen amino acid peptides overlapping by thirteen amino acids from PSCA peptide library is shown.

| amino acid no. | PSCA peptide sequence |
|---|---|
| 1-15 | MKAVLLALLMAGLAL |
| 3-17 | AVLLALLMAGLALQP |
| 5-19 | LLALLMAGLALQPGT |
| 7-21 | ALLMAGLALQPGTAL |
| 9-23 | LMAGLALQPGTALLC |
| 11-25 | AGLALQPGTALLCYS |
| 13-27 | LALQPGTALLCYSCK |
| 15-29 | LQPGTALLCYSCKAQ |
| 17-31 | PGTALLCYSCKAQVS |
| 19-33 | TALLCYSCKAQVSNE |
| 21-35 | LLCYSCKAQVSNEDC |
| 23-37 | CYSCKAQVSNEDCLQ |
| 25-39 | SCKAQVSNEDCLQVE |
| 27-41 | KAQVSNEDCLQVENC |
| 29-43 | QVSNEDCLQVENCTQ |
| 31-45 | SNEDCLQVENCTQLG |
| 33-47 | EDCLQVENCTQLGEQ |
| 35-49 | CLQVENCTQLGEQCW |
| 37-51 | QVENCTQLGEQCWTA |
| 39-53 | ENCTQLGEQCWTARI |
| 41-55 | CTQLGEQCWTARIRA |
| 43-57 | QLGEQCWTARIRAVG |
| 45-59 | GEQCWTARIRAVGLL |
| 47-61 | QCWTARIRAVGLLTV |
| 49-63 | WTARIRAVGLLTVIS |
| 51-65 | ARIRAVGLLTVISKG |
| 53-67 | IRAVGLLTVISKGCS |
| 55-69 | AVGLLTVISKGCSLN |
| 57-71 | GLLTVISKGCSLNCV |
| 59-73 | LTVISKGCSLNCVDD |
| 61-75 | VISKGCSLNCVDDSQ |
| 63-77 | SKGCSLNCVDDSQDY |
| 65-79 | GCSLNCVDDSQDYYV |
| 67-81 | SLNCVDDSQDYYVGK |
| 69-83 | NCVDDSQDYYVGKKN |
| 71-85 | VDDSQDYYVGKKNIT |
| 73-87 | DSQDYYVGKKNITCC |
| 75-89 | QDYYVGKKNITCCDT |
| 77-91 | YYVGKKNITCCDTDL |
| 79-93 | VGKKNITCCDTDLCN |
| 81-95 | KKNITCCDTDLCNAS |
| 83-97 | NITCCDTDLCNASGA |
| 85-99 | TCCDTDLCNASGAHA |

TABLE 26-continued

PSCA peptide pool: The amino acid position and sequence of fifteen amino acid peptides overlapping by thirteen amino acids from PSCA peptide library is shown.

| amino acid no. | PSCA peptide sequence |
|---|---|
| 87-101 | CDTDLCNASGAHALQ |
| 89-103 | TDLCNASGAHALQPA |
| 91-105 | LCNASGAHALQPAAA |
| 93-107 | NASGAHALQPAAAIL |
| 95-109 | SGAHALQPAAAILAL |
| 97-111 | AHALQPAAAILALLP |
| 99-113 | ALQPAAAILALLPAL |
| 101-115 | QPAAAILALLPALGL |
| 103-117 | AAAILALLPALGLLL |
| 105-119 | AILALLPALGLLLWG |
| 107-121 | LALLPALGLLLWGPG |
| 109-123 | LLPALGLLLWGPGQL |
| 111-125 | PALGLLLWGPGQL |

TABLE 27

IFNγ T cell responses induced by the single antigen (Group 1: Ad-PSMA; Group 2: Ad-PSA, Group 3: Ad-PSCA; Group 4: mix of Ad-PSMA, Ad-PSA and Ad-PSCA) or triple antigen expressing adenovirus vectors (Group 4: Ad-733; Group 6: Ad-734; Group 7: Ad-735; Group 8: Ad-796 and Group 9: Ad-809) after adenovirus prime with anti-CTLA-4 analyzed by ELISPOT assay.

| Response to PSMA | | animal ID | | | | | | | |
|---|---|---|---|---|---|---|---|---|---|
| peptides | | 1 | 2 | 3 | 4 | 5 | 6 | 7 | 8 |
| Group | 1 | 2356 | 988 | 1505 | 335 | 501 | 2145 | NA | NA |
| No. | 2 | 342 | 1776 | 154 | 329 | 158 | 438 | 321 | NA |
| | 3 | 0 | 1276 | 40 | 126 | 20 | 0 | NA | NA |
| | 4 | 304 | 1198 | 774 | 2007 | 1277 | 1310 | 1159 | 2774 |
| | 5 | 943 | 2670 | 2757 | 780 | 1082 | 2251 | 1566 | 544 |
| | 6 | 472 | 2092 | 4248 | 1369 | 1760 | 2964 | 1447 | 263 |
| | 7 | 2161 | 2202 | 939 | 869 | 3513 | 1654 | 3424 | 900 |
| | 8 | 1166 | 799 | 2566 | 663 | 1043 | 497 | 1334 | 560 |
| | 9 | 1621 | 3247 | 2031 | 980 | 2942 | 1882 | 1918 | 3805 |

| Response to PSA | | animal ID | | | | | | | |
|---|---|---|---|---|---|---|---|---|---|
| peptides | | 1 | 2 | 3 | 4 | 5 | 6 | 7 | 8 |
| Group | 1 | 0 | 0 | 0 | 48 | 0 | 42 | NA | NA |
| No. | 2 | 1419 | 1426 | 298 | 1223 | 1346 | 1120 | 1694 | NA |
| | 3 | 6 | 462 | 91 | 0 | 77 | 0 | NA | NA |
| | 4 | 790 | 1093 | 1611 | 790 | 186 | 783 | 2016 | 1964 |
| | 5 | 101 | 510 | 955 | 665 | 336 | 1512 | 1052 | 119 |
| | 6 | 236 | 673 | 2155 | 724 | 504 | 1600 | 930 | 83 |
| | 7 | 0 | 1086 | 494 | 663 | 2265 | 117 | 1712 | 84 |
| | 8 | 1893 | 2060 | 1490 | 1759 | 2352 | 1700 | 2232 | 1326 |
| | 9 | 1193 | 1432 | 207 | 1738 | 1886 | 949 | 492 | 1940 |

| Response to PSCA | | animal ID | | | | | | | |
|---|---|---|---|---|---|---|---|---|---|
| peptides | | 1 | 2 | 3 | 4 | 5 | 6 | 7 | 8 |
| Group | 1 | 795 | 425 | 874 | 1069 | 219 | 203 | NA | NA |
| No. | 2 | 669 | 713 | 391 | 199 | 164 | 560 | 461 | NA |
| | 3 | 510 | 1234 | 1099 | 1115 | 1194 | 339 | NA | NA |
| | 4 | 778 | 528 | 680 | 1101 | 165 | 531 | 1175 | 1009 |
| | 5 | 378 | 1061 | 1161 | 143 | 71 | 756 | 766 | 204 |
| | 6 | 118 | 380 | 1190 | 403 | 829 | 1225 | 148 | 261 |
| | 7 | 615 | 1141 | 794 | 564 | 1175 | 490 | 856 | 204 |
| | 8 | 968 | 1136 | 745 | 290 | 550 | 976 | 955 | 841 |
| | 9 | 929 | 434 | 1150 | 745 | 1120 | 246 | 1195 | 970 |

TABLE 28

IFNγ T cell responses induced by the single antigen (Group 1: PSMA; Group 2: PSA; Group 3: PSCA; Group 4: mix of PSMA, PSA and PSCA) or triple antigen expressing vectors (Groups 5-9) after adenovirus prime with anti-CTLA-4 and DNA electroporation boost immunizations analyzed by ELISPOT assay.

| Response to | | animal ID | | | | | | | |
|---|---|---|---|---|---|---|---|---|---|
| PSMA peptides | | 1 | 2 | 3 | 4 | 5 | 6 | 7 | 8 |
| Group No. | 1 | 1327 | 1535 | 1643 | 535 | 1506 | 1267 | NA | NA |
| | 2 | 15 | 266 | 26 | 191 | 10 | 46 | 1305 | NA |
| | 3 | 0 | 445 | 5 | 75 | 4 | 6 | NA | NA |
| | 4 | 365 | 675 | 731 | 1134 | 244 | 714 | 999 | 1683 |
| | 5 | 270 | 1623 | 2254 | 626 | 860 | 2245 | 1453 | 1046 |
| | 6 | 541 | 1151 | 2923 | 1094 | 1061 | 1746 | 691 | 489 |
| | 7 | 1183 | 1183 | 1453 | 1649 | 2844 | 1470 | 2321 | 991 |
| | 8 | 486 | 69 | 399 | 216 | 351 | 758 | 416 | 1389 |
| | 9 | 1430 | 2631 | 2015 | 475 | 1368 | 1826 | 1851 | 3141 |
| Response to PSA | | animal ID | | | | | | | |
| peptides | | 1 | 2 | 3 | 4 | 5 | 6 | 7 | 8 |
| Group No. | 1 | 0 | 0 | 0 | 1 | 0 | 26 | NA | NA |
| | 2 | 1883 | 1236 | 1574 | 393 | 461 | 941 | 1565 | NA |
| | 3 | 33 | 30 | 9 | 13 | 8 | 11 | NA | NA |
| | 4 | 571 | 1129 | 1180 | 210 | 88 | 274 | 924 | 360 |
| | 5 | 50 | 1255 | 1344 | 628 | 210 | 638 | 948 | 1161 |
| | 6 | 88 | 228 | 1390 | 489 | 1006 | 908 | 683 | 51 |
| | 7 | 0 | 211 | 321 | 156 | 1509 | 56 | 199 | 85 |
| | 8 | 414 | 611 | 85 | 105 | 544 | 1080 | 331 | 1883 |
| | 9 | 434 | 821 | 556 | 343 | 1160 | 510 | 144 | 1115 |
| Response to PSCA | | animal ID | | | | | | | |
| peptides | | 1 | 2 | 3 | 4 | 5 | 6 | 7 | 8 |
| Group No. | 1 | 615 | 799 | 533 | 74 | 258 | 61 | NA | NA |
| | 2 | 194 | 170 | 133 | 133 | 8 | 66 | 405 | NA |
| | 3 | 819 | 1071 | 873 | 839 | 1045 | 724 | NA | NA |
| | 4 | 543 | 506 | 664 | 470 | 70 | 673 | 761 | 1235 |
| | 5 | 154 | 455 | 1218 | 109 | 218 | 1094 | 285 | 569 |
| | 6 | 56 | 293 | 603 | 506 | 745 | 911 | 63 | 165 |
| | 7 | 429 | 298 | 939 | 589 | 1226 | 263 | 803 | 451 |
| | 8 | 279 | 214 | 871 | 61 | 144 | 511 | 193 | 963 |
| | 9 | 379 | 191 | 1196 | 73 | 699 | 198 | 616 | 836 |

Example 20. Reduction of STAT3 Phosphorylation by Sunitinib

The following example is provided to illustrate the capability of sunitinib to directly inhibit the phosphorylation of STAT3 (signal transducer of activator of transcription 3), a key mediator of immune suppression in the spleen.

Study Procedure.

The acute effect of Sutent on the phosphorylation status of STAT3 in the spleen was investigated in a subcutaneous tumor mouse model to evaluate the direct immunomodulatory effects of the compound. Briefly, 10-12 week old female BALB/neuT mice were implanted with 1e6 TUBO cells subcutaneously in the right flank. After forty one days post tumor implant, Sutent was given by oral gavage at 20 mg/kg. At 0, 1, 3, 7 and 24 hrs post Sutent dosing, three animals per timepoint were sacrificed under IAUCUC guidelines and spleens were immediately snap frozen in liquid nitrogen to preserve the phosphorylation status. Spleens from female BALB/c mice were snap frozen to use as healthy mice controls.

STAT3 Assay Procedures.

Snap frozen spleens were homogenized at 100 mg tissue per 500 μL lysis buffer (70 mM NaCl, 50 mM β-glycerol phosphate, 10 mM HEPES, 1% Triton X-100, 100 mM $Na_3VO_4$, 100 mM PMSF, 1 mg/mL leupeptin) using a polytron tissue homogenizer. Resulting digests were centrifuged at 10,000 g for 15 minutes. The supernatant was isolated and protein concentrations were determined using BCA protein assay kit (Pierce, Rockford, Ill.). Forty micrograms of protein were added to each well of either a total STAT3 (eBioscience, cat no. 85-86101-11) or phosphor-STAT3 (eBioscience, cat no. 85-86102-11) ELISA Kit. Relative levels of either protein were compared with standards provided in the kit and with standards purchased independently (Signaling Technologies, cat no. 9333-S).

Results.

Table 29 shows the result of a representative STAT assay that evaluates the effect of Sutent on the phosphorylation status of STAT3 in the spleen. Both spleen extracts from healthy or tumor bearing mice exhibited similar levels of STAT3 protein by ELISA (Total STAT3). However, compared to healthy BALB/c, the extracts from tumor bearing mice had significantly higher levels of phosphorylated STAT3 (Student's T-test, $P<0.001$). The phosphorylation levels rapidly decreased to levels similar to healthy animals only 1 hr after Sutent treatment and maintained at lower levels than the untreated mice up to 7 hrs. At 24 hrs the phosphorylation levels of STAT3 completely recovered to levels before Sutent treatment. The phosphorylation kinetics mirrors the levels of circulating Sutent in the blood. The rapid response of STAT3 phosphorylation in the spleen reflecting the pharmacokinetic profile of Sutent suggests a direct immunomodulatory function of Sutent in tumor bearing animals.

TABLE 29

The relative levels of phosphorylated STAT3 and total STAT3 from healthy BALB/c and tumor bearing BALB/neuT mice before or after Sutent treatment at multiple time points.

| Strain | Time Point, hrs | Phospho-STAT3 Individual values | Phospho-STAT3 Mean | Phospho-STAT3 SEM | Total STAT3 Individual values | Total STAT3 Mean | Total STAT3 SEM |
|---|---|---|---|---|---|---|---|
| Balb/c | 0 | 0.11 | 0.09 | 0.01 | 0.12 | 0.13 | 0.00 |
| | | 0.08 | | | 0.12 | | |
| | | 0.09 | | | 0.14 | | |
| Tumor bearing BALB/neuT | 0 | 1.08 | 1.31 | 0.12 | 0.08 | 0.09 | 0.01 |
| | | 1.38 | | | 0.11 | | |
| | | 1.46 | | | NA | | |
| | 1 | 0.26 | 0.23 | 0.02 | 0.12 | 0.09 | 0.01 |
| | | 0.25 | | | 0.08 | | |
| | | 0.19 | | | 0.08 | | |
| | 3 | 0.19 | 0.19 | 0.02 | 0.15 | 0.13 | 0.02 |
| | | 0.15 | | | 0.09 | | |
| | | 0.22 | | | 0.16 | | |
| | 7 | 0.19 | 0.27 | 0.04 | 0.10 | 0.08 | 0.01 |
| | | 0.31 | | | 0.07 | | |
| | | 0.29 | | | 0.08 | | |
| | 24 | 1.54 | 1.44 | 0.07 | 0.08 | 0.08 | 0.00 |
| | | 1.30 | | | 0.08 | | |
| | | 1.47 | | | 0.08 | | |

RAW SEQUENCE LISTING

AMINO ACID SEQUENCE OF THE FULL LENGTH HUMAN PSMA.

SEQ ID NO: 1

MWNLLHETDSAVATARRPRWLCAGALVLAGGFFLLGFLFGWFIKSSNEATNITPKHN

MKAFLDELKAENIKKFLYNFTQIPHLAGTEQNFQLAKQIQSQWKEFGLDSVELAHYDV

LLSYPNKTHPNYISIINEDGNEIFNTSLFEPPPPGYENVSDIVPPFSAFSPQGMPEGDL

VYVNYARTEDFFKLERDMKINCSGKIVIARYGKVFRGNKVKNAQLAGAKGVILYSDPA

DYFAPGVKSYPDGWNLPGGGVQRGNILNLNGAGDPLTPGYPANEYAYRRGIAEAVG

LPSIPVHPIGYYDAQKLLEKMGGSAPPDSSWRGSLKVPYNVGPGFTGNFSTQKVKM

HIHSTNEVTRIYNVIGTLRGAVEPDRYVILGGHRDSWVFGGIDPQSGAAVVHEIVRSF

GTLKKEGWRPRRTILFASWDAEEFGLLGSTEWAEENSRLLQERGVAYINADSSIEGN

YTLRVDCTPLMYSLVHNLTKELKSPDEGFEGKSLYESWTKKSPSPEFSGMPRISKLG

SGNDFEVFFQRLGIASGRARYTKNWETNKFSGYPLYHSVYETYELVEKFYDPMFKYH

LTVAQVRGGMVFELANSIVLPFDCRDYAVVLRKYADKIYSISMKHPQEMKTYSVSFDS

LFSAVKNFTEIASKFSERLQDFDKSNPIVLRMMNDQLMFLERAFIDPLGLPDRPFYRH

VIYAPSSHNKYAGESFPGIYDALFDIESKVDPSKAWGEVKRQIYVAAFTVQAAAETLSE

VA

NUCLEOTIDE SEQUENCE ENCODING THE FULL LENGTH HUMAN PSMA OF SEQ ID NO: 1.

SEQ ID NO: 2 atgtggaatctccttcacgaaaccgactcggctgtggccaccgcgcgccgcccgcgctggctgtgcgctggggcgctgg tgctggcgggtggcttctttctcctcggcttcctcttcgggtggtttataaaatcctccaatgaagctactaacattactccaaa gcataatatgaaagcattttttggatgaattgaaagctgagaacatcaagaagttcttatataattttacacagataccacatt tagcaggaacagaacaaaactttcagcttgcaaagcaaattcaatcccagtggaaagaatttggcctggattctgttgag ctagcacattatgatgtcctgttgtcctacccaaataagactcatcccaactacatctcaataattaatgaagatggaaatg agattttcaacacatcattatttgaaccacctcctccaggatatgaaaatgtttcggatattgtaccacctttcagtgctttctct cctcaaggaatgccagagggcgatctagtgtatgttaactatgcacgaactgaagacttctttaaattggaacgggacat gaaaatcaattgctctgggaaaattgtaattgccagatatgggaaagttttcagaggaaataaggttaaaaatgcccagc -continued tggcaggggccaaaggagtcattctctactccgaccctgctgactactttgctcctggggtgaagtcctatccagatggttg
gaatcttcctggaggtggtgtccagcgtggaaatatcctaaatctgaatggtgcaggagaccctctcacaccaggttacc
cagcaaatgaatatgcttataggcgtggaattgcagaggctgttggtcttccaagtattcctgttcatccaattggatactatg
atgcacagaagctcctagaaaaaatgggtggctcagcaccaccagatagcagctggagaggaagtctcaaagtgcc
ctacaatgttggacctggctttactggaaacttttctacacaaaaagtcaagatgcacatccactctaccaatgaagtgac
aagaatttacaatgtgataggtactctcagaggagcagtggaaccagacagatatgtcattctgggaggtcaccgggac
tcatgggtgtttggtggtattgaccctcagagtggagcagctgttgttcatgaaattgtgaggagctttggaacactgaaaa
aggaagggtggagacctagaagaacaattttgtttgcaagctgggatgcagaagaatttggtcttcttggttctactgagtg
ggcagaggagaattcaagactccttcaagagcgtggcgtggcttatattaatgctgactcatctatagaaggaaactaca
ctctgagagttgattgtacaccgctgatgtacagcttggtacacaacctaacaaaagagctgaaaagccctgatgaagg
ctttgaaggcaaatctctttatgaaagttggactaaaaaaagtccttccccagagttcagtggcatgcccaggataagca
aattgggatctggaaatgattttgaggtgttcttccaacgacttggaattgcttcaggcagagcacggtatactaaaaattg
ggaaacaaacaaattcagcggctatccactgtatcacagtgtctatgaaacatatgagttggtggaaaagttttatgatcc
aatgtttaaatatcacctcactgtggcccaggttcgaggagggatggtgtttgagctagccaattccatagtgctcccttttga
ttgtcgagattatgctgtagttttaagaaagtatgctgacaaaatctacagtatttctatgaaacatccacaggaaatgaag
acatacagtgtatcatttgattcactttttttctgcagtaaagaattttacagaaattgcttccaagttcagtgagagactccagg
actttgacaaaagcaacccaatagtattaagaatgatgaatgatcaactcatgtttctggaaagagcatttattgatccatta
gggttaccagacaggcctttttataggcatgtcatctatgctccaagcagccacaacaagtatgcaggggagtcattccc
aggaatttatgatgctctgtttgatattgaaagcaaagtggacccttccaaggcctggggagaagtgaagagacagattt
atgttgcagccttcacagtgcaggcagctgcagagactttgagtgaagtagcc

AMINO ACID SEQUENCE OF PSMA SHUFFLED ANTIGEN 1.

SEQ ID NO: 3

MASARRPRWLCAGALVLAGGFFLLGFLFGWFIKSSSEATNISPQHNVKAFLDEMKAE
NIKKFLYLFTQIPHLAGTEQNFQLAKQIQAEWKEFGLDSVELAHYDVLLSYPNETHPNY
ISIIDEDGNEIFNTSLFEPPPPGYENISDVVPPYSAFSPQGMPEGDLVYVNYARTEDFF
KLERELKINCSGKILIARYGKVFRGNKVKNAQLAGAKGIILYSDPADYFAPGVKSYPDG
WNLPGGGVQRGNVLNLNGAGDPLTPGYPANEYAYRRELAEAVGLPSIPVHPIGYYDA
QKLLEKMGGSAPPDSSWKGSLKVPYNVGPGFTGNFSTQKVKMHIHSTNEVTRIYNVI
GTIRGAVEPDRYVILGGHRDAWVFGGIDPQSGAAVVHEIVRSFGTLKKKGWRPRRTII
FASWDAEEFGLLGSTEWAEENSRLLQERGVAYINADSSIEGNYTLRVDCTPLMYSLV
YNLTKELQSPDEGFEGKSLYESWTKKSPSPEFSGVPRINKLGSGNDFEVFFQRLGIAS
GRARYTKNWKTNKFSGYPLYHSVYETYELVEKFYDPMFKYHLTVAQVRGGLVFELAD
SIVLPFDCQDYAVVLRKYADKIYNLAMKHPEELKTYSVSFDSLFSAVKNFTEIASKFNQ
RLQDFDKNNPLLVRMLNDQLMFLERAFVDPLGLPDRPFYRHVIYAPSSHNKYAGESF
PGIYDALFDIESKVDPSKAWGEVKRQIYVAAFTVQAAAETLSEVA

NUCLEOTIDE SEQUENCE ENCODING AMINO ACID SEQUENCE OF PSMA SHUFFLED ANTIGEN
1 OF SEQ ID NO: 3.

SEQ ID NO: 4 atggctagcgccagacggcccagatggctgtgcgccggagccctggtgctggccggaggattcttcctgctgggcttcct
gttcggctggttcatcaagagcagcagcgaggccaccaacatcagcccccagcacaacgtgaaggcctttctggacg
agatgaaggccgagaacatcaagaagtttctgtacctgttcacccagatcccccacctggccggcaccgagcagaact
tccagctggccaagcagattcaggctgagtggaaagagttcggcctggacagcgtggagctggcccactacgacgtg
ctgctgtcctaccccaacgagacacaccccaactacatcagcatcatcgacgaggacggcaacgagattttcaacacc -continued agcctgttcgagccccctcccccctggctacgagaacatctccgacgtggtgcccccctacagcgccttcagccctcagg gaatgcctgaaggcgacctggtgtacgtgaactacgcccggaccgaggacttcttcaagctggaacgggagctgaag atcaactgcagcggcaagatcctgatcgccagatacggcaaggtgttccggggcaacaaagtgaagaacgcacagc tggctggagccaagggcatcatcctgtacagcgaccccgccgactacttcgcccctggcgtgaagtcctaccctgacgg ctggaacctgcctggcggcggagtgcagcggggcaacgtgctgaacctgaacggagccggcgaccctctgacccca ggctaccccgccaacgagtacgcctaccggcgggagctggccgaagccgtgggcctgcccagcatccccgtgcacc ccatcggctactacgacgcccagaaactgctggaaaagatgggcggcagcgcccctcccgacagcagctggaagg gcagcctgaaggtgccctacaacgtgggccctggcttcaccggcaacttcagcacccagaaagtgaagatgcacatc cacagcaccaacgaagtgacccggatctacaacgtgatcggcaccatcagaggcgccgtggagcccgacagatac gtgatcctgggcggccaccgggacgcctgggtgttcggcggcatcgacccccagagcggagccgccgtggtgcacg agatcgtgcggagcttcggcaccctgaagaagaagggctggcggcccagacggaccatcatcttcgccagctgggac gccgaggaattcggactgctgggctctaccgagtgggccgaggaaaacagcagactgctgcaggaacggggcgtcg cctacatcaacgccgacagctccatcgagggcaactacaccctgcgggtggactgcacccccctgatgtacagcctgg tgtacaacctgaccaaagagctgcagagccccgacgagggcttcgagggcaagagcctgtacgagagctggacca agaagtcccccagccccgagttcagcggcgtgccccggatcaacaagctgggcagcggcaacgacttcgaggtgttc ttccagaggctgggcattgccagcggcagagcccggtacaccaagaactggaaaaccaacaagttctccggctaccc cctgtaccacagcgtgtacgagacatacgaactggtggagaagttctacgaccccatgttcaagtaccacctgaccgtg gcccaggtccggggagggctggtgttcgaactggccgacagcatcgtgctgcccttcgactgccaggactatgctgtggt gctgcggaagtacgccgacaaaatctacaacctggccatgaagcaccccgaggaactgaaaacctacagcgtgtcct tcgacagcctgttcagcgccgtgaagaacttcaccgagatcgccagcaagttcaaccagcggctgcaggacttcgaca agaacaaccccctgctggtccggatgctgaacgaccagctgatgttcctggaacgggccttcgtggacccccctgggcct gcctgaccggcccttctaccggcacgtgatctatgcccccagcagccacaacaagtacgctggcgagagcttccccgg catctacgatgccctgttcgacatcgagagcaaggtggaccccagcaaggcctggggcgaagtgaagcggcagatat acgtggccgccttcacagtgcaggccgctgccgagacactgagcgaggtggcc

AMINO ACID SEQUENCE OF PSMA SHUFFLED ANTIGEN 2.

SEQ ID NO: 5

MASARRPRWLCAGALVLAGGFFLLGFLFGWFIKSSSEATNITPQHNVKAFLDELKAEN

IKKFLYNFTQIPHLAGTEQNFELAKQIQAQWKEFGLDSVELSHYDVLLSYPNETHPNYI

SIIDEDGNEIFNTSLFEPPPPGYENISDVVPPYSAFSPQGMPEGDLVYVNYARTEDFFK

LERDMKINCSGKILIARYGKVFRGNKVKNAQLAGAKGIILYSDPADYFAPGVKSYPDG

WNLPGGGVQRGNVLNLNGAGDPLTPGYPANEYAYRRGIAEAVGLPSIPVHPIGYYDA

QKLLEKMGGAAPPDSSWKGSLQVPYNVGPGFTGNFSTQKVKMHIHSTNEVTRIYNVI

GTLKGAVEPDRYVILGGHRDAWVFGGIDPQSGAAVVHEIVRSFGTLKKKGWRPRRTI

LFASWDAEEFGLLGSTEWAEENSRLLQERGVAYINADSSIEGNYTLRVDCTPLMYSL

VYNLTKELQSPDEGFEGKSLFDSWTEKSPSPEFSGLPRISKLGSGNDFEVFFQRLGIA

SGRARYTKDWKTSKFSGYPLYHSVYETYELVEKFYDPMFKYHLTVAQVRGGIVFELA

NSVVLPFDCQDYAVVLKKYADKIYNISMKHPQEMKTYSVSFDSLFSAVKNFTEIASKF

NQRLQDFDKNNPILLRMMNDQLMFLERAFIDPLGLPDRPFYRHVIYAPSSHNKYAGES

FPGIYDALFDIESKVDPSKAWGEVKRQIYVAAFTVQAAAETLSEVA

NUCLEOTIDE SEQUENCE ENCODING AMINO ACID SEQUENCE OF PSMA SHUFFLED ANTIGEN 2 OF SEQ ID NO: 5.

-continued

SEQ ID NO: 6 atggctagcgccagacggcccagatggctgtgtgctggcgccctggtgctggctggcggctttttcctgctgggcttcctgtt cggctggttcatcaagagcagcagcgaggccaccaacatcacccccagcacaacgtgaaggcctttctggacgag ctgaaggccgagaatatcaagaagttcctgtacaacttcacccagatcccccacctggccggcaccgagcagaacttc gagctggccaagcagatccaggcccagtggaaagagttcggcctggacagcgtggaactgagccactacgacgtgc tgctgagctaccccaacgagacacaccccaactacatcagcatcatcgacgaggacggcaacgagattttcaacacc agcctgttcgagcccctccacccggctacgagaacatcagcgacgtggtgccccctacagcgcattcagtccacag ggaatgcccgagggcgacctggtgtacgtgaactacgcccggaccgaggacttcttcaagctggaacgggacatgaa gatcaactgcagcggcaagatcctgatcgccagatacggcaaggtgttccggggcaacaaagtgaagaacgcccag ctggcaggcgccaagggcatcatcctgtacagcgaccccgccgactacttcgcccctggcgtgaagtcctaccccgac ggctggaacctgcctggcggcggagtgcagaggggcaacgtgctgaacctgaacggcgctggcgaccctctgaccc ctggctaccccgccaacgagtacgcctacagacggggaatcgccgaggccgtgggcctgcctagcatccctgtgcac cccatcggctactacgacgcccagaaactgctggaaaagatgggcggagccgcccctcccgacagctcttggaagg gcagcctgcaggtcccctacaacgtgggccctggcttcaccggcaacttcagcacccagaaagtgaagatgcacatcc acagcaccaacgaagtgacccggatctacaacgtgatcggcaccctgaagggcgccgtggaacccgacagatacgt gatcctgggcggccaccgggacgcctgggtgttcggaggcatcgaccctcagagcggcgctgccgtggtgcacgaga tcgtgcggagcttcggcacactgaagaagaagggctggcggcccagacggaccatcctgttcgccagctgggacgcc gaggaattcggcctgctgggcagcaccgagtgggccgaggaaaacagtcggctgctgcaggaacggggcgtcgcct acatcaacgccgacagcagcatcgagggcaactacaccctgcgggtggactgcaccccccctgatgtacagcctggtg tacaacctgaccaaagagctgcagagccccgacgagggcttcgagggcaagtccctgttcgactcctggaccgagaa gtcccccagccccgagttcagcggcctgcccagaatcagcaagctgggcagcggcaacgacttcgaggtgttcttcca gcggctgggaatcgccagcggcagagcccggtacaccaaggactggaaaaccagcaagttctccggctaccccctg taccacagcgtgtacgagacatacgagctggtggaaaagttctacgaccccatgttcaagtaccacctgaccgtggccc aggtccgaggcggcatcgtgttcgaactggccaacagcgtggtgctgccattcgattgtcaggactacgccgtggtgctg aagaagtacgccgacaaaatctacaacatcagcatgaagcacccccaggaaatgaaaacctacagcgtgtccttcg acagcctgttcagcgccgtgaagaatttcaccgagatcgcctccaagttcaaccagagactgcaggacttcgacaaga acaaccccatcctgctgcggatgatgaacgaccagctgatgttcctggaacgggccttcatcgacccccctgggcctgcc cgaccggccccttttaccggcacgtgatctatgcccccagcagccacaacaaatacgccggcgagagtttccccggcat ctacgatgccctgttcgatatcgagagcaaggtggaccccagcaaggcctggggcgaagtgaagcggcagatttacgt ggccgcattcacagtgcaggctgctgccgagacactgagcgaggtggcc

AMINO ACID SEQUENCE OF PSMA SHUFFLED ANTIGEN 3.

SEQ ID NO: 7

MASARRPRWLCAGALVLAGGFFLLGFLFGWFIKSSNEATNITPKHNMKAFLDELKAE

NIKKFLYNFTQIPHLAGTEQNFQLAKQIQSQWKEFGLDSVELAHYDVLLSYPNKTHPN

YISIINEDGNEIFNTSLFEPPPPGYENVSDIVPPFSAFSPQGMPEGDLVYVNYARTEDF

FKLERDMKINCSGKIVIARYGKVFRGNKVKNAQLAGAKGVILYSDPADYFAPGVKSYP

DGWNLPGGGVQRGNILNLNGAGDPLTPGYPANEYAYRRGIAEAVGLPSIPVHPIGYY

DAQKLLEKMGGSAPPDSSWRGSLKVPYNVGPGFTGNFSAQKLKLHIHSNTKVTRIYN

VIGTLRGAVEPDRYVILGGHRDSWVFGGIDPQSGAAVVHEIVRTFGTLKKKGWRPRR

TILFASWDAEEFGLLGSTEWAEENSRLLQERGVAYINADSSIEGNYTLRVDCTPLLHS

LVYNLTKELKSPDEGFEGKSLYESWTKKSPSPELSGLPRISKLGSGNDFEVFFQRLGI

SSGRARYTKDWKTSKFSSYPLYHSIYETYELVVKFYDPMFKYHLTVAQVRGGMVFEL

-continued

ANSIVLPFDCRDYAVALKNHAENLYSISMKHPQEMKTYSVSFDSLFSAVKNFTEIASKF

SERLQDFDKSNPIVLRMMNDQLMFLERAFIDPLGLPDRPFYRHVIYAPSSHNKYAGES

FPGIYDALFDIESKVDPSKAWGEVKRQIYVAAFTVQAAAETLSEVA

NUCLEOTIDE SEQEUNCE ENCODING AMINO ACID SEQUENCE OF PSMA SHUFFLED ANTIGEN 3 OF SEQ ID NO: 7.

SEQ ID NO: 8 atggctagcgccagacggcccagatggctgtgtgctggcgccctggtgctggctggcggctttttcctgctgggcttcctgtt cggctggttcatcaagagcagcaacgaggccaccaacatcaccccccaagcacaacatgaaggcctttctggacgag ctgaaggccgagaatatcaagaagttcctgtacaacttcacccagatcccccacctggccggcaccgagcagaacttc cagctggccaagcagatccagagccagtggaaagagttcggcctggacagcgtggaactggcccactacgacgtgc tgctgagctaccccaacaagacccaccccaactacatcagcatcatcaacgaggacggcaacgagattttcaacacc agcctgttcgagccccctccacccggctacgagaacgtgtccgacatcgtgccccccattcagcgcattcagtccacagg gaatgcccgagggcgacctggtgtacgtgaactacgcccggaccgaggacttcttcaagctggaacgggacatgaag atcaactgcagcggcaagatcgtgatcgccagatacggcaaggtgttccggggcaacaaagtgaagaacgcccagc tggcaggcgccaagggcgtgatcctgtatagcgaccccgccgactacttcgcccctggcgtgaagtcctaccccgacg gctggaacctgcctggcggcggagtgcagcggggcaacatcctgaacctgaacggcgctggcgacccccctgacccct ggctatcccgccaacgagtacgcctacagacggggaatcgccgaggccgtgggcctgcctagcatccctgtgcaccc catcggctactacgacgcccagaaactgctggaaaagatgggcggcagcgcccctcccgatagctcttggagaggca gcctgaaggtgccctacaacgtgggccctggcttcaccggcaacttcagcgcccagaagctgaagctgcacatccaca gcaacaccaaagtgacccggatctacaacgtgatcggcaccctgagaggcgccgtggaacccgacagatacgtgat cctgggcggccaccgggacagctgggtgttcggcggcatcgaccctcagtctggcgccgctgtggtgcacgagatcgt gcggacctttggcaccctgaagaagaagggctggcggcccagacggaccatcctgttcgccagctgggacgccgag gaattcggcctgctgggcagcaccgagtgggccgaggaaaacagtcggctgctgcaggaacggggcgtcgcctaca tcaacgccgacagcagcatcgagggcaactacaccctgcgggtggactgcaccccccctgctgcacagcctggtgtac aacctgaccaaagagctgaagtcccccgacgagggcttcgagggcaagagcctgtacgagagctggaccaagaag tcccccagccccgagctgagcggcctgcccagaatcagcaagctgggcagcggcaacgacttcgaggtgttcttccag cggctgggcatcagcagcggcagagcccggtacaccaaggactggaaaaccagcaagttcagcagctacccccctgt accacagcatctacgagacatacgagctggtggtcaagttctacgaccccatgttcaagtaccacctgaccgtggccca ggtccgaggcggcatggtgttcgagctggccaacagcatcgtgctgcccttcgactgccgggactacgccgtggccctg aagaaccacgccgagaacctgtacagcatcagcatgaagcacccccaggaaatgaaaacctacagcgtgtccttcg acagcctgttcagcgccgtgaagaatttcaccgagatcgcctccaagttcagcgagcggctgcaggacttcgacaaga gcaaccccatcgtgctgagaatgatgaacgaccagctgatgttcctggaacgggccttcatcgacccccctgggcctgcc cgaccggcccttttaccggcacgtgatctatgcccccagcagccacaacaaatacgccggcgagagtttccccggcat ctacgatgccctgttcgacatcgagagcaaggtggaccccagcaaggcctggggcgaagtgaagcggcagatttacg tggccgcattcacagtgcaggccgctgccgagacactgagcgaggtggcc

AMINO ACID SEQUENCE OF A MEMBRANE-BOUND PSMA ANTIGEN.

SEQ ID NO: 9

MASARRPRWLCAGALVLAGGFFLLGFLFGWFIKSSNEATNITPKHNMKAFLDELKAE

NIKKFLYNFTQIPHLAGTEQNFQLAKQIQSQWKEFGLDSVELAHYDVLLSYPNKTHPN

YISIINEDGNEIFNTSLFEPPPPGYENVSDIVPPFSAFSPQGMPEGDLVYVNYARTEDF

FKLERDMKINCSGKIVIARYGKVFRGNKVKNAQLAGAKGVILYSDPADYFAPGVKSYP

DGWNLPGGGVQRGNILNLNGAGDPLTPGYPANEYAYRRGIAEAVGLPSIPVHPIGYY

DAQKLLEKMGGSAPPDSSWRGSLKVPYNVGPGFTGNFSTQKVKMHIHSTNEVTRIY

-continued

NVIGTLRGAVEPDRYVILGGHRDSWVFGGIDPQSGAAVVHEIVRSFGTLKKEGWRPR

RTILFASWDAEEFGLLGSTEWAEENSRLLQERGVAYINADSSIEGNYTLRVDCTPLMY

SLVHNLTKELKSPDEGFEGKSLYESWTKKSPSPEFSGMPRISKLGSGNDFEVFFQRL

GIASGRARYTKNWETNKFSGYPLYHSVYETYELVEKFYDPMFKYHLTVAQVRGGMV

FELANSIVLPFDCRDYAVVLRKYADKIYSISMKHPQEMKTYSVSFDSLFSAVKNFTEIA

SKFSERLQDFDKSNPIVLRMMNDQLMFLERAFIDPLGLPDRPFYRHVIYAPSSHNKYA

GESFPGIYDALFDIESKVDPSKAWGEVKRQIYVAAFTVQAAAETLSEVA

NUCLEOTIDE SEQEUNCE ENCODING AMINO ACID SEQUENCE OF THE MEMBRANE-BOUND PSMA ANTIGEN OF SEQ ID NO: 9.

SEQ ID NO: 10 atggctagcgcgcgccgcccgcgctggctgtgcgctggggcgctggtgctggcgggtggcttctttctcctcggcttcctcttcgggtggtttataaaatcctccaatgaagctactaacattactccaaagcataatatgaaagcatttttggatgaattgaaagctgagaacatcaagaagttcttatataattttacacagataccacatttagcaggaacagaacaaaactttcagcttgcaaagcaaattcaatcccagtggaaagaatttggcctggattctgttgagctggcacattatgatgtcctgttgtcctacccaaataagactcatcccaactacatctcaataattaatgaagatggaaatgagattttcaacacatcattatttgaaccacctcctccaggatatgaaaatgtttcggatattgtaccacctttcagtgctttctctcctcaaggaatgccagagggcgatctagtgtatgttaactatgcacgaactgaagacttctttaaattggaacgggacatgaaaatcaattgctctgggaaaattgtaattgccagatatgggaaagttttcagaggaaataaggttaaaaatgcccagctggcaggggccaaaggagtcattctctactccgaccctgctgactactttgctcctggggtgaagtcctatccagatggttggaatcttcctggaggtggtgtccagcgtggaaatatcctaaatctgaatggtgcaggagaccctctcacaccaggttacccagcaaatgaatatgcttataggcgtggaattgcagaggctgttggtcttccaagtattcctgttcatccaattggatactatgatgcacagaagctcctagaaaaaatgggtggctcagcaccaccagatagcagctggagaggaagtctcaaagtgccctacaatgttggacctggctttactggaaacttttctacacaaaaagtcaagatgcacatccactctaccaatgaagtgacaagaatttacaatgtgataggtactctcagaggagcagtggaaccagacagatatgtcattctgggaggtcaccgggactcatgggtgtttggtggtattgaccctcagagtggagcagctgttgttcatgaaattgtgaggagctttggaacactgaaaaaggaagggtggagacctagaagaacaattttgtttgcaagctgggatgcagaagaatttggtcttcttggttctactgagtgggcagaggagaattcaagactccttcaagagcgtggcgtggcttatattaatgctgactcatctatagaaggaaactacactctgagagttgattgtacaccgctgatgtacagcttggtacacaacctaacaaaagagctgaaaagccctgatgaaggctttgaaggcaaatctctttatgaaagttggactaaaaaaagtccttccccagagttcagtggcatgcccaggataagcaaattgggatctggaaatgattttgaggtgttcttccaacgacttggaattgcttcaggcagagcacggtatactaaaaattgggaaacaaacaaattcagcggctatccactgtatcacagtgtctatgaaacatatgagttggtggaaaagttttatgatccaatgtttaaatatcacctcactgtggcccaggttcgaggagggatggtgtttgagctggccaattccatagtgctcccttttgattgtcgagattatgctgtagttttaagaaagtatgctgacaaaatctacagtatttctatgaaacatccacaggaaatgaagacatacagtgtatcatttgattcactttttctgcagtaaagaattttacagaaattgcttccaagttcagtgagagactccaggactttgacaaaagcaacccaatagtattaagaatgatgaatgatcaactcatgtttctggaaagagcatttattgatccattagggttaccagacaggcctttttataggcatgtcatctatgctccaagcagccacaacaagtatgcaggggagtcattcccaggaatttatgatgctctgtttgatattgaaagcaaagtggacccttccaaggcctggggagaagtgaagagacagatttatgttgcagccttcacagtgcaggcagctgcagagactttgagtgaagtagcc

AMINO ACID SEQUENCE OF A CYTOSOLIC PSMA ANTIGEN.

SEQ ID NO: 11

MASKSSNEATNITPKHNMKAFLDELKAENIKKFLYNFTQIPHLAGTEQNFQLAKQIQSQ

WKEFGLDSVELAHYDVLLSYPNKTHPNYISIINEDGNEIFNTSLFEPPPPGYENVSDIVP

PFSAFSPQGMPEGDLVYVNYARTEDFFKLERDMKINCSGKIVIARYGKVFRGNKVKN

-continued

AQLAGAKGVILYSDPADYFAPGVKSYPDGWNLPGGGVQRGNILNLNGAGDPLTPGY

PANEYAYRRGIAEAVGLPSIPVHPIGYYDAQKLLEKMGGSAPPDSSWRGSLKVPYNV

GPGFTGNFSTQKVKMHIHSTNEVTRIYNVIGTLRGAVEPDRYVILGGHRDSWVFGGID

PQSGAAVVHEIVRSFGTLKKEGWRPRRTILFASWDAEEFGLLGSTEWAEENSRLLQE

RGVAYINADSSIEGNYTLRVDCTPLMYSLVHNLTKELKSPDEGFEGKSLYESWTKKSP

SPEFSGMPRISKLGSGNDFEVFFQRLGIASGRARYTKNWETNKFSGYPLYHSVYETY

ELVEKFYDPMFKYHLTVAQVRGGMVFELANSIVLPFDCRDYAVVLRKYADKIYSISMK

HPQEMKTYSVSFDSLFSAVKNFTEIASKFSERLQDFDKSNPIVLRMMNDQLMFLERAF

IDPLGLPDRPFYRHVIYAPSSHNKYAGESFPGIYDALFDIESKVDPSKAWGEVKRQIYV

AAFTVQAAAETLSEVA

NUCLEOTIDE SEQEUNCE ENCODING AMINO ACID SEQUENCE OF THE CYTOSOLIC PSMA ANTIGEN OF SEQ ID NO: 11.

SEQ ID NO: 12 atggctagcaaatcctccaatgaagctactaacattactccaaagcataatatgaaagcatttttggatgaattgaaagct gagaacatcaagaagttcttatataattttacacagataccacatttagcaggaacagaacaaaactttcagcttgcaaa gcaaattcaatcccagtggaaagaatttggcctggattctgttgagctggcacattatgatgtcctgttgtcctacccaaata agactcatcccaactacatctcaataattaatgaagatggaaatgagattttcaacacatcattatttgaaccacctcctcc aggatatgaaaatgtttcggatattgtaccacctttcagtgctttctctcctcaaggaatgccagagggcgatctagtgtatgt taactatgcacgaactgaagacttctttaaattggaacgggacatgaaaatcaattgctctgggaaaattgtaattgccag atatgggaaagttttcagaggaaataaggttaaaaatgcccagctggcaggggccaaaggagtcattctctactccgac cctgctgactactttgctcctggggtgaagtcctatccagatggttggaatcttcctggaggtggtgtccagcgtggaaatat cctaaatctgaatggtgcaggagaccctctcacaccaggttacccagcaaatgaatatgcttataggcgtggaattgcag aggctgttggtcttccaagtattcctgttcatccaattggatactatgatgcacagaagctcctagaaaaaatgggtggctc agcaccaccagatagcagctggagaggaagtctcaaagtgccctacaatgttggacctggctttactggaaacttttcta cacaaaaagtcaagatgcacatccactctaccaatgaagtgacaagaatttacaatgtgataggtactctcagaggag cagtggaaccagacagatatgtcattctgggaggtcaccgggactcatgggtgtttggtggtattgaccctcagagtgga gcagctgttgttcatgaaattgtgaggagctttggaacactgaaaaaggaagggtggagacctagaagaacaattttgttt gcaagctgggatgcagaagaatttggtcttcttggttctactgagtgggcagaggagaattcaagactccttcaagagcgt ggcgtggcttatattaatgctgactcatctatagaaggaaactacactctgagagttgattgtacaccgctgatgtacagctt ggtacacaacctaacaaaagagctgaaaagccctgatgaaggctttgaaggcaaatctctttatgaaagttggactaaa aaaagtccttccccagagttcagtggcatgcccaggataagcaaattgggatctggaaatgattttgaggtgttcttccaa cgacttggaattgcttcaggcagagcacggtatactaaaaattgggaaacaaacaaattcagcggctatccactgtatc acagtgtctatgaaacatatgagttggtggaaaagttttatgatccaatgtttaaatatcacctcactgtggcccaggttcga ggagggatggtgtttgagctggccaattccatagtgctcccttttgattgtcgagattatgctgtagttttaagaaagtatgctg acaaaatctacagtatttctatgaaacatccacaggaaatgaagacatacagtgtatcatttgattcactttttttctgcagtaa agaattttacagaaattgcttccaagttcagtgagagactccaggactttgacaaaagcaacccaatagtattaagaatg atgaatgatcaactcatgtttctggaaagagcatttattgatccattagggttaccagacaggccttttttataggcatgtcatct atgctccaagcagccacaacaagtatgcaggggagtcattcccaggaatttatgatgctctgtttgatattgaaagcaaa gtggacccttccaaggcctggggagaagtgaagagacagatttatgttgcagccttcacagtgcaggcagctgcagag actttgagtgaagtagcc

AMINO ACID SEQUENCE OF A SECRETED PSMA ANTIGEN.

-continued

SEQ ID NO: 13

MASETDTLLLWVLLLWVPGSTGDAAKSSNEATNITPKHNMKAFLDELKAENIKKFLYN

FTQIPHLAGTEQNFQLAKQIQSQWKEFGLDSVELAHYDVLLSYPNKTHPNYISIINEDG

NEIFNTSLFEPPPPGYENVSDIVPPFSAFSPQGMPEGDLVYVNYARTEDFFKLERDMK

INCSGKIVIARYGKVFRGNKVKNAQLAGAKGVILYSDPADYFAPGVKSYPDGWNLPG

GGVQRGNILNLNGAGDPLTPGYPANEYAYRRGIAEAVGLPSIPVHPIGYYDAQKLLEK

MGGSAPPDSSWRGSLKVPYNVGPGFTGNFSTQKVKMHIHSTNEVTRIYNVIGTLRGA

VEPDRYVILGGHRDSWVFGGIDPQSGAAVVHEIVRSFGTLKKEGWRPRRTILFASWD

AEEFGLLGSTEWAEENSRLLQERGVAYINADSSIEGNYTLRVDCTPLMYSLVHNLTKE

LKSPDEGFEGKSLYESWTKKSPSPEFSGMPRISKLGSGNDFEVFFQRLGIASGRARY

TKNWETNKFSGYPLYHSVYETYELVEKFYDPMFKYHLTVAQVRGGMVFELANSIVLP

FDCRDYAVVLRKYADKIYSISMKHPQEMKTYSVSFDSLFSAVKNFTEIASKFSERLQD

FDKSNPIVLRMMNDQLMFLERAFIDPLGLPDRPFYRHVIYAPSSHNKYAGESFPGIYD

ALFDIESKVDPSKAWGEVKRQIYVAAFTVQAAAETLSEVA

NUCLEOTIDE SEQUENCE ENCODING AMINO ACID SEQUENCE OF THE SECRETED PSMA ANTIGEN OF SEQ ID NO: 13.

SEQ ID NO: 14 atggctagcgaaaccgacactttgttgttgtgggtgcttttgctttgggtacccggatctactggtgatgctgctaaatcctcca atgaagctactaacattactccaaagcataatatgaaagcattttggatgaattgaaagctgagaacatcaagaagttct tatataattttacacagataccacatttagcaggaacagaacaaaactttcagcttgcaaagcaaattcaatcccagtgg aaagaatttggcctggattctgttgagctagcacattatgatgtcctgttgtcctacccaaataagactcatcccaactacat ctcaataattaatgaagatggaaatgagattttcaacacatcattatttgaaccacctcctccaggatatgaaaatgtttcgg atattgtaccacctttcagtgctttctctcctcaaggaatgccagagggcgatctagtgtatgttaactatgcacgaactgaa gacttctttaaattggaacgggacatgaaaatcaattgctctgggaaaattgtaattgccagatatgggaaagttttcagag gaaataaggttaaaaatgcccagctggcaggggccaaaggagtcattctctactccgaccctgctgactactttgctcct ggggtgaagtcctatccagatggttggaatcttcctggaggtggtgtccagcgtggaaatatcctaaatctgaatggtgca ggagaccctctcacaccaggttacccagcaaatgaatatgcttataggcgtggaattgcagaggctgttggtcttccaagt attcctgttcatccaattggatactatgatgcacagaagctcctagaaaaaatgggtggctcagcaccaccagatagcag ctggagaggaagtctcaaagtgccctacaatgttggacctggctttactggaaacttttctacacaaaaagtcaagatgc acatccactctaccaatgaagtgacaagaatttacaatgtgataggtactctcagaggagcagtggaaccagacagat atgtcattctgggaggtcaccgggactcatgggtgtttggtggtattgaccctcagagtggagcagctgttgttcatgaaatt gtgaggagctttggaacactgaaaaaggaagggtggagacctagaagaacaattttgtttgcaagctgggatgcagaa gaatttggtcttcttggttctactgagtgggcagaggagaattcaagactccttcaagagcgtggcgtggcttatattaatgct gactcatctatagaaggaaactacactctgagagttgattgtacaccgctgatgtacagcttggtacacaacctaacaaa agagctgaaaagccctgatgaaggctttgaaggcaaatctctttatgaaagttggactaaaaaaagtccttccccagagt tcagtggcatgcccaggataagcaaattgggatctggaaatgattttgaggtgttcttccaacgacttggaattgcttcagg cagagcacggtatactaaaaattgggaaacaaacaaattcagcggctatccactgtatcacagtgtctatgaaacatat gagttggtggaaaagttttatgatccaatgtttaaatatcacctcactgtggcccaggttcgaggagggatggtgtttgagct agccaattccatagtgctcccttttgattgtcgagattatgctgtagttttaagaaagtatgctgacaaaatctacagtatttcta tgaaacatccacaggaaatgaagacatacagtgtatcatttgattcactttttttctgcagtaaagaattttacagaaattgctt ccaagttcagtgagagactccaggactttgacaaaagcaacccaatagtattaagaatgatgaatgatcaactcatgttt ctggaaagagcatttattgatccattagggttaccagacaggcctttttataggcatgtcatctatgctccaagcagccaca -continued acaagtatgcaggggagtcattcccaggaatttatgatgctctgtttgatattgaaagcaaagtggacccttccaaggcct ggggagaagtgaagagacagatttatgttgcagccttcacagtgcaggcagctgcagagactttgagtgaagtagcc

AMINO ACID SEQUENCE OF THE FULL LENGTH HUMAN PSA.

SEQ ID NO: 15

MASWVPVVFLTLSVTWIGAAPLILSRIVGGWECEKHSQPWQVLVASRGRAVCGGVLV

HPQWVLTAAHCIRNKSVILLGRHSLFHPEDTGQVFQVSHSFPHPLYDMSLLKNRFLRP

GDDSSHDLMLLRLSEPAELTDAVKVMDLPTQEPALGTTCYASGWGSIEPEEFLTPKK

LQCVDLHVISNDVCAQVHPQKVTKFMLCAGRWTGGKSTCSGDSGGPLVCNGVLQGI

TSWGSEPCALPERPSLYTKVVHYRKWIKDTIVANP

NUCLEOTIDE SEQUENCE ENCODING AMINO ACID SEQUENCE OF THE FULL LENGTH HUMAN PSA OF SEQ ID NO: 15.

SEQ ID NO: 16 atggctagctgggtcccggttgtcttcctcaccctgtccgtgacgtggattggcgctgcgcccctcatcctgtctcggattgtg ggaggctgggagtgcgagaagcattcccaaccctggcaggtgcttgtggcctctcgtggcagggcagtctgcggcggt gttctggtgcacccccagtgggtcctcacagctgcccactgcatcaggaacaaaagcgtgatcttgctgggtcggcaca gcttgtttcatcctgaagacacaggccaggtatttcaggtcagccacagcttcccacacccgctctacgatatgagcctcct gaagaatcgattcctcaggccaggtgatgactccagccacgacctcatgctgctccgcctgtcagagcctgccgagctc acggatgctgtgaaggtcatggacctgcccacccaggagccagcactggggaccacctgctacgcctcaggctgggg cagcattgaaccagaggagttcttgaccccaaagaaacttcagtgtgtggacctccatgttatttccaatgacgtgtgtgcg caagttcaccctcagaaggtgaccaagttcatgctgtgtgctggacgctggacagggggcaaaagcacctgctcgggt gattctgggggcccacttgtctgtaatggtgtgcttcaaggtatcacgtcatggggcagtgaaccatgtgccctgcccgaa aggccttccctgtacaccaaggtggtgcattaccggaagtggatcaaggacaccatcgtggccaacccc

AMINO ACID SEQUENCE OF A CYTOSOLIC PSA ANTIGEN.

SEQ ID NO: 17

MASIVGGWECEKHSQPWQVLVASRGRAVCGGVLVHPQWVLTAAHCIRNKSVILLGR

HSLFHPEDTGQVFQVSHSFPHPLYDMSLLKNRFLRPGDDSSHDLMLLRLSEPAELTD

AVKVMDLPTQEPALGTTCYASGWGSIEPEEFLTPKKLQCVDLHVISNDVCAQVHPQK

VTKFMLCAGRWTGGKSTCSGDSGGPLVCNGVLQGITSWGSEPCALPERPSLYTKVV

HYRKWIKDTIVANP

NUCLEOTIDE SEQEUNCE ENCODING AMINO ACID SEQUENCE OF THE CYTOSOLIC PSA ANTIGEN OF SEQ ID NO: 17.

SEQ ID NO: 18 atggctagcattgtgggaggctgggagtgcgagaagcattcccaaccctggcaggtgcttgtggcctctcgtggcaggg cagtctgcggcggtgttctggtgcacccccagtgggtcctcacagctgcccactgcatcaggaacaaaagcgtgatcttg ctgggtcggcacagcttgtttcatcctgaagacacaggccaggtatttcaggtcagccacagcttcccacacccgctctac gatatgagcctcctgaagaatcgattcctcaggccaggtgatgactccagccacgacctcatgctgctccgcctgtcaga gcctgccgagctcacggatgctgtgaaggtcatggacctgcccacccaggagccagcactggggaccacctgctacg cctcaggctggggcagcattgaaccagaggagttcttgaccccaaagaaacttcagtgtgtggacctccatgttatttcca atgacgtgtgtgcgcaagttcaccctcagaaggtgaccaagttcatgctgtgtgctggacgctggacagggggcaaaa gcacctgctcgggtgattctgggggcccacttgtctgtaatggtgtgcttcaaggtatcacgtcatggggcagtgaaccatg tgccctgcccgaaaggccttccctgtacaccaaggtggtgcattaccggaagtggatcaaggacaccatcgtggccaa cccc

AMINO ACID SEQUENCE OF A MEMBRANE-BOUND PSA ANTIGEN.

SEQ ID NO: 19

MASARRPRWLCAGALVLAGGFFLLGFLFGWFIKSSNEATNITPGIVGGWECEKHSQP

WQVLVASRGRAVCGGVLVHPQWVLTAAHCIRNKSVILLGRHSLFHPEDTGQVFQVS

HSFPHPLYDMSLLKNRFLRPGDDSSHDLMLLRLSEPAELTDAVKVMDLPTQEPALGT

-continued

TCYASGWGSIEPEEFLTPKKLQCVDLHVISNDVCAQVHPQKVTKFMLCAGRWTGGK

STCSGDSGGPLVCNGVLQGITSWGSEPCALPERPSLYTKVVHYRKWIKDTIVANP

NUCLEOTIDE SEQUENCE ENCODING AMINO ACID SEQUENCE OF THE MEMBRANE-BOUND PSA ANTIGEN OF SEQ ID NO: 19.

SEQ ID NO: 20 atggctagcgcgcgccgcccgcgctggctgtgcgctggggcgctggtgctggcgggtggcttctttctcctcggcttcctctt cgggtggtttataaaatcctccaatgaagctactaacattactccaggaattgtgggaggctgggagtgcgagaagcatt cccaaccctggcaggtgcttgtggcctctcgtggcagggcagtctgcggcggtgttctggtgcacccccagtgggtcctc acagctgcccactgcatcaggaacaaaagcgtgatcttgctgggtcggcacagcttgtttcatcctgaagacacaggcc aggtatttcaggtcagccacagcttcccacacccgctctacgatatgagcctcctgaagaatcgattcctcaggccaggt gatgactccagccacgacctcatgctgctccgcctgtcagagcctgccgagctcacggatgctgtgaaggtcatggacc tgcccacccaggagccagcactggggaccacctgctacgcctcaggctggggcagcattgaaccagaggagttcttg accccaaagaaacttcagtgtgtggacctccatgttatttccaatgacgtgtgtgcgcaagttcaccctcagaaggtgacc aagttcatgctgtgtgctggacgctggacagggggcaaaagcacctgctcgggtgattctgggggcccacttgtctgtaat ggtgtgcttcaaggtatcacgtcatggggcagtgaaccatgtgccctgcccgaaaggccttccctgtacaccaaggtggt gcattaccggaagtggatcaaggacaccatcgtggccaacccctga

AMINO ACID SEQUENCE OF THE FULL LENGTH HUMAN PSCA.

SEQ ID NO: 21

MASKAVLLALLMAGLALQPGTALLCYSCKAQVSNEDCLQVENCTQLGEQCWTARIRA

VGLLTVISKGCSLNCVDDSQDYYVGKKNITCCDTDLCNASGAHALQPAAAILALLPAL

GLLLWGPGQL

NUCLEOTIDE SEQUENCE ENCODING AMINO ACID SEQUENCE OF THE FULL LENGTH HUMAN PSCA OF SEQ ID NO: 21.

SEQ ID NO: 22 atggctagcaaggctgtgctgcttgccctgttgatggcaggcttggccctgcagccaggcactgccctgctgtgctactcct gcaaagcccaggtgagcaacgaggactgcctgcaggtggagaactgcacccagctgggggagcagtgctggaccg cgcgcatccgcgcagttggcctcctgaccgtcatcagcaaaggctgcagcttgaactgcgtggatgactcacaggacta ctacgtgggcaagaagaacatcacgtgctgtgacaccgacttgtgcaacgccagcggggcccatgccctgcagccgg ctgccgccatccttgcgctgctccctgcactcggcctgctgctctggggacccggccagcta

NUCLEOTIDE SEQUENCE OF PLASMID 5166.

SEQ ID NO: 23

GGCGTAATGCTCTGCCAGTGTTACAACCAATTAACCAATTCTGATTAGAAAAACTC

ATCGAGCATCAAATGAAACTGCAATTTATTCATATCAGGATTATCAATACCATATTT

TTGAAAAAGCCGTTTCTGTAATGAAGGAGAAAACTCACCGAGGCAGTTCCATAGG

ATGGCAAGATCCTGGTATCGGTCTGCGATTCCGACTCGTCCAACATCAATACAAC

CTATTAATTTCCCCTCGTCAAAAATAAGGTTATCAAGTGAGAAATCACCATGAGTG

ACGACTGAATCCGGTGAGAATGGCAAAAGCTTATGCATTTCTTTCCAGACTTGTTC

AACAGGCCAGCCATTACGCTCGTCATCAAAATCACTCGCATCAACCAAACCGTTA

TTCATTCGTGATTGCGCCTGAGCGAGACGAAATACGCGATCGCTGTTAAAAGGAC

AATTACAAACAGGAATCAAATGCAACCGGCGCAGGAACACTGCCAGCGCATCAAC

AATATTTTCACCTGAATCAGGATATTCTTCTAATACCTGGAATGCTGTTTTCCCGG

GGATCGCAGTGGTGAGTAACCATGCATCATCAGGAGTACGGATAAAATGCTTGAT

GGTCGGAAGAGGCATAAATTCCGTCAGCCAGTTTAGTCTGACCATCTCATCTGTA

ACATCATTGGCAACGCTACCTTTGCCATGTTTCAGAAACAACTCTGGCGCATCGG

GCTTCCCATACAATCGATAGATTGTCGCACCTGATTGCCCGACATTATCGCGAGC

CCATTTATACCCATATAAATCAGCATCCATGTTGGAATTTAATCGCGGCCTCGAGC

-continued

AAGACGTTTCCCGTTGAATATGGCTCATAACACCCCTTGTATTACTGTTTATGTAA

GCAGACAGGTCGACAATATTGGCTATTGGCCATTGCATACGTTGTATCTATATCAT

AATATGTACATTTATATTGGCTCATGTCCAATATGACCGCCATGTTGACATTGATTA

TTGACTAGTTATTAATAGTAATCAATTACGGGGTCATTAGTTCATAGCCCATATATG

GAGTTCCGCGTTACATAACTTACGGTAAATGGCCCGCCTGGCTGACCGCCCAAC

GACCCCCGCCCATTGACGTCAATAATGACGTATGTTCCCATAGTAACGCCAATAG

GGACTTTCCATTGACGTCAATGGGTGGAGTATTTACGGTAAACTGCCCACTTGGC

AGTACATCAAGTGTATCATATGCCAAGTCCGCCCCCTATTGACGTCAATGACGGT

AAATGGCCCGCCTGGCATTATGCCCAGTACATGACCTTACGGGACTTTCCTACTT

GGCAGTACATCTACGTATTAGTCATCGCTATTACCATGGTGATGCGGTTTTGGCA

GTACACCAATGGGCGTGGATAGCGGTTTGACTCACGGGGATTTCCAAGTCTCCAC

CCCATTGACGTCAATGGGAGTTTGTTTTGGCACCAAAATCAACGGGACTTTCCAA

AATGTCGTAATAACCCCGCCCCGTTGACGCAAATGGGCGGTAGGCGTGTACGGT

GGGAGGTCTATATAAGCAGAGCTCGTTTAGTGAACCGTCAGATCGCCTGGAGAC

GCCATCCACGCTGTTTTGACCTCCATAGAAGACACCGGGACCGATCCAGCCTCC

GCGGCCGGGAACGGTGCATTGGAACGCGGATTCCCCGTGCCAAGAGTGACTCA

CCGTCCGGATCTCAGCAAGCAGGTATGTACTCTCCAGGGTGGGCCTGGCTTCCC

CAGTCAAGACTCCAGGGATTTGAGGGACGCTGTGGGCTCTTCTCTTACATGTACC

TTTTGCTTGCCTCAACCCTGACTATCTTCCAGGTCAGGATCCCAGAGTCAGGGGT

CTGTATTTTCCTGCTGGTGGCTCCAGTTCAGGAACAGTAAACCCTGCTCCGAATA

TTGCCTCTCACATCTCGTCAATCTCCGCGAGGACTGGGGACCCTGTGACGAACAT

GGCTAGCGCGCGCCGCCCGCGCTGGCTGTGCGCTGGGGCGCTGGTGCTGGCG

GGTGGCTTCTTTCTCCTCGGCTTCCTCTTCGGGTGGTTTATAAAATCCTCCAATGA

AGCTACTAACATTACTCCAAAGCATAATATGAAAGCATTTTTGGATGAATTGAAAG

CTGAGAACATCAAGAAGTTCTTATATAATTTTACACAGATACCACATTTAGCAGGA

ACAGAACAAAACTTTCAGCTTGCAAAGCAAATTCAATCCCAGTGGAAAGAATTTGG

CCTGGATTCTGTTGAGCTGGCACATTATGATGTCCTGTTGTCCTACCCAAATAAGA

CTCATCCCAACTACATCTCAATAATTAATGAAGATGGAAATGAGATTTTCAACACAT

CATTATTTGAACCACCTCCTCCAGGATATGAAAATGTTTCGGATATTGTACCACCT

TTCAGTGCTTTCTCTCCTCAAGGAATGCCAGAGGGCGATCTAGTGTATGTTAACTA

TGCACGAACTGAAGACTTCTTTAAATTGGAACGGGACATGAAAATCAATTGCTCTG

GGAAAATTGTAATTGCCAGATATGGGAAAGTTTTCAGAGGAAATAAGGTTAAAAAT

GCCCAGCTGGCAGGGGCCAAAGGAGTCATTCTCTACTCCGACCCTGCTGACTAC

TTTGCTCCTGGGGTGAAGTCCTATCCAGATGGTTGGAATCTTCCTGGAGGTGGTG

TCCAGCGTGGAAATATCCTAAATCTGAATGGTGCAGGAGACCCTCTCACACCAGG

TTACCCAGCAAATGAATATGCTTATAGGCGTGGAATTGCAGAGGCTGTTGGTCTT

CCAAGTATTCCTGTTCATCCAATTGGATACTATGATGCACAGAAGCTCCTAGAAAA

AATGGGTGGCTCAGCACCACCAGATAGCAGCTGGAGAGGAAGTCTCAAAGTGCC

CTACAATGTTGGACCTGGCTTTACTGGAAACTTTTCTACACAAAAAGTCAAGATGC

ACATCCACTCTACCAATGAAGTGACAAGAATTTACAATGTGATAGGTACTCTCAGA

GGAGCAGTGGAACCAGACAGATATGTCATTCTGGGAGGTCACCGGGACTCATGG

-continued

GTGTTTGGTGGTATTGACCCTCAGAGTGGAGCAGCTGTTGTTCATGAAATTGTGA

GGAGCTTTGGAACACTGAAAAAGGAAGGGTGGAGACCTAGAAGAACAATTTTGTT

TGCAAGCTGGGATGCAGAAGAATTTGGTCTTCTTGGTTCTACTGAGTGGGCAGAG

GAGAATTCAAGACTCCTTCAAGAGCGTGGCGTGGCTTATATTAATGCTGACTCAT

CTATAGAAGGAAACTACACTCTGAGAGTTGATTGTACACCGCTGATGTACAGCTT

GGTACACAACCTAACAAAAGAGCTGAAAAGCCCTGATGAAGGCTTTGAAGGCAAA

TCTCTTTATGAAAGTTGGACTAAAAAAAGTCCTTCCCCAGAGTTCAGTGGCATGCC

CAGGATAAGCAAATTGGGATCTGGAAATGATTTTGAGGTGTTCTTCCAACGACTTG

GAATTGCTTCAGGCAGAGCACGGTATACTAAAAATTGGGAAACAAACAAATTCAG

CGGCTATCCACTGTATCACAGTGTCTATGAAACATATGAGTTGGTGGAAAAGTTTT

ATGATCCAATGTTTAAATATCACCTCACTGTGGCCCAGGTTCGAGGAGGGATGGT

GTTTGAGCTGGCCAATTCCATAGTGCTCCCTTTTGATTGTCGAGATTATGCTGTAG

TTTTAAGAAAGTATGCTGACAAAATCTACAGTATTTCTATGAAACATCCACAGGAAA

TGAAGACATACAGTGTATCATTTGATTCACTTTTTTCTGCAGTAAAGAATTTTACAG

AAATTGCTTCCAAGTTCAGTGAGAGACTCCAGGACTTTGACAAAAGCAACCCAATA

GTATTAAGAATGATGAATGATCAACTCATGTTTCTGGAAAGAGCATTTATTGATCC

ATTAGGGTTACCAGACAGGCCTTTTTATAGGCATGTCATCTATGCTCCAAGCAGC

CACAACAAGTATGCAGGGGAGTCATTCCCAGGAATTTATGATGCTCTGTTTGATAT

TGAAAGCAAAGTGGACCCTTCCAAGGCCTGGGGAGAAGTGAAGAGACAGATTTAT

GTTGCAGCCTTCACAGTGCAGGCAGCTGCAGAGACTTTGAGTGAAGTAGCCTAAA

GATCTGGGCCCTAACAAAACAAAAAGATGGGGTTATTCCCTAAACTTCATGGGTTA

CGTAATTGGAAGTTGGGGGACATTGCCACAAGATCATATTGTACAAAAGATCAAA

CACTGTTTTAGAAAACTTCCTGTAAACAGGCCTATTGATTGGAAAGTATGTCAAAG

GATTGTGGGTCTTTTGGGCTTTGCTGCTCCATTTACACAATGTGGATATCCTGCCT

TAATGCCTTTGTATGCATGTATACAAGCTAAACAGGCTTTCACTTTCTCGCCAACT

TACAAGGCCTTTCTAAGTAAACAGTACATGAACCTTTACCCCGTTGCTCGGCAAC

GGCCTGGTCTGTGCCAAGTGTTTGCTGACGCAACCCCCACTGGCTGGGGCTTGG

CCATAGGCCATCAGCGCATGCGTGGAACCTTTGTGGCTCCTCTGCCGATCCATAC

TGCGGAACTCCTAGCCGCTTGTTTTGCTCGCAGCCGGTCTGGAGCAAAGCTCATA

GGAACTGACAATTCTGTCGTCCTCTCGCGGAAATATACATCGTTTCGATCTACGTA

TGATCTTTTTCCCTCTGCCAAAAATTATGGGGACATCATGAAGCCCCTTGAGCATC

TGACTTCTGGCTAATAAAGGAAATTTATTTTCATTGCAATAGTGTGTTGGAATTTTT

TGTGTCTCTCACTCGGAAGGAATTCTGCATTAATGAATCGGCCAACGCGCGGGGA

GAGGCGGTTTGCGTATTGGGCGCTCTTCCGCTTCCTCGCTCACTGACTCGCTGC

GCTCGGTCGTTCGGCTGCGGCGAGCGGTATCAGCTCACTCAAAGGCGGTAATAC

GGTTATCCACAGAATCAGGGGATAACGCAGGAAAGAACATGTGAGCAAAAGGCC

AGCAAAAGGCCAGGAACCGTAAAAAGGCCGCGTTGCTGGCGTTTTTCCATAGGC

TCCGCCCCCCTGACGAGCATCACAAAAATCGACGCTCAAGTCAGAGGTGGCGAA

ACCCGACAGGACTATAAAGATACCAGGCGTTTCCCCCTGGAAGCTCCCTCGTGC

GCTCTCCTGTTCCGACCCTGCCGCTTACCGGATACCTGTCCGCCTTTCTCCCTTC

GGGAAGCGTGGCGCTTTCTCATAGCTCACGCTGTAGGTATCTCAGTTCGGTGTAG

-continued

GTCGTTCGCTCCAAGCTGGGCTGTGTGCACGAACCCCCCGTTCAGCCCGACCGC

TGCGCCTTATCCGGTAACTATCGTCTTGAGTCCAACCCGGTAAGACACGACTTAT

CGCCACTGGCAGCAGCCACTGGTAACAGGATTAGCAGAGCGAGGTATGTAGGCG

GTGCTACAGAGTTCTTGAAGTGGTGGCCTAACTACGGCTACACTAGAAGAACAGT

ATTTGGTATCTGCGCTCTGCTGAAGCCAGTTACCTTCGGAAAAAGAGTTGGTAGC

TCTTGATCCGGCAAACAAACCACCGCTGGTAGCGGTGGTTTTTTTGTTTGCAAGC

AGCAGATTACGCGCAGAAAAAAAGGATCTCAAGAAGATCCTTTGATCTTTTCTACG

GGGTCTGACGCTCAGTGGAACGAAAACTCACGTTAAGGGATTTTGGTCATGAGAT

TATCAAAAAGGATCTTCACCTAGATCCTTTTAAATTAAAAATGAAGTTTTAAATCAA

TCTAAAGTATATATGAGTAAACTTGGTCTGACAGTTACCAATGCTTAATCAGTGAG

GCACCTATCTCAGCGATCTGTCTATTTCGTTCATCCATAGTTGCCTGACTC

NUCLEOTIDE SEQUENCE OF PLASMID 5259.

SEQ ID NO: 24

GGCGTAATGCTCTGCCAGTGTTACAACCAATTAACCAATTCTGATTAGAAAAACTC

ATCGAGCATCAAATGAAACTGCAATTTATTCATATCAGGATTATCAATACCATATTT

TTGAAAAAGCCGTTTCTGTAATGAAGGAGAAAACTCACCGAGGCAGTTCCATAGG

ATGGCAAGATCCTGGTATCGGTCTGCGATTCCGACTCGTCCAACATCAATACAAC

CTATTAATTTCCCCTCGTCAAAAATAAGGTTATCAAGTGAGAAATCACCATGAGTG

ACGACTGAATCCGGTGAGAATGGCAAAAGCTTATGCATTTCTTTCCAGACTTGTTC

AACAGGCCAGCCATTACGCTCGTCATCAAAATCACTCGCATCAACCAAACCGTTA

TTCATTCGTGATTGCGCCTGAGCGAGACGAAATACGCGATCGCTGTTAAAAGGAC

AATTACAAACAGGAATCAAATGCAACCGGCGCAGGAACACTGCCAGCGCATCAAC

AATATTTTCACCTGAATCAGGATATTCTTCTAATACCTGGAATGCTGTTTTCCCGG

GGATCGCAGTGGTGAGTAACCATGCATCATCAGGAGTACGGATAAAATGCTTGAT

GGTCGGAAGAGGCATAAATTCCGTCAGCCAGTTTAGTCTGACCATCTCATCTGTA

ACATCATTGGCAACGCTACCTTTGCCATGTTTCAGAAACAACTCTGGCGCATCGG

GCTTCCCATACAATCGATAGATTGTCGCACCTGATTGCCCGACATTATCGCGAGC

CCATTTATACCCATATAAATCAGCATCCATGTTGGAATTTAATCGCGGCCTCGAGC

AAGACGTTTCCCGTTGAATATGGCTCATAACACCCCTTGTATTACTGTTTATGTAA

GCAGACAGGTCGACAATATTGGCTATTGGCCATTGCATACGTTGTATCTATATCAT

AATATGTACATTTATATTGGCTCATGTCCAATATGACCGCCATGTTGACATTGATTA

TTGACTAGTTATTAATAGTAATCAATTACGGGGTCATTAGTTCATAGCCCATATATG

GAGTTCCGCGTTACATAACTTACGGTAAATGGCCCGCCTGGCTGACCGCCCAAC

GACCCCCGCCCATTGACGTCAATAATGACGTATGTTCCCATAGTAACGCCAATAG

GGACTTTCCATTGACGTCAATGGGTGGAGTATTTACGGTAAACTGCCCACTTGGC

AGTACATCAAGTGTATCATATGCCAAGTCCGCCCCCTATTGACGTCAATGACGGT

AAATGGCCCGCCTGGCATTATGCCCAGTACATGACCTTACGGGACTTTCCTACTT

GGCAGTACATCTACGTATTAGTCATCGCTATTACCATGGTGATGCGGTTTTGGCA

GTACACCAATGGGCGTGGATAGCGGTTTGACTCACGGGGATTTCCAAGTCTCCAC

CCCATTGACGTCAATGGGAGTTTGTTTTGGCACCAAAATCAACGGGACTTTCCAA

AATGTCGTAATAACCCCGCCCCGTTGACGCAAATGGGCGGTAGGCGTGTACGGT

GGGAGGTCTATATAAGCAGAGCTCGTTTAGTGAACCGTCAGATCGCCTGGAGAC

-continued

GCCATCCACGCTGTTTTGACCTCCATAGAAGACACCGGGACCGATCCAGCCTCC

GCGGCCGGGAACGGTGCATTGGAACGCGGATTCCCCGTGCCAAGAGTGACTCA

CCGTCCGGATCTCAGCAAGCAGGTATGTACTCTCCAGGGTGGGCCTGGCTTCCC

CAGTCAAGACTCCAGGGATTTGAGGGACGCTGTGGGCTCTTCTCTTACATGTACC

TTTTGCTTGCCTCAACCCTGACTATCTTCCAGGTCAGGATCCCAGAGTCAGGGGT

CTGTATTTTCCTGCTGGTGGCTCCAGTTCAGGAACAGTAAACCCTGCTCCGAATA

TTGCCTCTCACATCTCGTCAATCTCCGCGAGGACTGGGGACCCTGTGACGAACAT

GGCTAGCAAGGCTGTGCTGCTTGCCCTGTTGATGGCAGGCTTGGCCCTGCAGCC

AGGCACTGCCCTGCTGTGCTACTCCTGCAAAGCCCAGGTGAGCAACGAGGACTG

CCTGCAGGTGGAGAACTGCACCCAGCTGGGGGAGCAGTGCTGGACCGCGCGCA

TCCGCGCAGTTGGCCTCCTGACCGTCATCAGCAAAGGCTGCAGCTTGAACTGCG

TGGATGACTCACAGGACTACTACGTGGGCAAGAAGAACATCACGTGCTGTGACAC

CGACTTGTGCAACGCCAGCGGGGCCCATGCCCTGCAGCCGGCTGCCGCCATCC

TTGCGCTGCTCCCTGCACTCGGCCTGCTGCTCTGGGGACCCGGCCAGCTATAGA

GATCTGGGCCCTAACAAAACAAAAAGATGGGGTTATTCCCTAAACTTCATGGGTTA

CGTAATTGGAAGTTGGGGGACATTGCCACAAGATCATATTGTACAAAAGATCAAA

CACTGTTTTAGAAAACTTCCTGTAAACAGGCCTATTGATTGGAAAGTATGTCAAAG

GATTGTGGGTCTTTTGGGCTTTGCTGCTCCATTTACACAATGTGGATATCCTGCCT

TAATGCCTTTGTATGCATGTATACAAGCTAAACAGGCTTTCACTTTCTCGCCAACT

TACAAGGCCTTTCTAAGTAAACAGTACATGAACCTTTACCCCGTTGCTCGGCAAC

GGCCTGGTCTGTGCCAAGTGTTTGCTGACGCAACCCCCACTGGCTGGGGCTTGG

CCATAGGCCATCAGCGCATGCGTGGAACCTTTGTGGCTCCTCTGCCGATCCATAC

TGCGGAACTCCTAGCCGCTTGTTTTGCTCGCAGCCGGTCTGGAGCAAAGCTCATA

GGAACTGACAATTCTGTCGTCCTCTCGCGGAAATATACATCGTTTCGATCTACGTA

TGATCTTTTTCCCTCTGCCAAAAATTATGGGGACATCATGAAGCCCCTTGAGCATC

TGACTTCTGGCTAATAAAGGAAATTTATTTTCATTGCAATAGTGTGTTGGAATTTTT

TGTGTCTCTCACTCGGAAGGAATTCTGCATTAATGAATCGGCCAACGCGCGGGGA

GAGGCGGTTTGCGTATTGGGCGCTCTTCCGCTTCCTCGCTCACTGACTCGCTGC

GCTCGGTCGTTCGGCTGCGGCGAGCGGTATCAGCTCACTCAAAGGCGGTAATAC

GGTTATCCACAGAATCAGGGGATAACGCAGGAAAGAACATGTGAGCAAAAGGCC

AGCAAAAGGCCAGGAACCGTAAAAAGGCCGCGTTGCTGGCGTTTTTCCATAGGC

TCCGCCCCCCTGACGAGCATCACAAAAATCGACGCTCAAGTCAGAGGTGGCGAA

ACCCGACAGGACTATAAAGATACCAGGCGTTTCCCCCTGGAAGCTCCCTCGTGC

GCTCTCCTGTTCCGACCCTGCCGCTTACCGGATACCTGTCCGCCTTTCTCCCTTC

GGGAAGCGTGGCGCTTTCTCATAGCTCACGCTGTAGGTATCTCAGTTCGGTGTAG

GTCGTTCGCTCCAAGCTGGGCTGTGTGCACGAACCCCCCGTTCAGCCCGACCGC

TGCGCCTTATCCGGTAACTATCGTCTTGAGTCCAACCCGGTAAGACACGACTTAT

CGCCACTGGCAGCAGCCACTGGTAACAGGATTAGCAGAGCGAGGTATGTAGGCG

GTGCTACAGAGTTCTTGAAGTGGTGGCCTAACTACGGCTACACTAGAAGAACAGT

ATTTGGTATCTGCGCTCTGCTGAAGCCAGTTACCTTCGGAAAAAGAGTTGGTAGC

TCTTGATCCGGCAAACAAACCACCGCTGGTAGCGGTGGTTTTTTTGTTTGCAAGC

-continued

AGCAGATTACGCGCAGAAAAAAAGGATCTCAAGAAGATCCTTTGATCTTTTCTACG

GGGTCTGACGCTCAGTGGAACGAAAACTCACGTTAAGGGATTTTGGTCATGAGAT

TATCAAAAAGGATCTTCACCTAGATCCTTTTAAATTAAAAATGAAGTTTTAAATCAA

TCTAAAGTATATATGAGTAAACTTGGTCTGACAGTTACCAATGCTTAATCAGTGAG

GCACCTATCTCAGCGATCTGTCTATTTCGTTCATCCATAGTTGCCTGACTC

NUCLEOTIDE SEQUENCE OF PLASMID 5297.

SEQ ID NO: 25

GGCGTAATGCTCTGCCAGTGTTACAACCAATTAACCAATTCTGATTAGAAAAACTC

ATCGAGCATCAAATGAAACTGCAATTTATTCATATCAGGATTATCAATACCATATTT

TTGAAAAAGCCGTTTCTGTAATGAAGGAGAAAACTCACCGAGGCAGTTCCATAGG

ATGGCAAGATCCTGGTATCGGTCTGCGATTCCGACTCGTCCAACATCAATACAAC

CTATTAATTTCCCCTCGTCAAAAATAAGGTTATCAAGTGAGAAATCACCATGAGTG

ACGACTGAATCCGGTGAGAATGGCAAAAGCTTATGCATTTCTTTCCAGACTTGTTC

AACAGGCCAGCCATTACGCTCGTCATCAAAATCACTCGCATCAACCAAACCGTTA

TTCATTCGTGATTGCGCCTGAGCGAGACGAAATACGCGATCGCTGTTAAAAGGAC

AATTACAAACAGGAATCAAATGCAACCGGCGCAGGAACACTGCCAGCGCATCAAC

AATATTTTCACCTGAATCAGGATATTCTTCTAATACCTGGAATGCTGTTTTCCCGG

GGATCGCAGTGGTGAGTAACCATGCATCATCAGGAGTACGGATAAAATGCTTGAT

GGTCGGAAGAGGCATAAATTCCGTCAGCCAGTTTAGTCTGACCATCTCATCTGTA

ACATCATTGGCAACGCTACCTTTGCCATGTTTCAGAAACAACTCTGGCGCATCGG

GCTTCCCATACAATCGATAGATTGTCGCACCTGATTGCCCGACATTATCGCGAGC

CCATTTATACCCATATAAATCAGCATCCATGTTGGAATTTAATCGCGGCCTCGAGC

AAGACGTTTCCCGTTGAATATGGCTCATAACACCCCTTGTATTACTGTTTATGTAA

GCAGACAGGTCGACAATATTGGCTATTGGCCATTGCATACGTTGTATCTATATCAT

AATATGTACATTTATATTGGCTCATGTCCAATATGACCGCCATGTTGACATTGATTA

TTGACTAGTTATTAATAGTAATCAATTACGGGGTCATTAGTTCATAGCCCATATATG

GAGTTCCGCGTTACATAACTTACGGTAAATGGCCCGCCTGGCTGACCGCCCAAC

GACCCCCGCCCATTGACGTCAATAATGACGTATGTTCCCATAGTAACGCCAATAG

GGACTTTCCATTGACGTCAATGGGTGGAGTATTTACGGTAAACTGCCCACTTGGC

AGTACATCAAGTGTATCATATGCCAAGTCCGCCCCCTATTGACGTCAATGACGGT

AAATGGCCCGCCTGGCATTATGCCCAGTACATGACCTTACGGGACTTTCCTACTT

GGCAGTACATCTACGTATTAGTCATCGCTATTACCATGGTGATGCGGTTTTGGCA

GTACACCAATGGGCGTGGATAGCGGTTTGACTCACGGGGATTTCCAAGTCTCCAC

CCCATTGACGTCAATGGGAGTTTGTTTTGGCACCAAAATCAACGGGACTTTCCAA

AATGTCGTAATAACCCCGCCCCGTTGACGCAAATGGGCGGTAGGCGTGTACGGT

GGGAGGTCTATATAAGCAGAGCTCGTTTAGTGAACCGTCAGATCGCCTGGAGAC

GCCATCCACGCTGTTTTGACCTCCATAGAAGACACCGGGACCGATCCAGCCTCC

GCGGCCGGGAACGGTGCATTGGAACGCGGATTCCCCGTGCCAAGAGTGACTCA

CCGTCCGGATCTCAGCAAGCAGGTATGTACTCTCCAGGGTGGGCCTGGCTTCCC

CAGTCAAGACTCCAGGGATTTGAGGGACGCTGTGGGCTCTTCTCTTACATGTACC

TTTTGCTTGCCTCAACCCTGACTATCTTCCAGGTCAGGATCCCAGAGTCAGGGGT

CTGTATTTTCCTGCTGGTGGCTCCAGTTCAGGAACAGTAAACCCTGCTCCGAATA

-continued

TTGCCTCTCACATCTCGTCAATCTCCGCGAGGACTGGGGACCCTGTGACGAACAT

GGCTAGCATTGTGGGAGGCTGGGAGTGCGAGAAGCATTCCCAACCCTGGCAGGT

GCTTGTGGCCTCTCGTGGCAGGGCAGTCTGCGGCGGTGTTCTGGTGCACCCCCA

GTGGGTCCTCACAGCTGCCCACTGCATCAGGAACAAAAGCGTGATCTTGCTGGG

TCGGCACAGCTTGTTTCATCCTGAAGACACAGGCCAGGTATTTCAGGTCAGCCAC

AGCTTCCCACACCCGCTCTACGATATGAGCCTCCTGAAGAATCGATTCCTCAGGC

CAGGTGATGACTCCAGCCACGACCTCATGCTGCTCCGCCTGTCAGAGCCTGCCG

AGCTCACGGATGCTGTGAAGGTCATGGACCTGCCCACCCAGGAGCCAGCACTGG

GGACCACCTGCTACGCCTCAGGCTGGGGCAGCATTGAACCAGAGGAGTTCTTGA

CCCCAAAGAAACTTCAGTGTGTGGACCTCCATGTTATTTCCAATGACGTGTGTGC

GCAAGTTCACCCTCAGAAGGTGACCAAGTTCATGCTGTGTGCTGGACGCTGGAC

AGGGGGCAAAAGCACCTGCTCGGGTGATTCTGGGGGCCCACTTGTCTGTAATGG

TGTGCTTCAAGGTATCACGTCATGGGGCAGTGAACCATGTGCCCTGCCCGAAAG

GCCTTCCCTGTACACCAAGGTGGTGCATTACCGGAAGTGGATCAAGGACACCATC

GTGGCCAACCCCTGAAGATCTGGGCCCTAACAAAACAAAAAGATGGGGTTATTCC

CTAAACTTCATGGGTTACGTAATTGGAAGTTGGGGGACATTGCCACAAGATCATAT

TGTACAAAAGATCAAACACTGTTTTAGAAAACTTCCTGTAAACAGGCCTATTGATT

GGAAAGTATGTCAAAGGATTGTGGGTCTTTTGGGCTTTGCTGCTCCATTTACACAA

TGTGGATATCCTGCCTTAATGCCTTTGTATGCATGTATACAAGCTAAACAGGCTTT

CACTTTCTCGCCAACTTACAAGGCCTTTCTAAGTAAACAGTACATGAACCTTTACC

CCGTTGCTCGGCAACGGCCTGGTCTGTGCCAAGTGTTTGCTGACGCAACCCCCA

CTGGCTGGGGCTTGGCCATAGGCCATCAGCGCATGCGTGGAACCTTTGTGGCTC

CTCTGCCGATCCATACTGCGGAACTCCTAGCCGCTTGTTTTGCTCGCAGCCGGTC

TGGAGCAAAGCTCATAGGAACTGACAATTCTGTCGTCCTCTCGCGGAAATATACA

TCGTTTCGATCTACGTATGATCTTTTTCCCTCTGCCAAAAATTATGGGGACATCAT

GAAGCCCCTTGAGCATCTGACTTCTGGCTAATAAAGGAAATTTATTTTCATTGCAA

TAGTGTGTTGGAATTTTTTGTGTCTCTCACTCGGAAGGAATTCTGCATTAATGAAT

CGGCCAACGCGCGGGGAGAGGCGGTTTGCGTATTGGGCGCTCTTCCGCTTCCTC

GCTCACTGACTCGCTGCGCTCGGTCGTTCGGCTGCGGCGAGCGGTATCAGCTCA

CTCAAAGGCGGTAATACGGTTATCCACAGAATCAGGGGATAACGCAGGAAAGAAC

ATGTGAGCAAAAGGCCAGCAAAAGGCCAGGAACCGTAAAAAGGCCGCGTTGCTG

GCGTTTTTCCATAGGCTCCGCCCCCCTGACGAGCATCACAAAAATCGACGCTCAA

GTCAGAGGTGGCGAAACCCGACAGGACTATAAAGATACCAGGCGTTTCCCCCTG

GAAGCTCCCTCGTGCGCTCTCCTGTTCCGACCCTGCCGCTTACCGGATACCTGTC

CGCCTTTCTCCCTTCGGGAAGCGTGGCGCTTTCTCATAGCTCACGCTGTAGGTAT

CTCAGTTCGGTGTAGGTCGTTCGCTCCAAGCTGGGCTGTGTGCACGAACCCCCC

GTTCAGCCCGACCGCTGCGCCTTATCCGGTAACTATCGTCTTGAGTCCAACCCGG

TAAGACACGACTTATCGCCACTGGCAGCAGCCACTGGTAACAGGATTAGCAGAG

CGAGGTATGTAGGCGGTGCTACAGAGTTCTTGAAGTGGTGGCCTAACTACGGCT

ACACTAGAAGAACAGTATTTGGTATCTGCGCTCTGCTGAAGCCAGTTACCTTCGG

AAAAAGAGTTGGTAGCTCTTGATCCGGCAAACAAACCACCGCTGGTAGCGGTGGT

-continued

TTTTTTGTTTGCAAGCAGCAGATTACGCGCAGAAAAAAAGGATCTCAAGAAGATCC

TTTGATCTTTTCTACGGGGTCTGACGCTCAGTGGAACGAAAACTCACGTTAAGGG

ATTTTGGTCATGAGATTATCAAAAAGGATCTTCACCTAGATCCTTTTAAATTAAAAA

TGAAGTTTTAAATCAATCTAAAGTATATATGAGTAAACTTGGTCTGACAGTTACCAA

TGCTTAATCAGTGAGGCACCTATCTCAGCGATCTGTCTATTTCGTTCATCCATAGT

TGCCTGACTC

NUCLEOTIDE SEQUENCE OF PLASMID 460.

SEQ ID NO: 26

GAATTCTGCATTAATGAATCGGCCAACGCGCGGGGAGAGGCGGTTTGCGTATTG

GGCGCTCTTCCGCTTCCTCGCTCACTGACTCGCTGCGCTCGGTCGTTCGGCTGC

GGCGAGCGGTATCAGCTCACTCAAAGGCGGTAATACGGTTATCCACAGAATCAG

GGGATAACGCAGGAAAGAACATGTGAGCAAAAGGCCAGCAAAAGGCCAGGAACC

GTAAAAAGGCCGCGTTGCTGGCGTTTTTCCATAGGCTCCGCCCCCCTGACGAGC

ATCACAAAAATCGACGCTCAAGTCAGAGGTGGCGAAACCCGACAGGACTATAAAG

ATACCAGGCGTTTCCCCCTGGAAGCTCCCTCGTGCGCTCTCCTGTTCCGACCCTG

CCGCTTACCGGATACCTGTCCGCCTTTCTCCCTTCGGGAAGCGTGGCGCTTTCTC

ATAGCTCACGCTGTAGGTATCTCAGTTCGGTGTAGGTCGTTCGCTCCAAGCTGGG

CTGTGTGCACGAACCCCCCGTTCAGCCCGACCGCTGCGCCTTATCCGGTAACTA

TCGTCTTGAGTCCAACCCGGTAAGACACGACTTATCGCCACTGGCAGCAGCCACT

GGTAACAGGATTAGCAGAGCGAGGTATGTAGGCGGTGCTACAGAGTTCTTGAAG

TGGTGGCCTAACTACGGCTACACTAGAAGAACAGTATTTGGTATCTGCGCTCTGC

TGAAGCCAGTTACCTTCGGAAAAAGAGTTGGTAGCTCTTGATCCGGCAAACAAAC

CACCGCTGGTAGCGGTGGTTTTTTTGTTTGCAAGCAGCAGATTACGCGCAGAAAA

AAAGGATCTCAAGAAGATCCTTTGATCTTTTCTACGGGGTCTGACGCTCAGTGGA

ACGAAAACTCACGTTAAGGGATTTTGGTCATGAGATTATCAAAAAGGATCTTCACC

TAGATCCTTTTAAATTAAAAATGAAGTTTTAAATCAATCTAAAGTATATATGAGTAAA

CTTGGTCTGACAGTTACCAATGCTTAATCAGTGAGGCACCTATCTCAGCGATCTGT

CTATTTCGTTCATCCATAGTTGCCTGACTCGGCGTAATGCTCTGCCAGTGTTACAA

CCAATTAACCAATTCTGATTAGAAAAACTCATCGAGCATCAAATGAAACTGCAATTT

ATTCATATCAGGATTATCAATACCATATTTTTGAAAAAGCCGTTTCTGTAATGAAGG

AGAAAACTCACCGAGGCAGTTCCATAGGATGGCAAGATCCTGGTATCGGTCTGC

GATTCCGACTCGTCCAACATCAATACAACCTATTAATTTCCCCTCGTCAAAAATAA

GGTTATCAAGTGAGAAATCACCATGAGTGACGACTGAATCCGGTGAGAATGGCAA

AAGCTTATGCATTTCTTTCCAGACTTGTTCAACAGGCCAGCCATTACGCTCGTCAT

CAAAATCACTCGCATCAACCAAACCGTTATTCATTCGTGATTGCGCCTGAGCGAG

ACGAAATACGCGATCGCTGTTAAAAGGACAATTACAAACAGGAATCAAATGCAAC

CGGCGCAGGAACACTGCCAGCGCATCAACAATATTTTCACCTGAATCAGGATATT

CTTCTAATACCTGGAATGCTGTTTTCCCGGGGATCGCAGTGGTGAGTAACCATGC

ATCATCAGGAGTACGGATAAAATGCTTGATGGTCGGAAGAGGCATAAATTCCGTC

AGCCAGTTTAGTCTGACCATCTCATCTGTAACATCATTGGCAACGCTACCTTTGCC

ATGTTTCAGAAACAACTCTGGCGCATCGGGCTTCCCATACAATCGATAGATTGTC

GCACCTGATTGCCCGACATTATCGCGAGCCCATTTATACCCATATAAATCAGCATC

-continued

CATGTTGGAATTTAATCGCGGCCTCGAGCAAGACGTTTCCCGTTGAATATGGCTC

ATAACACCCCTTGTATTACTGTTTATGTAAGCAGACAGGGTACCAATCTTCCGAGT

GAGAGACACAAAAAATTCCAACACACTATTGCAATGAAAATAAATTTCCTTTATTAG

CCAGAAGTCAGATGCTCAAGGGGCTTCATGATGTCCCCATAATTTTTGGCAGAGG

GAAAAAGATCATACGTAGATCGAAACGATGTATATTTCCGCGAGAGGACGACAGA

ATTGTCAGTTCCTATGAGCTTTGCTCCAGACCGGCTGCGAGCAAAACAAGCGGCT

AGGAGTTCCGCAGTATGGATCGGCAGAGGAGCCACAAAGGTTCCACGCATGCGC

TGATGGCCTATGGCCAAGCCCCAGCCAGTGGGGGTTGCGTCAGCAAACACTTGG

CACAGACCAGGCCGTTGCCGAGCAACGGGGTAAAGGTTCATGTACTGTTTACTTA

GAAAGGCCTTGTAAGTTGGCGAGAAAGTGAAAGCCTGTTTAGCTTGTATACATGC

ATACAAAGGCATTAAGGCAGGATATCCACATTGTGTAAATGGAGCAGCAAAGCCC

AAAAGACCCACAATCCTTTGACATACTTTCCAATCAATAGGCCTGTTTACAGGAAG

TTTTCTAAAACAGTGTTTGATCTTTTGTACAATATGATCTTGTGGCAATGTCCCCCA

ACTTCCAATTACGTAACCCATGAAGTTTAGGGAATAACCCCATCTTTTTGTTTTGTT

AGGGCCCAGATCTTTAGGCTACTTCACTCAAAGTCTCTGCAGCTGCCTGCACTGT

GAAGGCTGCAACATAAATCTGTCTCTTCACTTCTCCCCAGGCCTTGGAAGGGTCC

ACTTTGCTTTCAATATCAAACAGAGCATCATAAATTCCTGGGAATGACTCCCCTGC

ATACTTGTTGTGGCTGCTTGGAGCATAGATGACATGCCTATAAAAAGGCCTGTCT

GGTAACCCTAATGGATCAATAAATGCTCTTTCCAGAAACATGAGTTGATCATTCAT

CATTCTTAATACTATTGGGTTGCTTTTGTCAAAGTCCTGGAGTCTCTCACTGAACTT

GGAAGCAATTTCTGTAAAATTCTTTACTGCAGAAAAAAGTGAATCAAATGATACAC

TGTATGTCTTCATTTCCTGTGGATGTTTCATAGAAATACTGTAGATTTTGTCAGCAT

ACTTTCTTAAAACTACAGCATAATCTCGACAATCAAAAGGGAGCACTATGGAATTG

GCCAGCTCAAACACCATCCCTCCTCGAACCTGGGCCACAGTGAGGTGATATTTAA

ACATTGGATCATAAAACTTTTCCACCAACTCATATGTTTCATAGACACTGTGATACA

GTGGATAGCCGCTGAATTTGTTTGTTTCCCAATTTTTAGTATACCGTGCTCTGCCT

GAAGCAATTCCAAGTCGTTGGAAGAACACCTCAAAATCATTTCCAGATCCCAATTT

GCTTATCCTGGGCATGCCACTGAACTCTGGGGAAGGACTTTTTTTAGTCCAACTTT

CATAAAGAGATTTGCCTTCAAAGCCTTCATCAGGGCTTTTCAGCTCTTTTGTTAGG

TTGTGTACCAAGCTGTACATCAGCGGTGTACAATCAACTCTCAGAGTGTAGTTTCC

TTCTATAGATGAGTCAGCATTAATATAAGCCACGCCACGCTCTTGAAGGAGTCTTG

AATTCTCCTCTGCCCACTCAGTAGAACCAAGAAGACCAAATTCTTCTGCATCCCAG

CTTGCAAACAAAATTGTTCTTCTAGGTCTCCACCCTTCCTTTTTCAGTGTTCCAAAG

CTCCTCACAATTTCATGAACAACAGCTGCTCCACTCTGAGGGTCAATACCACCAAA

CACCCATGAGTCCCGGTGACCTCCCAGAATGACATATCTGTCTGGTTCCACTGCT

CCTCTGAGAGTACCTATCACATTGTAAATTCTTGTCACTTCATTGGTAGAGTGGAT

GTGCATCTTGACTTTTTGTGTAGAAAAGTTTCCAGTAAAGCCAGGTCCAACATTGT

AGGGCACTTTGAGACTTCCTCTCCAGCTGCTATCTGGTGGTGCTGAGCCACCCAT

TTTTTCTAGGAGCTTCTGTGCATCATAGTATCCAATTGGATGAACAGGAATACTTG

GAAGACCAACAGCCTCTGCAATTCCACGCCTATAAGCATATTCATTTGCTGGGTAA

CCTGGTGTGAGAGGGTCTCCTGCACCATTCAGATTTAGGATATTTCCACGCTGGA

-continued

CACCACCTCCAGGAAGATTCCAACCATCTGGATAGGACTTCACCCCAGGAGCAAA

GTAGTCAGCAGGGTCGGAGTAGAGAATGACTCCTTTGGCCCCTGCCAGCTGGGC

ATTTTTAACCTTATTTCCTCTGAAAACTTTCCCATATCTGGCAATTACAATTTTCCCA

GAGCAATTGATTTTCATGTCCCGTTCCAATTTAAAGAAGTCTTCAGTTCGTGCATA

GTTAACATACACTAGATCGCCCTCTGGCATTCCTTGAGGAGAGAAAGCACTGAAA

GGTGGTACAATATCCGAAACATTTTCATATCCTGGAGGAGGTGGTTCAAATAATGA

TGTGTTGAAAATCTCATTTCCATCTTCATTAATTATTGAGATGTAGTTGGGATGAGT

CTTATTTGGGTAGGACAACAGGACATCATAATGTGCCAGCTCAACAGAATCCAGG

CCAAATTCTTTCCACTGGGATTGAATTTGCTTTGCAAGCTGAAAGTTTTGTTCTGTT

CCTGCTAAATGTGGTATCTGTGTAAAATTATATAAGAACTTCTTGATGTTCTCAGCT

TTCAATTCATCCAAAAATGCTTTCATATTATGCTTTGGAGTAATGTTAGTAGCTTCA

TTGGAGGATTTTATAAACCACCCGAAGAGGAAGCCGAGGAGAAAGAAGCCACCC

GCCAGCACCAGCGCCCCAGCGCACAGCCAGCGCGGGCGGCGCGCGCTAGCCA

TGTTCGTCACAGGGTCCCCAGTCCTCGCGGAGATTGACGAGATGTGAGAGGCAA

TATTCGGAGCAGGGTTTACTGTTCCTGAACTGGAGCCACCAGCAGGAAAATACAG

ACCCCTGACTCTGGGATCCTGACCTGGAAGATAGTCAGGGTTGAGGCAAGCAAA

AGGTACATGTAAGAGAAGAGCCCACAGCGTCCCTCAAATCCCTGGAGTCTTGACT

GGGGAAGCCAGGCCCACCCTGGAGAGTACATACCTGCTTGCTGAGATCCGGACG

GTGAGTCACTCTTGGCACGGGGAATCCGCGTTCCAATGCACCGTTCCCGGCCGC

GGAGGCTGGATCGGTCCCGGTGTCTTCTATGGAGGTCAAAACAGCGTGGATGGC

GTCTCCAGGCGATCTGACGGTTCACTAAACGAGCTCTGCTTATATAGACCTCCCA

CCGTACACGCCTACCGCCCATTTGCGTCAACGGGGCGGGGTTATTACGACATTTT

GGAAAGTCCCGTTGATTTTGGTGCTCGACCTGCAGGGTACCAATATTGGCTATTG

GCCATTGCATACGTTGTATCTATATCATAATATGTACATTTATATTGGCTCATGTCC

AATATGACCGCCATGTTGACATTGATTATTGACTAGTTATTAATAGTAATCAATTAC

GGGGTCATTAGTTCATAGCCCATATATGGAGTTCCGCGTTACATAACTTACGGTAA

ATGGCCCGCCTGGCTGACCGCCCAACGACCCCCGCCCATTGACGTCAATAATGA

CGTATGTTCCCATAGTAACGCCAATAGGGACTTTCCATTGACGTCAATGGGTGGA

GTATTTACGGTAAACTGCCCACTTGGCAGTACATCAAGTGTATCATATGCCAAGTC

CGCCCCCTATTGACGTCAATGACGGTAAATGGCCCGCCTGGCATTATGCCCAGTA

CATGACCTTACGGGACTTTCCTACTTGGCAGTACATCTACGTATTAGTCATCGCTA

TTACCATGGTGATGCGGTTTTGGCAGTACACCAATGGGCGTGGATAGCGGTTTGA

CTCACGGGGATTTCCAAGTCTCCACCCCATTGACGTCAATGGGAGTTTGTTTTGG

CACCAAAATCAACGGGACTTTCCAAAATGTCGTAATAACCCCGCCCCGTTGACGC

AAATGGGCGGTAGGCGTGTACGGTGGGAGGTCTATATAAGCAGAGCTCGTTTAG

TGAACCGTCAGATCGCCTGGAGACGCCATCCACGCTGTTTTGACCTCCATAGAAG

ACACCGGGACCGATCCAGCCTCCGCGGCCGGGAACGGTGCATTGGAACGCGGA

TTCCCCGTGCCAAGAGTGACTCACCGTCCGGATCTCAGCAAGCAGGTATGTACTC

TCCAGGGTGGGCCTGGCTTCCCCAGTCAAGACTCCAGGGATTTGAGGGACGCTG

TGGGCTCTTCTCTTACATGTACCTTTTGCTTGCCTCAACCCTGACTATCTTCCAGG

TCAGGATCCCAGAGTCAGGGGTCTGTATTTTCCTGCTGGTGGCTCCAGTTCAGGA

-continued

ACAGTAAACCCTGCTCCGAATATTGCCTCTCACATCTCGTCAATCTCCGCGAGGA

CTGGGGACCCTGTGACGAACATGGCTAGCAAGGCTGTGCTGCTTGCCCTGTTGA

TGGCAGGCTTGGCCCTGCAGCCAGGCACTGCCCTGCTGTGCTACTCCTGCAAAG

CCCAGGTGAGCAACGAGGACTGCCTGCAGGTGGAGAACTGCACCCAGCTGGGG

GAGCAGTGCTGGACCGCGCGCATCCGCGCAGTTGGCCTCCTGACCGTCATCAGC

AAAGGCTGCAGCTTGAACTGCGTGGATGACTCACAGGACTACTACGTGGGCAAG

AAGAACATCACGTGCTGTGACACCGACTTGTGCAACGCCAGCGGGGCCCATGCC

CTGCAGCCGGCTGCCGCCATCCTTGCGCTGCTCCCTGCACTCGGCCTGCTGCTC

TGGGGACCCGGCCAGCTATAGAGATCTGGGCCCTAACAAAACAAAAAGATGGGG

TTATTCCCTAAACTTCATGGGTTACGTAATTGGAAGTTGGGGGACATTGCCACAAG

ATCATATTGTACAAAAGATCAAACACTGTTTTAGAAAACTTCCTGTAAACAGGCCTA

TTGATTGGAAAGTATGTCAAAGGATTGTGGGTCTTTTGGGCTTTGCTGCTCCATTT

ACACAATGTGGATATCCTGCCTTAATGCCTTTGTATGCATGTATACAAGCTAAACA

GGCTTTCACTTTCTCGCCAACTTACAAGGCCTTTCTAAGTAAACAGTACATGAACC

TTTACCCCGTTGCTCGGCAACGGCCTGGTCTGTGCCAAGTGTTTGCTGACGCAAC

CCCCACTGGCTGGGGCTTGGCCATAGGCCATCAGCGCATGCGTGGAACCTTTGT

GGCTCCTCTGCCGATCCATACTGCGGAACTCCTAGCCGCTTGTTTTGCTCGCAGC

CGGTCTGGAGCAAAGCTCATAGGAACTGACAATTCTGTCGTCCTCTCGCGGAAAT

ATACATCGTTTCGATCTACGTATGATCTTTTTCCCTCTGCCAAAAATTATGGGGAC

ATCATGAAGCCCCTTGAGCATCTGACTTCTGGCTAATAAAGGAAATTTATTTTCATT

GCAATAGTGTGTTGGAATTTTTTGTGTCTCTCACTCGGAAGC

NUCLEOTIDE SEQUENCE OF PLASMID 451.

SEQ ID NO: 27

GGCGTAATGCTCTGCCAGTGTTACAACCAATTAACCAATTCTGATTAGAAAAACTC

ATCGAGCATCAAATGAAACTGCAATTTATTCATATCAGGATTATCAATACCATATTT

TTGAAAAAGCCGTTTCTGTAATGAAGGAGAAAACTCACCGAGGCAGTTCCATAGG

ATGGCAAGATCCTGGTATCGGTCTGCGATTCCGACTCGTCCAACATCAATACAAC

CTATTAATTTCCCCTCGTCAAAAATAAGGTTATCAAGTGAGAAATCACCATGAGTG

ACGACTGAATCCGGTGAGAATGGCAAAAGCTTATGCATTTCTTTCCAGACTTGTTC

AACAGGCCAGCCATTACGCTCGTCATCAAAATCACTCGCATCAACCAAACCGTTA

TTCATTCGTGATTGCGCCTGAGCGAGACGAAATACGCGATCGCTGTTAAAAGGAC

AATTACAAACAGGAATCAAATGCAACCGGCGCAGGAACACTGCCAGCGCATCAAC

AATATTTTCACCTGAATCAGGATATTCTTCTAATACCTGGAATGCTGTTTTCCCGG

GGATCGCAGTGGTGAGTAACCATGCATCATCAGGAGTACGGATAAAATGCTTGAT

GGTCGGAAGAGGCATAAATTCCGTCAGCCAGTTTAGTCTGACCATCTCATCTGTA

ACATCATTGGCAACGCTACCTTTGCCATGTTTCAGAAACAACTCTGGCGCATCGG

GCTTCCCATACAATCGATAGATTGTCGCACCTGATTGCCCGACATTATCGCGAGC

CCATTTATACCCATATAAATCAGCATCCATGTTGGAATTTAATCGCGGCCTCGAGC

AAGACGTTTCCCGTTGAATATGGCTCATAACACCCCTTGTATTACTGTTTATGTAA

GCAGACAGGTCGACAATATTGGCTATTGGCCATTGCATACGTTGTATCTATATCAT

AATATGTACATTTATATTGGCTCATGTCCAATATGACCGCCATGTTGACATTGATTA

-continued

TTGACTAGTTATTAATAGTAATCAATTACGGGGTCATTAGTTCATAGCCCATATATG

GAGTTCCGCGTTACATAACTTACGGTAAATGGCCCGCCTGGCTGACCGCCCAAC

GACCCCCGCCCATTGACGTCAATAATGACGTATGTTCCCATAGTAACGCCAATAG

GGACTTTCCATTGACGTCAATGGGTGGAGTATTTACGGTAAACTGCCCACTTGGC

AGTACATCAAGTGTATCATATGCCAAGTCCGCCCCCTATTGACGTCAATGACGGT

AAATGGCCCGCCTGGCATTATGCCCAGTACATGACCTTACGGGACTTTCCTACTT

GGCAGTACATCTACGTATTAGTCATCGCTATTACCATGGTGATGCGGTTTTGGCA

GTACACCAATGGGCGTGGATAGCGGTTTGACTCACGGGGATTTCCAAGTCTCCAC

CCCATTGACGTCAATGGGAGTTTGTTTTGGCACCAAAATCAACGGGACTTTCCAA

AATGTCGTAATAACCCCGCCCCGTTGACGCAAATGGGCGGTAGGCGTGTACGGT

GGGAGGTCTATATAAGCAGAGCTCGTTTAGTGAACCGTCAGATCGCCTGGAGAC

GCCATCCACGCTGTTTTGACCTCCATAGAAGACACCGGGACCGATCCAGCCTCC

GCGGCCGGGAACGGTGCATTGGAACGCGGATTCCCCGTGCCAAGAGTGACTCA

CCGTCCGGATCTCAGCAAGCAGGTATGTACTCTCCAGGGTGGGCCTGGCTTCCC

CAGTCAAGACTCCAGGGATTTGAGGGACGCTGTGGGCTCTTCTCTTACATGTACC

TTTTGCTTGCCTCAACCCTGACTATCTTCCAGGTCAGGATCCCAGAGTCAGGGGT

CTGTATTTTCCTGCTGGTGGCTCCAGTTCAGGAACAGTAAACCCTGCTCCGAATA

TTGCCTCTCACATCTCGTCAATCTCCGCGAGGACTGGGGACCCTGTGACGAACAT

GGCTAGCGCGCGCCGCCCGCGCTGGCTGTGCGCTGGGGCGCTGGTGCTGGCG

GGTGGCTTCTTTCTCCTCGGCTTCCTCTTCGGGTGGTTTATAAAATCCTCCAATGA

AGCTACTAACATTACTCCAAAGCATAATATGAAAGCATTTTTGGATGAATTGAAAG

CTGAGAACATCAAGAAGTTCTTATATAATTTTACACAGATACCACATTTAGCAGGA

ACAGAACAAAACTTTCAGCTTGCAAAGCAAATTCAATCCCAGTGGAAAGAATTTGG

CCTGGATTCTGTTGAGCTGGCACATTATGATGTCCTGTTGTCCTACCCAAATAAGA

CTCATCCCAACTACATCTCAATAATTAATGAAGATGGAAATGAGATTTTCAACACAT

CATTATTTGAACCACCTCCTCCAGGATATGAAAATGTTTCGGATATTGTACCACCT

TTCAGTGCTTTCTCTCCTCAAGGAATGCCAGAGGGCGATCTAGTGTATGTTAACTA

TGCACGAACTGAAGACTTCTTTAAATTGGAACGGGACATGAAAATCAATTGCTCTG

GGAAAATTGTAATTGCCAGATATGGGAAAGTTTTCAGAGGAAATAAGGTTAAAAAT

GCCCAGCTGGCAGGGGCCAAAGGAGTCATTCTCTACTCCGACCCTGCTGACTAC

TTTGCTCCTGGGGTGAAGTCCTATCCAGATGGTTGGAATCTTCCTGGAGGTGGTG

TCCAGCGTGGAAATATCCTAAATCTGAATGGTGCAGGAGACCCTCTCACACCAGG

TTACCCAGCAAATGAATATGCTTATAGGCGTGGAATTGCAGAGGCTGTTGGTCTT

CCAAGTATTCCTGTTCATCCAATTGGATACTATGATGCACAGAAGCTCCTAGAAAA

AATGGGTGGCTCAGCACCACCAGATAGCAGCTGGAGAGGAAGTCTCAAAGTGCC

CTACAATGTTGGACCTGGCTTTACTGGAAACTTTTCTACACAAAAAGTCAAGATGC

ACATCCACTCTACCAATGAAGTGACAAGAATTTACAATGTGATAGGTACTCTCAGA

GGAGCAGTGGAACCAGACAGATATGTCATTCTGGGAGGTCACCGGGACTCATGG

GTGTTTGGTGGTATTGACCCTCAGAGTGGAGCAGCTGTTGTTCATGAAATTGTGA

GGAGCTTTGGAACACTGAAAAAGGAAGGGTGGAGACCTAGAAGAACAATTTTGTT

TGCAAGCTGGGATGCAGAAGAATTTGGTCTTCTTGGTTCTACTGAGTGGGCAGAG

-continued

GAGAATTCAAGACTCCTTCAAGAGCGTGGCGTGGCTTATATTAATGCTGACTCAT

CTATAGAAGGAAACTACACTCTGAGAGTTGATTGTACACCGCTGATGTACAGCTT

GGTACACAACCTAACAAAAGAGCTGAAAAGCCCTGATGAAGGCTTTGAAGGCAAA

TCTCTTTATGAAAGTTGGACTAAAAAAAGTCCTTCCCCAGAGTTCAGTGGCATGCC

CAGGATAAGCAAATTGGGATCTGGAAATGATTTTGAGGTGTTCTTCCAACGACTTG

GAATTGCTTCAGGCAGAGCACGGTATACTAAAAATTGGGAAACAAACAAATTCAG

CGGCTATCCACTGTATCACAGTGTCTATGAAACATATGAGTTGGTGGAAAAGTTTT

ATGATCCAATGTTTAAATATCACCTCACTGTGGCCCAGGTTCGAGGAGGGATGGT

GTTTGAGCTGGCCAATTCCATAGTGCTCCCTTTTGATTGTCGAGATTATGCTGTAG

TTTTAAGAAAGTATGCTGACAAAATCTACAGTATTTCTATGAAACATCCACAGGAAA

TGAAGACATACAGTGTATCATTTGATTCACTTTTTTCTGCAGTAAAGAATTTTACAG

AAATTGCTTCCAAGTTCAGTGAGAGACTCCAGGACTTTGACAAAAGCAACCCAATA

GTATTAAGAATGATGAATGATCAACTCATGTTTCTGGAAAGAGCATTTATTGATCC

ATTAGGGTTACCAGACAGGCCTTTTTATAGGCATGTCATCTATGCTCCAAGCAGC

CACAACAAGTATGCAGGGGAGTCATTCCCAGGAATTTATGATGCTCTGTTTGATAT

TGAAAGCAAAGTGGACCCTTCCAAGGCCTGGGGAGAAGTGAAGAGACAGATTTAT

GTTGCAGCCTTCACAGTGCAGGCAGCTGCAGAGACTTTGAGTGAAGTAGCCGGA

TCCGAAGGTAGGGGTTCATTATTGACCTGTGGAGATGTCGAAGAAAACCCAGGAC

CCGCAAGCAAGGCTGTGCTGCTTGCCCTGTTGATGGCAGGCTTGGCCCTGCAGC

CAGGCACTGCCCTGCTGTGCTACTCCTGCAAAGCCCAGGTGAGCAACGAGGACT

GCCTGCAGGTGGAGAACTGCACCCAGCTGGGGGAGCAGTGCTGGACCGCGCGC

ATCCGCGCAGTTGGCCTCCTGACCGTCATCAGCAAAGGCTGCAGCTTGAACTGC

GTGGATGACTCACAGGACTACTACGTGGGCAAGAAGAACATCACGTGCTGTGAC

ACCGACTTGTGCAACGCCAGCGGGGCCCATGCCCTGCAGCCGGCTGCCGCCAT

CCTTGCGCTGCTCCCTGCACTCGGCCTGCTGCTCTGGGGACCCGGCCAGCTATA

GAGATCTGGGCCCTAACAAAACAAAAAGATGGGGTTATTCCCTAAACTTCATGGG

TTACGTAATTGGAAGTTGGGGGACATTGCCACAAGATCATATTGTACAAAAGATCA

AACACTGTTTTAGAAAACTTCCTGTAAACAGGCCTATTGATTGGAAAGTATGTCAA

AGGATTGTGGGTCTTTTGGGCTTTGCTGCTCCATTTACACAATGTGGATATCCTGC

CTTAATGCCTTTGTATGCATGTATACAAGCTAAACAGGCTTTCACTTTCTCGCCAA

CTTACAAGGCCTTTCTAAGTAAACAGTACATGAACCTTTACCCCGTTGCTCGGCAA

CGGCCTGGTCTGTGCCAAGTGTTTGCTGACGCAACCCCCACTGGCTGGGGCTTG

GCCATAGGCCATCAGCGCATGCGTGGAACCTTTGTGGCTCCTCTGCCGATCCATA

CTGCGGAACTCCTAGCCGCTTGTTTTGCTCGCAGCCGGTCTGGAGCAAAGCTCAT

AGGAACTGACAATTCTGTCGTCCTCTCGCGGAAATATACATCGTTTCGATCTACGT

ATGATCTTTTTCCCTCTGCCAAAAATTATGGGGACATCATGAAGCCCCTTGAGCAT

CTGACTTCTGGCTAATAAAGGAAATTTATTTTCATTGCAATAGTGTGTTGGAATTTT

TTGTGTCTCTCACTCGGAAGGAATTCTGCATTAATGAATCGGCCAACGCGCGGGG

AGAGGCGGTTTGCGTATTGGGCGCTCTTCCGCTTCCTCGCTCACTGACTCGCTG

CGCTCGGTCGTTCGGCTGCGGCGAGCGGTATCAGCTCACTCAAAGGCGGTAATA

-continued

CGGTTATCCACAGAATCAGGGGATAACGCAGGAAAGAACATGTGAGCAAAAGGC

CAGCAAAAGGCCAGGAACCGTAAAAAGGCCGCGTTGCTGGCGTTTTTCCATAGG

CTCCGCCCCCCTGACGAGCATCACAAAAATCGACGCTCAAGTCAGAGGTGGCGA

AACCCGACAGGACTATAAAGATACCAGGCGTTTCCCCCTGGAAGCTCCCTCGTGC

GCTCTCCTGTTCCGACCCTGCCGCTTACCGGATACCTGTCCGCCTTTCTCCCTTC

GGGAAGCGTGGCGCTTTCTCATAGCTCACGCTGTAGGTATCTCAGTTCGGTGTAG

GTCGTTCGCTCCAAGCTGGGCTGTGTGCACGAACCCCCCGTTCAGCCCGACCGC

TGCGCCTTATCCGGTAACTATCGTCTTGAGTCCAACCCGGTAAGACACGACTTAT

CGCCACTGGCAGCAGCCACTGGTAACAGGATTAGCAGAGCGAGGTATGTAGGCG

GTGCTACAGAGTTCTTGAAGTGGTGGCCTAACTACGGCTACACTAGAAGAACAGT

ATTTGGTATCTGCGCTCTGCTGAAGCCAGTTACCTTCGGAAAAAGAGTTGGTAGC

TCTTGATCCGGCAAACAAACCACCGCTGGTAGCGGTGGTTTTTTTGTTTGCAAGC

AGCAGATTACGCGCAGAAAAAAAGGATCTCAAGAAGATCCTTTGATCTTTTCTACG

GGGTCTGACGCTCAGTGGAACGAAAACTCACGTTAAGGGATTTTGGTCATGAGAT

TATCAAAAAGGATCTTCACCTAGATCCTTTTAAATTAAAAATGAAGTTTTAAATCAA

TCTAAAGTATATATGAGTAAACTTGGTCTGACAGTTACCAATGCTTAATCAGTGAG

GCACCTATCTCAGCGATCTGTCTATTTCGTTCATCCATAGTTGCCTGACTC

NUCLEOTIDE SEQUENCE OF PLASMID 454.

SEQ ID NO: 28

GGCGTAATGCTCTGCCAGTGTTACAACCAATTAACCAATTCTGATTAGAAAAACTC

ATCGAGCATCAAATGAAACTGCAATTTATTCATATCAGGATTATCAATACCATATTT

TTGAAAAAGCCGTTTCTGTAATGAAGGAGAAAACTCACCGAGGCAGTTCCATAGG

ATGGCAAGATCCTGGTATCGGTCTGCGATTCCGACTCGTCCAACATCAATACAAC

CTATTAATTTCCCCTCGTCAAAAATAAGGTTATCAAGTGAGAAATCACCATGAGTG

ACGACTGAATCCGGTGAGAATGGCAAAAGCTTATGCATTTCTTTCCAGACTTGTTC

AACAGGCCAGCCATTACGCTCGTCATCAAAATCACTCGCATCAACCAAACCGTTA

TTCATTCGTGATTGCGCCTGAGCGAGACGAAATACGCGATCGCTGTTAAAAGGAC

AATTACAAACAGGAATCAAATGCAACCGGCGCAGGAACACTGCCAGCGCATCAAC

AATATTTTCACCTGAATCAGGATATTCTTCTAATACCTGGAATGCTGTTTTCCCGG

GGATCGCAGTGGTGAGTAACCATGCATCATCAGGAGTACGGATAAAATGCTTGAT

GGTCGGAAGAGGCATAAATTCCGTCAGCCAGTTTAGTCTGACCATCTCATCTGTA

ACATCATTGGCAACGCTACCTTTGCCATGTTTCAGAAACAACTCTGGCGCATCGG

GCTTCCCATACAATCGATAGATTGTCGCACCTGATTGCCCGACATTATCGCGAGC

CCATTTATACCCATATAAATCAGCATCCATGTTGGAATTTAATCGCGGCCTCGAGC

AAGACGTTTCCCGTTGAATATGGCTCATAACACCCCTTGTATTACTGTTTATGTAA

GCAGACAGGTCGACAATATTGGCTATTGGCCATTGCATACGTTGTATCTATATCAT

AATATGTACATTTATATTGGCTCATGTCCAATATGACCGCCATGTTGACATTGATTA

TTGACTAGTTATTAATAGTAATCAATTACGGGGTCATTAGTTCATAGCCCATATATG

GAGTTCCGCGTTACATAACTTACGGTAAATGGCCCGCCTGGCTGACCGCCCAAC

GACCCCCGCCCATTGACGTCAATAATGACGTATGTTCCCATAGTAACGCCAATAG

GGACTTTCCATTGACGTCAATGGGTGGAGTATTTACGGTAAACTGCCCACTTGGC

AGTACATCAAGTGTATCATATGCCAAGTCCGCCCCCTATTGACGTCAATGACGGT

-continued

AAATGGCCCGCCTGGCATTATGCCCAGTACATGACCTTACGGGACTTTCCTACTT

GGCAGTACATCTACGTATTAGTCATCGCTATTACCATGGTGATGCGGTTTTGGCA

GTACACCAATGGGCGTGGATAGCGGTTTGACTCACGGGGATTTCCAAGTCTCCAC

CCCATTGACGTCAATGGGAGTTTGTTTTGGCACCAAAATCAACGGGACTTTCCAA

AATGTCGTAATAACCCCGCCCCGTTGACGCAAATGGGCGGTAGGCGTGTACGGT

GGGAGGTCTATATAAGCAGAGCTCGTTTAGTGAACCGTCAGATCGCCTGGAGAC

GCCATCCACGCTGTTTTGACCTCCATAGAAGACACCGGGACCGATCCAGCCTCC

GCGGCCGGGAACGGTGCATTGGAACGCGGATTCCCCGTGCCAAGAGTGACTCA

CCGTCCGGATCTCAGCAAGCAGGTATGTACTCTCCAGGGTGGGCCTGGCTTCCC

CAGTCAAGACTCCAGGGATTTGAGGGACGCTGTGGGCTCTTCTCTTACATGTACC

TTTTGCTTGCCTCAACCCTGACTATCTTCCAGGTCAGGATCCCAGAGTCAGGGGT

CTGTATTTTCCTGCTGGTGGCTCCAGTTCAGGAACAGTAAACCCTGCTCCGAATA

TTGCCTCTCACATCTCGTCAATCTCCGCGAGGACTGGGGACCCTGTGACGAACAT

GGCTAGCAAGGCTGTGCTGCTTGCCCTGTTGATGGCAGGCTTGGCCCTGCAGCC

AGGCACTGCCCTGCTGTGCTACTCCTGCAAAGCCCAGGTGAGCAACGAGGACTG

CCTGCAGGTGGAGAACTGCACCCAGCTGGGGGAGCAGTGCTGGACCGCGCGCA

TCCGCGCAGTTGGCCTCCTGACCGTCATCAGCAAAGGCTGCAGCTTGAACTGCG

TGGATGACTCACAGGACTACTACGTGGGCAAGAAGAACATCACGTGCTGTGACAC

CGACTTGTGCAACGCCAGCGGGGCCCATGCCCTGCAGCCGGCTGCCGCCATCC

TTGCGCTGCTCCCTGCACTCGGCCTGCTGCTCTGGGGACCCGGCCAGCTAGGAT

CCCAGACCCTGAACTTTGATCTGCTGAAACTGGCAGGCGATGTGGAAAGCAACC

CAGGCCCAATGGCAAGCGCGCGCCGCCCGCGCTGGCTGTGCGCTGGGGCGCT

GGTGCTGGCGGGTGGCTTCTTTCTCCTCGGCTTCCTCTTCGGGTGGTTTATAAAA

TCCTCCAATGAAGCTACTAACATTACTCCAAAGCATAATATGAAAGCATTTTTGGAT

GAATTGAAAGCTGAGAACATCAAGAAGTTCTTATATAATTTTACACAGATACCACAT

TTAGCAGGAACAGAACAAAACTTTCAGCTTGCAAAGCAAATTCAATCCCAGTGGAA

AGAATTTGGCCTGGATTCTGTTGAGCTGGCACATTATGATGTCCTGTTGTCCTACC

CAAATAAGACTCATCCCAACTACATCTCAATAATTAATGAAGATGGAAATGAGATTT

TCAACACATCATTATTTGAACCACCTCCTCCAGGATATGAAAATGTTTCGGATATT

GTACCACCTTTCAGTGCTTTCTCTCCTCAAGGAATGCCAGAGGGCGATCTAGTGT

ATGTTAACTATGCACGAACTGAAGACTTCTTTAAATTGGAACGGGACATGAAAATC

AATTGCTCTGGGAAAATTGTAATTGCCAGATATGGGAAAGTTTTCAGAGGAAATAA

GGTTAAAAATGCCCAGCTGGCAGGGGCCAAAGGAGTCATTCTCTACTCCGACCCT

GCTGACTACTTTGCTCCTGGGGTGAAGTCCTATCCAGATGGTTGGAATCTTCCTG

GAGGTGGTGTCCAGCGTGGAAATATCCTAAATCTGAATGGTGCAGGAGACCCTCT

CACACCAGGTTACCCAGCAAATGAATATGCTTATAGGCGTGGAATTGCAGAGGCT

GTTGGTCTTCCAAGTATTCCTGTTCATCCAATTGGATACTATGATGCACAGAAGCT

CCTAGAAAAAATGGGTGGCTCAGCACCACCAGATAGCAGCTGGAGAGGAAGTCT

CAAAGTGCCCTACAATGTTGGACCTGGCTTTACTGGAAACTTTTCTACACAAAAAG

TCAAGATGCACATCCACTCTACCAATGAAGTGACAAGAATTTACAATGTGATAGGT

-continued

ACTCTCAGAGGAGCAGTGGAACCAGACAGATATGTCATTCTGGGAGGTCACCGG

GACTCATGGGTGTTTGGTGGTATTGACCCTCAGAGTGGAGCAGCTGTTGTTCATG

AAATTGTGAGGAGCTTTGGAACACTGAAAAAGGAAGGGTGGAGACCTAGAAGAAC

AATTTTGTTTGCAAGCTGGGATGCAGAAGAATTTGGTCTTCTTGGTTCTACTGAGT

GGGCAGAGGAGAATTCAAGACTCCTTCAAGAGCGTGGCGTGGCTTATATTAATGC

TGACTCATCTATAGAAGGAAACTACACTCTGAGAGTTGATTGTACACCGCTGATGT

ACAGCTTGGTACACAACCTAACAAAAGAGCTGAAAAGCCCTGATGAAGGCTTTGA

AGGCAAATCTCTTTATGAAAGTTGGACTAAAAAAAGTCCTTCCCCAGAGTTCAGTG

GCATGCCCAGGATAAGCAAATTGGGATCTGGAAATGATTTTGAGGTGTTCTTCCA

ACGACTTGGAATTGCTTCAGGCAGAGCACGGTATACTAAAAATTGGGAAACAAAC

AAATTCAGCGGCTATCCACTGTATCACAGTGTCTATGAAACATATGAGTTGGTGGA

AAAGTTTTATGATCCAATGTTTAAATATCACCTCACTGTGGCCCAGGTTCGAGGAG

GGATGGTGTTTGAGCTGGCCAATTCCATAGTGCTCCCTTTTGATTGTCGAGATTAT

GCTGTAGTTTTAAGAAAGTATGCTGACAAAATCTACAGTATTTCTATGAAACATCCA

CAGGAAATGAAGACATACAGTGTATCATTTGATTCACTTTTTTCTGCAGTAAAGAAT

TTTACAGAAATTGCTTCCAAGTTCAGTGAGAGACTCCAGGACTTTGACAAAAGCAA

CCCAATAGTATTAAGAATGATGAATGATCAACTCATGTTTCTGGAAAGAGCATTTA

TTGATCCATTAGGGTTACCAGACAGGCCTTTTTATAGGCATGTCATCTATGCTCCA

AGCAGCCACAACAAGTATGCAGGGGAGTCATTCCCAGGAATTTATGATGCTCTGT

TTGATATTGAAAGCAAAGTGGACCCTTCCAAGGCCTGGGGAGAAGTGAAGAGACA

GATTTATGTTGCAGCCTTCACAGTGCAGGCAGCTGCAGAGACTTTGAGTGAAGTA

GCCTAAAGATCTGGGCCCTAACAAAACAAAAAGATGGGGTTATTCCCTAAACTTCA

TGGGTTACGTAATTGGAAGTTGGGGGACATTGCCACAAGATCATATTGTACAAAA

GATCAAACACTGTTTTAGAAAACTTCCTGTAAACAGGCCTATTGATTGGAAAGTAT

GTCAAAGGATTGTGGGTCTTTTGGGCTTTGCTGCTCCATTTACACAATGTGGATAT

CCTGCCTTAATGCCTTTGTATGCATGTATACAAGCTAAACAGGCTTTCACTTTCTC

GCCAACTTACAAGGCCTTTCTAAGTAAACAGTACATGAACCTTTACCCCGTTGCTC

GGCAACGGCCTGGTCTGTGCCAAGTGTTTGCTGACGCAACCCCCACTGGCTGGG

GCTTGGCCATAGGCCATCAGCGCATGCGTGGAACCTTTGTGGCTCCTCTGCCGA

TCCATACTGCGGAACTCCTAGCCGCTTGTTTTGCTCGCAGCCGGTCTGGAGCAAA

GCTCATAGGAACTGACAATTCTGTCGTCCTCTCGCGGAAATATACATCGTTTCGAT

CTACGTATGATCTTTTTCCCTCTGCCAAAAATTATGGGGACATCATGAAGCCCCTT

GAGCATCTGACTTCTGGCTAATAAAGGAAATTTATTTTCATTGCAATAGTGTGTTG

GAATTTTTTGTGTCTCTCACTCGGAAGGAATTCTGCATTAATGAATCGGCCAACGC

GCGGGGAGAGGCGGTTTGCGTATTGGGCGCTCTTCCGCTTCCTCGCTCACTGAC

TCGCTGCGCTCGGTCGTTCGGCTGCGGCGAGCGGTATCAGCTCACTCAAAGGCG

GTAATACGGTTATCCACAGAATCAGGGGATAACGCAGGAAAGAACATGTGAGCAA

AAGGCCAGCAAAAGGCCAGGAACCGTAAAAAGGCCGCGTTGCTGGCGTTTTTCC

ATAGGCTCCGCCCCCCTGACGAGCATCACAAAAATCGACGCTCAAGTCAGAGGT

GGCGAAACCCGACAGGACTATAAAGATACCAGGCGTTTCCCCCTGGAAGCTCCC

TCGTGCGCTCTCCTGTTCCGACCCTGCCGCTTACCGGATACCTGTCCGCCTTTCT

-continued

CCCTTCGGGAAGCGTGGCGCTTTCTCATAGCTCACGCTGTAGGTATCTCAGTTCG

GTGTAGGTCGTTCGCTCCAAGCTGGGCTGTGTGCACGAACCCCCCGTTCAGCCC

GACCGCTGCGCCTTATCCGGTAACTATCGTCTTGAGTCCAACCCGGTAAGACACG

ACTTATCGCCACTGGCAGCAGCCACTGGTAACAGGATTAGCAGAGCGAGGTATG

TAGGCGGTGCTACAGAGTTCTTGAAGTGGTGGCCTAACTACGGCTACACTAGAAG

AACAGTATTTGGTATCTGCGCTCTGCTGAAGCCAGTTACCTTCGGAAAAAGAGTT

GGTAGCTCTTGATCCGGCAAACAAACCACCGCTGGTAGCGGTGGTTTTTTTGTTT

GCAAGCAGCAGATTACGCGCAGAAAAAAAGGATCTCAAGAAGATCCTTTGATCTT

TTCTACGGGGTCTGACGCTCAGTGGAACGAAAACTCACGTTAAGGGATTTTGGTC

ATGAGATTATCAAAAAGGATCTTCACCTAGATCCTTTTAAATTAAAAATGAAGTTTT

AAATCAATCTAAAGTATATATGAGTAAACTTGGTCTGACAGTTACCAATGCTTAATC

AGTGAGGCACCTATCTCAGCGATCTGTCTATTTCGTTCATCCATAGTTGCCTGACT

C

NUCLEOTIDE SEQUENCE OF PLASMID 5300.

SEQ ID NO: 29

GGCGTAATGCTCTGCCAGTGTTACAACCAATTAACCAATTCTGATTAGAAAAACTC

ATCGAGCATCAAATGAAACTGCAATTTATTCATATCAGGATTATCAATACCATATTT

TTGAAAAAGCCGTTTCTGTAATGAAGGAGAAAACTCACCGAGGCAGTTCCATAGG

ATGGCAAGATCCTGGTATCGGTCTGCGATTCCGACTCGTCCAACATCAATACAAC

CTATTAATTTCCCCTCGTCAAAAATAAGGTTATCAAGTGAGAAATCACCATGAGTG

ACGACTGAATCCGGTGAGAATGGCAAAAGCTTATGCATTTCTTTCCAGACTTGTTC

AACAGGCCAGCCATTACGCTCGTCATCAAAATCACTCGCATCAACCAAACCGTTA

TTCATTCGTGATTGCGCCTGAGCGAGACGAAATACGCGATCGCTGTTAAAAGGAC

AATTACAAACAGGAATCAAATGCAACCGGCGCAGGAACACTGCCAGCGCATCAAC

AATATTTTCACCTGAATCAGGATATTCTTCTAATACCTGGAATGCTGTTTTCCCGG

GGATCGCAGTGGTGAGTAACCATGCATCATCAGGAGTACGGATAAAATGCTTGAT

GGTCGGAAGAGGCATAAATTCCGTCAGCCAGTTTAGTCTGACCATCTCATCTGTA

ACATCATTGGCAACGCTACCTTTGCCATGTTTCAGAAACAACTCTGGCGCATCGG

GCTTCCCATACAATCGATAGATTGTCGCACCTGATTGCCCGACATTATCGCGAGC

CCATTTATACCCATATAAATCAGCATCCATGTTGGAATTTAATCGCGGCCTCGAGC

AAGACGTTTCCCGTTGAATATGGCTCATAACACCCCTTGTATTACTGTTTATGTAA

GCAGACAGGTCGACAATATTGGCTATTGGCCATTGCATACGTTGTATCTATATCAT

AATATGTACATTTATATTGGCTCATGTCCAATATGACCGCCATGTTGACATTGATTA

TTGACTAGTTATTAATAGTAATCAATTACGGGGTCATTAGTTCATAGCCCATATATG

GAGTTCCGCGTTACATAACTTACGGTAAATGGCCCGCCTGGCTGACCGCCCAAC

GACCCCCGCCCATTGACGTCAATAATGACGTATGTTCCCATAGTAACGCCAATAG

GGACTTTCCATTGACGTCAATGGGTGGAGTATTTACGGTAAACTGCCCACTTGGC

AGTACATCAAGTGTATCATATGCCAAGTCCGCCCCCTATTGACGTCAATGACGGT

AAATGGCCCGCCTGGCATTATGCCCAGTACATGACCTTACGGGACTTTCCTACTT

GGCAGTACATCTACGTATTAGTCATCGCTATTACCATGGTGATGCGGTTTTGGCA

GTACACCAATGGGCGTGGATAGCGGTTTGACTCACGGGGATTTCCAAGTCTCCAC

-continued
CCCATTGACGTCAATGGGAGTTTGTTTTGGCACCAAAATCAACGGGACTTTCCAA
AATGTCGTAATAACCCCGCCCCGTTGACGCAAATGGGCGGTAGGCGTGTACGGT
GGGAGGTCTATATAAGCAGAGCTCGTTTAGTGAACCGTCAGATCGCCTGGAGAC
GCCATCCACGCTGTTTTGACCTCCATAGAAGACACCGGGACCGATCCAGCCTCC
GCGGCCGGGAACGGTGCATTGGAACGCGGATTCCCCGTGCCAAGAGTGACTCA
CCGTCCGGATCTCAGCAAGCAGGTATGTACTCTCCAGGGTGGGCCTGGCTTCCC
CAGTCAAGACTCCAGGGATTTGAGGGACGCTGTGGGCTCTTCTCTTACATGTACC
TTTTGCTTGCCTCAACCCTGACTATCTTCCAGGTCAGGATCCCAGAGTCAGGGGT
CTGTATTTTCCTGCTGGTGGCTCCAGTTCAGGAACAGTAAACCCTGCTCCGAATA
TTGCCTCTCACATCTCGTCAATCTCCGCGAGGACTGGGGACCCTGTGACGAACAT
GGCTAGCATTGTGGGAGGCTGGGAGTGCGAGAAGCATTCCCAACCCTGGCAGGT
GCTTGTGGCCTCTCGTGGCAGGGCAGTCTGCGGCGGTGTTCTGGTGCACCCCCA
GTGGGTCCTCACAGCTGCCCACTGCATCAGGAACAAAAGCGTGATCTTGCTGGG
TCGGCACAGCTTGTTTCATCCTGAAGACACAGGCCAGGTATTTCAGGTCAGCCAC
AGCTTCCCACACCCGCTCTACGATATGAGCCTCCTGAAGAATCGATTCCTCAGGC
CAGGTGATGACTCCAGCCACGACCTCATGCTGCTCCGCCTGTCAGAGCCTGCCG
AGCTCACGGATGCTGTGAAGGTCATGGACCTGCCCACCCAGGAGCCAGCACTGG
GGACCACCTGCTACGCCTCAGGCTGGGGCAGCATTGAACCAGAGGAGTTCTTGA
CCCCAAAGAAACTTCAGTGTGTGGACCTCCATGTTATTTCCAATGACGTGTGTGC
GCAAGTTCACCCTCAGAAGGTGACCAAGTTCATGCTGTGTGCTGGACGCTGGAC
AGGGGGCAAAAGCACCTGCTCGGGTGATTCTGGGGGCCCACTTGTCTGTAATGG
TGTGCTTCAAGGTATCACGTCATGGGGCAGTGAACCATGTGCCCTGCCCGAAAG
GCCTTCCCTGTACACCAAGGTGGTGCATTACCGGAAGTGGATCAAGGACACCATC
GTGGCCAACCCCGGATCCCAGACCCTGAACTTTGATCTGCTGAAACTGGCAGGC
GATGTGGAAAGCAACCCAGGCCCAATGGCAAGCGCGCGCCGCCCCGCGCTGGCT
GTGCGCTGGGGCGCTGGTGCTGGCGGGTGGCTTCTTTCTCCTCGGCTTCCTCTT
CGGGTGGTTTATAAAATCCTCCAATGAAGCTACTAACATTACTCCAAAGCATAATA
TGAAAGCATTTTTGGATGAATTGAAAGCTGAGAACATCAAGAAGTTCTTATATAATT
TTACACAGATACCACATTTAGCAGGAACAGAACAAAACTTTCAGCTTGCAAAGCAA
ATTCAATCCCAGTGGAAAGAATTTGGCCTGGATTCTGTTGAGCTGGCACATTATGA
TGTCCTGTTGTCCTACCCAAATAAGACTCATCCCAACTACATCTCAATAATTAATGA
AGATGGAAATGAGATTTTCAACACATCATTATTTGAACCACCTCCTCCAGGATATG
AAAATGTTTCGGATATTGTACCACCTTTCAGTGCTTTCTCTCCTCAAGGAATGCCA
GAGGGCGATCTAGTGTATGTTAACTATGCACGAACTGAAGACTTCTTTAAATTGGA
ACGGGACATGAAAATCAATTGCTCTGGGAAAATTGTAATTGCCAGATATGGGAAA
GTTTTCAGAGGAAATAAGGTTAAAAATGCCCAGCTGGCAGGGGCCAAAGGAGTCA
TTCTCTACTCCGACCCTGCTGACTACTTTGCTCCTGGGGTGAAGTCCTATCCAGA
TGGTTGGAATCTTCCTGGAGGTGGTGTCCAGCGTGGAAATATCCTAAATCTGAAT
GGTGCAGGAGACCCTCTCACACCAGGTTACCCAGCAAATGAATATGCTTATAGGC
GTGGAATTGCAGAGGCTGTTGGTCTTCCAAGTATTCCTGTTCATCCAATTGGATAC -continued
TATGATGCACAGAAGCTCCTAGAAAAAATGGGTGGCTCAGCACCACCAGATAGCA
GCTGGAGAGGAAGTCTCAAAGTGCCCTACAATGTTGGACCTGGCTTTACTGGAAA
CTTTTCTACACAAAAAGTCAAGATGCACATCCACTCTACCAATGAAGTGACAAGAA
TTTACAATGTGATAGGTACTCTCAGAGGAGCAGTGGAACCAGACAGATATGTCAT
TCTGGGAGGTCACCGGGACTCATGGGTGTTTGGTGGTATTGACCCTCAGAGTGG
AGCAGCTGTTGTTCATGAAATTGTGAGGAGCTTTGGAACACTGAAAAAGGAAGGG
TGGAGACCTAGAAGAACAATTTTGTTTGCAAGCTGGGATGCAGAAGAATTTGGTC
TTCTTGGTTCTACTGAGTGGGCAGAGGAGAATTCAAGACTCCTTCAAGAGCGTGG
CGTGGCTTATATTAATGCTGACTCATCTATAGAAGGAAACTACACTCTGAGAGTTG
ATTGTACACCGCTGATGTACAGCTTGGTACACAACCTAACAAAAGAGCTGAAAAG
CCCTGATGAAGGCTTTGAAGGCAAATCTCTTTATGAAAGTTGGACTAAAAAAAGTC
CTTCCCCAGAGTTCAGTGGCATGCCCAGGATAAGCAAATTGGGATCTGGAAATGA
TTTTGAGGTGTTCTTCCAACGACTTGGAATTGCTTCAGGCAGAGCACGGTATACTA
AAAATTGGGAAACAAACAAATTCAGCGGCTATCCACTGTATCACAGTGTCTATGAA
ACATATGAGTTGGTGGAAAAGTTTTATGATCCAATGTTTAAATATCACCTCACTGT
GGCCCAGGTTCGAGGAGGGATGGTGTTTGAGCTGGCCAATTCCATAGTGCTCCC
TTTTGATTGTCGAGATTATGCTGTAGTTTTAAGAAAGTATGCTGACAAAATCTACAG
TATTTCTATGAAACATCCACAGGAAATGAAGACATACAGTGTATCATTTGATTCACT
TTTTTCTGCAGTAAAGAATTTTACAGAAATTGCTTCCAAGTTCAGTGAGAGACTCC
AGGACTTTGACAAAAGCAACCCAATAGTATTAAGAATGATGAATGATCAACTCATG
TTTCTGGAAAGAGCATTTATTGATCCATTAGGGTTACCAGACAGGCCTTTTTATAG
GCATGTCATCTATGCTCCAAGCAGCCACAACAAGTATGCAGGGGAGTCATTCCCA
GGAATTTATGATGCTCTGTTTGATATTGAAAGCAAAGTGGACCCTTCCAAGGCCTG
GGGAGAAGTGAAGAGACAGATTTATGTTGCAGCCTTCACAGTGCAGGCAGCTGC
AGAGACTTTGAGTGAAGTAGCCTAAAGATCTGGGCCCTAACAAAACAAAAAGATG
GGGTTATTCCCTAAACTTCATGGGTTACGTAATTGGAAGTTGGGGGACATTGCCA
CAAGATCATATTGTACAAAAGATCAAACACTGTTTTAGAAAACTTCCTGTAAACAG
GCCTATTGATTGGAAAGTATGTCAAAGGATTGTGGGTCTTTTGGGCTTTGCTGCTC
CATTTACACAATGTGGATATCCTGCCTTAATGCCTTTGTATGCATGTATACAAGCT
AAACAGGCTTTCACTTTCTCGCCAACTTACAAGGCCTTTCTAAGTAAACAGTACAT
GAACCTTTACCCCGTTGCTCGGCAACGGCCTGGTCTGTGCCAAGTGTTTGCTGAC
GCAACCCCCACTGGCTGGGGCTTGGCCATAGGCCATCAGCGCATGCGTGGAACC
TTTGTGGCTCCTCTGCCGATCCATACTGCGGAACTCCTAGCCGCTTGTTTTGCTC
GCAGCCGGTCTGGAGCAAAGCTCATAGGAACTGACAATTCTGTCGTCCTCTCGC
GGAAATATACATCGTTTCGATCTACGTATGATCTTTTTCCCTCTGCCAAAAATTATG
GGGACATCATGAAGCCCCTTGAGCATCTGACTTCTGGCTAATAAAGGAAATTTATT
TTCATTGCAATAGTGTGTTGGAATTTTTTGTGTCTCTCACTCGGAAGGAATTCTGC
ATTAATGAATCGGCCAACGCGCGGGGAGAGGCGGTTTGCGTATTGGGCGCTCTT
CCGCTTCCTCGCTCACTGACTCGCTGCGCTCGGTCGTTCGGCTGCGGCGAGCGG
TATCAGCTCACTCAAAGGCGGTAATACGGTTATCCACAGAATCAGGGGATAACGC
AGGAAAGAACATGTGAGCAAAAGGCCAGCAAAAGGCCAGGAACCGTAAAAAGGC -continued

CGCGTTGCTGGCGTTTTTCCATAGGCTCCGCCCCCCTGACGAGCATCACAAAAAT

CGACGCTCAAGTCAGAGGTGGCGAAACCCGACAGGACTATAAAGATACCAGGCG

TTTCCCCCTGGAAGCTCCCTCGTGCGCTCTCCTGTTCCGACCCTGCCGCTTACCG

GATACCTGTCCGCCTTTCTCCCTTCGGGAAGCGTGGCGCTTTCTCATAGCTCACG

CTGTAGGTATCTCAGTTCGGTGTAGGTCGTTCGCTCCAAGCTGGGCTGTGTGCAC

GAACCCCCCGTTCAGCCCGACCGCTGCGCCTTATCCGGTAACTATCGTCTTGAGT

CCAACCCGGTAAGACACGACTTATCGCCACTGGCAGCAGCCACTGGTAACAGGA

TTAGCAGAGCGAGGTATGTAGGCGGTGCTACAGAGTTCTTGAAGTGGTGGCCTA

ACTACGGCTACACTAGAAGAACAGTATTTGGTATCTGCGCTCTGCTGAAGCCAGT

TACCTTCGGAAAAAGAGTTGGTAGCTCTTGATCCGGCAAACAAACCACCGCTGGT

AGCGGTGGTTTTTTTGTTTGCAAGCAGCAGATTACGCGCAGAAAAAAAGGATCTC

AAGAAGATCCTTTGATCTTTTCTACGGGGTCTGACGCTCAGTGGAACGAAAACTC

ACGTTAAGGGATTTTGGTCATGAGATTATCAAAAAGGATCTTCACCTAGATCCTTT

TAAATTAAAAATGAAGTTTTAAATCAATCTAAAGTATATATGAGTAAACTTGGTCTG

ACAGTTACCAATGCTTAATCAGTGAGGCACCTATCTCAGCGATCTGTCTATTTCGT

TCATCCATAGTTGCCTGACTC

NUCLEOTIDE SEQUENCE OF PLASMID 449.

SEQ ID NO: 30

GGCGTAATGCTCTGCCAGTGTTACAACCAATTAACCAATTCTGATTAGAAAAACTC

ATCGAGCATCAAATGAAACTGCAATTTATTCATATCAGGATTATCAATACCATATTT

TTGAAAAAGCCGTTTCTGTAATGAAGGAGAAAACTCACCGAGGCAGTTCCATAGG

ATGGCAAGATCCTGGTATCGGTCTGCGATTCCGACTCGTCCAACATCAATACAAC

CTATTAATTTCCCCTCGTCAAAAATAAGGTTATCAAGTGAGAAATCACCATGAGTG

ACGACTGAATCCGGTGAGAATGGCAAAAGCTTATGCATTTCTTTCCAGACTTGTTC

AACAGGCCAGCCATTACGCTCGTCATCAAAATCACTCGCATCAACCAAACCGTTA

TTCATTCGTGATTGCGCCTGAGCGAGACGAAATACGCGATCGCTGTTAAAAGGAC

AATTACAAACAGGAATCAAATGCAACCGGCGCAGGAACACTGCCAGCGCATCAAC

AATATTTTCACCTGAATCAGGATATTCTTCTAATACCTGGAATGCTGTTTTCCCGG

GGATCGCAGTGGTGAGTAACCATGCATCATCAGGAGTACGGATAAAATGCTTGAT

GGTCGGAAGAGGCATAAATTCCGTCAGCCAGTTTAGTCTGACCATCTCATCTGTA

ACATCATTGGCAACGCTACCTTTGCCATGTTTCAGAAACAACTCTGGCGCATCGG

GCTTCCCATACAATCGATAGATTGTCGCACCTGATTGCCCGACATTATCGCGAGC

CCATTTATACCCATATAAATCAGCATCCATGTTGGAATTTAATCGCGGCCTCGAGC

AAGACGTTTCCCGTTGAATATGGCTCATAACACCCCTTGTATTACTGTTTATGTAA

GCAGACAGGTCGACAATATTGGCTATTGGCCATTGCATACGTTGTATCTATATCAT

AATATGTACATTTATATTGGCTCATGTCCAATATGACCGCCATGTTGACATTGATTA

TTGACTAGTTATTAATAGTAATCAATTACGGGGTCATTAGTTCATAGCCCATATATG

GAGTTCCGCGTTACATAACTTACGGTAAATGGCCCGCCTGGCTGACCGCCCAAC

GACCCCCGCCCATTGACGTCAATAATGACGTATGTTCCCATAGTAACGCCAATAG

GGACTTTCCATTGACGTCAATGGGTGGAGTATTTACGGTAAACTGCCCACTTGGC

AGTACATCAAGTGTATCATATGCCAAGTCCGCCCCCTATTGACGTCAATGACGGT

-continued

AAATGGCCCGCCTGGCATTATGCCCAGTACATGACCTTACGGGACTTTCCTACTT

GGCAGTACATCTACGTATTAGTCATCGCTATTACCATGGTGATGCGGTTTTGGCA

GTACACCAATGGGCGTGGATAGCGGTTTGACTCACGGGGATTTCCAAGTCTCCAC

CCCATTGACGTCAATGGGAGTTTGTTTTGGCACCAAAATCAACGGGACTTTCCAA

AATGTCGTAATAACCCCGCCCCGTTGACGCAAATGGGCGGTAGGCGTGTACGGT

GGGAGGTCTATATAAGCAGAGCTCGTTTAGTGAACCGTCAGATCGCCTGGAGAC

GCCATCCACGCTGTTTTGACCTCCATAGAAGACACCGGGACCGATCCAGCCTCC

GCGGCCGGGAACGGTGCATTGGAACGCGGATTCCCCGTGCCAAGAGTGACTCA

CCGTCCGGATCTCAGCAAGCAGGTATGTACTCTCCAGGGTGGGCCTGGCTTCCC

CAGTCAAGACTCCAGGGATTTGAGGGACGCTGTGGGCTCTTCTCTTACATGTACC

TTTTGCTTGCCTCAACCCTGACTATCTTCCAGGTCAGGATCCCAGAGTCAGGGGT

CTGTATTTTCCTGCTGGTGGCTCCAGTTCAGGAACAGTAAACCCTGCTCCGAATA

TTGCCTCTCACATCTCGTCAATCTCCGCGAGGACTGGGGACCCTGTGACGAACAT

GGCTAGCGCGCGCCGCCCGCGCTGGCTGTGCGCTGGGGCGCTGGTGCTGGCG

GGTGGCTTCTTTCTCCTCGGCTTCCTCTTCGGGTGGTTTATAAAATCCTCCAATGA

AGCTACTAACATTACTCCAAAGCATAATATGAAAGCATTTTTGGATGAATTGAAAG

CTGAGAACATCAAGAAGTTCTTATATAATTTTACACAGATACCACATTTAGCAGGA

ACAGAACAAAACTTTCAGCTTGCAAAGCAAATTCAATCCCAGTGGAAAGAATTTGG

CCTGGATTCTGTTGAGCTGGCACATTATGATGTCCTGTTGTCCTACCCAAATAAGA

CTCATCCCAACTACATCTCAATAATTAATGAAGATGGAAATGAGATTTTCAACACAT

CATTATTTGAACCACCTCCTCCAGGATATGAAAATGTTTCGGATATTGTACCACCT

TTCAGTGCTTTCTCTCCTCAAGGAATGCCAGAGGGCGATCTAGTGTATGTTAACTA

TGCACGAACTGAAGACTTCTTTAAATTGGAACGGGACATGAAAATCAATTGCTCTG

GGAAAATTGTAATTGCCAGATATGGGAAAGTTTTCAGAGGAAATAAGGTTAAAAAT

GCCCAGCTGGCAGGGGCCAAAGGAGTCATTCTCTACTCCGACCCTGCTGACTAC

TTTGCTCCTGGGGTGAAGTCCTATCCAGATGGTTGGAATCTTCCTGGAGGTGGTG

TCCAGCGTGGAAATATCCTAAATCTGAATGGTGCAGGAGACCCTCTCACACCAGG

TTACCCAGCAAATGAATATGCTTATAGGCGTGGAATTGCAGAGGCTGTTGGTCTT

CCAAGTATTCCTGTTCATCCAATTGGATACTATGATGCACAGAAGCTCCTAGAAAA

AATGGGTGGCTCAGCACCACCAGATAGCAGCTGGAGAGGAAGTCTCAAAGTGCC

CTACAATGTTGGACCTGGCTTTACTGGAAACTTTTCTACACAAAAAGTCAAGATGC

ACATCCACTCTACCAATGAAGTGACAAGAATTTACAATGTGATAGGTACTCTCAGA

GGAGCAGTGGAACCAGACAGATATGTCATTCTGGGAGGTCACCGGGACTCATGG

GTGTTTGGTGGTATTGACCCTCAGAGTGGAGCAGCTGTTGTTCATGAAATTGTGA

GGAGCTTTGGAACACTGAAAAAGGAAGGGTGGAGACCTAGAAGAACAATTTTGTT

TGCAAGCTGGGATGCAGAAGAATTTGGTCTTCTTGGTTCTACTGAGTGGGCAGAG

GAGAATTCAAGACTCCTTCAAGAGCGTGGCGTGGCTTATATTAATGCTGACTCAT

CTATAGAAGGAAACTACACTCTGAGAGTTGATTGTACACCGCTGATGTACAGCTT

GGTACACAACCTAACAAAAGAGCTGAAAAGCCCTGATGAAGGCTTTGAAGGCAAA

TCTCTTTATGAAAGTTGGACTAAAAAAAGTCCTTCCCCAGAGTTCAGTGGCATGCC

CAGGATAAGCAAATTGGGATCTGGAAATGATTTTGAGGTGTTCTTCCAACGACTTG

-continued

GAATTGCTTCAGGCAGAGCACGGTATACTAAAAATTGGGAAACAAACAAATTCAG

CGGCTATCCACTGTATCACAGTGTCTATGAAACATATGAGTTGGTGGAAAAGTTTT

ATGATCCAATGTTTAAATATCACCTCACTGTGGCCCAGGTTCGAGGAGGGATGGT

GTTTGAGCTGGCCAATTCCATAGTGCTCCCTTTTGATTGTCGAGATTATGCTGTAG

TTTTAAGAAAGTATGCTGACAAAATCTACAGTATTTCTATGAAACATCCACAGGAAA

TGAAGACATACAGTGTATCATTTGATTCACTTTTTTCTGCAGTAAAGAATTTTACAG

AAATTGCTTCCAAGTTCAGTGAGAGACTCCAGGACTTTGACAAAAGCAACCCAATA

GTATTAAGAATGATGAATGATCAACTCATGTTTCTGGAAAGAGCATTTATTGATCC

ATTAGGGTTACCAGACAGGCCTTTTTATAGGCATGTCATCTATGCTCCAAGCAGC

CACAACAAGTATGCAGGGGAGTCATTCCCAGGAATTTATGATGCTCTGTTTGATAT

TGAAAGCAAAGTGGACCCTTCCAAGGCCTGGGGAGAAGTGAAGAGACAGATTTAT

GTTGCAGCCTTCACAGTGCAGGCAGCTGCAGAGACTTTGAGTGAAGTAGCCTAAA

GATCTGACCCCCTAACGTTACTGGCCGAAGCCGCTTGGAATAAGGCCGGTGTGC

GTTTGTCTATATGTTATTTTCCACCATATTGCCGTCTTTTGGCAATGTGAGGGCCC

GGAAACCTGGCCCTGTCTTCTTGACGAGCATTCCTAGGGGTCTTTCCCCTCTCGC

CAAAGGAATGCAAGGTCTGTTGAATGTCGTGAAGGAAGCAGTTCCTCTGGAAGCT

TCTTGAAGACAAACAACGTCTGTAGCGACCCTTTGCAGGCAGCGGAACCCCCCA

CCTGGCGACAGGTGCCTCTGCGGCCAAAAGCCACGTGTATAAGATACACCTGCA

AAGGCGGCACAACCCCAGTGCCACGTTGTGAGTTGGATAGTTGTGGAAAGAGTC

AAATGGCTCTCCTCAAGCGTATTCAACAAGGGGCTGAAGGATGCCCAGAAGGTAC

CCCATTGTATGGGATCTGATCTGGGGCCTCGGTGCACATGCTTTACATGTGTTTA

GTCGAGGTTAAAAAACGTCTAGGCCCCCCGAACCACGGGGACGTGGTTTTCCTTT

GAAAAACACGATGATAATATGGCCAGCAAGGCTGTGCTGCTTGCCCTGTTGATGG

CAGGCTTGGCCCTGCAGCCAGGCACTGCCCTGCTGTGCTACTCCTGCAAAGCCC

AGGTGAGCAACGAGGACTGCCTGCAGGTGGAGAACTGCACCCAGCTGGGGGAG

CAGTGCTGGACCGCGCGCATCCGCGCAGTTGGCCTCCTGACCGTCATCAGCAAA

GGCTGCAGCTTGAACTGCGTGGATGACTCACAGGACTACTACGTGGGCAAGAAG

AACATCACGTGCTGTGACACCGACTTGTGCAACGCCAGCGGGGCCCATGCCCTG

CAGCCGGCTGCCGCCATCCTTGCGCTGCTCCCTGCACTCGGCCTGCTGCTCTGG

GGACCCGGCCAGCTATAGGGATCTGGGCCCTAACAAAACAAAAAGATGGGGTTA

TTCCCTAAACTTCATGGGTTACGTAATTGGAAGTTGGGGGACATTGCCACAAGAT

CATATTGTACAAAAGATCAAACACTGTTTTAGAAAACTTCCTGTAAACAGGCCTATT

GATTGGAAAGTATGTCAAAGGATTGTGGGTCTTTTGGGCTTTGCTGCTCCATTTAC

ACAATGTGGATATCCTGCCTTAATGCCTTTGTATGCATGTATACAAGCTAAACAGG

CTTTCACTTTCTCGCCAACTTACAAGGCCTTTCTAAGTAAACAGTACATGAACCTTT

ACCCCGTTGCTCGGCAACGGCCTGGTCTGTGCCAAGTGTTTGCTGACGCAACCC

CCACTGGCTGGGGCTTGGCCATAGGCCATCAGCGCATGCGTGGAACCTTTGTGG

CTCCTCTGCCGATCCATACTGCGGAACTCCTAGCCGCTTGTTTTGCTCGCAGCCG

GTCTGGAGCAAAGCTCATAGGAACTGACAATTCTGTCGTCCTCTCGCGGAAATAT

ACATCGTTTCGATCTACGTATGATCTTTTTCCCTCTGCCAAAAATTATGGGGACAT

-continued

CATGAAGCCCCTTGAGCATCTGACTTCTGGCTAATAAAGGAAATTTATTTTCATTG

CAATAGTGTGTTGGAATTTTTTGTGTCTCTCACTCGGAAGGAATTCTGCATTAATG

AATCGGCCAACGCGCGGGGAGAGGCGGTTTGCGTATTGGGCGCTCTTCCGCTTC

CTCGCTCACTGACTCGCTGCGCTCGGTCGTTCGGCTGCGGCGAGCGGTATCAGC

TCACTCAAAGGCGGTAATACGGTTATCCACAGAATCAGGGGATAACGCAGGAAAG

AACATGTGAGCAAAAGGCCAGCAAAAGGCCAGGAACCGTAAAAAGGCCGCGTTG

CTGGCGTTTTTCCATAGGCTCCGCCCCCCTGACGAGCATCACAAAAATCGACGCT

CAAGTCAGAGGTGGCGAAACCCGACAGGACTATAAAGATACCAGGCGTTTCCCC

CTGGAAGCTCCCTCGTGCGCTCTCCTGTTCCGACCCTGCCGCTTACCGGATACCT

GTCCGCCTTTCTCCCTTCGGGAAGCGTGGCGCTTTCTCATAGCTCACGCTGTAGG

TATCTCAGTTCGGTGTAGGTCGTTCGCTCCAAGCTGGGCTGTGTGCACGAACCCC

CCGTTCAGCCCGACCGCTGCGCCTTATCCGGTAACTATCGTCTTGAGTCCAACCC

GGTAAGACACGACTTATCGCCACTGGCAGCAGCCACTGGTAACAGGATTAGCAG

AGCGAGGTATGTAGGCGGTGCTACAGAGTTCTTGAAGTGGTGGCCTAACTACGG

CTACACTAGAAGAACAGTATTTGGTATCTGCGCTCTGCTGAAGCCAGTTACCTTC

GGAAAAAGAGTTGGTAGCTCTTGATCCGGCAAACAAACCACCGCTGGTAGCGGT

GGTTTTTTTGTTTGCAAGCAGCAGATTACGCGCAGAAAAAAAGGATCTCAAGAAG

ATCCTTTGATCTTTTCTACGGGGTCTGACGCTCAGTGGAACGAAAACTCACGTTAA

GGGATTTTGGTCATGAGATTATCAAAAAGGATCTTCACCTAGATCCTTTTAAATTAA

AAATGAAGTTTTAAATCAATCTAAAGTATATATGAGTAAACTTGGTCTGACAGTTAC

CAATGCTTAATCAGTGAGGCACCTATCTCAGCGATCTGTCTATTTCGTTCATCCAT

AGTTGCCTGACTC

NUCLEOTIDE SEQUENCE OF PLASMID 603.

SEQ ID NO: 31

GGCGTAATGCTCTGCCAGTGTTACAACCAATTAACCAATTCTGATTAGAAAAACTC

ATCGAGCATCAAATGAAACTGCAATTTATTCATATCAGGATTATCAATACCATATTT

TTGAAAAAGCCGTTTCTGTAATGAAGGAGAAAACTCACCGAGGCAGTTCCATAGG

ATGGCAAGATCCTGGTATCGGTCTGCGATTCCGACTCGTCCAACATCAATACAAC

CTATTAATTTCCCCTCGTCAAAAATAAGGTTATCAAGTGAGAAATCACCATGAGTG

ACGACTGAATCCGGTGAGAATGGCAAAAGCTTATGCATTTCTTTCCAGACTTGTTC

AACAGGCCAGCCATTACGCTCGTCATCAAAATCACTCGCATCAACCAAACCGTTA

TTCATTCGTGATTGCGCCTGAGCGAGACGAAATACGCGATCGCTGTTAAAAGGAC

AATTACAAACAGGAATCAAATGCAACCGGCGCAGGAACACTGCCAGCGCATCAAC

AATATTTTCACCTGAATCAGGATATTCTTCTAATACCTGGAATGCTGTTTTCCCGG

GGATCGCAGTGGTGAGTAACCATGCATCATCAGGAGTACGGATAAAATGCTTGAT

GGTCGGAAGAGGCATAAATTCCGTCAGCCAGTTTAGTCTGACCATCTCATCTGTA

ACATCATTGGCAACGCTACCTTTGCCATGTTTCAGAAACAACTCTGGCGCATCGG

GCTTCCCATACAATCGATAGATTGTCGCACCTGATTGCCCGACATTATCGCGAGC

CCATTTATACCCATATAAATCAGCATCCATGTTGGAATTTAATCGCGGCCTCGAGC

AAGACGTTTCCCGTTGAATATGGCTCATAACACCCCTTGTATTACTGTTTATGTAA

GCAGACAGGTCGACAATATTGGCTATTGGCCATTGCATACGTTGTATCTATATCAT

AATATGTACATTTATATTGGCTCATGTCCAATATGACCGCCATGTTGACATTGATTA

-continued

TTGACTAGTTATTAATAGTAATCAATTACGGGGTCATTAGTTCATAGCCCATATATG

GAGTTCCGCGTTACATAACTTACGGTAAATGGCCCGCCTGGCTGACCGCCCAAC

GACCCCCGCCCATTGACGTCAATAATGACGTATGTTCCCATAGTAACGCCAATAG

GGACTTTCCATTGACGTCAATGGGTGGAGTATTTACGGTAAACTGCCCACTTGGC

AGTACATCAAGTGTATCATATGCCAAGTCCGCCCCCTATTGACGTCAATGACGGT

AAATGGCCCGCCTGGCATTATGCCCAGTACATGACCTTACGGGACTTTCCTACTT

GGCAGTACATCTACGTATTAGTCATCGCTATTACCATGGTGATGCGGTTTTGGCA

GTACACCAATGGGCGTGGATAGCGGTTTGACTCACGGGGATTTCCAAGTCTCCAC

CCCATTGACGTCAATGGGAGTTTGTTTTGGCACCAAAATCAACGGGACTTTCCAA

AATGTCGTAATAACCCCGCCCCGTTGACGCAAATGGGCGGTAGGCGTGTACGGT

GGGAGGTCTATATAAGCAGAGCTCGTTTAGTGAACCGTCAGATCGCCTGGAGAC

GCCATCCACGCTGTTTTGACCTCCATAGAAGACACCGGGACCGATCCAGCCTCC

GCGGCCGGGAACGGTGCATTGGAACGCGGATTCCCCGTGCCAAGAGTGACTCA

CCGTCCGGATCTCAGCAAGCAGGTATGTACTCTCCAGGGTGGGCCTGGCTTCCC

CAGTCAAGACTCCAGGGATTTGAGGGACGCTGTGGGCTCTTCTCTTACATGTACC

TTTTGCTTGCCTCAACCCTGACTATCTTCCAGGTCAGGATCCCAGAGTCAGGGGT

CTGTATTTTCCTGCTGGTGGCTCCAGTTCAGGAACAGTAAACCCTGCTCCGAATA

TTGCCTCTCACATCTCGTCAATCTCCGCGAGGACTGGGGACCCTGTGACGAACAT

GGCTAGCAAGGCTGTGCTGCTTGCCCTGTTGATGGCAGGCTTGGCCCTGCAGCC

AGGCACTGCCCTGCTGTGCTACTCCTGCAAAGCCCAGGTGAGCAACGAGGACTG

CCTGCAGGTGGAGAACTGCACCCAGCTGGGGGAGCAGTGCTGGACCGCGCGCA

TCCGCGCAGTTGGCCTCCTGACCGTCATCAGCAAAGGCTGCAGCTTGAACTGCG

TGGATGACTCACAGGACTACTACGTGGGCAAGAAGAACATCACGTGCTGTGACAC

CGACTTGTGCAACGCCAGCGGGGCCCATGCCCTGCAGCCGGCTGCCGCCATCC

TTGCGCTGCTCCCTGCACTCGGCCTGCTGCTCTGGGGACCCGGCCAGCTATAGA

GATCTGACCCCCTAACGTTACTGGCCGAAGCCGCTTGGAATAAGGCCGGTGTGC

GTTTGTCTATATGTTATTTTCCACCATATTGCCGTCTTTTGGCAATGTGAGGGCCC

GGAAACCTGGCCCTGTCTTCTTGACGAGCATTCCTAGGGGTCTTTCCCCTCTCGC

CAAAGGAATGCAAGGTCTGTTGAATGTCGTGAAGGAAGCAGTTCCTCTGGAAGCT

TCTTGAAGACAAACAACGTCTGTAGCGACCCTTTGCAGGCAGCGGAACCCCCCA

CCTGGCGACAGGTGCCTCTGCGGCCAAAAGCCACGTGTATAAGATACACCTGCA

AAGGCGGCACAACCCCAGTGCCACGTTGTGAGTTGGATAGTTGTGGAAAGAGTC

AAATGGCTCTCCTCAAGCGTATTCAACAAGGGGCTGAAGGATGCCCAGAAGGTAC

CCCATTGTATGGGATCTGATCTGGGGCCTCGGTGCACATGCTTTACATGTGTTTA

GTCGAGGTTAAAAAACGTCTAGGCCCCCCGAACCACGGGGACGTGGTTTTCCTTT

GAAAAACACGATGATAATATGGCCACAACCATGGCGCGCCGCCCGCGCTGGCTG

TGCGCTGGGGCGCTGGTGCTGGCGGGTGGCTTCTTTCTCCTCGGCTTCCTCTTC

GGGTGGTTTATAAAATCCTCCAATGAAGCTACTAACATTACTCCAAAGCATAATAT

GAAAGCATTTTTGGATGAATTGAAAGCTGAGAACATCAAGAAGTTCTTATATAATTT

TACACAGATACCACATTTAGCAGGAACAGAACAAAACTTTCAGCTTGCAAAGCAAA

-continued

TTCAATCCCAGTGGAAAGAATTTGGCCTGGATTCTGTTGAGCTGGCACATTATGAT

GTCCTGTTGTCCTACCCAAATAAGACTCATCCCAACTACATCTCAATAATTAATGA

AGATGGAAATGAGATTTTCAACACATCATTATTTGAACCACCTCCTCCAGGATATG

AAAATGTTTCGGATATTGTACCACCTTTCAGTGCTTTCTCTCCTCAAGGAATGCCA

GAGGGCGATCTAGTGTATGTTAACTATGCACGAACTGAAGACTTCTTTAAATTGGA

ACGGGACATGAAAATCAATTGCTCTGGGAAAATTGTAATTGCCAGATATGGGAAA

GTTTTCAGAGGAAATAAGGTTAAAAATGCCCAGCTGGCAGGGGCCAAAGGAGTCA

TTCTCTACTCCGACCCTGCTGACTACTTTGCTCCTGGGGTGAAGTCCTATCCAGA

TGGTTGGAATCTTCCTGGAGGTGGTGTCCAGCGTGGAAATATCCTAAATCTGAAT

GGTGCAGGAGACCCTCTCACACCAGGTTACCCAGCAAATGAATATGCTTATAGGC

GTGGAATTGCAGAGGCTGTTGGTCTTCCAAGTATTCCTGTTCATCCAATTGGATAC

TATGATGCACAGAAGCTCCTAGAAAAAATGGGTGGCTCAGCACCACCAGATAGCA

GCTGGAGAGGAAGTCTCAAAGTGCCCTACAATGTTGGACCTGGCTTTACTGGAAA

CTTTTCTACACAAAAAGTCAAGATGCACATCCACTCTACCAATGAAGTGACAAGAA

TTTACAATGTGATAGGTACTCTCAGAGGAGCAGTGGAACCAGACAGATATGTCAT

TCTGGGAGGTCACCGGGACTCATGGGTGTTTGGTGGTATTGACCCTCAGAGTGG

AGCAGCTGTTGTTCATGAAATTGTGAGGAGCTTTGGAACACTGAAAAAGGAAGGG

TGGAGACCTAGAAGAACAATTTTGTTTGCAAGCTGGGATGCAGAAGAATTTGGTC

TTCTTGGTTCTACTGAGTGGGCAGAGGAGAATTCAAGACTCCTTCAAGAGCGTGG

CGTGGCTTATATTAATGCTGACTCATCTATAGAAGGAAACTACACTCTGAGAGTTG

ATTGTACACCGCTGATGTACAGCTTGGTACACAACCTAACAAAAGAGCTGAAAAG

CCCTGATGAAGGCTTTGAAGGCAAATCTCTTTATGAAAGTTGGACTAAAAAAAGTC

CTTCCCCAGAGTTCAGTGGCATGCCCAGGATAAGCAAATTGGGATCTGGAAATGA

TTTTGAGGTGTTCTTCCAACGACTTGGAATTGCTTCAGGCAGAGCACGGTATACTA

AAAATTGGGAAACAAACAAATTCAGCGGCTATCCACTGTATCACAGTGTCTATGAA

ACATATGAGTTGGTGGAAAAGTTTTATGATCCAATGTTTAAATATCACCTCACTGT

GGCCCAGGTTCGAGGAGGGATGGTGTTTGAGCTGGCCAATTCCATAGTGCTCCC

TTTTGATTGTCGAGATTATGCTGTAGTTTTAAGAAAGTATGCTGACAAAATCTACAG

TATTTCTATGAAACATCCACAGGAAATGAAGACATACAGTGTATCATTTGATTCACT

TTTTTCTGCAGTAAAGAATTTTACAGAAATTGCTTCCAAGTTCAGTGAGAGACTCC

AGGACTTTGACAAAAGCAACCCAATAGTATTAAGAATGATGAATGATCAACTCATG

TTTCTGGAAAGAGCATTTATTGATCCATTAGGGTTACCAGACAGGCCTTTTTATAG

GCATGTCATCTATGCTCCAAGCAGCCACAACAAGTATGCAGGGGAGTCATTCCCA

GGAATTTATGATGCTCTGTTTGATATTGAAAGCAAAGTGGACCCTTCCAAGGCCTG

GGGAGAAGTGAAGAGACAGATTTATGTTGCAGCCTTCACAGTGCAGGCAGCTGC

AGAGACTTTGAGTGAAGTAGCCTAAAGATCTGGGCCCTAACAAAACAAAAAGATG

GGGTTATTCCCTAAACTTCATGGGTTACGTAATTGGAAGTTGGGGGACATTGCCA

CAAGATCATATTGTACAAAAGATCAAACACTGTTTTAGAAAACTTCCTGTAAACAG

GCCTATTGATTGGAAAGTATGTCAAAGGATTGTGGGTCTTTTGGGCTTTGCTGCTC

CATTTACACAATGTGGATATCCTGCCTTAATGCCTTTGTATGCATGTATACAAGCT

AAACAGGCTTTCACTTTCTCGCCAACTTACAAGGCCTTTCTAAGTAAACAGTACAT

-continued

GAACCTTTACCCCGTTGCTCGGCAACGGCCTGGTCTGTGCCAAGTGTTTGCTGAC

GCAACCCCCACTGGCTGGGGCTTGGCCATAGGCCATCAGCGCATGCGTGGAACC

TTTGTGGCTCCTCTGCCGATCCATACTGCGGAACTCCTAGCCGCTTGTTTTGCTC

GCAGCCGGTCTGGAGCAAAGCTCATAGGAACTGACAATTCTGTCGTCCTCTCGC

GGAAATATACATCGTTTCGATCTACGTATGATCTTTTTCCCTCTGCCAAAAATTATG

GGGACATCATGAAGCCCCTTGAGCATCTGACTTCTGGCTAATAAAGGAAATTTATT

TTCATTGCAATAGTGTGTTGGAATTTTTTGTGTCTCTCACTCGGAAGGAATTCTGC

ATTAATGAATCGGCCAACGCGCGGGGAGAGGCGGTTTGCGTATTGGGCGCTCTT

CCGCTTCCTCGCTCACTGACTCGCTGCGCTCGGTCGTTCGGCTGCGGCGAGCGG

TATCAGCTCACTCAAAGGCGGTAATACGGTTATCCACAGAATCAGGGGATAACGC

AGGAAAGAACATGTGAGCAAAAGGCCAGCAAAAGGCCAGGAACCGTAAAAAGGC

CGCGTTGCTGGCGTTTTTCCATAGGCTCCGCCCCCCTGACGAGCATCACAAAAAT

CGACGCTCAAGTCAGAGGTGGCGAAACCCGACAGGACTATAAAGATACCAGGCG

TTTCCCCCTGGAAGCTCCCTCGTGCGCTCTCCTGTTCCGACCCTGCCGCTTACCG

GATACCTGTCCGCCTTTCTCCCTTCGGGAAGCGTGGCGCTTTCTCATAGCTCACG

CTGTAGGTATCTCAGTTCGGTGTAGGTCGTTCGCTCCAAGCTGGGCTGTGTGCAC

GAACCCCCCGTTCAGCCCGACCGCTGCGCCTTATCCGGTAACTATCGTCTTGAGT

CCAACCCGGTAAGACACGACTTATCGCCACTGGCAGCAGCCACTGGTAACAGGA

TTAGCAGAGCGAGGTATGTAGGCGGTGCTACAGAGTTCTTGAAGTGGTGGCCTA

ACTACGGCTACACTAGAAGAACAGTATTTGGTATCTGCGCTCTGCTGAAGCCAGT

TACCTTCGGAAAAAGAGTTGGTAGCTCTTGATCCGGCAAACAAACCACCGCTGGT

AGCGGTGGTTTTTTTGTTTGCAAGCAGCAGATTACGCGCAGAAAAAAAGGATCTC

AAGAAGATCCTTTGATCTTTTCTACGGGGTCTGACGCTCAGTGGAACGAAAACTC

ACGTTAAGGGATTTTGGTCATGAGATTATCAAAAAGGATCTTCACCTAGATCCTTT

TAAATTAAAAATGAAGTTTTAAATCAATCTAAAGTATATATGAGTAAACTTGGTCTG

ACAGTTACCAATGCTTAATCAGTGAGGCACCTATCTCAGCGATCTGTCTATTTCGT

TCATCCATAGTTGCCTGACTC

NUCLEOTIDE SEQUENCE OF PLASMID 455.

SEQ ID NO: 32

GGCGTAATGCTCTGCCAGTGTTACAACCAATTAACCAATTCTGATTAGAAAAACTC

ATCGAGCATCAAATGAAACTGCAATTTATTCATATCAGGATTATCAATACCATATTT

TTGAAAAAGCCGTTTCTGTAATGAAGGAGAAAACTCACCGAGGCAGTTCCATAGG

ATGGCAAGATCCTGGTATCGGTCTGCGATTCCGACTCGTCCAACATCAATACAAC

CTATTAATTTCCCCTCGTCAAAAATAAGGTTATCAAGTGAGAAATCACCATGAGTG

ACGACTGAATCCGGTGAGAATGGCAAAAGCTTATGCATTTCTTTCCAGACTTGTTC

AACAGGCCAGCCATTACGCTCGTCATCAAAATCACTCGCATCAACCAAACCGTTA

TTCATTCGTGATTGCGCCTGAGCGAGACGAAATACGCGATCGCTGTTAAAAGGAC

AATTACAAACAGGAATCAAATGCAACCGGCGCAGGAACACTGCCAGCGCATCAAC

AATATTTTCACCTGAATCAGGATATTCTTCTAATACCTGGAATGCTGTTTTCCCGG

GGATCGCAGTGGTGAGTAACCATGCATCATCAGGAGTACGGATAAAATGCTTGAT

GGTCGGAAGAGGCATAAATTCCGTCAGCCAGTTTAGTCTGACCATCTCATCTGTA

-continued

ACATCATTGGCAACGCTACCTTTGCCATGTTTCAGAAACAACTCTGGCGCATCGG

GCTTCCCATACAATCGATAGATTGTCGCACCTGATTGCCCGACATTATCGCGAGC

CCATTTATACCCATATAAATCAGCATCCATGTTGGAATTTAATCGCGGCCTCGAGC

AAGACGTTTCCCGTTGAATATGGCTCATAACACCCCTTGTATTACTGTTTATGTAA

GCAGACAGGTCGACAATATTGGCTATTGGCCATTGCATACGTTGTATCTATATCAT

AATATGTACATTTATATTGGCTCATGTCCAATATGACCGCCATGTTGACATTGATTA

TTGACTAGTTATTAATAGTAATCAATTACGGGGTCATTAGTTCATAGCCCATATATG

GAGTTCCGCGTTACATAACTTACGGTAAATGGCCCGCCTGGCTGACCGCCCAAC

GACCCCCGCCCATTGACGTCAATAATGACGTATGTTCCCATAGTAACGCCAATAG

GGACTTTCCATTGACGTCAATGGGTGGAGTATTTACGGTAAACTGCCCACTTGGC

AGTACATCAAGTGTATCATATGCCAAGTCCGCCCCCTATTGACGTCAATGACGGT

AAATGGCCCGCCTGGCATTATGCCCAGTACATGACCTTACGGGACTTTCCTACTT

GGCAGTACATCTACGTATTAGTCATCGCTATTACCATGGTGATGCGGTTTTGGCA

GTACACCAATGGGCGTGGATAGCGGTTTGACTCACGGGGATTTCCAAGTCTCCAC

CCCATTGACGTCAATGGGAGTTTGTTTTGGCACCAAAATCAACGGGACTTTCCAA

AATGTCGTAATAACCCCGCCCCGTTGACGCAAATGGGCGGTAGGCGTGTACGGT

GGGAGGTCTATATAAGCAGAGCTCGTTTAGTGAACCGTCAGATCGCCTGGAGAC

GCCATCCACGCTGTTTTGACCTCCATAGAAGACACCGGGACCGATCCAGCCTCC

GCGGCCGGGAACGGTGCATTGGAACGCGGATTCCCCGTGCCAAGAGTGACTCA

CCGTCCGGATCTCAGCAAGCAGGTATGTACTCTCCAGGGTGGGCCTGGCTTCCC

CAGTCAAGACTCCAGGGATTTGAGGGACGCTGTGGGCTCTTCTCTTACATGTACC

TTTTGCTTGCCTCAACCCTGACTATCTTCCAGGTCAGGATCCCAGAGTCAGGGGT

CTGTATTTTCCTGCTGGTGGCTCCAGTTCAGGAACAGTAAACCCTGCTCCGAATA

TTGCCTCTCACATCTCGTCAATCTCCGCGAGGACTGGGGACCCTGTGACGAACAT

GGCTAGCAAGGCTGTGCTGCTTGCCCTGTTGATGGCAGGCTTGGCCCTGCAGCC

AGGCACTGCCCTGCTGTGCTACTCCTGCAAAGCCCAGGTGAGCAACGAGGACTG

CCTGCAGGTGGAGAACTGCACCCAGCTGGGGGAGCAGTGCTGGACCGCGCGCA

TCCGCGCAGTTGGCCTCCTGACCGTCATCAGCAAAGGCTGCAGCTTGAACTGCG

TGGATGACTCACAGGACTACTACGTGGGCAAGAAGAACATCACGTGCTGTGACAC

CGACTTGTGCAACGCCAGCGGGGCCCATGCCCTGCAGCCGGCTGCCGCCATCC

TTGCGCTGCTCCCTGCACTCGGCCTGCTGCTCTGGGGACCCGGCCAGCTATAGA

GATCTGACCCCCTAACGTTACTGGCCGAAGCCGCTTGGAATAAGGCCGGTGTGC

GTTTGTCTATATGTTATTTTCCACCATATTGCCGTCTTTTGGCAATGTGAGGGCCC

GGAAACCTGGCCCTGTCTTCTTGACGAGCATTCCTAGGGGTCTTTCCCCTCTCGC

CAAAGGAATGCAAGGTCTGTTGAATGTCGTGAAGGAAGCAGTTCCTCTGGAAGCT

TCTTGAAGACAAACAACGTCTGTAGCGACCCTTTGCAGGCAGCGGAACCCCCCA

CCTGGCGACAGGTGCCTCTGCGGCCAAAAGCCACGTGTATAAGATACACCTGCA

AAGGCGGCACAACCCCAGTGCCACGTTGTGAGTTGGATAGTTGTGGAAAGAGTC

AAATGGCTCTCCTCAAGCGTATTCAACAAGGGGCTGAAGGATGCCCAGAAGGTAC

CCCATTGTATGGGATCTGATCTGGGGCCTCGGTGCACATGCTTTACATGTGTTTA

GTCGAGGTTAAAAAACGTCTAGGCCCCCCGAACCACGGGGACGTGGTTTTCCTTT

-continued

GAAAAACACGATGATAATATGGCCAGCATTGTGGGAGGCTGGGAGTGCGAGAAG

CATTCCCAACCCTGGCAGGTGCTTGTGGCCTCTCGTGGCAGGGCAGTCTGCGGC

GGTGTTCTGGTGCACCCCCAGTGGGTCCTCACAGCTGCCCACTGCATCAGGAAC

AAAAGCGTGATCTTGCTGGGTCGGCACAGCTTGTTTCATCCTGAAGACACAGGCC

AGGTATTTCAGGTCAGCCACAGCTTCCCACACCCGCTCTACGATATGAGCCTCCT

GAAGAATCGATTCCTCAGGCCAGGTGATGACTCCAGCCACGACCTCATGCTGCTC

CGCCTGTCAGAGCCTGCCGAGCTCACGGATGCTGTGAAGGTCATGGACCTGCCC

ACCCAGGAGCCAGCACTGGGGACCACCTGCTACGCCTCAGGCTGGGGCAGCAT

TGAACCAGAGGAGTTCTTGACCCCAAAGAAACTTCAGTGTGTGGACCTCCATGTT

ATTTCCAATGACGTGTGTGCGCAAGTTCACCCTCAGAAGGTGACCAAGTTCATGC

TGTGTGCTGGACGCTGGACAGGGGGCAAAAGCACCTGCTCGGGTGATTCTGGG

GGCCCACTTGTCTGTAATGGTGTGCTTCAAGGTATCACGTCATGGGGCAGTGAAC

CATGTGCCCTGCCCGAAAGGCCTTCCCTGTACACCAAGGTGGTGCATTACCGGA

AGTGGATCAAGGACACCATCGTGGCCAACCCCTGAGGATCTGGGCCCTAACAAA

ACAAAAAGATGGGGTTATTCCCTAAACTTCATGGGTTACGTAATTGGAAGTTGGG

GGACATTGCCACAAGATCATATTGTACAAAAGATCAAACACTGTTTTAGAAAACTT

CCTGTAAACAGGCCTATTGATTGGAAAGTATGTCAAAGGATTGTGGGTCTTTTGG

GCTTTGCTGCTCCATTTACACAATGTGGATATCCTGCCTTAATGCCTTTGTATGCA

TGTATACAAGCTAAACAGGCTTTCACTTTCTCGCCAACTTACAAGGCCTTTCTAAG

TAAACAGTACATGAACCTTTACCCCGTTGCTCGGCAACGGCCTGGTCTGTGCCAA

GTGTTTGCTGACGCAACCCCCACTGGCTGGGGCTTGGCCATAGGCCATCAGCGC

ATGCGTGGAACCTTTGTGGCTCCTCTGCCGATCCATACTGCGGAACTCCTAGCCG

CTTGTTTTGCTCGCAGCCGGTCTGGAGCAAAGCTCATAGGAACTGACAATTCTGT

CGTCCTCTCGCGGAAATATACATCGTTTCGATCTACGTATGATCTTTTTCCCTCTG

CCAAAAATTATGGGGACATCATGAAGCCCCTTGAGCATCTGACTTCTGGCTAATAA

AGGAAATTTATTTTCATTGCAATAGTGTGTTGGAATTTTTTGTGTCTCTCACTCGGA

AGGAATTCTGCATTAATGAATCGGCCAACGCGCGGGGAGAGGCGGTTTGCGTAT

TGGGCGCTCTTCCGCTTCCTCGCTCACTGACTCGCTGCGCTCGGTCGTTCGGCT

GCGGCGAGCGGTATCAGCTCACTCAAAGGCGGTAATACGGTTATCCACAGAATC

AGGGGATAACGCAGGAAAGAACATGTGAGCAAAAGGCCAGCAAAAGGCCAGGAA

CCGTAAAAAGGCCGCGTTGCTGGCGTTTTTCCATAGGCTCCGCCCCCCTGACGA

GCATCACAAAAATCGACGCTCAAGTCAGAGGTGGCGAAACCCGACAGGACTATAA

AGATACCAGGCGTTTCCCCCTGGAAGCTCCCTCGTGCGCTCTCCTGTTCCGACC

CTGCCGCTTACCGGATACCTGTCCGCCTTTCTCCCTTCGGGAAGCGTGGCGCTTT

CTCATAGCTCACGCTGTAGGTATCTCAGTTCGGTGTAGGTCGTTCGCTCCAAGCT

GGGCTGTGTGCACGAACCCCCCGTTCAGCCCGACCGCTGCGCCTTATCCGGTAA

CTATCGTCTTGAGTCCAACCCGGTAAGACACGACTTATCGCCACTGGCAGCAGCC

ACTGGTAACAGGATTAGCAGAGCGAGGTATGTAGGCGGTGCTACAGAGTTCTTGA

AGTGGTGGCCTAACTACGGCTACACTAGAAGAACAGTATTTGGTATCTGCGCTCT

GCTGAAGCCAGTTACCTTCGGAAAAAGAGTTGGTAGCTCTTGATCCGGCAAACAA

-continued

ACCACCGCTGGTAGCGGTGGTTTTTTTGTTTGCAAGCAGCAGATTACGCGCAGAA

AAAAAGGATCTCAAGAAGATCCTTTGATCTTTTCTACGGGGTCTGACGCTCAGTG

GAACGAAAACTCACGTTAAGGGATTTTGGTCATGAGATTATCAAAAAGGATCTTCA

CCTAGATCCTTTTAAATTAAAAATGAAGTTTTAAATCAATCTAAAGTATATATGAGTA

AACTTGGTCTGACAGTTACCAATGCTTAATCAGTGAGGCACCTATCTCAGCGATCT

GTCTATTTCGTTCATCCATAGTTGCCTGACTC

NUCLEOTIDE SEQUENCE OF PLASMID 456.

SEQ ID NO: 33

GGCGTAATGCTCTGCCAGTGTTACAACCAATTAACCAATTCTGATTAGAAAAACTC

ATCGAGCATCAAATGAAACTGCAATTTATTCATATCAGGATTATCAATACCATATTT

TTGAAAAAGCCGTTTCTGTAATGAAGGAGAAAACTCACCGAGGCAGTTCCATAGG

ATGGCAAGATCCTGGTATCGGTCTGCGATTCCGACTCGTCCAACATCAATACAAC

CTATTAATTTCCCCTCGTCAAAAATAAGGTTATCAAGTGAGAAATCACCATGAGTG

ACGACTGAATCCGGTGAGAATGGCAAAAGCTTATGCATTTCTTTCCAGACTTGTTC

AACAGGCCAGCCATTACGCTCGTCATCAAAATCACTCGCATCAACCAAACCGTTA

TTCATTCGTGATTGCGCCTGAGCGAGACGAAATACGCGATCGCTGTTAAAAGGAC

AATTACAAACAGGAATCAAATGCAACCGGCGCAGGAACACTGCCAGCGCATCAAC

AATATTTTCACCTGAATCAGGATATTCTTCTAATACCTGGAATGCTGTTTTCCCGG

GGATCGCAGTGGTGAGTAACCATGCATCATCAGGAGTACGGATAAAATGCTTGAT

GGTCGGAAGAGGCATAAATTCCGTCAGCCAGTTTAGTCTGACCATCTCATCTGTA

ACATCATTGGCAACGCTACCTTTGCCATGTTTCAGAAACAACTCTGGCGCATCGG

GCTTCCCATACAATCGATAGATTGTCGCACCTGATTGCCCGACATTATCGCGAGC

CCATTTATACCCATATAAATCAGCATCCATGTTGGAATTTAATCGCGGCCTCGAGC

AAGACGTTTCCCGTTGAATATGGCTCATAACACCCCTTGTATTACTGTTTATGTAA

GCAGACAGGTCGACAATATTGGCTATTGGCCATTGCATACGTTGTATCTATATCAT

AATATGTACATTTATATTGGCTCATGTCCAATATGACCGCCATGTTGACATTGATTA

TTGACTAGTTATTAATAGTAATCAATTACGGGGTCATTAGTTCATAGCCCATATATG

GAGTTCCGCGTTACATAACTTACGGTAAATGGCCCGCCTGGCTGACCGCCCAAC

GACCCCCGCCCATTGACGTCAATAATGACGTATGTTCCCATAGTAACGCCAATAG

GGACTTTCCATTGACGTCAATGGGTGGAGTATTTACGGTAAACTGCCCACTTGGC

AGTACATCAAGTGTATCATATGCCAAGTCCGCCCCCTATTGACGTCAATGACGGT

AAATGGCCCGCCTGGCATTATGCCCAGTACATGACCTTACGGGACTTTCCTACTT

GGCAGTACATCTACGTATTAGTCATCGCTATTACCATGGTGATGCGGTTTTGGCA

GTACACCAATGGGCGTGGATAGCGGTTTGACTCACGGGGATTTCCAAGTCTCCAC

CCCATTGACGTCAATGGGAGTTTGTTTTGGCACCAAAATCAACGGGACTTTCCAA

AATGTCGTAATAACCCCGCCCCGTTGACGCAAATGGGCGGTAGGCGTGTACGGT

GGGAGGTCTATATAAGCAGAGCTCGTTTAGTGAACCGTCAGATCGCCTGGAGAC

GCCATCCACGCTGTTTTGACCTCCATAGAAGACACCGGGACCGATCCAGCCTCC

GCGGCCGGGAACGGTGCATTGGAACGCGGATTCCCCGTGCCAAGAGTGACTCA

CCGTCCGGATCTCAGCAAGCAGGTATGTACTCTCCAGGGTGGGCCTGGCTTCCC

CAGTCAAGACTCCAGGGATTTGAGGGACGCTGTGGGCTCTTCTCTTACATGTACC

TTTTGCTTGCCTCAACCCTGACTATCTTCCAGGTCAGGATCCCAGAGTCAGGGGT

-continued

```
CTGTATTTTCCTGCTGGTGGCTCCAGTTCAGGAACAGTAAACCCTGCTCCGAATA
TTGCCTCTCACATCTCGTCAATCTCCGCGAGGACTGGGGACCCTGTGACGAACAT
GGCTAGCATTGTGGGAGGCTGGGAGTGCGAGAAGCATTCCCAACCCTGGCAGGT
GCTTGTGGCCTCTCGTGGCAGGGCAGTCTGCGGCGGTGTTCTGGTGCACCCCCA
GTGGGTCCTCACAGCTGCCCACTGCATCAGGAACAAAAGCGTGATCTTGCTGGG
TCGGCACAGCTTGTTTCATCCTGAAGACACAGGCCAGGTATTTCAGGTCAGCCAC
AGCTTCCCACACCCGCTCTACGATATGAGCCTCCTGAAGAATCGATTCCTCAGGC
CAGGTGATGACTCCAGCCACGACCTCATGCTGCTCCGCCTGTCAGAGCCTGCCG
AGCTCACGGATGCTGTGAAGGTCATGGACCTGCCCACCCAGGAGCCAGCACTGG
GGACCACCTGCTACGCCTCAGGCTGGGGCAGCATTGAACCAGAGGAGTTCTTGA
CCCCAAAGAAACTTCAGTGTGTGGACCTCCATGTTATTTCCAATGACGTGTGTGC
GCAAGTTCACCCTCAGAAGGTGACCAAGTTCATGCTGTGTGCTGGACGCTGGAC
AGGGGGCAAAAGCACCTGCTCGGGTGATTCTGGGGGCCCACTTGTCTGTAATGG
TGTGCTTCAAGGTATCACGTCATGGGGCAGTGAACCATGTGCCCTGCCCGAAAG
GCCTTCCCTGTACACCAAGGTGGTGCATTACCGGAAGTGGATCAAGGACACCATC
GTGGCCAACCCCGGATCCCAGACCCTGAACTTTGATCTGCTGAAACTGGCAGGC
GATGTGGAAAGCAACCCAGGCCCAATGGCAAGCGCGCGCCGCCCGCGCTGGCT
GTGCGCTGGGGCGCTGGTGCTGGCGGGTGGCTTCTTTCTCCTCGGCTTCCTCTT
CGGGTGGTTTATAAAATCCTCCAATGAAGCTACTAACATTACTCCAAAGCATAATA
TGAAAGCATTTTTGGATGAATTGAAAGCTGAGAACATCAAGAAGTTCTTATATAATT
TTACACAGATACCACATTTAGCAGGAACAGAACAAAACTTTCAGCTTGCAAAGCAA
ATTCAATCCCAGTGGAAAGAATTTGGCCTGGATTCTGTTGAGCTGGCACATTATGA
TGTCCTGTTGTCCTACCCAAATAAGACTCATCCCAACTACATCTCAATAATTAATGA
AGATGGAAATGAGATTTTCAACACATCATTATTTGAACCACCTCCTCCAGGATATG
AAAATGTTTCGGATATTGTACCACCTTTCAGTGCTTTCTCTCCTCAAGGAATGCCA
GAGGGCGATCTAGTGTATGTTAACTATGCACGAACTGAAGACTTCTTTAAATTGGA
ACGGGACATGAAAATCAATTGCTCTGGGAAAATTGTAATTGCCAGATATGGGAAA
GTTTTCAGAGGAAATAAGGTTAAAAATGCCCAGCTGGCAGGGGCCAAAGGAGTCA
TTCTCTACTCCGACCCTGCTGACTACTTTGCTCCTGGGGTGAAGTCCTATCCAGA
TGGTTGGAATCTTCCTGGAGGTGGTGTCCAGCGTGGAAATATCCTAAATCTGAAT
GGTGCAGGAGACCCTCTCACACCAGGTTACCCAGCAAATGAATATGCTTATAGGC
GTGGAATTGCAGAGGCTGTTGGTCTTCCAAGTATTCCTGTTCATCCAATTGGATAC
TATGATGCACAGAAGCTCCTAGAAAAAATGGGTGGCTCAGCACCACCAGATAGCA
GCTGGAGAGGAAGTCTCAAAGTGCCCTACAATGTTGGACCTGGCTTTACTGGAAA
CTTTTCTACACAAAAAGTCAAGATGCACATCCACTCTACCAATGAAGTGACAAGAA
TTTACAATGTGATAGGTACTCTCAGAGGAGCAGTGGAACCAGACAGATATGTCAT
TCTGGGAGGTCACCGGGACTCATGGGTGTTTGGTGGTATTGACCCTCAGAGTGG
AGCAGCTGTTGTTCATGAAATTGTGAGGAGCTTTGGAACACTGAAAAAGGAAGGG
TGGAGACCTAGAAGAACAATTTTGTTTGCAAGCTGGGATGCAGAAGAATTTGGTC
TTCTTGGTTCTACTGAGTGGGCAGAGGAGAATTCAAGACTCCTTCAAGAGCGTGG
```

-continued

CGTGGCTTATATTAATGCTGACTCATCTATAGAAGGAAACTACACTCTGAGAGTTG

ATTGTACACCGCTGATGTACAGCTTGGTACACAACCTAACAAAAGAGCTGAAAAG

CCCTGATGAAGGCTTTGAAGGCAAATCTCTTTATGAAAGTTGGACTAAAAAAAGTC

CTTCCCCAGAGTTCAGTGGCATGCCCAGGATAAGCAAATTGGGATCTGGAAATGA

TTTTGAGGTGTTCTTCCAACGACTTGGAATTGCTTCAGGCAGAGCACGGTATACTA

AAAATTGGGAAACAAACAAATTCAGCGGCTATCCACTGTATCACAGTGTCTATGAA

ACATATGAGTTGGTGGAAAAGTTTTATGATCCAATGTTTAAATATCACCTCACTGT

GGCCCAGGTTCGAGGAGGGATGGTGTTTGAGCTGGCCAATTCCATAGTGCTCCC

TTTTGATTGTCGAGATTATGCTGTAGTTTTAAGAAAGTATGCTGACAAAATCTACAG

TATTTCTATGAAACATCCACAGGAAATGAAGACATACAGTGTATCATTTGATTCACT

TTTTTCTGCAGTAAAGAATTTTACAGAAATTGCTTCCAAGTTCAGTGAGAGACTCC

AGGACTTTGACAAAAGCAACCCAATAGTATTAAGAATGATGAATGATCAACTCATG

TTTCTGGAAAGAGCATTTATTGATCCATTAGGGTTACCAGACAGGCCTTTTTATAG

GCATGTCATCTATGCTCCAAGCAGCCACAACAAGTATGCAGGGGAGTCATTCCCA

GGAATTTATGATGCTCTGTTTGATATTGAAAGCAAAGTGGACCCTTCCAAGGCCTG

GGGAGAAGTGAAGAGACAGATTTATGTTGCAGCCTTCACAGTGCAGGCAGCTGC

AGAGACTTTGAGTGAAGTAGCCTAAAGATCTGACCCCCTAACGTTACTGGCCGAA

GCCGCTTGGAATAAGGCCGGTGTGCGTTTGTCTATATGTTATTTTCCACCATATTG

CCGTCTTTTGGCAATGTGAGGGCCCGGAAACCTGGCCCTGTCTTCTTGACGAGC

ATTCCTAGGGGTCTTTCCCCTCTCGCCAAAGGAATGCAAGGTCTGTTGAATGTCG

TGAAGGAAGCAGTTCCTCTGGAAGCTTCTTGAAGACAAACAACGTCTGTAGCGAC

CCTTTGCAGGCAGCGGAACCCCCCACCTGGCGACAGGTGCCTCTGCGGCCAAAA

GCCACGTGTATAAGATACACCTGCAAAGGCGGCACAACCCCAGTGCCACGTTGT

GAGTTGGATAGTTGTGGAAAGAGTCAAATGGCTCTCCTCAAGCGTATTCAACAAG

GGGCTGAAGGATGCCCAGAAGGTACCCCATTGTATGGGATCTGATCTGGGGCCT

CGGTGCACATGCTTTACATGTGTTTAGTCGAGGTTAAAAAACGTCTAGGCCCCCC

GAACCACGGGGACGTGGTTTTCCTTTGAAAAACACGATGATAATATGGCCAGCAA

GGCTGTGCTGCTTGCCCTGTTGATGGCAGGCTTGGCCCTGCAGCCAGGCACTGC

CCTGCTGTGCTACTCCTGCAAAGCCCAGGTGAGCAACGAGGACTGCCTGCAGGT

GGAGAACTGCACCCAGCTGGGGGAGCAGTGCTGGACCGCGCGCATCCGCGCAG

TTGGCCTCCTGACCGTCATCAGCAAAGGCTGCAGCTTGAACTGCGTGGATGACTC

ACAGGACTACTACGTGGGCAAGAAGAACATCACGTGCTGTGACACCGACTTGTG

CAACGCCAGCGGGGCCCATGCCCTGCAGCCGGCTGCCGCCATCCTTGCGCTGC

TCCCTGCACTCGGCCTGCTGCTCTGGGGACCCGGCCAGCTATAGGGATCTGGGC

CCTAACAAAACAAAAAGATGGGGTTATTCCCTAAACTTCATGGGTTACGTAATTGG

AAGTTGGGGGACATTGCCACAAGATCATATTGTACAAAAGATCAAACACTGTTTTA

GAAAACTTCCTGTAAACAGGCCTATTGATTGGAAAGTATGTCAAAGGATTGTGGGT

CTTTTGGGCTTTGCTGCTCCATTTACACAATGTGGATATCCTGCCTTAATGCCTTT

GTATGCATGTATACAAGCTAAACAGGCTTTCACTTTCTCGCCAACTTACAAGGCCT

TTCTAAGTAAACAGTACATGAACCTTTACCCCGTTGCTCGGCAACGGCCTGGTCT

GTGCCAAGTGTTTGCTGACGCAACCCCCACTGGCTGGGGCTTGGCCATAGGCCA

-continued

TCAGCGCATGCGTGGAACCTTTGTGGCTCCTCTGCCGATCCATACTGCGGAACTC

CTAGCCGCTTGTTTTGCTCGCAGCCGGTCTGGAGCAAAGCTCATAGGAACTGACA

ATTCTGTCGTCCTCTCGCGGAAATATACATCGTTTCGATCTACGTATGATCTTTTTC

CCTCTGCCAAAAATTATGGGGACATCATGAAGCCCCTTGAGCATCTGACTTCTGG

CTAATAAAGGAAATTTATTTTCATTGCAATAGTGTGTTGGAATTTTTTGTGTCTCTC

ACTCGGAAGGAATTCTGCATTAATGAATCGGCCAACGCGCGGGGAGAGGCGGTT

TGCGTATTGGGCGCTCTTCCGCTTCCTCGCTCACTGACTCGCTGCGCTCGGTCGT

TCGGCTGCGGCGAGCGGTATCAGCTCACTCAAAGGCGGTAATACGGTTATCCAC

AGAATCAGGGGATAACGCAGGAAAGAACATGTGAGCAAAAGGCCAGCAAAAGGC

CAGGAACCGTAAAAAGGCCGCGTTGCTGGCGTTTTTCCATAGGCTCCGCCCCCC

TGACGAGCATCACAAAAATCGACGCTCAAGTCAGAGGTGGCGAAACCCGACAGG

ACTATAAAGATACCAGGCGTTTCCCCCTGGAAGCTCCCTCGTGCGCTCTCCTGTT

CCGACCCTGCCGCTTACCGGATACCTGTCCGCCTTTCTCCCTTCGGGAAGCGTG

GCGCTTTCTCATAGCTCACGCTGTAGGTATCTCAGTTCGGTGTAGGTCGTTCGCT

CCAAGCTGGGCTGTGTGCACGAACCCCCCGTTCAGCCCGACCGCTGCGCCTTAT

CCGGTAACTATCGTCTTGAGTCCAACCCGGTAAGACACGACTTATCGCCACTGGC

AGCAGCCACTGGTAACAGGATTAGCAGAGCGAGGTATGTAGGCGGTGCTACAGA

GTTCTTGAAGTGGTGGCCTAACTACGGCTACACTAGAAGAACAGTATTTGGTATCT

GCGCTCTGCTGAAGCCAGTTACCTTCGGAAAAAGAGTTGGTAGCTCTTGATCCGG

CAAACAAACCACCGCTGGTAGCGGTGGTTTTTTTGTTTGCAAGCAGCAGATTACG

CGCAGAAAAAAAGGATCTCAAGAAGATCCTTTGATCTTTTCTACGGGGTCTGACG

CTCAGTGGAACGAAAACTCACGTTAAGGGATTTTGGTCATGAGATTATCAAAAAG

GATCTTCACCTAGATCCTTTTAAATTAAAAATGAAGTTTTAAATCAATCTAAAGTATA

TATGAGTAAACTTGGTCTGACAGTTACCAATGCTTAATCAGTGAGGCACCTATCTC

AGCGATCTGTCTATTTCGTTCATCCATAGTTGCCTGACTC

NUCLEOTIDE SEQUENCE OF PLASMID 457.

SEQ ID NO: 34

GGCGTAATGCTCTGCCAGTGTTACAACCAATTAACCAATTCTGATTAGAAAAACTC

ATCGAGCATCAAATGAAACTGCAATTTATTCATATCAGGATTATCAATACCATATTT

TTGAAAAAGCCGTTTCTGTAATGAAGGAGAAAACTCACCGAGGCAGTTCCATAGG

ATGGCAAGATCCTGGTATCGGTCTGCGATTCCGACTCGTCCAACATCAATACAAC

CTATTAATTTCCCCTCGTCAAAAATAAGGTTATCAAGTGAGAAATCACCATGAGTG

ACGACTGAATCCGGTGAGAATGGCAAAAGCTTATGCATTTCTTTCCAGACTTGTTC

AACAGGCCAGCCATTACGCTCGTCATCAAAATCACTCGCATCAACCAAACCGTTA

TTCATTCGTGATTGCGCCTGAGCGAGACGAAATACGCGATCGCTGTTAAAAGGAC

AATTACAAACAGGAATCAAATGCAACCGGCGCAGGAACACTGCCAGCGCATCAAC

AATATTTTCACCTGAATCAGGATATTCTTCTAATACCTGGAATGCTGTTTTTCCCGG

GGATCGCAGTGGTGAGTAACCATGCATCATCAGGAGTACGGATAAAATGCTTGAT

GGTCGGAAGAGGCATAAATTCCGTCAGCCAGTTTAGTCTGACCATCTCATCTGTA

ACATCATTGGCAACGCTACCTTTGCCATGTTTCAGAAACAACTCTGGCGCATCGG

GCTTCCCATACAATCGATAGATTGTCGCACCTGATTGCCCGACATTATCGCGAGC

-continued

CCATTTATACCCATATAAATCAGCATCCATGTTGGAATTTAATCGCGGCCTCGAGC

AAGACGTTTCCCGTTGAATATGGCTCATAACACCCCTTGTATTACTGTTTATGTAA

GCAGACAGGTCGACAATATTGGCTATTGGCCATTGCATACGTTGTATCTATATCAT

AATATGTACATTTATATTGGCTCATGTCCAATATGACCGCCATGTTGACATTGATTA

TTGACTAGTTATTAATAGTAATCAATTACGGGGTCATTAGTTCATAGCCCATATATG

GAGTTCCGCGTTACATAACTTACGGTAAATGGCCCGCCTGGCTGACCGCCCAAC

GACCCCCGCCCATTGACGTCAATAATGACGTATGTTCCCATAGTAACGCCAATAG

GGACTTTCCATTGACGTCAATGGGTGGAGTATTTACGGTAAACTGCCCACTTGGC

AGTACATCAAGTGTATCATATGCCAAGTCCGCCCCCTATTGACGTCAATGACGGT

AAATGGCCCGCCTGGCATTATGCCCAGTACATGACCTTACGGGACTTTCCTACTT

GGCAGTACATCTACGTATTAGTCATCGCTATTACCATGGTGATGCGGTTTTGGCA

GTACACCAATGGGCGTGGATAGCGGTTTGACTCACGGGGATTTCCAAGTCTCCAC

CCCATTGACGTCAATGGGAGTTTGTTTTGGCACCAAAATCAACGGGACTTTCCAA

AATGTCGTAATAACCCCGCCCCGTTGACGCAAATGGGCGGTAGGCGTGTACGGT

GGGAGGTCTATATAAGCAGAGCTCGTTTAGTGAACCGTCAGATCGCCTGGAGAC

GCCATCCACGCTGTTTTGACCTCCATAGAAGACACCGGGACCGATCCAGCCTCC

GCGGCCGGGAACGGTGCATTGGAACGCGGATTCCCCGTGCCAAGAGTGACTCA

CCGTCCGGATCTCAGCAAGCAGGTATGTACTCTCCAGGGTGGGCCTGGCTTCCC

CAGTCAAGACTCCAGGGATTTGAGGGACGCTGTGGGCTCTTCTCTTACATGTACC

TTTTGCTTGCCTCAACCCTGACTATCTTCCAGGTCAGGATCCCAGAGTCAGGGGT

CTGTATTTTCCTGCTGGTGGCTCCAGTTCAGGAACAGTAAACCCTGCTCCGAATA

TTGCCTCTCACATCTCGTCAATCTCCGCGAGGACTGGGGACCCTGTGACGAACAT

GGCTAGCATTGTGGGAGGCTGGGAGTGCGAGAAGCATTCCCAACCCTGGCAGGT

GCTTGTGGCCTCTCGTGGCAGGGCAGTCTGCGGCGGTGTTCTGGTGCACCCCCA

GTGGGTCCTCACAGCTGCCCACTGCATCAGGAACAAAAGCGTGATCTTGCTGGG

TCGGCACAGCTTGTTTCATCCTGAAGACACAGGCCAGGTATTTCAGGTCAGCCAC

AGCTTCCCACACCCGCTCTACGATATGAGCCTCCTGAAGAATCGATTCCTCAGGC

CAGGTGATGACTCCAGCCACGACCTCATGCTGCTCCGCCTGTCAGAGCCTGCCG

AGCTCACGGATGCTGTGAAGGTCATGGACCTGCCCACCCAGGAGCCAGCACTGG

GGACCACCTGCTACGCCTCAGGCTGGGGCAGCATTGAACCAGAGGAGTTCTTGA

CCCCAAAGAAACTTCAGTGTGTGGACCTCCATGTTATTTCCAATGACGTGTGTGC

GCAAGTTCACCCTCAGAAGGTGACCAAGTTCATGCTGTGTGCTGGACGCTGGAC

AGGGGGCAAAAGCACCTGCTCGGGTGATTCTGGGGGCCCACTTGTCTGTAATGG

TGTGCTTCAAGGTATCACGTCATGGGGCAGTGAACCATGTGCCCTGCCCGAAAG

GCCTTCCCTGTACACCAAGGTGGTGCATTACCGGAAGTGGATCAAGGACACCATC

GTGGCCAACCCCGGATCCCAGACCCTGAACTTTGATCTGCTGAAACTGGCAGGC

GATGTGGAAAGCAACCCAGGCCCAATGGCAAGCGCGCGCCGCCCCGCGCTGGCT

GTGCGCTGGGGCGCTGGTGCTGGCGGGTGGCTTCTTTCTCCTCGGCTTCCTCTT

CGGGTGGTTTATAAAATCCTCCAATGAAGCTACTAACATTACTCCAAAGCATAATA

TGAAAGCATTTTTGGATGAATTGAAAGCTGAGAACATCAAGAAGTTCTTATATAATT

TTACACAGATACCACATTTAGCAGGAACAGAACAAAACTTTCAGCTTGCAAAGCAA

-continued

ATTCAATCCCAGTGGAAAGAATTTGGCCTGGATTCTGTTGAGCTGGCACATTATGA

TGTCCTGTTGTCCTACCCAAATAAGACTCATCCCAACTACATCTCAATAATTAATGA

AGATGGAAATGAGATTTTCAACACATCATTATTTGAACCACCTCCTCCAGGATATG

AAAATGTTTCGGATATTGTACCACCTTTCAGTGCTTTCTCTCCTCAAGGAATGCCA

GAGGGCGATCTAGTGTATGTTAACTATGCACGAACTGAAGACTTCTTTAAATTGGA

ACGGGACATGAAAATCAATTGCTCTGGGAAAATTGTAATTGCCAGATATGGGAAA

GTTTTCAGAGGAAATAAGGTTAAAAATGCCCAGCTGGCAGGGGCCAAAGGAGTCA

TTCTCTACTCCGACCCTGCTGACTACTTTGCTCCTGGGGTGAAGTCCTATCCAGA

TGGTTGGAATCTTCCTGGAGGTGGTGTCCAGCGTGGAAATATCCTAAATCTGAAT

GGTGCAGGAGACCCTCTCACACCAGGTTACCCAGCAAATGAATATGCTTATAGGC

GTGGAATTGCAGAGGCTGTTGGTCTTCCAAGTATTCCTGTTCATCCAATTGGATAC

TATGATGCACAGAAGCTCCTAGAAAAAATGGGTGGCTCAGCACCACCAGATAGCA

GCTGGAGAGGAAGTCTCAAAGTGCCCTACAATGTTGGACCTGGCTTTACTGGAAA

CTTTTCTACACAAAAAGTCAAGATGCACATCCACTCTACCAATGAAGTGACAAGAA

TTTACAATGTGATAGGTACTCTCAGAGGAGCAGTGGAACCAGACAGATATGTCAT

TCTGGGAGGTCACCGGGACTCATGGGTGTTTGGTGGTATTGACCCTCAGAGTGG

AGCAGCTGTTGTTCATGAAATTGTGAGGAGCTTTGGAACACTGAAAAAGGAAGGG

TGGAGACCTAGAAGAACAATTTTGTTTGCAAGCTGGGATGCAGAAGAATTTGGTC

TTCTTGGTTCTACTGAGTGGGCAGAGGAGAATTCAAGACTCCTTCAAGAGCGTGG

CGTGGCTTATATTAATGCTGACTCATCTATAGAAGGAAACTACACTCTGAGAGTTG

ATTGTACACCGCTGATGTACAGCTTGGTACACAACCTAACAAAAGAGCTGAAAAG

CCCTGATGAAGGCTTTGAAGGCAAATCTCTTTATGAAAGTTGGACTAAAAAAAGTC

CTTCCCCAGAGTTCAGTGGCATGCCCAGGATAAGCAAATTGGGATCTGGAAATGA

TTTTGAGGTGTTCTTCCAACGACTTGGAATTGCTTCAGGCAGAGCACGGTATACTA

AAAATTGGGAAACAAACAAATTCAGCGGCTATCCACTGTATCACAGTGTCTATGAA

ACATATGAGTTGGTGGAAAAGTTTTATGATCCAATGTTTAAATATCACCTCACTGT

GGCCCAGGTTCGAGGAGGGATGGTGTTTGAGCTGGCCAATTCCATAGTGCTCCC

TTTTGATTGTCGAGATTATGCTGTAGTTTTAAGAAAGTATGCTGACAAAATCTACAG

TATTTCTATGAAACATCCACAGGAAATGAAGACATACAGTGTATCATTTGATTCACT

TTTTTCTGCAGTAAAGAATTTTACAGAAATTGCTTCCAAGTTCAGTGAGAGACTCC

AGGACTTTGACAAAAGCAACCCAATAGTATTAAGAATGATGAATGATCAACTCATG

TTTCTGGAAAGAGCATTTATTGATCCATTAGGGTTACCAGACAGGCCTTTTTATAG

GCATGTCATCTATGCTCCAAGCAGCCACAACAAGTATGCAGGGGAGTCATTCCCA

GGAATTTATGATGCTCTGTTTGATATTGAAAGCAAAGTGGACCCTTCCAAGGCCTG

GGGAGAAGTGAAGAGACAGATTTATGTTGCAGCCTTCACAGTGCAGGCAGCTGC

AGAGACTTTGAGTGAAGTAGCCGGATCCGAAGGTAGGGGTTCATTATTGACCTGT

GGAGATGTCGAAGAAAACCCAGGACCCGCAAGCAAGGCTGTGCTGCTTGCCCTG

TTGATGGCAGGCTTGGCCCTGCAGCCAGGCACTGCCCTGCTGTGCTACTCCTGC

AAAGCCCAGGTGAGCAACGAGGACTGCCTGCAGGTGGAGAACTGCACCCAGCTG

GGGGAGCAGTGCTGGACCGCGCGCATCCGCGCAGTTGGCCTCCTGACCGTCAT

-continued

CAGCAAAGGCTGCAGCTTGAACTGCGTGGATGACTCACAGGACTACTACGTGGG

CAAGAAGAACATCACGTGCTGTGACACCGACTTGTGCAACGCCAGCGGGGCCCA

TGCCCTGCAGCCGGCTGCCGCCATCCTTGCGCTGCTCCCTGCACTCGGCCTGCT

GCTCTGGGGACCCGGCCAGCTATAGAGATCTGGGCCCTAACAAAACAAAAAGAT

GGGGTTATTCCCTAAACTTCATGGGTTACGTAATTGGAAGTTGGGGGACATTGCC

ACAAGATCATATTGTACAAAAGATCAAACACTGTTTTAGAAAACTTCCTGTAAACAG

GCCTATTGATTGGAAAGTATGTCAAAGGATTGTGGGTCTTTTGGGCTTTGCTGCTC

CATTTACACAATGTGGATATCCTGCCTTAATGCCTTTGTATGCATGTATACAAGCT

AAACAGGCTTTCACTTTCTCGCCAACTTACAAGGCCTTTCTAAGTAAACAGTACAT

GAACCTTTACCCCGTTGCTCGGCAACGGCCTGGTCTGTGCCAAGTGTTTGCTGAC

GCAACCCCCACTGGCTGGGGCTTGGCCATAGGCCATCAGCGCATGCGTGGAACC

TTTGTGGCTCCTCTGCCGATCCATACTGCGGAACTCCTAGCCGCTTGTTTTGCTC

GCAGCCGGTCTGGAGCAAAGCTCATAGGAACTGACAATTCTGTCGTCCTCTCGC

GGAAATATACATCGTTTCGATCTACGTATGATCTTTTTCCCTCTGCCAAAAATTATG

GGGACATCATGAAGCCCCTTGAGCATCTGACTTCTGGCTAATAAAGGAAATTTATT

TTCATTGCAATAGTGTGTTGGAATTTTTTGTGTCTCTCACTCGGAAGGAATTCTGC

ATTAATGAATCGGCCAACGCGCGGGGAGAGGCGGTTTGCGTATTGGGCGCTCTT

CCGCTTCCTCGCTCACTGACTCGCTGCGCTCGGTCGTTCGGCTGCGGCGAGCGG

TATCAGCTCACTCAAAGGCGGTAATACGGTTATCCACAGAATCAGGGGATAACGC

AGGAAAGAACATGTGAGCAAAAGGCCAGCAAAAGGCCAGGAACCGTAAAAAGGC

CGCGTTGCTGGCGTTTTTCCATAGGCTCCGCCCCCCTGACGAGCATCACAAAAAT

CGACGCTCAAGTCAGAGGTGGCGAAACCCGACAGGACTATAAAGATACCAGGCG

TTTCCCCCTGGAAGCTCCCTCGTGCGCTCTCCTGTTCCGACCCTGCCGCTTACCG

GATACCTGTCCGCCTTTCTCCCTTCGGGAAGCGTGGCGCTTTCTCATAGCTCACG

CTGTAGGTATCTCAGTTCGGTGTAGGTCGTTCGCTCCAAGCTGGGCTGTGTGCAC

GAACCCCCCGTTCAGCCCGACCGCTGCGCCTTATCCGGTAACTATCGTCTTGAGT

CCAACCCGGTAAGACACGACTTATCGCCACTGGCAGCAGCCACTGGTAACAGGA

TTAGCAGAGCGAGGTATGTAGGCGGTGCTACAGAGTTCTTGAAGTGGTGGCCTA

ACTACGGCTACACTAGAAGAACAGTATTTGGTATCTGCGCTCTGCTGAAGCCAGT

TACCTTCGGAAAAAGAGTTGGTAGCTCTTGATCCGGCAAACAAACCACCGCTGGT

AGCGGTGGTTTTTTTGTTTGCAAGCAGCAGATTACGCGCAGAAAAAAAGGATCTC

AAGAAGATCCTTTGATCTTTTCTACGGGGTCTGACGCTCAGTGGAACGAAAACTC

ACGTTAAGGGATTTTGGTCATGAGATTATCAAAAAGGATCTTCACCTAGATCCTTT

TAAATTAAAAATGAAGTTTTAAATCAATCTAAAGTATATATGAGTAAACTTGGTCTG

ACAGTTACCAATGCTTAATCAGTGAGGCACCTATCTCAGCGATCTGTCTATTTCGT

TCATCCATAGTTGCCTGACTC

NUCLEOTIDE SEQUENCE OF PLASMID 458.

SEQ ID NO: 35

GGCGTAATGCTCTGCCAGTGTTACAACCAATTAACCAATTCTGATTAGAAAAACTC

ATCGAGCATCAAATGAAACTGCAATTTATTCATATCAGGATTATCAATACCATATTT

TTGAAAAAGCCGTTTCTGTAATGAAGGAGAAAACTCACCGAGGCAGTTCCATAGG

ATGGCAAGATCCTGGTATCGGTCTGCGATTCCGACTCGTCCAACATCAATACAAC

-continued

CTATTAATTTCCCCTCGTCAAAAATAAGGTTATCAAGTGAGAAATCACCATGAGTG

ACGACTGAATCCGGTGAGAATGGCAAAAGCTTATGCATTTCTTTCCAGACTTGTTC

AACAGGCCAGCCATTACGCTCGTCATCAAAATCACTCGCATCAACCAAACCGTTA

TTCATTCGTGATTGCGCCTGAGCGAGACGAAATACGCGATCGCTGTTAAAAGGAC

AATTACAAACAGGAATCAAATGCAACCGGCGCAGGAACACTGCCAGCGCATCAAC

AATATTTTCACCTGAATCAGGATATTCTTCTAATACCTGGAATGCTGTTTTCCCGG

GGATCGCAGTGGTGAGTAACCATGCATCATCAGGAGTACGGATAAAATGCTTGAT

GGTCGGAAGAGGCATAAATTCCGTCAGCCAGTTTAGTCTGACCATCTCATCTGTA

ACATCATTGGCAACGCTACCTTTGCCATGTTTCAGAAACAACTCTGGCGCATCGG

GCTTCCCATACAATCGATAGATTGTCGCACCTGATTGCCCGACATTATCGCGAGC

CCATTTATACCCATATAAATCAGCATCCATGTTGGAATTTAATCGCGGCCTCGAGC

AAGACGTTTCCCGTTGAATATGGCTCATAACACCCCTTGTATTACTGTTTATGTAA

GCAGACAGGTCGACAATATTGGCTATTGGCCATTGCATACGTTGTATCTATATCAT

AATATGTACATTTATATTGGCTCATGTCCAATATGACCGCCATGTTGACATTGATTA

TTGACTAGTTATTAATAGTAATCAATTACGGGGTCATTAGTTCATAGCCCATATATG

GAGTTCCGCGTTACATAACTTACGGTAAATGGCCCGCCTGGCTGACCGCCCAAC

GACCCCCGCCCATTGACGTCAATAATGACGTATGTTCCCATAGTAACGCCAATAG

GGACTTTCCATTGACGTCAATGGGTGGAGTATTTACGGTAAACTGCCCACTTGGC

AGTACATCAAGTGTATCATATGCCAAGTCCGCCCCCTATTGACGTCAATGACGGT

AAATGGCCCGCCTGGCATTATGCCCAGTACATGACCTTACGGGACTTTCCTACTT

GGCAGTACATCTACGTATTAGTCATCGCTATTACCATGGTGATGCGGTTTTGGCA

GTACACCAATGGGCGTGGATAGCGGTTTGACTCACGGGGATTTCCAAGTCTCCAC

CCCATTGACGTCAATGGGAGTTTGTTTTGGCACCAAAATCAACGGGACTTTCCAA

AATGTCGTAATAACCCCGCCCCGTTGACGCAAATGGGCGGTAGGCGTGTACGGT

GGGAGGTCTATATAAGCAGAGCTCGTTTAGTGAACCGTCAGATCGCCTGGAGAC

GCCATCCACGCTGTTTTGACCTCCATAGAAGACACCGGGACCGATCCAGCCTCC

GCGGCCGGGAACGGTGCATTGGAACGCGGATTCCCCGTGCCAAGAGTGACTCA

CCGTCCGGATCTCAGCAAGCAGGTATGTACTCTCCAGGGTGGGCCTGGCTTCCC

CAGTCAAGACTCCAGGGATTTGAGGGACGCTGTGGGCTCTTCTCTTACATGTACC

TTTTGCTTGCCTCAACCCTGACTATCTTCCAGGTCAGGATCCCAGAGTCAGGGGT

CTGTATTTTCCTGCTGGTGGCTCCAGTTCAGGAACAGTAAACCCTGCTCCGAATA

TTGCCTCTCACATCTCGTCAATCTCCGCGAGGACTGGGGACCCTGTGACGAACAT

GGCTAGCATTGTGGGAGGCTGGGAGTGCGAGAAGCATTCCCAACCCTGGCAGGT

GCTTGTGGCCTCTCGTGGCAGGGCAGTCTGCGGCGGTGTTCTGGTGCACCCCCA

GTGGGTCCTCACAGCTGCCCACTGCATCAGGAACAAAAGCGTGATCTTGCTGGG

TCGGCACAGCTTGTTTCATCCTGAAGACACAGGCCAGGTATTTCAGGTCAGCCAC

AGCTTCCCACACCCGCTCTACGATATGAGCCTCCTGAAGAATCGATTCCTCAGGC

CAGGTGATGACTCCAGCCACGACCTCATGCTGCTCCGCCTGTCAGAGCCTGCCG

AGCTCACGGATGCTGTGAAGGTCATGGACCTGCCCACCCAGGAGCCAGCACTGG

GGACCACCTGCTACGCCTCAGGCTGGGGCAGCATTGAACCAGAGGAGTTCTTGA

-continued

CCCCAAAGAAACTTCAGTGTGTGGACCTCCATGTTATTTCCAATGACGTGTGTGC

GCAAGTTCACCCTCAGAAGGTGACCAAGTTCATGCTGTGTGCTGGACGCTGGAC

AGGGGGCAAAAGCACCTGCTCGGGTGATTCTGGGGGCCCACTTGTCTGTAATGG

TGTGCTTCAAGGTATCACGTCATGGGGCAGTGAACCATGTGCCCTGCCCGAAAG

GCCTTCCCTGTACACCAAGGTGGTGCATTACCGGAAGTGGATCAAGGACACCATC

GTGGCCAACCCCGGATCCGAAGGTAGGGGTTCATTATTGACCTGTGGAGATGTC

GAAGAAAACCCAGGACCCGCTAGCAAGGCTGTGCTGCTTGCCCTGTTGATGGCA

GGCTTGGCCCTGCAGCCAGGCACTGCCCTGCTGTGCTACTCCTGCAAAGCCCAG

GTGAGCAACGAGGACTGCCTGCAGGTGGAGAACTGCACCCAGCTGGGGGAGCA

GTGCTGGACCGCGCGCATCCGCGCAGTTGGCCTCCTGACCGTCATCAGCAAAGG

CTGCAGCTTGAACTGCGTGGATGACTCACAGGACTACTACGTGGGCAAGAAGAA

CATCACGTGCTGTGACACCGACTTGTGCAACGCCAGCGGGGCCCATGCCCTGCA

GCCGGCTGCCGCCATCCTTGCGCTGCTCCCTGCACTCGGCCTGCTGCTCTGGGG

ACCCGGCCAGCTAGGATCCCAGACCCTGAACTTTGATCTGCTGAAACTGGCAGG

CGATGTGGAAAGCAACCCAGGCCCAATGGCAAGCGCGCGCCGCCCGCGCTGGC

TGTGCGCTGGGGCGCTGGTGCTGGCGGGTGGCTTCTTTCTCCTCGGCTTCCTCT

TCGGGTGGTTTATAAAATCCTCCAATGAAGCTACTAACATTACTCCAAAGCATAAT

ATGAAAGCATTTTTGGATGAATTGAAAGCTGAGAACATCAAGAAGTTCTTATATAAT

TTTACACAGATACCACATTTAGCAGGAACAGAACAAAACTTTCAGCTTGCAAAGCA

AATTCAATCCCAGTGGAAAGAATTTGGCCTGGATTCTGTTGAGCTGGCACATTATG

ATGTCCTGTTGTCCTACCCAAATAAGACTCATCCCAACTACATCTCAATAATTAATG

AAGATGGAAATGAGATTTTCAACACATCATTATTTGAACCACCTCCTCCAGGATAT

GAAAATGTTTCGGATATTGTACCACCTTTCAGTGCTTTCTCTCCTCAAGGAATGCC

AGAGGGCGATCTAGTGTATGTTAACTATGCACGAACTGAAGACTTCTTTAAATTGG

AACGGGACATGAAAATCAATTGCTCTGGGAAAATTGTAATTGCCAGATATGGGAA

AGTTTTCAGAGGAAATAAGGTTAAAAATGCCCAGCTGGCAGGGGCCAAAGGAGTC

ATTCTCTACTCCGACCCTGCTGACTACTTTGCTCCTGGGGTGAAGTCCTATCCAG

ATGGTTGGAATCTTCCTGGAGGTGGTGTCCAGCGTGGAAATATCCTAAATCTGAA

TGGTGCAGGAGACCCTCTCACACCAGGTTACCCAGCAAATGAATATGCTTATAGG

CGTGGAATTGCAGAGGCTGTTGGTCTTCCAAGTATTCCTGTTCATCCAATTGGATA

CTATGATGCACAGAAGCTCCTAGAAAAAATGGGTGGCTCAGCACCACCAGATAGC

AGCTGGAGAGGAAGTCTCAAAGTGCCCTACAATGTTGGACCTGGCTTTACTGGAA

ACTTTTCTACACAAAAAGTCAAGATGCACATCCACTCTACCAATGAAGTGACAAGA

ATTTACAATGTGATAGGTACTCTCAGAGGAGCAGTGGAACCAGACAGATATGTCA

TTCTGGGAGGTCACCGGGACTCATGGGTGTTTGGTGGTATTGACCCTCAGAGTG

GAGCAGCTGTTGTTCATGAAATTGTGAGGAGCTTTGGAACACTGAAAAAGGAAGG

GTGGAGACCTAGAAGAACAATTTTGTTTGCAAGCTGGGATGCAGAAGAATTTGGT

CTTCTTGGTTCTACTGAGTGGGCAGAGGAGAATTCAAGACTCCTTCAAGAGCGTG

GCGTGGCTTATATTAATGCTGACTCATCTATAGAAGGAAACTACACTCTGAGAGTT

GATTGTACACCGCTGATGTACAGCTTGGTACACAACCTAACAAAAGAGCTGAAAA

GCCCTGATGAAGGCTTTGAAGGCAAATCTCTTTATGAAAGTTGGACTAAAAAAAGT

-continued

CCTTCCCCAGAGTTCAGTGGCATGCCCAGGATAAGCAAATTGGGATCTGGAAATG

ATTTTGAGGTGTTCTTCCAACGACTTGGAATTGCTTCAGGCAGAGCACGGTATACT

AAAAATTGGGAAACAAACAAATTCAGCGGCTATCCACTGTATCACAGTGTCTATGA

AACATATGAGTTGGTGGAAAAGTTTTATGATCCAATGTTTAAATATCACCTCACTGT

GGCCCAGGTTCGAGGAGGGATGGTGTTTGAGCTGGCCAATTCCATAGTGCTCCC

TTTTGATTGTCGAGATTATGCTGTAGTTTTAAGAAAGTATGCTGACAAAATCTACAG

TATTTCTATGAAACATCCACAGGAAATGAAGACATACAGTGTATCATTTGATTCACT

TTTTTCTGCAGTAAAGAATTTTACAGAAATTGCTTCCAAGTTCAGTGAGAGACTCC

AGGACTTTGACAAAAGCAACCCAATAGTATTAAGAATGATGAATGATCAACTCATG

TTTCTGGAAAGAGCATTTATTGATCCATTAGGGTTACCAGACAGGCCTTTTTATAG

GCATGTCATCTATGCTCCAAGCAGCCACAACAAGTATGCAGGGGAGTCATTCCCA

GGAATTTATGATGCTCTGTTTGATATTGAAAGCAAAGTGGACCCTTCCAAGGCCTG

GGGAGAAGTGAAGAGACAGATTTATGTTGCAGCCTTCACAGTGCAGGCAGCTGC

AGAGACTTTGAGTGAAGTAGCCTAAAGATCTGGGCCCTAACAAAACAAAAAGATG

GGGTTATTCCCTAAACTTCATGGGTTACGTAATTGGAAGTTGGGGGACATTGCCA

CAAGATCATATTGTACAAAAGATCAAACACTGTTTTAGAAAACTTCCTGTAAACAG

GCCTATTGATTGGAAAGTATGTCAAAGGATTGTGGGTCTTTTGGGCTTTGCTGCTC

CATTTACACAATGTGGATATCCTGCCTTAATGCCTTTGTATGCATGTATACAAGCT

AAACAGGCTTTCACTTTCTCGCCAACTTACAAGGCCTTTCTAAGTAAACAGTACAT

GAACCTTTACCCCGTTGCTCGGCAACGGCCTGGTCTGTGCCAAGTGTTTGCTGAC

GCAACCCCCACTGGCTGGGGCTTGGCCATAGGCCATCAGCGCATGCGTGGAACC

TTTGTGGCTCCTCTGCCGATCCATACTGCGGAACTCCTAGCCGCTTGTTTTGCTC

GCAGCCGGTCTGGAGCAAAGCTCATAGGAACTGACAATTCTGTCGTCCTCTCGC

GGAAATATACATCGTTTCGATCTACGTATGATCTTTTTCCCTCTGCCAAAAATTATG

GGGACATCATGAAGCCCCTTGAGCATCTGACTTCTGGCTAATAAAGGAAATTTATT

TTCATTGCAATAGTGTGTTGGAATTTTTTGTGTCTCTCACTCGGAAGGAATTCTGC

ATTAATGAATCGGCCAACGCGCGGGGAGAGGCGGTTTGCGTATTGGGCGCTCTT

CCGCTTCCTCGCTCACTGACTCGCTGCGCTCGGTCGTTCGGCTGCGGCGAGCGG

TATCAGCTCACTCAAAGGCGGTAATACGGTTATCCACAGAATCAGGGGATAACGC

AGGAAAGAACATGTGAGCAAAAGGCCAGCAAAAGGCCAGGAACCGTAAAAAGGC

CGCGTTGCTGGCGTTTTTCCATAGGCTCCGCCCCCCTGACGAGCATCACAAAAAT

CGACGCTCAAGTCAGAGGTGGCGAAACCCGACAGGACTATAAAGATACCAGGCG

TTTCCCCCTGGAAGCTCCCTCGTGCGCTCTCCTGTTCCGACCCTGCCGCTTACCG

GATACCTGTCCGCCTTTCTCCCTTCGGGAAGCGTGGCGCTTTCTCATAGCTCACG

CTGTAGGTATCTCAGTTCGGTGTAGGTCGTTCGCTCCAAGCTGGGCTGTGTGCAC

GAACCCCCCGTTCAGCCCGACCGCTGCGCCTTATCCGGTAACTATCGTCTTGAGT

CCAACCCGGTAAGACACGACTTATCGCCACTGGCAGCAGCCACTGGTAACAGGA

TTAGCAGAGCGAGGTATGTAGGCGGTGCTACAGAGTTCTTGAAGTGGTGGCCTA

ACTACGGCTACACTAGAAGAACAGTATTTGGTATCTGCGCTCTGCTGAAGCCAGT

TACCTTCGGAAAAAGAGTTGGTAGCTCTTGATCCGGCAAACAAACCACCGCTGGT

-continued

AGCGGTGGTTTTTTTGTTTGCAAGCAGCAGATTACGCGCAGAAAAAAAGGATCTC

AAGAAGATCCTTTGATCTTTTCTACGGGGTCTGACGCTCAGTGGAACGAAAACTC

ACGTTAAGGGATTTTGGTCATGAGATTATCAAAAAGGATCTTCACCTAGATCCTTT

TAAATTAAAAATGAAGTTTTAAATCAATCTAAAGTATATATGAGTAAACTTGGTCTG

ACAGTTACCAATGCTTAATCAGTGAGGCACCTATCTCAGCGATCTGTCTATTTCGT

TCATCCATAGTTGCCTGACTC

NUCLEOTIDE SEQUENCE OF PLASMID 459.

SEQ ID NO: 36

GGCGTAATGCTCTGCCAGTGTTACAACCAATTAACCAATTCTGATTAGAAAAACTC

ATCGAGCATCAAATGAAACTGCAATTTATTCATATCAGGATTATCAATACCATATTT

TTGAAAAAGCCGTTTCTGTAATGAAGGAGAAAACTCACCGAGGCAGTTCCATAGG

ATGGCAAGATCCTGGTATCGGTCTGCGATTCCGACTCGTCCAACATCAATACAAC

CTATTAATTTCCCCTCGTCAAAAATAAGGTTATCAAGTGAGAAATCACCATGAGTG

ACGACTGAATCCGGTGAGAATGGCAAAAGCTTATGCATTTCTTTCCAGACTTGTTC

AACAGGCCAGCCATTACGCTCGTCATCAAAATCACTCGCATCAACCAAACCGTTA

TTCATTCGTGATTGCGCCTGAGCGAGACGAAATACGCGATCGCTGTTAAAAGGAC

AATTACAAACAGGAATCAAATGCAACCGGCGCAGGAACACTGCCAGCGCATCAAC

AATATTTTCACCTGAATCAGGATATTCTTCTAATACCTGGAATGCTGTTTTCCCGG

GGATCGCAGTGGTGAGTAACCATGCATCATCAGGAGTACGGATAAAATGCTTGAT

GGTCGGAAGAGGCATAAATTCCGTCAGCCAGTTTAGTCTGACCATCTCATCTGTA

ACATCATTGGCAACGCTACCTTTGCCATGTTTCAGAAACAACTCTGGCGCATCGG

GCTTCCCATACAATCGATAGATTGTCGCACCTGATTGCCCGACATTATCGCGAGC

CCATTTATACCCATATAAATCAGCATCCATGTTGGAATTTAATCGCGGCCTCGAGC

AAGACGTTTCCCGTTGAATATGGCTCATAACACCCCTTGTATTACTGTTTATGTAA

GCAGACAGGTCGACAATATTGGCTATTGGCCATTGCATACGTTGTATCTATATCAT

AATATGTACATTTATATTGGCTCATGTCCAATATGACCGCCATGTTGACATTGATTA

TTGACTAGTTATTAATAGTAATCAATTACGGGGTCATTAGTTCATAGCCCATATATG

GAGTTCCGCGTTACATAACTTACGGTAAATGGCCCGCCTGGCTGACCGCCCAAC

GACCCCCGCCCATTGACGTCAATAATGACGTATGTTCCCATAGTAACGCCAATAG

GGACTTTCCATTGACGTCAATGGGTGGAGTATTTACGGTAAACTGCCCACTTGGC

AGTACATCAAGTGTATCATATGCCAAGTCCGCCCCCTATTGACGTCAATGACGGT

AAATGGCCCGCCTGGCATTATGCCCAGTACATGACCTTACGGGACTTTCCTACTT

GGCAGTACATCTACGTATTAGTCATCGCTATTACCATGGTGATGCGGTTTTGGCA

GTACACCAATGGGCGTGGATAGCGGTTTGACTCACGGGGATTTCCAAGTCTCCAC

CCCATTGACGTCAATGGGAGTTTGTTTTGGCACCAAAATCAACGGGACTTTCCAA

AATGTCGTAATAACCCCGCCCCGTTGACGCAAATGGGCGGTAGGCGTGTACGGT

GGGAGGTCTATATAAGCAGAGCTCGTTTAGTGAACCGTCAGATCGCCTGGAGAC

GCCATCCACGCTGTTTTGACCTCCATAGAAGACACCGGGACCGATCCAGCCTCC

GCGGCCGGGAACGGTGCATTGGAACGCGGATTCCCCGTGCCAAGAGTGACTCA

CCGTCCGGATCTCAGCAAGCAGGTATGTACTCTCCAGGGTGGGCCTGGCTTCCC

CAGTCAAGACTCCAGGGATTTGAGGGACGCTGTGGGCTCTTCTCTTACATGTACC

TTTTGCTTGCCTCAACCCTGACTATCTTCCAGGTCAGGATCCCAGAGTCAGGGGT

-continued

CTGTATTTTCCTGCTGGTGGCTCCAGTTCAGGAACAGTAAACCCTGCTCCGAATA

TTGCCTCTCACATCTCGTCAATCTCCGCGAGGACTGGGGACCCTGTGACGAACAT

GGCTAGCAAGGCTGTGCTGCTTGCCCTGTTGATGGCAGGCTTGGCCCTGCAGCC

AGGCACTGCCCTGCTGTGCTACTCCTGCAAAGCCCAGGTGAGCAACGAGGACTG

CCTGCAGGTGGAGAACTGCACCCAGCTGGGGGAGCAGTGCTGGACCGCGCGCA

TCCGCGCAGTTGGCCTCCTGACCGTCATCAGCAAAGGCTGCAGCTTGAACTGCG

TGGATGACTCACAGGACTACTACGTGGGCAAGAAGAACATCACGTGCTGTGACAC

CGACTTGTGCAACGCCAGCGGGGCCCATGCCCTGCAGCCGGCTGCCGCCATCC

TTGCGCTGCTCCCTGCACTCGGCCTGCTGCTCTGGGGACCCGGCCAGCTAGGAT

CCCAGACCCTGAACTTTGATCTGCTGAAACTGGCAGGCGATGTGGAAAGCAACC

CAGGCCCAATGGCAAGCGCGCGCCGCCCGCGCTGGCTGTGCGCTGGGGCGCT

GGTGCTGGCGGGTGGCTTCTTTCTCCTCGGCTTCCTCTTCGGGTGGTTTATAAAA

TCCTCCAATGAAGCTACTAACATTACTCCAAAGCATAATATGAAAGCATTTTTGGAT

GAATTGAAAGCTGAGAACATCAAGAAGTTCTTATATAATTTTACACAGATACCACAT

TTAGCAGGAACAGAACAAAACTTTCAGCTTGCAAAGCAAATTCAATCCCAGTGGAA

AGAATTTGGCCTGGATTCTGTTGAGCTGGCACATTATGATGTCCTGTTGTCCTACC

CAAATAAGACTCATCCCAACTACATCTCAATAATTAATGAAGATGGAAATGAGATTT

TCAACACATCATTATTTGAACCACCTCCTCCAGGATATGAAAATGTTTCGGATATT

GTACCACCTTTCAGTGCTTTCTCTCCTCAAGGAATGCCAGAGGGCGATCTAGTGT

ATGTTAACTATGCACGAACTGAAGACTTCTTTAAATTGGAACGGGACATGAAAATC

AATTGCTCTGGGAAAATTGTAATTGCCAGATATGGGAAAGTTTTCAGAGGAAATAA

GGTTAAAAATGCCCAGCTGGCAGGGGCCAAAGGAGTCATTCTCTACTCCGACCCT

GCTGACTACTTTGCTCCTGGGGTGAAGTCCTATCCAGATGGTTGGAATCTTCCTG

GAGGTGGTGTCCAGCGTGGAAATATCCTAAATCTGAATGGTGCAGGAGACCCTCT

CACACCAGGTTACCCAGCAAATGAATATGCTTATAGGCGTGGAATTGCAGAGGCT

GTTGGTCTTCCAAGTATTCCTGTTCATCCAATTGGATACTATGATGCACAGAAGCT

CCTAGAAAAAATGGGTGGCTCAGCACCACCAGATAGCAGCTGGAGAGGAAGTCT

CAAAGTGCCCTACAATGTTGGACCTGGCTTTACTGGAAACTTTTCTACACAAAAAG

TCAAGATGCACATCCACTCTACCAATGAAGTGACAAGAATTTACAATGTGATAGGT

ACTCTCAGAGGAGCAGTGGAACCAGACAGATATGTCATTCTGGGAGGTCACCGG

GACTCATGGGTGTTTGGTGGTATTGACCCTCAGAGTGGAGCAGCTGTTGTTCATG

AAATTGTGAGGAGCTTTGGAACACTGAAAAAGGAAGGGTGGAGACCTAGAAGAAC

AATTTTGTTTGCAAGCTGGGATGCAGAAGAATTTGGTCTTCTTGGTTCTACTGAGT

GGGCAGAGGAGAATTCAAGACTCCTTCAAGAGCGTGGCGTGGCTTATATTAATGC

TGACTCATCTATAGAAGGAAACTACACTCTGAGAGTTGATTGTACACCGCTGATGT

ACAGCTTGGTACACAACCTAACAAAAGAGCTGAAAAGCCCTGATGAAGGCTTTGA

AGGCAAATCTCTTTATGAAAGTTGGACTAAAAAAAGTCCTTCCCCAGAGTTCAGTG

GCATGCCCAGGATAAGCAAATTGGGATCTGGAAATGATTTTGAGGTGTTCTTCCA

ACGACTTGGAATTGCTTCAGGCAGAGCACGGTATACTAAAAATTGGGAAACAAAC

AAATTCAGCGGCTATCCACTGTATCACAGTGTCTATGAAACATATGAGTTGGTGGA

-continued

AAAGTTTTATGATCCAATGTTTAAATATCACCTCACTGTGGCCCAGGTTCGAGGAG

GGATGGTGTTTGAGCTGGCCAATTCCATAGTGCTCCCTTTTGATTGTCGAGATTAT

GCTGTAGTTTTAAGAAAGTATGCTGACAAAATCTACAGTATTTCTATGAAACATCCA

CAGGAAATGAAGACATACAGTGTATCATTTGATTCACTTTTTTCTGCAGTAAAGAAT

TTTACAGAAATTGCTTCCAAGTTCAGTGAGAGACTCCAGGACTTTGACAAAAGCAA

CCCAATAGTATTAAGAATGATGAATGATCAACTCATGTTTCTGGAAAGAGCATTTA

TTGATCCATTAGGGTTACCAGACAGGCCTTTTTATAGGCATGTCATCTATGCTCCA

AGCAGCCACAACAAGTATGCAGGGGAGTCATTCCCAGGAATTTATGATGCTCTGT

TTGATATTGAAAGCAAAGTGGACCCTTCCAAGGCCTGGGGAGAAGTGAAGAGACA

GATTTATGTTGCAGCCTTCACAGTGCAGGCAGCTGCAGAGACTTTGAGTGAAGTA

GCCTAAAGATCTGACCCCCTAACGTTACTGGCCGAAGCCGCTTGGAATAAGGCC

GGTGTGCGTTTGTCTATATGTTATTTTCCACCATATTGCCGTCTTTTGGCAATGTG

AGGGCCCGGAAACCTGGCCCTGTCTTCTTGACGAGCATTCCTAGGGGTCTTTCC

CCTCTCGCCAAAGGAATGCAAGGTCTGTTGAATGTCGTGAAGGAAGCAGTTCCTC

TGGAAGCTTCTTGAAGACAAACAACGTCTGTAGCGACCCTTTGCAGGCAGCGGAA

CCCCCCACCTGGCGACAGGTGCCTCTGCGGCCAAAAGCCACGTGTATAAGATAC

ACCTGCAAAGGCGGCACAACCCCAGTGCCACGTTGTGAGTTGGATAGTTGTGGA

AAGAGTCAAATGGCTCTCCTCAAGCGTATTCAACAAGGGGCTGAAGGATGCCCAG

AAGGTACCCCATTGTATGGGATCTGATCTGGGGCCTCGGTGCACATGCTTTACAT

GTGTTTAGTCGAGGTTAAAAAACGTCTAGGCCCCCCGAACCACGGGGACGTGGT

TTTCCTTTGAAAAACACGATGATAATATGGCCAGCATTGTGGGAGGCTGGGAGTG

CGAGAAGCATTCCCAACCCTGGCAGGTGCTTGTGGCCTCTCGTGGCAGGGCAGT

CTGCGGCGGTGTTCTGGTGCACCCCCAGTGGGTCCTCACAGCTGCCCACTGCAT

CAGGAACAAAAGCGTGATCTTGCTGGGTCGGCACAGCTTGTTTCATCCTGAAGAC

ACAGGCCAGGTATTTCAGGTCAGCCACAGCTTCCCACACCCGCTCTACGATATGA

GCCTCCTGAAGAATCGATTCCTCAGGCCAGGTGATGACTCCAGCCACGACCTCAT

GCTGCTCCGCCTGTCAGAGCCTGCCGAGCTCACGGATGCTGTGAAGGTCATGGA

CCTGCCCACCCAGGAGCCAGCACTGGGGACCACCTGCTACGCCTCAGGCTGGG

GCAGCATTGAACCAGAGGAGTTCTTGACCCCAAAGAAACTTCAGTGTGTGGACCT

CCATGTTATTTCCAATGACGTGTGTGCGCAAGTTCACCCTCAGAAGGTGACCAAG

TTCATGCTGTGTGCTGGACGCTGGACAGGGGGCAAAAGCACCTGCTCGGGTGAT

TCTGGGGGCCCACTTGTCTGTAATGGTGTGCTTCAAGGTATCACGTCATGGGGCA

GTGAACCATGTGCCCTGCCCGAAAGGCCTTCCCTGTACACCAAGGTGGTGCATTA

CCGGAAGTGGATCAAGGACACCATCGTGGCCAACCCCTGAGGATCTGGGCCCTA

ACAAAACAAAAAGATGGGGTTATTCCCTAAACTTCATGGGTTACGTAATTGGAAGT

TGGGGGACATTGCCACAAGATCATATTGTACAAAAGATCAAACACTGTTTTAGAAA

ACTTCCTGTAAACAGGCCTATTGATTGGAAAGTATGTCAAAGGATTGTGGGTCTTT

TGGGCTTTGCTGCTCCATTTACACAATGTGGATATCCTGCCTTAATGCCTTTGTAT

GCATGTATACAAGCTAAACAGGCTTTCACTTTCTCGCCAACTTACAAGGCCTTTCT

AAGTAAACAGTACATGAACCTTTACCCCGTTGCTCGGCAACGGCCTGGTCTGTGC

CAAGTGTTTGCTGACGCAACCCCCACTGGCTGGGGCTTGGCCATAGGCCATCAG

-continued

CGCATGCGTGGAACCTTTGTGGCTCCTCTGCCGATCCATACTGCGGAACTCCTAG

CCGCTTGTTTTGCTCGCAGCCGGTCTGGAGCAAAGCTCATAGGAACTGACAATTC

TGTCGTCCTCTCGCGGAAATATACATCGTTTCGATCTACGTATGATCTTTTTCCCT

CTGCCAAAAATTATGGGGACATCATGAAGCCCCTTGAGCATCTGACTTCTGGCTA

ATAAAGGAAATTTATTTTCATTGCAATAGTGTGTTGGAATTTTTTGTGTCTCTCACT

CGGAAGGAATTCTGCATTAATGAATCGGCCAACGCGCGGGGAGAGGCGGTTTGC

GTATTGGGCGCTCTTCCGCTTCCTCGCTCACTGACTCGCTGCGCTCGGTCGTTCG

GCTGCGGCGAGCGGTATCAGCTCACTCAAAGGCGGTAATACGGTTATCCACAGA

ATCAGGGGATAACGCAGGAAAGAACATGTGAGCAAAAGGCCAGCAAAAGGCCAG

GAACCGTAAAAAGGCCGCGTTGCTGGCGTTTTTCCATAGGCTCCGCCCCCCTGA

CGAGCATCACAAAAATCGACGCTCAAGTCAGAGGTGGCGAAACCCGACAGGACT

ATAAAGATACCAGGCGTTTCCCCCTGGAAGCTCCCTCGTGCGCTCTCCTGTTCCG

ACCCTGCCGCTTACCGGATACCTGTCCGCCTTTCTCCCTTCGGGAAGCGTGGCG

CTTTCTCATAGCTCACGCTGTAGGTATCTCAGTTCGGTGTAGGTCGTTCGCTCCA

AGCTGGGCTGTGTGCACGAACCCCCCGTTCAGCCCGACCGCTGCGCCTTATCCG

GTAACTATCGTCTTGAGTCCAACCCGGTAAGACACGACTTATCGCCACTGGCAGC

AGCCACTGGTAACAGGATTAGCAGAGCGAGGTATGTAGGCGGTGCTACAGAGTT

CTTGAAGTGGTGGCCTAACTACGGCTACACTAGAAGAACAGTATTTGGTATCTGC

GCTCTGCTGAAGCCAGTTACCTTCGGAAAAAGAGTTGGTAGCTCTTGATCCGGCA

AACAAACCACCGCTGGTAGCGGTGGTTTTTTTGTTTGCAAGCAGCAGATTACGCG

CAGAAAAAAAGGATCTCAAGAAGATCCTTTGATCTTTTCTACGGGGTCTGACGCTC

AGTGGAACGAAAACTCACGTTAAGGGATTTTGGTCATGAGATTATCAAAAAGGATC

TTCACCTAGATCCTTTTAAATTAAAAATGAAGTTTTAAATCAATCTAAAGTATATATG

AGTAAACTTGGTCTGACAGTTACCAATGCTTAATCAGTGAGGCACCTATCTCAGC

GATCTGTCTATTTCGTTCATCCATAGTTGCCTGACTC

NUCLEOTIDE SEQUENCE OF PSHUTTLE IRES.

SEQ ID NO: 37

CATCATCAATAATATACCTTATTTTGGATTGAAGCCAATATGATAATGAGGGGGTG

GAGTTTGTGACGTGGCGCGGGGCGTGGGAACGGGGCGGGTGACGTAGTAGTGT

GGCGGAAGTGTGATGTTGCAAGTGTGGCGGAACACATGTAAGCGACGGATGTGG

CAAAAGTGACGTTTTTGGTGTGCGCCGGTGTACACAGGAAGTGACAATTTTCGCG

CGGTTTTAGGCGGATGTTGTAGTAAATTTGGGCGTAACCGAGTAAGATTTGGCCA

TTTTCGCGGGAAAACTGAATAAGAGGAAGTGAAATCTGAATAATTTTGTGTTACTC

ATAGCGCGTAATACTGTAATAGTAATCAATTACGGGGTCATTAGTTCATAGCCCAT

ATATGGAGTTCCGCGTTACATAACTTACGGTAAATGGCCCGCCTGGCTGACCGCC

CAACGACCCCCGCCCATTGACGTCAATAATGACGTATGTTCCCATAGTAACGCCA

ATAGGGACTTTCCATTGACGTCAATGGGTGGAGTATTTACGGTAAACTGCCCACT

TGGCAGTACATCAAGTGTATCATATGCCAAGTACGCCCCCTATTGACGTCAATGA

CGGTAAATGGCCCGCCTGGCATTATGCCCAGTACATGACCTTATGGGACTTTCCT

ACTTGGCAGTACATCTACGTATTAGTCATCGCTATTACCATGGTGATGCGGTTTTG

GCAGTACATCAATGGGCGTGGATAGCGGTTTGACTCACGGGGATTTCCAAGTCTC

-continued

CACCCCATTGACGTCAATGGGAGTTTGTTTTGGCACCAAAATCAACGGGACTTTC

CAAAATGTCGTAACAACTCCGCCCCATTGACGCAAATGGGCGGTAGGCGTGTAC

GGTGGGAGGTCTATATAAGCAGAGCTGGTTTAGTGAACCGTCAGATCCGCTAGA

GATCCACCATGGCTAGCGGTGCCCCGACGTTGCCCCCTGCCTGGCAGCCCTTTC

TCAAGGACCACCGCATCTCTACATTCAAGAACTGGCCCTTCTTGGAGGGCTGCGC

CTGCGCCCCGGAGCGGATGGCCGAGGCTGGCTTCATCCACTGCCCCACTGAGA

ACGAGCCAGACTTGGCCCAGTGTTTCTTCTGCTTCAAGGAGCTGGAAGGCTGGG

AGCCAGATGACGACCCCATAGAGGAACATAAAAAGCATTCGTCCGGTTGCGCTTT

CCTTTCTGTCAAGAAGCAGTTTGAAGAATTAACCCTTGGTGAATTTTTGAAACTGG

ACAGAGAAAGAGCCAAGAACAAAATTGCAAAGGAAACCAACAATAAGAAGAAAGA

ATTTGAGGAAACTGCGGAGAAAGTGCGCCGTGCCATCGAGCAGCTGGCTGCCAT

GGATTAGAGATCTGACCCCCTAACGTTACTGGCCGAAGCCGCTTGGAATAAGGC

CGGTGTGCGTTTGTCTATATGTTATTTTCCACCATATTGCCGTCTTTTGGCAATGT

GAGGGCCCGGAAACCTGGCCCTGTCTTCTTGACGAGCATTCCTAGGGGTCTTTC

CCCTCTCGCCAAAGGAATGCAAGGTCTGTTGAATGTCGTGAAGGAAGCAGTTCCT

CTGGAAGCTTCTTGAAGACAAACAACGTCTGTAGCGACCCTTTGCAGGCAGCGGA

ACCCCCCACCTGGCGACAGGTGCCTCTGCGGCCAAAAGCCACGTGTATAAGATA

CACCTGCAAAGGCGGCACAACCCCAGTGCCACGTTGTGAGTTGGATAGTTGTGG

AAAGAGTCAAATGGCTCTCCTCAAGCGTATTCAACAAGGGGCTGAAGGATGCCCA

GAAGGTACCCCATTGTATGGGATCTGATCTGGGGCCTCGGTGCACATGCTTTACA

TGTGTTTAGTCGAGGTTAAAAAACGTCTAGGCCCCCCGAACCACGGGGACGTGG

TTTTCCTTTGAAAAACACGATAATATGGCGGCCGCTCGAGCCTAAGCTTCTAGATA

AGATATCCGATCCACCGGATCTAGATAACTGATCATAATCAGCCATACCACATTTG

TAGAGGTTTTACTTGCTTTAAAAAACCTCCCACACCTCCCCCTGAACCTGAAACAT

AAAATGAATGCAATTGTTGTTGTTAACTTGTTTATTGCAGCTTATAATGGTTACAAA

TAAAGCAATAGCATCACAAATTTCACAAATAAAGCATTTTTTTCACTGCATTCTAGT

TGTGGTTTGTCCAAACTCATCAATGTATCTTAACGCGGATCTGGGCGTGGTTAAG

GGTGGGAAAGAATATATAAGGTGGGGGTCTTATGTAGTTTTGTATCTGTTTTGCAG

CAGCCGCCGCCGCCATGAGCACCAACTCGTTTGATGGAAGCATTGTGAGCTCAT

ATTTGACAACGCGCATGCCCCCATGGGCCGGGGTGCGTCAGAATGTGATGGGCT

CCAGCATTGATGGTCGCCCCGTCCTGCCCGCAAACTCTACTACCTTGACCTACGA

GACCGTGTCTGGAACGCCGTTGGAGACTGCAGCCTCCGCCGCCGCTTCAGCCG

CTGCAGCCACCGCCCGCGGGATTGTGACTGACTTTGCTTTCCTGAGCCCGCTTG

CAAGCAGTGCAGCTTCCCGTTCATCCGCCCGCGATGACAAGTTGACGGCTCTTTT

GGCACAATTGGATTCTTTGACCCGGGAACTTAATGTCGTTTCTCAGCAGCTGTTG

GATCTGCGCCAGCAGGTTTCTGCCCTGAAGGCTTCCTCCCCTCCCAATGCGGTTT

AAAACATAAATAAAAAACCAGACTCTGTTTGGATTTGGATCAAGCAAGTGTCTTGC

TGTCTTTATTTAGGGGTTTTGCGCGCGCGGTAGGCCCGGGACCAGCGGTCTCGG

TCGTTGAGGGTCCTGTGTATTTTTTCCAGGACGTGGTAAAGGTGACTCTGGATGT

TCAGATACATGGGCATAAGCCCGTCTCTGGGGTGGAGGTAGCACCACTGCAGAG

CTTCATGCTGCGGGGTGGTGTTGTAGATGATCCAGTCGTAGCAGGAGCGCTGGG

-continued

CGTGGTGCCTAAAAATGTCTTTCAGTAGCAAGCTGATTGCCAGGGGCAGGCCCTT

GGTGTAAGTGTTTACAAAGCGGTTAAGCTGGGATGGGTGCATACGTGGGGATAT

GAGATGCATCTTGGACTGTATTTTTAGGTTGGCTATGTTCCCAGCCATATCCCTCC

GGGGATTCATGTTGTGCAGAACCACCAGCACAGTGTATCCGGTGCACTTGGGAA

ATTTGTCATGTAGCTTAGAAGGAAATGCGTGGAAGAACTTGGAGACGCCCTTGTG

ACCTCCAAGATTTTCCATGCATTCGTCCATAATGATGGCAATGGGCCCACGGGCG

GCGGCCTGGGCGAAGATATTTCTGGGATCACTAACGTCATAGTTGTGTTCCAGGA

TGAGATCGTCATAGGCCATTTTTACAAAGCGCGGGCGGAGGGTGCCAGACTGCG

GTATAATGGTTCCATCCGGCCCAGGGGCGTAGTTACCCTCACAGATTTGCATTTC

CCACGCTTTGAGTTCAGATGGGGGGATCATGTCTACCTGCGGGGCGATGAAGAA

AACGGTTTCCGGGGTAGGGGAGATCAGCTGGGAAGAAAGCAGGTTCCTGAGCAG

CTGCGACTTACCGCAGCCGGTGGGCCCGTAAATCACACCTATTACCGGCTGCAA

CTGGTAGTTAAGAGAGCTGCAGCTGCCGTCATCCCTGAGCAGGGGGGCCACTTC

GTTAAGCATGTCCCTGACTCGCATGTTTTCCCTGACCAAATCCGCCAGAAGGCGC

TCGCCGCCCAGCGATAGCAGTTCTTGCAAGGAAGCAAAGTTTTTCAACGGTTTGA

GACCGTCCGCCGTAGGCATGCTTTTGAGCGTTTGACCAAGCAGTTCCAGGCGGT

CCCACAGCTCGGTCACCTGCTCTACGGCATCTCGATCCAGCATATCTCCTCGTTT

CGCGGGTTGGGGCGGCTTTCGCTGTACGGCAGTAGTCGGTGCTCGTCCAGACG

GGCCAGGGTCATGTCTTTCCACGGGCGCAGGGTCCTCGTCAGCGTAGTCTGGGT

CACGGTGAAGGGGTGCGCTCCGGGCTGCGCGCTGGCCAGGGTGCGCTTGAGGC

TGGTCCTGCTGGTGCTGAAGCGCTGCCGGTCTTCGCCCTGCGCGTCGGCCAGGT

AGCATTTGACCATGGTGTCATAGTCCAGCCCCTCCGCGGCGTGGCCCTTGGCGC

GCAGCTTGCCCTTGGAGGAGGCGCCGCACGAGGGGCAGTGCAGACTTTTGAGG

GCGTAGAGCTTGGGCGCGAGAAATACCGATTCCGGGGAGTAGGCATCCGCGCC

GCAGGCCCCGCAGACGGTCTCGCATTCCACGAGCCAGGTGAGCTCTGGCCGTTC

GGGGTCAAAAACCAGGTTTCCCCCATGCTTTTTGATGCGTTTCTTACCTCTGGTTT

CCATGAGCCGGTGTCCACGCTCGGTGACGAAAAGGCTGTCCGTGTCCCCGTATA

CAGACTTGAGAGGGAGTTTAAACGAATTCAATAGCTTGTTGCATGGGCGGCGATA

TAAAATGCAAGGTGCTGCTCAAAAAATCAGGCAAAGCCTCGCGCAAAAAAGAAAG

CACATCGTAGTCATGCTCATGCAGATAAAGGCAGGTAAGCTCCGGAACCACCACA

GAAAAAGACACCATTTTTCTCTCAAACATGTCTGCGGGTTTCTGCATAAACACAAA

ATAAAATAACAAAAAAACATTTAAACATTAGAAGCCTGTCTTACAACAGGAAAAACA

ACCCTTATAAGCATAAGACGGACTACGGCCATGCCGGCGTGACCGTAAAAAAACT

GGTCACCGTGATTAAAAAGCACCACCGACAGCTCCTCGGTCATGTCCGGAGTCAT

AATGTAAGACTCGGTAAACACATCAGGTTGATTCACATCGGTCAGTGCTAAAAAG

CGACCGAAATAGCCCGGGGGAATACATACCCGCAGGCGTAGAGACAACATTACA

GCCCCCATAGGAGGTATAACAAAATTAATAGGAGAGAAAAACACATAAACACCTG

AAAAACCCTCCTGCCTAGGCAAAATAGCACCCTCCCGCTCCAGAACAACATACAG

CGCTTCCACAGCGGCAGCCATAACAGTCAGCCTTACCAGTAAAAAAGAAAACCTA

TTAAAAAAACACCACTCGACACGGCACCAGCTCAATCAGTCACAGTGTAAAAAAG

-continued

GGCCAAGTGCAGAGCGAGTATATATAGGACTAAAAAATGACGTAACGGTTAAAGT

CCACAAAAAACACCCAGAAAACCGCACGCGAACCTACGCCCAGAAACGAAAGCC

AAAAAACCCACAACTTCCTCAAATCGTCACTTCCGTTTTCCCACGTTACGTCACTT

CCCATTTTAAGAAAACTACAATTCCCAACACATACAAGTTACTCCGCCCTAAAACC

TACGTCACCCGCCCCGTTCCCACGCCCCGCGCCACGTCACAAACTCCACCCCCT

CATTATCATATTGGCTTCAATCCAAAATAAGGTATATTATTGATGATGTTAATTAAC

ATGCATGGATCCATATGCGGTGTGAAATACCGCACAGATGCGTAAGGAGAAAATA

CCGCATCAGGCGCTCTTCCGCTTCCTCGCTCACTGACTCGCTGCGCTCGGTCGT

TCGGCTGCGGCGAGCGGTATCAGCTCACTCAAAGGCGGTAATACGGTTATCCAC

AGAATCAGGGGATAACGCAGGAAAGAACATGTGAGCAAAAGGCCAGCAAAAGGC

CAGGAACCGTAAAAAGGCCGCGTTGCTGGCGTTTTTCCATAGGCTCCGCCCCCC

TGACGAGCATCACAAAAATCGACGCTCAAGTCAGAGGTGGCGAAACCCGACAGG

ACTATAAAGATACCAGGCGTTTCCCCCTGGAAGCTCCCTCGTGCGCTCTCCTGTT

CCGACCCTGCCGCTTACCGGATACCTGTCCGCCTTTCTCCCTTCGGGAAGCGTG

GCGCTTTCTCATAGCTCACGCTGTAGGTATCTCAGTTCGGTGTAGGTCGTTCGCT

CCAAGCTGGGCTGTGTGCACGAACCCCCCGTTCAGCCCGACCGCTGCGCCTTAT

CCGGTAACTATCGTCTTGAGTCCAACCCGGTAAGACACGACTTATCGCCACTGGC

AGCAGCCACTGGTAACAGGATTAGCAGAGCGAGGTATGTAGGCGGTGCTACAGA

GTTCTTGAAGTGGTGGCCTAACTACGGCTACACTAGAAGGACAGTATTTGGTATC

TGCGCTCTGCTGAAGCCAGTTACCTTCGGAAAAAGAGTTGGTAGCTCTTGATCCG

GCAAACAAACCACCGCTGGTAGCGGTGGTTTTTTTGTTTGCAAGCAGCAGATTAC

GCGCAGAAAAAAAGGATCTCAAGAAGATCCTTTGATCTTTTCTACGGGGTCTGAC

GCTCAGTGGAACGAAAACTCACGTTAAGGGATTTTGGTCATGAGATTATCAAAAA

GGATCTTCACCTAGATCCTTTTAAATTAAAAATGAAGTTTTAAATCAATCTAAAGTA

TATATGAGTAAACTTGGTCTGACAGTTACCAATGCTTAATCAGTGAGGCACCTATC

TCAGCGATCTGTCTATTTCGTTCATCCATAGTTGCCTGACTCCCCGTCGTGTAGAT

AACTACGATACGGGAGGGCTTACCATCTGGCCCCAGTGCTGCAATGATACCGCG

AGACCCACGCTCACCGGCTCCAGATTTATCAGCAATAAACCAGCCAGCCGGAAG

GGCCGAGCGCAGAAGTGGTCCTGCAACTTTATCCGCCTCCATCCAGTCTATTAAT

TGTTGCCGGGAAGCTAGAGTAAGTAGTTCGCCAGTTAATAGTTTGCGCAACGTTG

TTGCCATTGCTGCAGCCATGAGATTATCAAAAAGGATCTTCACCTAGATCCTTTTC

ACGTAGAAAGCCAGTCCGCAGAAACGGTGCTGACCCCGGATGAATGTCAGCTAC

TGGGCTATCTGGACAAGGGAAAACGCAAGCGCAAAGAGAAAGCAGGTAGCTTGC

AGTGGGCTTACATGGCGATAGCTAGACTGGGCGGTTTTATGGACAGCAAGCGAA

CCGGAATTGCCAGCTGGGGCGCCCTCTGGTAAGGTTGGGAAGCCCTGCAAAGTA

AACTGGATGGCTTTCTTGCCGCCAAGGATCTGATGGCGCAGGGGATCAAGCTCT

GATCAAGAGACAGGATGAGGATCGTTTCGCATGATTGAACAAGATGGATTGCACG

CAGGTTCTCCGGCCGCTTGGGTGGAGAGGCTATTCGGCTATGACTGGGCACAAC

AGACAATCGGCTGCTCTGATGCCGCCGTGTTCCGGCTGTCAGCGCAGGGGCGC

CCGGTTCTTTTTGTCAAGACCGACCTGTCCGGTGCCCTGAATGAACTGCAAGACG

AGGCAGCGCGGCTATCGTGGCTGGCCACGACGGGCGTTCCTTGCGCAGCTGTG

-continued

CTCGACGTTGTCACTGAAGCGGGAAGGGACTGGCTGCTATTGGGCGAAGTGCCG

GGGCAGGATCTCCTGTCATCTCACCTTGCTCCTGCCGAGAAAGTATCCATCATGG

CTGATGCAATGCGGCGGCTGCATACGCTTGATCCGGCTACCTGCCCATTCGACC

ACCAAGCGAAACATCGCATCGAGCGAGCACGTACTCGGATGGAAGCCGGTCTTG

TCGATCAGGATGATCTGGACGAAGAGCATCAGGGGCTCGCGCCAGCCGAACTGT

TCGCCAGGCTCAAGGCGAGCATGCCCGACGGCGAGGATCTCGTCGTGACCCAT

GGCGATGCCTGCTTGCCGAATATCATGGTGGAAAATGGCCGCTTTTCTGGATTCA

TCGACTGTGGCCGGCTGGGTGTGGCGGACCGCTATCAGGACATAGCGTTGGCTA

CCCGTGATATTGCTGAAGAGCTTGGCGGCGAATGGGCTGACCGCTTCCTCGTGC

TTTACGGTATCGCCGCTCCCGATTCGCAGCGCATCGCCTTCTATCGCCTTCTTGA

CGAGTTCTTCTGAATTTTGTTAAAATTTTTGTTAAATCAGCTCATTTTTTAACCAATA

GGCCGAAATCGGCACCATCCCTTATAAATCAAAAGAATAGACCGAGATAGGGTTG

AGTGTTGTTCCAGTTTGGAACAAGAGTCCACTATTAAAGAACGTGGACTCCAACG

TCAAAGGGCGAAAAACCGTCTATCAGGGCGATGGCCCACTACGTGAACCATCAC

CCTAATCAAGTTTTTTGTGGTCGAGGTGCCGTAAAGCACTAAATCGGAACCCTAAA

GGGAGCCCCCGATTTAGAGCTTGACGGGGAAAGCCGGCGAACGTGGCGAGAAA

GGAAGGGAAGAAAGCGAAAGGAGCGGGCGCTAGGGCGCTGGCAAGTGTAGCGG

TCACGCTGCGCGTAACCACCACACCCGCGCGCTTAATGCGCCGCTACAGGGCGC

GTCCATTCGCCATTCAGGATCGAATTAATTCTTAATTAA

Amino acid sequence of Her-2 antigen:.

SEQ ID NO: 38

MASELAALCRWGLLLALLPPGAASTQVCTGTDMKLRLPASPETHLDMLRHLYQGCQ

VVQGNLELTYLPTNASLSFLQDIQEVQGYVLIAHNQVRQVPLQRLRIVRGTQLFEDNY

ALAVLDNGDPLDSVAPAAGATPGGLQELQLRSLTEILKGGVLIRRSPQLCHQDTVLWE

DVFRKNNQLALVLMDTNRSRACHPCAPMCKANHCWGESSQDCQTLTRTICTSACAR

CKAPLPTDCCHEQCAAGCTGPKHSDCLACLHFNHSGICELHCPALVTYNTDTFESMP

NPEGRYTFGASCVTACPYNYLSTDVGSCTLVCPLHNQEVTAEDGTQRCEKCSKPCA

RVCYGLGMEHLREARAITSANVQDFVGCKKIFGSLAFLPESFDGDPASGTAPLQPEQ

LQVFETLEEITGYLYISAWPDSFPNLSVFQNLRVIRGRILHNGAYSLTLQGLGISWLGL

RSLQELGSGLALVHRNARLCFVHTVPWDQLFRNPHQALLHSGNRPEEDCVGEGFVC

YSLCAHGHCWGPGPTQCVNCSHFLRGQECVEECRVLQGLPREYVNARHCLPCHPE

CQPQNGSVTCFGPEADQCVACAHYKDPPFCVARCPSGVKPDLSYMPIWKFPDEEG

ACQPCPINCTHSCVDLDDKGCPAEQRASPLTSIISAVVGILLVVVLGVVFGILIKRRQQK

IRKYTMRRNEDLGPSSPMDSTFYRSLLEDEDMGELVDAEEYLVPQQGFFCPDPTPGT

GSTAHRRHRSSSARNGGGDLTLGMEPSGEGPPRSPRAPSEGTGSDVFDGDLAVGV

TKGLQSLSPQDLSPLQRYSEDPTLPLPSETDGKVAPLSCSPQPEFVNQSDVQPKSPL

TPEGPPSPARPTGATLERAKTLSPGKNGVVKDVFTFGGAVENPEFLAPREGTASPPH

PSPAFSPAFDNLFFWDQNSSEQGPPPSNFEGTPTAENPEFLGLDVPV
(signal sequence underlined)

Nucleic acid sequence encoding the Her-2 antigen
amino acid sequence of SEQ ID NO: 38.

SEQ ID NO: 39

ATGGCTAGCGAGCTGGCCGCCCTGTGTAGATGGGGACTGCTGCTGGCTCTGCTG

CCTCCTGGAGCCGCTTCTACACAGGTCTGCACCGGCACCGACATGAAGCTGAGA

-continued

CTGCCCGCCAGCCCCGAGACACACCTGGACATGCTGCGGCACCTGTACCAGGG

CTGCCAGGTGGTCCAGGGGAATCTGGAACTGACCTACCTGCCCACCAACGCCAG

CCTGAGCTTCCTGCAGGACATCCAGGAAGTGCAGGGCTACGTCCTGATCGCCCA

CAACCAGGTCCGCCAGGTGCCCCTGCAGCGGCTGAGAATCGTGCGGGGCACCC

AGCTGTTCGAGGACAACTACGCCCTGGCCGTGCTGGACAACGGCGACCCTCTGG

ATAGCGTGGCCCCTGCTGCTGGGGCTACACCTGGCGGACTGCAGGAACTGCAG

CTGCGGAGCCTGACCGAGATCCTGAAGGGCGGCGTGCTGATCAGGCGGAGCCC

TCAGCTGTGCCACCAGGACACCGTGCTGTGGGAGGACGTGTTCCGGAAGAACAA

CCAGCTGGCCCTCGTGCTGATGGACACCAACAGAAGCCGGGCCTGCCACCCCTG

CGCCCCCATGTGCAAGGCCAATCACTGCTGGGGAGAGAGCAGCCAGGACTGCC

AGACCCTGACCCGGACCATCTGCACCAGCGCCTGCGCCAGATGCAAGGCCCCC

CTGCCTACCGACTGCTGCCACGAACAGTGCGCCGCTGGCTGCACCGGCCCCAA

GCACAGCGATTGCCTGGCCTGCCTGCACTTCAACCACAGCGGCATCTGCGAGCT

GCACTGCCCTGCCCTGGTGACATACAACACCGACACCTTCGAGAGCATGCCCAA

CCCCGAGGGCCGGTACACCTTCGGCGCCAGCTGTGTGACCGCCTGCCCCTACAA

CTACCTGAGCACCGACGTGGGCAGCTGCACCCTGGTGTGCCCCCTGCACAACCA

GGAAGTGACCGCCGAGGACGGCACCCAGAGATGCGAGAAGTGCAGCAAGCCTT

GCGCCAGAGTGTGCTACGGCCTGGGCATGGAACACCTGAGAGAGGCCAGAGCC

ATCACCAGCGCCAACGTGCAGGACTTCGTGGGCTGCAAGAAGATTTTCGGCTCC

CTGGCCTTCCTGCCCGAGAGCTTCGACGGCGATCCTGCCTCTGGCACCGCCCCT

CTGCAGCCTGAGCAGCTGCAGGTCTTCGAGACACTGGAAGAGATCACCGGCTAC

CTGTACATCAGCGCCTGGCCCGACAGCTTCCCCAACCTGAGCGTGTTCCAGAAC

CTGAGAGTGATCCGGGGCAGAATCCTGCACAACGGCGCCTACAGCCTGACCCTG

CAGGGCCTGGGAATCAGCTGGCTGGGCCTGCGGAGCCTGCAGGAACTGGGATC

TGGCCTGGCTCTGGTGCACCGGAACGCCCGGCTGTGCTTCGTGCACACCGTGCC

CTGGGACCAGCTGTTCAGAAACCCCCACCAGGCTCTGCTGCACAGCGGCAACCG

GCCCGAAGAGGATTGCGTGGGCGAGGGCTTCGTGTGCTACTCCCTGTGCGCCCA

CGGCCACTGTTGGGGACCTGGCCCTACCCAGTGCGTGAACTGCAGCCACTTCCT

GCGGGGCCAAGAATGCGTGGAAGAGTGCCGGGTGCTGCAGGGACTGCCCCGGG

AATACGTGAACGCCAGACACTGCCTGCCTTGCCACCCCGAGTGCCAGCCCCAGA

ATGGCAGCGTGACCTGCTTCGGACCCGAGGCCGATCAGTGTGTGGCCTGCGCC

CACTACAAGGACCCCCCATTCTGCGTGGCCAGATGCCCCAGCGGCGTGAAGCCC

GACCTGAGCTACATGCCCATCTGGAAGTTCCCCGACGAGGAAGGCGCCTGCCAG

CCTTGCCCCATCAACTGCACCCACAGCTGCGTGGACCTGGACGACAAGGGCTGC

CCTGCCGAGCAGAGAGCCAGCCCCCTGACCAGCATCATCAGCGCCGTGGTGGG

AATCCTGCTGGTGGTGGTGCTGGGCGTGGTGTTCGGCATCCTGATCAAGCGGCG

GCAGCAGAAGATCCGGAAGTACACCATGCGGCGGAACGAGGACCTGGGCCCCT

CTAGCCCCATGGACAGCACCTTCTACCGGTCCCTGCTGGAAGATGAGGACATGG

GCGAGCTGGTGGACGCCGAGGAATACCTGGTGCCTCAGCAGGGCTTCTTCTGCC

CCGACCCTACCCCTGGCACCGGCTCTACCGCCCACAGACGGCACAGAAGCAGCA

-continued

GCGCCAGAAACGGCGGAGGCGACCTGACCCTGGGAATGGAACCTAGCGGCGAG

GGACCTCCCAGAAGCCCTAGAGCCCCTAGCGAGGGCACCGGCAGCGACGTGTT

CGATGGCGATCTGGCCGTGGGCGTGACCAAGGGACTGCAGAGCCTGAGCCCCC

AGGACCTGTCCCCCCTGCAGAGATACAGCGAGGACCCCACCCTGCCCCTGCCCA

GCGAGACAGATGGCAAGGTGGCCCCCCTGAGCTGCAGCCCTCAGCCCGAGTTC

GTGAACCAGAGCGACGTGCAGCCCAAGTCCCCCCTGACACCCGAGGGACCTCCA

AGCCCTGCCAGACCTACCGGCGCCACCCTGGAAAGAGCCAAGACCCTGAGCCC

CGGCAAGAACGGCGTGGTGAAAGACGTGTTCACCTTCGGAGGCGCCGTGGAAAA

CCCCGAGTTCCTGGCCCCCAGAGAGGGCACAGCCAGCCCTCCACACCCCAGCC

CAGCCTTCTCCCCCGCCTTCGACAACCTGTTCTTCTGGGACCAGAACAGCAGCGA

GCAGGGCCCACCCCCCAGCAATTTCGAGGGCACCCCCACCGCCGAGAATCCTGA

GTTCCTGGGCCTGGACGTGCCCGTGTGA

Amino acid sequence of heavy chain of the anti-CD40 antibody CP870,893:.

SEQ ID NO: 40

MDWTWRILFLVAAATGAHSQVQLVQSGAEVKKPGASVKVSCKASGYTFTGYYMHW

VRQAPGQGLEWMGWINPDSGGTNYAQKFQGRVTMTRDTSISTAYMELNRLRSDDT

AVYYCARDQPLGYCTNGVCSYFDYWGQGTLVTVSSASTKGPSVFPLAPCSRSTSES

TAALGCLVKDYFPEPVTVSWNSGALTSGVHTFPAVLQSSGLYSLSSVVTVPSSNFGT

QTYTCNVDHKPSNTKVDKTVERKCCVECPPCPAPPVAGPSVFLFPPKPKDTLMISRT

PEVTCVVVDVSHEDPEVQFNWYVDGVEVHNAKTKPREEQFNSTFRVVSVLTVVHQD

WLNGKEYKCKVSNKGLPAPIEKTISKTKGQPREPQVYTLPPSREEMTKNQVSLTCLV

KGFYPSDIAVEWESNGQPENNYKTTPPMLDSDGSFFLYSKLTVDKSRWQQGNVFSC

SVMHEALHNHYTQKSLSLSPGK.

Acid sequence of the light chain of the anti-CD40 antibody CP870,893:.

SEQ ID NO: 41

MRLPAQLLGLLLLWFPGSRCDIQMTQSPSSVSASVGDRVTITCRASQGIYSWLAWYQ

QKPGKAPNLLIYTASTLQSGVPSRFSGSGSGTDFTLTISSLQPEDFATYYCQQANIFPL

TFGGGTKVEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNR

GEC.

Acid sequence of the heavy chain of the anti-CTLA-4 antibody Tremelimumab.

SEQ ID NO: 42

QVQLVESGGGVVQPGRSLRLSCAASGFTFSSYGMHWVRQAPGKGLEWVAVIWYDG

SNKYYADSVKGRFTISRDNSKNTLYLQMNSLRAEDTAVYYCARDPRGATLYYYYYGM

DVWGQGTTVTVSSASTKGPSVFPLAPCSRSTSESTAALGCLVKDYFPEPVTVSWNS

GALTSGVHTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDPEVQFNWY

VDGVEVHNAKTKPREEQFNSTFRVVSVLTVVHQDWLNGKEYKCKVSNKGLPAPIEKT

ISKTKGQPREPQVYTLPPSREEMTKNQVSLTCLVKGFYPSDIAVEWESNGQPENNYK

TTPPMLDSDGSFFLYSKLTVDKSRWQQGNVFSCSVMHEALHNHYTQKSLSLSPGK

Acid sequence of the light chain of the anti-CTLA-4 antibody Tremelimumab.

-continued

SEQ ID NO: 43

DIQMTQSPSSLSASVGDRVTITCRASQSINSYLDWYQQKPGKAPKLLIYAASSLQSGV

PSRFSGSGSGTDFTLTISSLQPEDFATYYCQQYYSTPFTFGPGTKVEIKRTVAAPSVFI

FPPSDEQLKSGTASVVCLLNNFYPREAKVQWKVDNALQSGNSQESVTEQDSKDSTY

SLSSTLTLSKADYEKHKVYACEVTHQGLSSPVTKSFNRGEC

Nucleotide sequence of CpG 7909.

SEQ ID NO: 44

5' TCGTCGTTTTGTCGTTTTGTCGTT3'

Nucleotide sequence of CpG 24555.

SEQ ID NO: 45

5' TCGTCGTTTTTCGGTGCTTTT3'

Nucleotide sequence of CpG 10103.

SEQ ID NO: 46

5' TCGTCGTTTTTCGGTCGTTTT3'

Amino acid sequence of eGFP.

SEQ ID NO: 47

MVSKGEELFTGVVPILVELDGDVNGHKFSVSGEGEGDATYGKLTLKFICTTGKLPVP

WPTLVTTLTYGVQCFSRYPDHMKQHDFFKSAMPEGYVQERTIFFKDDGNYKTRAEV

KFEGDTLVNRIELKGIDFKEDGNILGHKLEYNYNSHNVYIMADKQKNGIKVNFKIRHNIE

DGSVQLADHYQQNTPIGDGPVLLPDNHYLSTQSALSKDPNEKRDHMVLLEFVTAAGI

TLGMDELYK

Amino acid sequence of HBV core antigen.

SEQ ID NO: 48

MDIDPYKEFGATVELLSFLPSDFFPSVRDLLDTASALYREALESPEHCSPHHTALRQAI

LCWGELMTLATWVGNNLEDPASRDLVVNYVNTNMGLKIRQLLWFHISCLTFGRETVL

EYLVSFGVWIRTPPAYRPPNAPILSTLPETTVVRRRGRGRSPRRRTPSPRRRRSQSP

RRRRSQSRESQC

Amino acid sequence of HBV surface antigen.

SEQ ID NO: 49

MENITSGFLGPLLVLQAGFFLLTRILTIPQSLDSWWTSLNFLGGSPVCLGQNSQSPTS

NHSPTSCPPICPGYRWMCLRRFIIFLFILLLCLIFLLVLLDYQGMLPVCPLIPGSTTTSTG

PCKTCTTPAQGNSMFPSCCCTKPTDGNCTCIPIPSSWAFAKYLWEWASVRFSWLSLL

VPFVQWFVGLSPTVWLSAIWMMWYWGPSLYSIVSPFlPLLPIFFCLWVYI

Amino acid sequence of Rhesus PSMA ECD protein:.

SEQ ID NO: 50

MASETDTLLLWVLLLWVPGSTGDAAHHHHHHKSSSEATNITPKHNMKAFLDELKAENI

KKFLHNFTQIPHLAGTEQNFQLAKQIQSQWKEFGLDSVELTHYDVLLSYPNKTHPNYI

SIINEDGNEIFNTSLFEPPPAGYENVSDIVPPFSAFSPQGMPEGDLVYVNYARTEDFFK

LERDMKINCSGKIVIARYGKVFRGNKVKNAQLAGATGVILYSDPADYFAPGVKSYPDG

WNLPGGGVQRGNILNLNGAGDPLTPGYPANEYAYRRGIAEAVGLPSIPVHPIGYYDA

QKLLEKMGGSASPDSSWRGSLKVPYNVGPGFTGNFSTQKVKMHIHSTSEVTRIYNVI

GTLRGAVEPDRYVILGGHRDSWVFGGIDPQSGAAVVHEIVRSFGTLKKEGWRPRRTI

LFASWDAEEFGLLGSTEWAEENSRLLQERGVAYINADSSIEGNYTLRVDCTPLMYSL

VYNLTKELESPDEGFEGKSLYESWTKSPSPEFSGMPRISKLGSGNDFEVFFQRLGIAS

GRARYTKNWETNKFSSYPLYHSVYETYELVEKFYDPMFKYHLTVAQVRGGMVFELA

NSVVLPFDCRDYAVVLRKYADKIYNISMKHPQEMKTYSVSFDSLFSAVKNFTEIASKFS

-continued

ERLRDFDKSNPILLRMMNDQLMFLERAFIDPLGLPDRPFYRHVIYAPSSHNKYAGESF

PGIYDALFDIESKVDPSQAWGEVKRQISIATFTVQAAAETLSEVA

Amino acid sequence of rat Her-2 p66 peptide (H-2d T cell epitope).

SEQ ID NO: 51

TYVPANASL

Amino acid sequence of rat Her-2 p169 peptide (H-2d T cell epitope).

SEQ ID NO: 52

DMVLWKDVFRKNNQL

Amino acid sequence of HBV core antigen p87 peptide.

SEQ ID NO: 53

SYVNTNMGL

Amino acid sequence of a Rat Her-2 Antigen (rHer-2):.

SEQ ID NO: 54

MASELAAWCRWGFLLALLPPGIAGTQVCTGTDMKLRLPASPETHLDMLRHLYQGCQ

VVQGNLELTYVPANASLSFLQDIQEVQGYMLIAHNQVKRVPLQRLRIVRGTQLFEDKY

ALAVLDNRDPQDNVAASTPGRTPEGLRELQLRSLTEILKGGVLIRGNPQLCYQDMVL

WKDVFRKNNQLAPVDIDTNRSRACPPCAPACKDNHCWGESPEDCQILTGTICTSGC

ARCKGRLPTDCCHEQCAAGCTGPKHSDCLACLHFNHSGICELHCPALVTYNTDTFES

MHNPEGRYTFGASCVTTCPYNYLSTEVGSCTLVCPPNNQEVTAEDGTQRCEKCSKP

CARVCYGLGMEHLRGARAITSDNVQEFDGCKKIFGSLAFLPESFDGDPSSGIAPLRPE

QLQVFETLEEITGYLYISAWPDSLRDLSVFQNLRIIRGRILHDGAYSLTLQGLGIHSLGL

RSLRELGSGLALIHRNAHLCFVHTVPWDQLFRNPHQALLHSGNRPEEDCGLEGLVCN

SLCAHGHCWGPGPTQCVNCSHFLRGQECVEECRVWKGLPREYVSDKRCLPCHPEC

QPQNSSETCFGSEADQCAACAHYKDSSSCVARCPSGVKPDLSYMPIWKYPDEEGIC

QPCPINCTHSCVDLDERGCPAEQRASPVTFIIATVVGVLLFLILVVVVGILIKRRRQKIRK

YTMRRNEDLGPSSPMDSTFYRSLLEDDDMGDLVDAEEYLVPQQGFFSPDPTPGTGS

TAHRRHRSSSTRSGGGELTLGLEPSEEGPPRSPLAPSEGAGSDVFDGDLAMGVTKG

LQSLSPHDLSPLQRYSEDPTLPLPPETDGYVAPLACSPQPEFVNQSEVQPQPPLTPE

GPLPPVRPAGATLERPKTLSPGKNGVVKDVFAFGGAVENPEFLVPREGTASPPHPSP

AFSPAFDNLFFWDQNSSEQGPPPSNFEGTPTAENPEFLGLDVPV

Amino Acid Sequence of Rhesus PSMA antigen:.

SEQ ID NO: 55

MASARRPRWLCAGALVLAGGFFLLGFLFGWFIKSSSEATNITPKHNMKAFLDELKAENIK

KFLHNFTQIPHLAGTEQNFQLAKQIQSQWKEFGLDSVELTHYDVLLSYPNKTHPNYISII

NEDGNEIFNTSLFEPPPAGYENVSDIVPPFSAFSPQGMPEGDLVYVNYARTEDFFKLERD

MKINCSGKIVIARYGKVFRGNKVKNAQLAGATGVILYSDPADYFAPGVKSYPDGWNLPGG

GVQRGNILNLNGAGDPLTPGYPANEYAYRRGIAEAVGLPSIPVHPIGYYDAQKLLEKMGG

SASPDSSWRGSLKVPYNVGPGFTGNFSTQKVKMHIHSTSEVTRIYNVIGTLRGAVEPDRY

VILGGHRDSWVFGGIDPQSGAAVVHEIVRSFGTLKKEGWRPRRTILFASWDAEEFGLLGS

TEWAEENSRLLQERGVAYINADSSIEGNYTLRVDCTPLMYSLVYNLTKELESPDEGFEGK

SLYESWTKKSPSPEFSGMPRISKLGSGNDFEVFFQRLGIASGRARYTKNWETNKFSSYPL

YHSVYETYELVEKFYDPMFKYHLTVAQVRGGMVFELANSVVLPFDCRDYAVVLRKYADKI

YNISMKHPQEMKTYSVSFDSLFSAVKNFTEIASKFSERLRDFDKSNPILLRMMNDQLMFL

-continued

ERAFIDPLGLPDRPFYRHVIYAPSSHNKYAGESFPGIYDALFDIESKVDPSQAWGEVKRQ

ISIATFTVQAAAETLSEVA

Nucleotide sequence encoding the rhesus PSMA antigen
of SEQ ID NO: 55"

SEQ ID NO: 56

ATGGCTAGCGCTAGAAGGCCCAGATGGCTGTGCGCTGGCGCCCTGGTGCTGGCTGGCGGATTCTT

CCTGCTGGGCTTCCTGTTCGGCTGGTTCATCAAGTCCTCCAGCGAGGCCACCAACATCACCCCCA

AGCACAACATGAAGGCCTTTCTGGACGAGCTGAAGGCCGAGAATATCAAGAAGTTCCTGCACAAC

TTCACCCAGATCCCCCACCTGGCCGGCACCGAGCAGAACTTCCAGCTGGCCAAGCAGATCCAGTC

CCAGTGGAAAGAGTTCGGCCTGGACTCCGTGGAACTGACCCACTACGACGTGCTGCTGTCCTACC

CCAACAAGACCCACCCCAACTACATCTCCATCATCAACGAGGACGGCAACGAAATCTTCAACACC

TCCCTGTTCGAGCCCCCACCAGCCGGCTACGAGAACGTGTCCGACATCGTGCCCCCATTCTCCGC

ATTCAGTCCACAAGGCATGCCCGAGGGCGACCTGGTGTACGTGAACTACGCCAGGACCGAGGACT

TCTTCAAGCTGGAAAGGGACATGAAGATCAACTGCTCCGGCAAGATCGTGATCGCCAGATACGGC

AAGGTGTTCAGGGGCAACAAAGTGAAGAACGCTCAGCTGGCTGGGGCCACCGGCGTGATCCTGTA

CTCTGACCCCGCCGACTACTTCGCCCCCAGGCGTGAAGTCCTACCCCGACGGCTGGAACCTGCCAG

GTGGCGGAGTGCAGAGGGGCAACATCCTGAACCTGAACGGCGCTGGCGACCCCCTGACCCCAGGA

TACCCCGCCAACGAGTACGCCTACAGAAGAGGAATCGCCGAGGCCGTGGGCCTGCCCTCTATCCC

AGTGCACCCCATCGGCTACTACGACGCCCAGAAACTGCTGGAAAAGATGGGCGGCTCCGCCTCCC

CCGACTCCTCTTGGAGAGGCTCCCTGAAGGTGCCCTACAACGTGGGCCCAGGCTTCACCGGCAAC

TTCTCCACCCAGAAAGTGAAGATGCACATCCACTCCACCTCCGAAGTGACCAGGATCTACAACGT

GATCGGCACCCTGAGAGGCGCCGTGGAACCCGACAGATACGTGATCCTGGGCGGCCACAGGGACA

GCTGGGTGTTCGGCGGCATCGACCCACAGTCTGGCGCCGCTGTGGTGCACGAGATCGTGCGGTCC

TTCGGAACCCTGAAGAAAGAGGGATGGCGCCCCAGAAGGACAATCCTGTTCGCCTCCTGGGACGC

CGAGGAATTCGGCCTGCTGGGATCCACCGAGTGGGCCGAGGAAAACTCCAGGCTGCTGCAGGAAA

GGGGCGTCGCCTACATCAACGCCGACTCCTCCATCGAGGGCAACTACACCCTGAGGGTGGACTGC

ACCCCCCTGATGTACTCCCTGGTGTACAACCTGACCAAAGAGCTGGAATCCCCCGACGAGGGCTT

CGAGGGCAAGTCCCTGTACGAGTCCTGGACCAAGAAGTCCCCATCCCCCGAGTTCTCCGGCATGC

CCAGGATCTCCAAGCTGGGCTCCGGCAACGACTTCGAGGTGTTCTTCCAGAGGCTGGGAATCGCC

TCCGGCAGGGCCAGATACACCAAGAACTGGGAGACAAACAAGTTCTCCTCCTACCCCCTGTACCA

CTCCGTGTACGAAACCTACGAGCTGGTGGAAAAGTTCTACGACCCCATGTTCAAGTACCACCTGA

CCGTGGCCCAGGTCCGCGGAGGCATGGTGTTCGAGCTGGCCAACTCCGTGGTGCTGCCCTTCGAC

TGCAGAGACTATGCTGTGGTGCTGAGGAAGTACGCCGACAAAATCTACAACATCTCCATGAAGCA

CCCCCAGGAAATGAAGACCTACTCCGTGTCCTTCGACTCCCTGTTCTCCGCCGTGAAGAATTTCA

CCGAGATCGCCTCCAAGTTCTCCGAGAGGCTGAGGGACTTCGACAAGTCCAACCCCATCCTGCTG

AGGATGATGAACGACCAGCTGATGTTCCTGGAAAGGGCCTTCATCGACCCCCTGGGCCTGCCAGA

CAGGCCCTTCTACAGGCACGTGATCTACGCCCCATCCTCCCACAACAAATACGCCGGCGAGTCCT

TCCCCGGCATCTACGATGCCCTGTTCGACATCGAGTCCAAGGTGGACCCCTCCCAGGCTTGGGGC

GAAGTGAAGAGGCAGATCAGTATCGCCACATTCACAGTGCAGGCCGCTGCCGAAACCCTGTCCGA

GGTGGCC

The invention claimed is:

1. A plasmid vector which comprises a multi-antigen construct encoding two different immunogenic polypeptides, wherein each of the immunogenic polypeptides is encoded by a coding nucleotide sequence on the multi-antigen construct, wherein the multi-antigen construct comprises a separator sequence between the two coding nucleotide sequences, wherein one of the two different immunogenic polypeptides is an immunogenic PSMA polypeptide and the other immunogenic polypeptide is an immunogenic PSA polypeptide, and wherein the immunogenic PSA polypeptide consists of an amino acid sequence selected from the group consisting of:
- (1) an amino acid sequence consisting of amino acids 27-263 of SEQ ID NO:15;
- (2) an amino acid sequence consisting of amino acids 4-240 of SEQ ID NO:17; and
- (3) the amino acid sequence of SEQ ID NO:17.

2. The plasmid vector according to claim 1, wherein the immunogenic PSMA polypeptide consists of an amino acid sequence selected from the group consisting of:
- (1) an amino acid sequence consisting of amino acids 15-750 of SEQ ID NO:1;
- (2) the amino acid sequence of SEQ ID NO:3;
- (3) the amino acid sequence of SEQ ID NO:5;
- (4) the amino acid sequence of SEQ ID NO:7;
- (5) an amino acid sequence consisting of amino acids 4-739 of SEQ ID NO:9;
- (6) an amino acid sequence consisting of amino acids 4-739 of SEQ ID NO:3;
- (7) an amino acid sequence consisting of amino acids 4-739 of SEQ ID NO:5;
- (8) an amino acid sequence consisting of amino acids 4-739 of SEQ ID NO:7; and
- (9) the amino acid sequence of SEQ ID NO:9.

3. The plasmid vector according to claim 1, wherein the separator sequence is selected from the group consisting of:
- (1) a nucleotide sequence encoding a 2A peptide sequence; and
- (2) an internal ribosomal entry site (IRES) sequence.

4. The plasmid vector according to claim 3, wherein the 2A peptide sequence is selected from the group consisting of the 2A-peptide sequence of FMDV, ERAV, PTV1, EMC-B, EMCV, TME-GD7, ERBV, TaV, DrosC, CrPV, ABPV, IFV, Porcine rotavirus, human rotavirus, *T brucei* TSR1, and *T cruzi* AP endonuclease.

5. The plasmid vector according to claim 4, wherein the 2A peptide sequence is selected from the group consisting of a FMDV 2A-peptide sequence and a TAV 2A peptide sequence.

6. The plasmid vector according to claim 3, wherein the IRES sequence is an EMCV IRES sequence.

7. The plasmid vector according to claim 1, wherein the nucleotide sequence encoding the immunogenic PSA polypeptide is selected from the group consisting of:

(1) the nucleotide sequence of SEQ ID NO:18;

(2) the nucleotide sequence of SEQ ID NO:20;

(3) a nucleotide sequence consisting of nucleotides 10-720 of SEQ ID NO:18; and (4) a degenerate variant of any of the nucleotide sequences provided in (1)-(3).

8. A pharmaceutical composition, comprising the plasmid vector according to claim 1 and a pharmaceutically acceptable excipient.

9. A method of treatment for prostate cancer in a patient in need thereof, comprising administering to the patient an effective amount of a plasmid vector according to claim 1.

10. The method according to claim 9, further comprising administering to the patient an effective amount of an immune modulator.

11. The method according to claim 10, wherein the immune modulator is selected from the group consisting of TNFR agonists, CTLA-4 antagonists, TLR agonists, programmed cell death protein 1 antagonists, programmed cell death protein 1 ligand antagonists.

12. The method according to claim 11, wherein the immune modulator is a CTLA-4 antagonist.

13. The method according to claim 12, wherein the CTLA-4 antagonist is an anti-CTLA-4 antibody.

14. The method according to claim 11, wherein the immune modulator is a TLR agonist.

15. The method according to claim 14, wherein the TLR agonist is a CpG oligonucleotide.

16. The method according to claim 11, wherein the immune modulator is sunitinib malate.

17. The method according to claim 11, wherein the immune modulator PD-L1 antagonist or PD-1 antagonist.

* * * * *

```
                              SEQUENCE LISTING


<160> NUMBER OF SEQ ID NOS: 56

<210> SEQ ID NO 1
<211> LENGTH: 750
<212> TYPE: PRT
<213> ORGANISM: Homo sapiens

<400> SEQUENCE: 1

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365
```

```
Asp Arg Tyr Val Ile Leu Gly Gly His Arg Asp Ser Trp Val Phe Gly
    370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
    450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
    610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr Ala Gly Glu Ser
    690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
            740                 745                 750
```

<210> SEQ ID NO 2
<211> LENGTH: 2250
<212> TYPE: DNA
<213> ORGANISM: Homo sapiens

<400> SEQUENCE: 2

```
atgtggaatc tccttcacga aaccgactcg gctgtggcca ccgcgcgccg cccgcgctgg     60
ctgtgcgctg gggcgctggt gctggcgggt ggcttctttc tcctcggctt cctcttcggg    120
tggtttataa aatcctccaa tgaagctact aacattactc caaagcataa tatgaaagca    180
tttttggatg aattgaaagc tgagaacatc aagaagttct tatataattt tacacagata    240
ccacatttag caggaacaga acaaaacttt cagcttgcaa agcaaattca atcccagtgg    300
aaagaatttg gcctggattc tgttgagcta gcacattatg atgtcctgtt gtcctaccca    360
aataagactc atcccaacta catctcaata attaatgaag atggaaatga gattttcaac    420
acatcattat ttgaaccacc tcctccagga tatgaaaatg tttcggatat tgtaccacct    480
ttcagtgctt tctctcctca aggaatgcca gagggcgatc tagtgtatgt taactatgca    540
cgaactgaag acttctttaa attggaacgg gacatgaaaa tcaattgctc tgggaaaatt    600
gtaattgcca gatatgggaa agttttcaga ggaaataagg ttaaaaatgc ccagctggca    660
ggggccaaag gagtcattct ctactccgac cctgctgact actttgctcc tggggtgaag    720
tcctatccag atggttggaa tcttcctgga ggtggtgtcc agcgtggaaa tatcctaaat    780
ctgaatggtg caggagaccc tctcacacca ggttacccag caaatgaata tgcttatagg    840
cgtggaattg cagaggctgt tggtcttcca agtattcctg ttcatccaat tggatactat    900
gatgcacaga agctcctaga aaaaatgggt ggctcagcac caccagatag cagctggaga    960
ggaagtctca aagtgcccta caatgttgga cctggcttta ctggaaactt ttctacacaa   1020
aaagtcaaga tgcacatcca ctctaccaat gaagtgacaa gaatttacaa tgtgataggt   1080
actctcagag gagcagtgga accagacaga tatgtcattc tgggaggtca ccgggactca   1140
tgggtgtttg gtggtattga ccctcagagt ggagcagctg ttgttcatga aattgtgagg   1200
agctttggaa cactgaaaaa ggaagggtgg agacctagaa gaacaatttt gtttgcaagc   1260
tgggatgcag aagaatttgg tcttcttggt tctactgagt gggcagagga gaattcaaga   1320
ctccttcaag agcgtggcgt ggcttatatt aatgctgact catctataga aggaaactac   1380
actctgagag ttgattgtac accgctgatg tacagcttgg tacacaacct aacaaaagag   1440
ctgaaaagcc ctgatgaagg ctttgaaggc aaatctcttt atgaaagttg gactaaaaaa   1500
agtccttccc cagagttcag tggcatgccc aggataagca aattgggatc tggaaatgat   1560
tttgaggtgt tcttccaacg acttggaatt gcttcaggca gagcacggta tactaaaaat   1620
tgggaaacaa acaaattcag cggctatcca ctgtatcaca gtgtctatga aacatatgag   1680
ttggtggaaa agttttatga tccaatgttt aaatatcacc tcactgtggc ccaggttcga   1740
ggagggatgg tgtttgagct agccaattcc atagtgctcc cttttgattg tcgagattat   1800
gctgtagttt taagaaagta tgctgacaaa atctacagta tttctatgaa acatccacag   1860
gaaatgaaga catacagtgt atcatttgat tcactttttt ctgcagtaaa gaattttaca   1920
gaaattgctt ccaagttcag tgagagactc caggactttg acaaaagcaa cccaatagta   1980
ttaagaatga tgaatgatca actcatgttt ctggaaagag catttattga tccattaggg   2040
ttaccagaca ggccttttta taggcatgtc atctatgctc caagcagcca caacaagtat   2100
gcaggggagt cattcccagg aatttatgat gctctgtttg atattgaaag caaagtggac   2160
ccttccaagg cctggggaga agtgaagaga cagatttatg ttgcagcctt cacagtgcag   2220
gcagctgcag agactttgag tgaagtagcc                                    2250
```

<210> SEQ ID NO 3

<211> LENGTH: 739
<212> TYPE: PRT
<213> ORGANISM: Artificial
<220> FEATURE:
<223> OTHER INFORMATION: synthetic construct

<400> SEQUENCE: 3

```
Met Ala Ser Ala Arg Arg Pro Arg Trp Leu Cys Ala Gly Ala Leu Val
1               5                   10                  15

Leu Ala Gly Gly Phe Phe Leu Leu Gly Phe Leu Phe Gly Trp Phe Ile
            20                  25                  30

Lys Ser Ser Ser Glu Ala Thr Asn Ile Ser Pro Gln His Asn Val Lys
        35                  40                  45

Ala Phe Leu Asp Glu Met Lys Ala Glu Asn Ile Lys Lys Phe Leu Tyr
    50                  55                  60

Leu Phe Thr Gln Ile Pro His Leu Ala Gly Thr Glu Gln Asn Phe Gln
65                  70                  75                  80

Leu Ala Lys Gln Ile Gln Ala Glu Trp Lys Glu Phe Gly Leu Asp Ser
                85                  90                  95

Val Glu Leu Ala His Tyr Asp Val Leu Leu Ser Tyr Pro Asn Glu Thr
            100                 105                 110

His Pro Asn Tyr Ile Ser Ile Ile Asp Glu Asp Gly Asn Glu Ile Phe
        115                 120                 125

Asn Thr Ser Leu Phe Glu Pro Pro Pro Pro Gly Tyr Glu Asn Ile Ser
    130                 135                 140

Asp Val Val Pro Pro Tyr Ser Ala Phe Ser Pro Gln Gly Met Pro Glu
145                 150                 155                 160

Gly Asp Leu Val Tyr Val Asn Tyr Ala Arg Thr Glu Asp Phe Phe Lys
                165                 170                 175

Leu Glu Arg Glu Leu Lys Ile Asn Cys Ser Gly Lys Ile Leu Ile Ala
            180                 185                 190

Arg Tyr Gly Lys Val Phe Arg Gly Asn Lys Val Lys Asn Ala Gln Leu
        195                 200                 205

Ala Gly Ala Lys Gly Ile Ile Leu Tyr Ser Asp Pro Ala Asp Tyr Phe
    210                 215                 220

Ala Pro Gly Val Lys Ser Tyr Pro Asp Gly Trp Asn Leu Pro Gly Gly
225                 230                 235                 240

Gly Val Gln Arg Gly Asn Val Leu Asn Leu Asn Gly Ala Gly Asp Pro
                245                 250                 255

Leu Thr Pro Gly Tyr Pro Ala Asn Glu Tyr Ala Tyr Arg Arg Glu Leu
            260                 265                 270

Ala Glu Ala Val Gly Leu Pro Ser Ile Pro Val His Pro Ile Gly Tyr
        275                 280                 285

Tyr Asp Ala Gln Lys Leu Leu Glu Lys Met Gly Gly Ser Ala Pro Pro
    290                 295                 300

Asp Ser Ser Trp Lys Gly Ser Leu Lys Val Pro Tyr Asn Val Gly Pro
305                 310                 315                 320

Gly Phe Thr Gly Asn Phe Ser Thr Gln Lys Val Lys Met His Ile His
                325                 330                 335

Ser Thr Asn Glu Val Thr Arg Ile Tyr Asn Val Ile Gly Thr Ile Arg
            340                 345                 350

Gly Ala Val Glu Pro Asp Arg Tyr Val Ile Leu Gly Gly His Arg Asp
        355                 360                 365

Ala Trp Val Phe Gly Gly Ile Asp Pro Gln Ser Gly Ala Ala Val Val
    370                 375                 380
```

His Glu Ile Val Arg Ser Phe Gly Thr Leu Lys Lys Lys Gly Trp Arg
385 390 395 400

Pro Arg Arg Thr Ile Ile Phe Ala Ser Trp Asp Ala Glu Glu Phe Gly
405 410 415

Leu Leu Gly Ser Thr Glu Trp Ala Glu Glu Asn Ser Arg Leu Leu Gln
420 425 430

Glu Arg Gly Val Ala Tyr Ile Asn Ala Asp Ser Ser Ile Glu Gly Asn
435 440 445

Tyr Thr Leu Arg Val Asp Cys Thr Pro Leu Met Tyr Ser Leu Val Tyr
450 455 460

Asn Leu Thr Lys Glu Leu Gln Ser Pro Asp Glu Gly Phe Glu Gly Lys
465 470 475 480

Ser Leu Tyr Glu Ser Trp Thr Lys Lys Ser Pro Ser Pro Glu Phe Ser
485 490 495

Gly Val Pro Arg Ile Asn Lys Leu Gly Ser Gly Asn Asp Phe Glu Val
500 505 510

Phe Phe Gln Arg Leu Gly Ile Ala Ser Gly Arg Ala Arg Tyr Thr Lys
515 520 525

Asn Trp Lys Thr Asn Lys Phe Ser Gly Tyr Pro Leu Tyr His Ser Val
530 535 540

Tyr Glu Thr Tyr Glu Leu Val Glu Lys Phe Tyr Asp Pro Met Phe Lys
545 550 555 560

Tyr His Leu Thr Val Ala Gln Val Arg Gly Gly Leu Val Phe Glu Leu
565 570 575

Ala Asp Ser Ile Val Leu Pro Phe Asp Cys Gln Asp Tyr Ala Val Val
580 585 590

Leu Arg Lys Tyr Ala Asp Lys Ile Tyr Asn Leu Ala Met Lys His Pro
595 600 605

Glu Glu Leu Lys Thr Tyr Ser Val Ser Phe Asp Ser Leu Phe Ser Ala
610 615 620

Val Lys Asn Phe Thr Glu Ile Ala Ser Lys Phe Asn Gln Arg Leu Gln
625 630 635 640

Asp Phe Asp Lys Asn Asn Pro Leu Leu Val Arg Met Leu Asn Asp Gln
645 650 655

Leu Met Phe Leu Glu Arg Ala Phe Val Asp Pro Leu Gly Leu Pro Asp
660 665 670

Arg Pro Phe Tyr Arg His Val Ile Tyr Ala Pro Ser Ser His Asn Lys
675 680 685

Tyr Ala Gly Glu Ser Phe Pro Gly Ile Tyr Asp Ala Leu Phe Asp Ile
690 695 700

Glu Ser Lys Val Asp Pro Ser Lys Ala Trp Gly Glu Val Lys Arg Gln
705 710 715 720

Ile Tyr Val Ala Ala Phe Thr Val Gln Ala Ala Ala Glu Thr Leu Ser
725 730 735

Glu Val Ala

<210> SEQ ID NO 4
<211> LENGTH: 2217
<212> TYPE: DNA
<213> ORGANISM: Artificial
<220> FEATURE:
<223> OTHER INFORMATION: Synthetic Construct

<400> SEQUENCE: 4

-continued

```
atggctagcg ccagacggcc cagatggctg tgcgccggag ccctggtgct ggccggagga     60
ttcttcctgc tgggcttcct gttcggctgg ttcatcaaga gcagcagcga ggccaccaac    120
atcagccccc agcacaacgt gaaggccttt ctggacgaga tgaaggccga gaacatcaag    180
aagtttctgt acctgttcac ccagatcccc cacctggccg gcaccgagca gaacttccag    240
ctggccaagc agattcaggc tgagtggaaa gagttcggcc tggacagcgt ggagctggcc    300
cactacgacg tgctgctgtc ctaccccaac gagacacacc ccaactacat cagcatcatc    360
gacgaggacg gcaacgagat tttcaacacc agcctgttcg agcccctcc ccctggctac     420
gagaacatct ccgacgtggt gccccctac agcgccttca gccctcaggg aatgcctgaa     480
ggcgacctgg tgtacgtgaa ctacgcccgg accgaggact tcttcaagct ggaacgggag    540
ctgaagatca actgcagcgg caagatcctg atcgccagat acggcaaggt gttccggggc    600
aacaaagtga agaacgcaca gctggctgga gccaagggca tcatcctgta cagcgacccc    660
gccgactact tcgcccctgg cgtgaagtcc taccctgacg gctggaacct gcctggcggc    720
ggagtgcagc ggggcaacgt gctgaacctg aacggagccg gcgaccctct gaccccaggc    780
taccccgcca acgagtacgc ctaccggcgg gagctggccg aagccgtggg cctgcccagc    840
atccccgtgc accccatcgg ctactacgac gcccagaaac tgctggaaaa gatgggcggc    900
agcgcccctc ccgacagcag ctggaagggc agcctgaagg tgccctacaa cgtgggccct    960
ggcttcaccg gcaacttcag cacccagaaa gtgaagatgc acatccacag caccaacgaa   1020
gtgacccgga tctacaacgt gatcggcacc atcagaggcg ccgtggagcc cgacagatac   1080
gtgatcctgg gcggccaccg ggacgcctgg gtgttcggcg gcatcgaccc ccagagcgga   1140
gccgccgtgg tgcacgagat cgtgcggagc ttcggcaccc tgaagaagaa gggctggcgg   1200
cccagacgga ccatcatctt cgccagctgg gacgccgagg aattcggact gctgggctct   1260
accgagtggg ccgaggaaaa cagcagactg ctgcaggaac ggggcgtcgc ctacatcaac   1320
gccgacagct ccatcgaggg caactacacc ctgcgggtgg actgcacccc cctgatgtac   1380
agcctggtgt acaacctgac caaagagctg cagagccccg acgagggctt cgagggcaag   1440
agcctgtacg agagctggac caagaagtcc cccagccccg agttcagcgg cgtgccccgg   1500
atcaacaagc tgggcagcgg caacgacttc gaggtgttct tccagaggct gggcattgcc   1560
agcggcagag cccggtacac caagaactgg aaaaccaaca agttctccgg ctaccccctg   1620
taccacagcg tgtacgagac atacgaactg gtggagaagt tctacgaccc catgttcaag   1680
taccacctga ccgtggccca ggtccgggga gggctggtgt tcgaactggc cgacagcatc   1740
gtgctgccct tcgactgcca ggactatgct gtggtgctgc ggaagtacgc cgacaaaatc   1800
tacaacctgg ccatgaagca ccccgaggaa ctgaaaacct acagcgtgtc cttcgacagc   1860
ctgttcagcg ccgtgaagaa cttcaccgag atcgccagca agttcaacca gcggctgcag   1920
gacttcgaca agaacaaccc cctgctggtc cggatgctga acgaccagct gatgttcctg   1980
gaacgggcct tcgtggaccc cctgggcctg cctgaccggc ccttctaccg gcacgtgatc   2040
tatgccccca gcagccacaa caagtacgct ggcgagagct tccccggcat ctacgatgcc   2100
ctgttcgaca tcgagagcaa ggtggacccc agcaaggcct ggggcgaagt gaagcggcag   2160
atatacgtgg ccgccttcac agtgcaggcc gctgccgaga cactgagcga ggtggcc      2217
```

<210> SEQ ID NO 5
<211> LENGTH: 739
<212> TYPE: PRT
<213> ORGANISM: Artificial

<220> FEATURE:
<223> OTHER INFORMATION: Synthetic Construct

<400> SEQUENCE: 5

```
Met Ala Ser Ala Arg Arg Pro Arg Trp Leu Cys Ala Gly Ala Leu Val
1               5                   10                  15

Leu Ala Gly Gly Phe Phe Leu Leu Gly Phe Leu Phe Gly Trp Phe Ile
            20                  25                  30

Lys Ser Ser Ser Glu Ala Thr Asn Ile Thr Pro Gln His Asn Val Lys
        35                  40                  45

Ala Phe Leu Asp Glu Leu Lys Ala Glu Asn Ile Lys Lys Phe Leu Tyr
    50                  55                  60

Asn Phe Thr Gln Ile Pro His Leu Ala Gly Thr Glu Gln Asn Phe Glu
65                  70                  75                  80

Leu Ala Lys Gln Ile Gln Ala Gln Trp Lys Glu Phe Gly Leu Asp Ser
                85                  90                  95

Val Glu Leu Ser His Tyr Asp Val Leu Leu Ser Tyr Pro Asn Glu Thr
            100                 105                 110

His Pro Asn Tyr Ile Ser Ile Ile Asp Glu Asp Gly Asn Glu Ile Phe
        115                 120                 125

Asn Thr Ser Leu Phe Glu Pro Pro Pro Pro Gly Tyr Glu Asn Ile Ser
    130                 135                 140

Asp Val Val Pro Pro Tyr Ser Ala Phe Ser Pro Gln Gly Met Pro Glu
145                 150                 155                 160

Gly Asp Leu Val Tyr Val Asn Tyr Ala Arg Thr Glu Asp Phe Phe Lys
                165                 170                 175

Leu Glu Arg Asp Met Lys Ile Asn Cys Ser Gly Lys Ile Leu Ile Ala
            180                 185                 190

Arg Tyr Gly Lys Val Phe Arg Gly Asn Lys Val Lys Asn Ala Gln Leu
        195                 200                 205

Ala Gly Ala Lys Gly Ile Ile Leu Tyr Ser Asp Pro Ala Asp Tyr Phe
    210                 215                 220

Ala Pro Gly Val Lys Ser Tyr Pro Asp Gly Trp Asn Leu Pro Gly Gly
225                 230                 235                 240

Gly Val Gln Arg Gly Asn Val Leu Asn Leu Asn Gly Ala Gly Asp Pro
                245                 250                 255

Leu Thr Pro Gly Tyr Pro Ala Asn Glu Tyr Ala Tyr Arg Arg Gly Ile
            260                 265                 270

Ala Glu Ala Val Gly Leu Pro Ser Ile Pro Val His Pro Ile Gly Tyr
        275                 280                 285

Tyr Asp Ala Gln Lys Leu Leu Glu Lys Met Gly Gly Ala Ala Pro Pro
    290                 295                 300

Asp Ser Ser Trp Lys Gly Ser Leu Gln Val Pro Tyr Asn Val Gly Pro
305                 310                 315                 320

Gly Phe Thr Gly Asn Phe Ser Thr Gln Lys Val Lys Met His Ile His
                325                 330                 335

Ser Thr Asn Glu Val Thr Arg Ile Tyr Asn Val Ile Gly Thr Leu Lys
            340                 345                 350

Gly Ala Val Glu Pro Asp Arg Tyr Val Ile Leu Gly Gly His Arg Asp
        355                 360                 365

Ala Trp Val Phe Gly Gly Ile Asp Pro Gln Ser Gly Ala Ala Val Val
    370                 375                 380

His Glu Ile Val Arg Ser Phe Gly Thr Leu Lys Lys Lys Gly Trp Arg
385                 390                 395                 400
```

```
Pro Arg Arg Thr Ile Leu Phe Ala Ser Trp Asp Ala Glu Glu Phe Gly
                405                 410                 415

Leu Leu Gly Ser Thr Glu Trp Ala Glu Glu Asn Ser Arg Leu Leu Gln
            420                 425                 430

Glu Arg Gly Val Ala Tyr Ile Asn Ala Asp Ser Ser Ile Glu Gly Asn
        435                 440                 445

Tyr Thr Leu Arg Val Asp Cys Thr Pro Leu Met Tyr Ser Leu Val Tyr
    450                 455                 460

Asn Leu Thr Lys Glu Leu Gln Ser Pro Asp Glu Gly Phe Glu Gly Lys
465                 470                 475                 480

Ser Leu Phe Asp Ser Trp Thr Glu Lys Ser Pro Ser Pro Glu Phe Ser
                485                 490                 495

Gly Leu Pro Arg Ile Ser Lys Leu Gly Ser Gly Asn Asp Phe Glu Val
            500                 505                 510

Phe Phe Gln Arg Leu Gly Ile Ala Ser Gly Arg Ala Arg Tyr Thr Lys
        515                 520                 525

Asp Trp Lys Thr Ser Lys Phe Ser Gly Tyr Pro Leu Tyr His Ser Val
    530                 535                 540

Tyr Glu Thr Tyr Glu Leu Val Glu Lys Phe Tyr Asp Pro Met Phe Lys
545                 550                 555                 560

Tyr His Leu Thr Val Ala Gln Val Arg Gly Gly Ile Val Phe Glu Leu
                565                 570                 575

Ala Asn Ser Val Val Leu Pro Phe Asp Cys Gln Asp Tyr Ala Val Val
            580                 585                 590

Leu Lys Lys Tyr Ala Asp Lys Ile Tyr Asn Ile Ser Met Lys His Pro
        595                 600                 605

Gln Glu Met Lys Thr Tyr Ser Val Ser Phe Asp Ser Leu Phe Ser Ala
    610                 615                 620

Val Lys Asn Phe Thr Glu Ile Ala Ser Lys Phe Asn Gln Arg Leu Gln
625                 630                 635                 640

Asp Phe Asp Lys Asn Asn Pro Ile Leu Leu Arg Met Met Asn Asp Gln
                645                 650                 655

Leu Met Phe Leu Glu Arg Ala Phe Ile Asp Pro Leu Gly Leu Pro Asp
            660                 665                 670

Arg Pro Phe Tyr Arg His Val Ile Tyr Ala Pro Ser Ser His Asn Lys
        675                 680                 685

Tyr Ala Gly Glu Ser Phe Pro Gly Ile Tyr Asp Ala Leu Phe Asp Ile
    690                 695                 700

Glu Ser Lys Val Asp Pro Ser Lys Ala Trp Gly Glu Val Lys Arg Gln
705                 710                 715                 720

Ile Tyr Val Ala Ala Phe Thr Val Gln Ala Ala Ala Glu Thr Leu Ser
                725                 730                 735

Glu Val Ala
```

<210> SEQ ID NO 6
<211> LENGTH: 2217
<212> TYPE: DNA
<213> ORGANISM: Artificial
<220> FEATURE:
<223> OTHER INFORMATION: Synthetic Construct

<400> SEQUENCE: 6

```
atggctagcg ccagacggcc cagatggctg tgtgctggcg ccctggtgct ggctggcggc      60

tttttcctgc tgggcttcct gttcggctgg ttcatcaaga gcagcagcga ggccaccaac     120
```

-continued

```
atcacccccc agcacaacgt gaaggccttt ctggacgagc tgaaggccga gaatatcaag    180
aagttcctgt acaacttcac ccagatcccc cacctggccg gcaccgagca gaacttcgag    240
ctggccaagc agatccaggc ccagtggaaa gagttcggcc tggacagcgt ggaactgagc    300
cactacgacg tgctgctgag ctaccccaac gagacacacc ccaactacat cagcatcatc    360
gacgaggacg gcaacgagat tttcaacacc agcctgttcg agccccctcc acccggctac    420
gagaacatca gcgacgtggt gccccctac agcgcattca gtccacaggg aatgcccgag    480
ggcgacctgg tgtacgtgaa ctacgcccgg accgaggact tcttcaagct ggaacgggac    540
atgaagatca actgcagcgg caagatcctg atcgccagat acggcaaggt gttccggggc    600
aacaaagtga agaacgccca gctggcaggc gccaagggca tcatcctgta cagcgacccc    660
gccgactact tcgcccctgg cgtgaagtcc taccccgacg gctggaacct gcctggcggc    720
ggagtgcaga ggggcaacgt gctgaacctg aacggcgctg gcgaccctct gacccctggc    780
taccccgcca acgagtacgc ctacagacgg ggaatcgccg aggccgtggg cctgcctagc    840
atccctgtgc accccatcgg ctactacgac gcccagaaac tgctggaaaa gatgggcgga    900
gccgcccctc ccgacagctc ttggaagggc agcctgcagg tcccctacaa cgtgggccct    960
ggcttcaccg gcaacttcag cacccagaaa gtgaagatgc acatccacag caccaacgaa   1020
gtgacccgga tctacaacgt gatcggcacc ctgaagggcg ccgtggaacc cgacagatac   1080
gtgatcctgg gcggccaccg ggacgcctgg gtgttcggag gcatcgaccc tcagagcggc   1140
gctgccgtgg tgcacgagat cgtgcggagc ttcggcacac tgaagaagaa gggctggcgg   1200
cccagacgga ccatcctgtt cgccagctgg gacgccgagg aattcggcct gctgggcagc   1260
accgagtggg ccgaggaaaa cagtcggctg ctgcaggaac ggggcgtcgc ctacatcaac   1320
gccgacagca gcatcgaggg caactacacc ctgcgggtgg actgcacccc cctgatgtac   1380
agcctggtgt acaacctgac caaagagctg cagagccccg acgagggctt cgagggcaag   1440
tccctgttcg actcctggac cgagaagtcc cccagccccg agttcagcgg cctgcccaga   1500
atcagcaagc tgggcagcgg caacgacttc gaggtgttct tccagcggct gggaatcgcc   1560
agcggcagag cccggtacac caaggactgg aaaaccagca agttctccgg ctaccccctg   1620
taccacagcg tgtacgagac atacgagctg gtggaaaagt tctacgaccc catgttcaag   1680
taccacctga ccgtggccca ggtccgaggc ggcatcgtgt tcgaactggc caacagcgtg   1740
gtgctgccat tcgattgtca ggactacgcc gtggtgctga agaagtacgc cgacaaaatc   1800
tacaacatca gcatgaagca cccccaggaa atgaaaacct acagcgtgtc cttcgacagc   1860
ctgttcagcg ccgtgaagaa tttcaccgag atcgcctcca agttcaacca gagactgcag   1920
gacttcgaca agaacaaccc catcctgctg cggatgatga acgaccagct gatgttcctg   1980
gaacgggcct tcatcgaccc cctgggcctg cccgaccggc ccttttaccg gcacgtgatc   2040
tatgccccca gcagccacaa caaatacgcc ggcgagagtt tccccggcat ctacgatgcc   2100
ctgttcgata tcgagagcaa ggtggacccc agcaaggcct ggggcgaagt gaagcggcag   2160
atttacgtgg ccgcattcac agtgcaggct gctgccgaga cactgagcga ggtggcc      2217
```

<210> SEQ ID NO 7
<211> LENGTH: 739
<212> TYPE: PRT
<213> ORGANISM: Artificial
<220> FEATURE:
<223> OTHER INFORMATION: Synthetic Construct -continued

<400> SEQUENCE: 7

```
Met Ala Ser Ala Arg Arg Pro Arg Trp Leu Cys Ala Gly Ala Leu Val
1               5                   10                  15

Leu Ala Gly Gly Phe Phe Leu Leu Gly Phe Leu Phe Gly Trp Phe Ile
            20                  25                  30

Lys Ser Ser Asn Glu Ala Thr Asn Ile Thr Pro Lys His Asn Met Lys
        35                  40                  45

Ala Phe Leu Asp Glu Leu Lys Ala Glu Asn Ile Lys Lys Phe Leu Tyr
    50                  55                  60

Asn Phe Thr Gln Ile Pro His Leu Ala Gly Thr Glu Gln Asn Phe Gln
65                  70                  75                  80

Leu Ala Lys Gln Ile Gln Ser Gln Trp Lys Glu Phe Gly Leu Asp Ser
                85                  90                  95

Val Glu Leu Ala His Tyr Asp Val Leu Leu Ser Tyr Pro Asn Lys Thr
            100                 105                 110

His Pro Asn Tyr Ile Ser Ile Ile Asn Glu Asp Gly Asn Glu Ile Phe
        115                 120                 125

Asn Thr Ser Leu Phe Glu Pro Pro Pro Pro Gly Tyr Glu Asn Val Ser
    130                 135                 140

Asp Ile Val Pro Pro Phe Ser Ala Phe Ser Pro Gln Gly Met Pro Glu
145                 150                 155                 160

Gly Asp Leu Val Tyr Val Asn Tyr Ala Arg Thr Glu Asp Phe Phe Lys
                165                 170                 175

Leu Glu Arg Asp Met Lys Ile Asn Cys Ser Gly Lys Ile Val Ile Ala
            180                 185                 190

Arg Tyr Gly Lys Val Phe Arg Gly Asn Lys Val Lys Asn Ala Gln Leu
        195                 200                 205

Ala Gly Ala Lys Gly Val Ile Leu Tyr Ser Asp Pro Ala Asp Tyr Phe
    210                 215                 220

Ala Pro Gly Val Lys Ser Tyr Pro Asp Gly Trp Asn Leu Pro Gly Gly
225                 230                 235                 240

Gly Val Gln Arg Gly Asn Ile Leu Asn Leu Asn Gly Ala Gly Asp Pro
                245                 250                 255

Leu Thr Pro Gly Tyr Pro Ala Asn Glu Tyr Ala Tyr Arg Arg Gly Ile
            260                 265                 270

Ala Glu Ala Val Gly Leu Pro Ser Ile Pro Val His Pro Ile Gly Tyr
        275                 280                 285

Tyr Asp Ala Gln Lys Leu Leu Glu Lys Met Gly Gly Ser Ala Pro Pro
    290                 295                 300

Asp Ser Ser Trp Arg Gly Ser Leu Lys Val Pro Tyr Asn Val Gly Pro
305                 310                 315                 320

Gly Phe Thr Gly Asn Phe Ser Ala Gln Lys Leu Lys Leu His Ile His
                325                 330                 335

Ser Asn Thr Lys Val Thr Arg Ile Tyr Asn Val Ile Gly Thr Leu Arg
            340                 345                 350

Gly Ala Val Glu Pro Asp Arg Tyr Val Ile Leu Gly Gly His Arg Asp
        355                 360                 365

Ser Trp Val Phe Gly Gly Ile Asp Pro Gln Ser Gly Ala Ala Val Val
    370                 375                 380

His Glu Ile Val Arg Thr Phe Gly Thr Leu Lys Lys Lys Gly Trp Arg
385                 390                 395                 400

Pro Arg Arg Thr Ile Leu Phe Ala Ser Trp Asp Ala Glu Glu Phe Gly
                405                 410                 415
```

```
Leu Leu Gly Ser Thr Glu Trp Ala Glu Glu Asn Ser Arg Leu Leu Gln
            420                 425                 430

Glu Arg Gly Val Ala Tyr Ile Asn Ala Asp Ser Ser Ile Glu Gly Asn
        435                 440                 445

Tyr Thr Leu Arg Val Asp Cys Thr Pro Leu Leu His Ser Leu Val Tyr
    450                 455                 460

Asn Leu Thr Lys Glu Leu Lys Ser Pro Asp Glu Gly Phe Glu Gly Lys
465                 470                 475                 480

Ser Leu Tyr Glu Ser Trp Thr Lys Lys Ser Pro Ser Pro Glu Leu Ser
                485                 490                 495

Gly Leu Pro Arg Ile Ser Lys Leu Gly Ser Gly Asn Asp Phe Glu Val
            500                 505                 510

Phe Phe Gln Arg Leu Gly Ile Ser Ser Gly Arg Ala Arg Tyr Thr Lys
        515                 520                 525

Asp Trp Lys Thr Ser Lys Phe Ser Ser Tyr Pro Leu Tyr His Ser Ile
    530                 535                 540

Tyr Glu Thr Tyr Glu Leu Val Val Lys Phe Tyr Asp Pro Met Phe Lys
545                 550                 555                 560

Tyr His Leu Thr Val Ala Gln Val Arg Gly Gly Met Val Phe Glu Leu
                565                 570                 575

Ala Asn Ser Ile Val Leu Pro Phe Asp Cys Arg Asp Tyr Ala Val Ala
            580                 585                 590

Leu Lys Asn His Ala Glu Asn Leu Tyr Ser Ile Ser Met Lys His Pro
        595                 600                 605

Gln Glu Met Lys Thr Tyr Ser Val Ser Phe Asp Ser Leu Phe Ser Ala
    610                 615                 620

Val Lys Asn Phe Thr Glu Ile Ala Ser Lys Phe Ser Glu Arg Leu Gln
625                 630                 635                 640

Asp Phe Asp Lys Ser Asn Pro Ile Val Leu Arg Met Met Asn Asp Gln
                645                 650                 655

Leu Met Phe Leu Glu Arg Ala Phe Ile Asp Pro Leu Gly Leu Pro Asp
            660                 665                 670

Arg Pro Phe Tyr Arg His Val Ile Tyr Ala Pro Ser Ser His Asn Lys
        675                 680                 685

Tyr Ala Gly Glu Ser Phe Pro Gly Ile Tyr Asp Ala Leu Phe Asp Ile
    690                 695                 700

Glu Ser Lys Val Asp Pro Ser Lys Ala Trp Gly Glu Val Lys Arg Gln
705                 710                 715                 720

Ile Tyr Val Ala Ala Phe Thr Val Gln Ala Ala Ala Glu Thr Leu Ser
                725                 730                 735

Glu Val Ala
```

<210> SEQ ID NO 8
<211> LENGTH: 2217
<212> TYPE: DNA
<213> ORGANISM: Artificial
<220> FEATURE:
<223> OTHER INFORMATION: Synthetic Construct

<400> SEQUENCE: 8

```
atggctagcg ccagacggcc cagatggctg tgtgctggcg ccctggtgct ggctggcggc     60

tttttcctgc tgggcttcct gttcggctgg ttcatcaaga gcagcaacga ggccaccaac    120

atcaccccca agcacaacat gaaggccttt ctggacgagc tgaaggccga gaatatcaag    180
```

aagttcctgt acaacttcac ccagatcccc cacctggccg gcaccgagca gaacttccag 240
ctggccaagc agatccagag ccagtggaaa gagttcggcc tggacagcgt ggaactggcc 300
cactacgacg tgctgctgag ctaccccaac aagacccacc ccaactacat cagcatcatc 360
aacgaggacg gcaacgagat tttcaacacc agcctgttcg agccccctcc acccggctac 420
gagaacgtgt ccgacatcgt gcccccattc agcgcattca gtccacaggg aatgcccgag 480
ggcgacctgg tgtacgtgaa ctacgcccgg accgaggact tcttcaagct ggaacgggac 540
atgaagatca actgcagcgg caagatcgtg atcgccagat acggcaaggt gttccggggc 600
aacaaagtga agaacgccca gctggcaggc gccaagggcg tgatcctgta tagcgacccc 660
gccgactact tcgcccctgg cgtgaagtcc taccccgacg gctggaacct gcctggcggc 720
ggagtgcagc ggggcaacat cctgaacctg aacggcgctg gcgacccccct gacccctggc 780 tatcccgcca acgagtacgc ctacagacgg ggaatcgccg aggccgtggg cctgcctagc 840
atccctgtgc accccatcgg ctactacgac gcccagaaac tgctggaaaa gatgggcggc 900
agcgcccctc ccgatagctc ttggagaggc agcctgaagg tgccctacaa cgtgggccct 960
ggcttcaccg gcaacttcag cgcccagaag ctgaagctgc acatccacag caacaccaaa 1020
gtgacccgga tctacaacgt gatcggcacc ctgagaggcg ccgtggaacc cgacagatac 1080
gtgatcctgg gcggccaccg ggacagctgg gtgttcggcg gcatcgaccc tcagtctggc 1140
gccgctgtgg tgcacgagat cgtgcggacc tttggcaccc tgaagaagaa gggctggcgg 1200
cccagacgga ccatcctgtt cgccagctgg gacgccgagg aattcggcct gctgggcagc 1260
accgagtggg ccgaggaaaa cagtcggctg ctgcaggaac ggggcgtcgc ctacatcaac 1320
gccgacagca gcatcgaggg caactacacc ctgcgggtgg actgcacccc cctgctgcac 1380
agcctggtgt acaacctgac caaagagctg aagtcccccg acgagggctt cgagggcaag 1440
agcctgtacg agagctggac caagaagtcc cccagccccg agctgagcgg cctgcccaga 1500
atcagcaagc tgggcagcgg caacgacttc gaggtgttct tccagcggct gggcatcagc 1560
agcggcagag cccggtacac caaggactgg aaaaccagca agttcagcag ctaccccctg 1620
taccacagca tctacgagac atacgagctg gtggtcaagt tctacgaccc catgttcaag 1680
taccacctga ccgtggccca ggtccgaggc ggcatggtgt tcgagctggc caacagcatc 1740
gtgctgccct tcgactgccg ggactacgcc gtggccctga agaaccacgc cgagaacctg 1800
tacagcatca gcatgaagca cccccaggaa atgaaaacct acagcgtgtc cttcgacagc 1860
ctgttcagcg ccgtgaagaa tttcaccgag atcgcctcca agttcagcga gcggctgcag 1920
gacttcgaca agagcaaccc catcgtgctg agaatgatga acgaccagct gatgttcctg 1980
gaacgggcct tcatcgaccc cctgggcctg cccgaccggc ccttttaccg gcacgtgatc 2040
tatgccccca gcagccacaa caaatacgcc ggcgagagtt tccccggcat ctacgatgcc 2100
ctgttcgaca tcgagagcaa ggtggacccc agcaaggcct ggggcgaagt gaagcggcag 2160
atttacgtgg ccgcattcac agtgcaggcc gctgccgaga cactgagcga ggtggcc 2217

<210> SEQ ID NO 9
<211> LENGTH: 739
<212> TYPE: PRT
<213> ORGANISM: Artificial
<220> FEATURE:
<223> OTHER INFORMATION: Synthetic Construct

<400> SEQUENCE: 9

Met Ala Ser Ala Arg Arg Pro Arg Trp Leu Cys Ala Gly Ala Leu Val

-continued 1 5 10 15

Leu Ala Gly Gly Phe Phe Leu Leu Gly Phe Leu Phe Gly Trp Phe Ile
20 25 30

Lys Ser Ser Asn Glu Ala Thr Asn Ile Thr Pro Lys His Asn Met Lys
35 40 45

Ala Phe Leu Asp Glu Leu Lys Ala Glu Asn Ile Lys Lys Phe Leu Tyr
50 55 60

Asn Phe Thr Gln Ile Pro His Leu Ala Gly Thr Glu Gln Asn Phe Gln
65 70 75 80

Leu Ala Lys Gln Ile Gln Ser Gln Trp Lys Glu Phe Gly Leu Asp Ser
85 90 95

Val Glu Leu Ala His Tyr Asp Val Leu Leu Ser Tyr Pro Asn Lys Thr
100 105 110

His Pro Asn Tyr Ile Ser Ile Ile Asn Glu Asp Gly Asn Glu Ile Phe
115 120 125

Asn Thr Ser Leu Phe Glu Pro Pro Pro Pro Gly Tyr Glu Asn Val Ser
130 135 140

Asp Ile Val Pro Pro Phe Ser Ala Phe Ser Pro Gln Gly Met Pro Glu
145 150 155 160

Gly Asp Leu Val Tyr Val Asn Tyr Ala Arg Thr Glu Asp Phe Phe Lys
165 170 175

Leu Glu Arg Asp Met Lys Ile Asn Cys Ser Gly Lys Ile Val Ile Ala
180 185 190

Arg Tyr Gly Lys Val Phe Arg Gly Asn Lys Val Lys Asn Ala Gln Leu
195 200 205

Ala Gly Ala Lys Gly Val Ile Leu Tyr Ser Asp Pro Ala Asp Tyr Phe
210 215 220

Ala Pro Gly Val Lys Ser Tyr Pro Asp Gly Trp Asn Leu Pro Gly Gly
225 230 235 240

Gly Val Gln Arg Gly Asn Ile Leu Asn Leu Asn Gly Ala Gly Asp Pro
245 250 255

Leu Thr Pro Gly Tyr Pro Ala Asn Glu Tyr Ala Tyr Arg Arg Gly Ile
260 265 270

Ala Glu Ala Val Gly Leu Pro Ser Ile Pro Val His Pro Ile Gly Tyr
275 280 285

Tyr Asp Ala Gln Lys Leu Leu Glu Lys Met Gly Gly Ser Ala Pro Pro
290 295 300

Asp Ser Ser Trp Arg Gly Ser Leu Lys Val Pro Tyr Asn Val Gly Pro
305 310 315 320

Gly Phe Thr Gly Asn Phe Ser Thr Gln Lys Val Lys Met His Ile His
325 330 335

Ser Thr Asn Glu Val Thr Arg Ile Tyr Asn Val Ile Gly Thr Leu Arg
340 345 350

Gly Ala Val Glu Pro Asp Arg Tyr Val Ile Leu Gly Gly His Arg Asp
355 360 365

Ser Trp Val Phe Gly Gly Ile Asp Pro Gln Ser Gly Ala Ala Val Val
370 375 380

His Glu Ile Val Arg Ser Phe Gly Thr Leu Lys Lys Glu Gly Trp Arg
385 390 395 400

Pro Arg Arg Thr Ile Leu Phe Ala Ser Trp Asp Ala Glu Glu Phe Gly
405 410 415

Leu Leu Gly Ser Thr Glu Trp Ala Glu Glu Asn Ser Arg Leu Leu Gln
420 425 430

```
Glu Arg Gly Val Ala Tyr Ile Asn Ala Asp Ser Ser Ile Glu Gly Asn
        435                 440                 445

Tyr Thr Leu Arg Val Asp Cys Thr Pro Leu Met Tyr Ser Leu Val His
    450                 455                 460

Asn Leu Thr Lys Glu Leu Lys Ser Pro Asp Glu Gly Phe Glu Gly Lys
465                 470                 475                 480

Ser Leu Tyr Glu Ser Trp Thr Lys Lys Ser Pro Ser Pro Glu Phe Ser
                485                 490                 495

Gly Met Pro Arg Ile Ser Lys Leu Gly Ser Gly Asn Asp Phe Glu Val
            500                 505                 510

Phe Phe Gln Arg Leu Gly Ile Ala Ser Gly Arg Ala Arg Tyr Thr Lys
        515                 520                 525

Asn Trp Glu Thr Asn Lys Phe Ser Gly Tyr Pro Leu Tyr His Ser Val
    530                 535                 540

Tyr Glu Thr Tyr Glu Leu Val Glu Lys Phe Tyr Asp Pro Met Phe Lys
545                 550                 555                 560

Tyr His Leu Thr Val Ala Gln Val Arg Gly Gly Met Val Phe Glu Leu
                565                 570                 575

Ala Asn Ser Ile Val Leu Pro Phe Asp Cys Arg Asp Tyr Ala Val Val
            580                 585                 590

Leu Arg Lys Tyr Ala Asp Lys Ile Tyr Ser Ile Ser Met Lys His Pro
        595                 600                 605

Gln Glu Met Lys Thr Tyr Ser Val Ser Phe Asp Ser Leu Phe Ser Ala
    610                 615                 620

Val Lys Asn Phe Thr Glu Ile Ala Ser Lys Phe Ser Glu Arg Leu Gln
625                 630                 635                 640

Asp Phe Asp Lys Ser Asn Pro Ile Val Leu Arg Met Met Asn Asp Gln
                645                 650                 655

Leu Met Phe Leu Glu Arg Ala Phe Ile Asp Pro Leu Gly Leu Pro Asp
            660                 665                 670

Arg Pro Phe Tyr Arg His Val Ile Tyr Ala Pro Ser Ser His Asn Lys
        675                 680                 685

Tyr Ala Gly Glu Ser Phe Pro Gly Ile Tyr Asp Ala Leu Phe Asp Ile
    690                 695                 700

Glu Ser Lys Val Asp Pro Ser Lys Ala Trp Gly Glu Val Lys Arg Gln
705                 710                 715                 720

Ile Tyr Val Ala Ala Phe Thr Val Gln Ala Ala Ala Glu Thr Leu Ser
                725                 730                 735

Glu Val Ala
```

<210> SEQ ID NO 10
<211> LENGTH: 2217
<212> TYPE: DNA
<213> ORGANISM: Artificial
<220> FEATURE:
<223> OTHER INFORMATION: Synthetic Construct

<400> SEQUENCE: 10

```
atggctagcg cgcgccgccc gcgctggctg tgcgctgggg cgctggtgct ggcgggtggc      60

ttctttctcc tcggcttcct cttcgggtgg tttataaaat cctccaatga agctactaac     120

attactccaa agcataatat gaaagcattt ttggatgaat tgaaagctga gaacatcaag     180

aagttcttat ataattttac acagatacca catttagcag gaacagaaca aaactttcag     240

cttgcaaagc aaattcaatc ccagtggaaa gaatttggcc tggattctgt tgagctggca     300
```

```
cattatgatg tcctgttgtc ctacccaaat aagactcatc ccaactacat ctcaataatt    360

aatgaagatg gaaatgagat tttcaacaca tcattatttg aaccacctcc tccaggatat    420

gaaaatgttt cggatattgt accacctttc agtgctttct ctcctcaagg aatgccagag    480

ggcgatctag tgtatgttaa ctatgcacga actgaagact tctttaaatt ggaacgggac    540

atgaaaatca attgctctgg gaaaattgta attgccagat atgggaaagt tttcagagga    600

aataaggtta aaaatgccca gctggcaggg gccaaaggag tcattctcta ctccgaccct    660

gctgactact ttgctcctgg ggtgaagtcc tatccagatg gttggaatct tcctggaggt    720

ggtgtccagc gtggaaatat cctaaatctg aatggtgcag gagaccctct cacaccaggt    780

tacccagcaa atgaatatgc ttataggcgt ggaattgcag aggctgttgg tcttccaagt    840

attcctgttc atccaattgg atactatgat gcacagaagc tcctagaaaa aatgggtggc    900

tcagcaccac cagatagcag ctggagagga agtctcaaag tgccctacaa tgttggacct    960

ggctttactg gaaacttttc tacacaaaaa gtcaagatgc acatccactc taccaatgaa   1020

gtgacaagaa tttacaatgt gataggtact ctcagaggag cagtggaacc agacagatat   1080

gtcattctgg gaggtcaccg ggactcatgg gtgtttggtg gtattgaccc tcagagtgga   1140

gcagctgttg ttcatgaaat tgtgaggagc tttggaacac tgaaaaagga agggtggaga   1200

cctagaagaa caattttgtt tgcaagctgg gatgcagaag aatttggtct tcttggttct   1260

actgagtggg cagaggagaa ttcaagactc cttcaagagc gtggcgtggc ttatattaat   1320

gctgactcat ctatagaagg aaactacact ctgagagttg attgtacacc gctgatgtac   1380

agcttggtac acaacctaac aaaagagctg aaaagccctg atgaaggctt tgaaggcaaa   1440

tctctttatg aaagttggac taaaaaaagt ccttccccag agttcagtgg catgcccagg   1500

ataagcaaat tgggatctgg aaatgatttt gaggtgttct tccaacgact tggaattgct   1560

tcaggcagag cacggtatac taaaaattgg gaaacaaaca aattcagcgg ctatccactg   1620

tatcacagtg tctatgaaac atatgagttg gtggaaaagt tttatgatcc aatgtttaaa   1680

tatcacctca ctgtggccca ggttcgagga gggatggtgt ttgagctggc caattccata   1740

gtgctccctt ttgattgtcg agattatgct gtagttttaa gaaagtatgc tgacaaaatc   1800

tacagtattt ctatgaaaca tccacaggaa atgaagacat acagtgtatc atttgattca   1860

ctttttctg cagtaaagaa ttttacagaa attgcttcca agttcagtga gagactccag   1920

gactttgaca aaagcaaccc aatagtatta agaatgatga atgatcaact catgtttctg   1980

gaaagagcat ttattgatcc attagggtta ccagacaggc ctttttatag gcatgtcatc   2040

tatgctccaa gcagccacaa caagtatgca ggggagtcat tcccaggaat ttatgatgct   2100

ctgtttgata ttgaaagcaa agtggaccct tccaaggcct ggggagaagt gaagagacag   2160

atttatgttg cagccttcac agtgcaggca gctgcagaga ctttgagtga agtagcc      2217
```

<210> SEQ ID NO 11
<211> LENGTH: 710
<212> TYPE: PRT
<213> ORGANISM: Artificial
<220> FEATURE:
<223> OTHER INFORMATION: Synthetic Construct

<400> SEQUENCE: 11

```
Met Ala Ser Lys Ser Ser Asn Glu Ala Thr Asn Ile Thr Pro Lys His
1               5                   10                  15

Asn Met Lys Ala Phe Leu Asp Glu Leu Lys Ala Glu Asn Ile Lys Lys
```

-continued

```
            20                  25                  30

Phe Leu Tyr Asn Phe Thr Gln Ile Pro His Leu Ala Gly Thr Glu Gln
        35                  40                  45

Asn Phe Gln Leu Ala Lys Gln Ile Gln Ser Gln Trp Lys Glu Phe Gly
    50                  55                  60

Leu Asp Ser Val Glu Leu Ala His Tyr Asp Val Leu Leu Ser Tyr Pro
65                  70                  75                  80

Asn Lys Thr His Pro Asn Tyr Ile Ser Ile Ile Asn Glu Asp Gly Asn
                85                  90                  95

Glu Ile Phe Asn Thr Ser Leu Phe Glu Pro Pro Pro Pro Gly Tyr Glu
            100                 105                 110

Asn Val Ser Asp Ile Val Pro Pro Phe Ser Ala Phe Ser Pro Gln Gly
        115                 120                 125

Met Pro Glu Gly Asp Leu Val Tyr Val Asn Tyr Ala Arg Thr Glu Asp
    130                 135                 140

Phe Phe Lys Leu Glu Arg Asp Met Lys Ile Asn Cys Ser Gly Lys Ile
145                 150                 155                 160

Val Ile Ala Arg Tyr Gly Lys Val Phe Arg Gly Asn Lys Val Lys Asn
                165                 170                 175

Ala Gln Leu Ala Gly Ala Lys Gly Val Ile Leu Tyr Ser Asp Pro Ala
            180                 185                 190

Asp Tyr Phe Ala Pro Gly Val Lys Ser Tyr Pro Asp Gly Trp Asn Leu
        195                 200                 205

Pro Gly Gly Gly Val Gln Arg Gly Asn Ile Leu Asn Leu Asn Gly Ala
    210                 215                 220

Gly Asp Pro Leu Thr Pro Gly Tyr Pro Ala Asn Glu Tyr Ala Tyr Arg
225                 230                 235                 240

Arg Gly Ile Ala Glu Ala Val Gly Leu Pro Ser Ile Pro Val His Pro
                245                 250                 255

Ile Gly Tyr Tyr Asp Ala Gln Lys Leu Leu Glu Lys Met Gly Gly Ser
            260                 265                 270

Ala Pro Pro Asp Ser Ser Trp Arg Gly Ser Leu Lys Val Pro Tyr Asn
        275                 280                 285

Val Gly Pro Gly Phe Thr Gly Asn Phe Ser Thr Gln Lys Val Lys Met
    290                 295                 300

His Ile His Ser Thr Asn Glu Val Thr Arg Ile Tyr Asn Val Ile Gly
305                 310                 315                 320

Thr Leu Arg Gly Ala Val Glu Pro Asp Arg Tyr Val Ile Leu Gly Gly
                325                 330                 335

His Arg Asp Ser Trp Val Phe Gly Gly Ile Asp Pro Gln Ser Gly Ala
            340                 345                 350

Ala Val Val His Glu Ile Val Arg Ser Phe Gly Thr Leu Lys Lys Glu
        355                 360                 365

Gly Trp Arg Pro Arg Arg Thr Ile Leu Phe Ala Ser Trp Asp Ala Glu
    370                 375                 380

Glu Phe Gly Leu Leu Gly Ser Thr Glu Trp Ala Glu Glu Asn Ser Arg
385                 390                 395                 400

Leu Leu Gln Glu Arg Gly Val Ala Tyr Ile Asn Ala Asp Ser Ser Ile
                405                 410                 415

Glu Gly Asn Tyr Thr Leu Arg Val Asp Cys Thr Pro Leu Met Tyr Ser
            420                 425                 430

Leu Val His Asn Leu Thr Lys Glu Leu Lys Ser Pro Asp Glu Gly Phe
        435                 440                 445
```

Glu Gly Lys Ser Leu Tyr Glu Ser Trp Thr Lys Lys Ser Pro Ser Pro
    450                 455                 460

Glu Phe Ser Gly Met Pro Arg Ile Ser Lys Leu Gly Ser Gly Asn Asp
465                 470                 475                 480

Phe Glu Val Phe Phe Gln Arg Leu Gly Ile Ala Ser Gly Arg Ala Arg
                485                 490                 495

Tyr Thr Lys Asn Trp Glu Thr Asn Lys Phe Ser Gly Tyr Pro Leu Tyr
            500                 505                 510

His Ser Val Tyr Glu Thr Tyr Glu Leu Val Glu Lys Phe Tyr Asp Pro
        515                 520                 525

Met Phe Lys Tyr His Leu Thr Val Ala Gln Val Arg Gly Gly Met Val
    530                 535                 540

Phe Glu Leu Ala Asn Ser Ile Val Leu Pro Phe Asp Cys Arg Asp Tyr
545                 550                 555                 560

Ala Val Val Leu Arg Lys Tyr Ala Asp Lys Ile Tyr Ser Ile Ser Met
                565                 570                 575

Lys His Pro Gln Glu Met Lys Thr Tyr Ser Val Ser Phe Asp Ser Leu
            580                 585                 590

Phe Ser Ala Val Lys Asn Phe Thr Glu Ile Ala Ser Lys Phe Ser Glu
        595                 600                 605

Arg Leu Gln Asp Phe Asp Lys Ser Asn Pro Ile Val Leu Arg Met Met
    610                 615                 620

Asn Asp Gln Leu Met Phe Leu Glu Arg Ala Phe Ile Asp Pro Leu Gly
625                 630                 635                 640

Leu Pro Asp Arg Pro Phe Tyr Arg His Val Ile Tyr Ala Pro Ser Ser
                645                 650                 655

His Asn Lys Tyr Ala Gly Glu Ser Phe Pro Gly Ile Tyr Asp Ala Leu
            660                 665                 670

Phe Asp Ile Glu Ser Lys Val Asp Pro Ser Lys Ala Trp Gly Glu Val
        675                 680                 685

Lys Arg Gln Ile Tyr Val Ala Ala Phe Thr Val Gln Ala Ala Ala Glu
    690                 695                 700

Thr Leu Ser Glu Val Ala
705                 710

<210> SEQ ID NO 12
<211> LENGTH: 2130
<212> TYPE: DNA
<213> ORGANISM: Artificial
<220> FEATURE:
<223> OTHER INFORMATION: Synthetic Construct

<400> SEQUENCE: 12
atggctagca aatcctccaa tgaagctact aacattactc caaagcataa tatgaaagca     60
tttttggatg aattgaaagc tgagaacatc aagaagttct tatataattt tacacagata    120
ccacatttag caggaacaga acaaaacttt cagcttgcaa agcaaattca atcccagtgg    180
aaagaatttg gcctggattc tgttgagctg gcacattatg atgtcctgtt gtcctaccca    240
aataagactc atcccaacta catctcaata attaatgaag atggaaatga gattttcaac    300
acatcattat ttgaaccacc tcctccagga tatgaaaatg tttcggatat tgtaccacct    360
ttcagtgctt tctctcctca aggaatgcca gagggcgatc tagtgtatgt taactatgca    420
cgaactgaag acttctttaa attggaacgg gacatgaaaa tcaattgctc tgggaaaatt    480
gtaattgcca gatatgggaa agttttcaga ggaaataagg ttaaaaatgc ccagctggca    540

```
ggggccaaag gagtcattct ctactccgac cctgctgact actttgctcc tggggtgaag    600

tcctatccag atggttggaa tcttcctgga ggtggtgtcc agcgtggaaa tatcctaaat    660

ctgaatggtg caggagaccc tctcacacca ggttacccag caaatgaata tgcttatagg    720

cgtggaattg cagaggctgt tggtcttcca agtattcctg ttcatccaat tggatactat    780

gatgcacaga agctcctaga aaaaatgggt ggctcagcac caccagatag cagctggaga    840

ggaagtctca aagtgcccta caatgttgga cctggcttta ctggaaactt ttctacacaa    900

aaagtcaaga tgcacatcca ctctaccaat gaagtgacaa gaatttacaa tgtgataggt    960

actctcagag gagcagtgga accagacaga tatgtcattc tgggaggtca ccgggactca   1020

tgggtgtttg gtggtattga ccctcagagt ggagcagctg ttgttcatga aattgtgagg   1080

agctttggaa cactgaaaaa ggaagggtgg agacctagaa gaacaatttt gtttgcaagc   1140

tgggatgcag aagaatttgg tcttcttggt tctactgagt gggcagagga gaattcaaga   1200

ctccttcaag agcgtggcgt ggcttatatt aatgctgact catctataga aggaaactac   1260

actctgagag ttgattgtac accgctgatg tacagcttgg tacacaacct aacaaaagag   1320

ctgaaaagcc ctgatgaagg ctttgaaggc aaatctcttt atgaaagttg gactaaaaaa   1380

agtccttccc cagagttcag tggcatgccc aggataagca aattgggatc tggaaatgat   1440

tttgaggtgt tcttccaacg acttggaatt gcttcaggca gagcacggta tactaaaaat   1500

tgggaaacaa acaaattcag cggctatcca ctgtatcaca gtgtctatga aacatatgag   1560

ttggtggaaa agttttatga tccaatgttt aaatatcacc tcactgtggc ccaggttcga   1620

ggagggatgg tgtttgagct ggccaattcc atagtgctcc cttttgattg tcgagattat   1680

gctgtagttt taagaaagta tgctgacaaa atctacagta tttctatgaa acatccacag   1740

gaaatgaaga catacagtgt atcatttgat tcactttttt ctgcagtaaa gaattttaca   1800

gaaattgctt ccaagttcag tgagagactc caggactttg acaaaagcaa cccaatagta   1860

ttaagaatga tgaatgatca actcatgttt ctggaaagag catttattga tccattaggg   1920

ttaccagaca ggccttttta taggcatgtc atctatgctc caagcagcca caacaagtat   1980

gcaggggagt cattcccagg aatttatgat gctctgtttg atattgaaag caaagtggac   2040

ccttccaagg cctggggaga agtgaagaga cagatttatg ttgcagcctt cacagtgcag   2100

gcagctgcag agactttgag tgaagtagcc                                    2130
```

```
<210> SEQ ID NO 13
<211> LENGTH: 732
<212> TYPE: PRT
<213> ORGANISM: Artificial
<220> FEATURE:
<223> OTHER INFORMATION: Synthetic Construct

<400> SEQUENCE: 13

Met Ala Ser Glu Thr Asp Thr Leu Leu Leu Trp Val Leu Leu Leu Trp
1               5                   10                  15

Val Pro Gly Ser Thr Gly Asp Ala Ala Lys Ser Ser Asn Glu Ala Thr
            20                  25                  30

Asn Ile Thr Pro Lys His Asn Met Lys Ala Phe Leu Asp Glu Leu Lys
        35                  40                  45

Ala Glu Asn Ile Lys Lys Phe Leu Tyr Asn Phe Thr Gln Ile Pro His
    50                  55                  60

Leu Ala Gly Thr Glu Gln Asn Phe Gln Leu Ala Lys Gln Ile Gln Ser
65                  70                  75                  80
```

-continued

```
Gln Trp Lys Glu Phe Gly Leu Asp Ser Val Glu Leu Ala His Tyr Asp
                85                  90                  95

Val Leu Leu Ser Tyr Pro Asn Lys Thr His Pro Asn Tyr Ile Ser Ile
            100                 105                 110

Ile Asn Glu Asp Gly Asn Glu Ile Phe Asn Thr Ser Leu Phe Glu Pro
        115                 120                 125

Pro Pro Pro Gly Tyr Glu Asn Val Ser Asp Ile Val Pro Pro Phe Ser
    130                 135                 140

Ala Phe Ser Pro Gln Gly Met Pro Glu Gly Asp Leu Val Tyr Val Asn
145                 150                 155                 160

Tyr Ala Arg Thr Glu Asp Phe Phe Lys Leu Glu Arg Asp Met Lys Ile
                165                 170                 175

Asn Cys Ser Gly Lys Ile Val Ile Ala Arg Tyr Gly Lys Val Phe Arg
            180                 185                 190

Gly Asn Lys Val Lys Asn Ala Gln Leu Ala Gly Ala Lys Gly Val Ile
        195                 200                 205

Leu Tyr Ser Asp Pro Ala Asp Tyr Phe Ala Pro Gly Val Lys Ser Tyr
    210                 215                 220

Pro Asp Gly Trp Asn Leu Pro Gly Gly Gly Val Gln Arg Gly Asn Ile
225                 230                 235                 240

Leu Asn Leu Asn Gly Ala Gly Asp Pro Leu Thr Pro Gly Tyr Pro Ala
                245                 250                 255

Asn Glu Tyr Ala Tyr Arg Arg Gly Ile Ala Glu Ala Val Gly Leu Pro
            260                 265                 270

Ser Ile Pro Val His Pro Ile Gly Tyr Tyr Asp Ala Gln Lys Leu Leu
        275                 280                 285

Glu Lys Met Gly Gly Ser Ala Pro Pro Asp Ser Ser Trp Arg Gly Ser
    290                 295                 300

Leu Lys Val Pro Tyr Asn Val Gly Pro Gly Phe Thr Gly Asn Phe Ser
305                 310                 315                 320

Thr Gln Lys Val Lys Met His Ile His Ser Thr Asn Glu Val Thr Arg
                325                 330                 335

Ile Tyr Asn Val Ile Gly Thr Leu Arg Gly Ala Val Glu Pro Asp Arg
            340                 345                 350

Tyr Val Ile Leu Gly Gly His Arg Asp Ser Trp Val Phe Gly Gly Ile
        355                 360                 365

Asp Pro Gln Ser Gly Ala Ala Val Val His Glu Ile Val Arg Ser Phe
    370                 375                 380

Gly Thr Leu Lys Lys Glu Gly Trp Arg Pro Arg Arg Thr Ile Leu Phe
385                 390                 395                 400

Ala Ser Trp Asp Ala Glu Glu Phe Gly Leu Leu Gly Ser Thr Glu Trp
                405                 410                 415

Ala Glu Glu Asn Ser Arg Leu Leu Gln Glu Arg Gly Val Ala Tyr Ile
            420                 425                 430

Asn Ala Asp Ser Ser Ile Glu Gly Asn Tyr Thr Leu Arg Val Asp Cys
        435                 440                 445

Thr Pro Leu Met Tyr Ser Leu Val His Asn Leu Thr Lys Glu Leu Lys
    450                 455                 460

Ser Pro Asp Glu Gly Phe Glu Gly Lys Ser Leu Tyr Glu Ser Trp Thr
465                 470                 475                 480

Lys Lys Ser Pro Ser Pro Glu Phe Ser Gly Met Pro Arg Ile Ser Lys
                485                 490                 495
```

-continued

```
Leu Gly Ser Gly Asn Asp Phe Glu Val Phe Phe Gln Arg Leu Gly Ile
            500                 505                 510

Ala Ser Gly Arg Ala Arg Tyr Thr Lys Asn Trp Glu Thr Asn Lys Phe
        515                 520                 525

Ser Gly Tyr Pro Leu Tyr His Ser Val Tyr Glu Thr Tyr Glu Leu Val
    530                 535                 540

Glu Lys Phe Tyr Asp Pro Met Phe Lys Tyr His Leu Thr Val Ala Gln
545                 550                 555                 560

Val Arg Gly Gly Met Val Phe Glu Leu Ala Asn Ser Ile Val Leu Pro
                565                 570                 575

Phe Asp Cys Arg Asp Tyr Ala Val Val Leu Arg Lys Tyr Ala Asp Lys
            580                 585                 590

Ile Tyr Ser Ile Ser Met Lys His Pro Gln Glu Met Lys Thr Tyr Ser
        595                 600                 605

Val Ser Phe Asp Ser Leu Phe Ser Ala Val Lys Asn Phe Thr Glu Ile
    610                 615                 620

Ala Ser Lys Phe Ser Glu Arg Leu Gln Asp Phe Asp Lys Ser Asn Pro
625                 630                 635                 640

Ile Val Leu Arg Met Met Asn Asp Gln Leu Met Phe Leu Glu Arg Ala
                645                 650                 655

Phe Ile Asp Pro Leu Gly Leu Pro Asp Arg Pro Phe Tyr Arg His Val
            660                 665                 670

Ile Tyr Ala Pro Ser Ser His Asn Lys Tyr Ala Gly Glu Ser Phe Pro
        675                 680                 685

Gly Ile Tyr Asp Ala Leu Phe Asp Ile Glu Ser Lys Val Asp Pro Ser
    690                 695                 700

Lys Ala Trp Gly Glu Val Lys Arg Gln Ile Tyr Val Ala Ala Phe Thr
705                 710                 715                 720

Val Gln Ala Ala Ala Glu Thr Leu Ser Glu Val Ala
                725                 730
```

<210> SEQ ID NO 14
<211> LENGTH: 2196
<212> TYPE: DNA
<213> ORGANISM: Artificial
<220> FEATURE:
<223> OTHER INFORMATION: Synthetic Construct

<400> SEQUENCE: 14

```
atggctagcg aaaccgacac tttgttgttg tgggtgcttt tgctttgggt acccggatct      60

actggtgatg ctgctaaatc ctccaatgaa gctactaaca ttactccaaa gcataatatg     120

aaagcatttt tggatgaatt gaaagctgag aacatcaaga agttcttata taattttaca     180

cagataccac atttagcagg aacagaacaa aactttcagc ttgcaaagca aattcaatcc     240

cagtggaaag aatttggcct ggattctgtt gagctagcac attatgatgt cctgttgtcc     300

tacccaaata agactcatcc caactacatc tcaataatta atgaagatgg aaatgagatt     360

ttcaacacat cattatttga accacctcct ccaggatatg aaaatgtttc ggatattgta     420

ccacctttca gtgctttctc tcctcaagga atgccagagg gcgatctagt gtatgttaac     480

tatgcacgaa ctgaagactt ctttaaattg gaacgggaca tgaaaatcaa ttgctctggg     540

aaaattgtaa ttgccagata tgggaaagtt ttcagaggaa ataaggttaa aaatgcccag     600

ctggcagggg ccaaaggagt cattctctac tccgaccctg ctgactactt tgctcctggg     660

gtgaagtcct atccagatgg ttggaatctt cctggaggtg gtgtccagcg tggaaatatc     720
```

-continued

```
ctaaatctga atggtgcagg agaccctctc acaccaggtt acccagcaaa tgaatatgct     780

tataggcgtg gaattgcaga ggctgttggt cttccaagta ttcctgttca tccaattgga     840

tactatgatg cacagaagct cctagaaaaa atgggtggct cagcaccacc agatagcagc     900

tggagaggaa gtctcaaagt gccctacaat gttggacctg gctttactgg aaacttttct     960

acacaaaaag tcaagatgca catccactct accaatgaag tgacaagaat ttacaatgtg    1020

ataggtactc tcagaggagc agtggaacca gacagatatg tcattctggg aggtcaccgg    1080

gactcatggg tgtttggtgg tattgaccct cagagtggag cagctgttgt tcatgaaatt    1140

gtgaggagct ttggaacact gaaaaaggaa gggtggagac ctagaagaac aattttgttt    1200

gcaagctggg atgcagaaga atttggtctt cttggttcta ctgagtgggc agaggagaat    1260

tcaagactcc ttcaagagcg tggcgtggct tatattaatg ctgactcatc tatagaagga    1320

aactacactc tgagagttga ttgtacaccg ctgatgtaca gcttggtaca caacctaaca    1380

aaagagctga aaagccctga tgaaggcttt gaaggcaaat ctctttatga aagttggact    1440

aaaaaaagtc cttccccaga gttcagtggc atgcccagga taagcaaatt gggatctgga    1500

aatgattttg aggtgttctt ccaacgactt ggaattgctt caggcagagc acggtatact    1560

aaaaattggg aaacaaacaa attcagcggc tatccactgt atcacagtgt ctatgaaaca    1620

tatgagttgg tggaaaagtt ttatgatcca atgtttaaat atcacctcac tgtggcccag    1680

gttcgaggag ggatggtgtt tgagctagcc aattccatag tgctcccttt tgattgtcga    1740

gattatgctg tagttttaag aaagtatgct gacaaaatct acagtatttc tatgaaacat    1800

ccacaggaaa tgaagacata cagtgtatca tttgattcac tttttctgc agtaaagaat     1860

tttacagaaa ttgcttccaa gttcagtgag agactccagg actttgacaa aagcaaccca    1920

atagtattaa gaatgatgaa tgatcaactc atgtttctgg aaagagcatt tattgatcca    1980

ttagggttac cagacaggcc tttttatagg catgtcatct atgctccaag cagccacaac    2040

aagtatgcag gggagtcatt cccaggaatt tatgatgctc tgtttgatat tgaaagcaaa    2100

gtggaccctt ccaaggcctg gggagaagtg aagagacaga tttatgttgc agccttcaca    2160

gtgcaggcag ctgcagagac tttgagtgaa gtagcc                              2196
```

<210> SEQ ID NO 15
<211> LENGTH: 263
<212> TYPE: PRT
<213> ORGANISM: Homo sapiens

<400> SEQUENCE: 15

```
Met Ala Ser Trp Val Pro Val Val Phe Leu Thr Leu Ser Val Thr Trp
1               5                   10                  15

Ile Gly Ala Ala Pro Leu Ile Leu Ser Arg Ile Val Gly Gly Trp Glu
            20                  25                  30

Cys Glu Lys His Ser Gln Pro Trp Gln Val Leu Val Ala Ser Arg Gly
        35                  40                  45

Arg Ala Val Cys Gly Gly Val Leu Val His Pro Gln Trp Val Leu Thr
    50                  55                  60

Ala Ala His Cys Ile Arg Asn Lys Ser Val Ile Leu Leu Gly Arg His
65                  70                  75                  80

Ser Leu Phe His Pro Glu Asp Thr Gly Gln Val Phe Gln Val Ser His
                85                  90                  95

Ser Phe Pro His Pro Leu Tyr Asp Met Ser Leu Leu Lys Asn Arg Phe
            100                 105                 110
```

```
Leu Arg Pro Gly Asp Asp Ser Ser His Asp Leu Met Leu Leu Arg Leu
        115                 120                 125

Ser Glu Pro Ala Glu Leu Thr Asp Ala Val Lys Val Met Asp Leu Pro
    130                 135                 140

Thr Gln Glu Pro Ala Leu Gly Thr Thr Cys Tyr Ala Ser Gly Trp Gly
145                 150                 155                 160

Ser Ile Glu Pro Glu Glu Phe Leu Thr Pro Lys Lys Leu Gln Cys Val
                165                 170                 175

Asp Leu His Val Ile Ser Asn Asp Val Cys Ala Gln Val His Pro Gln
            180                 185                 190

Lys Val Thr Lys Phe Met Leu Cys Ala Gly Arg Trp Thr Gly Gly Lys
        195                 200                 205

Ser Thr Cys Ser Gly Asp Ser Gly Gly Pro Leu Val Cys Asn Gly Val
    210                 215                 220

Leu Gln Gly Ile Thr Ser Trp Gly Ser Glu Pro Cys Ala Leu Pro Glu
225                 230                 235                 240

Arg Pro Ser Leu Tyr Thr Lys Val Val His Tyr Arg Lys Trp Ile Lys
                245                 250                 255

Asp Thr Ile Val Ala Asn Pro
            260


<210> SEQ ID NO 16
<211> LENGTH: 789
<212> TYPE: DNA
<213> ORGANISM: Homo sapiens

<400> SEQUENCE: 16

atggctagct gggtcccggt tgtcttcctc accctgtccg tgacgtggat tggcgctgcg      60

cccctcatcc tgtctcggat tgtgggaggc tgggagtgcg agaagcattc ccaaccctgg     120

caggtgcttg tggcctctcg tggcagggca gtctgcggcg gtgttctggt gcacccccag     180

tgggtcctca cagctgccca ctgcatcagg aacaaaagcg tgatcttgct gggtcggcac     240

agcttgtttc atcctgaaga cacaggccag gtatttcagg tcagccacag cttcccacac     300

ccgctctacg atatgagcct cctgaagaat cgattcctca ggccaggtga tgactccagc     360

cacgacctca tgctgctccg cctgtcagag cctgccgagc tcacggatgc tgtgaaggtc     420

atggacctgc ccacccagga gccagcactg gggaccacct gctacgcctc aggctggggc     480

agcattgaac cagaggagtt cttgacccca aagaaacttc agtgtgtgga cctccatgtt     540

atttccaatg acgtgtgtgc gcaagttcac cctcagaagg tgaccaagtt catgctgtgt     600

gctggacgct ggacaggggg caaaagcacc tgctcgggtg attctggggg cccacttgtc     660

tgtaatggtg tgcttcaagg tatcacgtca tggggcagtg aaccatgtgc cctgcccgaa     720

aggccttccc tgtacaccaa ggtggtgcat taccggaagt ggatcaagga caccatcgtg     780

gccaacccc                                                             789


<210> SEQ ID NO 17
<211> LENGTH: 240
<212> TYPE: PRT
<213> ORGANISM: Artificial
<220> FEATURE:
<223> OTHER INFORMATION: Synthetic Construct

<400> SEQUENCE: 17

Met Ala Ser Ile Val Gly Gly Trp Glu Cys Glu Lys His Ser Gln Pro
1               5                   10                  15
```

```
Trp Gln Val Leu Val Ala Ser Arg Gly Arg Ala Val Cys Gly Gly Val
            20                  25                  30

Leu Val His Pro Gln Trp Val Leu Thr Ala Ala His Cys Ile Arg Asn
        35                  40                  45

Lys Ser Val Ile Leu Leu Gly Arg His Ser Leu Phe His Pro Glu Asp
    50                  55                  60

Thr Gly Gln Val Phe Gln Val Ser His Ser Phe Pro His Pro Leu Tyr
65                  70                  75                  80

Asp Met Ser Leu Leu Lys Asn Arg Phe Leu Arg Pro Gly Asp Asp Ser
                85                  90                  95

Ser His Asp Leu Met Leu Leu Arg Leu Ser Glu Pro Ala Glu Leu Thr
            100                 105                 110

Asp Ala Val Lys Val Met Asp Leu Pro Thr Gln Glu Pro Ala Leu Gly
        115                 120                 125

Thr Thr Cys Tyr Ala Ser Gly Trp Gly Ser Ile Glu Pro Glu Glu Phe
    130                 135                 140

Leu Thr Pro Lys Lys Leu Gln Cys Val Asp Leu His Val Ile Ser Asn
145                 150                 155                 160

Asp Val Cys Ala Gln Val His Pro Gln Lys Val Thr Lys Phe Met Leu
                165                 170                 175

Cys Ala Gly Arg Trp Thr Gly Gly Lys Ser Thr Cys Ser Gly Asp Ser
            180                 185                 190

Gly Gly Pro Leu Val Cys Asn Gly Val Leu Gln Gly Ile Thr Ser Trp
        195                 200                 205

Gly Ser Glu Pro Cys Ala Leu Pro Glu Arg Pro Ser Leu Tyr Thr Lys
    210                 215                 220

Val Val His Tyr Arg Lys Trp Ile Lys Asp Thr Ile Val Ala Asn Pro
225                 230                 235                 240
```

<210> SEQ ID NO 18
<211> LENGTH: 720
<212> TYPE: DNA
<213> ORGANISM: Artificial
<220> FEATURE:
<223> OTHER INFORMATION: Synthetic Construct

<400> SEQUENCE: 18

```
atggctagca ttgtgggagg ctgggagtgc gagaagcatt cccaaccctg gcaggtgctt     60

gtggcctctc gtggcagggc agtctgcggc ggtgttctgg tgcacccccca gtgggtcctc    120

acagctgccc actgcatcag gaacaaaagc gtgatcttgc tgggtcggca cagcttgttt    180

catcctgaag acacaggcca ggtatttcag gtcagccaca gcttcccaca cccgctctac    240

gatatgagcc tcctgaagaa tcgattcctc aggccaggtg atgactccag ccacgacctc    300

atgctgctcc gcctgtcaga gcctgccgag ctcacggatg ctgtgaaggt catggacctg    360

cccacccagg agccagcact ggggaccacc tgctacgcct caggctgggg cagcattgaa    420

ccagaggagt tcttgacccc aaagaaactt cagtgtgtgg acctccatgt tatttccaat    480

gacgtgtgtg cgcaagttca ccctcagaag gtgaccaagt tcatgctgtg tgctggacgc    540

tggacagggg gcaaaagcac ctgctcgggt gattctgggg gcccacttgt ctgtaatggt    600

gtgcttcaag gtatcacgtc atggggcagt gaaccatgtg ccctgcccga aaggccttcc    660

ctgtacacca aggtggtgca ttaccggaag tggatcaagg acaccatcgt ggccaacccc    720
```

<210> SEQ ID NO 19
<211> LENGTH: 281

<212> TYPE: PRT
<213> ORGANISM: Artificial
<220> FEATURE:
<223> OTHER INFORMATION: Synthetic Construct

<400> SEQUENCE: 19

Met Ala Ser Ala Arg Arg Pro Arg Trp Leu Cys Ala Gly Ala Leu Val
1               5                   10                  15

Leu Ala Gly Gly Phe Phe Leu Leu Gly Phe Leu Phe Gly Trp Phe Ile
            20                  25                  30

Lys Ser Ser Asn Glu Ala Thr Asn Ile Thr Pro Gly Ile Val Gly Gly
        35                  40                  45

Trp Glu Cys Glu Lys His Ser Gln Pro Trp Gln Val Leu Val Ala Ser
    50                  55                  60

Arg Gly Arg Ala Val Cys Gly Gly Val Leu Val His Pro Gln Trp Val
65                  70                  75                  80

Leu Thr Ala Ala His Cys Ile Arg Asn Lys Ser Val Ile Leu Leu Gly
                85                  90                  95

Arg His Ser Leu Phe His Pro Glu Asp Thr Gly Gln Val Phe Gln Val
            100                 105                 110

Ser His Ser Phe Pro His Pro Leu Tyr Asp Met Ser Leu Leu Lys Asn
        115                 120                 125

Arg Phe Leu Arg Pro Gly Asp Asp Ser Ser His Asp Leu Met Leu Leu
    130                 135                 140

Arg Leu Ser Glu Pro Ala Glu Leu Thr Asp Ala Val Lys Val Met Asp
145                 150                 155                 160

Leu Pro Thr Gln Glu Pro Ala Leu Gly Thr Thr Cys Tyr Ala Ser Gly
                165                 170                 175

Trp Gly Ser Ile Glu Pro Glu Glu Phe Leu Thr Pro Lys Lys Leu Gln
            180                 185                 190

Cys Val Asp Leu His Val Ile Ser Asn Asp Val Cys Ala Gln Val His
        195                 200                 205

Pro Gln Lys Val Thr Lys Phe Met Leu Cys Ala Gly Arg Trp Thr Gly
    210                 215                 220

Gly Lys Ser Thr Cys Ser Gly Asp Ser Gly Gly Pro Leu Val Cys Asn
225                 230                 235                 240

Gly Val Leu Gln Gly Ile Thr Ser Trp Gly Ser Glu Pro Cys Ala Leu
                245                 250                 255

Pro Glu Arg Pro Ser Leu Tyr Thr Lys Val Val His Tyr Arg Lys Trp
            260                 265                 270

Ile Lys Asp Thr Ile Val Ala Asn Pro
        275                 280

<210> SEQ ID NO 20
<211> LENGTH: 846
<212> TYPE: DNA
<213> ORGANISM: Artificial
<220> FEATURE:
<223> OTHER INFORMATION: Synthetic Construct

<400> SEQUENCE: 20
atggctagcg cgcgccgccc gcgctggctg tgcgctgggg cgctggtgct ggcgggtggc 60
ttctttctcc tcggcttcct cttcgggtgg tttataaaat cctccaatga agctactaac 120
attactccag gaattgtggg aggctgggag tgcgagaagc attcccaacc ctggcaggtg 180
cttgtggcct ctcgtggcag ggcagtctgc ggcggtgttc tggtgcaccc ccagtgggtc 240

-continued

```
ctcacagctg cccactgcat caggaacaaa agcgtgatct tgctgggtcg gcacagcttg    300

tttcatcctg aagacacagg ccaggtattt caggtcagcc acagcttccc acacccgctc    360

tacgatatga gcctcctgaa gaatcgattc ctcaggccag gtgatgactc cagccacgac    420

ctcatgctgc tccgcctgtc agagcctgcc gagctcacgg atgctgtgaa ggtcatggac    480

ctgcccaccc aggagccagc actggggacc acctgctacg cctcaggctg gggcagcatt    540

gaaccagagg agttcttgac cccaaagaaa cttcagtgtg tggacctcca tgttatttcc    600

aatgacgtgt gtgcgcaagt tcaccctcag aaggtgacca agttcatgct gtgtgctgga    660

cgctggacag gggcaaaag cacctgctcg ggtgattctg gggcccact tgtctgtaat    720

ggtgtgcttc aaggtatcac gtcatggggc agtgaaccat gtgccctgcc cgaaaggcct    780

tccctgtaca ccaaggtggt gcattaccgg aagtggatca aggacaccat cgtggccaac    840

ccctga                                                                846
```

<210> SEQ ID NO 21
<211> LENGTH: 125
<212> TYPE: PRT
<213> ORGANISM: Homo sapiens

<400> SEQUENCE: 21

```
Met Ala Ser Lys Ala Val Leu Leu Ala Leu Leu Met Ala Gly Leu Ala
1               5                   10                  15

Leu Gln Pro Gly Thr Ala Leu Leu Cys Tyr Ser Cys Lys Ala Gln Val
            20                  25                  30

Ser Asn Glu Asp Cys Leu Gln Val Glu Asn Cys Thr Gln Leu Gly Glu
        35                  40                  45

Gln Cys Trp Thr Ala Arg Ile Arg Ala Val Gly Leu Leu Thr Val Ile
    50                  55                  60

Ser Lys Gly Cys Ser Leu Asn Cys Val Asp Asp Ser Gln Asp Tyr Tyr
65                  70                  75                  80

Val Gly Lys Lys Asn Ile Thr Cys Cys Asp Thr Asp Leu Cys Asn Ala
                85                  90                  95

Ser Gly Ala His Ala Leu Gln Pro Ala Ala Ala Ile Leu Ala Leu Leu
            100                 105                 110

Pro Ala Leu Gly Leu Leu Leu Trp Gly Pro Gly Gln Leu
        115                 120                 125
```

<210> SEQ ID NO 22
<211> LENGTH: 375
<212> TYPE: DNA
<213> ORGANISM: Homo sapiens

<400> SEQUENCE: 22

```
atggctagca aggctgtgct gcttgccctg ttgatggcag gcttggccct gcagccaggc     60

actgccctgc tgtgctactc ctgcaaagcc caggtgagca acgaggactg cctgcaggtg    120

gagaactgca cccagctggg ggagcagtgc tggaccgcgc gcatccgcgc agttggcctc    180

ctgaccgtca tcagcaaagg ctgcagcttg aactgcgtgg atgactcaca ggactactac    240

gtgggcaaga agaacatcac gtgctgtgac accgacttgt gcaacgccag cggggcccat    300

gccctgcagc cggctgccgc catccttgcg ctgctccctg cactcggcct gctgctctgg    360

ggacccggcc agcta                                                      375
```

<210> SEQ ID NO 23
<211> LENGTH: 5964

<212> TYPE: DNA
<213> ORGANISM: Artificial
<220> FEATURE:
<223> OTHER INFORMATION: Synthetic Construct

<400> SEQUENCE: 23
ggcgtaatgc tctgccagtg ttacaaccaa ttaaccaatt ctgattagaa aaactcatcg 60
agcatcaaat gaaactgcaa tttattcata tcaggattat caataccata tttttgaaaa 120
agccgtttct gtaatgaagg agaaaactca ccgaggcagt tccataggat ggcaagatcc 180
tggtatcggt ctgcgattcc gactcgtcca acatcaatac aacctattaa tttcccctcg 240
tcaaaaataa ggttatcaag tgagaaatca ccatgagtga cgactgaatc cggtgagaat 300
ggcaaaagct tatgcatttc tttccagact tgttcaacag gccagccatt acgctcgtca 360
tcaaaatcac tcgcatcaac caaaccgtta ttcattcgtg attgcgcctg agcgagacga 420
aatacgcgat cgctgttaaa aggacaatta caaacaggaa tcaaatgcaa ccggcgcagg 480
aacactgcca gcgcatcaac aatattttca cctgaatcag gatattcttc taatacctgg 540
aatgctgttt tcccggggat cgcagtggtg agtaaccatg catcatcagg agtacggata 600
aaatgcttga tggtcggaag aggcataaat tccgtcagcc agtttagtct gaccatctca 660
tctgtaacat cattggcaac gctacctttg ccatgtttca gaaacaactc tggcgcatcg 720
ggcttcccat acaatcgata gattgtcgca cctgattgcc cgacattatc gcgagcccat 780
ttatacccat ataaatcagc atccatgttg gaatttaatc gcggcctcga gcaagacgtt 840
tcccgttgaa tatggctcat aacacccctt gtattactgt ttatgtaagc agacaggtcg 900
acaatattgg ctattggcca ttgcatacgt tgtatctata tcataatatg tacatttata 960
ttggctcatg tccaatatga ccgccatgtt gacattgatt attgactagt tattaatagt 1020
aatcaattac ggggtcatta gttcatagcc catatatgga gttccgcgtt acataactta 1080
cggtaaatgg cccgcctggc tgaccgccca acgacccccg cccattgacg tcaataatga 1140
cgtatgttcc catagtaacg ccaataggga ctttccattg acgtcaatgg gtggagtatt 1200
tacggtaaac tgcccacttg gcagtacatc aagtgtatca tatgccaagt ccgcccccta 1260
ttgacgtcaa tgacggtaaa tggcccgcct ggcattatgc ccagtacatg accttacggg 1320
actttcctac ttggcagtac atctacgtat tagtcatcgc tattaccatg gtgatgcggt 1380
tttggcagta caccaatggg cgtggatagc ggtttgactc acggggattt ccaagtctcc 1440
accccattga cgtcaatggg agtttgtttt ggcaccaaaa tcaacgggac tttccaaaat 1500
gtcgtaataa ccccgccccg ttgacgcaaa tgggcggtag gcgtgtacgg tgggaggtct 1560
atataagcag agctcgttta gtgaaccgtc agatcgcctg gagacgccat ccacgctgtt 1620
ttgacctcca tagaagacac cgggaccgat ccagcctccg cggccgggaa cggtgcattg 1680
gaacgcggat tccccgtgcc aagagtgact caccgtccgg atctcagcaa gcaggtatgt 1740
actctccagg gtgggcctgg cttccccagt caagactcca gggatttgag ggacgctgtg 1800
ggctcttctc ttacatgtac cttttgcttg cctcaaccct gactatcttc caggtcagga 1860
tcccagagtc aggggtctgt attttcctgc tggtggctcc agttcaggaa cagtaaaccc 1920
tgctccgaat attgcctctc acatctcgtc aatctccgcg aggactgggg accctgtgac 1980
gaacatggct agcgcgcgcc gcccgcgctg gctgtgcgct ggggcgctgg tgctggcggg 2040
tggcttcttt ctcctcggct tcctcttcgg gtggtttata aaatcctcca atgaagctac 2100
taacattact ccaaagcata atatgaaagc atttttggat gaattgaaag ctgagaacat 2160

-continued

```
caagaagttc ttatataatt ttacacagat accacattta gcaggaacag aacaaaactt   2220
tcagcttgca aagcaaattc aatcccagtg gaaagaattt ggcctggatt ctgttgagct   2280
ggcacattat gatgtcctgt tgtcctaccc aaataagact catcccaact acatctcaat   2340
aattaatgaa gatggaaatg agattttcaa cacatcatta tttgaaccac ctcctccagg   2400
atatgaaaat gtttcggata ttgtaccacc tttcagtgct ttctctcctc aaggaatgcc   2460
agagggcgat ctagtgtatg ttaactatgc acgaactgaa gacttcttta aattggaacg   2520
ggacatgaaa atcaattgct ctgggaaaat tgtaattgcc agatatggga aagttttcag   2580
aggaaataag gttaaaaatg cccagctggc aggggccaaa ggagtcattc tctactccga   2640
ccctgctgac tactttgctc ctggggtgaa gtcctatcca gatggttgga atcttcctgg   2700
aggtggtgtc cagcgtggaa atatcctaaa tctgaatggt gcaggagacc ctctcacacc   2760
aggttaccca gcaaatgaat atgcttatag gcgtggaatt gcagaggctg ttggtcttcc   2820
aagtattcct gttcatccaa ttggatacta tgatgcacag aagctcctag aaaaaatggg   2880
tggctcagca ccaccagata gcagctggag aggaagtctc aaagtgccct acaatgttgg   2940
acctggcttt actggaaact ttctacaca aaaagtcaag atgcacatcc actctaccaa   3000
tgaagtgaca agaatttaca atgtgatagg tactctcaga ggagcagtgg aaccagacag   3060
atatgtcatt ctgggaggtc accgggactc atgggtgttt ggtggtattg accctcagag   3120
tggagcagct gttgttcatg aaattgtgag gagctttgga acactgaaaa aggaagggtg   3180
gagacctaga agaacaattt tgtttgcaag ctgggatgca gaagaatttg gtcttcttgg   3240
ttctactgag tgggcagagg agaattcaag actccttcaa gagcgtggcg tggcttatat   3300
taatgctgac tcatctatag aaggaaacta cactctgaga gttgattgta caccgctgat   3360
gtacagcttg gtacacaacc taacaaaaga gctgaaaagc cctgatgaag gctttgaagg   3420
caaatctctt tatgaaagtt ggactaaaaa aagtccttcc ccagagttca gtggcatgcc   3480
caggataagc aaattgggat ctggaaatga ttttgaggtg ttcttccaac gacttggaat   3540
tgcttcaggc agagcacggt atactaaaaa ttgggaaaca aacaaattca gcggctatcc   3600
actgtatcac agtgtctatg aaacatatga gttggtggaa aagttttatg atccaatgtt   3660
taaatatcac ctcactgtgg cccaggttcg aggagggatg gtgtttgagc tggccaattc   3720
catagtgctc ccttttgatt gtcgagatta tgctgtagtt ttaagaaagt atgctgacaa   3780
aatctacagt atttctatga aacatccaca ggaaatgaag acatacagtg tatcatttga   3840
ttcacttttt tctgcagtaa agaattttac agaaattgct tccaagttca gtgagagact   3900
ccaggacttt gacaaaagca acccaatagt attaagaatg atgaatgatc aactcatgtt   3960
tctggaaaga gcatttattg atccattagg gttaccagac aggccttttt ataggcatgt   4020
catctatgct ccaagcagcc acaacaagta tgcaggggag tcattcccag gaatttatga   4080
tgctctgttt gatattgaaa gcaaagtgga cccttccaag gcctggggag aagtgaagag   4140
acagatttat gttgcagcct tcacagtgca ggcagctgca gagactttga gtgaagtagc   4200
ctaaagatct gggccctaac aaaacaaaaa gatggggtta ttccctaaac ttcatgggtt   4260
acgtaattgg aagttggggg acattgccac aagatcatat tgtacaaaag atcaaacact   4320
gttttagaaa acttcctgta aacaggccta ttgattggaa agtatgtcaa aggattgtgg   4380
gtcttttggg ctttgctgct ccatttacac aatgtggata tcctgcctta atgcctttgt   4440
atgcatgtat acaagctaaa caggctttca ctttctcgcc aacttacaag gcctttctaa   4500
gtaaacagta catgaacctt taccccgttg ctcggcaacg gcctggtctg tgccaagtgt   4560
```

```
ttgctgacgc aaccccccact ggctggggct tggccatagg ccatcagcgc atgcgtggaa   4620

cctttgtggc tcctctgccg atccatactg cggaactcct agccgcttgt tttgctcgca   4680

gccggtctgg agcaaagctc ataggaactg acaattctgt cgtcctctcg cggaaatata   4740

catcgtttcg atctacgtat gatctttttc cctctgccaa aaattatggg gacatcatga   4800

agccccttga gcatctgact tctggctaat aaaggaaatt tattttcatt gcaatagtgt   4860

gttggaattt tttgtgtctc tcactcggaa ggaattctgc attaatgaat cggccaacgc   4920

gcggggagag gcggtttgcg tattgggcgc tcttccgctt cctcgctcac tgactcgctg   4980

cgctcggtcg ttcggctgcg gcgagcggta tcagctcact caaaggcggt aatacggtta   5040

tccacagaat caggggataa cgcaggaaag aacatgtgag caaaaggcca gcaaaaggcc   5100

aggaaccgta aaaaggccgc gttgctggcg tttttccata ggctccgccc ccctgacgag   5160

catcacaaaa atcgacgctc aagtcagagg tggcgaaacc cgacaggact ataaagatac   5220

caggcgtttc cccctggaag ctccctcgtg cgctctcctg ttccgaccct gccgcttacc   5280

ggatacctgt ccgcctttct cccttcggga agcgtggcgc tttctcatag ctcacgctgt   5340

aggtatctca gttcggtgta ggtcgttcgc tccaagctgg gctgtgtgca cgaacccccc   5400

gttcagcccg accgctgcgc cttatccggt aactatcgtc ttgagtccaa cccggtaaga   5460

cacgacttat cgccactggc agcagccact ggtaacagga ttagcagagc gaggtatgta   5520

ggcggtgcta cagagttctt gaagtggtgg cctaactacg gctacactag aagaacagta   5580

tttggtatct gcgctctgct gaagccagtt accttcggaa aaagagttgg tagctcttga   5640

tccggcaaac aaaccaccgc tggtagcggt ggtttttttg tttgcaagca gcagattacg   5700

cgcagaaaaa aaggatctca agaagatcct ttgatctttt ctacggggtc tgacgctcag   5760

tggaacgaaa actcacgtta agggattttg gtcatgagat tatcaaaaag gatcttcacc   5820

tagatccttt taaattaaaa atgaagtttt aaatcaatct aaagtatata tgagtaaact   5880

tggtctgaca gttaccaatg cttaatcagt gaggcaccta tctcagcgat ctgtctattt   5940

cgttcatcca tagttgcctg actc                                           5964
```

<210> SEQ ID NO 24
<211> LENGTH: 4122
<212> TYPE: DNA
<213> ORGANISM: Artificial
<220> FEATURE:
<223> OTHER INFORMATION: Synthetic Construct

<400> SEQUENCE: 24

```
ggcgtaatgc tctgccagtg ttacaaccaa ttaaccaatt ctgattagaa aaactcatcg     60

agcatcaaat gaaactgcaa tttattcata tcaggattat caataccata tttttgaaaa    120

agccgtttct gtaatgaagg agaaaactca ccgaggcagt tccataggat ggcaagatcc    180

tggtatcggt ctgcgattcc gactcgtcca acatcaatac aacctattaa tttcccctcg    240

tcaaaaataa ggttatcaag tgagaaatca ccatgagtga cgactgaatc cggtgagaat    300

ggcaaaagct tatgcatttc tttccagact tgttcaacag gccagccatt acgctcgtca    360

tcaaaatcac tcgcatcaac caaaccgtta ttcattcgtg attgcgcctg agcgagacga    420

aatacgcgat cgctgttaaa aggacaatta caaacaggaa tcaaatgcaa ccggcgcagg    480

aacactgcca gcgcatcaac aatattttca cctgaatcag gatattcttc taatacctgg    540

aatgctgttt tcccggggat cgcagtggtg agtaaccatg catcatcagg agtacggata    600
```

-continued

```
aaatgcttga tggtcggaag aggcataaat tccgtcagcc agtttagtct gaccatctca    660
tctgtaacat cattggcaac gctacctttg ccatgtttca gaaacaactc tggcgcatcg    720
ggcttcccat acaatcgata gattgtcgca cctgattgcc cgacattatc gcgagcccat    780
ttatacccat ataaatcagc atccatgttg gaatttaatc gcggcctcga gcaagacgtt    840
tcccgttgaa tatggctcat aacacccctt gtattactgt ttatgtaagc agacaggtcg    900
acaatattgg ctattggcca ttgcatacgt tgtatctata tcataatatg tacatttata    960
ttggctcatg tccaatatga ccgccatgtt gacattgatt attgactagt tattaatagt   1020
aatcaattac ggggtcatta gttcatagcc catatatgga gttccgcgtt acataactta   1080
cggtaaatgg cccgcctggc tgaccgccca acgacccccg cccattgacg tcaataatga   1140
cgtatgttcc catagtaacg ccaataggga ctttccattg acgtcaatgg gtggagtatt   1200
tacggtaaac tgcccacttg gcagtacatc aagtgtatca tatgccaagt ccgcccccta   1260
ttgacgtcaa tgacggtaaa tggcccgcct ggcattatgc ccagtacatg accttacggg   1320
actttcctac ttggcagtac atctacgtat tagtcatcgc tattaccatg gtgatgcggt   1380
tttggcagta caccaatggg cgtggatagc ggtttgactc acggggattt ccaagtctcc   1440
accccattga cgtcaatggg agtttgtttt ggcaccaaaa tcaacgggac tttccaaaat   1500
gtcgtaataa ccccgccccg ttgacgcaaa tgggcggtag gcgtgtacgg tgggaggtct   1560
atataagcag agctcgttta gtgaaccgtc agatcgcctg gagacgccat ccacgctgtt   1620
ttgacctcca tagaagacac cgggaccgat ccagcctccg cggccgggaa cggtgcattg   1680
gaacgcggat tccccgtgcc aagagtgact caccgtccgg atctcagcaa gcaggtatgt   1740
actctccagg gtgggcctgg cttccccagt caagactcca gggatttgag ggacgctgtg   1800
ggctcttctc ttacatgtac cttttgcttg cctcaaccct gactatcttc caggtcagga   1860
tcccagagtc aggggtctgt attttcctgc tggtggctcc agttcaggaa cagtaaaccc   1920
tgctccgaat attgcctctc acatctcgtc aatctccgcg aggactgggg accctgtgac   1980
gaacatggct agcaaggctg tgctgcttgc cctgttgatg gcaggcttgg ccctgcagcc   2040
aggcactgcc ctgctgtgct actcctgcaa agcccaggtg agcaacgagg actgcctgca   2100
ggtggagaac tgcacccagc tgggggagca gtgctggacc gcgcgcatcc gcgcagttgg   2160
cctcctgacc gtcatcagca aaggctgcag cttgaactgc gtggatgact cacaggacta   2220
ctacgtgggc aagaagaaca tcacgtgctg tgacaccgac ttgtgcaacg ccagcggggc   2280
ccatgccctg cagccggctg ccgccatcct tgcgctgctc cctgcactcg gcctgctgct   2340
ctggggaccc ggccagctat agagatctgg gccctaacaa aacaaaaaga tggggttatt   2400
ccctaaactt catgggttac gtaattggaa gttgggggac attgccacaa gatcatattg   2460
tacaaaagat caaacactgt tttagaaaac ttcctgtaaa caggcctatt gattggaaag   2520
tatgtcaaag gattgtgggt cttttgggct ttgctgctcc atttacacaa tgtggatatc   2580
ctgccttaat gcctttgtat gcatgtatac aagctaaaca ggctttcact ttctcgccaa   2640
cttacaaggc ctttctaagt aaacagtaca tgaaccttta ccccgttgct cggcaacggc   2700
ctggtctgtg ccaagtgttt gctgacgcaa cccccactgg ctggggcttg gccataggcc   2760
atcagcgcat gcgtggaacc tttgtggctc ctctgccgat ccatactgcg gaactcctag   2820
ccgcttgttt tgctcgcagc cggtctggag caaagctcat aggaactgac aattctgtcg   2880
tcctctcgcg gaaatataca tcgtttcgat ctacgtatga tctttttccc tctgccaaaa   2940
attatgggga catcatgaag ccccttgagc atctgacttc tggctaataa aggaaattta   3000
```

ttttcattgc aatagtgtgt tggaattttt tgtgtctctc actcggaagg aattctgcat 3060
taatgaatcg gccaacgcgc ggggagaggc ggtttgcgta ttgggcgctc ttccgcttcc 3120
tcgctcactg actcgctgcg ctcggtcgtt cggctgcggc gagcggtatc agctcactca 3180
aaggcggtaa tacggttatc cacagaatca ggggataacg caggaaagaa catgtgagca 3240
aaaggccagc aaaaggccag gaaccgtaaa aaggccgcgt tgctggcgtt tttccatagg 3300
ctccgccccc ctgacgagca tcacaaaaat cgacgctcaa gtcagaggtg gcgaaacccg 3360
acaggactat aaagatacca ggcgtttccc cctggaagct ccctcgtgcg ctctcctgtt 3420
ccgaccctgc cgcttaccgg atacctgtcc gcctttctcc cttcgggaag cgtggcgctt 3480
tctcatagct cacgctgtag gtatctcagt tcggtgtagg tcgttcgctc caagctgggc 3540
tgtgtgcacg aaccccccgt tcagcccgac cgctgcgcct tatccggtaa ctatcgtctt 3600
gagtccaacc cggtaagaca cgacttatcg ccactggcag cagccactgg taacaggatt 3660
agcagagcga ggtatgtagg cggtgctaca gagttcttga agtggtggcc taactacggc 3720
tacactagaa gaacagtatt tggtatctgc gctctgctga agccagttac cttcggaaaa 3780
agagttggta gctcttgatc cggcaaacaa accaccgctg gtagcggtgg tttttttgtt 3840
tgcaagcagc agattacgcg cagaaaaaaa ggatctcaag aagatccttt gatcttttct 3900
acggggtctg acgctcagtg gaacgaaaac tcacgttaag ggattttggt catgagatta 3960
tcaaaaagga tcttcaccta gatcctttta aattaaaaat gaagttttaa atcaatctaa 4020
agtatatatg agtaaacttg gtctgacagt taccaatgct taatcagtga ggcacctatc 4080
tcagcgatct gtctatttcg ttcatccata gttgcctgac tc 4122

<210> SEQ ID NO 25
<211> LENGTH: 4467
<212> TYPE: DNA
<213> ORGANISM: Artificial
<220> FEATURE:
<223> OTHER INFORMATION: Synthetic Construct

<400> SEQUENCE: 25
ggcgtaatgc tctgccagtg ttacaaccaa ttaaccaatt ctgattagaa aaactcatcg 60
agcatcaaat gaaactgcaa tttattcata tcaggattat caataccata tttttgaaaa 120
agccgtttct gtaatgaagg agaaaactca ccgaggcagt tccataggat ggcaagatcc 180
tggtatcggt ctgcgattcc gactcgtcca acatcaatac aacctattaa tttcccctcg 240
tcaaaaataa ggttatcaag tgagaaatca ccatgagtga cgactgaatc cggtgagaat 300
ggcaaaagct tatgcatttc tttccagact tgttcaacag gccagccatt acgctcgtca 360
tcaaaatcac tcgcatcaac caaaccgtta ttcattcgtg attgcgcctg agcgagacga 420
aatacgcgat cgctgttaaa aggacaatta caaacaggaa tcaaatgcaa ccggcgcagg 480
aacactgcca gcgcatcaac aatattttca cctgaatcag gatattcttc taatacctgg 540
aatgctgttt tcccggggat cgcagtggtg agtaaccatg catcatcagg agtacggata 600
aaatgcttga tggtcggaag aggcataaat tccgtcagcc agtttagtct gaccatctca 660
tctgtaacat cattggcaac gctacctttg ccatgtttca gaaacaactc tggcgcatcg 720
ggcttcccat acaatcgata gattgtcgca cctgattgcc cgacattatc gcgagcccat 780
ttatacccat ataaatcagc atccatgttg gaatttaatc gcggcctcga gcaagacgtt 840
tcccgttgaa tatggctcat aacacccctt gtattactgt ttatgtaagc agacaggtcg 900
acaatattgg ctattggcca ttgcatacgt tgtatctata tcataatatg tacatttata 960
ttggctcatg tccaatatga ccgccatgtt gacattgatt attgactagt tattaatagt 1020
aatcaattac ggggtcatta gttcatagcc catatatgga gttccgcgtt acataactta 1080
cggtaaatgg cccgcctggc tgaccgccca acgacccccg cccattgacg tcaataatga 1140
cgtatgttcc catagtaacg ccaataggga ctttccattg acgtcaatgg gtggagtatt 1200
tacggtaaac tgcccacttg gcagtacatc aagtgtatca tatgccaagt ccgcccccta 1260
ttgacgtcaa tgacggtaaa tggcccgcct ggcattatgc ccagtacatg accttacggg 1320
actttcctac ttggcagtac atctacgtat tagtcatcgc tattaccatg gtgatgcggt 1380
tttggcagta caccaatggg cgtggatagc ggtttgactc acggggattt ccaagtctcc 1440
accccattga cgtcaatggg agtttgtttt ggcaccaaaa tcaacgggac tttccaaaat 1500
gtcgtaataa ccccgccccg ttgacgcaaa tgggcggtag gcgtgtacgg tgggaggtct 1560
atataagcag agctcgttta gtgaaccgtc agatcgcctg gagacgccat ccacgctgtt 1620
ttgacctcca tagaagacac cgggaccgat ccagcctccg cggccgggaa cggtgcattg 1680
gaacgcggat tccccgtgcc aagagtgact caccgtccgg atctcagcaa gcaggtatgt 1740
actctccagg gtgggcctgg cttccccagt caagactcca gggatttgag ggacgctgtg 1800
ggctcttctc ttacatgtac cttttgcttg cctcaaccct gactatcttc caggtcagga 1860
tcccagagtc aggggtctgt attttcctgc tggtggctcc agttcaggaa cagtaaaccc 1920
tgctccgaat attgcctctc acatctcgtc aatctccgcg aggactgggg accctgtgac 1980
gaacatggct agcattgtgg gaggctggga gtgcgagaag cattcccaac cctggcaggt 2040
gcttgtggcc tctcgtggca gggcagtctg cggcggtgtt ctggtgcacc cccagtgggt 2100
cctcacagct gcccactgca tcaggaacaa aagcgtgatc ttgctgggtc ggcacagctt 2160
gtttcatcct gaagacacag gccaggtatt tcaggtcagc cacagcttcc cacacccgct 2220
ctacgatatg agcctcctga agaatcgatt cctcaggcca ggtgatgact ccagccacga 2280
cctcatgctg ctccgcctgt cagagcctgc cgagctcacg gatgctgtga aggtcatgga 2340
cctgcccacc caggagccag cactggggac cacctgctac gcctcaggct ggggcagcat 2400
tgaaccagag gagttcttga ccccaaagaa acttcagtgt gtggacctcc atgttatttc 2460
caatgacgtg tgtgcgcaag ttcaccctca gaaggtgacc aagttcatgc tgtgtgctgg 2520
acgctggaca gggggcaaaa gcacctgctc gggtgattct gggggcccac ttgtctgtaa 2580
tggtgtgctt caaggtatca cgtcatgggg cagtgaacca tgtgccctgc ccgaaaggcc 2640
ttccctgtac accaaggtgg tgcattaccg gaagtggatc aaggacacca tcgtggccaa 2700
cccctgaaga tctgggccct aacaaaacaa aaagatgggg ttattcccta aacttcatgg 2760
gttacgtaat tggaagttgg gggacattgc cacaagatca tattgtacaa aagatcaaac 2820
actgttttag aaaacttcct gtaaacaggc ctattgattg gaaagtatgt caaaggattg 2880
tgggtctttt gggctttgct gctccattta cacaatgtgg atatcctgcc ttaatgcctt 2940
tgtatgcatg tatacaagct aaacaggctt tcactttctc gccaacttac aaggcctttc 3000
taagtaaaca gtacatgaac ctttaccccg ttgctcggca acggcctggt ctgtgccaag 3060
tgtttgctga cgcaaccccc actggctggg gcttggccat aggccatcag cgcatgcgtg 3120
gaacctttgt ggctcctctg ccgatccata ctgcggaact cctagccgct tgttttgctc 3180
gcagccggtc tggagcaaag ctcataggaa ctgacaattc tgtcgtcctc tcgcggaaat 3240
atacatcgtt tcgatctacg tatgatcttt ttccctctgc caaaaattat ggggacatca 3300

```
tgaagcccct tgagcatctg acttctggct aataaaggaa atttattttc attgcaatag   3360
tgtgttggaa tttttgtgt ctctcactcg gaaggaattc tgcattaatg aatcggccaa    3420
cgcgcgggga gaggcggttt gcgtattggg cgctcttccg cttcctcgct cactgactcg   3480
ctgcgctcgg tcgttcggct gcggcgagcg gtatcagctc actcaaaggc ggtaatacgg   3540
ttatccacag aatcagggga taacgcagga aagaacatgt gagcaaaagg ccagcaaaag   3600
gccaggaacc gtaaaaaggc cgcgttgctg gcgtttttcc ataggctccg cccccctgac   3660
gagcatcaca aaaatcgacg ctcaagtcag aggtggcgaa acccgacagg actataaaga   3720
taccaggcgt ttccccctgg aagctccctc gtgcgctctc ctgttccgac cctgccgctt   3780
accggatacc tgtccgcctt tctcccttcg ggaagcgtgg cgctttctca tagctcacgc   3840
tgtaggtatc tcagttcggt gtaggtcgtt cgctccaagc tgggctgtgt gcacgaaccc   3900
cccgttcagc ccgaccgctg cgccttatcc ggtaactatc gtcttgagtc caacccggta   3960
agacacgact tatcgccact ggcagcagcc actggtaaca ggattagcag agcgaggtat   4020
gtaggcggtg ctacagagtt cttgaagtgg tggcctaact acggctacac tagaagaaca   4080
gtatttggta tctgcgctct gctgaagcca gttaccttcg gaaaaagagt tggtagctct   4140
tgatccggca aacaaaccac cgctggtagc ggtggttttt ttgtttgcaa gcagcagatt   4200
acgcgcagaa aaaaaggatc tcaagaagat cctttgatct tttctacggg gtctgacgct   4260
cagtggaacg aaaactcacg ttaagggatt ttggtcatga gattatcaaa aaggatcttc   4320
acctagatcc ttttaaatta aaaatgaagt tttaaatcaa tctaaagtat atatgagtaa   4380
acttggtctg acagttacca atgcttaatc agtgaggcac ctatctcagc gatctgtcta   4440
tttcgttcat ccatagttgc ctgactc                                       4467
```

<210> SEQ ID NO 26
<211> LENGTH: 7563
<212> TYPE: DNA
<213> ORGANISM: Artificial
<220> FEATURE:
<223> OTHER INFORMATION: Synthetic Construct

<400> SEQUENCE: 26

```
gaattctgca ttaatgaatc ggccaacgcg cggggagagg cggtttgcgt attgggcgct     60
cttccgcttc ctcgctcact gactcgctgc gctcggtcgt tcggctgcgg cgagcggtat    120
cagctcactc aaaggcggta atacggttat ccacagaatc aggggataac gcaggaaaga    180
acatgtgagc aaaaggccag caaaaggcca ggaaccgtaa aaaggccgcg ttgctggcgt    240
ttttccatag gctccgcccc cctgacgagc atcacaaaaa tcgacgctca agtcagaggt    300
ggcgaaaccc gacaggacta taaagatacc aggcgtttcc ccctggaagc tccctcgtgc    360
gctctcctgt tccgaccctg ccgcttaccg gatacctgtc cgcctttctc ccttcgggaa    420
gcgtggcgct ttctcatagc tcacgctgta ggtatctcag ttcggtgtag gtcgttcgct    480
ccaagctggg ctgtgtgcac gaacccccg ttcagcccga ccgctgcgcc ttatccggta     540
actatcgtct tgagtccaac ccggtaagac acgacttatc gccactggca gcagccactg    600
gtaacaggat tagcagagcg aggtatgtag gcggtgctac agagttcttg aagtggtggc    660
ctaactacgg ctacactaga agaacagtat ttggtatctg cgctctgctg aagccagtta    720
ccttcggaaa aagagttggt agctcttgat ccggcaaaca aaccaccgct ggtagcggtg    780
gttttttgt ttgcaagcag cagattacgc gcagaaaaaa aggatctcaa gaagatcctt     840
```

```
tgatcttttc tacggggtct gacgctcagt ggaacgaaaa ctcacgttaa gggattttgg    900
tcatgagatt atcaaaaagg atcttcacct agatcctttt aaattaaaaa tgaagtttta    960
aatcaatcta aagtatatat gagtaaactt ggtctgacag ttaccaatgc ttaatcagtg   1020
aggcacctat ctcagcgatc tgtctatttc gttcatccat agttgcctga ctcggcgtaa   1080
tgctctgcca gtgttacaac caattaacca attctgatta gaaaaactca tcgagcatca   1140
aatgaaactg caatttattc atatcaggat tatcaatacc atatttttga aaaagccgtt   1200
tctgtaatga aggagaaaac tcaccgaggc agttccatag gatggcaaga tcctggtatc   1260
ggtctgcgat tccgactcgt ccaacatcaa tacaacctat taatttcccc tcgtcaaaaa   1320
taaggttatc aagtgagaaa tcaccatgag tgacgactga atccggtgag aatggcaaaa   1380
gcttatgcat ttctttccag acttgttcaa caggccagcc attacgctcg tcatcaaaat   1440
cactcgcatc aaccaaaccg ttattcattc gtgattgcgc ctgagcgaga cgaaatacgc   1500
gatcgctgtt aaaaggacaa ttacaaacag gaatcaaatg caaccggcgc aggaacactg   1560
ccagcgcatc aacaatattt tcacctgaat caggatattc ttctaatacc tggaatgctg   1620
ttttcccggg gatcgcagtg gtgagtaacc atgcatcatc aggagtacgg ataaaatgct   1680
tgatggtcgg aagaggcata aattccgtca gccagtttag tctgaccatc tcatctgtaa   1740
catcattggc aacgctacct ttgccatgtt tcagaaacaa ctctggcgca tcgggcttcc   1800
catacaatcg atagattgtc gcacctgatt gcccgacatt atcgcgagcc catttatacc   1860
catataaatc agcatccatg ttggaattta atcgcggcct cgagcaagac gtttcccgtt   1920
gaatatggct cataacaccc cttgtattac tgtttatgta agcagacagg gtaccaatct   1980
tccgagtgag agacacaaaa aattccaaca cactattgca atgaaaataa atttccttta   2040
ttagccagaa gtcagatgct caaggggctt catgatgtcc ccataatttt tggcagaggg   2100
aaaaagatca tacgtagatc gaaacgatgt atatttccgc gagaggacga cagaattgtc   2160
agttcctatg agctttgctc cagaccggct gcgagcaaaa caagcggcta ggagttccgc   2220
agtatggatc ggcagaggag ccacaaaggt tccacgcatg cgctgatggc ctatggccaa   2280
gccccagcca gtgggggttg cgtcagcaaa cacttggcac agaccaggcc gttgccgagc   2340
aacggggtaa aggttcatgt actgtttact tagaaaggcc ttgtaagttg gcgagaaagt   2400
gaaagcctgt ttagcttgta tacatgcata caaaggcatt aaggcaggat atccacattg   2460
tgtaaatgga gcagcaaagc ccaaaagacc cacaatcctt tgacatactt tccaatcaat   2520
aggcctgttt acaggaagtt ttctaaaaca gtgtttgatc ttttgtacaa tatgatcttg   2580
tggcaatgtc ccccaacttc caattacgta acccatgaag tttagggaat aaccccatct   2640
ttttgttttg ttagggccca gatctttagg ctacttcact caaagtctct gcagctgcct   2700
gcactgtgaa ggctgcaaca taaatctgtc tcttcacttc tccccaggcc ttggaagggt   2760
ccactttgct ttcaatatca aacagagcat cataaattcc tgggaatgac tcccctgcat   2820
acttgttgtg gctgcttgga gcatagatga catgcctata aaaaggcctg tctggtaacc   2880
ctaatggatc aataaatgct ctttccagaa acatgagttg atcattcatc attcttaata   2940
ctattgggtt gcttttgtca aagtcctgga gtctctcact gaacttggaa gcaatttctg   3000
taaaattctt tactgcagaa aaaagtgaat caaatgatac actgtatgtc ttcatttcct   3060
gtggatgttt catagaaata ctgtagattt tgtcagcata ctttcttaaa actacagcat   3120
aatctcgaca atcaaaaggg agcactatgg aattggccag ctcaaacacc atccctcctc   3180
gaacctgggc cacagtgagg tgatatttaa acattggatc ataaaacttt tccaccaact   3240
```

```
catatgtttc atagacactg tgatacagtg gatagccgct gaatttgttt gtttcccaat   3300
ttttagtata ccgtgctctg cctgaagcaa ttccaagtcg ttggaagaac acctcaaaat   3360
catttccaga tcccaatttg cttatcctgg gcatgccact gaactctggg gaaggacttt   3420
ttttagtcca actttcataa agagatttgc cttcaaagcc ttcatcaggg cttttcagct   3480
cttttgttag gttgtgtacc aagctgtaca tcagcggtgt acaatcaact ctcagagtgt   3540
agtttccttc tatagatgag tcagcattaa tataagccac gccacgctct tgaaggagtc   3600
ttgaattctc ctctgcccac tcagtagaac caagaagacc aaattcttct gcatcccagc   3660
ttgcaaacaa aattgttctt ctaggtctcc acccttcctt tttcagtgtt ccaaagctcc   3720
tcacaatttc atgaacaaca gctgctccac tctgagggtc aataccacca aacacccatg   3780
agtcccggtg acctcccaga atgacatatc tgtctggttc cactgctcct ctgagagtac   3840
ctatcacatt gtaaattctt gtcacttcat tggtagagtg gatgtgcatc ttgacttttt   3900
gtgtagaaaa gtttccagta aagccaggtc caacattgta gggcactttg agacttcctc   3960
tccagctgct atctggtggt gctgagccac ccatttttc taggagcttc tgtgcatcat   4020
agtatccaat tggatgaaca ggaatacttg gaagaccaac agcctctgca attccacgcc   4080
tataagcata ttcatttgct gggtaacctg gtgtgagagg gtctcctgca ccattcagat   4140
ttaggatatt tccacgctgg acaccacctc caggaagatt ccaaccatct ggataggact   4200
tcaccccagg agcaaagtag tcagcagggt cggagtagag aatgactcct ttggcccctg   4260
ccagctgggc atttttaacc ttatttcctc tgaaaacttt cccatatctg gcaattacaa   4320
ttttcccaga gcaattgatt ttcatgtccc gttccaattt aaagaagtct tcagttcgtg   4380
catagttaac atacactaga tcgccctctg gcattccttg aggagagaaa gcactgaaag   4440
gtggtacaat atccgaaaca ttttcatatc ctggaggagg tggttcaaat aatgatgtgt   4500
tgaaaatctc atttccatct tcattaatta ttgagatgta gttgggatga gtcttatttg   4560
ggtaggacaa caggacatca taatgtgcca gctcaacaga atccaggcca aattctttcc   4620
actgggattg aatttgcttt gcaagctgaa agttttgttc tgttcctgct aaatgtggta   4680
tctgtgtaaa attatataag aacttcttga tgttctcagc tttcaattca tccaaaaatg   4740
ctttcatatt atgctttgga gtaatgttag tagcttcatt ggaggatttt ataaaccacc   4800
cgaagaggaa gccgaggaga aagaagccac ccgccagcac cagcgcccca gcgcacagcc   4860
agcgcgggcg gcgcgcgcta gccatgttcg tcacagggtc cccagtcctc gcggagattg   4920
acgagatgtg agaggcaata ttcggagcag ggtttactgt tcctgaactg gagccaccag   4980
caggaaaata cagacccctg actctgggat cctgacctgg aagatagtca gggttgaggc   5040
aagcaaaagg tacatgtaag agaagagccc acagcgtccc tcaaatccct ggagtcttga   5100
ctggggaagc caggcccacc ctggagagta catacctgct tgctgagatc cggacggtga   5160
gtcactcttg gcacggggaa tccgcgttcc aatgcaccgt tcccggccgc ggaggctgga   5220
tcggtcccgg tgtcttctat ggaggtcaaa acagcgtgga tggcgtctcc aggcgatctg   5280
acggttcact aaacgagctc tgcttatata gacctcccac cgtacacgcc taccgcccat   5340
ttgcgtcaac ggggcggggt tattacgaca ttttggaaag tcccgttgat tttggtgctc   5400
gacctgcagg gtaccaatat tggctattgg ccattgcata cgttgtatct atatcataat   5460
atgtacattt atattggctc atgtccaata tgaccgccat gttgacattg attattgact   5520
agttattaat agtaatcaat tacggggtca ttagttcata gcccatatat ggagttccgc   5580
```

gttacataac ttacggtaaa tggcccgcct ggctgaccgc ccaacgaccc ccgcccattg 5640
acgtcaataa tgacgtatgt tcccatagta acgccaatag ggactttcca ttgacgtcaa 5700
tgggtggagt atttacggta aactgcccac ttggcagtac atcaagtgta tcatatgcca 5760
agtccgcccc ctattgacgt caatgacggt aaatggcccg cctggcatta tgcccagtac 5820
atgaccttac gggactttcc tacttggcag tacatctacg tattagtcat cgctattacc 5880
atggtgatgc ggttttggca gtacaccaat gggcgtggat agcggtttga ctcacgggga 5940
tttccaagtc tccaccccat tgacgtcaat gggagtttgt tttggcacca aaatcaacgg 6000
gactttccaa aatgtcgtaa taaccccgcc ccgttgacgc aaatgggcgg taggcgtgta 6060
cggtgggagg tctatataag cagagctcgt ttagtgaacc gtcagatcgc ctggagacgc 6120
catccacgct gttttgacct ccatagaaga caccgggacc gatccagcct ccgcggccgg 6180
gaacggtgca ttggaacgcg gattccccgt gccaagagtg actcaccgtc cggatctcag 6240
caagcaggta tgtactctcc agggtgggcc tggcttcccc agtcaagact ccagggattt 6300
gagggacgct gtgggctctt ctcttacatg taccttttgc ttgcctcaac cctgactatc 6360
ttccaggtca ggatcccaga gtcaggggtc tgtattttcc tgctggtggc tccagttcag 6420
gaacagtaaa ccctgctccg aatattgcct ctcacatctc gtcaatctcc gcgaggactg 6480
gggaccctgt gacgaacatg gctagcaagg ctgtgctgct tgccctgttg atggcaggct 6540
tggccctgca gccaggcact gccctgctgt gctactcctg caaagcccag gtgagcaacg 6600
aggactgcct gcaggtggag aactgcaccc agctggggga gcagtgctgg accgcgcgca 6660
tccgcgcagt tggcctcctg accgtcatca gcaaaggctg cagcttgaac tgcgtggatg 6720
actcacagga ctactacgtg ggcaagaaga acatcacgtg ctgtgacacc gacttgtgca 6780
acgccagcgg ggcccatgcc ctgcagccgg ctgccgccat ccttgcgctg ctccctgcac 6840
tcggcctgct gctctgggga cccggccagc tatagagatc tgggccctaa caaaacaaaa 6900
agatggggtt attccctaaa cttcatgggt tacgtaattg gaagttgggg gacattgcca 6960
caagatcata ttgtacaaaa gatcaaacac tgttttagaa aacttcctgt aaacaggcct 7020
attgattgga aagtatgtca aaggattgtg ggtcttttgg gctttgctgc tccatttaca 7080
caatgtggat atcctgcctt aatgcctttg tatgcatgta tacaagctaa acaggctttc 7140
actttctcgc caacttacaa ggcctttcta agtaaacagt acatgaacct ttaccccgtt 7200
gctcggcaac ggcctggtct gtgccaagtg tttgctgacg caacccccac tggctggggc 7260
ttggccatag gccatcagcg catgcgtgga acctttgtgg ctcctctgcc gatccatact 7320
gcggaactcc tagccgcttg ttttgctcgc agccggtctg gagcaaagct cataggaact 7380
gacaattctg tcgtcctctc gcggaaatat acatcgtttc gatctacgta tgatcttttt 7440
ccctctgcca aaaattatgg ggacatcatg aagccccttg agcatctgac ttctggctaa 7500
taaaggaaat ttattttcat tgcaatagtg tgttggaatt ttttgtgtct ctcactcgga 7560
agc 7563

<210> SEQ ID NO 27
<211> LENGTH: 6396
<212> TYPE: DNA
<213> ORGANISM: Artificial
<220> FEATURE:
<223> OTHER INFORMATION: Synthetic Construct

<400> SEQUENCE: 27
ggcgtaatgc tctgccagtg ttacaaccaa ttaaccaatt ctgattagaa aaactcatcg 60
agcatcaaat gaaactgcaa tttattcata tcaggattat caataccata tttttgaaaa 120
agccgtttct gtaatgaagg agaaaactca ccgaggcagt tccataggat ggcaagatcc 180
tggtatcggt ctgcgattcc gactcgtcca acatcaatac aacctattaa tttcccctcg 240
tcaaaaataa ggttatcaag tgagaaatca ccatgagtga cgactgaatc cggtgagaat 300
ggcaaaagct tatgcatttc tttccagact tgttcaacag gccagccatt acgctcgtca 360
tcaaaatcac tcgcatcaac caaaccgtta ttcattcgtg attgcgcctg agcgagacga 420
aatacgcgat cgctgttaaa aggacaatta caaacaggaa tcaaatgcaa ccggcgcagg 480
aacactgcca gcgcatcaac aatattttca cctgaatcag gatattcttc taatacctgg 540
aatgctgttt tcccggggat cgcagtggtg agtaaccatg catcatcagg agtacggata 600
aaatgcttga tggtcggaag aggcataaat tccgtcagcc agtttagtct gaccatctca 660
tctgtaacat cattggcaac gctacctttg ccatgtttca gaaacaactc tggcgcatcg 720
ggcttcccat acaatcgata gattgtcgca cctgattgcc cgacattatc gcgagcccat 780
ttatacccat ataaatcagc atccatgttg gaatttaatc gcggcctcga gcaagacgtt 840
tcccgttgaa tatggctcat aacacccctt gtattactgt ttatgtaagc agacaggtcg 900
acaatattgg ctattggcca ttgcatacgt tgtatctata tcataatatg tacatttata 960
ttggctcatg tccaatatga ccgccatgtt gacattgatt attgactagt tattaatagt 1020
aatcaattac ggggtcatta gttcatagcc catatatgga gttccgcgtt acataactta 1080
cggtaaatgg cccgcctggc tgaccgccca acgacccccg cccattgacg tcaataatga 1140
cgtatgttcc catagtaacg ccaataggga ctttccattg acgtcaatgg gtggagtatt 1200
tacggtaaac tgcccacttg gcagtacatc aagtgtatca tatgccaagt ccgcccccta 1260
ttgacgtcaa tgacggtaaa tggcccgcct ggcattatgc ccagtacatg accttacggg 1320
actttcctac ttggcagtac atctacgtat tagtcatcgc tattaccatg gtgatgcggt 1380
tttggcagta caccaatggg cgtggatagc ggtttgactc acggggattt ccaagtctcc 1440
accccattga cgtcaatggg agtttgtttt ggcaccaaaa tcaacgggac tttccaaaat 1500
gtcgtaataa ccccgccccg ttgacgcaaa tgggcggtag gcgtgtacgg tgggaggtct 1560
atataagcag agctcgttta gtgaaccgtc agatcgcctg gagacgccat ccacgctgtt 1620
ttgacctcca tagaagacac cgggaccgat ccagcctccg cggccgggaa cggtgcattg 1680
gaacgcggat tccccgtgcc aagagtgact caccgtccgg atctcagcaa gcaggtatgt 1740
actctccagg gtgggcctgg cttccccagt caagactcca gggatttgag ggacgctgtg 1800
ggctcttctc ttacatgtac cttttgcttg cctcaaccct gactatcttc caggtcagga 1860
tcccagagtc aggggtctgt attttcctgc tggtggctcc agttcaggaa cagtaaaccc 1920
tgctccgaat attgcctctc acatctcgtc aatctccgcg aggactgggg accctgtgac 1980
gaacatggct agcgcgcgcc gcccgcgctg gctgtgcgct ggggcgctgg tgctggcggg 2040
tggcttcttt ctcctcggct tcctcttcgg gtggtttata aaatcctcca atgaagctac 2100
taacattact ccaaagcata atatgaaagc atttttggat gaattgaaag ctgagaacat 2160
caagaagttc ttatataatt ttacacagat accacattta gcaggaacag aacaaaactt 2220
tcagcttgca aagcaaattc aatcccagtg gaaagaattt ggcctggatt ctgttgagct 2280
ggcacattat gatgtcctgt tgtcctaccc aaataagact catcccaact acatctcaat 2340
aattaatgaa gatggaaatg agattttcaa cacatcatta tttgaaccac ctcctccagg 2400

-continued

```
atatgaaaat gtttcggata ttgtaccacc tttcagtgct ttctctcctc aaggaatgcc   2460
agagggcgat ctagtgtatg ttaactatgc acgaactgaa gacttcttta aattggaacg   2520
ggacatgaaa atcaattgct ctgggaaaat tgtaattgcc agatatggga aagttttcag   2580
aggaaataag gttaaaaatg cccagctggc aggggccaaa ggagtcattc tctactccga   2640
ccctgctgac tactttgctc ctggggtgaa gtcctatcca gatggttgga atcttcctgg   2700
aggtggtgtc cagcgtggaa atatcctaaa tctgaatggt gcaggagacc ctctcacacc   2760
aggttaccca gcaaatgaat atgcttatag gcgtggaatt gcagaggctg ttggtcttcc   2820
aagtattcct gttcatccaa ttggatacta tgatgcacag aagctcctag aaaaaatggg   2880
tggctcagca ccaccagata gcagctggag aggaagtctc aaagtgccct acaatgttgg   2940
acctggcttt actggaaact tttctacaca aaaagtcaag atgcacatcc actctaccaa   3000
tgaagtgaca agaatttaca atgtgatagg tactctcaga ggagcagtgg aaccagacag   3060
atatgtcatt ctgggaggtc accgggactc atgggtgttt ggtggtattg accctcagag   3120
tggagcagct gttgttcatg aaattgtgag gagctttgga acactgaaaa aggaagggtg   3180
gagacctaga agaacaattt tgtttgcaag ctgggatgca gaagaatttg gtcttcttgg   3240
ttctactgag tgggcagagg agaattcaag actccttcaa gagcgtggcg tggcttatat   3300
taatgctgac tcatctatag aaggaaacta cactctgaga gttgattgta caccgctgat   3360
gtacagcttg gtacacaacc taacaaaaga gctgaaaagc cctgatgaag gctttgaagg   3420
caaatctctt tatgaaagtt ggactaaaaa aagtccttcc ccagagttca gtggcatgcc   3480
caggataagc aaattgggat ctggaaatga ttttgaggtg ttcttccaac gacttggaat   3540
tgcttcaggc agagcacggt atactaaaaa ttgggaaaca aacaaattca gcggctatcc   3600
actgtatcac agtgtctatg aaacatatga gttggtggaa aagttttatg atccaatgtt   3660
taaatatcac ctcactgtgg cccaggttcg aggagggatg gtgtttgagc tggccaattc   3720
catagtgctc ccttttgatt gtcgagatta tgctgtagtt ttaagaaagt atgctgacaa   3780
aatctacagt atttctatga aacatccaca ggaaatgaag acatacagtg tatcatttga   3840
ttcacttttt tctgcagtaa agaattttac agaaattgct tccaagttca gtgagagact   3900
ccaggacttt gacaaaagca acccaatagt attaagaatg atgaatgatc aactcatgtt   3960
tctggaaaga gcatttattg atccattagg gttaccagac aggccttttt ataggcatgt   4020
catctatgct ccaagcagcc acaacaagta tgcagggggag tcattcccag gaatttatga   4080
tgctctgttt gatattgaaa gcaaagtgga cccttccaag gcctggggag aagtgaagag   4140
acagatttat gttgcagcct tcacagtgca ggcagctgca gagactttga gtgaagtagc   4200
cggatccgaa ggtaggggtt cattattgac ctgtggagat gtcgaagaaa acccaggacc   4260
cgcaagcaag gctgtgctgc ttgccctgtt gatggcaggc ttggccctgc agccaggcac   4320
tgccctgctg tgctactcct gcaaagccca ggtgagcaac gaggactgcc tgcaggtgga   4380
gaactgcacc cagctggggg agcagtgctg gaccgcgcgc atccgcgcag ttggcctcct   4440
gaccgtcatc agcaaaggct gcagcttgaa ctgcgtggat gactcacagg actactacgt   4500
gggcaagaag aacatcacgt gctgtgacac cgacttgtgc aacgccagcg gggcccatgc   4560
cctgcagccg gctgccgcca tccttgcgct gctccctgca ctcggcctgc tgctctgggg   4620
acccggccag ctatagagat ctgggcccta acaaaacaaa aagatggggt tattccctaa   4680
acttcatggg ttacgtaatt ggaagttggg ggacattgcc acaagatcat attgtacaaa   4740
agatcaaaca ctgttttaga aaacttcctg taaacaggcc tattgattgg aaagtatgtc   4800
```

aaaggattgt gggtcttttg ggctttgctg ctccatttac acaatgtgga tatcctgcct 4860
taatgccttt gtatgcatgt atacaagcta aacaggcttt cactttctcg ccaacttaca 4920
aggcctttct aagtaaacag tacatgaacc tttaccccgt tgctcggcaa cggcctggtc 4980
tgtgccaagt gtttgctgac gcaaccccca ctggctgggg cttggccata ggccatcagc 5040
gcatgcgtgg aacctttgtg gctcctctgc cgatccatac tgcggaactc ctagccgctt 5100
gttttgctcg cagccggtct ggagcaaagc tcataggaac tgacaattct gtcgtcctct 5160
cgcggaaata tacatcgttt cgatctacgt atgatctttt tccctctgcc aaaaattatg 5220
gggacatcat gaagcccctt gagcatctga cttctggcta ataaaggaaa tttattttca 5280
ttgcaatagt gtgttggaat tttttgtgtc tctcactcgg aaggaattct gcattaatga 5340
atcggccaac gcgcggggag aggcggtttg cgtattgggc gctcttccgc ttcctcgctc 5400
actgactcgc tgcgctcggt cgttcggctg cggcgagcgg tatcagctca ctcaaaggcg 5460
gtaatacggt tatccacaga atcaggggat aacgcaggaa agaacatgtg agcaaaaggc 5520
cagcaaaagg ccaggaaccg taaaaaggcc gcgttgctgg cgtttttcca taggctccgc 5580
ccccctgacg agcatcacaa aaatcgacgc tcaagtcaga ggtggcgaaa cccgacagga 5640
ctataaagat accaggcgtt tccccctgga agctccctcg tgcgctctcc tgttccgacc 5700
ctgccgctta ccggatacct gtccgccttt ctcccttcgg gaagcgtggc gctttctcat 5760
agctcacgct gtaggtatct cagttcggtg taggtcgttc gctccaagct gggctgtgtg 5820
cacgaacccc ccgttcagcc cgaccgctgc gccttatccg gtaactatcg tcttgagtcc 5880
aacccggtaa gacacgactt atcgccactg gcagcagcca ctggtaacag gattagcaga 5940
gcgaggtatg taggcggtgc tacagagttc ttgaagtggt ggcctaacta cggctacact 6000
agaagaacag tatttggtat ctgcgctctg ctgaagccag ttaccttcgg aaaaagagtt 6060
ggtagctctt gatccggcaa acaaaccacc gctggtagcg gtggtttttt tgtttgcaag 6120
cagcagatta cgcgcagaaa aaaaggatct caagaagatc ctttgatctt ttctacgggg 6180
tctgacgctc agtggaacga aaactcacgt taagggattt tggtcatgag attatcaaaa 6240
aggatcttca cctagatcct tttaaattaa aaatgaagtt ttaaatcaat ctaaagtata 6300
tatgagtaaa cttggtctga cagttaccaa tgcttaatca gtgaggcacc tatctcagcg 6360
atctgtctat ttcgttcatc catagttgcc tgactc 6396

<210> SEQ ID NO 28
<211> LENGTH: 6405
<212> TYPE: DNA
<213> ORGANISM: Artificial
<220> FEATURE:
<223> OTHER INFORMATION: Synthetic Construct

<400> SEQUENCE: 28
ggcgtaatgc tctgccagtg ttacaaccaa ttaaccaatt ctgattagaa aaactcatcg 60
agcatcaaat gaaactgcaa tttattcata tcaggattat caataccata tttttgaaaa 120
agccgtttct gtaatgaagg agaaaactca ccgaggcagt tccataggat ggcaagatcc 180
tggtatcggt ctgcgattcc gactcgtcca acatcaatac aacctattaa tttcccctcg 240
tcaaaaataa ggttatcaag tgagaaatca ccatgagtga cgactgaatc cggtgagaat 300
ggcaaaagct tatgcatttc tttccagact tgttcaacag gccagccatt acgctcgtca 360
tcaaaatcac tcgcatcaac caaaccgtta ttcattcgtg attgcgcctg agcgagacga 420

-continued

```
aatacgcgat cgctgttaaa aggacaatta caaacaggaa tcaaatgcaa ccggcgcagg    480
aacactgcca gcgcatcaac aatattttca cctgaatcag gatattcttc taatacctgg    540
aatgctgttt tcccggggat cgcagtggtg agtaaccatg catcatcagg agtacggata    600
aaatgcttga tggtcggaag aggcataaat tccgtcagcc agtttagtct gaccatctca    660
tctgtaacat cattggcaac gctacctttg ccatgtttca gaaacaactc tggcgcatcg    720
ggcttcccat acaatcgata gattgtcgca cctgattgcc cgacattatc gcgagcccat    780
ttatacccat ataaatcagc atccatgttg gaatttaatc gcggcctcga gcaagacgtt    840
tcccgttgaa tatggctcat aacacccctt gtattactgt ttatgtaagc agacaggtcg    900
acaatattgg ctattggcca ttgcatacgt tgtatctata tcataatatg tacatttata    960
ttggctcatg tccaatatga ccgccatgtt gacattgatt attgactagt tattaatagt   1020
aatcaattac ggggtcatta gttcatagcc catatatgga gttccgcgtt acataactta   1080
cggtaaatgg cccgcctggc tgaccgccca acgacccccg cccattgacg tcaataatga   1140
cgtatgttcc catagtaacg ccaataggga ctttccattg acgtcaatgg gtggagtatt   1200
tacggtaaac tgcccacttg gcagtacatc aagtgtatca tatgccaagt ccgcccccta   1260
ttgacgtcaa tgacggtaaa tggcccgcct ggcattatgc ccagtacatg accttacggg   1320
actttcctac ttggcagtac atctacgtat tagtcatcgc tattaccatg gtgatgcggt   1380
tttggcagta caccaatggg cgtggatagc ggtttgactc acggggattt ccaagtctcc   1440
accccattga cgtcaatggg agtttgtttt ggcaccaaaa tcaacgggac tttccaaaat   1500
gtcgtaataa ccccgccccg ttgacgcaaa tgggcggtag gcgtgtacgg tgggaggtct   1560
atataagcag agctcgttta gtgaaccgtc agatcgcctg gagacgccat ccacgctgtt   1620
ttgacctcca tagaagacac cgggaccgat ccagcctccg cggccgggaa cggtgcattg   1680
gaacgcggat tccccgtgcc aagagtgact caccgtccgg atctcagcaa gcaggtatgt   1740
actctccagg gtgggcctgg cttccccagt caagactcca gggatttgag ggacgctgtg   1800
ggctcttctc ttacatgtac cttttgcttg cctcaaccct gactatcttc caggtcagga   1860
tcccagagtc aggggtctgt attttcctgc tggtggctcc agttcaggaa cagtaaaccc   1920
tgctccgaat attgcctctc acatctcgtc aatctccgcg aggactgggg accctgtgac   1980
gaacatggct agcaaggctg tgctgcttgc cctgttgatg gcaggcttgg ccctgcagcc   2040
aggcactgcc ctgctgtgct actcctgcaa agcccaggtg agcaacgagg actgcctgca   2100
ggtggagaac tgcacccagc tgggggagca gtgctggacc gcgcgcatcc gcgcagttgg   2160
cctcctgacc gtcatcagca aaggctgcag cttgaactgc gtggatgact cacaggacta   2220
ctacgtgggc aagaagaaca tcacgtgctg tgacaccgac ttgtgcaacg ccagcggggc   2280
ccatgccctg cagccggctg ccgccatcct tgcgctgctc cctgcactcg gcctgctgct   2340
ctggggaccc ggccagctag gatcccagac cctgaacttt gatctgctga aactggcagg   2400
cgatgtggaa agcaacccag gcccaatggc aagcgcgcgc cgcccgcgct ggctgtgcgc   2460
tggggcgctg gtgctggcgg gtggcttctt tctcctcggc ttcctcttcg ggtggtttat   2520
aaaatcctcc aatgaagcta ctaacattac tccaaagcat aatatgaaag catttttgga   2580
tgaattgaaa gctgagaaca tcaagaagtt cttatataat tttacacaga taccacattt   2640
agcaggaaca gaacaaaact ttcagcttgc aaagcaaatt caatcccagt ggaaagaatt   2700
tggcctggat tctgttgagc tggcacatta tgatgtcctg ttgtcctacc caaataagac   2760
tcatcccaac tacatctcaa taattaatga agatggaaat gagattttca acacatcatt   2820
```

-continued

```
atttgaacca cctcctccag gatatgaaaa tgtttcggat attgtaccac ctttcagtgc   2880
tttctctcct caaggaatgc cagagggcga tctagtgtat gttaactatg cacgaactga   2940
agacttcttt aaattggaac gggacatgaa aatcaattgc tctgggaaaa ttgtaattgc   3000
cagatatggg aaagttttca gaggaaataa ggttaaaaat gcccagctgg caggggccaa   3060
aggagtcatt ctctactccg accctgctga ctactttgct cctggggtga agtcctatcc   3120
agatggttgg aatcttcctg gaggtggtgt ccagcgtgga aatatcctaa atctgaatgg   3180
tgcaggagac cctctcacac caggttaccc agcaaatgaa tatgcttata ggcgtggaat   3240
tgcagaggct gttggtcttc caagtattcc tgttcatcca attggatact atgatgcaca   3300
gaagctccta gaaaaaatgg gtggctcagc accaccagat agcagctgga gaggaagtct   3360
caaagtgccc tacaatgttg gacctggctt tactggaaac ttttctacac aaaaagtcaa   3420
gatgcacatc cactctacca atgaagtgac aagaatttac aatgtgatag gtactctcag   3480
aggagcagtg gaaccagaca gatatgtcat tctgggaggt caccgggact catgggtgtt   3540
tggtggtatt gaccctcaga gtggagcagc tgttgttcat gaaattgtga ggagctttgg   3600
aacactgaaa aaggaagggt ggagacctag aagaacaatt ttgtttgcaa gctgggatgc   3660
agaagaattt ggtcttcttg gttctactga gtgggcagag gagaattcaa gactccttca   3720
agagcgtggc gtggcttata ttaatgctga ctcatctata gaaggaaact acactctgag   3780
agttgattgt acaccgctga tgtacagctt ggtacacaac ctaacaaaag agctgaaaag   3840
ccctgatgaa ggctttgaag gcaaatctct ttatgaaagt tggactaaaa aaagtccttc   3900
cccagagttc agtggcatgc ccaggataag caaattggga tctggaaatg attttgaggt   3960
gttcttccaa cgacttggaa ttgcttcagg cagagcacgg tatactaaaa attgggaaac   4020
aaacaaattc agcggctatc cactgtatca cagtgtctat gaaacatatg agttggtgga   4080
aaagttttat gatccaatgt ttaaatatca cctcactgtg gcccaggttc gaggagggat   4140
ggtgtttgag ctggccaatt ccatagtgct cccttttgat tgtcgagatt atgctgtagt   4200
tttaagaaag tatgctgaca aaatctacag tatttctatg aaacatccac aggaaatgaa   4260
gacatacagt gtatcatttg attcactttt ttctgcagta aagaatttta cagaaattgc   4320
ttccaagttc agtgagagac tccaggactt tgacaaaagc aacccaatag tattaagaat   4380
gatgaatgat caactcatgt ttctggaaag agcatttatt gatccattag ggttaccaga   4440
caggcctttt tataggcatg tcatctatgc tccaagcagc cacaacaagt atgcagggga   4500
gtcattccca ggaatttatg atgctctgtt tgatattgaa agcaaagtgg acccttccaa   4560
ggcctgggga gaagtgaaga gacagattta tgttgcagcc ttcacagtgc aggcagctgc   4620
agagactttg agtgaagtag cctaaagatc tgggccctaa caaaacaaaa agatggggtt   4680
attccctaaa cttcatgggt tacgtaattg gaagttgggg gacattgcca caagatcata   4740
ttgtacaaaa gatcaaacac tgttttagaa aacttcctgt aaacaggcct attgattgga   4800
aagtatgtca aaggattgtg ggtcttttgg gctttgctgc tccatttaca caatgtggat   4860
atcctgcctt aatgcctttg tatgcatgta tacaagctaa acaggctttc actttctcgc   4920
caacttacaa ggcctttcta agtaaacagt acatgaacct ttaccccgtt gctcggcaac   4980
ggcctggtct gtgccaagtg tttgctgacg caacccccac tggctggggc ttggccatag   5040
gccatcagcg catgcgtgga acctttgtgg ctcctctgcc gatccatact gcggaactcc   5100
tagccgcttg ttttgctcgc agccggtctg gagcaaagct cataggaact gacaattctg   5160
```

tcgtcctctc gcggaaatat acatcgtttc gatctacgta tgatcttttt ccctctgcca 5220
aaaattatgg ggacatcatg aagccccttg agcatctgac ttctggctaa taaaggaaat 5280
ttattttcat tgcaatagtg tgttggaatt ttttgtgtct ctcactcgga aggaattctg 5340
cattaatgaa tcggccaacg cgcggggaga ggcggtttgc gtattgggcg ctcttccgct 5400
tcctcgctca ctgactcgct gcgctcggtc gttcggctgc ggcgagcggt atcagctcac 5460
tcaaaggcgg taatacggtt atccacagaa tcaggggata acgcaggaaa gaacatgtga 5520
gcaaaaggcc agcaaaaggc caggaaccgt aaaaaggccg cgttgctggc gtttttccat 5580
aggctccgcc cccctgacga gcatcacaaa aatcgacgct caagtcagag gtggcgaaac 5640
ccgacaggac tataaagata ccaggcgttt ccccctggaa gctccctcgt gcgctctcct 5700
gttccgaccc tgccgcttac cggatacctg tccgcctttc tcccttcggg aagcgtggcg 5760
ctttctcata gctcacgctg taggtatctc agttcggtgt aggtcgttcg ctccaagctg 5820
ggctgtgtgc acgaaccccc cgttcagccc gaccgctgcg ccttatccgg taactatcgt 5880
cttgagtcca acccggtaag acacgactta tcgccactgg cagcagccac tggtaacagg 5940
attagcagag cgaggtatgt aggcggtgct acagagttct tgaagtggtg gcctaactac 6000
ggctacacta gaagaacagt atttggtatc tgcgctctgc tgaagccagt taccttcgga 6060
aaaagagttg gtagctcttg atccggcaaa caaaccaccg ctggtagcgg tggttttttt 6120
gtttgcaagc agcagattac gcgcagaaaa aaaggatctc aagaagatcc tttgatcttt 6180
tctacggggt ctgacgctca gtggaacgaa aactcacgtt aagggatttt ggtcatgaga 6240
ttatcaaaaa ggatcttcac ctagatcctt ttaaattaaa aatgaagttt taaatcaatc 6300
taaagtatat atgagtaaac ttggtctgac agttaccaat gcttaatcag tgaggcacct 6360
atctcagcga tctgtctatt tcgttcatcc atagttgcct gactc 6405

<210> SEQ ID NO 29
<211> LENGTH: 6750
<212> TYPE: DNA
<213> ORGANISM: Artificial
<220> FEATURE:
<223> OTHER INFORMATION: Synthetic Construct

<400> SEQUENCE: 29
ggcgtaatgc tctgccagtg ttacaaccaa ttaaccaatt ctgattagaa aaactcatcg 60
agcatcaaat gaaactgcaa tttattcata tcaggattat caataccata tttttgaaaa 120
agccgtttct gtaatgaagg agaaaactca ccgaggcagt tccataggat ggcaagatcc 180
tggtatcggt ctgcgattcc gactcgtcca acatcaatac aacctattaa tttcccctcg 240
tcaaaaataa ggttatcaag tgagaaatca ccatgagtga cgactgaatc cggtgagaat 300
ggcaaaagct tatgcatttc tttccagact tgttcaacag gccagccatt acgctcgtca 360
tcaaaatcac tcgcatcaac caaaccgtta ttcattcgtg attgcgcctg agcgagacga 420
aatacgcgat cgctgttaaa aggacaatta caaacaggaa tcaaatgcaa ccggcgcagg 480
aacactgcca gcgcatcaac aatattttca cctgaatcag gatattcttc taatacctgg 540
aatgctgttt tcccggggat cgcagtggtg agtaaccatg catcatcagg agtacggata 600
aaatgcttga tggtcggaag aggcataaat tccgtcagcc agtttagtct gaccatctca 660
tctgtaacat cattggcaac gctacctttg ccatgtttca gaaacaactc tggcgcatcg 720
ggcttcccat acaatcgata gattgtcgca cctgattgcc cgacattatc gcgagcccat 780
ttatacccat ataaatcagc atccatgttg gaatttaatc gcggcctcga gcaagacgtt 840

```
tcccgttgaa tatggctcat aacacccctt gtattactgt ttatgtaagc agacaggtcg    900
acaatattgg ctattggcca ttgcatacgt tgtatctata tcataatatg tacatttata    960
ttggctcatg tccaatatga ccgccatgtt gacattgatt attgactagt tattaatagt   1020
aatcaattac ggggtcatta gttcatagcc catatatgga gttccgcgtt acataactta   1080
cggtaaatgg cccgcctggc tgaccgccca acgacccccg cccattgacg tcaataatga   1140
cgtatgttcc catagtaacg ccaataggga ctttccattg acgtcaatgg gtggagtatt   1200
tacggtaaac tgcccacttg gcagtacatc aagtgtatca tatgccaagt ccgcccccta   1260
ttgacgtcaa tgacggtaaa tggcccgcct ggcattatgc ccagtacatg accttacggg   1320
actttcctac ttggcagtac atctacgtat tagtcatcgc tattaccatg gtgatgcggt   1380
tttggcagta caccaatggg cgtggatagc ggtttgactc acggggattt ccaagtctcc   1440
accccattga cgtcaatggg agtttgtttt ggcaccaaaa tcaacgggac tttccaaaat   1500
gtcgtaataa ccccgccccg ttgacgcaaa tgggcggtag gcgtgtacgg tgggaggtct   1560
atataagcag agctcgttta gtgaaccgtc agatcgcctg gagacgccat ccacgctgtt   1620
ttgacctcca tagaagacac cgggaccgat ccagcctccg cggccgggaa cggtgcattg   1680
gaacgcggat tccccgtgcc aagagtgact caccgtccgg atctcagcaa gcaggtatgt   1740
actctccagg gtgggcctgg cttccccagt caagactcca gggatttgag ggacgctgtg   1800
ggctcttctc ttacatgtac cttttgcttg cctcaaccct gactatcttc caggtcagga   1860
tcccagagtc aggggtctgt attttcctgc tggtggctcc agttcaggaa cagtaaaccc   1920
tgctccgaat attgcctctc acatctcgtc aatctccgcg aggactgggg accctgtgac   1980
gaacatggct agcattgtgg gaggctggga gtgcgagaag cattcccaac cctggcaggt   2040
gcttgtggcc tctcgtggca gggcagtctg cggcggtgtt ctggtgcacc cccagtgggt   2100
cctcacagct gcccactgca tcaggaacaa aagcgtgatc ttgctgggtc ggcacagctt   2160
gtttcatcct gaagacacag gccaggtatt tcaggtcagc cacagcttcc cacacccgct   2220
ctacgatatg agcctcctga agaatcgatt cctcaggcca ggtgatgact ccagccacga   2280
cctcatgctg ctccgcctgt cagagcctgc cgagctcacg gatgctgtga aggtcatgga   2340
cctgcccacc caggagccag cactggggac cacctgctac gcctcaggct ggggcagcat   2400
tgaaccagag gagttcttga ccccaaagaa acttcagtgt gtggacctcc atgttatttc   2460
caatgacgtg tgtgcgcaag ttcaccctca gaaggtgacc aagttcatgc tgtgtgctgg   2520
acgctggaca gggggcaaaa gcacctgctc gggtgattct gggggcccac ttgtctgtaa   2580
tggtgtgctt caaggtatca cgtcatgggg cagtgaacca tgtgccctgc ccgaaaggcc   2640
ttccctgtac accaaggtgg tgcattaccg gaagtggatc aaggacacca tcgtggccaa   2700
ccccggatcc cagaccctga actttgatct gctgaaactg gcaggcgatg tggaaagcaa   2760
cccaggccca atggcaagcg cgcgccgccc gcgctggctg tgcgctgggg cgctggtgct   2820
ggcgggtggc ttctttctcc tcggcttcct cttcgggtgg tttataaaat cctccaatga   2880
agctactaac attactccaa agcataatat gaaagcattt ttggatgaat tgaaagctga   2940
gaacatcaag aagttcttat ataattttac acagatacca catttagcag gaacagaaca   3000
aaactttcag cttgcaaagc aaattcaatc ccagtggaaa gaatttggcc tggattctgt   3060
tgagctggca cattatgatg tcctgttgtc ctacccaaat aagactcatc ccaactacat   3120
ctcaataatt aatgaagatg gaaatgagat tttcaacaca tcattatttg aaccacctcc   3180
```

-continued

```
tccaggatat gaaaatgttt cggatattgt accacctttc agtgctttct ctcctcaagg   3240
aatgccagag ggcgatctag tgtatgttaa ctatgcacga actgaagact tctttaaatt   3300
ggaacgggac atgaaaatca attgctctgg gaaaattgta attgccagat atgggaaagt   3360
tttcagagga aataaggtta aaaatgccca gctggcaggg gccaaaggag tcattctcta   3420
ctccgaccct gctgactact ttgctcctgg ggtgaagtcc tatccagatg gttggaatct   3480
tcctggaggt ggtgtccagc gtggaaatat cctaaatctg aatggtgcag gagaccctct   3540
cacaccaggt tacccagcaa atgaatatgc ttataggcgt ggaattgcag aggctgttgg   3600
tcttccaagt attcctgttc atccaattgg atactatgat gcacagaagc tcctagaaaa   3660
aatgggtggc tcagcaccac cagatagcag ctggagagga agtctcaaag tgccctacaa   3720
tgttggacct ggctttactg gaaacttttc tacacaaaaa gtcaagatgc acatccactc   3780
taccaatgaa gtgacaagaa tttacaatgt gataggtact ctcagaggag cagtggaacc   3840
agacagatat gtcattctgg gaggtcaccg ggactcatgg gtgtttggtg gtattgaccc   3900
tcagagtgga gcagctgttg ttcatgaaat tgtgaggagc tttggaacac tgaaaaagga   3960
agggtggaga cctagaagaa caattttgtt tgcaagctgg gatgcagaag aatttggtct   4020
tcttggttct actgagtggg cagaggagaa ttcaagactc cttcaagagc gtggcgtggc   4080
ttatattaat gctgactcat ctatagaagg aaactacact ctgagagttg attgtacacc   4140
gctgatgtac agcttggtac acaacctaac aaaagagctg aaaagccctg atgaaggctt   4200
tgaaggcaaa tctctttatg aaagttggac taaaaaaagt ccttccccag agttcagtgg   4260
catgcccagg ataagcaaat tgggatctgg aaatgatttt gaggtgttct tccaacgact   4320
tggaattgct tcaggcagag cacggtatac taaaaattgg gaaacaaaca aattcagcgg   4380
ctatccactg tatcacagtg tctatgaaac atatgagttg gtggaaaagt tttatgatcc   4440
aatgtttaaa tatcacctca ctgtggccca ggttcgagga gggatggtgt ttgagctggc   4500
caattccata gtgctccctt ttgattgtcg agattatgct gtagttttaa gaaagtatgc   4560
tgacaaaatc tacagtattt ctatgaaaca tccacaggaa atgaagacat acagtgtatc   4620
atttgattca ctttttctg cagtaaagaa ttttacagaa attgcttcca agttcagtga   4680
gagactccag gactttgaca aaagcaaccc aatagtatta agaatgatga atgatcaact   4740
catgtttctg gaaagagcat ttattgatcc attagggtta ccagacaggc ctttttatag   4800
gcatgtcatc tatgctccaa gcagccacaa caagtatgca ggggagtcat tcccaggaat   4860
ttatgatgct ctgtttgata ttgaaagcaa agtggaccct tccaaggcct ggggagaagt   4920
gaagagacag atttatgttg cagccttcac agtgcaggca gctgcagaga ctttgagtga   4980
agtagcctaa agatctgggc cctaacaaaa caaaaagatg gggttattcc ctaaacttca   5040
tgggttacgt aattggaagt tgggggacat tgccacaaga tcatattgta caaaagatca   5100
aacactgttt tagaaaactt cctgtaaaca ggcctattga ttggaaagta tgtcaaagga   5160
ttgtgggtct tttgggcttt gctgctccat ttacacaatg tggatatcct gccttaatgc   5220
ctttgtatgc atgtatacaa gctaaacagg ctttcacttt ctcgccaact tacaaggcct   5280
ttctaagtaa acagtacatg aacctttacc ccgttgctcg gcaacggcct ggtctgtgcc   5340
aagtgtttgc tgacgcaacc cccactggct ggggcttggc cataggccat cagcgcatgc   5400
gtggaacctt tgtggctcct ctgccgatcc atactgcgga actcctagcc gcttgttttg   5460
ctcgcagccg gtctggagca aagctcatag gaactgacaa ttctgtcgtc ctctcgcgga   5520
aatatacatc gtttcgatct acgtatgatc tttttccctc tgccaaaaat tatggggaca   5580
```

```
tcatgaagcc ccttgagcat ctgacttctg gctaataaag gaaatttatt ttcattgcaa   5640
tagtgtgttg gaattttttg tgtctctcac tcggaaggaa ttctgcatta atgaatcggc   5700
caacgcgcgg ggagaggcgg tttgcgtatt gggcgctctt ccgcttcctc gctcactgac   5760
tcgctgcgct cggtcgttcg gctgcggcga gcggtatcag ctcactcaaa ggcggtaata   5820
cggttatcca cagaatcagg ggataacgca ggaaagaaca tgtgagcaaa aggccagcaa   5880
aaggccagga accgtaaaaa ggccgcgttg ctggcgtttt tccataggct ccgcccccct   5940
gacgagcatc acaaaaatcg acgctcaagt cagaggtggc gaaacccgac aggactataa   6000
agataccagg cgtttccccc tggaagctcc ctcgtgcgct ctcctgttcc gaccctgccg   6060
cttaccggat acctgtccgc ctttctccct tcgggaagcg tggcgctttc tcatagctca   6120
cgctgtaggt atctcagttc ggtgtaggtc gttcgctcca agctgggctg tgtgcacgaa   6180
ccccccgttc agcccgaccg ctgcgcctta tccggtaact atcgtcttga gtccaacccg   6240
gtaagacacg acttatcgcc actggcagca gccactggta acaggattag cagagcgagg   6300
tatgtaggcg gtgctacaga gttcttgaag tggtggccta actacggcta cactagaaga   6360
acagtatttg gtatctgcgc tctgctgaag ccagttacct tcggaaaaag agttggtagc   6420
tcttgatccg gcaaacaaac caccgctggt agcggtggtt tttttgtttg caagcagcag   6480
attacgcgca gaaaaaaagg atctcaagaa gatcctttga tcttttctac ggggtctgac   6540
gctcagtgga acgaaaactc acgttaaggg attttggtca tgagattatc aaaaaggatc   6600
ttcacctaga tccttttaaa ttaaaaatga agttttaaat caatctaaag tatatatgag   6660
taaacttggt ctgacagtta ccaatgctta atcagtgagg cacctatctc agcgatctgt   6720
ctatttcgtt catccatagt tgcctgactc                                    6750
```

<210> SEQ ID NO 30
<211> LENGTH: 6908
<212> TYPE: DNA
<213> ORGANISM: Artificial
<220> FEATURE:
<223> OTHER INFORMATION: Synthetic Construct

<400> SEQUENCE: 30

```
ggcgtaatgc tctgccagtg ttacaaccaa ttaaccaatt ctgattagaa aaactcatcg     60
agcatcaaat gaaactgcaa tttattcata tcaggattat caataccata tttttgaaaa    120
agccgtttct gtaatgaagg agaaaactca ccgaggcagt tccataggat ggcaagatcc    180
tggtatcggt ctgcgattcc gactcgtcca acatcaatac aacctattaa tttcccctcg    240
tcaaaaataa ggttatcaag tgagaaatca ccatgagtga cgactgaatc cggtgagaat    300
ggcaaaagct tatgcatttc tttccagact tgttcaacag gccagccatt acgctcgtca    360
tcaaaatcac tcgcatcaac caaaccgtta ttcattcgtg attgcgcctg agcgagacga    420
aatacgcgat cgctgttaaa aggacaatta caaacaggaa tcaaatgcaa ccggcgcagg    480
aacactgcca gcgcatcaac aatattttca cctgaatcag gatattcttc taatacctgg    540
aatgctgttt tcccggggat cgcagtggtg agtaaccatg catcatcagg agtacggata    600
aaatgcttga tggtcggaag aggcataaat tccgtcagcc agtttagtct gaccatctca    660
tctgtaacat cattggcaac gctacctttg ccatgtttca gaaacaactc tggcgcatcg    720
ggcttcccat acaatcgata gattgtcgca cctgattgcc cgacattatc gcgagcccat    780
ttatacccat ataaatcagc atccatgttg gaatttaatc gcggcctcga gcaagacgtt    840
```

-continued

```
tcccgttgaa tatggctcat aacacccctt gtattactgt ttatgtaagc agacaggtcg    900
acaatattgg ctattggcca ttgcatacgt tgtatctata tcataatatg tacatttata    960
ttggctcatg tccaatatga ccgccatgtt gacattgatt attgactagt tattaatagt   1020
aatcaattac ggggtcatta gttcatagcc catatatgga gttccgcgtt acataactta   1080
cggtaaatgg cccgcctggc tgaccgccca acgacccccg cccattgacg tcaataatga   1140
cgtatgttcc catagtaacg ccaataggga ctttccattg acgtcaatgg gtggagtatt   1200
tacggtaaac tgcccacttg gcagtacatc aagtgtatca tatgccaagt ccgcccccta   1260
ttgacgtcaa tgacggtaaa tggcccgcct ggcattatgc ccagtacatg accttacggg   1320
actttcctac ttggcagtac atctacgtat tagtcatcgc tattaccatg gtgatgcggt   1380
tttggcagta caccaatggg cgtggatagc ggtttgactc acggggattt ccaagtctcc   1440
accccattga cgtcaatggg agtttgtttt ggcaccaaaa tcaacgggac tttccaaaat   1500
gtcgtaataa ccccgccccg ttgacgcaaa tgggcggtag gcgtgtacgg tgggaggtct   1560
atataagcag agctcgttta gtgaaccgtc agatcgcctg gagacgccat ccacgctgtt   1620
ttgacctcca tagaagacac cgggaccgat ccagcctccg cggccgggaa cggtgcattg   1680
gaacgcggat tccccgtgcc aagagtgact caccgtccgg atctcagcaa gcaggtatgt   1740
actctccagg gtgggcctgg cttccccagt caagactcca gggatttgag ggacgctgtg   1800
ggctcttctc ttacatgtac cttttgcttg cctcaaccct gactatcttc caggtcagga   1860
tcccagagtc aggggtctgt attttcctgc tggtggctcc agttcaggaa cagtaaaccc   1920
tgctccgaat attgcctctc acatctcgtc aatctccgcg aggactgggg accctgtgac   1980
gaacatggct agcgcgcgcc gcccgcgctg gctgtgcgct ggggcgctgg tgctggcggg   2040
tggcttcttt ctcctcggct tcctcttcgg gtggtttata aaatcctcca atgaagctac   2100
taacattact ccaaagcata atatgaaagc atttttggat gaattgaaag ctgagaacat   2160
caagaagttc ttatataatt ttacacagat accacattta gcaggaacag aacaaaactt   2220
tcagcttgca aagcaaattc aatcccagtg gaaagaattt ggcctggatt ctgttgagct   2280
ggcacattat gatgtcctgt tgtcctaccc aaataagact catcccaact acatctcaat   2340
aattaatgaa gatggaaatg agattttcaa cacatcatta tttgaaccac ctcctccagg   2400
atatgaaaat gtttcggata ttgtaccacc tttcagtgct ttctctcctc aaggaatgcc   2460
agagggcgat ctagtgtatg ttaactatgc acgaactgaa gacttcttta aattggaacg   2520
ggacatgaaa atcaattgct ctgggaaaat tgtaattgcc agatatggga aagttttcag   2580
aggaaataag gttaaaaatg cccagctggc aggggccaaa ggagtcattc tctactccga   2640
ccctgctgac tactttgctc ctggggtgaa gtcctatcca gatggttgga atcttcctgg   2700
aggtggtgtc cagcgtggaa atatcctaaa tctgaatggt gcaggagacc ctctcacacc   2760
aggttaccca gcaaatgaat atgcttatag gcgtggaatt gcagaggctg ttggtcttcc   2820
aagtattcct gttcatccaa ttggatacta tgatgcacag aagctcctag aaaaaatggg   2880
tggctcagca ccaccagata gcagctggag aggaagtctc aaagtgccct acaatgttgg   2940
acctggcttt actggaaact tttctacaca aaaagtcaag atgcacatcc actctaccaa   3000
tgaagtgaca agaatttaca atgtgatagg tactctcaga ggagcagtgg aaccagacag   3060
atatgtcatt ctgggaggtc accgggactc atgggtgttt ggtggtattg accctcagag   3120
tggagcagct gttgttcatg aaattgtgag gagctttgga acactgaaaa aggaagggtg   3180
gagacctaga agaacaattt tgtttgcaag ctgggatgca gaagaatttg gtcttcttgg   3240
```

```
ttctactgag tgggcagagg agaattcaag actccttcaa gagcgtggcg tggcttatat   3300
taatgctgac tcatctatag aaggaaacta cactctgaga gttgattgta caccgctgat   3360
gtacagcttg gtacacaacc taacaaaaga gctgaaaagc cctgatgaag gctttgaagg   3420
caaatctctt tatgaaagtt ggactaaaaa aagtccttcc ccagagttca gtggcatgcc   3480
caggataagc aaattgggat ctggaaatga ttttgaggtg ttcttccaac gacttggaat   3540
tgcttcaggc agagcacggt atactaaaaa ttgggaaaca aacaaattca gcggctatcc   3600
actgtatcac agtgtctatg aaacatatga gttggtggaa aagttttatg atccaatgtt   3660
taaatatcac ctcactgtgg cccaggttcg aggagggatg gtgtttgagc tggccaattc   3720
catagtgctc ccttttgatt gtcgagatta tgctgtagtt ttaagaaagt atgctgacaa   3780
aatctacagt atttctatga aacatccaca ggaaatgaag acatacagtg tatcatttga   3840
ttcacttttt tctgcagtaa agaattttac agaaattgct tccaagttca gtgagagact   3900
ccaggacttt gacaaaagca acccaatagt attaagaatg atgaatgatc aactcatgtt   3960
tctggaaaga gcatttattg atccattagg gttaccagac aggccttttt ataggcatgt   4020
catctatgct ccaagcagcc acaacaagta tgcaggggag tcattcccag gaatttatga   4080
tgctctgttt gatattgaaa gcaaagtgga cccttccaag gcctggggag aagtgaagag   4140
acagatttat gttgcagcct tcacagtgca ggcagctgca gagactttga gtgaagtagc   4200
ctaaagatct gaccccctaa cgttactggc cgaagccgct tggaataagg ccggtgtgcg   4260
tttgtctata tgttattttc caccatattg ccgtcttttg gcaatgtgag ggcccggaaa   4320
cctggccctg tcttcttgac gagcattcct aggggtcttt cccctctcgc caaaggaatg   4380
caaggtctgt tgaatgtcgt gaaggaagca gttcctctgg aagcttcttg aagacaaaca   4440
acgtctgtag cgaccctttg caggcagcgg aaccccccac ctggcgacag gtgcctctgc   4500
ggccaaaagc cacgtgtata agatacacct gcaaaggcgg cacaacccca gtgccacgtt   4560
gtgagttgga tagttgtgga aagagtcaaa tggctctcct caagcgtatt caacaagggg   4620
ctgaaggatg cccagaaggt accccattgt atgggatctg atctggggcc tcggtgcaca   4680
tgctttacat gtgtttagtc gaggttaaaa aacgtctagg ccccccgaac cacggggacg   4740
tggttttcct ttgaaaaaca cgatgataat atggccagca aggctgtgct gcttgccctg   4800
ttgatggcag gcttggccct gcagccaggc actgccctgc tgtgctactc ctgcaaagcc   4860
caggtgagca acgaggactg cctgcaggtg gagaactgca cccagctggg ggagcagtgc   4920
tggaccgcgc gcatccgcgc agttggcctc ctgaccgtca tcagcaaagg ctgcagcttg   4980
aactgcgtgg atgactcaca ggactactac gtgggcaaga agaacatcac gtgctgtgac   5040
accgacttgt gcaacgccag cggggcccat gccctgcagc cggctgccgc catccttgcg   5100
ctgctccctg cactcggcct gctgctctgg ggacccggcc agctataggg atctgggccc   5160
taacaaaaca aaaagatggg gttattccct aaacttcatg ggttacgtaa ttggaagttg   5220
ggggacattg ccacaagatc atattgtaca aaagatcaaa cactgtttta gaaaacttcc   5280
tgtaaacagg cctattgatt ggaaagtatg tcaaaggatt gtgggtcttt tgggctttgc   5340
tgctccattt acacaatgtg gatatcctgc cttaatgcct ttgtatgcat gtatacaagc   5400
taaacaggct ttcactttct cgccaactta caaggccttt ctaagtaaac agtacatgaa   5460
cctttacccc gttgctcggc aacggcctgg tctgtgccaa gtgtttgctg acgcaacccc   5520
cactggctgg ggcttggcca taggccatca gcgcatgcgt ggaacctttg tggctcctct   5580
```

```
gccgatccat actgcggaac tcctagccgc ttgttttgct cgcagccggt ctggagcaaa   5640

gctcatagga actgacaatt ctgtcgtcct ctcgcggaaa tatacatcgt ttcgatctac   5700

gtatgatctt tttccctctg ccaaaaatta tggggacatc atgaagcccc ttgagcatct   5760

gacttctggc taataaagga aatttatttt cattgcaata gtgtgttgga atttttgtg    5820

tctctcactc ggaaggaatt ctgcattaat gaatcggcca acgcgcgggg agaggcggtt   5880

tgcgtattgg gcgctcttcc gcttcctcgc tcactgactc gctgcgctcg gtcgttcggc   5940

tgcggcgagc ggtatcagct cactcaaagg cggtaatacg gttatccaca gaatcagggg   6000

ataacgcagg aaagaacatg tgagcaaaag gccagcaaaa ggccaggaac cgtaaaaagg   6060

ccgcgttgct ggcgtttttc cataggctcc gcccccctga cgagcatcac aaaaatcgac   6120

gctcaagtca gaggtggcga aacccgacag gactataaag ataccaggcg tttccccctg   6180

gaagctccct cgtgcgctct cctgttccga ccctgccgct taccggatac ctgtccgcct   6240

ttctcccttc gggaagcgtg gcgctttctc atagctcacg ctgtaggtat ctcagttcgg   6300

tgtaggtcgt tcgctccaag ctgggctgtg tgcacgaacc ccccgttcag cccgaccgct   6360

gcgccttatc cggtaactat cgtcttgagt ccaacccggt aagacacgac ttatcgccac   6420

tggcagcagc cactggtaac aggattagca gagcgaggta tgtaggcggt gctacagagt   6480

tcttgaagtg gtggcctaac tacggctaca ctagaagaac agtatttggt atctgcgctc   6540

tgctgaagcc agttaccttc ggaaaaagag ttggtagctc ttgatccggc aaacaaacca   6600

ccgctggtag cggtggtttt tttgtttgca agcagcagat tacgcgcaga aaaaaaggat   6660

ctcaagaaga tcctttgatc ttttctacgg ggtctgacgc tcagtggaac gaaaactcac   6720

gttaagggat tttggtcatg agattatcaa aaaggatctt cacctagatc cttttaaatt   6780

aaaaatgaag ttttaaatca atctaaagta tatatgagta aacttggtct gacagttacc   6840

aatgcttaat cagtgaggca cctatctcag cgatctgtct atttcgttca tccatagttg   6900

cctgactc                                                            6908
```

<210> SEQ ID NO 31
<211> LENGTH: 6914
<212> TYPE: DNA
<213> ORGANISM: Artificial
<220> FEATURE:
<223> OTHER INFORMATION: Synthetic Construct

<400> SEQUENCE: 31

```
ggcgtaatgc tctgccagtg ttacaaccaa ttaaccaatt ctgattagaa aaactcatcg     60

agcatcaaat gaaactgcaa tttattcata tcaggattat caataccata tttttgaaaa    120

agccgtttct gtaatgaagg agaaaactca ccgaggcagt tccataggat ggcaagatcc    180

tggtatcggt ctgcgattcc gactcgtcca acatcaatac aacctattaa tttcccctcg    240

tcaaaaataa ggttatcaag tgagaaatca ccatgagtga cgactgaatc cggtgagaat    300

ggcaaaagct tatgcatttc tttccagact tgttcaacag gccagccatt acgctcgtca    360

tcaaaatcac tcgcatcaac caaaccgtta ttcattcgtg attgcgcctg agcgagacga    420

aatacgcgat cgctgttaaa aggacaatta caaacaggaa tcaaatgcaa ccggcgcagg    480

aacactgcca gcgcatcaac aatattttca cctgaatcag gatattcttc taatacctgg    540

aatgctgttt tcccggggat cgcagtggtg agtaaccatg catcatcagg agtacggata    600

aaatgcttga tggtcggaag aggcataaat tccgtcagcc agtttagtct gaccatctca    660

tctgtaacat cattggcaac gctacctttg ccatgtttca gaaacaactc tggcgcatcg    720
```

ggcttcccat acaatcgata gattgtcgca cctgattgcc cgacattatc gcgagcccat 780
ttatacccat ataaatcagc atccatgttg gaatttaatc gcggcctcga gcaagacgtt 840
tcccgttgaa tatggctcat aacacccctt gtattactgt ttatgtaagc agacaggtcg 900
acaatattgg ctattggcca ttgcatacgt tgtatctata tcataatatg tacatttata 960
ttggctcatg tccaatatga ccgccatgtt gacattgatt attgactagt tattaatagt 1020
aatcaattac ggggtcatta gttcatagcc catatatgga gttccgcgtt acataactta 1080
cggtaaatgg cccgcctggc tgaccgccca acgacccccg cccattgacg tcaataatga 1140
cgtatgttcc catagtaacg ccaataggga ctttccattg acgtcaatgg gtggagtatt 1200
tacggtaaac tgcccacttg gcagtacatc aagtgtatca tatgccaagt ccgcccccta 1260
ttgacgtcaa tgacggtaaa tggcccgcct ggcattatgc ccagtacatg accttacggg 1320
actttcctac ttggcagtac atctacgtat tagtcatcgc tattaccatg gtgatgcggt 1380
tttggcagta caccaatggg cgtggatagc ggtttgactc acggggattt ccaagtctcc 1440
accccattga cgtcaatggg agtttgtttt ggcaccaaaa tcaacgggac tttccaaaat 1500
gtcgtaataa ccccgccccg ttgacgcaaa tgggcggtag gcgtgtacgg tgggaggtct 1560
atataagcag agctcgttta gtgaaccgtc agatcgcctg gagacgccat ccacgctgtt 1620
ttgacctcca tagaagacac cgggaccgat ccagcctccg cggccgggaa cggtgcattg 1680
gaacgcggat tccccgtgcc aagagtgact caccgtccgg atctcagcaa gcaggtatgt 1740
actctccagg gtgggcctgg cttccccagt caagactcca gggatttgag ggacgctgtg 1800
ggctcttctc ttacatgtac cttttgcttg cctcaaccct gactatcttc caggtcagga 1860
tcccagagtc aggggtctgt attttcctgc tggtggctcc agttcaggaa cagtaaaccc 1920
tgctccgaat attgcctctc acatctcgtc aatctccgcg aggactgggg accctgtgac 1980
gaacatggct agcaaggctg tgctgcttgc cctgttgatg gcaggcttgg ccctgcagcc 2040
aggcactgcc ctgctgtgct actcctgcaa agcccaggtg agcaacgagg actgcctgca 2100
ggtggagaac tgcacccagc tgggggagca gtgctggacc gcgcgcatcc gcgcagttgg 2160
cctcctgacc gtcatcagca aaggctgcag cttgaactgc gtggatgact cacaggacta 2220
ctacgtgggc aagaagaaca tcacgtgctg tgacaccgac ttgtgcaacg ccagcggggc 2280
ccatgccctg cagccggctg ccgccatcct tgcgctgctc cctgcactcg gcctgctgct 2340
ctggggaccc ggccagctat agagatctga ccccctaacg ttactggccg aagccgcttg 2400
gaataaggcc ggtgtgcgtt tgtctatatg ttattttcca ccatattgcc gtcttttggc 2460
aatgtgaggg cccggaaacc tggccctgtc ttcttgacga gcattcctag gggtctttcc 2520
cctctcgcca aaggaatgca aggtctgttg aatgtcgtga aggaagcagt tcctctggaa 2580
gcttcttgaa gacaaacaac gtctgtagcg accctttgca ggcagcggaa ccccccacct 2640
ggcgacaggt gcctctgcgg ccaaaagcca cgtgtataag atacacctgc aaaggcggca 2700
caaccccagt gccacgttgt gagttggata gttgtggaaa gagtcaaatg gctctcctca 2760
agcgtattca acaaggggct gaaggatgcc cagaaggtac cccattgtat gggatctgat 2820
ctggggcctc ggtgcacatg ctttacatgt gtttagtcga ggttaaaaaa cgtctaggcc 2880
ccccgaacca cggggacgtg gttttccttt gaaaaacacg atgataatat ggccacaacc 2940
atggcgcgcc gcccgcgctg gctgtgcgct ggggcgctgg tgctggcggg tggcttcttt 3000
ctcctcggct tcctcttcgg gtggtttata aaatcctcca atgaagctac taacattact 3060

```
ccaaagcata atatgaaagc atttttggat gaattgaaag ctgagaacat caagaagttc   3120
ttatataatt ttacacagat accacattta gcaggaacag aacaaaactt tcagcttgca   3180
aagcaaattc aatcccagtg gaaagaattt ggcctggatt ctgttgagct ggcacattat   3240
gatgtcctgt tgtcctaccc aaataagact catcccaact acatctcaat aattaatgaa   3300
gatggaaatg agattttcaa cacatcatta tttgaaccac ctcctccagg atatgaaaat   3360
gtttcggata ttgtaccacc tttcagtgct ttctctcctc aaggaatgcc agagggcgat   3420
ctagtgtatg ttaactatgc acgaactgaa gacttcttta aattggaacg ggacatgaaa   3480
atcaattgct ctgggaaaat tgtaattgcc agatatggga aagttttcag aggaaataag   3540
gttaaaaatg cccagctggc aggggccaaa ggagtcattc tctactccga ccctgctgac   3600
tactttgctc ctggggtgaa gtcctatcca gatggttgga atcttcctgg aggtggtgtc   3660
cagcgtggaa atatcctaaa tctgaatggt gcaggagacc ctctcacacc aggttaccca   3720
gcaaatgaat atgcttatag gcgtggaatt gcagaggctg ttggtcttcc aagtattcct   3780
gttcatccaa ttggatacta tgatgcacag aagctcctag aaaaaatggg tggctcagca   3840
ccaccagata gcagctggag aggaagtctc aaagtgccct acaatgttgg acctggcttt   3900
actggaaact tttctacaca aaaagtcaag atgcacatcc actctaccaa tgaagtgaca   3960
agaatttaca atgtgatagg tactctcaga ggagcagtgg aaccagacag atatgtcatt   4020
ctgggaggtc accgggactc atgggtgttt ggtggtattg accctcagag tggagcagct   4080
gttgttcatg aaattgtgag gagctttgga acactgaaaa aggaagggtg gagacctaga   4140
agaacaattt tgtttgcaag ctgggatgca gaagaatttg gtcttcttgg ttctactgag   4200
tgggcagagg agaattcaag actccttcaa gagcgtggcg tggcttatat taatgctgac   4260
tcatctatag aaggaaacta cactctgaga gttgattgta caccgctgat gtacagcttg   4320
gtacacaacc taacaaaaga gctgaaaagc cctgatgaag gctttgaagg caaatctctt   4380
tatgaaagtt ggactaaaaa aagtccttcc ccagagttca gtggcatgcc caggataagc   4440
aaattgggat ctggaaatga ttttgaggtg ttcttccaac gacttggaat tgcttcaggc   4500
agagcacggt atactaaaaa ttgggaaaca aacaaattca gcggctatcc actgtatcac   4560
agtgtctatg aaacatatga gttggtggaa aagttttatg atccaatgtt taaatatcac   4620
ctcactgtgg cccaggttcg aggagggatg gtgtttgagc tggccaattc catagtgctc   4680
ccttttgatt gtcgagatta tgctgtagtt ttaagaaagt atgctgacaa aatctacagt   4740
atttctatga aacatccaca ggaaatgaag acatacagtg tatcatttga ttcacttttt   4800
tctgcagtaa agaattttac agaaattgct tccaagttca gtgagagact ccaggacttt   4860
gacaaaagca acccaatagt attaagaatg atgaatgatc aactcatgtt tctggaaaga   4920
gcatttattg atccattagg gttaccagac aggccttttt ataggcatgt catctatgct   4980
ccaagcagcc acaacaagta tgcaggggag tcattcccag gaatttatga tgctctgttt   5040
gatattgaaa gcaaagtgga cccttccaag gcctggggag aagtgaagag acagatttat   5100
gttgcagcct tcacagtgca ggcagctgca gagactttga gtgaagtagc ctaaagatct   5160
gggccctaac aaaacaaaaa gatggggtta ttccctaaac ttcatgggtt acgtaattgg   5220
aagttggggg acattgccac aagatcatat tgtacaaaag atcaaacact gttttagaaa   5280
acttcctgta aacaggccta ttgattggaa agtatgtcaa aggattgtgg gtcttttggg   5340
ctttgctgct ccatttacac aatgtggata tcctgcctta atgcctttgt atgcatgtat   5400
acaagctaaa caggctttca ctttctcgcc aacttacaag gcctttctaa gtaaacagta   5460
```

```
catgaacctt taccccgttg ctcggcaacg gcctggtctg tgccaagtgt ttgctgacgc   5520
aacccccact ggctggggct tggccatagg ccatcagcgc atgcgtggaa cctttgtggc   5580
tcctctgccg atccatactg cggaactcct agccgcttgt tttgctcgca gccggtctgg   5640
agcaaagctc ataggaactg acaattctgt cgtcctctcg cggaaatata catcgtttcg   5700
atctacgtat gatctttttc cctctgccaa aaattatggg gacatcatga agccccttga   5760
gcatctgact tctggctaat aaaggaaatt tattttcatt gcaatagtgt gttggaattt   5820
tttgtgtctc tcactcggaa ggaattctgc attaatgaat cggccaacgc gcggggagag   5880
gcggtttgcg tattgggcgc tcttccgctt cctcgctcac tgactcgctg cgctcggtcg   5940
ttcggctgcg gcgagcggta tcagctcact caaaggcggt aatacggtta tccacagaat   6000
caggggataa cgcaggaaag aacatgtgag caaaaggcca gcaaaaggcc aggaaccgta   6060
aaaaggccgc gttgctggcg tttttccata ggctccgccc ccctgacgag catcacaaaa   6120
atcgacgctc aagtcagagg tggcgaaacc cgacaggact ataaagatac caggcgtttc   6180
cccctggaag ctccctcgtg cgctctcctg ttccgaccct gccgcttacc ggatacctgt   6240
ccgcctttct cccttcggga agcgtggcgc tttctcatag ctcacgctgt aggtatctca   6300
gttcggtgta ggtcgttcgc tccaagctgg gctgtgtgca cgaacccccc gttcagcccg   6360
accgctgcgc cttatccggt aactatcgtc ttgagtccaa cccggtaaga cacgacttat   6420
cgccactggc agcagccact ggtaacagga ttagcagagc gaggtatgta ggcggtgcta   6480
cagagttctt gaagtggtgg cctaactacg gctacactag aagaacagta tttggtatct   6540
gcgctctgct gaagccagtt accttcggaa aaagagttgg tagctcttga tccggcaaac   6600
aaaccaccgc tggtagcggt ggtttttttg tttgcaagca gcagattacg cgcagaaaaa   6660
aaggatctca agaagatcct ttgatctttt ctacggggtc tgacgctcag tggaacgaaa   6720
actcacgtta agggattttg gtcatgagat tatcaaaaag gatcttcacc tagatccttt   6780
taaattaaaa atgaagtttt aaatcaatct aaagtatata tgagtaaact tggtctgaca   6840
gttaccaatg cttaatcagt gaggcaccta tctcagcgat ctgtctattt cgttcatcca   6900
tagttgcctg actc                                                     6914
```

```
<210> SEQ ID NO 32
<211> LENGTH: 5411
<212> TYPE: DNA
<213> ORGANISM: Artificial
<220> FEATURE:
<223> OTHER INFORMATION: Synthetic Construct

<400> SEQUENCE: 32
```

```
ggcgtaatgc tctgccagtg ttacaaccaa ttaaccaatt ctgattagaa aaactcatcg     60
agcatcaaat gaaactgcaa tttattcata tcaggattat caataccata tttttgaaaa    120
agccgtttct gtaatgaagg agaaaactca ccgaggcagt tccataggat ggcaagatcc    180
tggtatcggt ctgcgattcc gactcgtcca acatcaatac aacctattaa tttcccctcg    240
tcaaaaataa ggttatcaag tgagaaatca ccatgagtga cgactgaatc cggtgagaat    300
ggcaaaagct tatgcatttc tttccagact tgttcaacag gccagccatt acgctcgtca    360
tcaaaatcac tcgcatcaac caaaccgtta ttcattcgtg attgcgcctg agcgagacga    420
aatacgcgat cgctgttaaa aggacaatta caaacaggaa tcaaatgcaa ccggcgcagg    480
aacactgcca gcgcatcaac aatattttca cctgaatcag gatattcttc taatacctgg    540
```

```
aatgctgttt tcccggggat cgcagtggtg agtaaccatg catcatcagg agtacggata    600
aaatgcttga tggtcggaag aggcataaat tccgtcagcc agtttagtct gaccatctca    660
tctgtaacat cattggcaac gctacctttg ccatgtttca gaaacaactc tggcgcatcg    720
ggcttcccat acaatcgata gattgtcgca cctgattgcc cgacattatc gcgagcccat    780
ttatacccat ataaatcagc atccatgttg gaatttaatc gcggcctcga gcaagacgtt    840
tcccgttgaa tatggctcat aacacccctt gtattactgt ttatgtaagc agacaggtcg    900
acaatattgg ctattggcca ttgcatacgt tgtatctata tcataatatg tacatttata    960
ttggctcatg tccaatatga ccgccatgtt gacattgatt attgactagt tattaatagt   1020
aatcaattac ggggtcatta gttcatagcc catatatgga gttccgcgtt acataactta   1080
cggtaaatgg cccgcctggc tgaccgccca acgacccccg cccattgacg tcaataatga   1140
cgtatgttcc catagtaacg ccaataggga ctttccattg acgtcaatgg gtggagtatt   1200
tacggtaaac tgcccacttg gcagtacatc aagtgtatca tatgccaagt ccgcccccta   1260
ttgacgtcaa tgacggtaaa tggcccgcct ggcattatgc ccagtacatg accttacggg   1320
actttcctac ttggcagtac atctacgtat tagtcatcgc tattaccatg gtgatgcggt   1380
tttggcagta caccaatggg cgtggatagc ggtttgactc acggggattt ccaagtctcc   1440
accccattga cgtcaatggg agtttgtttt ggcaccaaaa tcaacgggac tttccaaaat   1500
gtcgtaataa ccccgccccg ttgacgcaaa tgggcggtag gcgtgtacgg tgggaggtct   1560
atataagcag agctcgttta gtgaaccgtc agatcgcctg gagacgccat ccacgctgtt   1620
ttgacctcca tagaagacac cgggaccgat ccagcctccg cggccgggaa cggtgcattg   1680
gaacgcggat tccccgtgcc aagagtgact caccgtccgg atctcagcaa gcaggtatgt   1740
actctccagg gtgggcctgg cttccccagt caagactcca gggatttgag ggacgctgtg   1800
ggctcttctc ttacatgtac cttttgcttg cctcaaccct gactatcttc caggtcagga   1860
tcccagagtc aggggtctgt attttcctgc tggtggctcc agttcaggaa cagtaaaccc   1920
tgctccgaat attgcctctc acatctcgtc aatctccgcg aggactgggg accctgtgac   1980
gaacatggct agcaaggctg tgctgcttgc cctgttgatg gcaggcttgg ccctgcagcc   2040
aggcactgcc ctgctgtgct actcctgcaa agcccaggtg agcaacgagg actgcctgca   2100
ggtggagaac tgcacccagc tgggggagca gtgctggacc gcgcgcatcc gcgcagttgg   2160
cctcctgacc gtcatcagca aaggctgcag cttgaactgc gtggatgact cacaggacta   2220
ctacgtgggc aagaagaaca tcacgtgctg tgacaccgac ttgtgcaacg ccagcggggc   2280
ccatgccctg cagccggctg ccgccatcct tgcgctgctc cctgcactcg gcctgctgct   2340
ctggggaccc ggccagctat agagatctga ccccctaacg ttactggccg aagccgcttg   2400
gaataaggcc ggtgtgcgtt tgtctatatg ttattttcca ccatattgcc gtcttttggc   2460
aatgtgaggg cccggaaacc tggccctgtc ttcttgacga gcattcctag gggtctttcc   2520
cctctcgcca aaggaatgca aggtctgttg aatgtcgtga aggaagcagt tcctctggaa   2580
gcttcttgaa gacaaacaac gtctgtagcg accctttgca ggcagcggaa ccccccacct   2640
ggcgacaggt gcctctgcgg ccaaaagcca cgtgtataag atacacctgc aaaggcggca   2700
caaccccagt gccacgttgt gagttggata gttgtggaaa gagtcaaatg gctctcctca   2760
agcgtattca acaaggggct gaaggatgcc cagaaggtac cccattgtat gggatctgat   2820
ctggggcctc ggtgcacatg ctttacatgt gtttagtcga ggttaaaaaa cgtctaggcc   2880
ccccgaacca cggggacgtg gttttccttt gaaaaacacg atgataatat ggccagcatt   2940
```

gtgggaggct gggagtgcga gaagcattcc caaccctggc aggtgcttgt ggcctctcgt 3000
ggcagggcag tctgcggcgg tgttctggtg cacccccagt gggtcctcac agctgcccac 3060
tgcatcagga acaaaagcgt gatcttgctg ggtcggcaca gcttgtttca tcctgaagac 3120
acaggccagg tatttcaggt cagccacagc ttcccacacc cgctctacga tatgagcctc 3180
ctgaagaatc gattcctcag gccaggtgat gactccagcc acgacctcat gctgctccgc 3240
ctgtcagagc ctgccgagct cacggatgct gtgaaggtca tggacctgcc cacccaggag 3300
ccagcactgg ggaccacctg ctacgcctca ggctggggca gcattgaacc agaggagttc 3360
ttgaccccaa agaaacttca gtgtgtggac ctccatgtta tttccaatga cgtgtgtgcg 3420
caagttcacc ctcagaaggt gaccaagttc atgctgtgtg ctggacgctg gacagggggc 3480
aaaagcacct gctcgggtga ttctgggggc ccacttgtct gtaatggtgt gcttcaaggt 3540
atcacgtcat ggggcagtga accatgtgcc ctgcccgaaa ggccttccct gtacaccaag 3600
gtggtgcatt accggaagtg gatcaaggac accatcgtgg ccaacccctg aggatctggg 3660
ccctaacaaa acaaaaagat ggggttattc cctaaacttc atgggttacg taattggaag 3720
ttgggggaca ttgccacaag atcatattgt acaaaagatc aaacactgtt ttagaaaact 3780
tcctgtaaac aggcctattg attggaaagt atgtcaaagg attgtgggtc ttttgggctt 3840
tgctgctcca tttacacaat gtggatatcc tgccttaatg cctttgtatg catgtataca 3900
agctaaacag gctttcactt tctcgccaac ttacaaggcc tttctaagta aacagtacat 3960
gaacctttac cccgttgctc ggcaacggcc tggtctgtgc caagtgtttg ctgacgcaac 4020
ccccactggc tggggcttgg ccataggcca tcagcgcatg cgtggaacct ttgtggctcc 4080
tctgccgatc catactgcgg aactcctagc cgcttgtttt gctcgcagcc ggtctggagc 4140
aaagctcata ggaactgaca attctgtcgt cctctcgcgg aaatatacat cgtttcgatc 4200
tacgtatgat ctttttccct ctgccaaaaa ttatggggac atcatgaagc cccttgagca 4260
tctgacttct ggctaataaa ggaaatttat tttcattgca atagtgtgtt ggaatttttt 4320
gtgtctctca ctcggaagga attctgcatt aatgaatcgg ccaacgcgcg gggagaggcg 4380
gtttgcgtat tgggcgctct tccgcttcct cgctcactga ctcgctgcgc tcggtcgttc 4440
ggctgcggcg agcggtatca gctcactcaa aggcggtaat acggttatcc acagaatcag 4500
gggataacgc aggaaagaac atgtgagcaa aaggccagca aaaggccagg aaccgtaaaa 4560
aggccgcgtt gctggcgttt ttccataggc tccgcccccc tgacgagcat cacaaaaatc 4620
gacgctcaag tcagaggtgg cgaaacccga caggactata aagataccag gcgtttcccc 4680
ctggaagctc cctcgtgcgc tctcctgttc cgaccctgcc gcttaccgga tacctgtccg 4740
cctttctccc ttcgggaagc gtggcgcttt ctcatagctc acgctgtagg tatctcagtt 4800
cggtgtaggt cgttcgctcc aagctgggct gtgtgcacga accccccgtt cagcccgacc 4860
gctgcgcctt atccggtaac tatcgtcttg agtccaaccc ggtaagacac gacttatcgc 4920
cactggcagc agccactggt aacaggatta gcagagcgag gtatgtaggc ggtgctacag 4980
agttcttgaa gtggtggcct aactacggct acactagaag aacagtattt ggtatctgcg 5040
ctctgctgaa gccagttacc ttcggaaaaa gagttggtag ctcttgatcc ggcaaacaaa 5100
ccaccgctgg tagcggtggt ttttttgttt gcaagcagca gattacgcgc agaaaaaaag 5160
gatctcaaga agatcctttg atcttttcta cggggtctga cgctcagtgg aacgaaaact 5220
cacgttaagg gattttggtc atgagattat caaaaaggat cttcacctag atccttttaa 5280
attaaaaatg aagttttaaa tcaatctaaa gtatatatga gtaaacttgg tctgacagtt 5340
accaatgctt aatcagtgag gcacctatct cagcgatctg tctatttcgt tcatccatag 5400
ttgcctgact c 5411

<210> SEQ ID NO 33
<211> LENGTH: 7694
<212> TYPE: DNA
<213> ORGANISM: Artificial
<220> FEATURE:
<223> OTHER INFORMATION: Synthetic Construct

<400> SEQUENCE: 33
ggcgtaatgc tctgccagtg ttacaaccaa ttaaccaatt ctgattagaa aaactcatcg 60
agcatcaaat gaaactgcaa tttattcata tcaggattat caataccata tttttgaaaa 120
agccgtttct gtaatgaagg agaaaactca ccgaggcagt tccataggat ggcaagatcc 180
tggtatcggt ctgcgattcc gactcgtcca acatcaatac aacctattaa tttcccctcg 240
tcaaaaataa ggttatcaag tgagaaatca ccatgagtga cgactgaatc cggtgagaat 300
ggcaaaagct tatgcatttc tttccagact tgttcaacag gccagccatt acgctcgtca 360
tcaaaatcac tcgcatcaac caaaccgtta ttcattcgtg attgcgcctg agcgagacga 420
aatacgcgat cgctgttaaa aggacaatta caaacaggaa tcaaatgcaa ccggcgcagg 480
aacactgcca gcgcatcaac aatattttca cctgaatcag gatattcttc taatacctgg 540
aatgctgttt tcccggggat cgcagtggtg agtaaccatg catcatcagg agtacggata 600
aaatgcttga tggtcggaag aggcataaat tccgtcagcc agtttagtct gaccatctca 660
tctgtaacat cattggcaac gctacctttg ccatgtttca gaaacaactc tggcgcatcg 720
ggcttcccat acaatcgata gattgtcgca cctgattgcc cgacattatc gcgagcccat 780
ttatacccat ataaatcagc atccatgttg gaatttaatc gcggcctcga gcaagacgtt 840
tcccgttgaa tatggctcat aacacccctt gtattactgt ttatgtaagc agacaggtcg 900
acaatattgg ctattggcca ttgcatacgt tgtatctata tcataatatg tacatttata 960
ttggctcatg tccaatatga ccgccatgtt gacattgatt attgactagt tattaatagt 1020
aatcaattac ggggtcatta gttcatagcc catatatgga gttccgcgtt acataactta 1080
cggtaaatgg cccgcctggc tgaccgccca acgacccccg cccattgacg tcaataatga 1140
cgtatgttcc catagtaacg ccaataggga ctttccattg acgtcaatgg gtggagtatt 1200
tacggtaaac tgcccacttg gcagtacatc aagtgtatca tatgccaagt ccgcccccta 1260
ttgacgtcaa tgacggtaaa tggcccgcct ggcattatgc ccagtacatg accttacggg 1320
actttcctac ttggcagtac atctacgtat tagtcatcgc tattaccatg gtgatgcggt 1380
tttggcagta caccaatggg cgtggatagc ggtttgactc acggggattt ccaagtctcc 1440
accccattga cgtcaatggg agtttgtttt ggcaccaaaa tcaacgggac tttccaaaat 1500
gtcgtaataa ccccgccccg ttgacgcaaa tgggcggtag gcgtgtacgg tgggaggtct 1560
atataagcag agctcgttta gtgaaccgtc agatcgcctg gagacgccat ccacgctgtt 1620
ttgacctcca tagaagacac cgggaccgat ccagcctccg cggccgggaa cggtgcattg 1680
gaacgcggat tccccgtgcc aagagtgact caccgtccgg atctcagcaa gcaggtatgt 1740
actctccagg gtgggcctgg cttccccagt caagactcca gggatttgag ggacgctgtg 1800
ggctcttctc ttacatgtac cttttgcttg cctcaaccct gactatcttc caggtcagga 1860
tcccagagtc aggggtctgt attttcctgc tggtggctcc agttcaggaa cagtaaaccc 1920

-continued

```
tgctccgaat attgcctctc acatctcgtc aatctccgcg aggactgggg accctgtgac   1980
gaacatggct agcattgtgg gaggctggga gtgcgagaag cattcccaac cctggcaggt   2040
gcttgtggcc tctcgtggca gggcagtctg cggcggtgtt ctggtgcacc cccagtgggt   2100
cctcacagct gcccactgca tcaggaacaa aagcgtgatc ttgctgggtc ggcacagctt   2160
gtttcatcct gaagacacag gccaggtatt tcaggtcagc cacagcttcc cacacccgct   2220
ctacgatatg agcctcctga agaatcgatt cctcaggcca ggtgatgact ccagccacga   2280
cctcatgctg ctccgcctgt cagagcctgc cgagctcacg gatgctgtga aggtcatgga   2340
cctgcccacc caggagccag cactggggac cacctgctac gcctcaggct ggggcagcat   2400
tgaaccagag gagttcttga ccccaaagaa acttcagtgt gtggacctcc atgttatttc   2460
caatgacgtg tgtgcgcaag ttcaccctca gaaggtgacc aagttcatgc tgtgtgctgg   2520
acgctggaca gggggcaaaa gcacctgctc gggtgattct gggggcccac ttgtctgtaa   2580
tggtgtgctt caaggtatca cgtcatgggg cagtgaacca tgtgccctgc ccgaaaggcc   2640
ttccctgtac accaaggtgg tgcattaccg gaagtggatc aaggacacca tcgtggccaa   2700
ccccggatcc cagaccctga actttgatct gctgaaactg gcaggcgatg tggaaagcaa   2760
cccaggccca atggcaagcg cgcgccgccc gcgctggctg tgcgctgggg cgctggtgct   2820
ggcgggtggc ttctttctcc tcggcttcct cttcgggtgg tttataaaat cctccaatga   2880
agctactaac attactccaa agcataatat gaaagcattt ttggatgaat tgaaagctga   2940
gaacatcaag aagttcttat ataattttac acagatacca catttagcag gaacagaaca   3000
aaactttcag cttgcaaagc aaattcaatc ccagtggaaa gaatttggcc tggattctgt   3060
tgagctggca cattatgatg tcctgttgtc ctacccaaat aagactcatc ccaactacat   3120
ctcaataatt aatgaagatg gaaatgagat tttcaacaca tcattatttg aaccacctcc   3180
tccaggatat gaaaatgttt cggatattgt accacctttc agtgctttct ctcctcaagg   3240
aatgccagag ggcgatctag tgtatgttaa ctatgcacga actgaagact tctttaaatt   3300
ggaacgggac atgaaaatca attgctctgg gaaaattgta attgccagat atgggaaagt   3360
tttcagagga aataaggtta aaaatgccca gctggcaggg gccaaaggag tcattctcta   3420
ctccgaccct gctgactact ttgctcctgg ggtgaagtcc tatccagatg gttggaatct   3480
tcctggaggt ggtgtccagc gtggaaatat cctaaatctg aatggtgcag gagaccctct   3540
cacaccaggt tacccagcaa atgaatatgc ttataggcgt ggaattgcag aggctgttgg   3600
tcttccaagt attcctgttc atccaattgg atactatgat gcacagaagc tcctagaaaa   3660
aatgggtggc tcagcaccac cagatagcag ctggagagga agtctcaaag tgccctacaa   3720
tgttggacct ggctttactg gaaacttttc tacacaaaaa gtcaagatgc acatccactc   3780
taccaatgaa gtgacaagaa tttacaatgt gataggtact ctcagaggag cagtggaacc   3840
agacagatat gtcattctgg gaggtcaccg ggactcatgg gtgtttggtg gtattgaccc   3900
tcagagtgga gcagctgttg ttcatgaaat tgtgaggagc tttggaacac tgaaaaagga   3960
agggtggaga cctagaagaa caattttgtt tgcaagctgg gatgcagaag aatttggtct   4020
tcttggttct actgagtggg cagaggagaa ttcaagactc cttcaagagc gtggcgtggc   4080
ttatattaat gctgactcat ctatagaagg aaactacact ctgagagttg attgtacacc   4140
gctgatgtac agcttggtac acaacctaac aaaagagctg aaaagccctg atgaaggctt   4200
tgaaggcaaa tctctttatg aaagttggac taaaaaaagt ccttccccag agttcagtgg   4260
```

-continued

```
catgcccagg ataagcaaat tgggatctgg aaatgatttt gaggtgttct tccaacgact    4320

tggaattgct tcaggcagag cacggtatac taaaaattgg gaaacaaaca aattcagcgg    4380

ctatccactg tatcacagtg tctatgaaac atatgagttg gtggaaaagt tttatgatcc    4440

aatgtttaaa tatcacctca ctgtggccca ggttcgagga gggatggtgt ttgagctggc    4500

caattccata gtgctccctt ttgattgtcg agattatgct gtagttttaa gaaagtatgc    4560

tgacaaaatc tacagtattt ctatgaaaca tccacaggaa atgaagacat acagtgtatc    4620

atttgattca cttttttctg cagtaaagaa ttttacagaa attgcttcca agttcagtga    4680

gagactccag gactttgaca aaagcaaccc aatagtatta agaatgatga atgatcaact    4740

catgtttctg gaaagagcat ttattgatcc attagggtta ccagacaggc cttttttatag   4800

gcatgtcatc tatgctccaa gcagccacaa caagtatgca ggggagtcat tcccaggaat    4860

ttatgatgct ctgtttgata ttgaaagcaa agtggaccct tccaaggcct ggggagaagt    4920

gaagagacag atttatgttg cagccttcac agtgcaggca gctgcagaga ctttgagtga    4980

agtagcctaa agatctgacc ccctaacgtt actggccgaa gccgcttgga ataaggccgg    5040

tgtgcgtttg tctatatgtt attttccacc atattgccgt cttttggcaa tgtgagggcc    5100

cggaaacctg gccctgtctt cttgacgagc attcctaggg gtctttcccc tctcgccaaa    5160

ggaatgcaag gtctgttgaa tgtcgtgaag gaagcagttc ctctggaagc ttcttgaaga    5220

caaacaacgt ctgtagcgac cctttgcagg cagcggaacc ccccacctgg cgacaggtgc    5280

ctctgcggcc aaaagccacg tgtataagat acacctgcaa aggcggcaca accccagtgc    5340

cacgttgtga gttggatagt tgtggaaaga gtcaaatggc tctcctcaag cgtattcaac    5400

aaggggctga aggatgccca gaaggtaccc cattgtatgg gatctgatct ggggcctcgg    5460

tgcacatgct ttacatgtgt ttagtcgagg ttaaaaaacg tctaggcccc ccgaaccacg    5520

gggacgtggt tttcctttga aaaacacgat gataatatgg ccagcaaggc tgtgctgctt    5580

gccctgttga tggcaggctt ggccctgcag ccaggcactg ccctgctgtg ctactcctgc    5640

aaagcccagg tgagcaacga ggactgcctg caggtggaga actgcaccca gctgggggag    5700

cagtgctgga ccgcgcgcat ccgcgcagtt ggcctcctga ccgtcatcag caaaggctgc    5760

agcttgaact gcgtggatga ctcacaggac tactacgtgg gcaagaagaa catcacgtgc    5820

tgtgacaccg acttgtgcaa cgccagcggg gcccatgccc tgcagccggc tgccgccatc    5880

cttgcgctgc tccctgcact cggcctgctg ctctggggac ccggccagct atagggatct    5940

gggccctaac aaaacaaaaa gatggggtta ttccctaaac ttcatgggtt acgtaattgg    6000

aagttggggg acattgccac aagatcatat tgtacaaaag atcaaacact gttttagaaa    6060

acttcctgta aacaggccta ttgattggaa agtatgtcaa aggattgtgg gtcttttggg    6120

ctttgctgct ccatttacac aatgtggata tcctgcctta atgcctttgt atgcatgtat    6180

acaagctaaa caggctttca ctttctcgcc aacttacaag gcctttctaa gtaaacagta    6240

catgaacctt taccccgttg ctcggcaacg gcctggtctg tgccaagtgt ttgctgacgc    6300

aacccccact ggctggggct tggccatagg ccatcagcgc atgcgtggaa cctttgtggc    6360

tcctctgccg atccatactg cggaactcct agccgcttgt tttgctcgca gccggtctgg    6420

agcaaagctc ataggaactg acaattctgt cgtcctctcg cggaaatata catcgtttcg    6480

atctacgtat gatcttttc cctctgccaa aaattatggg gacatcatga agccccttga    6540

gcatctgact tctggctaat aaaggaaatt tattttcatt gcaatagtgt gttggaattt    6600

tttgtgtctc tcactcggaa ggaattctgc attaatgaat cggccaacgc gcggggagag    6660
```

```
gcggtttgcg tattgggcgc tcttccgctt cctcgctcac tgactcgctg cgctcggtcg   6720
ttcggctgcg gcgagcggta tcagctcact caaaggcggt aatacggtta tccacagaat   6780
caggggataa cgcaggaaag aacatgtgag caaaaggcca gcaaaaggcc aggaaccgta   6840
aaaaggccgc gttgctggcg tttttccata ggctccgccc ccctgacgag catcacaaaa   6900
atcgacgctc aagtcagagg tggcgaaacc cgacaggact ataaagatac caggcgtttc   6960
cccctggaag ctccctcgtg cgctctcctg ttccgaccct gccgcttacc ggatacctgt   7020
ccgcctttct cccttcggga agcgtggcgc tttctcatag ctcacgctgt aggtatctca   7080
gttcggtgta ggtcgttcgc tccaagctgg gctgtgtgca cgaacccccc gttcagcccg   7140
accgctgcgc cttatccggt aactatcgtc ttgagtccaa cccggtaaga cacgacttat   7200
cgccactggc agcagccact ggtaacagga ttagcagagc gaggtatgta ggcggtgcta   7260
cagagttctt gaagtggtgg cctaactacg gctacactag aagaacagta tttggtatct   7320
gcgctctgct gaagccagtt accttcggaa aaagagttgg tagctcttga tccggcaaac   7380
aaaccaccgc tggtagcggt ggtttttttg tttgcaagca gcagattacg cgcagaaaaa   7440
aaggatctca agaagatcct ttgatctttt ctacggggtc tgacgctcag tggaacgaaa   7500
actcacgtta agggattttg gtcatgagat tatcaaaaag gatcttcacc tagatccttt   7560
taaattaaaa atgaagtttt aaatcaatct aaagtatata tgagtaaact tggtctgaca   7620
gttaccaatg cttaatcagt gaggcaccta tctcagcgat ctgtctattt cgttcatcca   7680
tagttgcctg actc                                                     7694
```

<210> SEQ ID NO 34
<211> LENGTH: 7182
<212> TYPE: DNA
<213> ORGANISM: Artificial
<220> FEATURE:
<223> OTHER INFORMATION: Synthetic Construct

<400> SEQUENCE: 34

```
ggcgtaatgc tctgccagtg ttacaaccaa ttaaccaatt ctgattagaa aaactcatcg     60
agcatcaaat gaaactgcaa tttattcata tcaggattat caataccata tttttgaaaa    120
agccgtttct gtaatgaagg agaaaactca ccgaggcagt tccataggat ggcaagatcc    180
tggtatcggt ctgcgattcc gactcgtcca acatcaatac aacctattaa tttcccctcg    240
tcaaaaataa ggttatcaag tgagaaatca ccatgagtga cgactgaatc cggtgagaat    300
ggcaaaagct tatgcatttc tttccagact tgttcaacag gccagccatt acgctcgtca    360
tcaaaatcac tcgcatcaac caaaccgtta ttcattcgtg attgcgcctg agcgagacga    420
aatacgcgat cgctgttaaa aggacaatta caaacaggaa tcaaatgcaa ccggcgcagg    480
aacactgcca gcgcatcaac aatattttca cctgaatcag gatattcttc taatacctgg    540
aatgctgttt tcccggggat cgcagtggtg agtaaccatg catcatcagg agtacggata    600
aaatgcttga tggtcggaag aggcataaat tccgtcagcc agtttagtct gaccatctca    660
tctgtaacat cattggcaac gctacctttg ccatgtttca gaaacaactc tggcgcatcg    720
ggcttcccat acaatcgata gattgtcgca cctgattgcc cgacattatc gcgagcccat    780
ttatacccat ataaatcagc atccatgttg gaatttaatc gcggcctcga gcaagacgtt    840
tcccgttgaa tatggctcat aacacccctt gtattactgt ttatgtaagc agacaggtcg    900
acaatattgg ctattggcca ttgcatacgt tgtatctata tcataatatg tacatttata    960
```

-continued

```
ttggctcatg tccaatatga ccgccatgtt gacattgatt attgactagt tattaatagt   1020
aatcaattac ggggtcatta gttcatagcc catatatgga gttccgcgtt acataactta   1080
cggtaaatgg cccgcctggc tgaccgccca acgacccccg cccattgacg tcaataatga   1140
cgtatgttcc catagtaacg ccaataggga ctttccattg acgtcaatgg gtggagtatt   1200
tacggtaaac tgcccacttg gcagtacatc aagtgtatca tatgccaagt ccgcccccta   1260
ttgacgtcaa tgacggtaaa tggcccgcct ggcattatgc ccagtacatg accttacggg   1320
actttcctac ttggcagtac atctacgtat tagtcatcgc tattaccatg gtgatgcggt   1380
tttggcagta caccaatggg cgtggatagc ggtttgactc acggggattt ccaagtctcc   1440
accccattga cgtcaatggg agtttgtttt ggcaccaaaa tcaacgggac tttccaaaat   1500
gtcgtaataa ccccgccccg ttgacgcaaa tgggcggtag gcgtgtacgg tgggaggtct   1560
atataagcag agctcgttta gtgaaccgtc agatcgcctg gagacgccat ccacgctgtt   1620
ttgacctcca tagaagacac cgggaccgat ccagcctccg cggccgggaa cggtgcattg   1680
gaacgcggat tccccgtgcc aagagtgact caccgtccgg atctcagcaa gcaggtatgt   1740
actctccagg gtgggcctgg cttccccagt caagactcca gggatttgag ggacgctgtg   1800
ggctcttctc ttacatgtac cttttgcttg cctcaaccct gactatcttc caggtcagga   1860
tcccagagtc aggggtctgt attttcctgc tggtggctcc agttcaggaa cagtaaaccc   1920
tgctccgaat attgcctctc acatctcgtc aatctccgcg aggactgggg accctgtgac   1980
gaacatggct agcattgtgg gaggctggga gtgcgagaag cattcccaac cctggcaggt   2040
gcttgtggcc tctcgtggca gggcagtctg cggcggtgtt ctggtgcacc cccagtgggt   2100
cctcacagct gcccactgca tcaggaacaa aagcgtgatc ttgctgggtc ggcacagctt   2160
gtttcatcct gaagacacag gccaggtatt tcaggtcagc cacagcttcc cacacccgct   2220
ctacgatatg agcctcctga agaatcgatt cctcaggcca ggtgatgact ccagccacga   2280
cctcatgctg ctccgcctgt cagagcctgc cgagctcacg gatgctgtga aggtcatgga   2340
cctgcccacc caggagccag cactggggac cacctgctac gcctcaggct ggggcagcat   2400
tgaaccagag gagttcttga ccccaaagaa acttcagtgt gtggacctcc atgttatttc   2460
caatgacgtg tgtgcgcaag ttcaccctca gaaggtgacc aagttcatgc tgtgtgctgg   2520
acgctggaca gggggcaaaa gcacctgctc gggtgattct gggggcccac ttgtctgtaa   2580
tggtgtgctt caaggtatca cgtcatgggg cagtgaacca tgtgccctgc ccgaaaggcc   2640
ttccctgtac accaaggtgg tgcattaccg gaagtggatc aaggacacca tcgtggccaa   2700
ccccggatcc cagaccctga actttgatct gctgaaactg gcaggcgatg tggaaagcaa   2760
cccaggccca atggcaagcg cgcgccgccc gcgctggctg tgcgctgggg cgctggtgct   2820
ggcgggtggc ttctttctcc tcggcttcct cttcgggtgg tttataaaat cctccaatga   2880
agctactaac attactccaa agcataatat gaaagcattt ttggatgaat tgaaagctga   2940
gaacatcaag aagttcttat ataattttac acagatacca catttagcag gaacagaaca   3000
aaactttcag cttgcaaagc aaattcaatc ccagtggaaa gaatttggcc tggattctgt   3060
tgagctggca cattatgatg tcctgttgtc ctacccaaat aagactcatc ccaactacat   3120
ctcaataatt aatgaagatg gaaatgagat tttcaacaca tcattatttg aaccacctcc   3180
tccaggatat gaaaatgttt cggatattgt accacctttc agtgctttct ctcctcaagg   3240
aatgccagag ggcgatctag tgtatgttaa ctatgcacga actgaagact tctttaaatt   3300
ggaacgggac atgaaaatca attgctctgg gaaaattgta attgccagat atgggaaagt   3360
```

```
tttcagagga aataaggtta aaaatgccca gctggcaggg gccaaaggag tcattctcta   3420
ctccgaccct gctgactact ttgctcctgg ggtgaagtcc tatccagatg gttggaatct   3480
tcctggaggt ggtgtccagc gtggaaatat cctaaatctg aatggtgcag gagaccctct   3540
cacaccaggt tacccagcaa atgaatatgc ttataggcgt ggaattgcag aggctgttgg   3600
tcttccaagt attcctgttc atccaattgg atactatgat gcacagaagc tcctagaaaa   3660
aatgggtggc tcagcaccac cagatagcag ctggagagga agtctcaaag tgccctacaa   3720
tgttggacct ggctttactg gaaacttttc tacacaaaaa gtcaagatgc acatccactc   3780
taccaatgaa gtgacaagaa tttacaatgt gataggtact ctcagaggag cagtggaacc   3840
agacagatat gtcattctgg gaggtcaccg ggactcatgg gtgtttggtg gtattgaccc   3900
tcagagtgga gcagctgttg ttcatgaaat tgtgaggagc tttggaacac tgaaaaagga   3960
agggtggaga cctagaagaa caattttgtt tgcaagctgg gatgcagaag aatttggtct   4020
tcttggttct actgagtggg cagaggagaa ttcaagactc cttcaagagc gtggcgtggc   4080
ttatattaat gctgactcat ctatagaagg aaactacact ctgagagttg attgtacacc   4140
gctgatgtac agcttggtac acaacctaac aaaagagctg aaaagccctg atgaaggctt   4200
tgaaggcaaa tctctttatg aaagttggac taaaaaaagt ccttccccag agttcagtgg   4260
catgcccagg ataagcaaat tgggatctgg aaatgatttt gaggtgttct tccaacgact   4320
tggaattgct tcaggcagag cacggtatac taaaaattgg gaaacaaaca aattcagcgg   4380
ctatccactg tatcacagtg tctatgaaac atatgagttg gtggaaaagt tttatgatcc   4440
aatgtttaaa tatcacctca ctgtggccca ggttcgagga gggatggtgt ttgagctggc   4500
caattccata gtgctccctt ttgattgtcg agattatgct gtagttttaa gaaagtatgc   4560
tgacaaaatc tacagtattt ctatgaaaca tccacaggaa atgaagacat acagtgtatc   4620
atttgattca ctttttctg cagtaaagaa ttttacagaa attgcttcca agttcagtga   4680
gagactccag gactttgaca aaagcaaccc aatagtatta agaatgatga atgatcaact   4740
catgtttctg gaaagagcat ttattgatcc attagggtta ccagacaggc ctttttatag   4800
gcatgtcatc tatgctccaa gcagccacaa caagtatgca ggggagtcat tcccaggaat   4860
ttatgatgct ctgtttgata ttgaaagcaa agtggaccct tccaaggcct ggggagaagt   4920
gaagagacag atttatgttg cagccttcac agtgcaggca gctgcagaga ctttgagtga   4980
agtagccgga tccgaaggta ggggttcatt attgacctgt ggagatgtcg aagaaaaccc   5040
aggacccgca agcaaggctg tgctgcttgc cctgttgatg gcaggcttgg ccctgcagcc   5100
aggcactgcc ctgctgtgct actcctgcaa agcccaggtg agcaacgagg actgcctgca   5160
ggtggagaac tgcacccagc tgggggagca gtgctggacc gcgcgcatcc gcgcagttgg   5220
cctcctgacc gtcatcagca aaggctgcag cttgaactgc gtggatgact cacaggacta   5280
ctacgtgggc aagaagaaca tcacgtgctg tgacaccgac ttgtgcaacg ccagcggggc   5340
ccatgccctg cagccggctg ccgccatcct tgcgctgctc cctgcactcg gcctgctgct   5400
ctggggaccc ggccagctat agagatctgg gccctaacaa aacaaaaaga tggggttatt   5460
ccctaaactt catgggttac gtaattggaa gttgggggac attgccacaa gatcatattg   5520
tacaaaagat caaacactgt tttagaaaac ttcctgtaaa caggcctatt gattggaaag   5580
tatgtcaaag gattgtgggt cttttgggct ttgctgctcc atttacacaa tgtggatatc   5640
ctgccttaat gcctttgtat gcatgtatac aagctaaaca ggctttcact ttctcgccaa   5700
```

```
cttacaaggc ctttctaagt aaacagtaca tgaaccttta ccccgttgct cggcaacggc   5760

ctggtctgtg ccaagtgttt gctgacgcaa cccccactgg ctggggcttg gccataggcc   5820

atcagcgcat gcgtggaacc tttgtggctc ctctgccgat ccatactgcg gaactcctag   5880

ccgcttgttt tgctcgcagc cggtctggag caaagctcat aggaactgac aattctgtcg   5940

tcctctcgcg gaaatataca tcgtttcgat ctacgtatga tctttttccc tctgccaaaa   6000

attatgggga catcatgaag ccccttgagc atctgacttc tggctaataa aggaaattta   6060

ttttcattgc aatagtgtgt tggaattttt tgtgtctctc actcggaagg aattctgcat   6120

taatgaatcg gccaacgcgc ggggagaggc ggtttgcgta ttgggcgctc ttccgcttcc   6180

tcgctcactg actcgctgcg ctcggtcgtt cggctgcggc gagcggtatc agctcactca   6240

aaggcggtaa tacggttatc cacagaatca ggggataacg caggaaagaa catgtgagca   6300

aaaggccagc aaaaggccag gaaccgtaaa aaggccgcgt tgctggcgtt tttccatagg   6360

ctccgccccc ctgacgagca tcacaaaaat cgacgctcaa gtcagaggtg gcgaaacccg   6420

acaggactat aaagatacca ggcgtttccc cctggaagct ccctcgtgcg ctctcctgtt   6480

ccgaccctgc cgcttaccgg atacctgtcc gcctttctcc cttcgggaag cgtggcgctt   6540

tctcatagct cacgctgtag gtatctcagt tcggtgtagg tcgttcgctc caagctgggc   6600

tgtgtgcacg aaccccccgt tcagcccgac cgctgcgcct tatccggtaa ctatcgtctt   6660

gagtccaacc cggtaagaca cgacttatcg ccactggcag cagccactgg taacaggatt   6720

agcagagcga ggtatgtagg cggtgctaca gagttcttga agtggtggcc taactacggc   6780

tacactagaa gaacagtatt tggtatctgc gctctgctga agccagttac cttcggaaaa   6840

agagttggta gctcttgatc cggcaaacaa accaccgctg gtagcggtgg tttttttgtt   6900

tgcaagcagc agattacgcg cagaaaaaaa ggatctcaag aagatccttt gatcttttct   6960

acggggtctg acgctcagtg gaacgaaaac tcacgttaag ggattttggt catgagatta   7020

tcaaaaagga tcttcaccta gatcctttta aattaaaaat gaagttttaa atcaatctaa   7080

agtatatatg agtaaacttg gtctgacagt taccaatgct taatcagtga ggcacctatc   7140

tcagcgatct gtctatttcg ttcatccata gttgcctgac tc                      7182
```

<210> SEQ ID NO 35
<211> LENGTH: 7182
<212> TYPE: DNA
<213> ORGANISM: Artificial
<220> FEATURE:
<223> OTHER INFORMATION: Synthetic Construct

<400> SEQUENCE: 35

```
ggcgtaatgc tctgccagtg ttacaaccaa ttaaccaatt ctgattagaa aaactcatcg     60

agcatcaaat gaaactgcaa tttattcata tcaggattat caataccata tttttgaaaa    120

agccgtttct gtaatgaagg agaaaactca ccgaggcagt tccataggat ggcaagatcc    180

tggtatcggt ctgcgattcc gactcgtcca acatcaatac aacctattaa tttcccctcg    240

tcaaaaataa ggttatcaag tgagaaatca ccatgagtga cgactgaatc cggtgagaat    300

ggcaaaagct tatgcatttc tttccagact tgttcaacag gccagccatt acgctcgtca    360

tcaaaatcac tcgcatcaac caaaccgtta ttcattcgtg attgcgcctg agcgagacga    420

aatacgcgat cgctgttaaa aggacaatta caaacaggaa tcaaatgcaa ccggcgcagg    480

aacactgcca gcgcatcaac aatattttca cctgaatcag gatattcttc taatacctgg    540

aatgctgttt tcccggggat cgcagtggtg agtaaccatg catcatcagg agtacggata    600
```

-continued

```
aaatgcttga tggtcggaag aggcataaat tccgtcagcc agtttagtct gaccatctca    660
tctgtaacat cattggcaac gctacctttg ccatgtttca gaaacaactc tggcgcatcg    720
ggcttcccat acaatcgata gattgtcgca cctgattgcc cgacattatc gcgagcccat    780
ttatacccat ataaatcagc atccatgttg gaatttaatc gcggcctcga gcaagacgtt    840
tcccgttgaa tatggctcat aacacccctt gtattactgt ttatgtaagc agacaggtcg    900
acaatattgg ctattggcca ttgcatacgt tgtatctata tcataatatg tacatttata    960
ttggctcatg tccaatatga ccgccatgtt gacattgatt attgactagt tattaatagt   1020
aatcaattac ggggtcatta gttcatagcc catatatgga gttccgcgtt acataactta   1080
cggtaaatgg cccgcctggc tgaccgccca acgacccccg cccattgacg tcaataatga   1140
cgtatgttcc catagtaacg ccaataggga ctttccattg acgtcaatgg gtggagtatt   1200
tacggtaaac tgcccacttg gcagtacatc aagtgtatca tatgccaagt ccgcccccta   1260
ttgacgtcaa tgacggtaaa tggcccgcct ggcattatgc ccagtacatg accttacggg   1320
actttcctac ttggcagtac atctacgtat tagtcatcgc tattaccatg gtgatgcggt   1380
tttggcagta caccaatggg cgtggatagc ggtttgactc acggggattt ccaagtctcc   1440
accccattga cgtcaatggg agtttgtttt ggcaccaaaa tcaacgggac tttccaaaat   1500
gtcgtaataa ccccgccccg ttgacgcaaa tgggcggtag gcgtgtacgg tgggaggtct   1560
atataagcag agctcgttta gtgaaccgtc agatcgcctg gagacgccat ccacgctgtt   1620
ttgacctcca tagaagacac cgggaccgat ccagcctccg cggccgggaa cggtgcattg   1680
gaacgcggat tccccgtgcc aagagtgact caccgtccgg atctcagcaa gcaggtatgt   1740
actctccagg gtgggcctgg cttccccagt caagactcca gggatttgag ggacgctgtg   1800
ggctcttctc ttacatgtac cttttgcttg cctcaaccct gactatcttc caggtcagga   1860
tcccagagtc aggggtctgt attttcctgc tggtggctcc agttcaggaa cagtaaaccc   1920
tgctccgaat attgcctctc acatctcgtc aatctccgcg aggactgggg accctgtgac   1980
gaacatggct agcattgtgg gaggctggga gtgcgagaag cattcccaac cctggcaggt   2040
gcttgtggcc tctcgtggca gggcagtctg cggcggtgtt ctggtgcacc cccagtgggt   2100
cctcacagct gcccactgca tcaggaacaa aagcgtgatc ttgctgggtc ggcacagctt   2160
gtttcatcct gaagacacag gccaggtatt tcaggtcagc cacagcttcc cacacccgct   2220
ctacgatatg agcctcctga agaatcgatt cctcaggcca ggtgatgact ccagccacga   2280
cctcatgctg ctccgcctgt cagagcctgc cgagctcacg gatgctgtga aggtcatgga   2340
cctgcccacc caggagccag cactggggac cacctgctac gcctcaggct ggggcagcat   2400
tgaaccagag gagttcttga ccccaaagaa acttcagtgt gtggacctcc atgttatttc   2460
caatgacgtg tgtgcgcaag ttcaccctca gaaggtgacc aagttcatgc tgtgtgctgg   2520
acgctggaca gggggcaaaa gcacctgctc gggtgattct gggggcccac ttgtctgtaa   2580
tggtgtgctt caaggtatca cgtcatgggg cagtgaacca tgtgccctgc ccgaaaggcc   2640
ttccctgtac accaaggtgg tgcattaccg gaagtggatc aaggacacca tcgtggccaa   2700
ccccggatcc gaaggtaggg gttcattatt gacctgtgga gatgtcgaag aaaacccagg   2760
acccgctagc aaggctgtgc tgcttgccct gttgatggca ggcttggccc tgcagccagg   2820
cactgccctg ctgtgctact cctgcaaagc ccaggtgagc aacgaggact gcctgcaggt   2880
ggagaactgc acccagctgg gggagcagtg ctggaccgcg cgcatccgcg cagttggcct   2940
```

-continued

```
cctgaccgtc atcagcaaag gctgcagctt gaactgcgtg gatgactcac aggactacta   3000
cgtgggcaag aagaacatca cgtgctgtga caccgacttg tgcaacgcca gcggggccca   3060
tgccctgcag ccggctgccg ccatccttgc gctgctccct gcactcggcc tgctgctctg   3120
gggacccggc cagctaggat cccagaccct gaactttgat ctgctgaaac tggcaggcga   3180
tgtggaaagc aacccaggcc caatggcaag cgcgcgccgc ccgcgctggc tgtgcgctgg   3240
ggcgctggtg ctggcgggtg gcttctttct cctcggcttc ctcttcgggt ggtttataaa   3300
atcctccaat gaagctacta acattactcc aaagcataat atgaaagcat ttttggatga   3360
attgaaagct gagaacatca agaagttctt atataatttt acacagatac cacatttagc   3420
aggaacagaa caaaactttc agcttgcaaa gcaaattcaa tcccagtgga aagaatttgg   3480
cctggattct gttgagctgg cacattatga tgtcctgttg tcctacccaa ataagactca   3540
tcccaactac atctcaataa ttaatgaaga tggaaatgag attttcaaca catcattatt   3600
tgaaccacct cctccaggat atgaaaatgt ttcggatatt gtaccacctt tcagtgcttt   3660
ctctcctcaa ggaatgccag agggcgatct agtgtatgtt aactatgcac gaactgaaga   3720
cttctttaaa ttggaacggg acatgaaaat caattgctct gggaaaattg taattgccag   3780
atatgggaaa gttttcagag gaaataaggt taaaaatgcc cagctggcag ggccaaagg    3840
agtcattctc tactccgacc ctgctgacta ctttgctcct ggggtgaagt cctatccaga   3900
tggttggaat cttcctggag gtggtgtcca gcgtggaaat atcctaaatc tgaatggtgc   3960
aggagaccct ctcacaccag gttacccagc aaatgaatat gcttataggc gtggaattgc   4020
agaggctgtt ggtcttccaa gtattcctgt tcatccaatt ggatactatg atgcacagaa   4080
gctcctagaa aaaatgggtg gctcagcacc accagatagc agctggagag gaagtctcaa   4140
agtgccctac aatgttggac ctggctttac tggaaacttt tctacacaaa aagtcaagat   4200
gcacatccac tctaccaatg aagtgacaag aatttacaat gtgataggta ctctcagagg   4260
agcagtggaa ccagacagat atgtcattct gggaggtcac cgggactcat gggtgtttgg   4320
tggtattgac cctcagagtg gagcagctgt tgttcatgaa attgtgagga gctttggaac   4380
actgaaaaag gaagggtgga gacctagaag aacaattttg tttgcaagct gggatgcaga   4440
agaatttggt cttcttggtt ctactgagtg ggcagaggag aattcaagac tccttcaaga   4500
gcgtggcgtg gcttatatta atgctgactc atctatagaa ggaaactaca ctctgagagt   4560
tgattgtaca ccgctgatgt acagcttggt acacaaccta acaaaagagc tgaaaagccc   4620
tgatgaaggc tttgaaggca aatctcttta tgaaagttgg actaaaaaaa gtccttcccc   4680
agagttcagt ggcatgccca ggataagcaa attgggatct ggaaatgatt ttgaggtgtt   4740
cttccaacga cttggaattg cttcaggcag agcacggtat actaaaaatt gggaaacaaa   4800
caaattcagc ggctatccac tgtatcacag tgtctatgaa acatatgagt tggtggaaaa   4860
gttttatgat ccaatgttta aatatcacct cactgtggcc caggttcgag gagggatggt   4920
gtttgagctg gccaattcca tagtgctccc ttttgattgt cgagattatg ctgtagtttt   4980
aagaaagtat gctgacaaaa tctacagtat ttctatgaaa catccacagg aaatgaagac   5040
atacagtgta tcatttgatt cacttttttc tgcagtaaag aattttacag aaattgcttc   5100
caagttcagt gagagactcc aggactttga caaaagcaac ccaatagtat taagaatgat   5160
gaatgatcaa ctcatgtttc tggaaagagc atttattgat ccattagggt taccagacag   5220
gcctttttat aggcatgtca tctatgctcc aagcagccac aacaagtatg caggggagtc   5280
attcccagga atttatgatg ctctgtttga tattgaaagc aaagtggacc cttccaaggc   5340
```

ctggggagaa gtgaagagac agatttatgt tgcagccttc acagtgcagg cagctgcaga 5400
gactttgagt gaagtagcct aaagatctgg gccctaacaa aacaaaaaga tggggttatt 5460
ccctaaactt catgggttac gtaattggaa gttgggggac attgccacaa gatcatattg 5520
tacaaaagat caaacactgt tttagaaaac ttcctgtaaa caggcctatt gattggaaag 5580
tatgtcaaag gattgtgggt cttttgggct ttgctgctcc atttacacaa tgtggatatc 5640
ctgccttaat gcctttgtat gcatgtatac aagctaaaca ggctttcact ttctcgccaa 5700
cttacaaggc ctttctaagt aaacagtaca tgaaccttta ccccgttgct cggcaacggc 5760
ctggtctgtg ccaagtgttt gctgacgcaa cccccactgg ctggggcttg gccataggcc 5820
atcagcgcat gcgtggaacc tttgtggctc ctctgccgat ccatactgcg gaactcctag 5880
ccgcttgttt tgctcgcagc cggtctggag caaagctcat aggaactgac aattctgtcg 5940
tcctctcgcg gaaatataca tcgtttcgat ctacgtatga tctttttccc tctgccaaaa 6000
attatgggga catcatgaag ccccttgagc atctgacttc tggctaataa aggaaattta 6060
ttttcattgc aatagtgtgt tggaattttt tgtgtctctc actcggaagg aattctgcat 6120
taatgaatcg gccaacgcgc ggggagaggc ggtttgcgta ttgggcgctc ttccgcttcc 6180
tcgctcactg actcgctgcg ctcggtcgtt cggctgcggc gagcggtatc agctcactca 6240
aaggcggtaa tacggttatc cacagaatca ggggataacg caggaaagaa catgtgagca 6300
aaaggccagc aaaaggccag gaaccgtaaa aaggccgcgt tgctggcgtt tttccatagg 6360
ctccgccccc ctgacgagca tcacaaaaat cgacgctcaa gtcagaggtg gcgaaacccg 6420
acaggactat aaagatacca ggcgtttccc cctggaagct ccctcgtgcg ctctcctgtt 6480
ccgaccctgc cgcttaccgg atacctgtcc gcctttctcc cttcgggaag cgtggcgctt 6540
tctcatagct cacgctgtag gtatctcagt tcggtgtagg tcgttcgctc caagctgggc 6600
tgtgtgcacg aaccccccgt tcagcccgac cgctgcgcct tatccggtaa ctatcgtctt 6660
gagtccaacc cggtaagaca cgacttatcg ccactggcag cagccactgg taacaggatt 6720
agcagagcga ggtatgtagg cggtgctaca gagttcttga agtggtggcc taactacggc 6780
tacactagaa gaacagtatt tggtatctgc gctctgctga agccagttac cttcggaaaa 6840
agagttggta gctcttgatc cggcaaacaa accaccgctg gtagcggtgg tttttttgtt 6900
tgcaagcagc agattacgcg cagaaaaaaa ggatctcaag aagatccttt gatcttttct 6960
acggggtctg acgctcagtg gaacgaaaac tcacgttaag ggattttggt catgagatta 7020
tcaaaaagga tcttcaccta gatcctttta aattaaaaat gaagttttaa atcaatctaa 7080
agtatatatg agtaaacttg gtctgacagt taccaatgct taatcagtga ggcacctatc 7140
tcagcgatct gtctatttcg ttcatccata gttgcctgac tc 7182

<210> SEQ ID NO 36
<211> LENGTH: 7694
<212> TYPE: DNA
<213> ORGANISM: Artificial
<220> FEATURE:
<223> OTHER INFORMATION: Synthetic Construct

<400> SEQUENCE: 36
ggcgtaatgc tctgccagtg ttacaaccaa ttaaccaatt ctgattagaa aaactcatcg 60
agcatcaaat gaaactgcaa tttattcata tcaggattat caataccata tttttgaaaa 120
agccgtttct gtaatgaagg agaaaactca ccgaggcagt tccataggat ggcaagatcc 180

-continued

```
tggtatcggt ctgcgattcc gactcgtcca acatcaatac aacctattaa tttcccctcg    240
tcaaaaataa ggttatcaag tgagaaatca ccatgagtga cgactgaatc cggtgagaat    300
ggcaaaagct tatgcatttc tttccagact tgttcaacag gccagccatt acgctcgtca    360
tcaaaatcac tcgcatcaac caaaccgtta ttcattcgtg attgcgcctg agcgagacga    420
aatacgcgat cgctgttaaa aggacaatta caaacaggaa tcaaatgcaa ccggcgcagg    480
aacactgcca gcgcatcaac aatattttca cctgaatcag gatattcttc taatacctgg    540
aatgctgttt tcccggggat cgcagtggtg agtaaccatg catcatcagg agtacggata    600
aaatgcttga tggtcggaag aggcataaat tccgtcagcc agtttagtct gaccatctca    660
tctgtaacat cattggcaac gctacctttg ccatgtttca gaaacaactc tggcgcatcg    720
ggcttcccat acaatcgata gattgtcgca cctgattgcc cgacattatc gcgagcccat    780
ttatacccat ataaatcagc atccatgttg gaatttaatc gcggcctcga gcaagacgtt    840
tcccgttgaa tatggctcat aacacccctt gtattactgt ttatgtaagc agacaggtcg    900
acaatattgg ctattggcca ttgcatacgt tgtatctata tcataatatg tacatttata    960
ttggctcatg tccaatatga ccgccatgtt gacattgatt attgactagt tattaatagt   1020
aatcaattac ggggtcatta gttcatagcc catatatgga gttccgcgtt acataactta   1080
cggtaaatgg cccgcctggc tgaccgccca acgacccccg cccattgacg tcaataatga   1140
cgtatgttcc catagtaacg ccaataggga ctttccattg acgtcaatgg gtggagtatt   1200
tacggtaaac tgcccacttg gcagtacatc aagtgtatca tatgccaagt ccgcccccta   1260
ttgacgtcaa tgacggtaaa tggcccgcct ggcattatgc ccagtacatg accttacggg   1320
actttcctac ttggcagtac atctacgtat tagtcatcgc tattaccatg gtgatgcggt   1380
tttggcagta caccaatggg cgtggatagc ggtttgactc acggggattt ccaagtctcc   1440
accccattga cgtcaatggg agtttgtttt ggcaccaaaa tcaacgggac tttccaaaat   1500
gtcgtaataa ccccgccccg ttgacgcaaa tgggcggtag gcgtgtacgg tgggaggtct   1560
atataagcag agctcgttta gtgaaccgtc agatcgcctg gagacgccat ccacgctgtt   1620
ttgacctcca tagaagacac cgggaccgat ccagcctccg cggccgggaa cggtgcattg   1680
gaacgcggat tccccgtgcc aagagtgact caccgtccgg atctcagcaa gcaggtatgt   1740
actctccagg gtgggcctgg cttccccagt caagactcca gggatttgag ggacgctgtg   1800
ggctcttctc ttacatgtac cttttgcttg cctcaaccct gactatcttc caggtcagga   1860
tcccagagtc aggggtctgt attttcctgc tggtggctcc agttcaggaa cagtaaaccc   1920
tgctccgaat attgcctctc acatctcgtc aatctccgcg aggactgggg accctgtgac   1980
gaacatggct agcaaggctg tgctgcttgc cctgttgatg gcaggcttgg ccctgcagcc   2040
aggcactgcc ctgctgtgct actcctgcaa agcccaggtg agcaacgagg actgcctgca   2100
ggtggagaac tgcacccagc tgggggagca gtgctggacc gcgcgcatcc gcgcagttgg   2160
cctcctgacc gtcatcagca aaggctgcag cttgaactgc gtggatgact cacaggacta   2220
ctacgtgggc aagaagaaca tcacgtgctg tgacaccgac ttgtgcaacg ccagcggggc   2280
ccatgccctg cagccggctg ccgccatcct tgcgctgctc cctgcactcg gcctgctgct   2340
ctggggaccc ggccagctag gatcccagac cctgaacttt gatctgctga aactggcagg   2400
cgatgtggaa agcaacccag gcccaatggc aagcgcgcgc cgcccgcgct ggctgtgcgc   2460
tggggcgctg gtgctggcgg gtggcttctt tctcctcggc ttcctcttcg ggtggtttat   2520
aaaatcctcc aatgaagcta ctaacattac tccaaagcat aatatgaaag catttttgga   2580
```

-continued

```
tgaattgaaa gctgagaaca tcaagaagtt cttatataat tttacacaga taccacattt   2640
agcaggaaca gaacaaaact ttcagcttgc aaagcaaatt caatcccagt ggaaagaatt   2700
tggcctggat tctgttgagc tggcacatta tgatgtcctg ttgtcctacc caaataagac   2760
tcatcccaac tacatctcaa taattaatga agatggaaat gagattttca acacatcatt   2820
atttgaacca cctcctccag gatatgaaaa tgtttcggat attgtaccac ctttcagtgc   2880
tttctctcct caaggaatgc cagagggcga tctagtgtat gttaactatg cacgaactga   2940
agacttcttt aaattggaac gggacatgaa aatcaattgc tctgggaaaa ttgtaattgc   3000
cagatatggg aaagttttca gaggaaataa ggttaaaaat gcccagctgg caggggccaa   3060
aggagtcatt ctctactccg accctgctga ctactttgct cctggggtga agtcctatcc   3120
agatggttgg aatcttcctg gaggtggtgt ccagcgtgga aatatcctaa atctgaatgg   3180
tgcaggagac cctctcacac caggttaccc agcaaatgaa tatgcttata ggcgtggaat   3240
tgcagaggct gttggtcttc caagtattcc tgttcatcca attggatact atgatgcaca   3300
gaagctccta gaaaaaatgg gtggctcagc accaccagat agcagctgga gaggaagtct   3360
caaagtgccc tacaatgttg gacctggctt tactggaaac ttttctacac aaaaagtcaa   3420
gatgcacatc cactctacca atgaagtgac aagaatttac aatgtgatag gtactctcag   3480
aggagcagtg gaaccagaca gatatgtcat tctgggaggt caccgggact catgggtgtt   3540
tggtggtatt gaccctcaga gtggagcagc tgttgttcat gaaattgtga ggagctttgg   3600
aacactgaaa aaggaagggt ggagacctag aagaacaatt ttgtttgcaa gctgggatgc   3660
agaagaattt ggtcttcttg gttctactga gtgggcagag gagaattcaa gactccttca   3720
agagcgtggc gtggcttata ttaatgctga ctcatctata gaaggaaact acactctgag   3780
agttgattgt acaccgctga tgtacagctt ggtacacaac ctaacaaaag agctgaaaag   3840
ccctgatgaa ggctttgaag gcaaatctct ttatgaaagt tggactaaaa aaagtccttc   3900
cccagagttc agtggcatgc ccaggataag caaattggga tctggaaatg attttgaggt   3960
gttcttccaa cgacttggaa ttgcttcagg cagagcacgg tatactaaaa attgggaaac   4020
aaacaaattc agcggctatc cactgtatca cagtgtctat gaaacatatg agttggtgga   4080
aaagttttat gatccaatgt ttaaatatca cctcactgtg gcccaggttc gaggagggat   4140
ggtgtttgag ctggccaatt ccatagtgct ccccttttgat tgtcgagatt atgctgtagt   4200
tttaagaaag tatgctgaca aaatctacag tatttctatg aaacatccac aggaaatgaa   4260
gacatacagt gtatcatttg attcactttt ttctgcagta aagaatttta cagaaattgc   4320
ttccaagttc agtgagagac tccaggactt tgacaaaagc aacccaatag tattaagaat   4380
gatgaatgat caactcatgt ttctggaaag agcatttatt gatccattag ggttaccaga   4440
caggcctttt tataggcatg tcatctatgc tccaagcagc cacaacaagt atgcagggga   4500
gtcattccca ggaatttatg atgctctgtt tgatattgaa agcaaagtgg acccttccaa   4560
ggcctgggga gaagtgaaga gacagattta tgttgcagcc ttcacagtgc aggcagctgc   4620
agagactttg agtgaagtag cctaaagatc tgacccccta acgttactgg ccgaagccgc   4680
ttggaataag gccggtgtgc gtttgtctat atgttatttt ccaccatatt gccgtctttt   4740
ggcaatgtga gggcccggaa acctggccct gtcttcttga cgagcattcc taggggtctt   4800
tcccctctcg ccaaaggaat gcaaggtctg ttgaatgtcg tgaaggaagc agttcctctg   4860
gaagcttctt gaagacaaac aacgtctgta gcgacccttt gcaggcagcg gaacccccca   4920
```

cctggcgaca ggtgcctctg cggccaaaag ccacgtgtat aagatacacc tgcaaaggcg 4980
gcacaacccc agtgccacgt tgtgagttgg atagttgtgg aaagagtcaa atggctctcc 5040
tcaagcgtat tcaacaaggg gctgaaggat gcccagaagg taccccattg tatgggatct 5100
gatctggggc ctcggtgcac atgctttaca tgtgtttagt cgaggttaaa aaacgtctag 5160
gccccccgaa ccacggggac gtggttttcc tttgaaaaac acgatgataa tatggccagc 5220
attgtgggag gctgggagtg cgagaagcat tcccaaccct ggcaggtgct tgtggcctct 5280
cgtggcaggg cagtctgcgg cggtgttctg gtgcaccccc agtgggtcct cacagctgcc 5340
cactgcatca ggaacaaaag cgtgatcttg ctgggtcggc acagcttgtt tcatcctgaa 5400
gacacaggcc aggtatttca ggtcagccac agcttcccac acccgctcta cgatatgagc 5460
ctcctgaaga atcgattcct caggccaggt gatgactcca gccacgacct catgctgctc 5520
cgcctgtcag agcctgccga gctcacggat gctgtgaagg tcatggacct gcccacccag 5580
gagccagcac tggggaccac ctgctacgcc tcaggctggg gcagcattga accagaggag 5640
ttcttgaccc caaagaaact tcagtgtgtg gacctccatg ttatttccaa tgacgtgtgt 5700
gcgcaagttc accctcagaa ggtgaccaag ttcatgctgt gtgctggacg ctggacaggg 5760
ggcaaaagca cctgctcggg tgattctggg ggcccacttg tctgtaatgg tgtgcttcaa 5820
ggtatcacgt catggggcag tgaaccatgt gccctgcccg aaaggccttc cctgtacacc 5880
aaggtggtgc attaccggaa gtggatcaag gacaccatcg tggccaaccc ctgaggatct 5940
gggccctaac aaaacaaaaa gatggggtta ttccctaaac ttcatgggtt acgtaattgg 6000
aagttggggg acattgccac aagatcatat tgtacaaaag atcaaacact gttttagaaa 6060
acttcctgta aacaggccta ttgattggaa agtatgtcaa aggattgtgg gtcttttggg 6120
ctttgctgct ccatttacac aatgtggata tcctgcctta atgcctttgt atgcatgtat 6180
acaagctaaa caggctttca ctttctcgcc aacttacaag gcctttctaa gtaaacagta 6240
catgaacctt taccccgttg ctcggcaacg gcctggtctg tgccaagtgt ttgctgacgc 6300
aacccccact ggctggggct tggccatagg ccatcagcgc atgcgtggaa cctttgtggc 6360
tcctctgccg atccatactg cggaactcct agccgcttgt tttgctcgca gccggtctgg 6420
agcaaagctc ataggaactg acaattctgt cgtcctctcg cggaaatata catcgtttcg 6480
atctacgtat gatctttttc cctctgccaa aaattatggg gacatcatga agccccttga 6540
gcatctgact tctggctaat aaaggaaatt tattttcatt gcaatagtgt gttggaattt 6600
tttgtgtctc tcactcggaa ggaattctgc attaatgaat cggccaacgc gcggggagag 6660
gcggtttgcg tattgggcgc tcttccgctt cctcgctcac tgactcgctg cgctcggtcg 6720
ttcggctgcg gcgagcggta tcagctcact caaaggcggt aatacggtta tccacagaat 6780
caggggataa cgcaggaaag aacatgtgag caaaaggcca gcaaaaggcc aggaaccgta 6840
aaaaggccgc gttgctggcg tttttccata ggctccgccc ccctgacgag catcacaaaa 6900
atcgacgctc aagtcagagg tggcgaaacc cgacaggact ataaagatac caggcgtttc 6960
cccctggaag ctccctcgtg cgctctcctg ttccgaccct gccgcttacc ggatacctgt 7020
ccgcctttct cccttcggga agcgtggcgc tttctcatag ctcacgctgt aggtatctca 7080
gttcggtgta ggtcgttcgc tccaagctgg gctgtgtgca cgaacccccc gttcagcccg 7140
accgctgcgc cttatccggt aactatcgtc ttgagtccaa cccggtaaga cacgacttat 7200
cgccactggc agcagccact ggtaacagga ttagcagagc gaggtatgta ggcggtgcta 7260
cagagttctt gaagtggtgg cctaactacg gctacactag aagaacagta tttggtatct 7320
gcgctctgct gaagccagtt accttcggaa aaagagttgg tagctcttga tccggcaaac 7380
aaaccaccgc tggtagcggt ggtttttttg tttgcaagca gcagattacg cgcagaaaaa 7440
aaggatctca agaagatcct ttgatctttt ctacggggtc tgacgctcag tggaacgaaa 7500
actcacgtta agggattttg gtcatgagat tatcaaaaag gatcttcacc tagatccttt 7560
taaattaaaa atgaagtttt aaatcaatct aaagtatata tgagtaaact tggtctgaca 7620
gttaccaatg cttaatcagt gaggcaccta tctcagcgat ctgtctattt cgttcatcca 7680
tagttgcctg actc 7694

<210> SEQ ID NO 37
<211> LENGTH: 8461
<212> TYPE: DNA
<213> ORGANISM: Artificial
<220> FEATURE:
<223> OTHER INFORMATION: Synthetic Construct

<400> SEQUENCE: 37
catcatcaat aatatacctt attttggatt gaagccaata tgataatgag ggggtggagt 60
ttgtgacgtg gcgcggggcg tgggaacggg gcgggtgacg tagtagtgtg gcggaagtgt 120
gatgttgcaa gtgtggcgga acacatgtaa gcgacggatg tggcaaaagt gacgtttttg 180
gtgtgcgccg gtgtacacag gaagtgacaa ttttcgcgcg gttttaggcg gatgttgtag 240
taaatttggg cgtaaccgag taagatttgg ccattttcgc gggaaaactg aataagagga 300
agtgaaatct gaataatttt gtgttactca tagcgcgtaa tactgtaata gtaatcaatt 360
acggggtcat tagttcatag cccatatatg gagttccgcg ttacataact tacggtaaat 420
ggcccgcctg gctgaccgcc caacgacccc cgcccattga cgtcaataat gacgtatgtt 480
cccatagtaa cgccaatagg gactttccat tgacgtcaat gggtggagta tttacggtaa 540
actgcccact tggcagtaca tcaagtgtat catatgccaa gtacgccccc tattgacgtc 600
aatgacggta aatggcccgc ctggcattat gcccagtaca tgaccttatg ggactttcct 660
acttggcagt acatctacgt attagtcatc gctattacca tggtgatgcg gttttggcag 720
tacatcaatg ggcgtggata gcggtttgac tcacggggat ttccaagtct ccaccccatt 780
gacgtcaatg ggagtttgtt ttggcaccaa aatcaacggg actttccaaa atgtcgtaac 840
aactccgccc cattgacgca aatgggcggt aggcgtgtac ggtgggaggt ctatataagc 900
agagctggtt tagtgaaccg tcagatccgc tagagatcca ccatggctag cggtgccccg 960
acgttgcccc ctgcctggca gccctttctc aaggaccacc gcatctctac attcaagaac 1020
tggcccttct tggagggctg cgcctgcgcc ccggagcgga tggccgaggc tggcttcatc 1080
cactgcccca ctgagaacga gccagacttg gcccagtgtt tcttctgctt caaggagctg 1140
gaaggctggg agccagatga cgaccccata gaggaacata aaaagcattc gtccggttgc 1200
gctttccttt ctgtcaagaa gcagtttgaa gaattaaccc ttggtgaatt tttgaaactg 1260
gacagagaaa gagccaagaa caaaattgca aaggaaacca acaataagaa gaaagaattt 1320
gaggaaactg cggagaaagt gcgccgtgcc atcgagcagc tggctgccat ggattagaga 1380
tctgaccccc taacgttact ggccgaagcc gcttggaata aggccggtgt gcgtttgtct 1440
atatgttatt ttccaccata ttgccgtctt ttggcaatgt gagggcccgg aaacctggcc 1500
ctgtcttctt gacgagcatt cctaggggtc tttcccctct cgccaaagga atgcaaggtc 1560
tgttgaatgt cgtgaaggaa gcagttcctc tggaagcttc ttgaagacaa acaacgtctg 1620

```
tagcgaccct ttgcaggcag cggaaccccc cacctggcga caggtgcctc tgcggccaaa   1680
agccacgtgt ataagataca cctgcaaagg cggcacaacc ccagtgccac gttgtgagtt   1740
ggatagttgt ggaaagagtc aaatggctct cctcaagcgt attcaacaag gggctgaagg   1800
atgcccagaa ggtaccccat tgtatgggat ctgatctggg gcctcggtgc acatgcttta   1860
catgtgttta gtcgaggtta aaaaacgtct aggccccccg aaccacgggg acgtggtttt   1920
cctttgaaaa acacgataat atggcggccg ctcgagccta agcttctaga taagatatcc   1980
gatccaccgg atctagataa ctgatcataa tcagccatac cacatttgta gaggttttac   2040
ttgctttaaa aaacctccca cacctccccc tgaacctgaa acataaaatg aatgcaattg   2100
ttgttgttaa cttgtttatt gcagcttata atggttacaa ataaagcaat agcatcacaa   2160
atttcacaaa taaagcattt ttttcactgc attctagttg tggtttgtcc aaactcatca   2220
atgtatctta acgcggatct gggcgtggtt aagggtggga aagaatatat aaggtggggg   2280
tcttatgtag ttttgtatct gttttgcagc agccgccgcc gccatgagca ccaactcgtt   2340
tgatggaagc attgtgagct catatttgac aacgcgcatg cccccatggg ccggggtgcg   2400
tcagaatgtg atgggctcca gcattgatgg tcgccccgtc ctgcccgcaa actctactac   2460
cttgacctac gagaccgtgt ctggaacgcc gttggagact gcagcctccg ccgccgcttc   2520
agccgctgca gccaccgccc gcgggattgt gactgacttt gctttcctga gcccgcttgc   2580
aagcagtgca gcttcccgtt catccgcccg cgatgacaag ttgacggctc ttttggcaca   2640
attggattct ttgacccggg aacttaatgt cgtttctcag cagctgttgg atctgcgcca   2700
gcaggtttct gccctgaagg cttcctcccc tcccaatgcg gtttaaaaca taaataaaaa   2760
accagactct gtttggattt ggatcaagca agtgtcttgc tgtctttatt taggggtttt   2820
gcgcgcgcgg taggcccggg accagcggtc tcggtcgttg agggtcctgt gtattttttc   2880
caggacgtgg taaaggtgac tctggatgtt cagatacatg ggcataagcc cgtctctggg   2940
gtggaggtag caccactgca gagcttcatg ctgcggggtg gtgttgtaga tgatccagtc   3000
gtagcaggag cgctgggcgt ggtgcctaaa aatgtctttc agtagcaagc tgattgccag   3060
gggcaggccc ttggtgtaag tgtttacaaa gcggttaagc tgggatgggt gcatacgtgg   3120
ggatatgaga tgcatcttgg actgtatttt taggttggct atgttcccag ccatatccct   3180
ccggggattc atgttgtgca gaaccaccag cacagtgtat ccggtgcact tgggaaattt   3240
gtcatgtagc ttagaaggaa atgcgtggaa gaacttggag acgcccttgt gacctccaag   3300
attttccatg cattcgtcca taatgatggc aatgggccca cgggcggcgg cctgggcgaa   3360
gatatttctg ggatcactaa cgtcatagtt gtgttccagg atgagatcgt cataggccat   3420
ttttacaaag cgcgggcgga gggtgccaga ctgcggtata atggttccat ccggcccagg   3480
ggcgtagtta ccctcacaga tttgcatttc ccacgctttg agttcagatg gggggatcat   3540
gtctacctgc ggggcgatga agaaaacggt ttccggggta ggggagatca gctgggaaga   3600
aagcaggttc ctgagcagct gcgacttacc gcagccggtg ggcccgtaaa tcacacctat   3660
taccggctgc aactggtagt taagagagct gcagctgccg tcatccctga gcagggggc    3720
cacttcgtta agcatgtccc tgactcgcat gttttccctg accaaatccg ccagaaggcg   3780
ctcgccgccc agcgatagca gttcttgcaa ggaagcaaag tttttcaacg gtttgagacc   3840
gtccgccgta ggcatgcttt tgagcgtttg accaagcagt tccaggcggt cccacagctc   3900
ggtcacctgc tctacggcat ctcgatccag catatctcct cgtttcgcgg gttggggcgg   3960
ctttcgctgt acggcagtag tcggtgctcg tccagacggg ccagggtcat gtctttccac   4020
```

gggcgcaggg tcctcgtcag cgtagtctgg gtcacggtga aggggtgcgc tccgggctgc 4080
gcgctggcca gggtgcgctt gaggctggtc ctgctggtgc tgaagcgctg ccggtcttcg 4140
ccctgcgcgt cggccaggta gcatttgacc atggtgtcat agtccagccc ctccgcggcg 4200
tggcccttgg cgcgcagctt gcccttggag gaggcgccgc acgaggggca gtgcagactt 4260
ttgagggcgt agagcttggg cgcgagaaat accgattccg gggagtaggc atccgcgccg 4320
caggccccgc agacggtctc gcattccacg agccaggtga gctctggccg ttcggggtca 4380
aaaaccaggt ttcccccatg ctttttgatg cgtttcttac ctctggtttc catgagccgg 4440
tgtccacgct cggtgacgaa aaggctgtcc gtgtccccgt atacagactt gagagggagt 4500
ttaaacgaat tcaatagctt gttgcatggg cggcgatata aaatgcaagg tgctgctcaa 4560
aaaatcaggc aaagcctcgc gcaaaaaaga aagcacatcg tagtcatgct catgcagata 4620
aaggcaggta agctccggaa ccaccacaga aaaagacacc atttttctct caaacatgtc 4680
tgcgggtttc tgcataaaca caaaataaaa taacaaaaaa acatttaaac attagaagcc 4740
tgtcttacaa caggaaaaac aacccttata agcataagac ggactacggc catgccggcg 4800
tgaccgtaaa aaaactggtc accgtgatta aaaagcacca ccgacagctc ctcggtcatg 4860
tccggagtca taatgtaaga ctcggtaaac acatcaggtt gattcacatc ggtcagtgct 4920
aaaaagcgac cgaaatagcc cgggggaata catacccgca ggcgtagaga caacattaca 4980
gcccccatag gaggtataac aaaattaata ggagagaaaa acacataaac acctgaaaaa 5040
ccctcctgcc taggcaaaat agcaccctcc cgctccagaa caacatacag cgcttccaca 5100
gcggcagcca taacagtcag ccttaccagt aaaaaagaaa acctattaaa aaaacaccac 5160
tcgacacggc accagctcaa tcagtcacag tgtaaaaaag ggccaagtgc agagcgagta 5220
tatataggac taaaaaatga cgtaacggtt aaagtccaca aaaaacaccc agaaaaccgc 5280
acgcgaacct acgcccagaa acgaaagcca aaaaacccac aacttcctca aatcgtcact 5340
tccgttttcc cacgttacgt cacttcccat tttaagaaaa ctacaattcc caacacatac 5400
aagttactcc gccctaaaac ctacgtcacc cgccccgttc ccacgccccg cgccacgtca 5460
caaactccac cccctcatta tcatattggc ttcaatccaa aataaggtat attattgatg 5520
atgttaatta acatgcatgg atccatatgc ggtgtgaaat accgcacaga tgcgtaagga 5580
gaaaataccg catcaggcgc tcttccgctt cctcgctcac tgactcgctg cgctcggtcg 5640
ttcggctgcg gcgagcggta tcagctcact caaaggcggt aatacggtta tccacagaat 5700
caggggataa cgcaggaaag aacatgtgag caaaaggcca gcaaaaggcc aggaaccgta 5760
aaaaggccgc gttgctggcg tttttccata ggctccgccc ccctgacgag catcacaaaa 5820
atcgacgctc aagtcagagg tggcgaaacc cgacaggact ataaagatac caggcgtttc 5880
cccctggaag ctccctcgtg cgctctcctg ttccgaccct gccgcttacc ggatacctgt 5940
ccgcctttct cccttcggga agcgtggcgc tttctcatag ctcacgctgt aggtatctca 6000
gttcggtgta ggtcgttcgc tccaagctgg gctgtgtgca cgaacccccc gttcagcccg 6060
accgctgcgc cttatccggt aactatcgtc ttgagtccaa cccggtaaga cacgacttat 6120
cgccactggc agcagccact ggtaacagga ttagcagagc gaggtatgta ggcggtgcta 6180
cagagttctt gaagtggtgg cctaactacg gctacactag aaggacagta tttggtatct 6240
gcgctctgct gaagccagtt accttcggaa aaagagttgg tagctcttga tccggcaaac 6300
aaaccaccgc tggtagcggt ggtttttttg tttgcaagca gcagattacg cgcagaaaaa 6360

-continued

```
aaggatctca agaagatcct ttgatctttt ctacggggtc tgacgctcag tggaacgaaa   6420
actcacgtta agggattttg gtcatgagat tatcaaaaag gatcttcacc tagatccttt   6480
taaattaaaa atgaagtttt aaatcaatct aaagtatata tgagtaaact tggtctgaca   6540
gttaccaatg cttaatcagt gaggcaccta tctcagcgat ctgtctattt cgttcatcca   6600
tagttgcctg actccccgtc gtgtagataa ctacgatacg ggagggctta ccatctggcc   6660
ccagtgctgc aatgataccg cgagacccac gctcaccggc tccagattta tcagcaataa   6720
accagccagc cggaagggcc gagcgcagaa gtggtcctgc aactttatcc gcctccatcc   6780
agtctattaa ttgttgccgg gaagctagag taagtagttc gccagttaat agtttgcgca   6840
acgttgttgc cattgctgca gccatgagat tatcaaaaag gatcttcacc tagatccttt   6900
tcacgtagaa agccagtccg cagaaacggt gctgaccccg gatgaatgtc agctactggg   6960
ctatctggac aagggaaaac gcaagcgcaa agagaaagca ggtagcttgc agtgggctta   7020
catggcgata gctagactgg gcggttttat ggacagcaag cgaaccggaa ttgccagctg   7080
gggcgccctc tggtaaggtt gggaagccct gcaaagtaaa ctggatggct ttcttgccgc   7140
caaggatctg atggcgcagg ggatcaagct ctgatcaaga gacaggatga ggatcgtttc   7200
gcatgattga acaagatgga ttgcacgcag gttctccggc cgcttgggtg gagaggctat   7260
tcggctatga ctgggcacaa cagacaatcg gctgctctga tgccgccgtg ttccggctgt   7320
cagcgcaggg gcgcccggtt ctttttgtca agaccgacct gtccggtgcc ctgaatgaac   7380
tgcaagacga ggcagcgcgg ctatcgtggc tggccacgac gggcgttcct tgcgcagctg   7440
tgctcgacgt tgtcactgaa gcgggaaggg actggctgct attgggcgaa gtgccggggc   7500
aggatctcct gtcatctcac cttgctcctg ccgagaaagt atccatcatg gctgatgcaa   7560
tgcggcggct gcatacgctt gatccggcta cctgcccatt cgaccaccaa gcgaaacatc   7620
gcatcgagcg agcacgtact cggatggaag ccggtcttgt cgatcaggat gatctggacg   7680
aagagcatca ggggctcgcg ccagccgaac tgttcgccag gctcaaggcg agcatgcccg   7740
acggcgagga tctcgtcgtg acccatggcg atgcctgctt gccgaatatc atggtggaaa   7800
atggccgctt ttctggattc atcgactgtg gccggctggg tgtggcggac cgctatcagg   7860
acatagcgtt ggctacccgt gatattgctg aagagcttgg cggcgaatgg gctgaccgct   7920
tcctcgtgct ttacggtatc gccgctcccg attcgcagcg catcgccttc tatcgccttc   7980
ttgacgagtt cttctgaatt ttgttaaaat tttgttaaa tcagctcatt ttttaaccaa    8040
taggccgaaa tcggcaccat cccttataaa tcaaaagaat agaccgagat agggttgagt   8100
gttgttccag tttggaacaa gagtccacta ttaaagaacg tggactccaa cgtcaaaggg   8160
cgaaaaaccg tctatcaggg cgatggccca ctacgtgaac catcacccta atcaagtttt   8220
ttgtggtcga ggtgccgtaa agcactaaat cggaacccta aagggagccc ccgatttaga   8280
gcttgacggg gaaagccggc gaacgtggcg agaaaggaag ggaagaaagc gaaaggagcg   8340
ggcgctaggg cgctggcaag tgtagcggtc acgctgcgcg taaccaccac acccgcgcgc   8400
ttaatgcgcc gctacagggc gcgtccattc gccattcagg atcgaattaa ttcttaatta   8460
a                                                                   8461
```

<210> SEQ ID NO 38
<211> LENGTH: 956
<212> TYPE: PRT
<213> ORGANISM: Artificial
<220> FEATURE:
<223> OTHER INFORMATION: Synthetic Construct

<400> SEQUENCE: 38

```
Met Ala Ser Glu Leu Ala Ala Leu Cys Arg Trp Gly Leu Leu Leu Ala
1               5                   10                  15

Leu Leu Pro Pro Gly Ala Ala Ser Thr Gln Val Cys Thr Gly Thr Asp
            20                  25                  30

Met Lys Leu Arg Leu Pro Ala Ser Pro Glu Thr His Leu Asp Met Leu
        35                  40                  45

Arg His Leu Tyr Gln Gly Cys Gln Val Val Gln Gly Asn Leu Glu Leu
    50                  55                  60

Thr Tyr Leu Pro Thr Asn Ala Ser Leu Ser Phe Leu Gln Asp Ile Gln
65                  70                  75                  80

Glu Val Gln Gly Tyr Val Leu Ile Ala His Asn Gln Val Arg Gln Val
                85                  90                  95

Pro Leu Gln Arg Leu Arg Ile Val Arg Gly Thr Gln Leu Phe Glu Asp
            100                 105                 110

Asn Tyr Ala Leu Ala Val Leu Asp Asn Gly Asp Pro Leu Asp Ser Val
        115                 120                 125

Ala Pro Ala Ala Gly Ala Thr Pro Gly Gly Leu Gln Glu Leu Gln Leu
    130                 135                 140

Arg Ser Leu Thr Glu Ile Leu Lys Gly Gly Val Leu Ile Arg Arg Ser
145                 150                 155                 160

Pro Gln Leu Cys His Gln Asp Thr Val Leu Trp Glu Asp Val Phe Arg
                165                 170                 175

Lys Asn Asn Gln Leu Ala Leu Val Leu Met Asp Thr Asn Arg Ser Arg
            180                 185                 190

Ala Cys His Pro Cys Ala Pro Met Cys Lys Ala Asn His Cys Trp Gly
        195                 200                 205

Glu Ser Ser Gln Asp Cys Gln Thr Leu Thr Arg Thr Ile Cys Thr Ser
    210                 215                 220

Ala Cys Ala Arg Cys Lys Ala Pro Leu Pro Thr Asp Cys Cys His Glu
225                 230                 235                 240

Gln Cys Ala Ala Gly Cys Thr Gly Pro Lys His Ser Asp Cys Leu Ala
                245                 250                 255

Cys Leu His Phe Asn His Ser Gly Ile Cys Glu Leu His Cys Pro Ala
            260                 265                 270

Leu Val Thr Tyr Asn Thr Asp Thr Phe Glu Ser Met Pro Asn Pro Glu
        275                 280                 285

Gly Arg Tyr Thr Phe Gly Ala Ser Cys Val Thr Ala Cys Pro Tyr Asn
    290                 295                 300

Tyr Leu Ser Thr Asp Val Gly Ser Cys Thr Leu Val Cys Pro Leu His
305                 310                 315                 320

Asn Gln Glu Val Thr Ala Glu Asp Gly Thr Gln Arg Cys Glu Lys Cys
                325                 330                 335

Ser Lys Pro Cys Ala Arg Val Cys Tyr Gly Leu Gly Met Glu His Leu
            340                 345                 350

Arg Glu Ala Arg Ala Ile Thr Ser Ala Asn Val Gln Asp Phe Val Gly
        355                 360                 365

Cys Lys Lys Ile Phe Gly Ser Leu Ala Phe Leu Pro Glu Ser Phe Asp
    370                 375                 380

Gly Asp Pro Ala Ser Gly Thr Ala Pro Leu Gln Pro Glu Gln Leu Gln
385                 390                 395                 400

Val Phe Glu Thr Leu Glu Glu Ile Thr Gly Tyr Leu Tyr Ile Ser Ala
```

405 410 415

Trp Pro Asp Ser Phe Pro Asn Leu Ser Val Phe Gln Asn Leu Arg Val
420 425 430

Ile Arg Gly Arg Ile Leu His Asn Gly Ala Tyr Ser Leu Thr Leu Gln
435 440 445

Gly Leu Gly Ile Ser Trp Leu Gly Leu Arg Ser Leu Gln Glu Leu Gly
450 455 460

Ser Gly Leu Ala Leu Val His Arg Asn Ala Arg Leu Cys Phe Val His
465 470 475 480

Thr Val Pro Trp Asp Gln Leu Phe Arg Asn Pro His Gln Ala Leu Leu
485 490 495

His Ser Gly Asn Arg Pro Glu Glu Asp Cys Val Gly Glu Gly Phe Val
500 505 510

Cys Tyr Ser Leu Cys Ala His Gly His Cys Trp Gly Pro Gly Pro Thr
515 520 525

Gln Cys Val Asn Cys Ser His Phe Leu Arg Gly Gln Glu Cys Val Glu
530 535 540

Glu Cys Arg Val Leu Gln Gly Leu Pro Arg Glu Tyr Val Asn Ala Arg
545 550 555 560

His Cys Leu Pro Cys His Pro Glu Cys Gln Pro Gln Asn Gly Ser Val
565 570 575

Thr Cys Phe Gly Pro Glu Ala Asp Gln Cys Val Ala Cys Ala His Tyr
580 585 590

Lys Asp Pro Pro Phe Cys Val Ala Arg Cys Pro Ser Gly Val Lys Pro
595 600 605

Asp Leu Ser Tyr Met Pro Ile Trp Lys Phe Pro Asp Glu Glu Gly Ala
610 615 620

Cys Gln Pro Cys Pro Ile Asn Cys Thr His Ser Cys Val Asp Leu Asp
625 630 635 640

Asp Lys Gly Cys Pro Ala Glu Gln Arg Ala Ser Pro Leu Thr Ser Ile
645 650 655

Ile Ser Ala Val Val Gly Ile Leu Leu Val Val Val Leu Gly Val Val
660 665 670

Phe Gly Ile Leu Ile Lys Arg Arg Gln Gln Lys Ile Arg Lys Tyr Thr
675 680 685

Met Arg Arg Asn Glu Asp Leu Gly Pro Ser Ser Pro Met Asp Ser Thr
690 695 700

Phe Tyr Arg Ser Leu Leu Glu Asp Glu Asp Met Gly Glu Leu Val Asp
705 710 715 720

Ala Glu Glu Tyr Leu Val Pro Gln Gln Gly Phe Phe Cys Pro Asp Pro
725 730 735

Thr Pro Gly Thr Gly Ser Thr Ala His Arg Arg His Arg Ser Ser Ser
740 745 750

Ala Arg Asn Gly Gly Gly Asp Leu Thr Leu Gly Met Glu Pro Ser Gly
755 760 765

Glu Gly Pro Pro Arg Ser Pro Arg Ala Pro Ser Glu Gly Thr Gly Ser
770 775 780

Asp Val Phe Asp Gly Asp Leu Ala Val Gly Val Thr Lys Gly Leu Gln
785 790 795 800

Ser Leu Ser Pro Gln Asp Leu Ser Pro Leu Gln Arg Tyr Ser Glu Asp
805 810 815

Pro Thr Leu Pro Leu Pro Ser Glu Thr Asp Gly Lys Val Ala Pro Leu
820 825 830

Ser Cys Ser Pro Gln Pro Glu Phe Val Asn Gln Ser Asp Val Gln Pro
835 840 845

Lys Ser Pro Leu Thr Pro Glu Gly Pro Pro Ser Pro Ala Arg Pro Thr
850 855 860

Gly Ala Thr Leu Glu Arg Ala Lys Thr Leu Ser Pro Gly Lys Asn Gly
865 870 875 880

Val Val Lys Asp Val Phe Thr Phe Gly Gly Ala Val Glu Asn Pro Glu
885 890 895

Phe Leu Ala Pro Arg Glu Gly Thr Ala Ser Pro Pro His Pro Ser Pro
900 905 910

Ala Phe Ser Pro Ala Phe Asp Asn Leu Phe Phe Trp Asp Gln Asn Ser
915 920 925

Ser Glu Gln Gly Pro Pro Pro Ser Asn Phe Glu Gly Thr Pro Thr Ala
930 935 940

Glu Asn Pro Glu Phe Leu Gly Leu Asp Val Pro Val
945 950 955

<210> SEQ ID NO 39
<211> LENGTH: 2871
<212> TYPE: DNA
<213> ORGANISM: Artificial
<220> FEATURE:
<223> OTHER INFORMATION: Synthetic Construct

<400> SEQUENCE: 39
atggctagcg agctggccgc cctgtgtaga tggggactgc tgctggctct gctgcctcct 60
ggagccgctt ctacacaggt ctgcaccggc accgacatga agctgagact gcccgccagc 120
cccgagacac acctggacat gctgcggcac ctgtaccagg gctgccaggt ggtccagggg 180
aatctggaac tgacctacct gcccaccaac gccagcctga gcttcctgca ggacatccag 240
gaagtgcagg gctacgtcct gatcgcccac aaccaggtcc gccaggtgcc cctgcagcgg 300
ctgagaatcg tgcggggcac ccagctgttc gaggacaact acgccctggc cgtgctggac 360
aacggcgacc ctctggatag cgtggcccct gctgctgggg ctacacctgg cggactgcag 420
gaactgcagc tgcggagcct gaccgagatc ctgaagggcg gcgtgctgat caggcggagc 480
cctcagctgt gccaccagga caccgtgctg tgggaggacg tgttccggaa gaacaaccag 540
ctggccctcg tgctgatgga caccaacaga agccgggcct gccacccctg cgcccccatg 600
tgcaaggcca atcactgctg gggagagagc agccaggact gccagaccct gacccggacc 660
atctgcacca gcgcctgcgc cagatgcaag gccccccctgc ctaccgactg ctgccacgaa 720
cagtgcgccg ctggctgcac cggccccaag cacagcgatt gcctggcctg cctgcacttc 780
aaccacagcg gcatctgcga gctgcactgc cctgccctgg tgacatacaa caccgacacc 840
ttcgagagca tgcccaaccc cgagggccgg tacaccttcg gcgccagctg tgtgaccgcc 900
tgcccctaca actacctgag caccgacgtg ggcagctgca ccctggtgtg cccccctgcac 960 aaccaggaag tgaccgccga ggacggcacc cagagatgcg agaagtgcag caagccttgc 1020
gccagagtgt gctacggcct gggcatggaa cacctgagag aggccagagc catcaccagc 1080
gccaacgtgc aggacttcgt gggctgcaag aagattttcg gctccctggc cttcctgccc 1140
gagagcttcg acggcgatcc tgcctctggc accgcccctc tgcagcctga gcagctgcag 1200
gtcttcgaga cactggaaga gatcaccggc tacctgtaca tcagcgcctg gcccgacagc 1260
ttccccaacc tgagcgtgtt ccagaacctg agagtgatcc ggggcagaat cctgcacaac 1320
ggcgcctaca gcctgaccct gcagggcctg ggaatcagct ggctgggcct gcggagcctg 1380
caggaactgg gatctggcct ggctctggtg caccggaacg cccggctgtg cttcgtgcac 1440
accgtgccct gggaccagct gttcagaaac cccccaccagg ctctgctgca cagcggcaac 1500
cggcccgaag aggattgcgt gggcgagggc ttcgtgtgct actccctgtg cgcccacggc 1560
cactgttggg gacctggccc tacccagtgc gtgaactgca gccacttcct gcggggccaa 1620
gaatgcgtgg aagagtgccg ggtgctgcag ggactgcccc gggaatacgt gaacgccaga 1680
cactgcctgc cttgccaccc cgagtgccag ccccagaatg gcagcgtgac ctgcttcgga 1740
cccgaggccg atcagtgtgt ggcctgcgcc cactacaagg acccccccatt ctgcgtggcc 1800 agatgcccca gcggcgtgaa gcccgacctg agctacatgc ccatctggaa gttccccgac 1860
gaggaaggcg cctgccagcc ttgccccatc aactgcaccc acagctgcgt ggacctggac 1920
gacaagggct gccctgccga gcagagagcc agcccccctga ccagcatcat cagcgccgtg 1980
gtgggaatcc tgctggtggt ggtgctgggc gtggtgttcg gcatcctgat caagcggcgg 2040
cagcagaaga tccggaagta caccatgcgg cggaacgagg acctgggccc ctctagcccc 2100
atggacagca ccttctaccg gtccctgctg gaagatgagg acatgggcga gctggtggac 2160
gccgaggaat acctggtgcc tcagcagggc ttcttctgcc ccgaccctac ccctggcacc 2220
ggctctaccg cccacagacg gcacagaagc agcagcgcca gaaacggcgg aggcgacctg 2280
accctgggaa tggaacctag cggcgaggga cctcccagaa gccctagagc ccctagcgag 2340
ggcaccggca gcgacgtgtt cgatggcgat ctggccgtgg gcgtgaccaa gggactgcag 2400
agcctgagcc cccaggacct gtccccccctg cagagataca gcgaggaccc caccctgccc 2460
ctgcccagcg agacagatgg caaggtggcc cccctgagct gcagccctca gcccgagttc 2520
gtgaaccaga gcgacgtgca gcccaagtcc cccctgacac ccgagggacc tccaagccct 2580
gccagaccta ccggcgccac cctggaaaga gccaagaccc tgagccccgg caagaacggc 2640
gtggtgaaag acgtgttcac cttcggaggc gccgtggaaa accccgagtt cctggccccc 2700
agagagggca cagccagccc tccacacccc agcccagcct tctcccccgc cttcgacaac 2760
ctgttcttct gggaccagaa cagcagcgag cagggcccac cccccagcaa tttcgagggc 2820
acccccaccg ccgagaatcc tgagttcctg ggcctggacg tgcccgtgtg a 2871

<210> SEQ ID NO 40
<211> LENGTH: 471
<212> TYPE: PRT
<213> ORGANISM: Artificial
<220> FEATURE:
<223> OTHER INFORMATION: Synthetic Construct

<400> SEQUENCE: 40

Met Asp Trp Thr Trp Arg Ile Leu Phe Leu Val Ala Ala Ala Thr Gly
1 5 10 15

Ala His Ser Gln Val Gln Leu Val Gln Ser Gly Ala Glu Val Lys Lys
20 25 30

Pro Gly Ala Ser Val Lys Val Ser Cys Lys Ala Ser Gly Tyr Thr Phe
35 40 45

Thr Gly Tyr Tyr Met His Trp Val Arg Gln Ala Pro Gly Gln Gly Leu
50 55 60

Glu Trp Met Gly Trp Ile Asn Pro Asp Ser Gly Gly Thr Asn Tyr Ala
65 70 75 80

Gln Lys Phe Gln Gly Arg Val Thr Met Thr Arg Asp Thr Ser Ile Ser
85 90 95

```
Thr Ala Tyr Met Glu Leu Asn Arg Leu Arg Ser Asp Asp Thr Ala Val
            100                 105                 110

Tyr Tyr Cys Ala Arg Asp Gln Pro Leu Gly Tyr Cys Thr Asn Gly Val
        115                 120                 125

Cys Ser Tyr Phe Asp Tyr Trp Gly Gln Gly Thr Leu Val Thr Val Ser
    130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Asn Phe Gly Thr Gln
    210                 215                 220

Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Gln Phe Asn Trp Tyr Val Asp
    290                 295                 300

Gly Val Glu Val His Asn Ala Lys Thr Lys Pro Arg Glu Glu Gln Phe
305                 310                 315                 320

Asn Ser Thr Phe Arg Val Val Ser Val Leu Thr Val Val His Gln Asp
                325                 330                 335

Trp Leu Asn Gly Lys Glu Tyr Lys Cys Lys Val Ser Asn Lys Gly Leu
            340                 345                 350

Pro Ala Pro Ile Glu Lys Thr Ile Ser Lys Thr Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Met Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470
```

<210> SEQ ID NO 41
<211> LENGTH: 234
<212> TYPE: PRT
<213> ORGANISM: Artificial
<220> FEATURE:

<223> OTHER INFORMATION: Synthetic Construct

<400> SEQUENCE: 41

Met Arg Leu Pro Ala Gln Leu Leu Gly Leu Leu Leu Leu Trp Phe Pro
1               5                   10                  15

Gly Ser Arg Cys Asp Ile Gln Met Thr Gln Ser Pro Ser Ser Val Ser
            20                  25                  30

Ala Ser Val Gly Asp Arg Val Thr Ile Thr Cys Arg Ala Ser Gln Gly
        35                  40                  45

Ile Tyr Ser Trp Leu Ala Trp Tyr Gln Gln Lys Pro Gly Lys Ala Pro
    50                  55                  60

Asn Leu Leu Ile Tyr Thr Ala Ser Thr Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Ala Asn
            100                 105                 110

Ile Phe Pro Leu Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 42
<211> LENGTH: 451
<212> TYPE: PRT
<213> ORGANISM: Artificial
<220> FEATURE:
<223> OTHER INFORMATION: Synthetic Construct

<400> SEQUENCE: 42

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Arg Gly Ala Thr Leu Tyr Tyr Tyr Tyr Tyr Gly Met
            100                 105                 110

```
Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 43
<211> LENGTH: 214
<212> TYPE: PRT
<213> ORGANISM: Artificial
<220> FEATURE:
<223> OTHER INFORMATION: Synthetic Construct

<400> SEQUENCE: 43

```
Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Ser Ile Asn Ser Tyr
            20                  25                  30

Leu Asp Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Phe
                85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 44
<211> LENGTH: 24
<212> TYPE: DNA
<213> ORGANISM: Artificial
<220> FEATURE:
<223> OTHER INFORMATION: Synthetic Construct

<400> SEQUENCE: 44
tcgtcgtttt gtcgttttgt cgtt 24

<210> SEQ ID NO 45
<211> LENGTH: 21
<212> TYPE: DNA
<213> ORGANISM: Artificial
<220> FEATURE:
<223> OTHER INFORMATION: Synthetic Construct

<400> SEQUENCE: 45
tcgtcgtttt tcggtgcttt t 21

<210> SEQ ID NO 46
<211> LENGTH: 21
<212> TYPE: DNA
<213> ORGANISM: Artificial
<220> FEATURE:
<223> OTHER INFORMATION: Synthetic Construct

<400> SEQUENCE: 46
tcgtcgtttt tcggtcgttt t 21

<210> SEQ ID NO 47
<211> LENGTH: 239

<212> TYPE: PRT
<213> ORGANISM: Artificial
<220> FEATURE:
<223> OTHER INFORMATION: Synthetic Construct

<400> SEQUENCE: 47

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 48
<211> LENGTH: 185
<212> TYPE: PRT
<213> ORGANISM: Orthohepadnavirus hepatitis B virus

<400> SEQUENCE: 48

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
```

100 105 110

Glu Thr Val Leu Glu Tyr Leu Val Ser Phe Gly Val Trp Ile Arg Thr
115 120 125

Pro Pro Ala Tyr Arg Pro Pro Asn Ala Pro Ile Leu Ser Thr Leu Pro
130 135 140

Glu Thr Thr Val Val Arg Arg Arg Gly Arg Gly Arg Ser Pro Arg Arg
145 150 155 160

Arg Thr Pro Ser Pro Arg Arg Arg Arg Ser Gln Ser Pro Arg Arg Arg
165 170 175

Arg Ser Gln Ser Arg Glu Ser Gln Cys
180 185

<210> SEQ ID NO 49
<211> LENGTH: 226
<212> TYPE: PRT
<213> ORGANISM: Orthohepadnavirus hepatitis B virus

<400> SEQUENCE: 49

Met Glu Asn Ile Thr Ser Gly Phe Leu Gly Pro Leu Leu Val Leu Gln
1 5 10 15

Ala Gly Phe Phe Leu Leu Thr Arg Ile Leu Thr Ile Pro Gln Ser Leu
20 25 30

Asp Ser Trp Trp Thr Ser Leu Asn Phe Leu Gly Gly Ser Pro Val Cys
35 40 45

Leu Gly Gln Asn Ser Gln Ser Pro Thr Ser Asn His Ser Pro Thr Ser
50 55 60

Cys Pro Pro Ile Cys Pro Gly Tyr Arg Trp Met Cys Leu Arg Arg Phe
65 70 75 80

Ile Ile Phe Leu Phe Ile Leu Leu Leu Cys Leu Ile Phe Leu Leu Val
85 90 95

Leu Leu Asp Tyr Gln Gly Met Leu Pro Val Cys Pro Leu Ile Pro Gly
100 105 110

Ser Thr Thr Thr Ser Thr Gly Pro Cys Lys Thr Cys Thr Thr Pro Ala
115 120 125

Gln Gly Asn Ser Met Phe Pro Ser Cys Cys Cys Thr Lys Pro Thr Asp
130 135 140

Gly Asn Cys Thr Cys Ile Pro Ile Pro Ser Ser Trp Ala Phe Ala Lys
145 150 155 160

Tyr Leu Trp Glu Trp Ala Ser Val Arg Phe Ser Trp Leu Ser Leu Leu
165 170 175

Val Pro Phe Val Gln Trp Phe Val Gly Leu Ser Pro Thr Val Trp Leu
180 185 190

Ser Ala Ile Trp Met Met Trp Tyr Trp Gly Pro Ser Leu Tyr Ser Ile
195 200 205

Val Ser Pro Phe Ile Pro Leu Leu Pro Ile Phe Phe Cys Leu Trp Val
210 215 220

Tyr Ile
225

<210> SEQ ID NO 50
<211> LENGTH: 737
<212> TYPE: PRT
<213> ORGANISM: Artificial
<220> FEATURE:
<223> OTHER INFORMATION: Synthetic Construct

<400> SEQUENCE: 50

```
Met Ala Ser Glu Thr Asp Thr Leu Leu Leu Trp Val Leu Leu Leu Trp
1               5                   10                  15

Val Pro Gly Ser Thr Gly Asp Ala Ala His His His His His His Lys
            20                  25                  30

Ser Ser Ser Glu Ala Thr Asn Ile Thr Pro Lys His Asn Met Lys Ala
        35                  40                  45

Phe Leu Asp Glu Leu Lys Ala Glu Asn Ile Lys Lys Phe Leu His Asn
    50                  55                  60

Phe Thr Gln Ile Pro His Leu Ala Gly Thr Glu Gln Asn Phe Gln Leu
65                  70                  75                  80

Ala Lys Gln Ile Gln Ser Gln Trp Lys Glu Phe Gly Leu Asp Ser Val
                85                  90                  95

Glu Leu Thr His Tyr Asp Val Leu Leu Ser Tyr Pro Asn Lys Thr His
            100                 105                 110

Pro Asn Tyr Ile Ser Ile Ile Asn Glu Asp Gly Asn Glu Ile Phe Asn
        115                 120                 125

Thr Ser Leu Phe Glu Pro Pro Pro Ala Gly Tyr Glu Asn Val Ser Asp
    130                 135                 140

Ile Val Pro Pro Phe Ser Ala Phe Ser Pro Gln Gly Met Pro Glu Gly
145                 150                 155                 160

Asp Leu Val Tyr Val Asn Tyr Ala Arg Thr Glu Asp Phe Phe Lys Leu
                165                 170                 175

Glu Arg Asp Met Lys Ile Asn Cys Ser Gly Lys Ile Val Ile Ala Arg
            180                 185                 190

Tyr Gly Lys Val Phe Arg Gly Asn Lys Val Lys Asn Ala Gln Leu Ala
        195                 200                 205

Gly Ala Thr Gly Val Ile Leu Tyr Ser Asp Pro Ala Asp Tyr Phe Ala
    210                 215                 220

Pro Gly Val Lys Ser Tyr Pro Asp Gly Trp Asn Leu Pro Gly Gly Gly
225                 230                 235                 240

Val Gln Arg Gly Asn Ile Leu Asn Leu Asn Gly Ala Gly Asp Pro Leu
                245                 250                 255

Thr Pro Gly Tyr Pro Ala Asn Glu Tyr Ala Tyr Arg Arg Gly Ile Ala
            260                 265                 270

Glu Ala Val Gly Leu Pro Ser Ile Pro Val His Pro Ile Gly Tyr Tyr
        275                 280                 285

Asp Ala Gln Lys Leu Leu Glu Lys Met Gly Gly Ser Ala Ser Pro Asp
    290                 295                 300

Ser Ser Trp Arg Gly Ser Leu Lys Val Pro Tyr Asn Val Gly Pro Gly
305                 310                 315                 320

Phe Thr Gly Asn Phe Ser Thr Gln Lys Val Lys Met His Ile His Ser
                325                 330                 335

Thr Ser Glu Val Thr Arg Ile Tyr Asn Val Ile Gly Thr Leu Arg Gly
            340                 345                 350

Ala Val Glu Pro Asp Arg Tyr Val Ile Leu Gly Gly His Arg Asp Ser
        355                 360                 365

Trp Val Phe Gly Gly Ile Asp Pro Gln Ser Gly Ala Ala Val Val His
    370                 375                 380

Glu Ile Val Arg Ser Phe Gly Thr Leu Lys Lys Glu Gly Trp Arg Pro
385                 390                 395                 400

Arg Arg Thr Ile Leu Phe Ala Ser Trp Asp Ala Glu Glu Phe Gly Leu
                405                 410                 415
```

```
Leu Gly Ser Thr Glu Trp Ala Glu Glu Asn Ser Arg Leu Leu Gln Glu
            420                 425                 430

Arg Gly Val Ala Tyr Ile Asn Ala Asp Ser Ser Ile Glu Gly Asn Tyr
        435                 440                 445

Thr Leu Arg Val Asp Cys Thr Pro Leu Met Tyr Ser Leu Val Tyr Asn
    450                 455                 460

Leu Thr Lys Glu Leu Glu Ser Pro Asp Glu Gly Phe Glu Gly Lys Ser
465                 470                 475                 480

Leu Tyr Glu Ser Trp Thr Lys Ser Pro Ser Pro Glu Phe Ser Gly Met
                485                 490                 495

Pro Arg Ile Ser Lys Leu Gly Ser Gly Asn Asp Phe Glu Val Phe Phe
            500                 505                 510

Gln Arg Leu Gly Ile Ala Ser Gly Arg Ala Arg Tyr Thr Lys Asn Trp
        515                 520                 525

Glu Thr Asn Lys Phe Ser Ser Tyr Pro Leu Tyr His Ser Val Tyr Glu
    530                 535                 540

Thr Tyr Glu Leu Val Glu Lys Phe Tyr Asp Pro Met Phe Lys Tyr His
545                 550                 555                 560

Leu Thr Val Ala Gln Val Arg Gly Gly Met Val Phe Glu Leu Ala Asn
                565                 570                 575

Ser Val Val Leu Pro Phe Asp Cys Arg Asp Tyr Ala Val Val Leu Arg
            580                 585                 590

Lys Tyr Ala Asp Lys Ile Tyr Asn Ile Ser Met Lys His Pro Gln Glu
        595                 600                 605

Met Lys Thr Tyr Ser Val Ser Phe Asp Ser Leu Phe Ser Ala Val Lys
    610                 615                 620

Asn Phe Thr Glu Ile Ala Ser Lys Phe Ser Glu Arg Leu Arg Asp Phe
625                 630                 635                 640

Asp Lys Ser Asn Pro Ile Leu Leu Arg Met Met Asn Asp Gln Leu Met
                645                 650                 655

Phe Leu Glu Arg Ala Phe Ile Asp Pro Leu Gly Leu Pro Asp Arg Pro
            660                 665                 670

Phe Tyr Arg His Val Ile Tyr Ala Pro Ser Ser His Asn Lys Tyr Ala
        675                 680                 685

Gly Glu Ser Phe Pro Gly Ile Tyr Asp Ala Leu Phe Asp Ile Glu Ser
    690                 695                 700

Lys Val Asp Pro Ser Gln Ala Trp Gly Glu Val Lys Arg Gln Ile Ser
705                 710                 715                 720

Ile Ala Thr Phe Thr Val Gln Ala Ala Ala Glu Thr Leu Ser Glu Val
                725                 730                 735

Ala


<210> SEQ ID NO 51
<211> LENGTH: 9
<212> TYPE: PRT
<213> ORGANISM: Artificial
<220> FEATURE:
<223> OTHER INFORMATION: Synthetic Construct

<400> SEQUENCE: 51

Thr Tyr Val Pro Ala Asn Ala Ser Leu
1               5


<210> SEQ ID NO 52
<211> LENGTH: 15
<212> TYPE: PRT
```

<213> ORGANISM: Artificial
<220> FEATURE:
<223> OTHER INFORMATION: Synthetic Construct

<400> SEQUENCE: 52

Asp Met Val Leu Trp Lys Asp Val Phe Arg Lys Asn Asn Gln Leu
1 5 10 15

<210> SEQ ID NO 53
<211> LENGTH: 9
<212> TYPE: PRT
<213> ORGANISM: Artificial
<220> FEATURE:
<223> OTHER INFORMATION: Synthetic Construct

<400> SEQUENCE: 53

Ser Tyr Val Asn Thr Asn Met Gly Leu
1 5

<210> SEQ ID NO 54
<211> LENGTH: 957
<212> TYPE: PRT
<213> ORGANISM: Artificial
<220> FEATURE:
<223> OTHER INFORMATION: Synthetic Construct

<400> SEQUENCE: 54

Met Ala Ser Glu Leu Ala Ala Trp Cys Arg Trp Gly Phe Leu Leu Ala
1 5 10 15

Leu Leu Pro Pro Gly Ile Ala Gly Thr Gln Val Cys Thr Gly Thr Asp
20 25 30

Met Lys Leu Arg Leu Pro Ala Ser Pro Glu Thr His Leu Asp Met Leu
35 40 45

Arg His Leu Tyr Gln Gly Cys Gln Val Val Gln Gly Asn Leu Glu Leu
50 55 60

Thr Tyr Val Pro Ala Asn Ala Ser Leu Ser Phe Leu Gln Asp Ile Gln
65 70 75 80

Glu Val Gln Gly Tyr Met Leu Ile Ala His Asn Gln Val Lys Arg Val
85 90 95

Pro Leu Gln Arg Leu Arg Ile Val Arg Gly Thr Gln Leu Phe Glu Asp
100 105 110

Lys Tyr Ala Leu Ala Val Leu Asp Asn Arg Asp Pro Gln Asp Asn Val
115 120 125

Ala Ala Ser Thr Pro Gly Arg Thr Pro Glu Gly Leu Arg Glu Leu Gln
130 135 140

Leu Arg Ser Leu Thr Glu Ile Leu Lys Gly Gly Val Leu Ile Arg Gly
145 150 155 160

Asn Pro Gln Leu Cys Tyr Gln Asp Met Val Leu Trp Lys Asp Val Phe
165 170 175

Arg Lys Asn Asn Gln Leu Ala Pro Val Asp Ile Asp Thr Asn Arg Ser
180 185 190

Arg Ala Cys Pro Pro Cys Ala Pro Ala Cys Lys Asp Asn His Cys Trp
195 200 205

Gly Glu Ser Pro Glu Asp Cys Gln Ile Leu Thr Gly Thr Ile Cys Thr
210 215 220

Ser Gly Cys Ala Arg Cys Lys Gly Arg Leu Pro Thr Asp Cys Cys His
225 230 235 240

Glu Gln Cys Ala Ala Gly Cys Thr Gly Pro Lys His Ser Asp Cys Leu
245 250 255

```
Ala Cys Leu His Phe Asn His Ser Gly Ile Cys Glu Leu His Cys Pro
            260                 265                 270

Ala Leu Val Thr Tyr Asn Thr Asp Thr Phe Glu Ser Met His Asn Pro
        275                 280                 285

Glu Gly Arg Tyr Thr Phe Gly Ala Ser Cys Val Thr Thr Cys Pro Tyr
    290                 295                 300

Asn Tyr Leu Ser Thr Glu Val Gly Ser Cys Thr Leu Val Cys Pro Pro
305                 310                 315                 320

Asn Asn Gln Glu Val Thr Ala Glu Asp Gly Thr Gln Arg Cys Glu Lys
                325                 330                 335

Cys Ser Lys Pro Cys Ala Arg Val Cys Tyr Gly Leu Gly Met Glu His
            340                 345                 350

Leu Arg Gly Ala Arg Ala Ile Thr Ser Asp Asn Val Gln Glu Phe Asp
        355                 360                 365

Gly Cys Lys Lys Ile Phe Gly Ser Leu Ala Phe Leu Pro Glu Ser Phe
    370                 375                 380

Asp Gly Asp Pro Ser Ser Gly Ile Ala Pro Leu Arg Pro Glu Gln Leu
385                 390                 395                 400

Gln Val Phe Glu Thr Leu Glu Glu Ile Thr Gly Tyr Leu Tyr Ile Ser
                405                 410                 415

Ala Trp Pro Asp Ser Leu Arg Asp Leu Ser Val Phe Gln Asn Leu Arg
            420                 425                 430

Ile Ile Arg Gly Arg Ile Leu His Asp Gly Ala Tyr Ser Leu Thr Leu
        435                 440                 445

Gln Gly Leu Gly Ile His Ser Leu Gly Leu Arg Ser Leu Arg Glu Leu
    450                 455                 460

Gly Ser Gly Leu Ala Leu Ile His Arg Asn Ala His Leu Cys Phe Val
465                 470                 475                 480

His Thr Val Pro Trp Asp Gln Leu Phe Arg Asn Pro His Gln Ala Leu
                485                 490                 495

Leu His Ser Gly Asn Arg Pro Glu Glu Asp Cys Gly Leu Glu Gly Leu
            500                 505                 510

Val Cys Asn Ser Leu Cys Ala His Gly His Cys Trp Gly Pro Gly Pro
        515                 520                 525

Thr Gln Cys Val Asn Cys Ser His Phe Leu Arg Gly Gln Glu Cys Val
    530                 535                 540

Glu Glu Cys Arg Val Trp Lys Gly Leu Pro Arg Glu Tyr Val Ser Asp
545                 550                 555                 560

Lys Arg Cys Leu Pro Cys His Pro Glu Cys Gln Pro Gln Asn Ser Ser
                565                 570                 575

Glu Thr Cys Phe Gly Ser Glu Ala Asp Gln Cys Ala Ala Cys Ala His
            580                 585                 590

Tyr Lys Asp Ser Ser Ser Cys Val Ala Arg Cys Pro Ser Gly Val Lys
        595                 600                 605

Pro Asp Leu Ser Tyr Met Pro Ile Trp Lys Tyr Pro Asp Glu Glu Gly
    610                 615                 620

Ile Cys Gln Pro Cys Pro Ile Asn Cys Thr His Ser Cys Val Asp Leu
625                 630                 635                 640

Asp Glu Arg Gly Cys Pro Ala Glu Gln Arg Ala Ser Pro Val Thr Phe
                645                 650                 655

Ile Ile Ala Thr Val Val Gly Val Leu Leu Phe Leu Ile Leu Val Val
            660                 665                 670
```

```
Val Val Gly Ile Leu Ile Lys Arg Arg Arg Gln Lys Ile Arg Lys Tyr
        675                 680                 685

Thr Met Arg Arg Asn Glu Asp Leu Gly Pro Ser Ser Pro Met Asp Ser
    690                 695                 700

Thr Phe Tyr Arg Ser Leu Leu Glu Asp Asp Asp Met Gly Asp Leu Val
705                 710                 715                 720

Asp Ala Glu Glu Tyr Leu Val Pro Gln Gln Gly Phe Phe Ser Pro Asp
                725                 730                 735

Pro Thr Pro Gly Thr Gly Ser Thr Ala His Arg Arg His Arg Ser Ser
            740                 745                 750

Ser Thr Arg Ser Gly Gly Gly Glu Leu Thr Leu Gly Leu Glu Pro Ser
        755                 760                 765

Glu Glu Gly Pro Pro Arg Ser Pro Leu Ala Pro Ser Glu Gly Ala Gly
    770                 775                 780

Ser Asp Val Phe Asp Gly Asp Leu Ala Met Gly Val Thr Lys Gly Leu
785                 790                 795                 800

Gln Ser Leu Ser Pro His Asp Leu Ser Pro Leu Gln Arg Tyr Ser Glu
                805                 810                 815

Asp Pro Thr Leu Pro Leu Pro Pro Glu Thr Asp Gly Tyr Val Ala Pro
            820                 825                 830

Leu Ala Cys Ser Pro Gln Pro Glu Phe Val Asn Gln Ser Glu Val Gln
        835                 840                 845

Pro Gln Pro Pro Leu Thr Pro Glu Gly Pro Leu Pro Pro Val Arg Pro
    850                 855                 860

Ala Gly Ala Thr Leu Glu Arg Pro Lys Thr Leu Ser Pro Gly Lys Asn
865                 870                 875                 880

Gly Val Val Lys Asp Val Phe Ala Phe Gly Gly Ala Val Glu Asn Pro
                885                 890                 895

Glu Phe Leu Val Pro Arg Glu Gly Thr Ala Ser Pro Pro His Pro Ser
            900                 905                 910

Pro Ala Phe Ser Pro Ala Phe Asp Asn Leu Phe Phe Trp Asp Gln Asn
        915                 920                 925

Ser Ser Glu Gln Gly Pro Pro Pro Ser Asn Phe Glu Gly Thr Pro Thr
    930                 935                 940

Ala Glu Asn Pro Glu Phe Leu Gly Leu Asp Val Pro Val
945                 950                 955
```

<210> SEQ ID NO 55
<211> LENGTH: 739
<212> TYPE: PRT
<213> ORGANISM: Artificial
<220> FEATURE:
<223> OTHER INFORMATION: Synthetic Construct

<400> SEQUENCE: 55

```
Met Ala Ser Ala Arg Arg Pro Arg Trp Leu Cys Ala Gly Ala Leu Val
1               5                   10                  15

Leu Ala Gly Gly Phe Phe Leu Leu Gly Phe Leu Phe Gly Trp Phe Ile
            20                  25                  30

Lys Ser Ser Ser Glu Ala Thr Asn Ile Thr Pro Lys His Asn Met Lys
        35                  40                  45

Ala Phe Leu Asp Glu Leu Lys Ala Glu Asn Ile Lys Lys Phe Leu His
    50                  55                  60

Asn Phe Thr Gln Ile Pro His Leu Ala Gly Thr Glu Gln Asn Phe Gln
65                  70                  75                  80
```

```
Leu Ala Lys Gln Ile Gln Ser Gln Trp Lys Glu Phe Gly Leu Asp Ser
                85                  90                  95

Val Glu Leu Thr His Tyr Asp Val Leu Leu Ser Tyr Pro Asn Lys Thr
            100                 105                 110

His Pro Asn Tyr Ile Ser Ile Ile Asn Glu Asp Gly Asn Glu Ile Phe
        115                 120                 125

Asn Thr Ser Leu Phe Glu Pro Pro Pro Ala Gly Tyr Glu Asn Val Ser
    130                 135                 140

Asp Ile Val Pro Pro Phe Ser Ala Phe Ser Pro Gln Gly Met Pro Glu
145                 150                 155                 160

Gly Asp Leu Val Tyr Val Asn Tyr Ala Arg Thr Glu Asp Phe Phe Lys
                165                 170                 175

Leu Glu Arg Asp Met Lys Ile Asn Cys Ser Gly Lys Ile Val Ile Ala
            180                 185                 190

Arg Tyr Gly Lys Val Phe Arg Gly Asn Lys Val Lys Asn Ala Gln Leu
        195                 200                 205

Ala Gly Ala Thr Gly Val Ile Leu Tyr Ser Asp Pro Ala Asp Tyr Phe
    210                 215                 220

Ala Pro Gly Val Lys Ser Tyr Pro Asp Gly Trp Asn Leu Pro Gly Gly
225                 230                 235                 240

Gly Val Gln Arg Gly Asn Ile Leu Asn Leu Asn Gly Ala Gly Asp Pro
                245                 250                 255

Leu Thr Pro Gly Tyr Pro Ala Asn Glu Tyr Ala Tyr Arg Arg Gly Ile
            260                 265                 270

Ala Glu Ala Val Gly Leu Pro Ser Ile Pro Val His Pro Ile Gly Tyr
        275                 280                 285

Tyr Asp Ala Gln Lys Leu Leu Glu Lys Met Gly Gly Ser Ala Ser Pro
    290                 295                 300

Asp Ser Ser Trp Arg Gly Ser Leu Lys Val Pro Tyr Asn Val Gly Pro
305                 310                 315                 320

Gly Phe Thr Gly Asn Phe Ser Thr Gln Lys Val Lys Met His Ile His
                325                 330                 335

Ser Thr Ser Glu Val Thr Arg Ile Tyr Asn Val Ile Gly Thr Leu Arg
            340                 345                 350

Gly Ala Val Glu Pro Asp Arg Tyr Val Ile Leu Gly Gly His Arg Asp
        355                 360                 365

Ser Trp Val Phe Gly Gly Ile Asp Pro Gln Ser Gly Ala Ala Val Val
    370                 375                 380

His Glu Ile Val Arg Ser Phe Gly Thr Leu Lys Lys Glu Gly Trp Arg
385                 390                 395                 400

Pro Arg Arg Thr Ile Leu Phe Ala Ser Trp Asp Ala Glu Glu Phe Gly
                405                 410                 415

Leu Leu Gly Ser Thr Glu Trp Ala Glu Glu Asn Ser Arg Leu Leu Gln
            420                 425                 430

Glu Arg Gly Val Ala Tyr Ile Asn Ala Asp Ser Ser Ile Glu Gly Asn
        435                 440                 445

Tyr Thr Leu Arg Val Asp Cys Thr Pro Leu Met Tyr Ser Leu Val Tyr
    450                 455                 460

Asn Leu Thr Lys Glu Leu Glu Ser Pro Asp Glu Gly Phe Glu Gly Lys
465                 470                 475                 480

Ser Leu Tyr Glu Ser Trp Thr Lys Lys Ser Pro Ser Pro Glu Phe Ser
                485                 490                 495

Gly Met Pro Arg Ile Ser Lys Leu Gly Ser Gly Asn Asp Phe Glu Val
```

-continued

```
            500                 505                 510

Phe Phe Gln Arg Leu Gly Ile Ala Ser Gly Arg Ala Arg Tyr Thr Lys
        515                 520                 525

Asn Trp Glu Thr Asn Lys Phe Ser Ser Tyr Pro Leu Tyr His Ser Val
    530                 535                 540

Tyr Glu Thr Tyr Glu Leu Val Glu Lys Phe Tyr Asp Pro Met Phe Lys
545                 550                 555                 560

Tyr His Leu Thr Val Ala Gln Val Arg Gly Gly Met Val Phe Glu Leu
                565                 570                 575

Ala Asn Ser Val Val Leu Pro Phe Asp Cys Arg Asp Tyr Ala Val Val
            580                 585                 590

Leu Arg Lys Tyr Ala Asp Lys Ile Tyr Asn Ile Ser Met Lys His Pro
        595                 600                 605

Gln Glu Met Lys Thr Tyr Ser Val Ser Phe Asp Ser Leu Phe Ser Ala
    610                 615                 620

Val Lys Asn Phe Thr Glu Ile Ala Ser Lys Phe Ser Glu Arg Leu Arg
625                 630                 635                 640

Asp Phe Asp Lys Ser Asn Pro Ile Leu Leu Arg Met Met Asn Asp Gln
                645                 650                 655

Leu Met Phe Leu Glu Arg Ala Phe Ile Asp Pro Leu Gly Leu Pro Asp
            660                 665                 670

Arg Pro Phe Tyr Arg His Val Ile Tyr Ala Pro Ser Ser His Asn Lys
        675                 680                 685

Tyr Ala Gly Glu Ser Phe Pro Gly Ile Tyr Asp Ala Leu Phe Asp Ile
    690                 695                 700

Glu Ser Lys Val Asp Pro Ser Gln Ala Trp Gly Glu Val Lys Arg Gln
705                 710                 715                 720

Ile Ser Ile Ala Thr Phe Thr Val Gln Ala Ala Ala Glu Thr Leu Ser
                725                 730                 735

Glu Val Ala


<210> SEQ ID NO 56
<211> LENGTH: 2217
<212> TYPE: DNA
<213> ORGANISM: Artificial
<220> FEATURE:
<223> OTHER INFORMATION: Synthetic Construct

<400> SEQUENCE: 56

atggctagcg ctagaaggcc cagatggctg tgcgctggcg ccctggtgct ggctggcgga      60

ttcttcctgc tgggcttcct gttcggctgg ttcatcaagt cctccagcga ggccaccaac     120

atcacccccca agcacaacat gaaggccttt ctggacgagc tgaaggccga gaatatcaag     180

aagttcctgc acaacttcac ccagatcccc cacctggccg gcaccgagca gaacttccag     240

ctggccaagc agatccagtc ccagtggaaa gagttcggcc tggactccgt ggaactgacc     300

cactacgacg tgctgctgtc ctaccccaac aagacccacc ccaactacat ctccatcatc     360

aacgaggacg gcaacgaaat cttcaacacc tccctgttcg agcccccacc agccggctac     420

gagaacgtgt ccgacatcgt gcccccattc tccgcattca gtccacaagg catgcccgag     480

ggcgacctgg tgtacgtgaa ctacgccagg accgaggact tcttcaagct ggaaagggac     540

atgaagatca actgctccgg caagatcgtg atcgccagat acggcaaggt gttcaggggc     600

aacaaagtga agaacgctca gctggctggg gccaccggcg tgatcctgta ctctgacccc     660

gccgactact tcgccccagg cgtgaagtcc taccccgacg gctggaacct gccaggtggc     720
```

-continued

```
ggagtgcaga ggggcaacat cctgaacctg aacggcgctg gcgacccccct gaccccagga    780

taccccgcca acgagtacgc ctacagaaga ggaatcgccg aggccgtggg cctgccctct    840

atcccagtgc accccatcgg ctactacgac gcccagaaac tgctggaaaa gatgggcggc    900

tccgcctccc ccgactcctc ttggagaggc tccctgaagg tgccctacaa cgtgggccca    960

ggcttcaccg gcaacttctc cacccagaaa gtgaagatgc acatccactc cacctccgaa   1020

gtgaccagga tctacaacgt gatcggcacc ctgagaggcg ccgtggaacc cgacagatac   1080

gtgatcctgg gcggccacag ggacagctgg gtgttcggcg gcatcgaccc acagtctggc   1140

gccgctgtgg tgcacgagat cgtgcggtcc ttcggaaccc tgaagaaaga gggatggcgc   1200

cccagaagga caatcctgtt cgcctcctgg gacgccgagg aattcggcct gctgggatcc   1260

accgagtggg ccgaggaaaa ctccaggctg ctgcaggaaa ggggcgtcgc ctacatcaac   1320

gccgactcct ccatcgaggg caactacacc ctgagggtgg actgcacccc cctgatgtac   1380

tccctggtgt acaacctgac caaagagctg gaatcccccg acgagggctt cgagggcaag   1440

tccctgtacg agtcctggac caagaagtcc ccatcccccg agttctccgg catgcccagg   1500

atctccaagc tgggctccgg caacgacttc gaggtgttct tccagaggct gggaatcgcc   1560

tccggcaggg ccagatacac caagaactgg gagacaaaca agttctcctc ctaccccctg   1620

taccactccg tgtacgaaac ctacgagctg gtggaaaagt tctacgaccc catgttcaag   1680

taccacctga ccgtggccca ggtccgcgga ggcatggtgt tcgagctggc caactccgtg   1740

gtgctgccct tcgactgcag agactatgct gtggtgctga ggaagtacgc cgacaaaatc   1800

tacaacatct ccatgaagca cccccaggaa atgaagacct actccgtgtc cttcgactcc   1860

ctgttctccg ccgtgaagaa tttcaccgag atcgcctcca agttctccga gaggctgagg   1920

gacttcgaca agtccaaccc catcctgctg aggatgatga acgaccagct gatgttcctg   1980

gaaagggcct tcatcgaccc cctgggcctg ccagacaggc ccttctacag gcacgtgatc   2040

tacgccccat cctcccacaa caaatacgcc ggcgagtcct tccccggcat ctacgatgcc   2100

ctgttcgaca tcgagtccaa ggtggacccc tcccaggctt ggggcgaagt gaagaggcag   2160

atcagtatcg ccacattcac agtgcaggcc gctgccgaaa ccctgtccga ggtggcc      2217
```